US008350009B2

(12) United States Patent
Jakobovits et al.

(10) Patent No.: US 8,350,009 B2
(45) Date of Patent: *Jan. 8, 2013

(54) ANTIBODIES AND RELATED MOLECULES THAT BIND TO 161P2F10B PROTEINS

(75) Inventors: Aya Jakobovits, Beverly Hills, CA (US); Steven B. Kanner, Santa Monica, CA (US); Pia M. Challita-Eid, Encino, CA (US); Juan J. Perez-Villar, Santa Monica, CA (US); Daulet Satpaev, Santa Monica, CA (US); Arthur B. Raitano, Los Angeles, CA (US); Robert Kendall Morrison, Santa Monica, CA (US); Karen Jane Meyrick Morrison, Santa Monica, CA (US); Xiao-chi Jia, Los Angeles, CA (US); Jean Gudas, Los Angeles, CA (US)

(73) Assignee: Agensys, Inc., Santa Monica, CA (US)

( * ) Notice: Subject to any disclaimer, the term of this patent is extended or adjusted under 35 U.S.C. 154(b) by 239 days.

This patent is subject to a terminal disclaimer.

(21) Appl. No.: 12/757,935

(22) Filed: Apr. 9, 2010

(65) Prior Publication Data

US 2010/0260756 A1 Oct. 14, 2010

Related U.S. Application Data

(60) Continuation-in-part of application No. 12/433,760, filed on Apr. 30, 2009, now Pat. No. 7,811,565, which is a continuation of application No. 12/196,039, filed on Aug. 21, 2008, now abandoned, which is a division of application No. 11/396,178, filed on Mar. 31, 2006, now Pat. No. 7,427,399.

(60) Provisional application No. 60/667,588, filed on Mar. 31, 2005, provisional application No. 60/700,975, filed on Jul. 20, 2005.

(51) Int. Cl.
C07K 16/00 (2006.01)
A61K 39/00 (2006.01)
C12P 21/08 (2006.01)

(52) U.S. Cl. ............. 530/388.1; 530/388.85; 530/391.3; 530/391.7; 424/139.1; 424/141.1; 424/178.1

(58) Field of Classification Search .................. None
See application file for complete search history.

(56) References Cited

U.S. PATENT DOCUMENTS

| 5,001,225 | A | 3/1991 | Taylor |
| 6,323,321 | B1 | 11/2001 | Buhring |
| 6,342,219 | B1 | 1/2002 | Thorpe et al. |
| 7,067,130 | B2 | 6/2006 | Challita-Eid et al. |
| 7,226,594 | B2 | 6/2007 | Jakobovits et al. |
| 7,405,290 | B2 | 7/2008 | Challita-Eid et al. |
| 7,811,565 | B2 | 10/2010 | Jakobovits et al. |
| 2002/0137139 | A1 | 9/2002 | Byatt et al. |
| 2003/0165505 | A1 | 9/2003 | Challita-Eid et al. |
| 2003/0191073 | A1 | 10/2003 | Challita-Eid et al. |
| 2003/0206905 | A1 | 11/2003 | Challita-Eid et al. |
| 2005/0055733 | A1 | 3/2005 | Sun et al. |
| 2005/0265921 | A1 | 12/2005 | Challita-Eid et al. |
| 2005/0265924 | A1 | 12/2005 | Challita-Eid et al. |
| 2006/0002993 | A1 | 1/2006 | Challita-Eid et al. |
| 2006/0233794 | A1 | 10/2006 | Law et al. |
| 2006/0275211 | A1 | 12/2006 | Challita-Eid et al. |
| 2007/0004913 | A1 | 1/2007 | Challita-Eid et al. |
| 2007/0031335 | A1 | 2/2007 | Jakobovits et al. |

FOREIGN PATENT DOCUMENTS

| WO | WO-99/60164 | 11/1999 |
| WO | WO-00/21990 | 4/2000 |
| WO | WO-01/57272 | 8/2001 |
| WO | WO-01/57273 | 8/2001 |
| WO | WO-01/57274 | 8/2001 |
| WO | WO-01/57275 | 8/2001 |
| WO | WO-01/57276 | 8/2001 |
| WO | WO-01/57277 | 8/2001 |
| WO | WO-01/57278 | 8/2001 |
| WO | WO-01/60860 | 8/2001 |
| WO | WO-01/75067 | 10/2001 |
| WO | WO-01/86003 | 11/2001 |
| WO | WO-02/079411 | 10/2002 |
| WO | WO-03/004514 | 1/2003 |
| WO | WO-03/016475 | 2/2003 |
| WO | WO-03/040340 | 5/2003 |
| WO | WO-03/048779 | 6/2003 |

OTHER PUBLICATIONS

Request for Continued Examination from U.S. Appl. No. 10/062,109, filed via facsimile on Mar. 2, 2005.
Notice of Allowance and Fee(s) Due from U.S. Appl. No. 10/860,769, mailed Jun. 1, 2007.
Notice of Allowance and Fee(s) Due from U.S. Appl. No. 10/859,643, mailed Jun. 8, 2007. Amendment in Response to Non-Final Office Action from U.S. Appl. No. 11/097,912, filed via EFS-Web on May 4, 2007.
Non-Final Office Action (2nd) from U.S. Appl. No. 11/097,912, mailed Jun. 27, 2007.
Amendment in Response to Non-Final Office Action (2nd) from U.S. Appl. No. 11/097,912, filed via EFS-Web on Dec. 13, 2007.
Amendment in Response to Non-Final Office Action from U.S. Appl. No. 11/097,864, filed via EFS-Web on Apr. 17, 2007.
Final Office Action from U.S. Appl. No. 11/097,864, mailed Jun. 27, 2007.
Request for Continued Examination from U.S. Appl. No. 11/097,864, filed via EFS-Web on Oct. 30, 2007.
Advisory Action Before the Filing of an Appeal Brief from U.S. Appl. No. 10/291,241, mailed May 19, 2006.
Notice of Allowance and Fee(s) Due from U.S. Appl. No. 10/291,241, mailed Oct. 4, 2006.
Non-Final Office Action for U.S. Appl. No. 11/655,822, mailed on Aug. 6, 2008, 19 pages.
Non-Final Office Action for U.S. Appl. No. 11/655,822, mailed on Feb. 23, 2009, 10 pages.

(Continued)

*Primary Examiner* — Laura B Goddard
(74) *Attorney, Agent, or Firm* — Morrison & Foerster LLP

(57) ABSTRACT

Antibodies and molecules derived therefrom that bind to 161P2F10B protein and variants thereof, are described wherein 161P2F10B exhibits tissue specific expression in normal adult tissue, and is aberrantly expressed in the cancers listed in Table I. Consequently, 161P2F10B provides a diagnostic, prognostic, prophylactic and/or therapeutic target for cancer. The 161P2F10B gene or fragment thereof, or its encoded protein, or variants thereof, or a fragment thereof, can be used to elicit a humoral or cellular immune response; antibodies or T cells reactive with 161P2F10B can be used in active or passive immunization.

8 Claims, 146 Drawing Sheets

OTHER PUBLICATIONS

International Search Report for PCT/US11/24055, mailed on Apr. 6, 2011, 3 pages.
Written Opinion of the International Searching Authority for PCT/US11/24055, mailed on Apr. 6, 2011, 4 pages.
Alcocer et al., J. Agric. Food Chem (2000) 48:4053-4059.
Non-Final Office Action for U.S. Appl. No. 12/641,261 mailed Jul. 21, 2010, 15 pages.
Amalfitano et al., Current Gene Therapy (2002) 2:111-133.
Andoh et al., "Genomic structure and promoter analysis of the ecto-phosphodiesterase I gene (PDNP3) expressed in glial cells," Biochimica et Biophysica Acta (1999) 1446(3):213-224.
Boehringer Mannheim Biochemicals, 1994 Catalog, p. 93.
Bollen et al., "Nucleotide pyrophosphatases/phosphodiesterases on the move," Critical Reviews in Biochemistry and Molecular Biology (2000) 35(6):393-432.
Buehring et al., Tissue Antigens (2000) 55(Suppl. 01):68.
Buhring et al., Blood 94(7):2343-2356 (1999).
Buhring et al., Blood 97(10):3303-3305 (2001).
Burgess et al., Journal of Cell Biology 111:2129-2138 (1990).
Colbern et al., J. Inorg. Biochem. (1999) 77:117-120.
Coleman, Research in Immunology 145:33-36 (1994).
Database EMBL [Online] Accession No. AK024899 (Sep. 29, 2000).
Database Geneseq [Online] Accession No. ADE56103 (Jan. 29, 2005).
Deissler et al., Journal of Biological Chemistry (1995) 270(17):9849-9855.
Dennis, Nature (2006) 442:739-741.
Dillman, Annals of Internal Medicine (1989) 111:592-603.
Goding et al., Biochimica et Biophysica Acta (2003) 1638(1):1-19.
Houdebine, Journal of Biotechnology (1994) 34:269-287.
Houghton and Scheinberg, Seminars in Oncology (1986) 13:165-179.
International Search Report for PCT/US02/36002, mailed on Jan. 5, 2005, 5 pages.
International Search Report and Written Opinion for PCT/US06/12314, mailed Jan. 11, 2008, 7 pages.
Jain, Scientific American (1994) 271:58-65.
Jiang et al., J. Biol. Chem. (2005) 280(6):4656-4662.
Jin-Hua et al., Genomics 45(2):412-415 (1997).
Lazar et al., Molecular and Cellular Biology 8(3):1247-1252 (1988).
Lederman et al., Molecular Immunology 28:1171-1181 (1991).
Lewin, ed., Genes VI, Chapter 29, pp. 847-848 (1997).
Li et al., Proc Natl Acad Sci USA 77:3211-3214 (1980).
Maurice et al., "Biosynthesis and intracellular transport of a bile canalicular plasma membrane protein: studies in vivo and in the perfused rat liver," Hepatology (1994) 19(3):648-655.
Maurice et al., "Characterization of rat hepatocyte plasma membrane domains by monoclonal antibodies," European Journal of Cell Biology (1985) 39(1):122-129.
McCormick, Nature Reviews (2001) 1:130-141.
Meibohm, ed., Pharmacokinetics and Pharmacodynamics of Biotech Drugs, Wiley-VHC, 2006, Chapter 3, pp. 45-91.
NCBI Accession No. NP_004439, Version: NP_004439.1, GI:4758298, PRI date: Oct. 14, 1999, pp. 1-4.
Pandha et al., Current Opinion in Investigational Drugs (2000) 1:122-134.
Paul (Ed.), Fundamental Immunology, 3rd ed., p. 242 (1993).
PN IM3575, 100 tests, 20 µL/test, IOTest Conjugated Antibodies, Immunotech, A Coulter Company, Vers. 01, Apr. 4, 2001, retrieved from Internet.
Reiger et al., Glossary of Genetics and Cytogenetics, Classical and Molecular, 4th Ed., Springer-Verlag, Berlin (1976).
Rolland, Advanced Drug Delivery Reviews (2005) 57:669-673.
Schwartz et al., Proc Natl Acad Sci USA 84:6408-6411 (1987).
Scott et al., "Biochemical and molecular identification of distinct forms of alkaline phosphodiesterase I expressed on the apical and basolateral plasma membrane surfaces of rat hepatocytes," Hepatology (1997) 25(4):995-1002.
Srivastava, Nature Immunology (2000) 1(5):363-366.
Stancoviski et al., PNAS USA (1991) 88:8691-8695.
Supplementary Partial European Search Report for EP 02 79 7088.8, mailed on Oct. 25, 2006, 7 pages.
Supplementary European Search Report for EP 02 79 7088, mailed on Feb. 5, 2007, 8 pages.
Supplementary European Search Report for EP 06749164.7, mailed Aug. 20, 2009, 12 pages.
Verma et al., Nature (1997) 389:239-242.
Weiner, Seminars in Oncology (1999) 26(Suppl. 12):41-50.
White et al., Ann Rev Med (2001) 52:125-145.
Yano et al., Cancer Letters (2004) 207(2):139-147.
Yano et al., International Journal of Molecular Medicine (2003) 12(5):763-766.
Restriction Requirement for U.S. Appl. No. 10/005,480, mailed on May 24, 2004.
Response to Restriction Requirement and Amendment Under 37 CFR § 1.111 for U.S. Appl. No. 10/005,480, filed Jun. 18, 2004.
Non-Final Office Action for U.S. Appl. No. 10/005,480, mailed on Aug. 17, 2004.
Restriction Requirement for U.S. Appl. No. 10/062,109, mailed on Jul. 9, 2004.
Response to Restriction Requirement for U.S. Appl. No. 10/062,109, filed Jul. 15, 2004.
Non-Final Office Action for U.S. Appl. No. 10/062,109, mailed on Aug. 25, 2004.
Amendment in Response to Non-Final Office Action for U.S. Appl. No. 10/062,109, filed Sep. 17, 2004.
Final Office Action for U.S. Appl. No. 10/062,109, mailed on Nov. 12, 2004.
Amendment After Final Action (37 CFR § 1.116) for U.S. Appl. No. 10/062,109, filed Dec. 1, 2004.
Notice of Allowance for U.S. Appl. No. 10/062,109, mailed on May 4, 2005.
Non-Final Office Action for U.S. Appl. No. 10/860,769, mailed on Dec. 5, 2006.
Amendment in Response to Non-Final Office Action for U.S. Appl. No. 10/860,769, filed Mar. 5, 2007.
Non-Final Office Action for U.S. Appl. No. 10/859,643, mailed on Nov. 13, 2006.
Amendment in Response to Non-Final Office Action for U.S. Appl. No. 10/859,643, filed Mar. 5, 2007.
Non-Final Office Action for U.S. Appl. No. 11/097,912, mailed on Nov. 6, 2006.
Non-Final Office Action for U.S. Appl. No. 11/097,864, mailed on Oct. 19, 2006.
Restriction Requirement for U.S. Appl. No. 10/291,241, mailed on Sep. 21, 2005.
Response to Restriction Requirement, filed on Nov. 18, 2005.
Non-Final Office Action for U.S. Appl. No. 10/291,241, mailed on Dec. 29, 2005.
Amendment in Response to Non-Final Office Action for U.S. Appl. No. 10/291,241, filed Jan. 10, 2006.
Final Office Action for U.S. Appl. No. 10/291,241, mailed on Apr. 5, 2006.
Amendment After Final Action (37 CFR § 1.116) for U.S. Appl. No. 10/291,241, filed Apr. 19, 2006.
Supplemental Amendment After Final Action (37 CFR § 1.116) for U.S. Appl. No. 10/291,241, filed Jun. 1, 2006.
Non-Final Office Action for U.S. Appl. No. 10/291,241, mailed on Jun. 28, 2006.
Amendment in Response to Non-Final Office Action for U.S. Appl. No. 10/291,241, filed Jul. 13, 2006.
Notice of Allowance for U.S. Appl. No. 10/291,241, mailed on Dec. 12, 2006.
Restriction Requirement for U.S. Appl. No. 11/396,178, mailed on Feb. 27, 2007.
Non-Final Office Action for U.S. Appl. No. 12/196,039, mailed on May 13, 2009, 13 pages.
Johnstone and Thorpe, Immunochemistry in Practice, 2nd Ed., Blackwell Scientific Publications, Oxford (1987) pp. 49-50.
Maynard et al., "Antibody Engineering," Annu. Rev. Biomed. Eng. (2000) 2:339-376.

Figure 1:

Figure 1A. The cDNA (SEQ ID NO:1) and amino acid sequence (SEQ ID NO:2) of 161P2F10B variant 1. The 3858 nucleotide sequence of 161P2F10B variant 1 is shown. The open reading frame extends from nucleic acid 44-2671 including the stop codon.

```
  1                                            M   E   S   T   L   T
  1  ctactttattctgataaaacaggtctatgcagctaccaggacaATGGAATCTACGTTGAC
  7  L   A   T   E   Q   P   V   K   K   N   T   L   K   K   Y   I   A   C   I
 61  TTTAGCAACGGAACAACCTGTTAAGAAGAACACTCTTAAGAAATATAAAATAGCTTGCAT
 27  V   L   A   L   L   V   I   M   S   L   G   L   G   L   G   L   R
121  TGTTCTTCTTGCTTTGCTGGTGATCATGTCACTTGGATTAGGCCTGGGGCTTGGACTCAG
 47  K   L   E   K   Q   G   S   C   R   K   K   C   F   D   A   S   F   R   G   L
181  GAAACTGGAAAAGCAAGGCAGCTGCAGGAAGAAGTGCTTTGATGCATCATTTAGAGGACT
 67  E   N   C   R   C   D   V   A   C   K   D   R   G   D   C   C   W   D   F   E
241  GGAGAACTGCCGGTGTGATGTGGCATGTAAAGACCGAGGTGATTGCTGCTGGGATTTTGA
 87  D   T   C   V   E   S   T   R   I   W   M   C   N   K   F   R   C   G   E   T
301  AGACACCTGTGTGGAATCAACTCGAATATGGATGTGCAATAAATTTCGTTGTGGAGAGAC
107  R   L   E   A   S   L   C   S   C   S   D   D   C   L   Q   K   K   D   C   C
361  CAGATTAGAGGCCAGCCTTTGCTCTTGTTCAGATGACTGTTTGCAGAAGAAAGATTGCTG
127  A   D   Y   K   S   V   C   Q   G   E   T   S   W   L   E   N   C   D   T
421  TGCTGACTATAAGAGTGTTTGCCAAGGAGAAACCTCATGGCTGGAAGAAAACTGTGACAC
147  A   Q   Q   S   Q   C   P   E   G   F   D   L   P   P   V   I   L   F   S   M
481  AGCCCAGCAGTCTCAGTGCCCAGAAGGGTTTGACCTGCCACCAGTTATCTTGTTTTCTAT
167  D   G   F   R   A   E   Y   L   Y   T   W   D   T   L   M   P   N   I   N   K
541  GGATGGATTTAGAGCTGAATATTTATACACATGGGATACTTTAATGCCAAATATCAATAA
187  L   K   T   C   G   I   H   S   K   Y   M   R   A   M   Y   P   T   K   T   F
601  ACTGAAAACATGTGGAATTCATTCAAAATACATGAGAGCTATGTATCCTACCAAAACCTT
207  P   N   H   Y   I   V   T   G   L   Y   P   E   S   H   G   I   I   D   N
661  CCCAAATCATTACACCATTGTCACGGGCTTGTATCCAGAGTCACATGGCATCATTGACAA
227  N   M   Y   D   V   N   L   K   N   F   S   L   S   S   K   E   Q   N   N
721  TAATATGTATGATGTAAATCTCAACAAGAATTTTTCACTTTCTTCAAAGGAACAAAATAA
247  P   A   W   W   H   G   Q   P   M   W   L   T   A   M   Y   Q   G   L   K   A
781  TCCAGCCTGGTGGCATGGGCAACCAATGTGGCTGACAGCAATGTATCAAGGTTTAAAAGC
267  A   T   Y   F   W   P   G   S   E   V   A   I   N   G   S   F   P   S   I   Y
841  CGCTACCTACTTTTGGCCCGGATCAGAAGTGGCTATAAATGGCTCCTTCCCTTCCATATA
287  M   P   Y   N   G   S   V   P   F   E   E   R   I   S   T   L   L   K   W   L
901  CATGCCTTACAACGGAAGTGTCCCATTTGAAGAGAGGATTTCTACACTGTTAAAATGGCT
307  D   L   P   K   A   E   R   P   R   F   Y   T   M   Y   F   E   E   P   D   S
961  GGACCTGCCCAAAGCTGAAAGACCCAGGTTTTATACCATGTATTTTGAAGAACCTGATTC
327  S   G   H   A   G   G   P   V   S   A   R   V   I   K   A   L   Q   V   V   D
1021 CTCTGGACATGCAGGTGGACCAGTCAGTGCCAGAGTAATTAAAGCCTTACAGGTAGTAGA
```

Figure 1A-2

```
 347  H  A  F  G  M  L  M  E  G  L  K  Q  R  N  L  H  N  C  V  N
1081  TCATGCTTTTGGGATGTTGATGGAAGGCCTGAAGCAGCGGAATTTGCACAACTGTGTCAA
 367  I  I  L  L  A  D  H  G  M  D  Q  T  Y  C  N  K  M  E  Y  M
1141  TATCATCCTTCTGGCTGACCATGGAATGGACCAGACTTATTGTAACAAGATGGAATACAT
 387  T  D  Y  F  P  R  I  N  F  F  Y  M  Y  E  G  P  A  P  R  I
1201  GACTGATTATTTTCCCAGAATAAACTTCTTCTACATGTACGAAGGGCCTGCCCCCCGCAT
 407  R  A  H  N  I  P  H  D  F  F  S  F  N  S  E  E  I  V  R  N
1261  CCGAGCTCATAATATACCTCATGACTTTTTTAGTTTTAATTCTGAGGAAATTGTTAGAAA
 427  L  S  C  R  K  P  D  Q  H  F  K  P  Y  L  T  P  D  L  P  K
1321  CCTCAGTTGCCGAAAACCTGATCAGCATTTCAAGCCCTATTTGACTCCTGATTTGCCAAA
 447  R  L  H  Y  A  K  N  V  R  I  D  K  V  H  L  F  V  D  Q  Q
1381  GCGACTGCACTATGCCAAGAACGTCAGAATCGACAAAGTTCATCTCTTTGTGGATCAACA
 467  W  L  A  V  R  S  K  S  N  T  N  C  G  G  G  N  H  G  Y  N
1441  GTGGCTGGCTGTTAGGAGTAAATCAAATACAAATTGTGGAGGAGGCAACCATGGTTATAA
 487  N  E  F  R  S  M  E  A  I  F  L  A  H  G  P  S  F  K  E  K
1501  CAATGAGTTTAGGAGCATGGAGGCTATCTTTCTGGCACATGGACCCAGTTTTAAAGAGAA
 507  T  E  V  E  P  F  E  N  I  E  V  Y  N  L  M  C  D  L  L  R
1561  GACTGAAGTTGAACCATTTGAAAATATTGAAGTCTATAACCTAATGTGTGATCTTCTACG
 527  I  Q  P  A  P  N  N  G  T  H  G  S  L  N  H  L  L  K  V  P
1621  CATTCAACCAGCACCAAACAATGGAACCCATGGTAGTTTAAACCATCTTCTGAAGGTGCC
 547  F  Y  E  P  S  H  A  E  E  V  S  K  F  S  V  C  G  F  A  N
1681  TTTTTATGAGCCATCCCATGCAGAGGAGGTGTCAAAGTTTTCTGTTTGTGGCTTTGCTAA
 567  P  L  P  T  E  S  L  D  C  F  C  P  H  L  Q  N  S  T  Q  L
1741  TCCATTGCCCACAGAGTCTCTTGACTGTTTCTGCCCTCACCTACAAAATAGTACTCAGCT
 587  E  Q  V  N  Q  M  L  N  L  T  Q  E  E  I  T  A  T  V  K  V
1801  GGAACAAGTGAATCAGATGCTAAATCTCACCCAAGAAGAAATAACAGCAACAGTGAAAGT
 607  N  L  P  F  G  R  P  R  V  L  Q  K  N  V  D  H  C  L  L  Y
1861  AAATTTGCCATTTGGGAGGCCTAGGGTACTGCAGAAGAACGTGGACCACTGTCTCCTTTA
 627  H  R  E  Y  V  S  G  F  G  K  A  M  R  M  P  M  W  S  S  Y
1921  CCACAGGGAATATGTCAGTGGATTTGGAAAAGCTATGAGGATGCCCATGTGGAGTTCATA
 647  T  V  P  Q  L  G  D  T  S  P  L  P  P  T  V  P  D  C  L  R
1981  CACAGTCCCCCAGTTGGGAGACACATCGCCTCTGCCTCCCACTGTCCCAGACTGTCTGCG
 667  A  D  V  R  V  P  P  S  E  S  Q  K  C  S  F  Y  L  A  D  K
2041  GGCTGATGTCAGGGTTCCTCCTTCTGAGAGCCAAAAATGTTCCTTCTATTTAGCAGACAA
 687  N  I  T  H  G  F  L  Y  P  P  A  S  N  R  T  S  D  S  Q  Y
2101  GAATATCACCCACGGCTTCCTCTATCCTCCTGCCAGCAATAGAACATCAGATAGCCAATA
 707  D  A  L  I  T  S  N  L  V  P  M  Y  E  E  F  R  K  M  W  D
2161  TGATGCTTTAATTACTAGCAATTTGGTACCTATGTATGAAGAATTCAGAAAAATGTGGGA
 727  Y  F  H  S  V  L  L  I  K  H  A  T  E  R  N  G  V  N  V  V
2221  CTACTTCCACAGTGTTCTTCTTATAAAACATGCCACAGAAAGAAATGGAGTAAATGTGGT
```

Figure 1A-3

```
747  S  G  P  I  F  D  Y  N  Y  D  G  H  F  D  A  P  D  E  I  T
2281 TAGTGGACCAATATTTGATTATAATTATGATGGCCATTTTGATGCTCCAGATGAAATTAC
767  K  H  L  A  N  T  D  V  P  I  P  T  H  Y  F  V  V  L  T  S
2341 CAAACATTTAGCCAACACTGATGTTCCCATCCCAACACACTACTTTGTGGTGCTGACCAG
787  C  K  N  K  S  H  T  P  E  N  C  P  G  W  L  D  V  L  P  F
2401 TTGTAAAAACAAGAGCCACACACCGGAAAACTGCCCTGGGTGGCTGGATGTCCTACCCTT
807  I  I  P  H  R  P  T  N  V  E  S  C  P  E  G  K  P  E  A  L
2461 TATCATCCCTCACCGACCTACCAACGTGGAGAGCTGTCCTGAAGGTAAACCAGAAGCTCT
827  W  V  E  E  R  F  T  A  H  I  A  R  V  R  D  V  E  L  L  T
2521 TTGGGTTGAAGAAAGATTTACAGCTCACATTGCCCGGGTCCGTGATGTAGAACTTCTCAC
847  G  L  D  F  Y  Q  D  K  V  Q  P  V  S  E  I  L  Q  L  K  T
2581 TGGGCTTGACTTCTATCAGGATAAAGTGCAGCCTGTCTCTGAAATTTTGCAACTAAAGAC
867  Y  L  P  T  F  E  T  T  I  *
2641 ATATTTACCAACATTTGAAACCACTATTTAActtaataatgtctacttaatatataattt
2701 actgtataaagtaattttggcaaaatataagtgattttttctggagaattgtaaaataaa
2761 gttttctattttccttaaaaaaaaaccggaattccgggcttgggaggctgaggcagga
2821 gactcgcttgaacccgggaggcagaggttgcagtgagccaagattgcgccattgcactcc
2881 agagcctgggtgacagagcaagactacatctcaaaaataaataaataaaataaaagtaa
2941 caataaaaataaaagaacagcagagagaatgagcaaggagaaatgtcacaaactattgc
3001 aaaatactgttacactgggttggctctccaagaagatactggaatctcttcagccatttg
3061 cttttcagaagtagaaaccagcaaaccacctctaagcggagaacatacgattctttatta
3121 agtagctctggggaaggaaagaataaagttgatagctccctgattgggaaaaaatgcac
3181 aattaataaagaatgaagatgaaagaaagcatgcttatgttgtaacacaaaaaaaattca
3241 caaacgttggtggaaggaaaacagtatagaaaacattactttaactaaaagctggaaaaa
3301 ttttcagttgggatgcgactgacaaaaagaacgggatttccaggcataaagttggcgtga
3361 gctacagagggcaccatgtggctcagtggaagacccttcaagattcaaagttccatttga
3421 cagagcaaaggcacttcgcaaggagaagggtttaaattatgggtccaaaagccaagtggt
3481 aaagcgagcaatttgcagcataactgcttctcctagacagggctgagtgggcaaaatacg
3541 acagtacacacagtgactattagccactgccagaaacaggctgaacagccctgggagaca
3601 agggaaggcaggtggtgggagttgttcatggagagaaggagagttttagaaccagcaca
3661 tccactggagatgctgggccaccagacccctcccagtcaataaagtctggtgcctcattt
3721 gatctcagcctcatcatgaccctggagagacctgataccatctgccagtccccgacagc
3781 ttaggcactccttgccatcaacctgaccccccgagtggttctccaggctccctgccccac
3841 ccattcaggccggaattc
```

Figure 1B: The cDNA (SEQ ID NO:3) and amino acid sequence (SEQ ID NO:4) of 161P2F10B variant 2. The 3858 nucleotide sequence of 161P2F10B variant 2 is shown. The open reading frame extends from nucleic acid 44-2671 including the stop codon.

```
    1                                              M  E  S  T  L  T
    1 ctactttattctgataaaacaggtctatgcagctaccaggacaATGGAATCTACGTTGAC
    7 L  A  T  E  Q  P  V  K  K  N  T  L  K  K  Y  K  I  A  C  I
   61 TTTAGCAACGGAACAACCTGTTAAGAAGAACACTCTTAAGAAATATAAAATAGCTTGCAT
   27 V  L  L  A  L  L  V  I  M  S  L  G  L  G  L  G  L  R
  121 TGTTCTTCTTGCTTTGCTGGTGATCATGTCACTTGGATTAGGCCTGGGGCTTGGACTCAG
   47 K  L  E  K  Q  G  S  C  R  K  K  C  F  D  A  S  F  R  G  L
  181 GAAACTGGAAAAGCAAGGCAGCTGCAGGAAGAAGTGCTTTGATGCATCATTTAGAGGACT
   67 E  N  C  R  C  D  V  A  C  K  D  R  G  D  C  C  W  D  F  E
  241 GGAGAACTGCCGGTGTGATGTGGCATGTAAAGACCGAGGTGATTGCTGCTGGGATTTTGA
   87 D  T  C  V  E  S  T  R  I  W  M  C  N  K  F  R  C  G  E  T
  301 AGACACCTGTGTGGAATCAACTCGAATATGGATGTGCAATAAATTTCGTTGTGGAGAGAC
  107 R  L  E  A  S  L  C  S  C  S  D  D  C  L  Q  R  K  D  C  C
  361 CAGATTAGAGGCCAGCCTTTCCTCTTGTTCAGATGACTGTTTGCAGAGCAAAGATTGCTG
  127 A  D  Y  K  S  V  C  Q  G  E  T  S  W  L  E  E  N  C  D  T
  421 TGCTGACTATAAGAGTGTTTGCCAAGGAGAAACCTCATGGCTGGAAGAAAACTGTGACAC
  147 A  Q  Q  S  Q  C  P  E  G  F  D  L  P  P  V  I  L  F  S  M
  481 AGCCCAGCAGTCTCAGTGCCCAGAAGGGTTTGACCTGCCACCAGTTATCTTGTTTTCTAT
  167 D  G  F  R  A  E  Y  L  Y  T  W  D  T  L  M  P  N  I  N  K
  541 GGATGGATTTAGAGCTGAATATTTATACACATGGGATACTTTAATGCCAAATATCAATAA
  187 L  K  T  C  G  I  H  S  K  Y  M  R  A  M  Y  P  T  K  T  F
  601 ACTGAAAACATGTGGAATTCATTCAAAATACATGAGAGCTATGTATCCTACCAAAACCTT
  207 P  N  H  Y  T  I  V  T  G  L  Y  P  E  S  H  G  I  I  D  N
  661 CCCAAATCATTACACCATTGTCACGGGCTTGTATCCAGAGTCACATGGCATCATTGACAA
  227 N  M  Y  D  V  N  L  N  K  N  F  S  L  S  S  K  E  Q  N  N
  721 TAATATGTATGATGTAAATCTCAACAAGAATTTTTCACTTTCTTCAAAGGAACAAAATAA
  247 P  A  W  H  G  Q  P  M  W  L  T  A  M  Y  Q  G  L  K  A
  781 TCCAGCCTGGTGGCATGGGCAACCAATGTGGCTGACAGCAATGTATCAAGCTTTAAAGC
  267 A  T  Y  F  W  P  G  S  E  V  A  I  N  G  S  F  P  S  I  Y
  841 CGCTACCTACTTTTGGCCCGGATCAGAAGTGGCTATAAATGGCTCCTTTCCTTCCATATA
  287 M  P  Y  N  G  S  V  P  F  E  E  R  I  S  T  L  L  K  W  L
  901 CATGCCTTACAACGGAAGTGTCCCATTTGAAGAGAGGATTTCTACACTGTTAAAATGGCT
  307 D  L  P  K  A  E  R  P  R  F  Y  T  M  Y  F  E  E  P  D  S
  961 GGACCTGCCCAAAGCTGAAAGACCCAGGTTTTATACCATGTATTTTGAAGAACCTGATTC
  327 S  C  H  A  G  C  P  V  S  A  R  V  I  K  A  L  Q  V  V  D
 1021 CTCTGGACATGCAGGTGGACCAGTCAGTGCCAGAGTAATTAAAGCCTTACAGGTAGTAGA
  347 H  A  F  G  M  L  M  E  G  L  K  Q  R  N  L  H  N  C  V  N
 1081 TCATGCTTTTGGGATGTTGATGGAAGGCCTGAAGCAGCGGAATTTGCACAACTGTGTCAA
  367 I  I  L  L  A  D  H  G  M  D  Q  T  Y  C  N  K  M  E  Y  M
 1141 TATCATCCTTCTGGCTGACCATGGAATGGACCAGACTTATTGTAACAAGATGGAATACAT
  387 T  D  Y  F  P  R  I  N  F  F  Y  M  Y  E  G  P  A  P  R  I
 1201 GACTGATTATTTTCCCACAATAAACTTCTTCTACATGTACCAAGGGCCTCCCCCCCCCAT
  407 R  A  H  N  I  P  H  D  F  F  S  F  N  S  E  E  I  V  R  N
 1261 CCGAGCTCATAATATACCTCATGACTTTTTTAGTTTTAATTCTGAGGAAATTGTTAGAAA
```

Figure 1B-2

```
 427  L  S  C  R  K  P  D  Q  H  F  K  P  Y  L  T  P  D  L  P  K
1321  CCTCAGTTGCCGAAAACCTGATCAGCATTTCAAGCCCTATTTGACTCCTGATTTGCCAAA
 447  R  L  H  Y  A  K  N  V  R  I  D  K  V  H  L  F  V  D  Q  Q
1381  GCGACTGCACTATGCCAAGAACGTCAGAATCGACAAAGTTCATCTCTTTGTGGATCAACA
 467  W  L  A  V  R  S  K  S  N  T  N  C  G  G  G  N  H  G  Y  N
1441  GTGGCTGGCTGTTAGGAGTAAATCAAATACAAATTGTGGAGGAGGCAACCATGGTTATAA
 487  N  E  F  R  S  M  E  A  I  F  L  A  H  G  P  S  F  K  E  K
1501  CAATGAGTTTAGGAGCATGGAGGCTATCTTTCTGGCACATGGACCCAGTTTTAAAGAGAA
 507  T  E  V  E  P  F  E  N  I  E  V  Y  N  L  M  C  D  L  L  R
1561  GACTGAAGTTGAACCATTTGAAAATATTGAAGTCTATAACCTAATGTGTGATCTTCTACG
 527  I  Q  P  A  P  N  N  G  T  H  G  S  L  N  H  L  L  K  V  P
1621  CATTCAACCAGCACCAAACAATGGAACCCATGGTAGTTTAAACCATCTTCTGAAGGTGCC
 547  F  Y  E  P  S  H  A  E  E  V  S  K  F  S  V  C  G  F  A  N
1681  TTTTTATGAGCCATCCCATGCAGAGGAGGTGTCAAAGTTTTCTGTTTGTGGCTTTGCTAA
 567  P  L  P  T  E  S  L  D  C  F  C  P  H  L  Q  N  S  T  Q  L
1741  TCCATTGCCCACAGAGTCTCTTGACTGTTTCTGCCCTCACCTACAAAATAGTACTCAGCT
 587  E  Q  V  N  Q  M  L  N  L  T  Q  E  E  I  T  A  T  V  K  V
1801  GGAACAAGTGAATCAGATGCTAAATCTCACCCAAGAAGAAATAACAGCAACAGTGAAAGT
 607  N  L  P  F  G  R  P  R  V  L  Q  K  N  V  D  H  C  L  L  Y
1861  AAATTTGCCATTTGGGAGGCCTAGGGTACTGCAGAAGAACGTGGACCACTGTCTCCTTTA
 627  H  R  E  Y  V  S  G  F  G  K  A  M  R  M  P  M  W  S  S  Y
1921  CCACAGGGAATATGTCAGTGGATTTGGAAAAGCTATGAGGATGCCCATGTGGAGTTCATA
 647  T  V  P  Q  L  G  D  T  S  P  L  P  P  T  V  P  D  C  L  R
1981  CACAGTCCCCCAGTTGGGAGACACATCGCCTCTGCCTCCCACTGTCCCAGACTGTCTGCG
 667  A  D  V  R  V  P  P  S  E  S  Q  K  C  S  F  Y  L  A  D  K
2041  GGCTGATGTCAGGGTTCCTCCTTCTGAGAGCCAAAAATGTTCCTTCTATTTAGCAGACAA
 687  N  I  T  H  G  F  L  Y  P  P  A  S  N  R  T  S  D  S  Q  Y
2101  GAATATCACCCACGGCTTCCTCTATCCTCCTGCCAGCAATAGAACATCAGATAGCCAATA
 707  D  A  L  I  T  S  N  L  V  P  M  Y  E  E  F  R  K  M  W  D
2161  TGATGCTTTAATTACTAGCAATTTGGTACCTATGTATGAAGAATTCAGAAAAATGTGGGA
 727  Y  F  H  S  V  L  L  I  K  H  A  T  E  R  N  G  V  N  V  V
2221  CTACTTCCACAGTGTTCTTCTTATAAAACATGCCACAGAAAGAAATGGAGTAAATGTGGT
 747  S  G  P  I  F  D  Y  N  Y  D  G  H  F  D  A  P  D  E  I  T
2281  TAGTGGACCAATATTTGATTATAATTATGATGGCCATTTTGATGCTCCAGATGAAATTAC
 767  K  H  L  A  N  T  D  V  P  I  P  T  H  Y  F  V  V  L  T  S
2341  CAAACATTTAGCCAACACTGATGTTCCCATCCCAACACACTACTTTGTGGTGCTGACCAG
 787  C  K  N  K  S  H  T  P  E  N  C  P  G  W  L  D  V  L  P  F
2401  TTGTAAAAACAAGAGCCACACACCGGAAAACTGCCCTGGGTGGCTGGATGTCCTACCCTT
 807  I  I  P  H  R  P  T  N  V  E  S  C  P  E  G  K  P  E  A  L
2461  TATCATCCCTCACCGACCTACCAACGTGGAGAGCTGTCCTGAAGGTAAACCAGAAGCTCT
 827  W  V  E  E  R  F  T  A  H  I  A  R  V  R  D  V  E  L  L  T
2521  TTGGGTTGAAGAAAGATTTACAGCTCACATTGCCCGGGTCCGTGATGTAGAACTTCTCAC
 847  G  L  D  F  Y  Q  D  K  V  Q  P  V  S  E  I  L  Q  L  K  T
2581  TGGGCTTGACTTCTATCAGGATAAAGTGCAGCCTGTCTCTGAAATTTTGCAACTAAAGAC
 867  Y  L  P  T  F  E  T  T  I  *
2641  ATATTTACCAACATTTGAAACCACTATTTAActtaataatgtctacttaatatataattt
```

Figure 1B-3

```
2701 actgtataaagtaattttggcaaaatataagtgattttttctggagaattgtaaaataaa
2761 gttttctatttttccttaaaaaaaaaaccggaattccgggcttgggaggctgaggcagga
2821 gactcgcttgaacccgggaggcagaggttgcagtgagccaagattgcgccattgcactcc
2881 agagcctgggtgacagagcaagactacatctcaaaaaataaataaataaaataaaagtaa
2941 caataaaataaaaagaacagcagagagaatgagcaaggagaaatgtcacaaactattgc
3001 aaaatactgttacactcggttggctctccaagaagatactggaatctcttcagccatttg
3061 cttttcagaagtagaaaccagcaaaccacctctaagcggagaacatacgattctttatta
3121 agtagctctggggaaggaaagaataaaagttgatagctccctgattgggaaaaaatgcac
3181 aattaataaagaatgaagatgaaagaaagcatgcttatgttgtaacacaaaaaaaattca
3241 caaacgttggtggaaggaaaacagtatagaaaacattactttaactaaaagctggaaaaa
3301 ttttcagttgggatgcgactgacaaaaagaacgggatttccaggcataaagttggcgtga
3361 gctacagagggcaccatgtggctcagtggaagaccttcaagattcaaagttccatttga
3421 cagagcaaaggcacttcgcaaggagaagggtttaaattatgggtccaaaagccaagtggt
3481 aaagcgagcaatttgcagcataactgctctcctagacagggctgagtgggcaaaatacg
3541 acagtacacacagtgactattagccactgccagaaacaggctgaacagccctgggagaca
3601 agggaaggcaggtggtgggagttgttcatggagagaaaggagagttttagaaccagcaca
3661 tccactggagatgctgggccaccagacccctcccagtcaataaagtctggtgcctcattt
3721 gatctcagcctcatcatgaccctggagagaccctgataccatctgccagtcccgacagc
3781 ttaggcactccttgccatcaacctgaccccgagtggttctccaggctccctgccccac
3841 ccattcaggccggaattc
```

Figure 1C: The cDNA (SEQ ID NO:5) and amino acid sequence (SEQ ID NO:6) of 161P2F10B variant 3. The 3858 nucleotide sequence of 161P2F10B variant 3 is shown. The open reading frame extends from nucleic acid 44-2671 including the stop codon.

```
                                              M  E  S  T  L  T
  1 ctactttattctgataaaacaggtctatgcagctaccaggacaATGGAATCTACGTTGAC
  7  L  A  T  E  Q  P  V  K  K  N  T  L  K  K  Y  K  I  A  C  I
 61 TTTAGCAACGGAACAACCTGTTAAGAAGAACACTCTTAAGAAATATAAAATAGCTTGCAT
 27  V  L  L  A  L  L  V  I  M  S  L  G  L  G  L  G  L  R
121 TGTTCTTCTTGCTTTGCTGGTGATCATGTCACTTGGATTAGGCCTGGGGCTTGGACTCAG
 47  K  L  E  K  Q  G  S  C  R  K  K  C  F  D  A  S  F  R  G  L
181 GAAACTGGAAAAGCAAGGCAGCTGCAGGAAGAAGTGCTTTGATGCATCATTTAGAGGACT
 67  E  N  C  R  C  D  V  A  C  K  D  R  G  D  C  C  W  D  F  E
241 GGAGAACTGCCGGTGTGATGTGGCATGTAAAGACCGAGGTGATTGCTGCTGGGATTTTGA
 87  D  T  C  V  E  S  T  R  I  W  M  C  N  K  F  C  G  E  T
301 AGACACCTGTGTGGAATCAACTCGAATATGGATGTGCAATAAATTTCGTTGTGGAGAGAC
107  R  L  E  A  S  L  C  S  C  S  D  D  C  L  Q  K  K  D  C  C
361 CAGATTAGAGGCCAGCCTTTGCTCTTGTTCAGATGACTGTTTGCAGAAGAAAGATTGCTG
127  A  D  Y  K  S  V  C  Q  G  E  T  S  W  L  E  E  N  C  D  T
421 TGCTGACTATAAGAGTGTTTGCCAAGGAGAAACCTCATGGCTGGAAGAAAACTGTGACAC
147  A  Q  Q  S  Q  C  P  E  G  F  D  L  P  P  V  I  L  F  S  M
481 AGCCCAGCAGTCTCAGTGCCCAGAAGGGTTTGACCTGCCACCAGTTATCTTGTTTTCTAT
167  D  G  F  R  A  E  Y  L  Y  T  W  D  T  L  M  P  N  I  N  K
541 GGATGGATTTAGAGCTGAATATTTATACACATGGGATACTTTAATGCCAAATATCAATAA
187  L  K  T  C  G  I  H  S  K  Y  M  R  A  M  Y  P  T  K  T  F
601 ACTGAAAACATGTGGAATTCATTCAAAATACATGAGAGCTATGTATCCTACCAAAACCTT
207  P  N  H  Y  T  I  V  T  G  L  Y  P  E  S  H  G  I  I  D  N
661 CCCAAATCATTACACCATTGTCACGGGCTTGTATCCAGAGTCACATGGCATCATTGACAA
227  N  M  Y  D  V  N  L  N  K  N  F  S  L  S  S  K  E  Q  N  N
721 TAATATGTATGATGTAAATCTCAACAAGAATTTTTCACTTTCTTCAAAGGAACAAAATAA
247  P  A  W  W  H  G  Q  P  M  W  L  T  A  M  Y  Q  G  L  K  A
781 TCCAGCCTGGTGGCATGGGCAACCAATGTGGCTGACAGCAATGTATCAAGGTTTAAAAGC
```

Figure 1C-2

```
 267  A   T   Y   F   W   P   G   S   E   V   A   I   N   G   S   F   P   S   I   Y
 841 CGCTACCTACTTTTGGCCCGGATCAGAAGTGGCTATAAATGGCTCCTTTCCTTCCATATA
 287  M   P   Y   N   G   S   V   P   F   E   E   R   I   S   T   L   L   K   W   L
 901 CATGCCTTACAACGGAAGTGTCCCATTTGAAGAGAGGATTTCTACACTGTTAAAATGGCT
 307  D   L   P   K   A   E   R   P   R   F   Y   T   M   Y   F   E   E   P   D   S
 961 GGACCTGCCCAAAGCTGAAAGACCCAGGTTTTATACCATGTATTTTGAAGAACCTGATTC
 327  S   G   H   A   G   G   P   V   S   A   R   V   I   K   A   L   Q   V   V   D
1021 CTCTGGACATGCAGGTGGACCAGTCAGTGCCAGAGTAATTAAAGCCTTACAGGTAGTAGA
 347  H   A   F   G   M   L   M   E   G   L   K   Q   R   N   L   H   N   C   V   N
1081 TCATGCTTTTGGGATGTTGATGGAAGGCCTGAAGCAGCGGAATTTGCACAACTGTGTCAA
 367  I   I   L   L   A   D   H   G   M   D   Q   T   Y   C   N   K   M   E   Y   M
1141 TATCATCCTTCTGGCTGACCATGGAATGGACCAGACTTATTGTAACAAGATGGAATACAT
 387  T   D   Y   F   P   R   T   N   F   F   Y   M   Y   E   G   P   A   P   R   T
1201 GACTGATTATTTTCCCAGAATAAACTTCTTCTACATGTACGAAGGGCCTGCCCCCCGCAT
 407  R   A   H   N   I   P   H   D   F   F   S   F   N   S   E   E   I   V   R   N
1261 CCGAGCTCATAATATACCTCATGACTTTTTTAGTTTTAATTCTGAGGAAATTGTTAGAAA
 427  L   S   C   R   K   P   D   Q   H   F   K   P   Y   L   T   P   D   L   P   K
1321 CCTCAGTTGCCGAAAACCTGATCAGCATTTCAAGCCCTATTTGACTCCTGATTTGCCAAA
 447  R   L   H   Y   A   K   N   V   R   I   D   K   V   H   L   F   V   D   Q   Q
1381 GCGACTGCACTATGCCAAGAACGTCAGAATCGACAAAGTTCATCTCTTTGTGGATCAACA
 467  W   L   A   V   R   S   K   S   N   T   N   C   G   G   G   N   H   G   Y   N
1441 GTGGCTGGCTGTTAGGAGTAAATCAAATACAAATTGTGGAGGAGGCAACCATGGTTATAA
 487  N   E   F   R   S   M   E   A   I   F   L   A   H   G   P   S   F   K   E   K
1501 CAATGAGTTTAGGAGCATGGAGGCTATCTTTCTGGCACATGGACCCAGTTTTAAAGAGAA
 507  T   E   V   E   P   F   E   N   I   E   V   Y   N   L   M   C   D   L   L   R
1561 GACTGAAGTTGAACCATTTGAAAATATTGAAGTCTATAACCTAATGTGTGATCTTCTACG
 527  I   Q   P   A   P   N   N   G   T   H   G   S   L   N   H   L   L   K   V   P
1621 CATTCAACCAGCACCAAACAATGGAACCCATGGTAGTTTAAACCATCTTCTGAAGGTGCC
 547  F   Y   E   P   S   H   A   E   E   V   S   K   F   S   V   C   G   F   A   N
1681 TTTTTATGAGCCATCCCATGCAGAGGAGGTGTCAAAGTTTTCTGTTTGTGGCTTTGCTAA
 567  P   L   P   T   E   S   L   D   C   F   C   P   H   L   Q   N   S   T   Q   L
1741 TCCATTGCCCACAGAGTCTCTTGACTGTTTCTGCCCTCACCTACAAAATAGTACTCAGCT
 587  E   Q   V   N   Q   M   L   N   L   T   Q   E   E   I   T   A   T   V   K   V
1801 GGAACAAGTGAATCAGATGCTAAATCTCACCCAAGAAGAAATAACAGCAACAGTGAAAGT
 607  N   L   P   F   G   R   P   R   V   L   Q   K   N   V   D   H   C   L   L   Y
1861 AAATTTGCCATTTGGGAGGCCTAGGGTACTGCAGAAGAACGTGGACCACTGTCTCCTTTA
 627  H   R   E   Y   V   S   G   F   G   K   A   M   R   M   P   M   W   S   S   Y
1921 CCACAGGGAATATGTCAGTGGATTTGGAAAAGCTATGAGGATGCCCATGTGGAGTTCATA
 647  T   V   P   Q   L   G   D   T   S   P   L   P   P   T   V   P   D   C   L   R
1981 CACAGTCCCCCAGTTGGGAGACACATCGCCTCTGCCTCCCACTGTCCCAGACTGTCTGCG
 667  A   D   V   R   V   P   P   S   E   S   Q   K   C   S   F   Y   L   A   D   K
2041 GGCTGATGTCAGGGTTCCTCCTTCTGAGAGCCAAAAATGTTCCTTCTATTTAGCAGACAA
 687  N   I   T   H   G   F   L   Y   P   P   A   S   N   R   T   S   D   S   Q   Y
2101 GAATATCACCCACGGCTTCCTCTATCCTCCTGCCAGCAATAGAACATCAGATAGCCAATA
 707  D   A   L   I   T   S   N   L   V   P   M   Y   E   E   F   R   K   M   W   D
2161 TGATGCTTTAATTACTAGCAATTTGGTACCTATGTATGAAGAATTCAGAAAAATGTGGGA
 727  Y   F   H   S   V   L   L   I   K   H   A   T   E   R   N   G   V   N   V   V
2221 CTACTTCCACAGTGTTCTTCTTATAAAACATGCCACAGAAAGAAATGGAGTAAATGTGGT
 747  S   G   P   I   F   D   Y   N   Y   D   G   H   F   D   A   P   D   E   I   T
2281 TAGTGGACCAATATTTGATTATAATTATGATGGCCATTTTGATGCTCCAGATGAAATTAC
 767  K   H   L   A   N   T   D   V   P   I   P   T   H   Y   F   V   V   L   T   S
2341 CAAACATTTAGCCAACACTGATGTTCCCATCCCAACACACTACTTTGTGGTGCTGACCAG
 787  C   K   N   K   S   H   T   P   E   N   C   P   G   W   L   D   V   L   P   F
2401 TTGTAAAAACAAGAGCCACACACCGGAAAACTGCCCTGGGTGGCTGGATGTCCTACCCTT
 807  I   I   P   H   R   P   T   N   V   E   S   C   P   G   G   K   P   E   A   L
2461 TATCATCCCTCACCGACCTACCAACGTGGAGAGCTGTCCTGGAGGTAAACCAGAAGCTCT
 827  W   V   E   E   R   F   T   A   H   I   A   R   V   R   D   V   E   L   L   T
2521 TTGGGTTGAAGAAAGATTTACAGCTCACATTGCCCGGGTCCGTGATGTAGAACTTCTCAC
 847  G   L   D   F   Y   Q   D   K   V   Q   P   V   S   E   I   L   Q   L   K   T
2581 TGGGCTTGACTTCTATCAGGATAAAGTGCAGCCTGTCTCTGAAATTTTGCAACTAAAGAC
 867  Y   L   P   T   F   E   T   T   I   *
2641 ATATTTACCAACATTTGAAACCACTATTTAActtaataatgtctacttaatatataattt
2701 actgtataaagtaattttggcaaaatataagtgatttttctggagaattgtaaaataaa
```

Figure 1C-3

```
2761 gttttctattttttccttaaaaaaaaaaccggaattccgggcttgggaggctgaggcagga
2821 gactcgcttgaacccggggaggcagaggttgcagtgagccaagattgcgccattgcactcc
2881 agagcctgggtgacagagcaagactacatctcaaaaaataaataaataaaataaaagtaa
2941 caataaaaataaaaagaacagcagagagaatgagcaaggagaaatgtcacaaactattgc
3001 aaaatactgttacactgggttggctctccaagaagatactggaatctcttcagccatttg
3061 cttttcagaagtagaaaccagcaaaccacctctaagcggagaacatacgattctttatta
3121 agtagctctggggaaggaaagaataaaagttgatagctccctgattgggaaaaaatgcac
3181 aattaataaagaatgaagatgaaagaaagcatgcttatgttgtaacacaaaaaaaattca
3241 caaacgttggtggaaggaaaacagtatagaaaacattactttaactaaaagctggaaaaa
3301 ttttcagttgggatgcgactgacaaaaagaacgggatttccaggcataaagttggcgtga
3361 gctacagaggcaccatgtggctcagtggaagaccttcaagattcaaagttccatttga
3421 cagagcaaaggcacttcgcaaggagaagggtttaaattatgggtccaaaagccaagtggt
3481 aaagcgagcaatttgcagcataactgcttctcctagacagggctgagtgggcaaaatacg
3541 acagtacacacagtgactattagccactgccagaaacaggctgaacagccctgggagaca
3601 agggaaggcaggtggtgggagttgttcatggagagaaaggagagttttagaaccagcaca
3661 tccactggagatgctgggccaccagacccctcccagtcaataaagtctggtgcctcattt
3721 gatctcagcctcatcatgaccctggagagaccctgataccatctgccagtccccgacagc
3781 ttaggcactccttgccatcaacctgaccccccgagtggttctccaggctccctgccccac
3841 ccattcaggccggaattc
```

Figure 1D: The cDNA (SEQ ID NO:7) and amino acid sequence (SEQ ID NO:8) of 161P2F10B variant
4. The 3858 nucleotide sequence of 161P2F10B variant 4 is shown. The open reading frame extends from nucleic acid 44-2671 including the stop codon.

```
                                                    M   E   S   T   L   T
  1 ctactttattctgataaaacaggtctatgcagctaccaggacaATGGAATCTACGTTGAC
  7 L   A   T   E   Q   P   V   K   K   N   T   L   K   K   Y   K   I   A   C   I
 61 TTTAGCAACGGAACAACCTGTTAAGAAGAACACTCTTAAGAAATATAAAATAGCTTGCAT
 27 V   L   L   A   L   L   V   I   M   S   L   G   L   G   L   G   L   R
121 TGTTCTTCTTGCTTTGCTGGTGATCATGTCACTTGGATTAGGCCTGGGGCTTGGACTCAG
 47 K   L   E   K   Q   G   S   C   R   K   K   C   F   D   A   S   F   R   G   L
181 GAAACTGGAAAAGCAAGGCAGCTGCAGGAAGAAGTGCTTTGATGCATCATTTAGAGGACT
 67 E   N   C   R   D   V   A   C   K   D   R   G   D   C   C   W   D   F   E
241 GGAGAACTGCCGGTGTGATGTGGCATGTAAAGACCGAGGTGATTGCTGCTGGGATTTTGA
 87 D   T   C   V   E   S   T   R   I   W   M   C   N   K   F   R   C   G   E   T
301 AGACACCTGTGTGGAATCAACTCGAATATGGATGTGCAATAAATTTCGTTGTGGAGAGAC
107 R   L   E   A   S   L   C   S   C   S   D   D   C   L   Q   K   K   D   C   C
361 CAGATTAGAGGCCAGCCTTTGCTCTTGTTCAGATGACTGTTTGCAGAAGAAAGATTGCTG
127 A   D   Y   K   S   V   C   Q   G   E   T   S   W   L   E   E   N   C   D   T
421 TGCTGACTATAAGAGTGTTTGCCAAGGAGAAACCTCATGGCTGGAAGAAAACTGTGACAC
147 A   Q   Q   S   Q   C   P   E   G   F   D   L   P   P   V   I   L   F   S   M
481 AGCCCAGCAGTCTCAGTGCCCAGAAGGGTTTGACCTGCCACCAGTTATCTTGTTTTCTAT
167 D   G   F   R   A   E   Y   L   Y   T   W   D   T   L   M   P   N   I   N   K
541 GGATGGATTTAGAGCTGAATATTTATACACATGGGATACTTTAATGCCAAATATCAATAA
187 L   K   T   C   G   I   H   S   K   Y   M   R   A   M   Y   P   T   K   T   F
601 ACTGAAAACATGTGGAATTCATTCAAAATACATGAGAGCTATGTATCCTACCAAAACCTT
207 P   N   H   Y   T   T   V   T   G   L   Y   P   E   S   H   G   I   I   D   N
661 CCCAAATCATTACACCATTGTCACGGGCTTGTATCCAGAGTCACATGGCATCATTGACAA
227 N   M   Y   D   V   N   L   N   K   N   F   S   L   S   S   K   E   Q   N   N
```

Figure 1D-2

```
 721  TAATATGTATGATGTAAATCTCAACAAGAATTTTTCACTTTCTTCAAAGGAACAAAATAA
 247   P  A  W  W  H  G  Q  P  M  W  L  T  A  M  Y  Q  G  L  K  A
 781  TCCAGCCTGGTGGCATGGGCAACCAATGTGGCTGACAGCAATGTATCAAGGTTTAAAAGC
 267   A  T  Y  F  W  P  G  S  E  V  A  I  N  G  S  F  P  S  I  Y
 841  CGCTACCTACTTTTGGCCCGGATCAGAAGTGGCTATAAATGGCTCCTTTCCTTCCATATA
 287   M  P  Y  N  G  S  V  P  F  E  E  R  I  S  T  L  L  K  W  L
 901  CATGCCTTACAACGGAAGTGTCCCATTTGAAGAGAGGATTTCTACACTGTTAAAATGGCT
 307   D  L  P  K  A  E  R  P  R  F  Y  T  M  Y  F  E  E  P  D  S
 961  GGACCTGCCCAAAGCTGAAAGACCCAGGTTTTATACCATGTATTTTGAAGAACCTGATTC
 327   S  G  H  A  G  G  P  V  S  A  R  V  I  K  A  L  Q  V  V  D
1021  CTCTGGACATGCAGGTGGACCAGTCAGTGCCAGAGTAATTAAAGCCTTACAGGTAGTAGA
 347   H  A  F  G  M  L  M  E  G  L  K  Q  R  N  L  H  N  C  V  N
1081  TCATGCTTTTGGGATGTTGATGGAAGGCCTGAAGCAGCGGAATTTGCACAACTGTGTCAA
 367   I  I  L  L  A  D  H  G  M  D  Q  T  Y  C  N  K  M  E  Y  M
1141  TATCATCCTTCTGGCTGACCATGGAATGGACCAGACTTATTGTAACAAGATGGAATACAT
 387   T  D  Y  F  P  R  I  N  F  F  Y  M  Y  E  G  P  A  P  R  I
1201  GACTGATTATTTTCCCAGAATAAACTTCTTCTACATGTACGAAGGGCCTGCCCCCCGCAT
 407   R  A  H  N  I  P  H  D  F  F  S  F  N  S  E  E  I  V  R  N
1261  CCGAGCTCATAATATACCTCATGACTTTTTTAGTTTTAATTCTGAGGAAATTGTTAGAAA
 427   L  S  C  R  K  P  D  Q  H  F  K  P  Y  L  T  P  D  L  P  K
1321  CCTCAGTTGCCGAAAACCTGATCAGCATTTCAAGCCCTATTTGACTCCTGATTTGCCAAA
 447   R  L  H  Y  A  K  N  V  R  I  D  K  V  H  L  F  V  D  Q  Q
1381  GCGACTGCACTATGCCAAGAACGTCAGAATCGACAAAGTTCATCTCTTTGTGGATCAACA
 467   W  L  A  V  R  S  K  S  N  T  N  C  G  G  G  N  H  G  Y  N
1441  GTGGCTGGCTGTTAGGAGTAAATCAAATACAAATTGTGGAGGAGGCAACCATGGTTATAA
 487   N  E  F  R  S  M  E  A  I  F  L  A  H  G  P  S  F  K  E  K
1501  CAATGAGTTTAGGAGCATGGAGGCTATCTTTCTGGCACATGGACCCAGTTTTAAAGAGAA
 507   T  E  V  E  P  F  E  N  I  E  V  Y  N  L  M  C  D  L  L  R
1561  GACTGAAGTTGAACCATTTGAAAATATTGAAGTCTATAACCTAATGTGTGATCTTCTACG
 527   I  Q  P  A  P  N  N  G  T  H  G  S  L  N  H  L  L  K  V  P
1621  CATTCAACCAGCACCAAACAATGGAACCCATGGTAGTTTAAACCATCTTCTGAAGGTGCC
 547   F  Y  E  P  S  H  A  E  E  V  S  K  F  S  V  C  G  F  A  N
1681  TTTTTATGAGCCATCCCATGCAGAGGAGGTGTCAAAGTTTTCTGTTTGTGGCTTTGCTAA
 567   P  L  P  T  E  S  L  D  C  F  C  P  H  L  Q  N  S  T  Q  L
1741  TCCATTGCCCACAGAGTCTCTTGACTGTTTCTGCCCTCACCTACAAAATAGTACTCAGCT
 587   E  Q  V  N  Q  M  L  N  L  T  Q  E  E  I  T  A  T  V  K  V
1801  GGAACAAGTGAATCAGATGCTAAATCTCACCCAAGAAGAAATAACAGCAACAGTGAAAGT
 607   N  L  P  F  G  R  P  R  V  L  Q  K  N  V  D  H  C  L  L  Y
1861  AAATTTGCCATTTGGGAGGCCTAGGGTACTGCAGAAGAACGTGGACCACTGTCTCCTTTA
 627   H  R  E  Y  V  S  G  F  G  K  A  M  R  M  P  M  W  S  S  Y
1921  CCACAGGGAATATGTCAGTGGATTTGGAAAAGCTATGAGGATGCCCATGTGGAGTTCATA
 647   T  V  P  Q  L  G  D  T  S  P  L  P  P  T  V  P  D  C  L  R
```

Figure 1D-3

```
1981 CACAGTCCCCCAGTTGGGAGACACATCGCCTCTGCCTCCCACTGTCCCAGACTGTCTGCG
 667  A  D  V  R  V  P  P  S  E  S  Q  K  C  S  F  Y  L  A  D  K
2041 GGCTGATGTCAGGGTTCCTCCTTCTGAGAGCCAAAAATGTTCCTTCTATTTAGCAGACAA
 687  N  I  T  H  G  F  L  Y  P  P  A  S  N  R  T  S  D  S  Q  Y
2101 GAATATCACCCACGGCTTCCTCTATCCTCCTGCCAGCAATAGAACATCAGATAGCCAATA
 707  D  A  L  I  T  S  N  L  V  P  M  Y  E  E  F  R  K  M  W  D
2161 TGATGCTTTAATTACTAGCAATTTGGTACCTATGTATGAAGAATTCAGAAAAATGTGGGA
 727  Y  F  H  S  V  L  L  I  K  H  A  T  E  R  N  G  V  N  V  V
2221 CTACTTCCACAGTGTTCTTCTTATAAAACATGCCACAGAAAGAAATGGAGTAAATGTGGT
 747  S  G  P  I  F  D  Y  N  Y  D  G  H  F  D  A  P  D  E  I  T
2281 TAGTGGACCAATATTTGATTATAATTATGATGGCCATTTTGATGCTCCAGATGAAATTAC
 767  K  H  L  A  N  T  D  V  P  I  P  T  H  Y  F  V  V  L  T  S
2341 CAAACATTTAGCCAACACTGATGTTCCATCCCAACACACTACTTTGTGGTGCTGACCAG
 787  C  K  N  K  S  H  T  P  E  N  C  P  G  W  L  D  V  L  P  F
2401 TTGTAAAAACAAGAGCCACACACCGGAAAACTGCCCTGGGTGGCTGGATGTCCTACCCTT
 807  I  I  P  H  R  P  T  N  V  E  S  C  P  E  G  K  P  E  A  L
2461 TATCATCCCTCACCGACCTACCAACGTGGAGAGCTGTCCTGAAGGTAAACCAGAAGCTCT
 827  W  V  E  E  R  F  T  A  H  I  A  R  V  R  D  V  E  L  L  T
2521 TTGGGTTGAAGAAAGATTTACAGCTCACATTGCCCGGGTCCGTGATGTAGAACTTCTCAC
 847  G  L  D  F  Y  Q  D  K  V  Q  P  V  S  E  I  L  Q  L  K  T
2581 TGGGCTTGACTTCTATCAGGATAAAGTGCAGCCTGTCTCTGAAATTTTGCAACTAAAGAC
 867  Y  L  P  T  F  E  T  P  I  *
2641 ATATTTACCAACATTTGAAACCCCTATTTAActtaataatgtctacttaatatataattt
2701 actgtataaagtaattttggcaaaatataagtgattttttctggagaattgtaaaataaa
2761 gttttctattttccttaaaaaaaaaaccggaattccgggcttgggaggctgaggcagga
2821 gactcgcttgaacccgggaggcagaggttgcagtgagccaagattgcgccattgcactcc
2881 agagcctgggtgacagagcaagactacatctcaaaaaataaataaataaaataaaagtaa
2941 caataaaaataaaaagaacagcagagagaatgagcaaggagaaatgtcacaaactattgc
3001 aaaatactgttacactgggttggctctccaagaagatactggaatctcttcagccatttg
3061 cttttcagaagtagaaaccagcaaaccacctctaagcggagaacatacgattctttatta
3121 agtagctctggggaaggaaagaataaaagttgatagctccctgattgggaaaaaatgcac
3181 aattaataaagaatgaagatgaaagaaagcatgcttatgttgtaacacaaaaaaaattca
3241 caaacgttggtggaaggaaaacagtatagaaaacattactttaactaaaagctggaaaaa
3301 ttttcagttgggatgcgactgacaaaaagaacgggatttccaggcataaagttggcgtga
3361 gctacagagggcaccatgtggctcagtggaagacccttcaagattcaaagttccatttga
3421 cagagcaaaggcacttcgcaaggagaagggtttaaattatgggtccaaaagccaagtggt
3481 aaagcgagcaatttgcagcataactgcttctcctagacagggctgagtgggcaaaatacg
3541 acagtacacacagtgactattagccactgccagaaacaggctgaacagccctgggagaca
3601 agggaaggcaggtggtgggagttgttcatggagagaaaggagagttttagaaccagcaca
3661 tccactggagatgctggccaccagacccctcccagtcaataaagtctggtgcctcattt
3721 gatctcagcctcatcatgaccctggagagaccctgataccatctgccagtccccgacagc
```

Figure 1D-4

```
3781 ttaggcactccttgccatcaacctgaccccccgagtggttctccaggctccctgccccac
3841 ccattcaggccggaattc
```

Figure 1E: The cDNA (SEQ ID NO: 9) and amino acid sequence (SEQ ID NO: 10) of 161P2F10B variant 5. The 3858 nucleotide sequence of 161P2F10B variant 5 is shown. The open reading frame extends from nucleic acid 44-2671 including the stop codon.

```
     1                                              M  E  S  T  L  T
     1 ctactttattctgataaaacaggtctatgcagctaccaggacaATGGAATCTACGTTGAC
     7  L  A  T  E  Q  P  V  K  K  N  T  L  K  K  Y  K  I  A  C  I
    61 TTTAGCAACGGAACAACCTGTTAAGAAGAACACTCTTAAGAAATATAAAATAGCTTGCAT
    27  V  L  L  A  L  L  V  I  M  S  L  G  L  G  L  G  L  G  L  R
   121 TGTTCTTCTTGCTTTGCTGGTGATCATGTCACTTGGATTAGGCCTGGGGCTTGGACTCAG
    47  K  L  E  K  Q  G  S  C  R  K  K  C  F  D  A  S  F  R  G  L
   181 GAAACTGGAAAAGCAAGGCAGCTGCAGGAAGAAGTGCTTTGATGCATCATTTAGAGGACT
    67  E  N  C  R  D  V  A  C  K  D  R  G  D  C  C  W  D  F  E
   241 GGAGAACTGCCGGTGTGATGTGGCATGTAAAGACCGAGGTGATTGCTGCTGGGATTTTGA
    87  D  T  C  V  E  S  T  R  I  W  M  C  N  K  F  R  C  G  E  T
   301 AGACACCTGTGTGGAATCAACTCGAATATGGATGTGCAATAAATTTCGTTGTGGAGAGAC
   107  R  L  E  A  S  L  C  S  C  S  D  D  C  L  Q  K  K  D  C  C
   361 CAGATTAGAGGCCAGCCTTTGCTCTTGTTCAGATGACTGTTTGCAGAAGAAAGATTGCTG
   127  A  D  Y  K  S  V  C  Q  G  E  T  S  W  L  E  E  N  C  D  T
   421 TGCTGACTATAAGAGTGTTTGCCAAGGAGAAACCTCATGGCTGGAAGAAAACTGTGACAC
   147  A  Q  Q  S  Q  C  P  E  G  F  D  L  P  P  V  I  L  F  S  M
   481 AGCCCAGCAGTCTCAGTGCCCAGAAGGGTTTGACCTGCCACCAGTTATCTTGTTTTCTAT
   167  D  G  F  R  A  E  Y  L  Y  T  W  D  T  L  M  P  N  I  N  K
   541 GGATGGATTTAGAGCTGAATATTTATACACATGGGATACTTTAATGCCAAATATCAATAA
   187  L  K  T  C  G  I  H  S  K  Y  M  R  A  M  Y  P  T  K  T  F
   601 ACTGAAAACATGTGGAATTCATTCAAAATACATGAGAGCTATGTATCCTACCAAAACCTT
   207  P  N  H  Y  T  I  V  T  G  L  Y  P  E  S  H  G  I  I  D  N
   661 CCCAAATCATTACACCATTGTCACGGGCTTGTATCCAGAGTCACATGGCATCATTGACAA
   227  N  M  Y  D  V  N  L  K  N  F  S  L  S  S  K  E  Q  N  N
   721 TAATATGTATGATGTAAATCTCAACAAGAATTTTTCACTTTCTTCAAAGGAACAAAATAA
   247  P  A  W  H  G  Q  P  M  W  L  T  A  M  Y  Q  G  L  K  A
   781 TCCAGCCTGGTGGCATGGGCAACCAATGTGGCTGACAGCAATGTATCAAGGTTTAAAAGC
   267  A  T  Y  F  W  P  G  S  E  V  A  I  N  G  S  F  P  S  I  Y
   841 CGCTACCTACTTTTGGCCCGGATCAGAAGTGGCTATAAATGGCTCCTTTCCTTCCATATA
   287  M  P  Y  N  G  S  V  P  F  E  E  R  I  S  T  L  L  K  W  L
   901 CATGCCTTACAACGGAAGTGTCCCATTTGAAGAGAGGATTTCTACACTGTTAAAATGGCT
   307  D  L  P  K  A  E  R  P  R  F  Y  T  M  Y  F  E  E  P  D  S
   961 GGACCTGCCCAAAGCTGAAAGACCCAGGTTTTATACCATGTATTTTGAAGAACCTGATTC
   327  S  G  H  A  G  G  P  V  S  A  R  V  I  K  A  L  Q  V  V  D
  1021 CTCTGGACATGCAGGTGGACCAGTCAGTGCCAGAGTAATTAAAGCCTTACAGGTAGTAGA
   347  H  A  F  G  M  L  M  E  G  L  K  Q  R  N  L  H  N  C  V  N
```

Figure 1E-2

```
1081 TCATGCTTTTGGGATGTTGATGGAAGGCCTGAAGCAGCGGAATTTGCACAACTGTGTCAA
 367   I  I  L  L  A  D  H  G  M  D  Q  T  Y  C  N  K  M  E  Y  M
1141 TATCATCCTTCTGGCTGACCATGGAATGGACCAGACTTATTGTAACAAGATGGAATACAT
 387   T  D  Y  F  P  R  I  N  F  F  Y  M  Y  E  G  P  A  P  R  I
1201 GACTGATTATTTTCCCAGAATAAACTTCTTCTACATGTACGAAGGGCCTGCCCCCCGCAT
 407   R  A  H  N  I  P  H  D  F  F  S  F  N  S  E  E  I  V  R  N
1261 CCGAGCTCATAATATACCTCATGACTTTTTTAGTTTTAATTCTGAGGAAATTGTTAGAAA
 427   L  S  C  R  K  P  D  Q  H  F  K  P  Y  L  T  P  D  L  P  K
1321 CCTCAGTTGCCGAAAACCTGATCAGCATTTCAAGCCCTATTTGACTCCTGATTTGCCAAA
 447   R  L  H  Y  A  K  N  V  R  I  D  K  V  H  L  F  V  D  Q  Q
1381 GCGACTGCACTATGCCAAGAACGTCAGAATCGACAAAGTTCATCTCTTTGTGGATCAACA
 467   W  L  A  V  R  S  K  S  N  T  N  C  G  G  G  N  H  G  Y  N
1441 GTGGCTGGCTGTTAGGAGTAAATCAAATACAAATTGTGGAGGAGGCAACCATGGTTATAA
 487   N  E  F  R  S  M  E  A  I  F  L  A  H  G  P  S  F  K  E  K
1501 CAATGAGTTTAGGAGCATGGAGGCTATCTTTCTGGCACATGGACCCAGTTTTAAAGAGAA
 507   T  E  V  E  P  F  E  N  I  E  V  Y  N  L  M  C  D  L  L  R
1561 GACTGAAGTTGAACCATTTGAAAATATTGAAGTCTATAACCTAATGTGTGATCTTCTACG
 527   I  Q  P  A  P  N  N  G  T  H  G  S  L  N  H  L  L  K  V  P
1621 CATTCAACCAGCACCAAACAATGGAACCCATGGTAGTTTAAACCATCTTCTGAAGGTGCC
 547   F  Y  E  P  S  H  A  E  E  V  S  K  F  S  V  C  G  F  A  N
1681 TTTTTATGAGCCATCCCATGCAGAGGAGGTGTCAAAGTTTTCTGTTTGTGGCTTTGCTAA
 567   P  L  P  T  E  S  L  D  C  F  C  P  H  L  Q  N  S  T  Q  L
1741 TCCATTGCCCACAGAGTCTCTTGACTGTTTCTGCCCTCACCTACAAAATAGTACTCAGCT
 587   E  Q  V  N  Q  M  L  N  L  T  Q  E  E  I  T  A  T  V  K  V
1801 GGAACAAGTGAATCAGATGCTAAATCTCACCCAAGAAGAAATAACAGCAACAGTGAAAGT
 607   N  L  P  F  G  R  P  R  V  L  Q  K  N  V  D  H  C  L  L  Y
1861 AAATTTGCCATTTGGGAGGCCTAGGGTACTGCAGAAGAACGTGGACCACTGTCTCCTTTA
 627   H  R  E  Y  V  S  G  F  G  K  A  M  R  M  P  M  W  S  S  Y
1921 CCACAGGGAATATGTCAGTGGATTTGGAAAAGCTATGAGGATGCCCATGTGGAGTTCATA
 647   T  V  P  Q  L  G  D  T  S  P  L  P  P  T  V  P  D  C  L  R
1981 CACAGTCCCCCAGTTGGGAGACACATCGCCTCTGCCTCCCACTGTCCCAGACTGTCTGCG
 667   A  D  V  R  V  P  P  S  E  S  Q  K  C  S  F  Y  L  A  D  K
2041 GGCTGATGTCAGGGTTCCTCCTTCTGAGAGCCAAAAATGTTCCTTCTATTTAGCAGACAA
 687   N  I  T  H  G  F  L  Y  P  P  A  S  N  R  T  S  D  S  Q  Y
2101 GAATATCACCCACGGCTTCCTCTATCCTCCTGCCAGCAATAGAACATCAGATAGCCAATA
 707   D  A  L  I  T  S  N  L  V  P  M  Y  E  E  F  R  K  M  W  D
2161 TGATGCTTTAATTACTAGCAATTTGGTACCTATGTATGAAGAATTCAGAAAAATGTGGGA
 727   Y  F  H  S  V  L  L  I  K  H  A  T  E  R  N  G  V  N  V  V
2221 CTACTTCCACAGTGTTCTTCTTATAAAACATGCCACAGAAAGAAATGGAGTAAATGTGGT
 747   S  G  P  I  F  D  Y  N  Y  D  G  H  F  D  A  P  D  E  I  T
2281 TAGTGGACCAATATTTGATTATAATTATGATGGCCATTTTGATGCTCCAGATGAAATTAC
 767   K  H  L  A  N  T  D  V  P  I  P  T  H  Y  F  V  V  L  T  S
```

Figure 1E-3

```
2341 CAAACATTTAGCCAACACTGATGTTCCCATCCCAACACACTACTTTGTGGTGCTGACCAG
 787  C  K  N  K  S  H  T  P  E  N  C  P  G  W  L  D  V  L  P  F
2401 TTGTAAAAACAAGAGCCACACACCGGAAAACTGCCCTGGGTGGCTGGATGTCCTACCCTT
 807  I  I  P  E  R  P  T  N  V  E  S  C  P  E  G  K  P  E  A  L
2461 TATCATCCCTCACCGACCTACCAACGTGGAGAGCTGTCCTGAAGGTAAACCAGAAGCTCT
 827  W  V  E  R  F  T  A  H  I  A  R  V  R  D  V  E  L  L  T
2521 TTGGGTTGAAGAAAGATTTACAGCTCACATTGCCCGGGTCCGTGATGTAGAACTTCTCAC
 847  G  L  D  F  Y  Q  D  K  V  Q  P  V  S  E  I  L  Q  L  K  T
2581 TGGGCTTGACTTCTATCAGGATAAAGTGCAGCCTGTCTCTGAAATTTTGCAACTAAAGAC
 867  Y  L  P  T  F  E  T  T  I  *
2641 ATATTTACCAACATTTGAAACCACTATTTAActtaataatgtctacttaatatataattt
2701 actgtataaagtaattttggcaaaatataagtgattttttctggagaattgtaaaataaa
2761 gttttctattttttccttaaaaaaaaaaccggaattccgggcttgggaggctgaggcagga
2821 gactcgcttgaacccgggaggcagaggttgcagtgagccaagattgcgccattgcactcc
2881 agagcctgggtgacagagcaagactacatctcaaaaaataaataaataaaataaaagtaa
2941 caataaaaataaaaagaacagcagagagaatgagcaaggagaaatgtcacaaactattgc
3001 aaaatactgttacactgggttggctctccaagaagatactggaatctcttcagccatttg
3061 cttttcagaagtagaaaccagcaaaccacctctaagcggagaacatacgattctttatta
3121 agtagctctggggaaggaaagaataaaagttgatagctccctgattgggaaaaaatgcac
3181 aattaataaagaatgaagatgaaagaaagcatgcttatgttgtaacacaaaacaaattca
3241 caaacgttggtggaaggaaaacagtatagaaaacattacttttaactaaaagctggaaaaa
3301 ttttcagttgggatgcgactgacaaaaagaacgggatttccaggcataaagttggcgtga
3361 gctacagaggcaccatgtggctcagtggaagaccctcaagattcaaagttccatttga
3421 cagagcaaaggcacttcgcaaggagaagggtttaaattatgggtccaaaagccaagtggt
3481 aaagcgagcaatttgcagcataactgcttctcctagacagggctgagtgggcaaaatacg
3541 acagtacacacagtgactattagccactgccagaaacaggctgaacagccctgggagaca
3601 agggaaggcaggtggtgggagttgttcatggagagaaaggagagttttagaaccagcaca
3661 tccactggagatgctgggccaccagacccctcccagtcaataaagtctggtgcctcattt
3721 gatctcagcctcatcatgaccctggagagacctgataccatctgccagtccccgacagc
3781 ttaggcactccttgccatcaacctgaccccccgagtggttctccaggctccctgccccac
3841 ccattcaggccggaattc
```

Figure 1F: The cDNA (SEQ ID NO: 11) and amino acid sequence (SEQ ID NO: 12) of 161P2F10B variant 6. The 3165 nucleotide sequence of 161P2F10B variant 6 is shown. The open reading frame extends from nucleic acid 84-2711 including the stop codon.

```
   1 atacagtttctctttgccagactagactaaagaaggagcactactttattctgataaaac
   1                                  M  E  S  T  L  T  L  A  T  E  Q  P  V
  61 aggtctatgcagctaccaggacaATGGAATCTACGTTGACTTTAGCAACGGAACAACCTG
  14  K  K  N  T  L  K  K  Y  K  I  A  C  I  V  L  L  A  L  L  V
 121 TTAAGAAGAACACTCTTAAGAAATATAAAATAGCTTGCATTGTTCTTCTTGCTTTGCTGG
  34  T  M  S  L  G  L  G  L  G  L  G  L  R  K  L  E  K  Q  G  S
```

Figure 1F-2

```
 181 TGATCATGTCACTTGGATTAGGCCTGGGGCTTGGACTCAGGAAACTGGAAAAGCAAGGCA
  54    C   R   K   K   C   F   D   A   S   F   R   G   L   E   N   C   R   C   D   V
 241 GCTGCAGGAAGAAGTGCTTTGATGCATCATTTAGAGGACTGGAGAACTGCCGGTGTGATG
  74    A   C   K   D   R   G   D   C   C   W   D   F   E   D   T   C   V   E   S   T
 301 TGGCATGTAAAGACCGAGGTGATTGCTGCTGGGATTTTGAAGACACCTGTGTGGAATCAA
  94    R   I   W   M   C   N   K   F   R   C   G   E   T   R   L   E   A   S   L   C
 361 CTCGAATATGGATGTGCAATAAATTTCGTTGTGGAGAGACCAGATTAGAGGCCAGCCTTT
 114    S   C   S   D   D   C   L   Q   R   K   D   C   C   A   D   Y   K   S   V   C
 421 GCTCTTGTTCAGATGACTGTTTGCAGAGGAAAGATTGCTGTGCTGACTATAAGAGTGTTT
 134    Q   G   E   T   S   W   L   E   E   N   C   D   T   A   Q   Q   S   Q   C   P
 481 GCCAAGGAGAAACCTCATGGCTGGAAGAAAACTGTGACACAGCCCAGCAGTCTCAGTGCC
 154    E   G   F   D   L   P   P   V   I   L   F   S   M   D   G   F   R   A   E   Y
 541 CAGAAGGGTTTGACCTGCCACCAGTTATCTTGTTTTCTATGGATGGATTTAGAGCTGAAT
 174    L   Y   T   W   D   T   L   M   P   N   I   N   K   L   K   T   C   G   I   H
 601 ATTTATACACATGGGATACTTTAATGCCAAATATCAATAAACTGAAAACATGTGGAATTC
 194    S   K   Y   M   R   A   M   Y   P   T   K   T   F   P   N   H   Y   T   I   V
 661 ATTCAAAATACATGAGAGCTATGTATCCTACCAAAACCTTCCCAAATCATTACACCATTG
 214    T   G   L   Y   P   E   S   H   G   I   I   D   N   N   M   Y   D   V   N   L
 721 TCACGGGCTTGTATCCGGAGTCACATGGCATCATTGACAATAATATGTATGATGTAAATC
 234    N   K   N   F   S   L   S   S   K   E   Q   N   N   P   A   W   W   H   G   Q
 781 TCAACAAGAATTTTTCACTTTCTTCAAAGGAACAAAATAATCCAGCCTGGTGGCATGGGC
 254    P   M   W   L   T   A   M   Y   Q   G   L   K   A   A   T   Y   F   W   P   G
 841 AACCAATGTGGCTGACAGCAATGTATCAAGGTTTAAAAGCCGCTACCTACTTTTGGCCCG
 274    S   E   V   A   I   N   G   S   F   P   S   I   Y   M   P   Y   N   G   S   V
 901 GATCAGAAGTGGCTATAAATGGCTCCTTTCCTTCCATATACATGCCTTACAACGGAAGTG
 294    P   F   E   E   R   I   S   T   L   L   K   W   D   L   P   K   A   E   R
 961 TCCCATTTGAAGAGAGGATTTCTACACTGTTAAAATGGCTGGACCTGCCCAAAGCTGAGA
 314    P   R   F   Y   T   M   F   F   E   E   P   D   S   S   G   H   A   G   G   P
1021 GACCCAGGTTTTATACCATGTTTTTTGAAGAACCTGATTCCTCTGGACATGCAGGTGGAC
 334    V   S   A   R   V   I   K   A   L   Q   V   V   D   H   A   F   G   M   L   M
1081 CAGTCAGTGCCAGAGTAATTAAAGCCTTACAGGTAGTAGATCATGCTTTTGGGATGTTGA
 354    E   G   L   K   Q   R   N   L   H   N   C   V   N   I   I   L   L   A   D   H
1141 TGGAAGGCCTGAAGCAGCGGAATTTGCACAACTGTGTCAATATCATCCTTCTGGCTGACC
 374    G   M   D   Q   T   Y   C   N   K   M   E   Y   M   T   D   Y   F   P   R   I
1201 ATGGAATGGACCAGACTTATTGTAACAAGATGGAATACATGACTGATTATTTTCCCAGAA
 394    N   F   F   Y   M   Y   E   G   P   A   P   R   V   R   A   H   N   I   P   H
1261 TAAACTTCTTCTACATGTACGAAGGGCCTGCCCCCGCGTCCGAGCTCATAATATACCTC
 414    D   F   F   S   F   N   S   E   E   I   V   R   N   L   S   C   R   K   P   D
1321 ATGACTTTTTTAGTTTTAATTCTGAGGAAATTGTTAGAAACCTCAGTTGCCGAAAACCTG
 434    Q   H   F   K   P   Y   L   T   P   D   L   P   K   R   L   H   Y   A   K   N
1381 ATCAGCATTTCAAGCCCTATTTGACTCCTGATTTGCCAAAGCGACTGCACTATGCCAAGA
```

Figure 1F-3

```
 454      V  R  I  D  K  V  H  L  F  V  D  Q  Q  W  L  A  V  R  S  K
1441 ACGTCAGAATCGACAAAGTTCATCTCTTTGTGGATCAACAGTGGCTGGCTGTTAGGAGTA
 474      S  N  T  N  C  G  G  G  N  H  G  Y  N  N  E  F  R  S  M  E
1501 AATCAAATACAAATTGTGGAGGAGGCAACCATGGTTATAACAATGAGTTTAGGAGCATGG
 494      A  T  F  L  A  H  G  P  S  F  K  E  K  T  E  V  E  P  F  E
1561 AGGCTATCTTTCTGGCACATGGACCCAGTTTTAAAGAGAAGACTGAAGTTGAACCATTTG
 514      N  I  E  V  Y  N  L  M  C  D  L  L  R  I  Q  P  A  P  N  N
1621 AAAATATTGAAGTCTATAACCTAATGTGTGATCTTCTACGCATTCAACCAGCACCAAACA
 534      G  T  H  G  S  L  N  H  L  L  K  V  P  F  Y  E  P  S  H  A
1681 ATGGAACCCATGGTAGTTTAAACCATCTTCTGAAGGTGCCTTTTTATGAGCCATCCCATG
 554      E  E  V  S  K  F  S  V  C  G  F  A  N  P  L  P  T  E  S  L
1741 CAGAGGAGGTGTCAAAGTTTTCTGTTTGTGGCTTTGCTAATCCATTGCCCACAGAGTCTC
 574      D  C  F  C  P  H  L  Q  N  S  T  Q  L  E  Q  V  N  Q  M  L
1801 TTGACTGTTTCTGCCCTCACCTACAAAATAGTACTCAGCTGGAACAAGTGAATCAGATGC
 594      N  L  T  Q  E  E  I  T  A  T  V  K  V  N  L  P  F  G  R  P
1861 TAAATCTCACCCAAGAAGAAATAACAGCAACAGTGAAAGTAAATTTGCCATTTGGGAGGC
 614      R  V  L  Q  K  N  V  D  H  C  L  L  Y  H  R  E  Y  V  S  G
1921 CTAGGGTACTGCAGAAGAACGTGGACCACTGTCTCCTTTACCACAGGGAATATGTCAGTG
 634      F  G  K  A  M  R  M  P  M  W  S  S  Y  T  V  P  Q  L  G  D
1981 GATTTGGAAAAGCTATGAGGATGCCCATGTGGAGTTCATACACAGTCCCCCAGTTGGGAG
 654      T  S  P  L  P  P  T  V  P  D  C  L  R  A  D  V  R  V  P  P
2041 ACACATCGCCTCTGCCTCCCACTGTCCCAGACTGTCTGCGGGCTGATGTCAGGGTTCCTC
 674      S  E  S  Q  K  C  S  F  Y  L  A  D  K  N  I  T  H  G  F  L
2101 CTTCTGAGAGCCAAAAATGTTCCTTCTATTTAGCAGACAACAATATCACCCACGGCTTCC
 694      Y  P  P  A  S  N  R  T  S  D  S  Q  Y  D  A  L  I  T  S  N
2161 TCTATCCTCCTGCCAGCAATAGAACATCAGATAGCCAATATGATGCTTTAATTACTAGCA
 714      L  V  P  M  Y  E  E  F  R  K  M  W  D  Y  F  H  S  V  L  L
2221 ATTTGGTACCTATGTATGAAGAATTCAGAAAAATGTGGGACTACTTCCACAGTGTTCTTC
 734      I  K  H  A  T  E  R  N  G  V  N  V  V  S  G  P  I  F  D  Y
2281 TTATAAAACATGCCACAGAAAGAAATGGAGTAAATGTGGTTAGTGGACCAATATTTGATT
 754      N  Y  D  G  H  F  D  A  P  D  E  I  T  K  H  L  A  N  T  D
2341 ATAATTATGATGGCCATTTTGATGCTCCAGATGAAATTACCAAACATTTAGCCAACACTG
 774      V  P  I  P  T  H  Y  F  V  V  L  T  S  C  K  N  K  S  H  T
2401 ATGTTCCCATCCCAACACACTACTTTGTGGTGCTGACCAGTTGTAAAAACAAGAGCCACA
 794      P  E  N  C  P  G  W  L  D  V  L  P  F  I  I  P  H  R  P  T
2461 CACCGGAAAACTGCCCTGGGTGGCTGGATGTCCTACCCTTTATCATCCCTCACCGACCTA
 814      N  V  E  S  C  P  E  G  K  P  E  A  L  W  V  E  E  R  F  T
2521 CCAACGTGGAGAGCTGTCCTGAAGGTAAACCAGAAGCTCTTTGGGTTGAAGAAAGATTTA
 834      A  H  I  A  R  V  R  D  V  E  L  L  T  G  L  D  F  Y  Q  D
2581 CAGCTCACATTGCCCGGGTCCGTGATGTAGAACTTCTCACTGGGCTTGACTTCTATCAGG
 854      K  V  Q  P  V  S  E  I  L  Q  L  K  T  Y  L  P  T  F  E  T
```

Figure 1F-4

```
2641 ATAAAGTGCAGCCTGTCTCTGAAATTTTGCAACTAAAGACATATTTACCAACATTTGAAA
 874  T  I  *
2701 CCACTATTTAActtaataatgtctacttaatatataatttactgtataaagtaattttgg
2761 caaaatataagtgatttttttctggagaattgtaaaataaagttttctattttttccttaa
2821 gtcccctaaaagccataattttttattattccttttttctctttttttcaattctatgaatat
2881 gtattattttaaagttatattttttcacacagagatgatgctatattacaccttcccttttt
2941 ttgttggtttcttaaactctaatctcatgacagattataccttccttattacttgttttta
3001 tcttactcagaatctttgaatatattttttctgcccagaattatctaaacaaaagggagaa
3061 caaaagaagtatgtctcacttgggaactgaatcaactctaaatcagttttgtcacaaaac
3121 tttttgtatttgactggcaatgctgattaaaattaaaaatgcaca
```

Figure 1G: The cDNA (SEQ ID NO: 13) and amino acid sequence (SEQ ID NO:14) of 161P2F10B variant 7. The 3988 nucleotide sequence of 161P2F10B variant 7 is shown. The open reading frame extends from nucleic acid 276-2801 including the stop codon.

```
   1 ctactttattctgataaaacaggtctatgcagctaccaggacaatggaatctacgttgac
  61 tttagcaacggaacaacctgttaagaagaacactcttaagaaatataaaatagcttgcat
 121 tacagggtctctctcctttgggatctcacctcaccacaacctctgtttcccaggctcaag
 181 tgatcctcctgcctcagcctcctgagtagcttggaccacaggcacatgccacaaggctca
   1                                            M  S  L  G  L  G  L
 241 gctaagttttgttcttcttgctttgctggtgatcATGTCACTTGGATTAGGCCTGGGGC
  10  G  L  R  K  L  E  K  Q  G  S  C  R  K  K  C  F  D  A  S  F
 301 TTGGACTCAGGAAACTGGAAAAGCAAGGCAGCTGCAGGAAGAAGTGCTTTGATGCATCAT
  30  R  G  L  E  N  C  R  D  V  A  C  K  D  R  G  D  C  C  W
 361 TTAGAGGACTGGAGAACTGCCGGTGTGATGTGGCATGTAAAGACCGAGGTGATTGCTGCT
  50  D  F  E  D  T  C  V  E  S  T  R  I  W  M  C  N  K  F  R  C
 421 GGGATTTTGAAGACACCTGTGTGGAATCAACTCGAATATGGATGTGCAATAAATTTCGTT
  70  G  E  T  R  L  E  A  S  L  C  S  C  S  D  D  C  L  Q  K  K
 481 GTGGAGAGACCAGATTAGAGGCCAGCCTTTGCTCTTGTTCAGATGACTGTTTGCAGAAGA
  90  D  C  C  A  D  Y  K  S  V  C  Q  G  E  T  S  W  L  E  E  N
 541 AAGATTGCTGTGCTGACTATAAGAGTGTTTGCCAAGGAGAAACCTCATGGCTGGAAGAAA
 110  C  D  T  A  Q  Q  S  Q  C  P  E  G  F  D  L  P  P  V  I  L
 601 ACTGTGACACAGCCCAGCAGTCTCAGTGCCCAGAAGGGTTTGACCTGCCACCAGTTATCT
 130  F  S  M  D  G  F  R  A  E  Y  L  Y  T  W  D  T  L  M  P  N
 661 TGTTTTCTATGGATGGATTTAGAGCTGAATATTTATACACATGGGATACTTTAATGCCAA
 150  I  N  K  L  K  T  C  G  I  H  S  K  Y  M  R  A  M  Y  P  T
 721 ATATCAATAAACTGAAAACATGTGGAATTCATTCAAAATACATGAGAGCTATGTATCCTA
 170  K  T  F  P  N  H  Y  T  I  V  T  G  L  Y  P  E  S  H  G  I
 781 CCAAAACCTTCCCAAATCATTACACCATTGTCACGGGCTTGTATCCAGAGTCACATGGCA
 190  I  D  N  K  M  Y  D  V  N  L  N  K  N  F  S  L  S  S  K  E
 841 TCATTGACAATAAATATGTATGATGTAAATCTCAACAAGAATTTTTCACTTTCTTCAAAGG
 210  Q  N  N  P  A  W  W  H  G  Q  P  M  W  L  T  A  M  Y  Q  G
 901 AACAAAATAATCCAGCCTGGTGGCATGGGCAACCAATGTGGCTGACAGCAATGTATCAAG
 230  L  K  A  A  T  Y  F  W  P  G  S  E  V  A  I  N  G  S  F  P
 961 GTTTAAAAGCCGCTACCTACTTTTGGCCCGGATCAGAAGTGGCTATAAATGGCTCCTTTC
 250  S  I  Y  M  P  Y  N  G  S  V  P  F  E  E  R  I  S  T  L  L
1021 CTTCCATATACATGCCTTACAACGGAAGTGTCCCATTTGAAGAGAGGATTTCTACACTGT
 270  K  W  L  D  L  P  K  A  E  R  P  R  F  Y  T  M  Y  F  E  E
1081 TAAAATGGCTGGACCTGCCCAAAGCTGAAAGACCCAGGTTTTATACCATGTATTTTGAAG
 290  P  D  S  S  G  H  A  G  G  P  V  S  A  R  V  I  K  A  L  Q
1141 AACCTGATTCCTCTGGACATGCAGGTGGACCAGTCAGTGCCAGAGTAATTAAAGCCTTAC
 310  V  V  D  H  A  F  G  M  L  E  G  L  K  Q  R  N  L  H  N
1201 AGGTAGTAGATCATGCTTTTGGGATGTTGATGGAAGGCCTGAAGCAGCGGAATTTGCACA
 330  C  V  N  I  I  L  L  A  D  H  G  M  D  Q  T  Y  C  N  K  M
```

Figure 1G-2

```
1261 ACTGTGTCAATATCATCCTTCTGGCTGACCATGGAATGGACCAGACTTATTGTAACAAGA
 350   E  Y  M  T  D  Y  F  P  R  I  N  F  F  Y  M  Y  E  G  P  A
1321 TGGAATACATGACTGATTATTTTCCCAGAATAAACTTCTTCTACATGTACGAAGGGCCTG
 370   P  R  I  R  A  H  N  I  P  H  D  F  F  S  F  N  S  E  E  I
1381 CCCCCCGCATCCGAGCTCATAATATACCTCATGACTTTTTTAGTTTTAATTCTGAGGAAA
 390   V  R  N  L  S  C  R  K  P  D  Q  H  F  K  P  Y  L  T  P  D
1441 TTGTTAGAAACCTCAGTTGCCGAAAACCTGATCAGCATTTCAAGCCCTATTTGACTCCTG
 410   L  P  K  R  L  H  Y  A  K  N  V  R  I  D  K  V  H  L  F  V
1501 ATTTGCCAAAGCGACTGCACTATGCCAAGAACGTCAGAATCGACAAAGTTCATCTCTTTG
 430   D  Q  Q  W  L  A  V  R  S  K  S  N  T  N  C  G  G  N  H
1561 TGGATCAACAGTGGCTGGCTGTTAGGAGTAAATCAAATACAAATTGTGGAGGAGGCAACC
 450   G  Y  N  N  E  F  R  S  M  E  A  I  F  L  A  H  G  P  S  F
1621 ATGGTTATAACAATGAGTTTAGGAGCATGGAGGCTATCTTTCTGGCACATGGACCCAGTT
 470   K  E  K  T  E  V  E  P  F  E  N  I  E  V  Y  N  L  M  C  D
1681 TTAAAGAGAAGACTGAAGTTGAACCATTTGAAAATATTGAAGTCTATAACCTAATGTGTG
 490   L  L  R  I  Q  P  A  P  N  N  G  T  H  G  S  L  N  H  L  L
1741 ATCTTCTACGCATTCAACCAGCACCAAACAATGGAACCCATGGTAGTTTAAACCATCTTC
 510   K  V  P  F  Y  E  P  S  H  A  E  E  V  S  K  F  S  V  C  G
1801 TGAAGGTGCCTTTTTATGAGCCATCCCATGCAGAGGAGGTGTCAAAGTTTTCTGTTTGTG
 530   F  A  N  P  L  P  T  E  S  L  D  C  F  C  P  H  L  Q  N  S
1861 GCTTTGCTAATCCATTGCCCACAGAGTCTCTTGACTGTTTCTGCCCTCACCTACAAAATA
 550   T  Q  L  E  Q  V  N  Q  M  L  N  L  T  Q  E  E  I  T  A  T
1921 GTACTCAGCTGGAACAAGTGAATCAGATGCTAAATCTCACCCAAGAAGAAATAACAGCAA
 570   V  K  V  N  L  P  F  G  R  P  R  V  L  Q  K  N  V  D  H  C
1981 CAGTGAAAGTAAATTTGCCATTTGGGAGGCCTAGGGTACTGCAGAAGAACGTGGACCACT
 590   L  L  Y  H  R  E  Y  V  S  G  F  G  K  A  M  R  M  P  M  W
2041 GTCTCCTTTACCACAGGGAATATGTCAGTGGATTTGGAAAAGCTATGAGGATGCCCATGT
 610   S  S  Y  I  V  P  Q  L  G  D  T  S  P  L  P  P  T  V  P  D
2101 GGAGTTCATACACAGTCCCCCAGTTGGGAGACACATCGCCTCTGCCTCCCACTGTCCCAG
 630   C  L  R  A  D  V  R  V  P  P  S  E  S  Q  K  C  S  F  Y  L
2161 ACTGTCTGCGGGCTGATGTCAGGGTTCCTCCTTCTGAGAGCCAAAAATGTTCCTTCTATT
 650   A  D  K  N  I  T  H  G  F  L  Y  P  P  A  S  N  R  T  S  D
2221 TAGCAGACAAGAATATCACCCACGGCTTCCTCTATCCTCCTGCCAGCAATAGAACATCAG
 670   S  Q  Y  D  A  L  I  T  S  N  L  V  P  M  Y  E  E  F  R  K
2281 ATAGCCAATATGATGCTTTAATTACTAGCAATTTGGTACCTATGTATGAAGAATTCAGAA
 690   M  W  D  Y  F  H  S  V  L  L  I  K  H  A  T  E  R  N  G  V
2341 AAATGTGGGACTACTTCCACAGTGTTCTTCTTATAAAACATGCCACAGAAAGAAATGGAG
 710   N  V  V  S  G  P  I  F  D  Y  N  Y  D  G  H  F  D  A  P  D
2401 TAAATGTGGTTAGTGGACCAATATTTGATTATAATTATGATGGCCATTTTGATGCTCCAG
 730   E  I  T  K  H  L  A  N  T  D  V  P  I  P  T  H  Y  F  V  V
2461 ATGAAATTACCAAACATTTAGCCAACACTGATGTTCCCATCCCAACACACTACTTTGTGG
```

Figure 1G-3

```
 750   L  T  S  C  K  N  K  S  H  T  P  E  N  C  P  G  W  L  D  V
2521  TGCTGACCAGTTGTAAAAACAAGAGCCACACACCGGAAAACTGCCCTGGGTGGCTGGATG
 770   L  P  F  I  I  P  H  R  P  T  N  V  E  S  C  P  E  G  K  P
2581  TCCTACCCTTTATCATCCCTCACCGACCTACCAACGTGGAGAGCTGTCCTGAAGGTAAAC
 790   E  A  L  W  V  E  E  R  F  T  A  H  I  A  R  V  R  D  V  E
2641  CAGAAGCTCTTTGGGTTGAAGAAAGATTTACAGCTCACATTGCCCGGGTCCGTGATGTAG
 810   L  L  T  G  L  D  F  Y  Q  D  K  V  Q  P  V  S  E  I  L  Q
2701  AACTTCTCACTGGGCTTGACTTCTATCAGGATAAAGTGCAGCCTGTCTCTGAAATTTTGC
 830   L  K  T  Y  L  P  T  F  E  T  T  I  *
2761  AACTAAAGACATATTTACCAACATTTGAAACCACTATTTAActtaataatgtctacttaa
2821  tatataatttactgtataaagtaattttggcaaaatataagtgattttttctggagaatt
2881  gtaaaataaagttttctattttccttaaaaaaaaaaccggaattccgggcttgggaggc
2941  tgaggcaggagactcgcttgaacccggagcagaggttgcagtgagccaagattgcgcc
3001  attgcactccagagcctgggtgacagagcaagactacatctcaaaaataaataataaa
3061  ataaaagtaacaataaaaataaaaagaacagcagagagaatgagcaaggagaaatgtcac
3121  aaactattgcaaaatactgttacactgggttggctctccaagaagatactggaatctctt
3181  cagccatttgcttttcagaagtagaaaccagcaaaccacctctaagcggagaacatacga
3241  ttctttattaagtagctctggggaaggaaagaataaaagttgatagctccctgattggga
3301  aaaaatgcacaattaataaagaatgaagatgaaagaaagcatgcttatgttgtaacacaa
3361  aaaaaattcacaaacgttggtggaaggaaaacagtatagaaaacattactttaactaaaa
3421  gctggaaaaattttcagttgggatgcgactgacaaaaagaacgggatttccaggcataaa
3481  gttggcgtgagctacagagggcaccatgtggctcagtggaagacccttcaagattcaaag
3541  ttccatttgacagagcaaaggcacttcgcaaggagaagggtttaaattatgggtccaaaa
3601  gccaagtggtaaagcgagcaatttgcagcataactgcttctcctagacagggctgagtgg
3661  gcaaaatacgacagtacacacagtgactattagccactgccagaaacaggctgaacagcc
3721  ctgggagacaagggaaggcaggtggtgggagttgttcatggagagaaggagagttttag
3781  aaccagcacatccactggagatgctgggccaccagacccctcccagtcaataaagtctgg
3841  tgcctcatttgatctcagcctcatcatgaccctggagagaccctgataccatctgccagt
3901  ccccgacagcttaggcactccttgccatcaacctgacccccgagtggttctccaggctc
3961  cctgccccacccattcaggccggaattc
```

Figure 2:

<u>Figure 2A</u> The cDNA (SEQ ID NO:15) and amino acid sequence (SEQ ID NO:16) of H16-7.213 VH.
Underlined is a portion of the heavy chain constant region.

```
  1   W  G  L  S  E  V  S  C  K  A  S  G  Y  T  F  T  G  Y  Y  M
  1 ctggggcctcagtgaggtctcctgcaaggcttctggatacaccttcaccggctactatat
 21   H  W  V  R  Q  A  P  G  Q  G  L  E  W  M  G  W  I  N  P  N
 61 gcactgggtgcgacaggcccctggacaagggcttgagtggatgggatggatcaaccctaa
 41   S  G  G  T  N  Y  A  Q  K  F  Q  G  R  V  T  M  T  R  D  T
121 cagtggtggcacaaactatgcacagaagtttcagggcagagtcaccatgaccagggacac
 61   S  I  S  T  A  Y  M  E  L  S  R  L  R  S  D  D  T  A  V  Y
181 gtccatcagcacagcctacatggagctgagcaggctgagatctgacgacacggccgtgta
 81   Y  C  A  R  E  L  R  Y  F  G  W  L  L  S  S  L  D  Y  W  G
241 ttactgtgcgcgagaattacgatattttggctggttattatcctcccttgactactgggg
101   Q  G  T  L  V  T  V  S  S  A  S  T  K  G  P  S  V  F  P  L
301 ccagggaaccctggtcaccgtctcctcagcctccaccaagggcccatcggtcttcccccT
121   A  P  C  S  R  S  T  S  E  S  T  A  A  L  G  C  L  V  K  D
361 ggcgccctgctccaggagcacctccgagagcacagcggccctgggctgcctggtcaagga
141   Y  F  P  E  P  V  T  V  S  W  N  S  G  A  L  T  S  G  V  H
421 ctacttccccgaaccggtgacggtgtcgtggaactcaggcgctctgaccagcggcgtgca
161   T  F  P  A  V  L  Q  S  S  G  L  Y  S  L  S  S  V  V  T  V
481 caccttcccagctgtcctacagtcctcaggactctactccctcagcagcgtggtgaccgt
181   P  S  S  N  F  G  T  Q  T  Y  T  C  N  V  D  H  K  P  S  N
541 gccctccagcaacttcggcacccagacctacacctgcaacgtagatcacaagcccagcaa
201   T  K  V  D  K  T  V  E  R  K  C  C  V  E  C  P  P  C  P  A
601 caccaaggtggacaagacagttgagcgcaaatgttgtgtcgagtgcccaccgtgcccagc
221   P  P  V  A  G  P  S  V  F  L  F  P  P  K  P  K  D  T  L  M
661 accacctgtggcaggaccgtcagtcttcctcttccccccaaaacccaagacaccctcat
241   I  S  R  T  P  E  V  T  C  V  V  V  D  V  S  H  E  D  P  E
721 gatctcccggacccctgaggtcacgtgcgtggtggtggacgtgagccacgaagaccccga
261   V  Q  F  N  W  Y  V  D  G  V  E  V  H  N  A  K  T  K  P  R
781 ggtccagttcaactggtacgtggacggcgtggaggtgcataatgccaagacaaagccacg
281   E  E  Q  F  N  S  T  F  R  V  V  S  V  L  T  V  V  H  Q  D
841 ggaggagcagttcaacagcacgttccgtgtggtcagcgtcctcaccgttgtgcaccagga
301   W  L  N  G  K  E  Y  K  C  K  V  S  N  K  G  L  P  A  P  I
901 ctggctgaacggcaaggagtacaagtgcaaggtctccaacaaaggcctcccagcccccat
321   E  K  T  I  S  K  T  K  G  Q  P  R  E  P  Q  V  Y  T  L  P
961 cgagaaaaccatctccaaaaccaaagggcagccccgagaaccacaggtgtacaccctgcc
341   P  S  R  E  E  M  T  K  N  Q  V  S  L  T  C  L  V  K  G  F
1021 cccatcccgggaggagatgaccaagaaccaggtcagcctgacctgcctggtcaaaggctt
361   Y  P  S  D  I  A  V  E  W  E  S  N  G  Q  P  E  N  N  Y  K
1081 ctaccccagcgacatcgccgtggagtgggagagcaatgggcagccggagaacaactacaa
381   T  T  P  P  M  L  D  S  D  G  S  F  F  L  Y  S  K  L  T  V
1141 gaccacacctcccatgctggactccgacggctccttcttcctttacagcaagctcaccgt
401   D  K  S  R  W  Q  Q  G  N  V  F  S  C  S  V  M  H  E  A  L
1201 ggacaagagcaggtggcagcaggggaacgtcttctcatgctccgtgatgcatgaggctct
421   H
1261 gcacaa
```

<u>Figure 2B</u> The cDNA (SEQ ID NO:17) and amino acid sequence (SEQ ID NO:18) of H16-7.213 VL.
Underlined is a portion of the light chain constant region.

```
  1   L  L  G  L  L  L  L  W  L  R  G  A  R  C  D  I  Q  M  T  Q
  1 agctcctggggctcctgctactctggctccgaggtgccagatgtgacatccagatgaccc
 21   S  P  S  S  L  S  A  S  V  G  D  R  V  T  I  T  C  R  A  S
 61 agtctccatcctccctgtctgcatctgtaggagacagagtcaccatcacttgccgggcaa
 41   Q  S  I  S  S  Y  L  N  W  F  Q  Q  K  P  G  K  A  P  K  L
121 gtcagagcattagcagctatttaaattggttcagcagaaaccagggaaagcccctaagc
 61   L  I  Y  A  A  S  S  L  Q  S  G  V  P  S  R  F  S  G  S  E
181 tcctgatctatgctgcatccagtttgcaaagtggggtcccatcaaggttcagtggcagtg
 81   S  G  T  D  F  T  L  T  I  S  S  L  Q  P  E  D  F  A  T  Y
241 aatctgggacagatttcactctcaccatcagcagtctgcaacctgaagattttgctactt
101   S  C  Q  Q  S  Y  S  F  P  L  T  F  G  G  G  T  K  V  E  I
```

Figure 2B-2

```
301 actcctgtcaacagagttacagtttcccgctcactttcggcggagggaccaaggtggaga
121    K  R  T  V  A  A  P  S  V  F  I  F  P  P  S  D  E  Q  L  K
361 tcaaacgaactgtggctgcaccatctgtcttcatcttcccgccatctgatcagcagttga
141    S  G  T  A  S  V  V  C  L  L  N  N  F  Y  P  R  E  A  K  V
421 aatctggaactgcctctgttgtgtgcctgctgaataacttctatcccagacaggccaaag
161    Q  W  K  V  D  N  A  L  Q  S  G  N  S  Q  E  S  V  T  E  Q
481 tacagtggaaggtggataacgccctccaatcgggtaactcccaggagagtgtcacagagc
181    D  S  K  D  S  T  Y  S  L  S  S  T  L  T  L  S  K  A  D  Y
541 aggacagcaaggacagcacctacagcctcagcagcaccctgacgctgagcaaagcagact
201    E  K  H  K  V  Y  A  C  E  V  T  H  Q  G  L  S  S  P  V  T
601 acgagaaacacaaagtctacgcctgcgaagtcacccatcagggcctgagctcgcccgtca
221    K  S  F  N  R  G
661 caaagagcttcaacaggggga
```

Figure 2C The cDNA (SEQ ID NO:19) and amino acid sequence (SEQ ID NO:20) of H16-9.69 VH.
Double-underlined is the leader sequence, and underlined is a portion of the heavy chain constant region.

```
                                                                   M  D
    1 CTCAACAACCACATCTGTCCTCTAGAGAAAACCCTGTGAGCACAGCTCCTCACCATGGAC
        W  T  W  R  I  L  F  L  V  A  A  A  T  S  A  H  S  Q  V  Q
   61 TGGACCTGGAGGATCCTCTTCTTGGTGGCAGCAGCTACAAGTGCCCACTCCCAGGTGCAG
        L  V  Q  S  G  A  E  V  K  K  P  G  A  S  V  K  V  S  C  K
  121 CTGGTGCAGTCTGGGGCTGAGGTGAAGAAGCCTGGGGCCTCAGTGAAGGTCTCCTGCAAG
        A  S  G  Y  T  F  T  S  Y  D  I  H  W  V  R  Q  A  T  G  Q
  181 GCTTCTGGATACACCTTCACCAGTTATGATATCCACTGGGTGCGACAGGCCACTGGACAA
        G  L  E  W  M  G  W  M  N  P  N  S  G  N  T  V  Y  A  Q  K
  241 GGGCTTGAGTGGATGGGATGGATGAACCCTAACAGTGGTAACACAGTCTATGCACAGAAG
        F  Q  G  R  V  T  M  T  R  N  T  S  I  S  T  A  Y  M  E  L
  301 TTCCAGGGCAGAGTCACCATGACCAGGAACACCTCCATAAGCACAGCCTACATGGAGCTG
        S  S  L  R  S  E  D  T  A  V  Y  Y  C  A  R  T  V  L  L  W
  361 AGCAGCCTGAGATCTGAGGACACGGCCGTGTATTACTGTGCGAGAACAGTATTACTATGG
        P  F  D  Y  W  G  Q  G  T  L  V  T  V  S  S  A  S  T  K  G
  421 CCCTTTGACTACTGGGGCCAGGGAACCCTGGTCACCGTCTCCTCAGCCTCCACCAAGGGC
        P  S  V  F  P  L  A  P  C  S  R  S  T  S  E  S  T  A  A  L
  481 CCATCGGTCTTCCCCCTGGCGCCCTGCTCCAGGAGCACCTCCGAGAGCACAGCGGCCCTG
        G  C  L  V  K  D  Y  F  P  E  P  V  T  V  S  W  N  S  G  A
  541 GGCTGCCTGGTCAAGGACTACTTCCCCGAACCGGTGACGGTGTCGTGGAACTCAGGCGCT
        L  T  S  G  V  H  T  F  P  A  V  L  Q  S  S  G  L  Y  S  L
  601 CTGACCAGCGGCGTGCACACCTTCCCAGCTGTCCTACAGTCCTCAGGACTCTACTCCCTC
        S  S  V  V  T  V  P  S  S  N  F  G  T  Q  T  Y  T  C  N  V
  661 AGCAGCGTGGTGACCGTGCCCTCCAGCAACTTCGGCACCCAGACCTACACCTGCAACGTA
        D  H  K  P  S  N  T  K  V  D  K  T  V  E  R  K  C  C  V  E
  721 GATCACAAGCCCAGCAACACCAAGGTGGACAAGACAGTTGAGCGCAAATGTTGTGTCGAG
        C  P  P  C  P  A  P  P  V  A  G  P  S  V  F  L  F  P  P  K
  781 TGCCCACCGTGCCCAGCACCACCTGTGGCAGGACCGTCAGTCTTCCTCTTCCCCCCAAAA
        P  K  D  T  L  M  I  S  R  T  P  E  V  T  C  V  V  V  D  V
  841 CCCAAGGACACCCTCATGATCTCCCGGACCCCTGAGGTCACGTGCGTGGTGGTGGACGTG
        S  H  E  D  P  E  V  Q  F  N  W  Y  V  D  G  V  E  V  H  N
  901 AGCCACGAAGACCCCGAGGTCCAGTTCAACTGGTACGTGGACGGCGTGGAGGTGCATAAT
        A  K  T  K  P  R  E  E  Q  F  N  S  T  F  R  V  V  S  V  L
  961 GCCAAGACAAAGCCACGGGAGGAGCAGTTCAACAGCACGTTCCGTGTGGTCAGCGTCCTC
        T  V  V  H  Q  D  W  L  N  G  K  E  Y  K  C  K  V  S  N  K
 1021 ACCGTTGTGCACCAGGACTGGCTGAACGGCAAGGAGTACAAGTGCAAGGTCTCCAACAAA
        G  L  P  A  P  I  E  K  T  I  S  K  T  K  G  Q  P  R  E  P
 1081 GGCCTCCCAGCCCCCATCGAGAAAACCATCTCCAAAACCAAAGGGCAGCCCCGAGAACCA
        Q  V  Y  T  L  P  P  S  R  E  E  M  T  K  N  Q  V  S  L  T
 1141 CAGGTGTACACCCTGCCCCCATCCCGGGAGGAGATGACCAAGAACCAGGTCAGCCTGACC
        C  L  V  K  G  F  Y  P  S  D  I  A  V  E  W  E  S  N  G  Q
 1201 TGCCTGGTCAAAGGCTTCTACCCCAGCGACATCGCCGTGGAGTGGGAGAGCAATGGGCAG
        P  E  N  N  Y  K  T  T  P  P  M  L  D  S  D  G  S  F  F  L
 1261 CCGGAGAACAACTACAAGACCACACCTCCCATGCTGGACTCCGACGGCTCCTTCTTCCTT
        Y  S  K  L  T  V  D  K  S  R  X  Q  Q  G  N  V  F  S  C  S
```

Figure 2C-2

```
1321 TACAGCAAGCTCACCGTGGACAAGAGCAGGNGGCAGCAGGGGAACGTCTTCTCATGCTCC
        V  M  H  E  A  L  H  N
1381 GTGATGCATGAGGCTCTGCACAACC
```

Figure 2D The cDNA (SEQ ID NO:21) and amino acid sequence (SEQ ID NO:22) of H16-9.69 VL.

Double-underlined is the leader sequence and underlined is a portion of the heavy chain constant region.

```
  1   W  I  S  G  A  Y  G  D  I  V  M  T  Q  S  P  D  S  L  A  V
  1 tctggatctctggtgcctacggggacatcgtgatgacccagtctccagactccctggctg
 21   S  L  G  E  R  A  T  I  N  C  K  S  S  Q  S  V  L  Y  S  S
 61 tgtctctgggcgagagggccaccatcaactgcaagtccagccagagtgttttatacagct
 41   K  N  K  N  Y  L  A  W  Y  Q  Q  K  P  G  Q  P  P  K  L  L
121 ccaagaataagaactacttagcttggtaccagcagaaaccaggacagcctcctaagctgc
 61   I  Y  W  A  S  T  R  E  S  G  V  P  D  R  F  S  G  S  G  S
181 tcatttactgggcatctaccCgggaatccggggtccctgaccgattcagtggcagcggt
 81   G  T  D  F  T  L  T  T  S  S  L  Q  A  E  D  V  A  V  Y  Y
241 ctgggacagatttcactctcaccatcagcagcctgcaggctgaagatgtggcagtttatt
101   C  Q  Q  Y  Y  S  T  P  P  W  T  F  G  Q  G  T  K  V  E  I
301 actgtcagcaatattatagtactcctccgtggacgttcggccaagggaccaagGtggaaa
121   K  R  T  V  A  A  P  S  V  F  I  F  P  P  S  D  E  Q  L  K
361 tcaaacgaactgtggctgcaccatctgtcttcatcttcccgccatctgatgagcagttga
141   S  G  T  A  S  V  V  C  L  L  N  N  F  Y  P  R  E  A  K  V
421 aatctgaactgcctctgttgtgtgcctgctgaataacttctatcccagagaggccaaag
161   Q  W  K  V  D  N  A  L  Q  S  G  N  S  Q  E  S  V  T  E  Q
481 tacagtggaaggtggataacgccctccaatcgggtaactcccaggagagtgtcacagagc
181   D  S  K  D  S  T  Y  S  L  S  S  T  L  T  L  S  K  A  D  Y
541 aggacagccaaggacagcacctacagcctcagcagcaccctgacgctgagcaaagcagact
201   E  K  H  K  V  Y  A  C  E  V  T  H  Q  G  L  S  S  P  V  T
601 acgagaaacacaaagtctacgcctgcgaagtcacccatcagggcctgagctcgcccgtca
221   K  S  F  N  R  G  E
661 caaagagcttcaacaggggagagtg
```

Figure 2E The cDNA (SEQ ID. NO. : 23) and amino acid sequence (SEQ ID. NO. : 24) of H16-1.52 VH.

Underlined is a portion of the heavy chain constant region.

```
  1   S  G  G  G  L  V  Q  P  G  G  S  L  R  L  S  C  A  A  S  G
  1 agtctgcggGaggcttggtacagcctgggGggtccctgagactctcctgtgcagcctctg
 21   F  T  F  S  S  Y  A  M  S  W  V  R  Q  A  P  G  K  G  L  E
 61 gattcacctttagcagctatgccatgagctgggtccgccaggctccagggaaggggctgg
 41   W  V  S  A  I  S  G  S  D  G  S  P  Y  Y  A  D  S  V  K  G
121 agtgggtctcagctattagtggtagtgatggtagcccatactacgcagactccgtgaagg
 61   R  F  T  I  S  R  D  N  S  K  N  T  L  Y  L  Q  M  N  S  L
181 gccggttcaccatctccagagacaattccaagaacacgctgtatctgcaaatgaacagcc
 81   R  A  E  D  T  A  V  Y  Y  C  A  K  D  G  Y  S  S  G  W  N
241 tgagagccgaggacacggccgtatattactgtgcgaaagatggttatagcagtggctgga
101   Y  F  D  Y  W  G  Q  G  T  L  V  T  V  S  S  A  S  T  K  G
301 actactttgactactggggccagggaaccctggtcaccgtctcctcagcctccaccaagg
121   P  S  V  F  P  L  A  P
361 gcccatcggtcttccccctggcaccct
```

Figure 2F The cDNA (SEQ ID NO:25) and amino acid sequence (SEQ ID NO:26) of H16-1.52 VL.

Underlined is a portion of the light chain constant region.

```
 1 W  I  S  G  A  Y  G  D  I  V  M  T  Q  S  P  D  S  L  A  V
   1 tggatctctggtgcctacggggacatcgtgatgacccagtctccagactccctggctgtg
21 S  L  G  E  R  A  T  I  N  C  K  S  S  Q  S  V  L  Y  S  S
  61 tctctgggcgagagggccaccatcaactgcaagtccagccagagtgttttatacagctcc
41 N  N  K  N  Y  L  A  W  Y  Q  Q  K  P  G  Q  P  P  K  L  L
```

Figure 2F-2

```
121 aacaataagaactacttagcttggtaccagcagaaaccaggacagcctcccaagctgctc
 61  I  Y  W  A  S  T  R  E  S  G  V  P  D  R  F  S  G  S  G  S
181 atttactgggcatctacccgggaatccggggtccctgaccgattcagtggcagcgggtct
 81  G  T  D  F  T  L  T  I  S  S  L  Q  A  E  D  V  A  V  Y  Y
241 gggacagatttcactctcaccatcagcagcctgcaggctgaagatgtggcagtttattac
101  C  Q  E  Y  Y  S  T  M  C  S  F  G  Q  G  T  K  L  E  I  K
301 tgtcaggaatattatagtaccatgtgcagttttggccaggggaccaagctggagatcaaa
121  R  T  V  A  A  P  S  V  F  I  F  P  P  S  D  E  Q  L  K  S
361 cgaactgtggctgcaccatctgtcttcatcttcccgccatctgatgagcagttgaaatct
141  G  T  A  S  V  V  C  L  L  N  N  F  Y  P  R  E  A  K  V  Q
421 ggaactgcctctgttgtgtgcctgctgaataacttctatcccagagaggccaaagtacag
161  W  K  V  D  N  A  L  Q  S  G  N  S  Q  E  S  V  T  E  Q  D
481 tggaaggtggataacgccctccaatcgggtaactcccaggagagtgtcacagagcaggac
181  S  K  D  S  T  Y  S  L  S  S  T  L  T  L  S  K  A  D  Y  E
541 agcaaggacagcacctacagcctcagcagcaccctgacgctgagcaaagcagactacgag
201  K  H  K  V  Y  A  C  E  V  T  H  Q  G  L  S  S  P  V  T  K
601 aaacacaaagtctacgcctgcgaagtcacccatcagggcctgagctcgcccgtcacaaag
221  S  F  N  R  G  E
661 agcttcaacaggggagagtg
```

Figure 2G The cDNA (SEQ ID NO:27) and amino acid sequence (SEQ ID NO:28) of Ha16-1(1)23 VH.
Underlined is a portion of the heavy chain constant region.

```
  1  V  E  S  G  G  G  V  V  Q  P  G  R  S  L  R  L  S  C  A  A
  1 gtggagtctgggggaggcgtggtccagcctgggaggtccctgagactctcctgtgcagcg
 21  S  G  F  T  F  R  S  Y  G  M  H  W  V  R  Q  A  P  G  K  G
 61 tctggattcaccttcagaagctatggcatgcactgggtccgccaggctccaggcaagggg
 41  L  E  W  V  A  V  I  W  S  D  G  S  N  K  Y  Y  A  D  S  V
121 ctggagtgggtggcagttatatggtctgatggaagtaataaatactatgcagactccgtg
 61  K  G  R  F  T  I  S  R  D  N  S  K  N  T  L  Y  L  Q  M  N
181 aaggggccgatttaccatctccagagacaattccaagaacacgctgtatctgcaaatgaac
 81  S  L  R  A  E  D  T  A  V  Y  Y  C  A  R  E  G  Y  Y  G  S
241 agcctgagagccgaggacacggctgtgtattactgtgcgagagaggggtactatggttcg
101  G  S  Y  Y  Y  Y  Y  G  M  D  V  W  G  Q  G  T  T  V  T  V
301 gggagttattactactactacggtatggacgtctggggccaagggaccacggtcaccgtc
121  S  S  A  S  T  K  G  P  S  V  F  P  L  A  P  S
361 tcctcagcctccaccaagggcccatcggtcttccccctggcaccctcc
```

Figure 2H The cDNA (SEQ ID NO:29) and amino acid sequence (SEQ ID NO:30) of Ha16-1(1)23 VL.
Underlined is a portion of the light chain constant region.

```
  1  L  L  T  L  L  T  H  S  A  V  S  V  V  Q  A  G  L  T  Q  P
  1 ctcctgaccctcctcactcactctgcagtgtcagtggtccaggcagggctgactcagcca
 21  P  S  V  S  K  G  L  R  Q  T  A  T  L  T  C  T  G  N  S  N
 61 ccctcggtgtccaaggggcttgagacagaccgccacactcacctgcactgggaacagcaac
 41  N  V  G  T  Q  G  A  A  W  L  Q  Q  H  Q  G  H  P  P  K  L
121 aatgttggcacccaaggagcagcttggctgcagcagcaccagggccacccctcccaaactc
 61  L  S  Y  R  N  N  R  P  S  G  I  S  E  R  L  S  A  S  T
181 ctttcctacaggaataacaaccggccctcagggatctcagagagattatctgcatccacg
 81  S  G  N  T  A  S  L  T  I  T  G  L  Q  P  E  D  E  A  D  Y
241 tcaggaaacacagcctccctgaccattactggactccagcctgaggacgaggctgactat
101  Y  C  S  A  W  D  S  S  L  S  A  V  V  F  G  G  G  T  K  L
301 tactgctcagcatgggacagcagcctcagtgctgtggtattcggcggagggaccaagctg
121  T  V  L  G  Q  P  K  A  A  P  S  V  T  L  F  P  P  S  S  E
361 accgtcctaggtcagcccaaggctgccccctcggtcactctgttcccgccctcctctgag
141  E  L  Q  A  N  K  A  T  L  V  C  L  I  S  D  F  Y  P  G  A
421 gagcttcaagccaacaaggccacactggtgtgtctcataagtgacttctacccgggagcc
161  V  T  V  A  W  K  A  D  S  S  P  V  K  A  G  V  E  T  T  T
481 gtgacagtggcctggaaggcagatagcagccccgtcaaggcgggagtggagaccaccaca
181  P  S  K  Q  S  N  N  K  Y  A  A  S  S  Y  L  S  L  T  P  E
```

Figure 2H-2

```
541 ccctccaaacaaagcaacaacaagtacgcggccagcagctatctgagcctgacgcctgag
201  Q   W   K   S   H   R   S   Y   S   C   Q   V   T   H   E   G   S   T   V   E
601 cagtggaagtcccacagaagctacagctgccagctcacgcatgaagggagcaccgtggag
221  K   T   V   A   P   T
661 aagacagtggcccctaca
```

Figure 2I The cDNA (SEQ ID NO:31) and amino acid sequence (SEQ ID NO:32) of Ha16-9.44 VH.
Underlined is a portion of the heavy chain constant region.

```
   1  L   S   L   T   C   T   V   S   G   G   S   I   S   S   Y   Y   W   S   W   I
   1 cctgtccctcacctgcactgtctctggtggctccatcagtagttactactggagctggat
  21  R   Q   S   A   G   K   G   L   E   W   I   G   R   I   Y   T   G   V   S   T
  61 ccggcagtccgccgggaagggactggagtggattgggcgtatctataccggtgtgagcac
  41  N   Y   N   P   S   L   K   S   R   V   T   M   S   V   D   T   S   K   N   Q
 121 caactacaaccctccctcaagagtcgagtcaccatgtcagtagacacgtccaagaacca
  61  F   S   L   K   L   S   S   V   T   A   A   D   T   A   V   Y   Y   C   A   R
 181 gttctccctgaagctgagctctgtgaccgccgcggacacggccgtgtattactgtgcgag
  81  D   Y   Y   D   S   S   G   Y   Y   P   F   D   Y   W   G   Q   G   T   L   V
 241 agattactatgatagtagtggttattaccccctttgactactggggccagggaaccctggt
 101  T   V   S   S   A   S   T   K   G   P   S   V   F   P   L   A   P   C   S   R
 301 caccgtctcctcagcctccaccaagggcccatcggtcttccccctggcgccctgctccag
 121  S   T   S   E   S   T   A   A   L   G   C   L   V   K   D   Y   F   P   E   P
 361 gagcacctccgagagcacagcggccctgggctgcctggtcaaggactacttccccgaacc
 141  V   T   V   S   W   N   S   G   A   L   T   S   G   V   H   T   F   P   A   V
 421 ggtgacggtgtcgtggaactcaggcgctctgaccagcggcgtgcacaccttcccagctgt
 161  L   Q   S   S   G   L   Y   S   L   S   S   V   V   T   V   P   S   S   N   F
 481 cctacagtcctcaggactctactccctcagcagcgtggtgaccgtgccctccagcaactt
 181  G   T   Q   T   Y   T   C   N   V   D   H   K   P   S   N   T   K   V   D   K
 541 cggcacccagacctacacctgcaacgtagatcacaagcccagcaacaccaaggtggacaa
 201  T   V   E   R   K   C   C   V   E   C   P   P   C   P   A   P   P   V   A   G
 601 gacagttgagcgcaaatgttgtgtcgagtgcccaccgtgcccagcaccacctgtggcagg
 221  P   S   V   F   L   F   P   P   K   P   K   D   T   L   M   I   S   R   T   P
 661 accgtcagtcttcctcttccccccaaaacccaaggacaccctcatgatctcccggacccc
 241  E   V   T   C   V   V   V   D   V   S   H   E   D   P   E   V   Q   F   N   W
 721 tgaggtcacgtgcgtggtggtggacgtgagccacgaagaccccgaggtccagttcaactg
 261  Y   V   D   G   V   E   V   H   N   A   K   T   K   P   R   E   E   Q   F   N
 781 gtacgtggacggcgtggaggtgcataatgccaagacaaagccacggggaggagcagttcaa
 281  S   T   F   R   V   V   S   V   L   T   V   V   H   Q   D   W   L   N   G   K
 841 cagcacgttccgtgtggtcagcgtcctcaccgttgtgcaccaggactggctgaacggcaa
 301  E   Y   K   C   K   V   S   N   K   G   L   P   A   P   I   E   K   T   I   S
 901 ggagtacaagtgcaaggtctccaacaaaggcctcccagcccccatcgagaaaaccatctc
 321  K   T   K   G   Q   P   R   E   P   Q   V   Y   T   L   P   P   S   R   E   E
 961 caaaaccaaagggcagccccgagaaccacaggtgtacaccctgcccccatcccgggagga
 341  M   T   K   N   Q   V   S   L   T   C   L   V   K   G   F   Y   P   S   D   I
1021 gatgaccaagaaccaggtcagcctgacctgcctggtcaaaggcttctaccccagcgacat
 361  A   V   E   W   E   S   N   G   Q   P   E   N   N   Y   K   T   T   P   P   M
1081 cgccgtggagtgggagagcaatgggcagccggagaacaactacaagaccacacctcccat
 381  L   D   S   D   G   S   F   F   L   Y   S   K   L   T   V   D   K   S   R   W
1141 gctggactccgacggctccttcttcctttacagcaagctcaccgtggacaagagcaggtg
 401  Q   Q   G   N   V   F   S   C   S   V   M   H   E   A   L   H
1201 gcagcaggcgaacgtcttctcatgctccgtgatgcatgaggctctgcaca
```

Figure 2J The cDNA (SEQ ID NO:33) and amino acid sequence (SEQ ID NO:34) of H16-9.44 VL.
Underlined is a portion of the light chain constant region.

```
  1 L   L   G   L   L   L   L   C   F   P   G   A   R   C   D   I   Q   M   T   Q
  1 ctcctggggctcctgctgctctgtttcccaggtgccagatgtgacatccagatgacccag
 21 S   P   S   S   L   S   A   S   V   G   D   R   V   T   I   S   C   R   A   S
 61 tctccatcctcactgtctgcatctgtaggagacagagtcaccatcagttgtcggcgagt
 41 Q   G   I   S   N   Y   L   A   W   F   Q   Q   K   P   G   K   A   P   K   S
121 cagggcattagcaattatttagcctggtttcagcagaaaccagggaaagcccctaagtcc
 61 L   I   Y   A   A   S   S   L   E   N   G   V   P   S   K   F   S   G   S   G
```

Figure 2J-2

```
181 ctgatctatgctgcatccagtttggaaaatggggtcccatcaaagttcagcggcagtgga
 81  S  G  T  D  F  T  L  T  I  S  S  L  Q  P  E  D  F  A  T  Y
241 tctgggacagatttcactctcaccatcagcagcctgcagcctgaagattttgcaacttat
101  Y  C  Q  Q  Y  N  S  S  P  F  T  F  G  P  G  T  K  V  D  I
301 tactgccaacagtataatagttccccattcactttcggccctgggaccaaagtggatatc
121  R  R  T  V  A  A  P  S  V  F  I  F  P  P  S  D  E  Q  L  K
361 agacgaactgtggctgcaccatctgtcttcatcttcccgccatctgatgagcagttgaaa
141  S  G  T  A  S  V  V  C  L  L  N  N  F  Y  P  R  E  A  K  V
421 tctggaactgcctctgttgtgtgcctgctgaataacttctatcccagagaggccaaagta
161  Q  W  K  V  D  N  A  L  Q  S  G  N  S  Q  E  S  V  T  E  Q
481 cagtggaaggtggataacgccctccaatcgggtaactcccaggagagtgtcacagagcag
181  D  S  K  D  S  T  Y  S  L  S  S  T  L  T  L  S  K  A  D  Y
541 gacagcaaggacagcacctacagcctcagcagcaccctgacgctgagcaaagcagactac
201  E  K  H  K  V  Y  A  C  E  V  T  H  Q  G  L  S  S  P  V  T
601 gagaaacacaaagtctacgcctgcgaagtcacccatcagggcctgagctcgcccgtcaca
221  K  S  F  N  R  G
661 aagagcttcaacaggga
```

Figure 2K The cDNA (SEQ ID NO:35) and amino acid sequence (SEQ ID NO:36) of H16-1.67 VH.

```
  1  V  E  S  G  P  G  L  V  K  P  S  Q  T  L  S  L  T  C  T  V
  1 tggtggagtctggcccaggactggtgaagccttcacagaccctgtccctcacctgcactg
 21  S  G  G  S  I  N  S  F  G  Y  Y  W  S  W  I  R  Q  Y  P  G
 61 tctctggtggctccatcaacagttttggttactactggagctggatccgccagtatccag
 41  K  G  L  E  W  I  G  S  T  L  Y  F  T  G  S  T  Y  Y  N  P
121 gaaagggcctggagtggattgggttcctctatttcactgggagcacctactacaacccgt
 61  L  K  S  R  V  T  I  S  V  D  T  S  K  S  Q  F  S  L  K  L
181 ccctcaagagtcgagttaccatatcagtagacacgtctaagagccagttctccctgaagc
 81  S  S  V  T  A  D  T  A  V  Y  Y  C  A  R  A  G  T  M  V
241 tgagctctgtgactgccgcggacacggccgtgtattactgtgcgagagcaggtactatgg
101  R  G  A  H  Y  Y  G  M  D  V  W  G  Q  G  T  T  V  T  V  S
301 ttcggggagccactactacggtatggacgtctggggccaagggaccacggtcaccgtct
121  S  A  S  T  K  G  P  S  V  F  P  L  A  P  S
361 cctcagcctccaccaagggcccatcggtcttccccctggcaccctcc
```

Figure 2L The cDNA (SEQ ID NO:37) and amino acid sequence (SEQ ID NO:38) of H16-1.67 VL.
Underlined is the light chain constant region.

```
  1  Q  L  L  G  L  L  L  L  W  L  R  G  G  R  C  D  T  Q  M  T
  1 ctcagctcctggggctcctgctactctggctccgaggaggcagatgtgacatccagatga
 21  Q  S  P  S  S  L  S  A  S  V  G  D  R  V  T  I  T  C  R  A
 61 cccagtctccatcctccctgtctgcatctgtaggagacagagtcaccatcacttgccggg
 41  S  Q  S  I  S  N  Y  L  N  W  Y  Q  Q  K  P  G  K  A  P  K
121 caagtcagagtattagtaactatttaaattggtatcagcagaaaccagggaaagccccta
 61  L  L  I  Y  A  A  S  S  L  Q  S  G  V  P  S  R  F  S  G  S
181 agctcctgatctatgctgcatccagtttgcaaagtggggtcccatcaagttcagtggca
 81  G  S  G  T  D  F  T  L  T  I  S  S  L  Q  P  E  D  F  A  T
241 gtggatctgggacagatttcactctcaccatcagcagtctgcaacctgaagattttgcaa
101  Y  Y  C  Q  Q  I  Y  S  T  P  P  E  W  T  F  G  Q  G  T  K
301 cttactactgtcaacagatttacagtacccctccggagtggacgttcggccaagggacca
121  V  E  I  K  R  T  V  A  A  P  S  V  F  I  F  P  P  S  D  E
361 aggtggaaatcaaacgaactgtggctgcaccatctgtcttcatcttcccgccatctgatg
141  Q  L  K  S  G  T  A  S  V  V  C  L  L  N  N  F  Y  P  R  E
421 agcagttgaaatctggaactgcctctgttgtgtgcctgctgaataacttctatcccagag
161  A  K  V  Q  W  K  V  D  N  A  L  Q  S  G  N  S  Q  E  S  V
481 aggccaaagtacagtggaaggtggataacgccctccaatcgggtaactcccaggagagtg
181  T  E  Q  D  S  K  D  S  T  Y  S  L  S  S  T  L  T  L  S  K
541 tcacagagcaggacagcaaggacagcacctacagcctcagcagcaccctgacgctgagca
201  A  D  Y  E  K  H  K  V  Y  A  C  E  V  T  H  Q  G  L  S  S
601 aagcagactacgagaaacacaaagtctacgcctgcgaagtcacccatcagggcctgagct
221  P  V  T  K  S  F  N  R  G  E  C  *
661 cgcccgtcacaaagagcttcaacaggggagagtgttagag
```

Figure 2M The cDNA (SEQ ID NO:39) and amino acid sequence (SEQ ID NO:40) of Ha16-1(3,5)36 VH. Underlined is a portion of the heavy chain constant region.

```
  1 E   V   Q   L   V   E   S   G   P   G   L   V   K   P   S   E   T   L   S   L
  1 gaggtgcagctggtggagtctggcccaggactggtgaagccttcggagaccctgtccctc
 21 T   C   T   V   S   G   G   S   I   S   S   S   S   Y   Y   W   G   W   I   R
 61 acctgcactgtctctggtggctccatcagcagtagtagttattactggggctggatccgc
 41 Q   P   P   G   K   G   L   E   W   I   G   S   M   Y   Y   S   G   S   T   Y
121 cagcccccagggaagggctggagtggattgggagtatgtattatagtgggagcacctac
 61 H   N   P   S   L   K   S   R   V   I   I   S   V   D   T   S   K   N   Q   F
181 cacaacccgtccctcaagagtcgagtcatcatatccgtagacacgtccaagaaccagttc
 81 S   L   K   L   S   S   V   T   A   A   D   T   A   V   Y   Y   C   A   R   H
241 tccctgaagctgagctctgtgaccgccgcagacacggctgtgtattactgtgcgagacat
101 Y   I   T   V   A   G   I   F   D   Y   W   G   Q   G   T   L   V   T   V   S
301 tatataacagtggctggtatctttgactactggggccagggaaccctggtcaccgtctcc
121 S   A   S   T   K   G   P   S   V   F   P   L   A   P   S   S
361 tcagcctccaccaagggcccatcggtcttccccctggcaccctcctcc
```

Figure 2N The cDNA (SEQ ID NO:41) and amino acid sequence (SEQ ID NO:42) of Ha16-1(3,5)36 VL. Underlined is a portion of the light chain constant region.

```
  1     L   L   T   L   L   T   H   C   A   G   S   W   A   Q   S   V   L   T   Q   P
  1 tcctcctcaccctcctcactcactgtgcagggtcctgggcccagtctgtactgactcagc
 21     P   S   A   S   G   T   P   G   Q   R   A   T   I   S   C   S   G   S   S   T
 61 caccctcagcgtctgggaccccggcagagggccaccatctcttgttctggaagcagca
 41     N   I   G   S   T   I   V   N   W   Y   Q   Q   V   P   G   T   A   P   K   L
121 ccaatatcggaagtactattgtaaactggtaccagcaggtcccaggaacggcccccaaac
 61     L   I   Y   S   N   N   Q   R   P   S   G   V   P   D   R   F   S   G   S   K
181 tcctcatctatagtaataatcagcggcctcaggggtccctgaccgattctctggctcca
 81     S   G   T   S   A   S   L   A   I   S   G   L   Q   S   E   D   E   A   D   Y
241 agtctggcacctcagcctccctggccatcagtgggctccagtctgaggatgaggctgatt
101     Y   C   A   A   W   D   A   S   L   N   G   P   V   F   G   G   G   T   K   L
301 attactgtgcagcatgggatgccagcctgaatggtccggtattcggcggagggaccaagc
121     T   V   L   G   Q   P   K   A   A   P   S   V   T   L   F   P   P   S   S   E
361 tgaccgtcctaggtcagcccaaggctgccccctcggtcactctgttcccgccctcctctg
141     E   L   Q   A   N   K   A   T   L   V   C   L   I   S   D   F   Y   P   G   A
421 aggagcttcaagccaacaaggccacactggtgtgtctcataagtgacttctacccgggag
161     V   T   V   A   W   K   A   D   S   S   P   V   K   A   G   V   E   T   T   T
481 ccgtgacagtggcctggaaggcagatagcagccccgtcaaggcgggagtggagaccacca
181     P   S   K   Q   S   N   N   K   Y   A   A   S   S   Y   L   S   L   T   P   E
541 caccctccaaacaaagcaacaacaagtacgcggccagcagctatctgagcctgacgcctg
201     Q   W   K   S   H   R   S   Y   S   C   Q   V   T   H   E   G   S   T   V   E
601 agcagtggaagtcccacagaagctacagctgccaggtcacgcatgaagggagcaccgtgg
221     K   T   V   A   P   T
661 agaagacagtggcccctaca
```

Figure 2O The cDNA (SEQ ID NO:43) and amino acid sequence (SEQ ID NO:44) of H16-1.86 VH. Underlined is a portion of the heavy chain constant region.

```
  1 V   E   S   G   P   G   L   V   K   P   S   E   T   L   S   L   T   C   T   V
  1 gtggagtctggcccaggactggtgaagccttcggagaccctgtccctcacctgcactgtc
 21 S   G   G   S   I   S   S   Y   Y   W   S   W   I   R   Q   P   P   G   K   G
 61 tctggtggctccatcagtagttactactggagctggatccggcagcccccagggaaggga
 41 L   E   W   I   G   Y   I   Y   Y   S   G   S   T   N   Y   N   P   S   L   K
121 ctggagtggattgggtatatctattacagtgggagcaccaactacaacccctccctcaag
 61 S   R   V   T   I   S   V   D   T   S   K   N   Q   F   S   L   K   L   S   S
181 agtcgagtcaccatatcagtagacacgtccaagaaccagttctccctgaagctgagctct
 81 V   T   A   A   D   T   A   V   Y   Y   C   A   R   A   Y   G   Y   Y   Y   Y
241 gtgaccgctgcggacacggccgtgtattactgtgcgagagcctacggctactactactac
101 G   M   D   V   W   G   Q   G   T   T   V   T   V   S   S   A   S   T   K   G
301 ggtatggacgtctggggccaagggaccacggtcaccgtctcctcagcctccaccaagggc
121 P   S   V   F   P   L   A   P   S
361 ccatcggtcttccccctggcaccctcctc
```

Figure 2P The cDNA (SEQ ID NO:45) and amino acid sequence (SEQ ID NO:46) of H16-1.86 VL.
Underlined is a portion of the light chain constant region.

```
  1 Q   L   L   G   L   L   L   L   W   L   R   G   A   R   C   D   I   Q   M   T
  1 cagctcctggggctcctgctactctggctccgaggtgccagatgtgacatccagatgacc
 21 Q   S   P   S   S   L   S   A   S   V   G   D   R   V   T   I   T   C   R   T
 61 cagtctccatcctccctgtctgcatctgtaggagacagagtcaccatcacttgccggaca
 41 S   Q   S   I   S   S   Y   L   N   W   Y   Q   Q   K   P   G   K   A   P   N
121 agtcagagcattagcagctatttaaattggtatcagcagaaaccagggaaagccccta ac
 61 L   L   I   Y   A   A   S   S   L   Q   S   G   V   P   S   R   F   S   G   S
181 ctcctgatctatgctgcatccagtttgcaaagtgggtcccatcaaggttcagtggcagt
 81 G   S   G   T   D   F   T   L   T   I   S   S   L   Q   P   E   D   F   A   T
241 ggatctgggacagatttcactctcaccatcagcagtctgcaacctgaagatttt gcaact
101 Y   Y   C   Q   Q   T   Y   S   S   P   P   W   T   F   G   Q   G   T   K   V
301 tactactgtcaacagacttacagttcccctcgtggacgttcggccaagggaccaaggtg
121 E   I   K   R   T   V   A   A   P   S   V   F   I   F   P   P   S   D   E   Q
361 gaaatcaaacgaactgtggctgcaccatctgtcttcatcttcccgccatctgatgagcag
141 L   K   S   G   T   A   S   V   V   C   L   L   N   N   F   Y   P   R   E   A
421 ttgaaatctggaactgcctctgttgtgtgcctgctgaataacttctatcccagagaggcc
161 K   V   Q   W   K   V   D   N   A   L   Q   S   G   N   S   Q   E   S   V   T
481 aaagtacagtggaaggtggataacgccctccaatcgggtaactcccaggagagtgtcaca
181 E   Q   D   S   K   D   S   T   Y   S   L   S   S   T   L   T   L   S   K   A
541 gagcaggacagcaaggacagcacctacagcctcagcagcaccctgacgctgagcaaagca
201 D   Y   E   K   H   K   V   Y   A   C   E   V   T   H   Q   G   L   S   S   P
601 gactacgagaaacacaaagtctacgcctgcgaagtcacccatcagggcctgagctcgccc
221 V   T   K   S   F   N   R   G
661 gtcacaaagagcttcaacaggga
```

Figure 2Q The cDNA (SEQ ID NO:47) and amino acid sequence (SEQ ID NO:48) of Ha16- 9.10 VH.
Underlined is a portion of the heavy chain constant region.

```
  1 L   L   E   S   G   P   G   L   V   K   P   S   Q   T   L   S   L   T   C   A
  1 ctgttggagtctggtccaggactggtgaagccctcgcagaccctctcactcacctgtgcc
 21 I   S   G   D   S   V   S   S   N   S   A   A   W   N   W   I   R   Q   S   P
 61 atctccggggacagtgtctctagcaacagtgctgcttggaactggatcaggcagtcccca
 41 S   R   G   L   E   W   L   G   R   T   Y   Y   R   S   K   W   Y   N   A   Y
121 tcgagaggccttgagtggctggggaaggacatactacaggtccaagtggtataatgcttat
 61 A   V   S   V   K   S   R   M   T   I   N   P   D   T   S   K   N   Q   F   S
181 gcagtatctgtgaaagtcgaatgaccatcaacccagacacatccaagaaccagttctcc
 81 L   Q   L   N   S   V   T   P   E   D   T   A   V   Y   Y   C   A   R   E   A
241 ctgcagctgaactctgtgactcccgaggacacggctgtgtattactgtgcaagagaggcg
101 G   G   W   F   D   P   W   G   Q   G   T   L   V   T   V   S   S   A   S   T
301 gggggctggttcgaccctggggccagggaaccctggtcaccgtctcctcagcctccacc
121 K
361 aagg
```

Figure 2R The cDNA (SEQ ID NO:49) and amino acid sequence (SEQ ID NO:50) of H16-9.10 VL.
Underlined is a portion of the light chain constant region.

```
  1   Q   L   L   G   L   L   L   W   F   P   G   S   R   C   D   I   Q   M   T
  1 ctcagctcctggggctcctgctgctctggttcccaggttccagatgcgacatccagatga
 21   Q   S   P   S   S   V   S   A   S   V   G   D   R   V   T   I   T   C   R   A
 61 cccagtctccatcttccgtgtctgcatctgtaggagacagagtcaccatcacttgtcggg
 41   S   Q   G   I   R   S   W   L   A   W   Y   Q   Q   K   P   G   K   A   P   K
121 cgagtcagggtattcgcagctggttagcctggtatcagcagaaaccagggaaagccccta
 61   L   L   I   Y   A   A   S   S   L   Q   S   G   V   P   S   R   F   S   G   S
181 agctcctgatctatgctgcatccagtttgcaaagtgggtcccatcaaggttcagcggca
 81   G   S   G   T   D   F   T   L   T   I   S   S   L   Q   P   E   D   F   A   T
241 gtggatctgggacagatttcactctcaccatcagcagcctgcagcctgaagatttt gcaa
101   Y   Y   C   Q   Q   A   N   S   F   P   P   T   F   G   G   G   T   K   V   E
301 cttactattgtcaacaggctaacagtttccctcccactttcggcggagggaccaaggtgg
121   I   K   R   T   V   A   A   P   S   V   F   I   F   P   P   S   D   E   Q   L
```

Figure 2R-2

```
361 agatcaaacgaactgtggctgcaccatctgtcttcatcttcccgccatctgatgagcagt
141  K  S  G  T  A  S  V  V  C  L  L  N  N  F  Y  P  R  E  A  K
421 tgaaatctggaactgcctctgttgtgtgcctgctgaataacttctatcccagagaggcca
161  V  Q  W  K  V  D  N  A  L  Q  S  G  N  S  Q  E  S  V  T  E
481 aagtacagtggaaggtggataacgccctccaatcgggtaactcccaggagagtgtcacag
181  Q  D  S  K  D  S  T  Y  S  L  S  S  T  L  T  L  S  K  A  D
541 agcaggacagcaaggacagcacctacagcctcagcagcaccctgacgctgagcaaagcag
201  Y  E  K  H  K  V  Y  A  C  E  V  T  H  Q  G  L  S  S  P  V
601 actacgagaaacacaaagtctacgcctgcgaagtcacccatcagggcctgagctcgcccg
221  T  K  S  F  N  R  G
661 tcacaaagagcttcaacagggga
```

Figure 2S  The cDNA (SEQ ID NO:51) and amino acid sequence (SEQ ID NO:52) of H16-9.33 VH.
Underlined is a portion of the heavy chain constant region.

```
  1  E  V  Q  L  L  E  S  G  P  G  L  V  K  P  S  Q  T  L  S  L
  1 gaggtgcagctgttggagtctggtccaggactggtgaagccctcgcagaccctctcactc
 21  T  C  A  I  S  G  D  S  V  S  S  N  S  A  A  W  N  W  I  R
 61 acctgtgccatctccggggacagtgtctctagcaacagtgctgcttggaactggatcagg
 41  Q  S  P  S  R  G  L  E  W  L  G  R  T  Y  Y  R  S  K  Y  Y
121 cagtcccccatcgagaggccttgagtggctgggaaggacatactacaggtccaagtattat
 61  N  A  Y  P  V  S  V  K  S  R  I  T  I  N  P  D  T  S  K  N
181 aatgcttatccagtatctgtgaaaagtcgaataaccatcaacccagacacatccaagaac
 81  Q  F  S  L  Q  L  N  S  V  T  P  E  D  T  A  V  Y  Y  C  A
241 cagttctccctgcagctgaactctgtgactcccgaggacacggctgtgtattactgtgca
101  R  E  A  G  G  W  F  D  P  W  G  Q  G  T  L  V  T  V  S  S
301 agagaggcggggggctggttcgacccctggggccagggaaccctggtcaccgtctcctca
121  A  S  T
361 gcctccaccaa
```

Figure 2T  The cDNA (SEQ ID NO:53) and amino acid sequence (SEQ ID NO:54) of H16-9.33 VL.
Underlined is a portion of the light chain constant region.

```
  1  L  L  G  L  L  L  L  W  F  P  G  S  R  C  D  I  Q  M  T  Q
  1 agctcctggggctcctgctgctctggttcccaggttccagatgcgacatccagatgaccc
 21  S  P  S  S  V  S  A  S  V  G  D  R  V  T  I  T  C  R  A  N
 61 agtctccatcttccgtgtctgcatctgtaggagagacagagtcaccatcacttgtcgggcga
 41  Q  G  I  R  S  W  L  A  W  Y  Q  Q  K  P  G  K  A  P  K  L
121 atcagggtattaggagttggttagcctggtatcagcagaaaccagggaaagcccccaaagc
 61  L  I  Y  A  A  S  S  L  Q  S  G  V  P  S  R  F  S  G  S  G
181 tcctgatctatgctgcatccagtttgcaaagtggggtcccatcaaggttcagcggcagtg
 81  S  G  T  D  F  T  L  T  I  S  S  L  Q  P  E  D  F  A  T  Y
241 gatctgggacagatttcactctcaccatcagcagcctgcagcctgaagattttgcaactt
101  Y  C  Q  Q  A  N  S  F  P  P  T  F  G  G  G  T  K  V  E  I
301 actattgtcaacaggctaacagtttccctcccactttcggcggagggaccaaggtggaga
121  K  R  T  V  A  A  P  S  V  F  I  F  P  P  S  D  E  Q  L  K
361 tcaaacgaactgtggctgcaccatctgtcttcatcttcccgccatctgatgagcagttga
141  S  G  T  A  S  V  V  C  L  L  N  N  F  Y  P  R  E  A  K  V
421 aatctggaactgcctctgttgtgtgcctgctgaataacttctatcccagagaggccaaag
161  Q  W  K  V  D  N  A  L  Q  S  G  N  S  Q  E  S  V  T  E  Q
481 tacagtggaaggtggataacgccctccaatcgggtaactcccaggagagtgtcacagagc
181  D  S  K  D  S  T  Y  S  L  S  S  T  L  T  L  S  K  A  D  Y
541 aggacagcaaggacagcacctacagcctcagcagcaccctgacgctgagcaaagcagact
201  E  K  H  K  V  Y  A  C  E  V  T  H  Q  G  L  S  S  P  V  T
601 acgagaaacacaaagtctacgcctgcgaagtcacccatcagggcctgagctcgcccgtca
221  K  S  F  N  R
661 caaagagcttcaacagggg
```

Figure 2U The cDNA (SEQ ID NO:55) and amino acid sequence (SEQ ID NO:56) of H16-1.68 VH.
Underlined is a portion of the heavy chain constant region.

```
  1 E   V   H   L   V   E   S   G   G   G   V   V   Q   P   G   R   S   L   R   L
  1 gaggtgcatctggtggagtctgggggaggcgtggtccagcctggGaggtccctgagactc
 21 S   C   A   A   S   G   F   T   F   R   S   Y   G   M   H   W   V   R   Q   A
 61 tcctgtgcagcgtctggattcaccttcagaagctatggcatgcactgggtccgccagGct
 41 P   G   K   G   L   E   W   V   A   V   I   W   Y   D   G   S   N   K   Y   Y
121 ccaggcaaggggctggagtgggtggcagttatatggtatgatggaagtaataaatactat
 61 A   D   S   V   K   G   R   F   T   I   S   R   D   N   S   K   N   T   L   Y
181 gcagactccgtgaagggccgattcaccatctccagagacaattccaagaacacgctgtat
 81 L   Q   M   N   S   L   R   A   E   D   M   A   M   Y   Y   C   A   R   S   R
241 ctgcaaatgaacagcctgagagccgaggacatggctatgtattactgtgcgaggtccaga
101 I   T   I   F   G   V   V   H   Y   G   M   D   V   W   G   Q   G   T   T   V
301 attacgattttTggagtggttcactacggtatggacgtctggggccaagggaccacggtc
121 T   V   S   S   A   S   T   K   G   P   S   V   F   P   L   A   P   S   S   K
361 accgtctcctcagcctccaccaagggcccatcggtcttccccctggcaccctcctccaag
141 S   T
421 agcacct
```

Figure 2V The cDNA (SEQ ID NO:57) and amino acid sequence (SEQ ID NO:58) of H16-1.68 VL.
Underlined is a portion of the light chain constant region.

```
  1 T   Q   L   T   Q   S   P   S   S   L   S   A   S   V   G   D   R   V   T   I
  1 acgcagctgacgcagtctccatcctccctgtctgcatctgttggagacagagtcaccatc
 21 T   C   R   A   S   Q   N   I   N   S   Y   L   N   W   Y   Q   Q   K   P   G
 61 acttgccgggcaagtcagaacattaacagctatttaaattggtatcagcagaaaccaggg
 41 K   A   P   K   L   L   I   Y   A   A   S   S   L   Q   S   G   V   P   S   R
121 aaagcccctaagctcctgatctatgctgcatccagtttgcaaagtggggtcccatcaagg
 61 F   S   G   S   G   S   G   T   D   F   T   L   T   I   S   S   L   Q   P   E
181 ttcagtggcagtggatctgggacagatttcactctcaccatcagcagtctacaacctgaa
 81 D   F   T   T   Y   Y   C   Q   Q   S   Y   S   S   A   P   T   F   G   G   G
241 gattttacaacttactactgtcagcagagttacagttccgcccccacttTcggcggcggg
101 T   K   L   E   I   K   R   T   V   A   A   P   S   V   F   I   F   P   P   S
301 accaagctggagatcaaacgaactgtggctgcaccatctgtcttcatcttcccgccatct
121 D   E   Q   L   K   S   G   T   A   S   V   V   C   L   L   N   N   F   Y   P
361 gatgagcagttgaaatctggaactgcctctgttgtgtgcctgctgaataacttctatccc
141 R   E   A   K   V   Q   W   K   V   D   N   A   L   Q   S   G
421 agagaggccaaagtacagtggaaggtggataacgccctccaatcgggt
```

Figure 2W The cDNA (SEQ ID NO:59) and amino acid sequence (SEQ ID NO:60) of Ha16-1(1)11 VH.
Underlined is a portion of the heavy chain constant region.

```
  1 G   P   G   L   V   K   P   S   E   T   L   S   L   T   C   T   V   S   G   G
  1 ggcccaggactggtgaagccttcggagaccctgtccctcacctgcactgtctctggtggc
 21 S   I   S   S   Y   Y   W   S   W   I   R   Q   P   P   G   K   G   L   E   W
 61 tccatcagtagttactactggagctggatccggcagcccccagggaagggactggagtgg
 41 I   G   Y   I   Y   Y   S   G   S   T   N   Y   N   P   S   L   K   S   R   V
121 attgggtatatctattacagtgggagcaccaactacaacccctccctcaagagtcgagtc
 61 T   I   S   V   D   T   S   K   N   Q   F   S   L   K   L   S   S   V   T   A
181 accatatcagtagacacgtccaagaaccagttctccctgaagctgagctctgtgaccgct
 81 A   D   T   A   V   Y   Y   C   A   R   A   V   S   Y   Y   Y   Y   G   M   D
241 gcggacacggccgtgtattactgtgcgagagcggtgtcctactactactacggtatggac
101 V   W   G   Q   G   T   T   V   T   V   S   S   A   S   T   K   G   P   S   V
301 gtctggggccaagggaccacggtcaccgtctcctcagcctccaccaagggcccatcggtc
121 F   P   L   A   P   S   S   K   S   T
361 ttccccctggcaccctcctccaagagcaccta
```

Figure 2X The cDNA (SEQ ID NO:61) and amino acid sequence (SEQ ID NO:62) of Ha16-1(1)11 VL. Underlined is a portion of the light chain constant region.

```
     1 V P A Q L L G L L L L W L R G A R C D I
     1 gtccccgctcagctcctggggctcctgctactctggctccgaggtgccagatgtgacatc
    21 Q M T Q S P S S L S A S V G D R V T I T
    61 cagatgacccagtctccatcctccctgtctgcatctgtaggagacagagtcaccatcact
    41 C R T I Q N I N S Y L N W Y Q Q R P G K
   121 tgccggacaattcagaacattaacagctatttaaattggtatcagcagagaccagggaaa
    61 A P K L L I Y A T S S L Q S G V P S R F
   181 gcccctaagctcctgatctatgctacatccagtttgcaaagtggggtcccatcaaggttc
    81 S G S G S G T D F T L T I S S L Q P E D
   241 agtggcagtggatctgggacagatttcactctcaccatcagcagtctgcaacctgaagat
   101 F A T Y Y C Q Q T Y S T L F T F G P G T
   301 tttgcaacttactactgtcaacagacttacagtaccctattcactttcggccctgggacc
   121 K V D I K R T V A A P S V F I F P P S D
   361 aaagtggatatcaaacgaactgtggctgcaccatctgtcttcatcttcccgccatctgat
   141 E Q L K S G T A S V V C L L N N F Y P R
   421 gagcagttgaaatctggaactgcctctgttgtgtgcctgctgaataacttctatcccaga
   161 E A K V Q W K V D N A L Q S G N S Q E S
   481 gaggccaaagtacagtggaaggtggataacgccctccaatcgggtaactcccaggagagt
   181 V T E Q D S K D S T Y S L S S T L T L S
   541 gtcacagagcaggacagcaaggacagcacctacagcctcagcagcaccctgacgctgagc
   201 K A D Y E K H K V Y A C E V T H Q G L S
   601 aaagcagactacgagaaacacaaagtctacgcctgcgaagtcacccatcagggcctgagc
   221 S P V T K S F N R G E W L E
   661 tcgcccgtcacaaagagcttcaacaggggagagtggttagaga
```

Figure 2Y The cDNA (SEQ ID NO:63) and amino acid sequence (SEQ ID NO:64) of Ha16-1(3,5)18 heavy chain. Underlined is the leader sequence and double-underlined is the heavy chain variable region. Dashed underline shows the human IgG1 constant region.

```
                           M D L L H K N M K H L W F F ·
     1 AAAAAACTTTCTGAGACTCATGGACCTCCTGCACAAGAACATGAAACACCTGTGGTTCTT
       · L L L V A A P R W V L S Q V Q L Q E S G ·
    61 CCTCCTGCTGGTGGCAGCTCCCAGATGGGTCCTGTCCCAGGTGCAGCTGCAGGAGTCGGG
       · P G L V K P S E T L S L T C T V P G G S ·
   121 CCCAGGACTGGTGAAGCCTTCGGAGACCCTGTCCCTCACCTGCACTGTCCCTGGTGGCTC
       · I R S Y F W S W I R Q P A G K G L E W I ·
   181 CATCAGGAGTTACTTCTGGAGCTGGATCCGGCAGCCCGCCGGGAAGGGACTGGAGTGGAT
       · G R F Y F S G S T N Y N P S L K S R V T ·
   241 TGGGCGTTTCTATTTCAGTGGGAGCACCAACTACAACCCCTCCCTCAAGAGTCGAGTCAC
       · M S V D T S K N Q F S L K L S S V T A A ·
   301 CATGTCAGTAGACACGTCCAAGAACCAGTTCTCCCTGAAGTTGAGCTCTGTGACCGCCGC
       · D T A V Y Y C A R D Y G D H Y Y Y Y G M ·
   361 GGACACGGCCGTGTATTACTGTGCGAGAGACTACGGTGACCACTACTACTACTACGGTAT
       · D V W G Q G T T V T V S S A S T K G P S ·
   421 GGACGTCTGGGGCCAAGGGACCACGGTCACCGTCTCCTCAGCATCCACCAAGGGCCCATC
       · V F P L A P S S K S T S G G T A A L G C ·
   481 GGTCTTCCCCCTGGCACCCTCCTCCAAGAGCACCTCTGGGGGCACAGCGGCCCTGGGCTG
       · L V K D Y F P E P V T V S W N S G A L T ·
   541 CCTGGTCAAGGACTACTTCCCCGAACCGGTGACGGTGTCGTGGAACTCAGGCGCCCTGAC
       · S G V H T F P A V L Q S S G L Y S L S S ·
   601 CAGCGGCGTGCACACCTTCCCGGCTGTCCTACAGTCCTCAGGACTCTACTCCCTCAGCAG
       · V V T V P S S S L G T Q T Y I C N V N H ·
   661 CGTGGTGACCGTGCCCTCCAGCAGCTTGGGCACCCAGACCTACATCTGCAACGTGAATCA
       · K P S N T K V D K R V E P K S C D K T H ·
   721 CAAGCCCAGCAACACCAAGGTGGACAAGAGAGTTGAGCCCAAATCTTGTGACAAAACTCA
       · T C P P C P A P E L L G G P S V F L F P ·
   781 CACATGCCCACCGTGCCCAGCACCTGAACTCCTGGGGGGACCGTCAGTCTTCCTCTTCCC
       · P K P K D T L M I S R T P E V T C V V V ·
   841 CCCAAAACCCAAGGACACCCTCATGATCTCCCGGACCCCTGAGGTCACATGCGTGGTGGT
```

Figure 2Y-2

```
            · D   V   S   H   E   D   P   E   V   K   F   N   W   Y   V   D   G   V   E   V ·
    901 GGACGTGAGCCACGAAGACCCTGAGGTCAAGTTCAACTGGTACGTGGACGGCGTGGAGGT
            · H   N   A   K   T   K   P   R   E   E   Q   Y   N   S   T   Y   R   V   V   S ·
    961 GCATAATGCCAAGACAAAGCCGCGGGAGGAGCAGTACAACAGCACGTACCGTGTGGTCAG
            · V   L   T   V   L   H   Q   D   W   L   N   G   K   E   Y   K   C   K   V   S ·
   1021 CGTCCTCACCGTCCTGCACCAGGACTGGCTGAATGGCAAGGAGTACAAGTGCAAGGTCTC
            · N   K   A   L   P   A   P   I   E   K   T   I   S   K   A   K   G   Q   P   R ·
   1081 CAACAAAGCCCTCCCAGCCCCCATCGAGAAAACCATCTCCAAAGCCAAAGGGCAGCCCCG
            · E   P   Q   V   Y   T   L   P   P   S   R   E   E   M   T   K   N   Q   V   S ·
   1141 AGAACCACAGGTGTACACCCTGCCCCCATCCCGGGAGGAGATGACCAAGAACCAGGTCAG
            · L   T   C   L   V   K   G   F   Y   P   S   D   I   A   V   E   W   E   S   N ·
   1201 CCTGACCTGCCTGGTCAAAGGCTTCTATCCCAGCGACATCGCCGTGGAGTGGGAGAGCAA
            · G   Q   P   E   N   N   Y   K   T   T   P   P   V   L   D   S   D   G   S   F ·
   1261 TGGGCAGCCGGAGAACAACTACAAGACCACGCCTCCCGTGCTGGACTCCGACGGCTCCTT
            · F   L   Y   S   K   L   T   V   D   K   S   R   W   Q   Q   G   N   V   F   S ·
   1321 CTTCCTCTATAGCAAGCTCACCGTGGACAAGAGCAGGTGGCAGCAGGGGAACGTCTTCTC
            · C   S   V   M   H   E   A   L   H   N   H   Y   T   Q   K   S   L   S   L   S ·
   1381 ATGCTCCGTGATGCATGAGGCTCTGCACAACCACTACACGCAGAAGAGCCTCTCCCTGTC
            · P   G   K   *
   1441 CCCGGGTAAATGA
```

<u>Figure 2Z</u> The cDNA (SEQ ID NO:65) and amino acid sequence (SEQ ID NO:66) of Ha16-1(3,5)18 light chain Double-underlined is the light chain variable region. Dashed underline shows the human Ig lambda constant region.

```
              Q   S   V   L   T   Q   P   P   S   V   S   A   A   P   G   Q   K   V   T   I
      1 CAGTCTGTGCTGACGCAGCCGCCCTCAGTGTCTGCGGCCCCAGGACAGAAGGTCACCATC
              S   C   S   G   S   S   S   N   I   G   N   N   Y   V   S   W   Y   Q   Q   F
     61 TCCTGCTCTGGAAGCAGCTCCAATATTGGGAATAATTATGTATCCTGGTACCAGCAGTTC
              P   G   T   A   P   K   F   L   I   Y   D   N   N   K   R   S   S   G   I   P
    121 CCAGGAACAGCCCCCAAATTCCTCATTTATGACAATAATAAGCGATCCTCAGGGATTCCT
              D   R   F   S   G   S   K   S   G   T   S   A   T   L   G   I   T   G   L   Q
    181 GACCGATTCTCTGGCTCCAAGTCTGGCACGTCAGCCACCCTGGGCATCACCGGACTCCAG
              T   G   D   E   A   D   Y   Y   C   G   T   W   D   S   S   L   S   A   V   I
    241 ACTGGGGACGAGGCCGATTATTACTGCGGAACATGGGATAGCAGCCTGAGTGCTGTGATA
              F   G   G   G   T   K   L   T   V   L   G   Q   P   K   A   A   P   S   V   T
    301 TTCGGCGGAGGGACCAAGCTGACCGTCCTAGGTCAGCCCAAGGCTGCCCCCTCGGTCACT
              L   F   P   P   S   S   E   E   L   Q   A   N   K   A   T   L   V   C   L   I
    361 CTGTTCCCGCCCTCCTCTGAGGAGCTTCAAGCCAACAAGGCCACACTGGTGTGTCTCATA
              S   D   F   Y   P   G   A   V   T   V   A   W   K   A   D   S   S   P   V   K
    421 AGTGACTTCTACCCGGGAGCCGTGACAGTGGCCTGGAAGGCAGATAGCAGCCCCGTCAAG
              A   G   V   E   T   T   T   P   S   K   Q   S   N   N   K   Y   A   A   S   S
    481 GCGGGAGTGGAGACCACCACACCCTCCAAACAAAGCAACAACAAGTACGCGGCCAGCAGC
              Y   L   S   L   T   P   E   Q   W   K   S   H   R   S   Y   S   C   Q   V   T
    541 TATCTGAGCCTGACGCCTGAGCAGTGGAAGTCCCACAGAAGCTACAGCTGCCAGGTCACG
              H   E   G   S   T   V   E   K   T   V   A   P   T   E   C   S   *
    601 CATGAAGGGAGCACCGTGGAGAAGACAGTGGCCCCTACAGAATGTTCATAG
```

<u>Figure 2AA</u> The cDNA (SEQ ID NO:67) and amino acid sequence (SEQ ID NO:68) of Ha16-1(2,4)4 VH.

```
      1 G   F   T   F   S   S   Y   G   M   H   W   V   R   Q   A   P   G   K   G   L
      1 ggattcaccttcagtagctatggcatgcactgggtccgccaggctccaggcaaggggctg
     21 E   W   V   A   I   I   W   Y   D   E   S   N   K   Y   Y   A   D   S   V   K
     61 gagtgggtggcaattatatggtatgatgaaagtaataaatactatgcagactccgtgaag
     41 G   R   F   T   T   S   R   D   N   S   K   N   T   L   Y   L   Q   M   N   S
    121 ggccgattcaccatctccagagacaattccaagaacacgctgtatctgcaaatgaacagc
     61 L   R   A   E   D   T   A   V   Y   Y   C   A   R   A   Y   S   G   S   Y   G
    181 ctgagagccgaggacacggctgtgtattactgtgcgagagcttatagtgggagctacggg
```

Figure 2AB The cDNA (SEQ ID. NO:69) and amino acid sequence (SEQ ID NO:70) of Ha16-1(2,4)4 VL.
Underlined is a portion of the light chain constant region.

```
  1 Q   D   R   Q   P   A   S   P   G   S   G   D   K   L   G   D   K   Y   A   C
  1 caggacagacagccagcatcacctggctctggagataaattgggggataaatatgcttgc
 21 W   Y   Q   Q   K   P   G   Q   S   P   V   L   V   I   Y   Q   D   S   K   R
 61 tggtatcagcagaagccaggccagtcccctgtgctcgtcatctatcaagatagcaagcgg
 41 P   S   G   I   P   E   R   F   S   G   S   N   S   G   N   T   A   T   L   T
121 ccctcagggatccctgagcgattctctggctccaactctgggaacacagccactctgacc
 61 I   S   G   T   Q   A   M   D   E   A   D   Y   Y   C   Q   A   W   D   N   R
181 atcagcgggacccaggctatggatgaggctgactattactgtcaggcgtgggacaacaga
 81 T   A   V   F   G   G   G   T   K   L   T   V   L   G   Q   P   K   A   A   P
241 actgcggtattcggcggagggaccaagctgaccgtcctaggtcagcccaaggctgccccc
101 S   V   T   L   F   P   P   S   S   E   E   L   Q   A   N   K   A   T   L   V
301 tcggtcactctgttcccgccctcctctgaggagcttcaagccaacaaggccacactggtg
121 C   L   I   S   D   F   Y   P   G   A   V   T   V   A   W   K   A   D   S   S
361 tgtctcataagtgacttctaccgggagccgtgacagtggcctggaagcagatagcagc
141 P   V   K   A   G   V   E   T   T   T   P   S   K   Q   S   N   N   K   Y   A
421 cccgtcaaggcgggagtggagaccaccacaccctccaaacaaagcaacaacaagtacgcg
161 A   S   S   Y   L   S   L   T   P   E   Q   W   K   S   H   R   S   Y   S   C
481 gccagcagctatctgagcctgacgcctgagcagtggaagtcccacagaagctacagctgc
181 Q
541 cag
```

Figure 2AC The cDNA (SEQ ID NO:71) and amino acid sequence (SEQ ID NO:72) of Ha16-1(3,5)56 VH.
Underlined is a portion of the heavy chain constant region.

```
  1 R   C   R   L   V   E   S   G   A   E   V   K   K   P   G   E   S   L   K   I
  1 aggtgcaggctggtggagtctgcagcagaggtgaaaaagcccggggagtctctgaagatc
 21 S   C   K   G   S   G   Y   R   F   T   S   Y   W   I   G   W   V   R   Q   M
 61 tcctgtaagggttctggatacagatttaccagctactggatcggctgggtgcgccagatg
 41 P   G   K   G   L   E   W   M   G   I   I   Y   P   G   D   S   D   T   R   Y
121 cccgggaaaggcctggagtggatggggatcatctatcctggtgactctgataccagatac
 61 S   P   S   F   Q   G   Q   V   T   I   S   A   D   K   S   I   S   T   A   Y
181 agcccgtccttccaaggccaggtcaccatctcagccgacaagtccatcagcaccgcctac
 81 L   Q   W   R   S   L   K   A   S   D   T   A   M   Y   Y   C   A   R   K   D
241 ctgcagtggcgcagcctgaaggcctcggacaccgccatgtattactgtgcgagaaaggac
101 Y   Y   Y   Y   V   M   D   V   W   G   Q   G   T   T   V   T   V   S   S   A
301 tactactactacgttatggacgtctggggccaagggaccacggtcaccgtctcctcagcc
121 S   T   K   G   P   S   V   F   P   L   A   P   S
361 tccaccaagggcccatcggtcttccccctggcaccctcctc
```

Figure 2AD The cDNA (SEQ ID NO:73) and amino acid sequence (SEQ ID NO:74) of Ha16-1(3,5)56 VL.
Underlined is a portion of the light chain constant region.

```
  1 D   T   I   S   C   T   G   T   S   S   D   V   G   N   Y   N   Y   V   S   W
  1 gataccatctcctgcactggaaccagcagtgacgttggtaattataactatgtctcctgg
 21 Y   Q   Q   H   P   G   K   A   P   K   L   M   I   Y   A   V   N   N   R   P
 61 taccaacaacacccaggcaaagcccccaaactcatgatttatgcggtcaataatcggccc
 41 S   G   V   S   N   R   F   S   G   S   K   S   G   N   T   A   S   L   T   I
121 tcaggggtttctaatcgcttctctggctccaagtctggcaacacggcctccctgaccatc
 61 S   G   L   Q   A   E   D   E   A   D   Y   Y   C   S   S   Y   T   S   S   R
181 tctgggctccaggctgaggacgaggctgattattactgcagctcatatacaagcagcagg
 81 N   L   V   V   F   G   G   G   T   K   L   T   V   L   G   Q   P   K   A   A
241 aatcttgtagttttcggcggcgggaccaagctgaccgtcctaggtcagcccaaggctgcc
101 P   S   V   T   L   F   P   P   S   S   E   E   L   Q   A   N   K   A   T   L
301 ccctcggtcactctgttcccgccctcctctgaggagcttcaagccaacaaggccacactg
121 V   C   L   I   S   D   F   Y   P   G   A   V   T   V   A   W   K   A   D   S
361 gtgtgtctcataagtgacttctaccgggagccgtgacagtggcctggaaggcagatagc
141 S   P   V   K   A   G   V   E   T   T   T   P   S   K   Q   S   N   N   K   Y
421 agccccgtcaaggcgggagtggagaccaccacaccctccaaacaaagcaacaacaagtac
161 A   A   S   S   Y   L   S   L   T   P   E   Q   W   K   S   H   R   S   Y   S
```

Figure 2AD-2

```
481 gcggccagcagctatctgagcctgacgcctgagcagtggaagtcccacagaagctacagc
181  C  Q  V  T  H  E  G  S  T  V  E  K  T  V  A  P  T
541 tgccaggtcacgcatgaagggagcaccgtggagaagacagtggcccctaca
```

Figure 2AE  The cDNA (SEQ ID NO:75) and amino acid sequence (SEQ ID NO:76) of H16-1.93 VH.
Double-underlined is the leader sequence, and underlined is a portion of the heavy chain constant region.

```
  1 GGAGCACGAGGACACTGACATGGACTGAAGGAGTAGAAAACCCAAAAACCACACCCCTCC
                                             M  D  W  T  W  S  I  L  F
 61 TTGGGAGAATCCCCTAGATCACAGCTCCTCACCATGGACTGGACCTGGAGCATCCTTTTC
     L  V  A  A  A  T  G  A  H  S  Q  V  Q  L  V  Q  S  G  A  E
121 TTGGTGGCAGCAGCAACAGGTGCCCACTCCCAGGTTCAGCTGGTGCAGTCTGGAGCTGAG
     V  K  K  P  G  A  S  V  K  V  S  C  K  A  S  G  Y  T  F  T
181 GTGAAGAAGCCTGGGGCCTCAGTGAAGGTCTCCTGCAAGGCTTCTGGTTACACCTTTACC
     S  Y  G  I  S  W  V  R  Q  A  P  G  Q  G  L  E  W  M  G  W
241 AGCTATGGTATCAGCTGGGTGCGACAGGCCCCTGGACAAGGGCTTGAGTGGATGGGATGG
     I  S  A  Y  N  G  N  T  Y  Y  A  Q  K  L  Q  A  R  V  T  M
301 ATCAGCGCTTACAATGGTAACACATACTATGCACAGAAGCTCCAGGCCAGAGTCACCATG
     T  T  D  T  S  T  S  T  A  Y  M  E  L  R  S  L  R  S  D  D
361 ACCACAGACACATCCACGAGCACAGCCTACATGGAGCTGAGGAGCCTGAGATCTGACGAC
     T  A  V  Y  Y  C  A  R  D  G  Y  S  S  S  W  S  L  L  H  Y
421 ACGGCCGTGTATTACTGTGCGAGAGATGGGTATAGCAGCAGCTGGTCCCTCCTGCACTAC
     Y  G  M  D  V  W  G  Q  G  T  T  V  T  V  S  S  A  S  T  K
481 TACGGTATGGACGTCTGGGGCCAAGGGACCACGGTCACCGTCTCCTCAGCCTCCACCAAG
     G  P  S  V  F  P  L  A  P  S  S  K  S  T  S  G  G  T  A  A
541 GGCCCATCGGTCTTCCCCCTGGCACCCTCCTCCAAGAGCACCTCTGGGGGCACAGCGGCC
     L  G  C  L  V  K  D  Y  F  P  E  P  V  T  V  S  W  N  S  A
601 CTGGGCTGCCTGGTCAAGGACTACTTCCCCGAACCGGTGACGGTGTCGTGGAACTCAGCG
```

Figure 2AF  The cDNA (SEQ ID NO:77) and amino acid sequence (SEQ ID NO:78) of H16-1.93 VL.
Double-underlined is the leader sequence, and underlined is a portion of the light chain constant region.

```
            S  D  T  R  C  D  I  Q  M  T  Q  S  P  S  S  L  S  A  S  V
  1 TCAGATACCAGATGTGACATCCAGATGACCCAGTCTCCATCCTCCCTGTCTGCATCTGTA
     G  D  R  I  T  I  T  W  R  S  S  Q  G  I  Y  N  S  L  A  W
 61 GGAGACAGAATCACCATCACTTGGCGGTCGAGTCAGGGCATTTACAATTCTTTAGCCTGG
     Y  Q  Q  K  P  G  K  V  P  K  L  L  I  Y  A  A  S  T  L  H
121 TATCAGCAGAAACCAGGGAAAGTTCCTAAGCTCCTGATCTATGCTGCATCCACTTTGCAC
     S  G  V  P  S  R  F  S  G  S  G  S  G  T  D  F  T  L  T  I
181 TCAGGGGTCCCATCTCGGTTCAGTGGCAGTGGATCTGGGACAGATTTCACTCTCACCATC
     S  S  L  Q  P  E  D  V  A  T  Y  Y  C  Q  K  Y  N  S  A  P
241 AGCAGCCTGCAGCCTGAAGATGTTGCAACTTATTACTGTCAAAAATATAACAGTGCCCCA
     F  T  F  G  P  G  T  K  V  D  I  K  R  T  V  A  A  P  S  V
301 TTCACTTTCGGCCCTGGGACCAAAGTGGATATCAAACGAACTGTGGCTGCACCATCTGTC
     F  I  F  P  P  S  D  E  Q  L  K  S  G  T  A  S  V  V  C  L
361 TTCATCTTCCCGCCATCTGATGAGCAGTTGAAATCTGGAACTGCCTCTGTTGTGTGCCTG
     L  N  N  F  Y  P  R  E  A  K  V  Q  W  K  V  D  N  A  L  Q
421 CTGAATAACTTCTATCCCAGAGAGGCCAAAGTACAGTGGAAGGTGGATAACGCCCTCCAA
     S  G  N  S  Q  E  S  V  T  E  Q  D  S  K  D  S  T  Y  S  L
481 TCGGGTAACTCCCAGGAGAGTGTCACAGAGCAGGACAGCAAGGACAGCACCTACAGCCTC
     S  S  T  L  T  L  S  K  A  D  Y  E  K  H  K  V  Y  A  C  E
541 AGCAGCACCCTGACGCTGAGCAAAGCAGACTACGAGAAACACAAAGTCTACGCCTGCGAA
     V  T  H  Q  G  L  S  S  P  V  T  K  S  F  N  R  G
601 GTCACCCATCAGGGCCTGAGCTCGCCCGTCACAAAGAGCTTCAACAGGGGA
```

Figure 2AG The cDNA (SEQ ID NO:79) and amino acid sequence (SEQ ID NO:80) of H16-7.8 VH.
Double-underlined is the leader sequence, and underlined is a portion of the heavy chain constant region.

```
                                                M   K   H   L   W   F   F   L   L
   1   TTTCTGAGAGTCCTGGACCTCCTGTGCAAGAACATGAAACACCTGTGGTTCTTCCTCCTG
         L   V   A   A   P   R   W   V   L   S   Q   V   Q   L   Q   E   S   G   P   G
  61   CTGGTGGCAGCTCCCAGATGGGTCCTGTCCCAGGTGCAGCTGCAGGAGTCGGGCCCAGGA
         L   V   K   P   S   Q   T   L   S   L   T   C   T   V   S   G   G   S   I   S
 121   CTGGTGAAGCCTTCACAGACCCTGTCCCTCACCTGCACTGTCTCTGGTGGCTCCATCAGC
         S   G   G   Y   Y   W   S   W   I   R   Q   H   P   G   K   G   L   E   W   I
 181   AGTGGTGGTTACTACTGGAGCTGGATCCGCCAGCACCCAGGGAAGGGCCTGGAGTGGATT
         G   I   I   Y   Y   S   G   S   T   Y   Y   N   P   S   L   K   S   R   V   T
 241   GGGATCATCTATTACAGTGGGAGCACCTACTACAACCCGTCCCTCAAGAGTCGAGTTACC
         I   S   V   D   T   S   K   N   Q   F   S   L   K   L   N   S   V   T   A   A
 301   ATATCAGTAGACACGTCTAAGAACCAGTTCTCCCTGAAGCTGAACTCTGTGACTGCCGCG
         D   T   A   V   F   Y   C   A   R   V   A   I   V   T   T   I   P   G   G   M
 361   GACACGGCCGTGTTTTACTGTGCGAGAGTGGCTATAGTGACTACGATCCCGGGCGGTATG
         D   V   W   G   Q   G   T   T   V   T   V   S   S   A   S   T   K   G   P   S
 421   GACGTCTGGGGCCAAGGGACCACGGTCACCGTCTCCTCAGCCTCCACCAAGGGCCCATCG
         V   F   P   L   A   P   C   S   R   S   T   S   E   S   T   A   A   L   G   C
 481   GTCTTCCCCCTGGCGCCCTGCTCCAGGAGCACCTCCGAGAGCACAGCGGCCCTGGGCTGC
         L   V   K   D   Y   F   P   E   P   V   T   V   S   W   N   S   G   A   L   T
 541   CTGGTCAAGGACTACTTCCCCGAACCGGTGACGGTGTCGTGGAACTCAGGCGCTCTGACC
         S   G   V   H   T   F   P   A   V   L   Q   S   S   G   L   Y   S   L   S   S
 601   AGCGGCGTGCACACCTTCCCAGCTGTCCTACAGTCCTCAGGACTCTACTCCCTCAGCAGC
         V   V   T   V   P   S   S   N   F   G   T   Q   T   Y   T   C   N   V   D   H
 661   GTGGTGACCGTGCCCTCCAGCAACTTCGGCACCCAGACCTACACCTGCAACGTAGATCAC
         K   P   S   N   T   K   V   D   K   T   V   E   R   K   C   C   V   E   C   P
 721   AAGCCCAGCAACACCAAGGTGGACAAGACAGTTGAGCGCAAATGTTGTGTCGAGTGCCCA
         P   C   P   A   P   P   V   A   G   P   S   V   F   L   F   P   P   K   P   K
 781   CCGTGCCCAGCACCACCTGTGGCAGGACCGTCAGTCTTCCTCTTCCCCCCAAAACCCAAG
         D   T   L   M   I   S   R   T   P   E   V   T   C   V   V   V   D   V   S   H
 841   GACACCCTCATGATCTCCCGGACCCCTGAGGTCACGTGCGTGGTGGTGGACGTGAGCCAC
         E   D   P   E   V   Q   F   N   W   Y   V   D   G   V   E   V   H   N   A   K
 901   GAAGACCCCGAGGTCCAGTTCAACTGGTACGTGGACGGCGTGGAGGTGCATAATGCCAAG
         T   K   P   R   E   E   Q   F   N   S   T   F   R   V   V   S   V   L   T   V
 961   ACAAAGCCACGGGAGGAGCAGTTCAACAGCACGTTCCGTGTGGTCAGCGTCCTCACCGTT
         V   H   Q   D   W   L   N   G   K   E   Y   K   C   K   V   S   N   K   G   L
1021   GTGCACCAGGACTGGCTGAACGGCAAGGAGTACAAGTGCAAGGTCTCCAACAAAGGCCTC
         P   A   P   I   E   K   T   I   S   K   T   K   G   Q   P   R   E   P   Q   V
1081   CCAGCCCCCATCGAGAAAACCATCTCCAAAACCAAAGGGCAGCCCCGAGAACCACAGGTG
         Y   T   L   P   P   S   R   E   E   M   T   K   N   Q   V   S   L   T   C   L
1141   TACACCCTGCCCCCATCCCGGGAGGAGATGACCAAGAACCAGGTCAGCCTGACCTGCCTG
         V   K   G   F   Y   P   S   D   I   A   V   E   W   E   S   N   G   Q   P   E
1201   GTCAAAGGCTTCTACCCCAGCGACATCGCCGTGGAGTGGGAGAGCAATGGGCAGCCGGAG
         N   N   Y   K   T   T   P   P   M   L   D   S   D   G   S   F   F   L   Y   S
1261   AACAACTACAAGACCACACCTCCCATGCTGGACTCCGACGGCTCCTTCTTCCTTTACAGC
         K   L   T   V   D   K   S   R   W   Q   Q   G   N   V   F   S   C   S   V   M
1321   AAGCTCACCGTGGACAAGAGCAGGTGGCAGCAGGGGAACGTCTTCTCATGCTCCGTGATG
         H   E   A   L   H
1381   CATGAGGCTCTGCACA
```

Figure 2AH The cDNA (SEQ ID NO:81) and amino acid sequence (SEQ ID NO:82) of H16-7.8 VL.
Double-underlined is the leader sequence, and underlined is a portion of the light chain constant region.

```
                                                        M   L   P   S   Q   L
   1   AGGAGTAGAAAATGAGCAAAACTGACAAGTCAAGGCAGGAAGATGTTGCCATCACAACTC
         I   G   F   L   L   L   W   V   P   A   S   R   G   E   I   V   L   T   Q   S
  61   ATTGGGTTTCTGCTGCTCTGGGTTCCAGCCTCCAGGGGTGAAATTGTGCTGACTCAGTCT
         P   D   F   Q   S   V   T   P   K   E   V   T   I   T   C   R   A   S   Q
 121   CCAGACTTTCAGTCTGTGACTCCAAAGGAGAAAGTCACCATCACCTGCCGGGCCAGTCAG
         S   I   G   I   S   L   H   W   Y   Q   Q   K   P   D   Q   S   P   K   L   L
```

Figure 2AH-2

```
181 AGCATTGGTATTAGCTTACACTGGTACCAGCAGAAACCAGATCAGTCTCCAAAGCTCCTC
      I  K  Y  A  S  Q  S  F  S  G  V  P  S  R  F  S  G  S  G  S
241 ATCAAGTATGCTTCCCAGTCCTTCTCAGGGGTCCCCTCGAGGTTCAGTGGCAGTGGATCT
      G  T  D  F  T  L  T  I  N  S  L  E  A  E  D  A  A  T  Y  Y
301 GGGACAGATTTCACCCTCACCATCAATAGCCTGGAAGCTGAAGATGCTGCAACGTATTAC
      C  H  Q  S  R  S  F  P  W  T  F  G  Q  G  T  K  V  E  I  K
361 TGTCATCAGAGTAGGAGTTTCCCGTGGACGTTCGGCCAAGGGACCAAGGTGGAAATCAAA
      R  T  V  A  A  P  S  V  F  I  F  P  P  S  D  E  Q  L  K  S
421 CGAACTGTGGCTGCACCATCTGTCTTCATCTTCCCGCCATCTGATGAGCAGTTGAAATCT
      G  T  A  S  V  V  C  L  L  N  N  F  Y  P  R  E  A  K  V  Q
481 GGAACTGCCTCTGTTGTGTGCCTGCTGAATAACTTCTATCCCAGAGAGGCCAAAGTACAG
      W  K  V  D  N  A  L  Q  S  G  N  S  Q  E  S  V  T  E  Q  D
541 TGGAAGGTGGATAACGCCCTCCAATCGGGTAACTCCCAGGAGAGTGTCACAGAGCAGGAC
      S  K  D  S  T  Y  S  L  S  S  T  L  T  L  S  K  A  D  Y  E
601 AGCAAGGACAGCACCTACAGCCTCAGCAGCACCCTGACGCTGAGCAAAGCAGACTACGAG
      K  H  K  V  Y  A  C  E  V  T  H  Q  G
661 AAACACAAAGTCTACGCCTGCGAAGTCACCCATCAGGGCC
```

<u>Figure 2AI</u> The cDNA (SEQ ID NO:83) and amino acid sequence (SEQ ID NO:84) of Ha16-1(3,5)27.1 VH. Underlined is a portion of the heavy chain constant region.

```
      L  V  E  S  G  A  E  V  K  K  P  G  E  S  L  K  I  S  C  K
  1 TTGGTGGAGTCTGGAGCAGAGGTGAAAAAGCCCGGGGAGTCTCTGAAGATCTCCTGTAAG
      G  S  G  Y  R  F  T  S  Y  W  I  G  W  V  R  Q  M  P  G  K
 61 GGTTCTGGATACAGATTTACCAGCTACTGGATCGGCTGGGTGCGCCAGATGCCCGGGAAA
      G  L  E  W  M  G  I  I  Y  P  G  D  S  D  T  R  Y  S  P  S
121 GGCCTGGAGTGGATGGGGATCATCTATCCTGGTGACTCTGATACCAGATACAGCCCGTCC
      F  Q  G  Q  V  T  I  S  A  D  K  S  I  S  T  A  Y  L  Q  W
181 TTCCAAGGCCAGGTCACCATCTCAGCCGACAAGTCCATCAGTACCGCCTACCTGCAGTGG
      S  S  L  K  A  S  D  T  A  M  Y  Y  C  A  R  K  D  Y  Y  Y
241 AGCAGCCTGAAGGCCTCGGACACCGCCATGTATTACTGTGCGAGAAAGGACTACTACTAC
      Y  S  M  D  V  W  G  Q  G  T  T  V  T  V  S  S  A  S  T  K
301 TACAGTATGGACGTCTGGGGCCAAGGGACCACGGTCACCGTCTCCTCAGCCTCCACCAAG
      G  P  S  V  F  P  L  E  P  S  S  K
361 GGCCCATCGGTCTTCCCCCTGGAACCCTCCTCCAAA
```

<u>Figure 2AJ</u> The cDNA (SEQ ID NO:85) and amino acid sequence (SEQ ID NO:86) of Ha16-1(3,5)27 VL. Underlined is a portion of the light chain constant region.

```
      G  Q  S  A  L  T  Q  P  A  S  V  S  G  S  P  G  Q  S  I  T
  1 GGCCAGTCTGCCCTGACTCAACCTGCCTCCGTGTCTGGGTCTCCTGGACAGTCGATCACC
      I  S  C  T  G  T  S  S  D  V  G  G  Y  N  Y  V  S  W  Y  Q
 61 ATCTCCTGCACTGGAACCAGCAGTGACGTTGGTGGTTATAATTATGTCTCCTGGTACCAA
      Q  H  P  G  Q  A  P  K  L  L  I  Y  G  V  N  I  R  P  S  G
121 CAGCACCCAGGCCAAGCCCCCAAACTCCTGATTTATGGGGTCAATATTCGGCCCTCAGGG
      V  S  T  R  F  S  G  S  K  S  G  N  T  A  S  L  T  I  S  G
181 GTTTCTACTCGCTTCTCTGGCTCCAAGTCTGGCAACACGGCCTCCCTGACCATCTCTGGG
      L  Q  A  E  D  E  A  D  Y  Y  C  S  S  Y  T  R  S  S  I  L
241 CTCCAGGCTGAGGACGAGGCCGATTATTATTGTAGTTCATATACAAGAAGCAGCATTCTT
      V  V  F  A  G  G  T  K  L  T  V  L  G  Q  P  K  A  A  P  S
301 GTGGTTTTCGCCGGAGGGACCAAACTGACCGTCCTAGGTCAGCCCAAGGCTGCCCCCTCG
      V  T  L  F  P  P  S  S  E  E  L  Q  A  N  K  A  T  L  V  C
361 GTCACTCTGTTCCCGCCCTCCTCTGAGGAGCTTCAAGCCAACAAGGCCACACTGGTGTGT
      L  I  S  D  F  Y  P  G  A  V  T  V  A  W  K  A  D  S  S  P
421 CTCATAAGTGACTTCTACCCGGGAGCCGTGACAGTGGCCTGGAAGGCAGATAGCAGCCCC
      V  K  A  G  V  E  T  T  T  P  S  K  Q  S  N  N  K  Y  A  A
481 GTCAAGGCGGGAGTGGAGACCACCACACCCTCCAAACAAAGCAACAACAAGTACGCGGCC
      S  S  Y  L  S  L  T  P  E  Q
541 AGCAGCTATCTGAGCCTGACGCCTGAGCAG
```

Figure 2AK The cDNA (SEQ ID NO:87) and amino acid sequence (SEQ ID NO:88) of H16-1.61 VH.
Underlined is a portion of the heavy chain constant region.

```
    1  E   V   Q   L   V   E   S   G   G   G   V   V   Q   P   G   R   S   L   R   L
    1  GAGGTGCAGCTGGTGGAGTCTGGGGGAGGCGTGGTCCAGCCTGGGAGGTCCCTGAGACTC
   21  S   C   A   A   S   G   F   T   F   S   S   Y   G   M   H   W   V   R   Q   A
   61  TCCTGTGCAGCGTCTGGATTCACCTTCAGTAGCTATGGCATGCACTGGGTCCGCCAGGCT
   41  P   G   K   G   L   E   W   V   A   V   I   W   Y   D   G   S   N   K   Y   Y
  121  CCAGGCAAGGGGCTGGAGTGGGTGGCAGTTATATGGTATGATGGAAGTAATAAATACTAT
   61  A   D   S   V   K   G   R   F   T   I   S   R   D   N   S   K   N   T   L   Y
  181  GCAGACTCCGTGAAGGGCCGATTCACCATCTCCAGAGACAATTCCAAGAACACGCTGTAT
   81  L   Q   M   N   S   L   R   A   E   D   T   A   V   Y   Y   C   A   R   S   R
  241  CTGCAAATGAACAGCCTGAGAGCCGAGGACACGGCTGTGTATTACTGTGCGAGGTCCAGA
  101  I   T   I   F   G   V   V   H   Y   G   M   D   V   W   G   Q   G   T   T   V
  301  ATTACGATTTTTGGAGTGGTTCACTACGGTATGGACGTCTGGGGCCAAGGGACCACGGTC
  121  T   V   S   S   A   S   T   K   G   P   S   V   F   P   L   A   P   S   S   K
  361  ACCGTCTCCTCAGCCTCCACCAAGGGCCCATCGGTCTTCCCCCTGGCACCCTCCTCCAAG
  141  S   T
  421  AGCACCT
```

Figure 2AL The cDNA (SEQ ID NO:89) and amino acid sequence (SEQ ID NO:90) of H16-1.61 VL.
Underlined is a portion of the light chain constant region.

```
    1  D   T   Q   L   T   Q   S   P   S   S   L   S   A   S   V   G   D   R   V   T
    1  GACACGCAGCTGACTCAGTCTCCATCCTCCCTGTCTGCATCTGTAGGAGACAGAGTCACC
   21  I   T   C   R   A   S   Q   S   I   S   S   Y   L   N   W   Y   Q   L   K   P
   61  ATCACTTGCCGGGCAAGTCAGAGCATTAGCAGCTATTTAAATTGGTATCAGCTGAAACCA
   41  G   K   A   P   K   L   L   I   Y   A   A   S   S   L   E   S   G   V   P   S
  121  GGGAAAGCCCCTAAGCTCCTGATCTATGCTGCATCCAGTTTAGAAAGTGGGGTCCCATCA
   61  R   F   S   G   S   E   S   G   T   D   F   T   L   T   I   S   S   L   Q   P
  181  AGGTTCAGTGGCAGTGAATCTGGGACAGATTTCACTCTCACCATCAGCAGTCTGCAACCT
   81  E   D   F   A   T   Y   Y   C   Q   Q   S   Y   N   S   P   I   T   F   G   P
  241  GAAGATTTTGCAACTTACTACTGTCAACAGAGTTACAATTCCCCAATCACTTTCGGCCCT
  101  G   T   K   V   D   I   K   R   T   V   A   A   P   S   V   F   I   F   P   P
  301  GGGACCAAAGTGGATATCAAACGAACTGTGGCTGCACCATCTGTCTTCATCTTCCCGCCA
  121  S   D   E   Q   L   K   S   G   T   A   S   V   V   C   L   L   N   N   F   Y
  361  TCTGATGAGCAGTTGAAATCTGGAACTGCCTCTGTTGTGTGCCTGCTGAATAACTTCTAT
  141  P   R   E   A   K   V   Q   W   K   V   D   N   A   L   Q   S
  421  CCCAGAGAGGCCAAAGTACAGTGGAAGGTGGATAACGCCCTCCAATCGGG
```

Figure 2AM The cDNA (SEQ ID NO:91) and amino acid sequence (SEQ ID NO:92) of H16-1(3,5)5 VH.
Double-underlined is the leader sequence, and underlined is a portion of the heavy chain constant region.

```
    1  AGAAGAGTCTCCCTCACTGCCCAGCTGGGATCTCAGGGCTTCATTTTCTGTCCTCCACCA
          M   G   S   T   A   I   L   A   L   L   A   V   L   Q   G   V   C   A   E
   61  ATGGGGTCAACCGCCATCCTCGCCCTCCTCCTGGCTGTTCTCCAAGGAGTCTGTGCCGAG
          V   Q   L   V   Q   S   G   A   E   V   K   K   P   G   E   S   L   K   I   S
  121  GTGCAACTAGTGCAGTCTGGAGCAGAGGTGAAAAAGCCCGGGGAGTCTCTGAAGATCTCC
          C   K   G   S   G   Y   R   F   T   S   Y   W   I   G   W   V   R   Q   M   P
  181  TGTAAGGGTTCTGGATACAGGTTTACCAGCTACTGGATCGGCTGGGTGCGCCAGATGCCC
          G   K   G   L   E   W   M   G   I   I   Y   P   G   D   S   D   T   R   Y   S
  241  GGGAAAGGCCTGGAGTGGATGGGGATCATCTATCCTGGTGACTCTGATACCAGATACAGC
          P   S   F   Q   G   Q   V   T   I   S   A   D   K   S   I   S   T   A   Y   L
  301  CCGTCCTTCCAAGGCCAGGTCACCATCTCAGCCGACAAGTCCATCAGCACCGCCTACCTG
          Q   W   S   S   L   K   A   S   D   T   A   M   Y   Y   C   A   R   K   D   Y
  361  CAGTGGAGCAGCCTGAAGGCCTCGGACACCGCCATGTATTACTGTGCGAGAAAGGACTAC
          Y   Y   Y   T   M   D   V   W   G   Q   G   T   T   V   T   V   S   S   A   S
  421  TACTACTACACTATGGACGTCTGGGGCCAAGGGACCACGGTCACCGTCTCCTCAGCCTCC
          T   K   G   P   S   V   F   P   L   A   P   S   S   K   S   T   S   G   G   T
```

Figure 2AM-2

```
481 ACCAAGGGCCCATCGGTCTTCCCCCTGGCACCCTCCTCCAAGAGCACCTCTGGGGGCACA
     A  A  L  G  C  L  V  K  D  Y  F  P  E  P  V  T  V  S
541 GCGGCCCTGGGCTGCCTGGTCAAGGACTACTTCCCCGAACCGGTGACGGTGTCG
```

Figure 2AN The cDNA (SEQ ID NO:93) and amino acid sequence (SEQ ID NO:94) of H16-1(3,5)5 VL.

Double-underlined is part of the leader sequence, and underlined is a portion of the light chain constant region.

```
        L  G  Q  S  A  L  T  Q  P  A  S  V  S  G  S  P  G  Q  S  I
  1 CTGGGCCAGTCTGCCCTGACTCAGCCTGCCTCCGTGTCTGGGTCTCCTGGACAGTCGATC
     T  I  S  C  T  G  T  S  S  D  V  G  G  Y  N  Y  V  S  W  Y
 61 ACCATCTCCTGCACTGGAACCAGCAGTGACGTTGGTGGTTATAACTATGTCTCCTGGTAC
     Q  Q  H  P  G  K  A  P  K  L  M  I  Y  A  V  S  N  R  P  S
121 CAACAACACCCAGGCAAAGCCCCCAAACTCATGATTTATGCGGTCAGTAATCGGCCCTCA
     G  V  S  N  R  F  S  G  S  K  S  G  N  T  A  S  L  T  I  S
181 GGGGTTTCTAATCGCTTCTCTGGCTCCAAGTCTGGCAACACGGCCTCCCTGACCATCTCT
     G  L  Q  A  E  D  E  A  D  Y  Y  C  S  S  Y  T  I  S  R  I
241 GGGCTCCAGGCTGAGGACGAGGCTGATTATTACTGCAGCTCATATACAATCAGCAGGATT
     L  V  V  F  G  G  G  T  K  L  T  V  L  G  Q  P  K  A  A  P
301 CTTGTGGTTTTCGGCGGGGGGACCAAGCTGACCGTCCTAGGTCAGCCCAAGGCTGCCCCC
     S  V  T  L  F  P  P  S  S  E  E  L  Q  A  N  K  A  T  L  V
361 TCGGTCACTCTGTTCCCGCCCTCCTCTGAGGAGCTTCAAGCCAACAAGGCCACACTGGTG
     C  L  I  S  D  F  Y  P  G  A  V  T  V  A  W  K  A  D  S  S
421 TGTCTCATAAGTGACTTCTACCCGGGAGCCGTGACAGTGGCCTGGAAGGCAGATAGCAGC
     P  V  K  A  G  V  E  T  T  T  P  S  K  Q  S  N  N  K  Y  A
481 CCCGTCAAGGCGGGAGTGGAGACCACCACACCCTCCAAACAAAGCAACAACAAGTACGCG
     A  S  S  Y  L  S  L  T  P  E  Q  W  K  S  H  R  S  Y  S  C
541 GCCAGCAGCTATCTGAGCCTGACGCCTGAGCAGTGGAAGTCCCACAGAAGCTACAGCTGC
     Q  V  T  H  E  G  S  T  V  E  K  T  V  A  P  T
601 CAGGTCACGCATGAAGGGAGCACCGTGGAGAAGACAGTGGCCCCTACA
```

Figure 2AO The cDNA (SEQ ID NO:95) and amino acid sequence (SEQ ID NO:96) of H16-7.200 VH.

Double-underlined is the leader sequence, and underlined is a portion of the heavy chain constant region.

```
                                                M  K  H  L  W  F  F
  1 AAATACTTTCTGAGAGTCCTGGACCTCCTGTGCAAGAACATGAAACACCTGTGGTTCTTC
     L  L  L  V  A  A  P  R  W  V  L  S  Q  V  Q  L  Q  E  S  G
 61 CTCCTGCTGGTGGCAGCTCCCAGATGGGTCCTGTCCCAGGTGCAGCTGCAGGAGTCGGGC
     P  G  L  V  K  P  S  Q  T  L  S  L  T  C  T  V  S  G  G  S
121 CCAGGACTGGTGAAGCCTTCACAGACCCTGTCCCTCACCTGCACTGTCTCTGGTGGCTCC
     I  T  S  G  D  Y  Y  W  S  W  I  R  Q  H  P  G  K  G  L  E
181 ATCACCAGTGGTGATTACTACTGGAGCTGGATCCGCCAGCACCCAGGGAAGGGCCTGGAG
     W  F  G  F  I  Y  Y  S  G  S  A  Y  Y  N  P  S  L  K  S  R
241 TGGTTTGGGTTCATCTATTACAGTGGGAGCGCCTACTACAACCCGTCCCTCAAGAGTCGA
     I  T  I  S  V  D  T  S  K  N  Q  F  S  L  K  L  S  S  V  T
301 ATTACCATATCAGTAGACACGTCTAAGAACCAGTTCTCCCTGAAGCTGAGCTCTGTGACT
     A  A  D  T  A  V  Y  Y  C  A  R  E  R  N  Y  G  G  N  S  F
361 GCCGCGGACACGGCCGTGTATTACTGTGCGAGAGAGAGGAACTACGGTGGTAACTCGTTT
     D  Y  W  G  Q  G  T  L  V  T  V  S  S  A  S  T  K  G  P  S
421 GACTACTGGGGCCAGGGAACCCTGGTCACCGTCTCCTCAGCCTCCACCAAGGGCCCATCG
     V  F  P  L  A  P  C  S  R  S  T  S  E  S  T  A  A  L  G  C
481 GTCTTCCCCCTGGCGCCCTGCTCCAGGAGCACCTCCGAGAGCACAGCGGCCCTGGGCTGC
     L  V  K  D  Y  F  P  E  P  V  T  V  S  W  N  S  G  A  L  T
541 CTGGTCAAGGACTACTTCCCCGAACCGGTGACGGTGTCGTGGAACTCAGGCGCTCTGACC
     S  G  V  H  T  F  P  A  V  L  Q  S  S  G  L  Y  S  L  S  S
601 AGCGGCGTGCACACCTTCCCAGCTGTCCTACAGTCCTCAGGACTCTACTCCCTCAGCAGC
     V  V  T  V  P  S  S  T
661 GTGGTGACCGTGCCCTCCAGCACTCG
```

Figure 2AP The cDNA (SEQ ID NO:97) and amino acid sequence (SEQ ID NO:98) of H16-7.200 VL. Double-underlined is part of the leader sequence, and underlined is a portion of the light chain constant region.

```
         W  I  S  G  S  S  G  D  I  V  M  T  Q  S  P  L  S  L  P  V
  1  TGGATCTCTGGATCCAGTGGGGATATTGTGATGACTCAGTCTCCACTCTCCCTGCCCGTC
         T  P  G  E  P  A  S  I  S  C  R  S  S  Q  S  L  L  H  S  N
 61  ACCCCTGGAGAGCCGGCCTCCATCTCCTGCAGGTCTAGTGAGCCTCCTGCATAGTAAT
         G  Y  N  Y  L  D  W  Y  L  Q  K  P  G  Q  S  P  Q  L  L  I
121  GGATACAACTATTTGGATTGGTACCTGCAGAAGCCAGGGCAGTCTCCACAGCTCCTGATC
         Y  L  G  S  N  R  A  S  G  V  P  D  R  F  S  G  S  G  S  G
181  TATTTGGGTTCTAATCGGGCCTCCGGGGTCCCTGACAGGTTCAGTGGCAGTGGATCAGGC
         T  D  F  T  L  K  I  S  R  V  E  A  E  D  V  G  V  Y  Y  C
241  ACAGATTTTACACTGAAAATCAGCAGAGTGGAGGCTGAGGATGTTGGGGTTTATTACTGC
         M  Q  A  L  Q  T  I  T  F  G  Q  G  T  R  L  E  I  K  R  T
301  ATGCAAGCTCTACAAACTATCACCTTCGGCCAAGGGACACGACTGGAGATTAAACGAACT
         V  A  A  P  S  V  F  I  F  P  P  S  D  E  Q  L  K  S  G  T
361  GTGGCTGCACCATCTGTCTTCATCTTCCCGCCATCTGATGAGCAGTTGAAATCTGGAACT
         A  S  V  V  C  L  L  N  N  F  Y  P  R  E  A  K  V  Q  W  K
421  GCCTCTGTTGTGTGCCTGCTGAATAACTTCTATCCCAGAGAGGCCAAAGTACAGTGGAAG
         V  D  N  A  L  Q  S  G  N  S  Q  E  S  V  T  E  Q  D  S  K
481  GTGGATAACGCCCTCCAATCGGGTAACTCCCAGGAGAGTGTCACAGAGCAGGACAGCAAG
         D  S  T  Y  S  L  S  S  T  L  T  L  S  K  A  D  Y  E  K  H
541  GACAGCACCTACAGCCTCAGCAGCACCCTGACGCTGAGCAAAGCAGACTACGAGAAACAC
         K  V  Y  A  C  E  V  T  H  Q  X  L  S  S  P  V  T  K  S  F
601  AAAGTCTACGCCTGCGAAGTCACCCATCAGGSCCTGAGCTCGCCCGTCACAAAGAGCTTC
         N  R  G
661  AACAGGGGAGA
```

Figure 2AQ The cDNA (SEQ ID NO:99) and amino acid sequence (SEQ ID NO:100) of Ha16-1(3,5)42 VH. Double-underlined is the leader sequence, and underlined is a portion of the heavy chain constant region.

```
                                                                   M
  1  AGTCTCCCTCACTGCCCAGCTGGGATCTCAGGGCTTCATTTTCTGTCCTCCACCATCATG
         G  S  T  A  I  L  A  L  L  L  A  V  L  Q  G  V  C  A  E  V
 61  GGGTCAACCGCCATCCTCGCCCTCCTCCTGGCTGTTCTCCAAGGAGTCTGTGCCGAGGTG
         Q  L  V  Q  S  G  A  E  V  K  K  P  G  E  S  L  K  I  S  C
121  CAGCTGGTGCAGTCTGGAGCAGAGGTGAAAAAGCCCGGGGAGTCTCTGAAGATCTCCTGT
         K  G  S  G  Y  R  F  T  S  Y  W  I  G  W  V  R  Q  M  P  G
181  AAGGGTTCTGGATACAGGTTTACCAGCTACTGGATCGGCTGGGTGCGCCAGATGCCCGGG
         K  G  L  E  W  M  G  I  I  Y  P  G  D  S  D  T  R  Y  S  P
241  AAAGGCCTGGAGTGGATGGGGATCATCTATCCTGGTGACTCTGATACCAGATACAGCCCG
         S  F  Q  G  Q  V  T  I  S  A  D  K  S  I  S  T  A  Y  L  Q
301  TCCTTCCAAGGCCAGGTCACCATCTCAGCCGACAAGTCCATCAGCACCGCCTACCTGCAG
         W  S  S  L  K  A  S  D  T  A  M  Y  Y  C  A  R  K  D  Y  Y
361  TGGAGCAGCCTGAAGGCCTCGGACACCGCCATGTATTACTGTGCGAGAAAGGACTACTAC
         Y  Y  S  M  D  V  W  G  Q  G  T  T  V  T  V  S  S  A  S  T
421  TACTACAGTATGGACGTCTGGGGCCAAGGGACCACGGTCACCGTCTCCTCAGCCTCCACC
         K  G  P  S  V  F  P  L  A  P  S  S  K  S  T  S  G  G  T  A
481  AAGGGCCCATCGGTCTTCCCCCTGGCACCCTCCTCCAAGAGCACCTCTGGGGGCACAGCG
         A  L  G  C  L  V  K  D  Y  F  P  E  P  S  D  C  R  E  L
541  GCCCTGGGCTGCCTGGTCAAGGACTACTTCCCCGAACCGAGTGACGAGTGTCGTGAACTC
         S
601  AGCG
```

Figure 2AR The cDNA (SEQ ID NO:101) and amino acid sequence (SEQ ID NO:102) of Ha16-1(3,5)42 VL.

Double-underlined is part of the leader sequence, and underlined is a portion of the light chain constant region.

```
          G  L  G  Q  S  A  L  T  Q  P  A  S  V  S  G  S  P  G  Q  S
    1   GGTCTGGGCCAGTCTGCCCTGACTCAGCCTGCCTCCGTGTCTGGGTCTCCTGGACAGTCG
          I  T  I  S  C  T  G  T  S  S  D  V  G  R  F  N  Y  V  S  W
   61   ATCACCATCTCCTGCACTGGAACCAGCAGTGACGTTGGTCGTTTTAACTATGTCTCCTGG
          Y  Q  Q  R  P  G  K  A  P  K  L  M  I  Y  A  V  N  I  R  P
  121   TACCAACAGCGCCCAGGCAAAGCCCCCAAACTCATGATTTATGCGGTCAATATTCGGCCC
          S  G  V  S  N  R  F  S  G  S  K  S  G  N  T  A  S  L  T  I
  181   TCAGGGGTTTCTAATCGCTTCTCTGGCTCCAAGTCTGGCAACACGGCCTCCCTGACCATC
          S  G  L  Q  A  E  D  E  A  G  Y  Y  C  S  S  Y  T  S  S  S
  241   TCTGGGCTCCAGGCTGAGGACGAGGCTGGTTATTACTGCAGCTCATATACAAGCAGCAGC
          T  L  L  V  F  G  G  G  T  K  L  T  V  L  G  Q  P  K  A  A
  301   ACTCTTCTGGTTTTCGGCGGAGGGACCAAGCTGACCGTCCTGGGTCAGCCCAAGGCTGCC
          P  S  V  T  L  F  P  P  S  S  E  L  Q  A  N  K  A  T  L
  361   CCCTCGGTCACTCTGTTCCCGCCCTCCTCTGAGGAGCTTCAAGCCAACAAGGCCACACTG
          V  C  L  I  S  D  F  Y  P  G  A  V  T  V  A  W  K  A  D  S
  421   GTGTGTCTCATAAGTGACTTCTACCCGGGAGCCGTGACAGTGGCCTGGAAGGCAGATAGC
          S  P  V  K  A  G  V  E  T  T  T  P  S  K  Q  S  N  N  K  Y
  481   AGCCCCGTCAAGGCGGGAGTGGAGACCACCACACCCTCCAAACAAAGCAACAACAAGTAC
          A  A  S  S  Y  L  S  L  T  P  E  Q  W  K  S  H  R  S  Y  S
  541   GCGGCCAGCAGCTATCTGAGCCTGACGCCTGAGCAGTGGAAGTCCCACAGAAGCTACAGC
          C  Q  V  T  H  E  G  S  T  V  E  K  T  V  A  P  T
  601   TGCCAGGTCACGCATGAAGGGAGCACCGTGGAGAAGACAGTGGCCCCTACA
```

Figure 2AS The cDNA (SEQ ID NO:103) and amino acid sequence (SEQ ID NO:104) of H16-9.65 VH.

Double-underlined is the leader sequence, and underlined is a portion of the heavy chain constant region.

```
    1   CTGGGAGAGGAGCCCAGCACTAGAAGTCGGCGGTGTTTCCATTCGGTGATCAGCACTGAA
                                    M  E  F  G  L  S  W  V  F  L  V  A  L  L  R
   61   CACAGAGGACTCACCATGGAGTTTGGGCTGAGCTGGGTTTTCCTCGTTGCTCTTTTAAGA
          G  V  Q  C  Q  V  Q  L  V  E  S  G  G  G  V  V  Q  P  G  R
  121   GGTGTCCAGTGTCAGGTGCAGCTGGTGGAGTCTGGGGGAGGCGTGGTCCAGCCTGGGAGG
          S  L  R  L  S  C  A  A  S  G  F  T  F  S  S  Y  G  M  H  W
  181   TCCCTGAGACTCTCCTGTGCAGCGTCTGGATTCACCTTCAGTAGCTATGGCATGCACTGG
          V  R  Q  A  P  G  K  G  L  E  W  V  A  T  I  W  F  D  G  S
  241   GTCCGCCAGGCTCCAGGCAAGGGGCTGGAGTGGGTGGCAACTATATGGTTTGATGGAAGT
          N  G  Y  Y  A  D  S  V  K  G  R  F  T  I  S  R  D  N  S  K
  301   AATGGATACTATGCAGACTCCGTGAAGGGCCGATTCACCATCTCCAGAGACAATTCCAAG
          N  T  L  Y  L  Q  M  N  S  L  R  A  E  D  T  A  V  Y  Y  C
  361   AACACGTTGTATCTGCAAATGAACAGCCTGAGAGCCGAGGACACGGCTGTGTATTACTGT
          A  R  D  S  S  G  S  Y  D  H  F  D  Y  W  G  Q  G  T  L  V
  421   GCGAGAGACAGCAGTGGGAGCTACGACCACTTTGACTACTGGGGCCAGGGAACCCTGGTC
          T  V  S  S  A  S  T  K  G  P  S  V  F  P  L  A  P  C  S  R
  481   ACCGTCTCCTCAGCCTCCACCAAGGGCCCATCGGTCTTCCCCCTGGCGCCCTGCTCCAGG
          S  T  S  E  S  T  A  A  L  G  C  L  V  K  D  Y  F  P  E  P
  541   AGCACCTCCGAGAGCACAGCGGCCCTGGGCTGCCTGGTCAAGGACTACTTCCCCGAACCG
          V
  601   GTG
```

Figure 2AT The cDNA (SEQ ID NO:105) and amino acid sequence (SEQ ID NO:106) of H16-9.65 VL.

Double-underlined is part of the leader sequence, and underlined is a portion of the light chain constant region.

```
          D  Q  W  D  I  V  M  T  Q  S  P  L  S  L  P  V  T  P  G  E
    1   GATCAGTGGGATATTGTGATGACTCAGTCTCCACTCTCCCTGCCCGTCACCCCTGGAGAG
          P  A  S  I  S  C  R  S  S  Q  S  L  L  H  S  N  G  Y  N  C
   61   CCGGCCTCCATCTCCTGCAGGTCTAGTCAGAGCCTCCTGCATAGTAATGGATACAACTGT
          L  D  W  Y  L  Q  K  P  G  Q  S  P  Q  L  L  I  Y  L  G  S
  121   TTGGATTGGTACCTGCAGAAGCCAGGGCAGTCTCCACAGCTCCTGATCTATTTGGGTTCT
          N  R  A  S  G  V  P  D  R  F  S  G  S  G  S  G  T  D  F  T
  181   AATCGGGCCTCCGGGGTCCCTGACAGGTTCAGTGGCAGTGGATCAGGCACAGATTTTACA
```

Figure 2AT-2

```
        L   K   I   S   R   V   E   A   E   D   V   G   V   Y   Y   C   M   Q   A   L
241   CTGAAAATCAGCAGAGTGGAGGCTGAGGATGTTGGGGTTTATTACTGCATGCAAGCACTA
        Q   T   P   I   T   F   G   Q   G   T   R   V   E   I   K   R   T   V   A   A
301   CAAACTCCGATCACCTTCGGCCAAGGGACACGAGTGGAGATTAAACGAACTGTGGCTGCA
        P   S   V   F   I   F   P   P   S   D   E   Q   L   K   S   G   T   A   S   V
361   CCATCTGTCTTCATCTTCCCGCCATCTGATGAGCAGTTGAAATCTGGAACTGCCTCTGTT
        V   C   L   L   N   N   F   Y   P   R   E   A   K   V   Q   W   K   V   D   N
421   GTGTGCCTGCTGAATAACTTCTATCCCAGAGAGGCCAAAGTACAGTGGAAGGTGGATAAC
        A   L   Q   S   G   N   S   Q   E   S   V   T   E   Q   D   S   K   D   S   T
481   GCCCTCCAATCGGGTAACTCCCAGGAGAGTGTCACAGAGCAGGACAGCAAGGACAGCACC
        Y   S   L   S   S   T   L   T   L   S   K   A   D   Y   E   K   H   K   V   Y
541   TACAGCCTCAGCAGCACCCTGACGCTGAGCAAAGCAGACTACGAGAAACACAAAGTCTAC
        A   C   E   V   T   H   Q   G   L   S   S   P   V   T   K   S   F   N   R   G
601   GCCTGCGAAGTCACCCATCAGGGCCTGAGCTCGCCCGTCACAAAGAGCTTCAACAGGGGA
        E   C
661   GAGTGTTA
```

Figure 2AU  The cDNA (SEQ ID NO:107) and amino acid sequence (SEQ ID NO:108) of H16-1.29 VH. Underlined is a portion of the heavy chain constant region.

```
        C   R   L   V   E   S   G   A   E   V   K   K   P   G   A   S   V   K   V   S
  1   TGCAGGCTGGTGGAGTCTGGGGCTGAGGTGAAGAAGCCTGGGGCCTCAGTGAAGGTCTCC
        C   K   A   S   G   Y   T   F   T   G   Y   Y   M   H   W   V   R   Q   A   P
 61   TGCAAGGCTTCTGGATACACCTTCACCGGCTACTATATGCACTGGGTGCGACAGGCCCCT
        G   Q   G   L   E   W   M   G   W   I   N   P   N   S   G   G   T   N   Y   A
121   GGACAAGGGCTTGAGTGGATGGGATGGATCAACCCTAACAGTGGTGGCACAAACTATGCA
        Q   K   F   Q   G   R   V   T   M   T   R   D   T   S   I   S   T   A   Y   M
181   CAGAAGTTTCAGGGCAGGGTCACCATGACCAGGGACACGTCCATCAGCACAGCCTACATG
        E   L   S   R   L   R   S   D   D   T   A   V   Y   Y   C   A   R   D   Q   V
241   GAGCTGAGCAGGCTGAGATCTGACGACACGGCCGTGTATTACTGTGCGAGAGATCAGGTG
        D   I   V   A   T   R   Y   Y   Y   Y   Y   Y   G   M   D   V   W   G   Q   G
301   GATATAGTGGCTACCCGTTATTACTACTACTACTACGGTATGGACGTCTGGGGCCAAGGG
        T   T   V   T   V   S   S   A   S   T   K   G   P   S   V   F   P   L   A   P
361   ACCACGGTCACCGTCTCCTCAGCCTCCACCAAGGGCCCATCGGTCTTCCCCCTGGCACCC
        S   S   K   S   T
421   TCCTCCAAGAGCACC
```

Figure 2AV  The cDNA (SEQ ID NO:109) and amino acid sequence (SEQ ID NO:110) of H16-3.4 VH. Underlined is a portion of the heavy chain constant region.

```
        V   E   S   G   P   G   L   V   K   P   S   Q   T   L   S   L   T   C   T   V
  1   GTGGAGTCTGGCCCAGGACTGGTGAAGCCTTCACAGACCCTGTCCCTCACCTGCACTGTC
        S   G   G   S   I   S   S   G   G   Y   Y   W   S   W   I   R   Q   H   P   G
 61   TCTGGTGGCTCCATCAGCAGTGGTGGTTACTACTGGAGCTGGATCCGCCAGCACCCAGGG
        K   G   L   E   W   I   G   Y   I   Y   Y   S   G   S   T   Y   Y   N   P   S
121   AAGGGCCTGGAGTGGATTGGGTACATCTATTACAGTGGGAGCACCTACTACAACCCGTCC
        L   K   S   R   V   T   I   S   V   D   T   S   K   N   Q   F   S   L   K   L
181   CTCAAGAGTCGAGTTACCATATCAGTAGACACGTCTAAGAACCAGTTCTCCCTGAAGCTG
        S   S   V   T   A   A   D   T   A   V   Y   Y   C   A   R   V   D   I   V   A
241   AGCTCTGTGACTGCCGCGGACACGGCCGTGTATTACTGTGCGAGAGTGGATATAGTGGCT
        T   I   P   L   I   F   D   Y   W   G   Q   G   T   L   V   T   V   S   S   A
301   ACGATCCCACTTATCTTTGACTACTGGGGCCAGGGAACCCTGGTCACCGTCTCCTCAGCC
        S   T   K   G   P   S   V   F   P   L   A   P
361   TCCACCAAGGGCCCATCGGTCTTCCCCCTGGCACCCT
```

Figure 2AW  The cDNA (SEQ ID NO:111) and amino acid sequence (SEQ ID NO:112) of H16-1.92 VH.
Underlined is a portion of the heavy chain constant region.

```
        E  V  L  L  V  E  S  G  P  G  L  V  K  P  S  E  T  L  S  L
  1   GAGGTGCTGCTGGTGGAGTCTGGCCCAGGACTGGTGAAGCCTTCGGAGACCCTGTCCCTC
        T  C  T  V  S  G  G  S  I  S  S  S  S  Y  F  W  G  W  I  R
 61   ACCTGCACTGTCTCTGGTGGCTCCATCAGCAGTAGTAGTTACTTCTGGGGCTGGATCCGC
        Q  P  P  G  K  G  L  E  W  I  G  S  I  Y  Y  S  G  N  T  Y
121   CAGCCCCCAGGGAAGGGGCTGGAGTGGATTGGGAGTATCTATTATAGTGGAAACACCTAC
        Y  N  P  S  L  K  S  R  V  T  I  S  V  D  T  S  K  N  R  F
181   TACAACCCGTCCCTCAAGAGTCGAGTCACCATATCCGTAGACACGTCCAAGAACCGGTTC
        S  L  K  L  S  S  V  T  A  A  D  T  A  V  Y  C  C  A  S  A
241   TCCCTGAAGCTGAGCTCTGTGACCGCCGCAGACACGGCTGTGTATTGCTGTGCGAGCGCC
        T  T  V  T  T  A  F  D  I  W  G  Q  G  T  M  V  T  V  S  S
301   ACTACAGTAACTACAGCTTTTGATATCTGGGGCCAAGGGACAATGGTCACCGTCTCTTCA
        A  S  T  K  G  P  S  V  F  P  L  A  P  S  S
361   GCCTCCACCAAGGGCCCATCGGTCTTCCCCCTGGCACCCTCCTCCA
```

Figure 2AX  The cDNA (SEQ ID NO:113) and amino acid sequence (SEQ ID NO:114) of Ha16-1(3,5)19 VL.
Double-underlined is part of the leader sequence, and underlined is a portion of the light chain constant region.

```
        L  G  Q  S  A  L  T  Q  P  A  S  V  S  G  S  P  G  Q  S  I
  1   CTGGGCCAGTCTGCCCTGACTCAGCCTGCCTCCGTGTCTGGGTCTCCTGGACAGTCGATC
        T  I  S  C  T  G  T  S  S  D  V  G  R  Y  N  Y  V  S  W  Y
 61   ACCATCTCCTGTACTGGAACCAGCAGTGACGTTGGTCGTTATAACTATGTCTCCTGGTAC
        Q  Q  H  P  G  Q  A  P  K  L  M  I  Y  G  I  S  I  R  P  S
121   CAACAGCACCCAGGCCAAGCCCCCAAACTCATGATTTATGGGATCAGTATTCGGCCCTCA
        G  V  S  P  R  F  S  G  S  K  S  G  N  T  A  S  L  T  I  S
181   GGGGTTTCTCCTCGCTTCTCTGGCTCCAAGTCTGGCAACACGGCCTCCCTGACCATCTCT
        G  L  Q  A  E  D  E  A  D  Y  Y  C  S  S  H  T  S  N  S  T
241   GGGCTCCAGGCTGAGGACGAGGCTGATTATTACTGCAGCTCACATACAAGCAACAGCACT
        L  V  V  F  A  G  G  T  K  L  T  V  L  G  Q  P  K  A  A  P
301   CTTGTGGTATTCGCCGGAGGGACCAAACTGACCGTCCTAGGTCAGCCCAAGGCTGCCCCC
        S  V  T  L  F  P  P  S  S  E  E  L  Q  A  N  K  A  T  L  V
361   TCGGTCACTCTGTTCCCGCCCTCCTCTGAGGAGCTTCAAGCCAACAAGGCCACACTGGTG
        C  L  I  S  D  F  Y  P  G  A  V  T  V  A  W  K  A  D  S  S
421   TGTCTCATAAGTGACTTCTACCCGGGAGCCGTGACAGTGGCCTGGAAGGCAGATAGCAGC
        P  V  K  A  G  V  E  T  T  T  P  S  K  Q  S  N  N  K  Y  A
481   CCCGTCAAGGCGGGAGTGGAGACCACCACACCCTCCAAACAAAGCAACAACAAGTACGCG
        A  S  S  Y  L  S  L  T  P  E  Q  W  K  S  H  R  S  Y  S  C
541   GCCAGCAGCTATCTGAGCCTGACGCCTGAGCAGTGGAAGTCCCACAGAAGCTACAGCTGC
        Q  V  T  H  E  G  S  T  V  E  K  T  V  A  P  T
601   CAGGTCACGCATGAAGGGAGCACCGTGGAGAAGACAGTGGCCCCTACA
```

Figure 2AY  The cDNA (SEQ ID NO:169) and amino acid sequence (SEQ ID NO:170) of Ha16-1(3,5)19 VH.
Double-underlined is part of the leader sequence, and underlined is a portion of the light chain constant region.

```
  1   TGACATGGACTGAAGGAGTAGAAAAGAAGTCTCCCTCACTGCCCAGCTGGGATCTCAGGG
                        M  G  S  T  A  I  L  A  L  L  L  A
 61   CTTCATTTTCTGTCCTCCACCATCATGGGGTCAACCGCCATCCTCGCCCTCCTCCTGGCT
        V  L  Q  G  V  C  A  E  V  Q  L  V  Q  S  G  A  E  V  K  K
121   GTTCTCCAAGGAGTCTGTGCCGAGGTGCAGCTGGTGCAGTCTGGAGCAGAGGTGAAAAAG
        P  G  E  S  L  K  I  S  C  K  G  S  G  Y  R  F  T  S  Y  W
181   CCCGGGGAGTCTCTGAAGATCTCCTGTAAGGGTTCTGGATACAGGTTTACCAGCTACTGG
        I  G  W  V  R  Q  M  P  G  K  G  L  E  W  M  G  I  I  Y  P
241   ATCGGCTGGGTGCGCCAGATGCCCGGGAAAGGCCTGGAGTGGATGGGGATCATCTATCCT
        G  D  S  D  T  R  Y  S  P  S  F  Q  G  Q  V  T  I  S  A  D
301   GGTGACTCTGATACCAGATACAGCCCGTCCTTCCAAGGCCAGGTCACCATCTCAGCCGAC
```

Figure 2AY-2

```
       K  S  I  S  T  A  Y  L  Q  W  S  S  L  K  A  S  D  T  A  M
361    AAGTCCATCAGTACCGCCTACCTGCAGTGGAGCAGCCTGAAGGCCTCGGACACCGCCATG
       Y  Y  C  A  R  K  D  Y  Y  Y  Y  A  M  D  V  W  G  Q  G  T
421    TATTACTGTGCGAGAAAGGACTACTACTACTACGCTATGGACGTCTGGGGCCAAGGGACC
       T  V  T  V  S  S  A  S  T  K  G  P  S  V  F  P  L  A  P  S
481    ACGGTCACCGTCTCCTCAGCCTCCACCAAGGGCCCATCGGTCTTCCCCCTGGCACCCTCC
       S  K  S  T
541    TCCAAAAGCACC
```

Figure 2AZ The cDNA (SEQ ID NO:171) and amino acid sequence (SEQ ID NO:172) of Ha16-1.80 VH. Double-underlined is part of the leader sequence, and underlined is a portion of the light chain constant region.

```
                                                  M  K  H  L  W  F  F
  1    AAAAACTTTTTGAGAGTCCTGGACCTCCTGTGCAAGAACATGAAACATCTGTGGTTCTTC
       L  L  L  V  A  A  P  R  W  V  L  S  Q  V  Q  L  Q  E  S  G
 61    CTTCTCCTGGTGGCAGCTCCCAGATGGGTCCTGTCCCAGGTGCAGCTGCAGGAGTCGGGC
       P  G  L  V  K  P  S  E  T  L  S  L  T  C  T  V  S  G  G  S
121    CCAGGACTGGTGAAGCCTTCGGAGACCCTGTCCCTCACCTGCACTGTCTCTGGTGGCTCC
       I  S  S  Y  Y  W  S  W  I  R  Q  P  P  G  K  G  L  E  W  I
181    ATCAGTAGTTACTACTGGAGCTGGATCCGGCAGCCCCCAGGGAAGGGACTGGAGTGGATT
       G  Y  V  Y  F  S  G  S  T  N  Y  N  P  S  L  K  S  R  V  T
241    GGGTATGTCTATTTCAGTGGGAGCACCAACTACAACCCCTCCCTCAAGAGTCGAGTCACC
       I  S  V  D  T  S  K  N  Q  F  S  L  K  L  S  S  V  T  A  A
301    ATATCAGTAGACACGTCCAAGAACCAGTTCTCCCTGAAGCTGAGCTCTGTGACCGCTGCG
       D  T  A  V  Y  Y  C  A  R  A  T  R  D  Y  Y  Y  Y  G  M  D
361    GACACGGCCGTGTATTACTGTGCGAGAGCTACAAGAGACTACTACTACTACGGTATGGAC
       V  W  G  Q  G  T  T  V  T  V  S  S  A  S  T  K  G  P  S  V
421    GTCTGGGGCCAAGGGACCACGGTCACCGTCTCCTCAGCCTCCACCAAGGGCCCATCGGTC
       F  P  L  A  P  S  S  K  S  T  S  G  G  T  A  A  L  G  C  L
481    TTCCCCCTGGCACCCTCCTCCAAGAGCACCTCTGGGGGCACAGCGGCCCTGGGCTGCCTG
       V  K  D  Y  F  P  E  P  V  T  V  S  W  E  L  S
541    GTCAAGGACTACTTCCCCGAACCGGTGACGGTGTCGTGGGAACTCAGCG
```

Figure 2AAA The cDNA (SEQ ID NO:173) and amino acid sequence (SEQ ID NO:174) of Ha16-1.80 VL. Double-underlined is part of the leader sequence, and underlined is a portion of the light chain constant region.

```
          Q  L  L  G  L  L  L  L  W  L  R  G  A  R  C  D  I  Q  M  T
  1    CAGCTCCTGGGGCTCCTGCTACTCTGGCTCCGAGGTGCCAGATGTGACATCCAGATGACC
       Q  S  P  S  S  L  S  A  S  V  G  D  R  V  T  I  T  C  R  T
 61    CAGTCTCCATCCTCCCTGTCTGCATCTGTAGGAGACAGAGTCACCATCACTTGCCGGACA
       S  H  D  I  S  N  Y  L  N  W  Y  Q  Q  K  P  G  K  A  P  K
121    AGTCATGACATTAGTAACTATTTAAATTGGTATCAGCAGAAACCAGGGAAAGCCCCTAAG
       L  L  I  Y  A  A  S  S  L  Q  S  G  V  P  S  R  F  S  G  S
181    CTCCTGATCTATGCTGCATCCAGTTTGCAAAGTGGGGTCCCATCAAGGTTCAGTGGCAGT
       R  S  G  T  D  F  T  L  T  I  S  S  L  Q  P  E  D  F  A  T
241    AGATCTGGGACAGATTTCACTCTCACCATCAGCAGTCTGCAACCTGAAGATTTTGCAACT
       Y  Y  C  Q  Q  T  Y  S  T  L  F  T  F  G  P  G  T  K  V  D
301    TACTACTGTCAACAGACTTACAGTACCCTCTTCACTTTCGGCCCTGGGACCAAAGTGGAT
       I  K  R  T  V  A  A  P  S  V  F  I  F  P  P  S  D  E  Q  L
361    ATCAAACGAACTGTGGCTGCACCATCTGTCTTCATCTTCCCGCCATCTGATGAGCAGTTG
       K  S  G  T  A  S  V  V  C  L  L  N  N  F  Y  P  R  E  A  K
421    AAATCTGGAACTGCCTCTGTTGTGTGCCTGCTGAATAACTTCTATCCCAGAGAGGCCAAA
       V  Q  W  K  V  D  N  A  L  Q  S  G  N  S  Q  E  S  V  T  E
481    GTACAGTGGAAGGTGGATAACGCCCTCCAATCGGGTAACTCCCAGGAGAGTGTCACAGAG
       Q  D  S  K  D  S  T  Y  S  L  S  S  T  L  T  L  S  K  A  D
541    CAGGACAGCAAGGACAGCACCTACAGCCTCAGCAGCACCCTGACGCTGAGCAAAGCAGAC
       Y  E  K  H  K  V  Y  A  C  E  V  T  H  Q  G  L  S  S  P  V
601    TACGAGAAACACAAAGTCTACGCCTGCGAAGTCACCCATCAGGGCCTGAGCTCGCCCGTC
       T  K  S  F  N  R
661    ACAAAGAGCTTCAACAGGG
```

Figure 3:

Figure 3A  The amino acid sequence (SEQ ID NO:115) of H16-7.213 VH. Underlined is a portion of the heavy chain constant region.

```
  1 WGLSEVSCKA SGYTFTGYYM HWVRQAPGQG LEWMGWINPN SGGTNYAQKF QGRVTMTRDT
 61 SISTAYMELS RLRSDDTAVY YCARELRYFG WLLSSLDYWG QGTLVTVSSA STKGPSVFPL
121 APCSRSTSES TAALGCLVKD YFPEPVTVSW NSGALTSGVH TFPAVLQSSG LYSLSSVVTV
181 PSSNFGTQTY TCNVDHKPSN TKVDKTVERK CCVECPPCPA PPVAGPSVFL FPPKPKDTLM
241 ISRTPEVTCV VVDVSHEDPE VQFNWYVDGV EVHNAKTKPR EEQFNSTFRV VSVLTVVHQD
301 WLNGKEYKCK VSNKGLPAPI EKTISKTKGQ PREPQVYTLP PSREEMTKNQ VSLTCLVKGF
361 YPSDIAVEWE SNGQPENNYK TTPPMLDSDG SFFLYSKLTV DKSRWQQGNV FSCSVMHEAL
421 E
```

Figure 3B  The amino acid sequence (SEQ ID NO:116) of H16-7.213 VL. Underlined is a portion of the light Chain constant region.

```
  1 LLGLLLLWLR GARCDIQMTQ SPSSLSASVG DRVTITCRAS QSISSYLNWF QQKPGKAPKL
 61 LIYAASSLQS GVPSRFSGSE SGTDFTLTIS SLQPEDFATY SCQQSYSFPL TFGGGTKVEI
121 KRTVAAPSVF IFPPSDEQLK SGTASVVCLL NNFYPREAKV QWKVDNALQS GNSQESVTEQ
181 DSKDSTYSLS STLTLSKADY EKHKVYACEV THQGLSSPVT KSFNRG
```

Figure 3C  The amino acid sequence (SEQ ID NO:117) of H16-9.69 VH. Underlined is a portion of the heavy chain constant region.

```
  1 WGLSEVSCKA SGYTFTSYDI HWVRQATGQG LEWMGWMNPN SGNTVYAQKF QGRVTMTRNT
 61 SISTAYMELS SLRSEDTAVY YCARTVLLWP FDYWGQGTLV TVSSASTKGP SVFPLAPCSR
121 STSESTAALG CLVKDYFPEP VTVSWNSGAL TSGVHTFPAV LQSSGLYSLS SVVTVPSSNF
181 GTQTYTCNVD HKPSNTKVDK TVERKCCVEC PPCPAPPVAG PSVFLFPPKP KDTLMISRTP
241 EVTCVVVDVS HEDPEVQFNW YVDGVEVHNA KTKPREEQFN STFRVVSVLT VVHQDWLNGK
301 EYKCKVSNKG LPAPIEKTIS KTKGQPREPQ VYTLPPSREE MTKNQVSLTC LVKGFYPSDI
361 AVEWESNGQP ENNYKTTPPM LDSDGSFFLY SKLTVDKSR
```

Figure 3D  The amino acid sequence (SEQ ID NO:118) of H16-9.69 VL. Underlined is a portion of the light chain constant region.

```
  1 WISGAYGDIV MTQSPDSLAV SLGERATINC KSSQSVLYSS KNKNYLAWYQ QKPGQPPKLL
 61 IYWASTRESG VPDRFSGSGS GTDFTLTISS LQAEDVAVYY CQQYYSTPPW TFGQGTKVEI
121 KRTVAAPSVF IFPPSDEQLK SGTASVVCLL NNFYPREAKV QWKVDNALQS GNSQESVTEQ
181 DSKDSTYSLS STLTLSKADY EKHKVYACEV THQGLSSPVT KSFNRGE
```

Figure 3E  The amino acid sequence (SEQ ID NO:119) of H16-1.52 VH. Underlined is a portion of the heavy chain constant region.

```
  1 SGGGLVQPGG SLRLSCAASG FTFSSYAMSW VRQAPGKGLE WVSAISGSDG SPYYADSVKG
 61 RFTISRDNSK NTLYLQMNSL RAEDTAVYYC AKDGYSSGWN YFDYWGQGTL VTVSSASTKG
121 PSVFPLAP
```

Figure 3F  The amino acid sequence (SEQ ID NO:120) of H16-1.52 VL.  Underlined is a portion of the light chain constant region.

```
  1 WISGAYGDIV MTQSPDSLAV SLGERATINC KSSQSVLYSS NNKNYLAWYQ QKPGQPPKLL
 61 IYWASTRESG VPDRFSGSGS GTDFTLTISS LQAEDVAVYY CQEYYSTMCS FGQGTKLEIK
121 RTVAAPSVFI FPPSDEQLKS GTASVVCLLN NFYPREAKVQ WKVDNALQSG NSQESVTEQD
181 SKDSTYSLSS TLTLSKADYE KHKVYACEVT HQGLSSPVTK SFNRGE
```

Figure 3G  The amino acid sequence (SEQ ID. NO:121) of Ha16-1(1)23 VH.  Underlined is a portion of the heavy chain constant region.

```
  1 VESGGGVVQP GRSLRLSCAA SGFTFRSYGM HWVRQAPGKG LEWVAVIWSD GSNKYYADSV
 61 KGRFTISRDN SKNTLYLQMN SLRAEDTAVY YCAREGYYGS GSYYYYYGMD VWGQGTTVTV
121 SSASTKGPSV FPLAPS
```

Figure 3H  The amino acid sequence (SEQ ID NO:122) of Ha16-1(1)23 VL.  Underlined is a portion of the light chain constant region.

```
  1 LLTLLLTHSAV SVVQAGLTQP PSVSKGLRQT ATLTCTGNSN NVGTQGAAWL QQHQGHPPKL
 61 LSYRNNNRPS GISERLSAST SGNTASLTIT GLQPEDEADY YCSAWDSSLS AVVFGGGTKL
121 TVLGQPKAAP SVTLFPPSSE ELQANKATLV CLISDFYPGA VTVAWKADSS PVKAGVETTT
181 PSKQSNNKYA ASSYLSLTPE QWKSHRSYSC QVTHEGSTVE KTVAPT
```

Figure 3I  The amino acid sequence (SEQ ID NO:123) of H16-9.44 VH.  Underlined is a portion of the heavy chain constant region.

```
  1 LSLTCTVSGG SISSYYWSWI RQSAGKGLEW IGRIYTGVST NYNPSLKSRV TMSVDTSKNQ
 61 FSLKLSSVTA ADTAVYYCAR DYYDSSGYYP FDYWGQGTLV TVSSASTKGP SVFPLAPCSR
121 STSESTAALG CLVKDYFPEP VTVSWNSGAL TSGVHTFPAV LQSSGLYSLS SVVTVPSSNF
181 GTQTYTCNVD HKPSNTKVDK TVERKCCVEC PPCPAPPVAG PSVFLFPPKP KDTLMISRTP
241 EVTCVVVDVS HEDPEVQFNW YVDGVEVHNA KTKPREEQFN STFRVVSVLT VVHQDWLNGK
301 EYKCKVSNKG LPAPIEKTIS KTKGQPREPQ VYTLPPSREE MTKNQVSLTC LVKGFYPSDI
361 AVEWESNGQP ENNYKTTPPM LDSDGSFFLY SKLTVDKSRW QQGNVFSCSV MHEALH
```

Figure 3J  The amino acid sequence (SEQ ID NO:124) of H16-9.44 VL.  Underlined is a portion of the light chain constant region.

```
  1 LLGLLLLCFP GARCDIQMTQ SPSSLSASVG DRVTISCRAS QGISNYLAWF QQKPGKAPKS
 61 LIYAASSLEN GVPSKFSGSG SGTDFTLTIS SLQPEDFATY YCQQYNSSPF TFGPGTKVDI
121 RRTVAAPSVF IFPPSDEQLK SGTASVVCLL NNFYPREAKV QWKVDNALQS GNSQESVTEQ
181 DSKDSTYSLS STLTLSKADY EKHKVYACEV THQGLSSPVT KSFNRG
```

Figure 3K The amino acid sequence (SEQ ID NO:125) of H16-1.67 VH. Underlined is a portion of the heavy chain constant region.

```
  1 VESGPGLVKP SQTLSLTCTV SGGSINSFGY YWSWIRQYPG KGLEWIGFLY FTGSTYYNPS
 61 LKSRVTISVD TSKSQFSLKL SSVTAADTAV YYCARAGTMV RGAHYYGMDV WGQGTTVTVS
121 SASTKGPSVF PLAPS
```

Figure 3L The amino acid sequence (SEQ ID NO:126) of H16-1.67 VL. Underlined is the light chain constant region.

```
  1 QLLGLLLLWL RGGRCDIQMT QSPSSLSASV GDRVTITCRA SQSISNYLNW YQQKPGKAPK
 61 LLIYAASSLQ SGVPSRFSGS GSGTDFTLTI SSLQPEDFAT YYCQQIYSTP PEWTFGQGTK
121 VEIKRTVAAP SVFIFPPSDE QLKSGTASVV CLLNNFYPRE AKVQWKVDNA LQSGNSQESV
181 TEQDSKDSTY SLSSTLTLSK ADYEKHKVYA CEVTHQGLSS PVTKSFNRGE C
```

Figure 3M The amino acid sequence (SEQ ID NO:127) of Ha16-1(3,5)36 VH. Underlined is a portion of the heavy chain constant region.

```
  1 EVQLVESGPG LVKPSETLSL TCTVSGGSIS SSSYYWGWIR QPPGKGLEWI GSMYYSGSTY
 61 HNPSLKSRVT ISVDTSKNQF SLKLSSVTAA DTAVYYCARH YTTVAGTFDY WGQGTLVTVS
121 SASTKGPSVF PLAPSS
```

Figure 3N The amino acid sequence (SEQ ID NO:128) of Ha16-1(3,5)36 VL. Underlined is a portion of the light chain constant region.

```
  1 LLTLLLTHCAG SWAQSVLTQP PSASGTPGQR ATISCSGSST NIGSTIVNWY QQVPGTAPKL
 61 LIYSNNQRPS GVPDRFSGSK SGTSASLAIS GLQSEDEADY YCAAWDASLN GPVFGGGTKL
121 TVLGQPKAAP SVTLFPPSSE ELQANKATLV CLISDFYPGA VTVAWKADSS PVKAGVETTT
181 PSKQSNNKYA ASSYLSLTPE QWKSHRSYSC QVTHEGSTVE KTVAPT
```

Figure 3O The amino acid sequence (SEQ ID NO:129) of H16-1.86 VH. Underlined is a portion of the heavy chain constant region.

```
  1 VESGPGLVKP SETLSLTCTV SGGSISSYYW SWIRQPPGKG LEWIGYIYYS GSTNYNPSLK
 61 SRVTISVDTS KNQFSLKLSS VTAADTAVYY CARAYGYYYY GMDVWGQGTT VTVSSASTKG
121 PSVFPLAPS
```

Figure 3P The amino acid sequence (SEQ ID NO:130) of H16-1.86 VL. Underlined is a portion of the light chain constant region.

```
  1 QLLGLLLLWL RGARCDIQMT QSPSSLSASV GDRVTITCRT SQSISSYLNW YQQKPGKAPN
 61 LLIYAASSLQ SGVPSRFSGS GSGTDFTLTI SSLQPEDFAT YYCQQTYSSP PWTFGQGTKV
121 EIKRTVAAPS VFIFPPSDEQ LKSGTASVVC LLNNFYPREA KVQWKVDNAL QSGNSQESVT
181 EQDSKDSTYS LSSTLTLSKA DYEKHKVYAC EVTHQGLSSP VTKSFNRG
```

Figure 3Q The amino acid sequence (SEQ ID NO:131) of H16-9.10 VH. Underlined is a portion of the heavy chain constant region.

```
  1 LLESGPGLVK PSQTLSLTCA ISGDSVSSNS AAWNWIRQSP SRGLEWLGRT YYRSKWYNAY
 61 AVSVKSRMTI NPDTSKNQFS LQLNSVTPED TAVYYCAREA GGWFDPWGQG TLVTVSSAST
121 K
```

Figure 3R The amino acid sequence (SEQ ID NO:132) of H16-9.10 VL. Underlined is a portion of the light chain constant region.

```
  1 QLLGLLLLWF PGSRCDIQMT QSPSSVSASV GDRVTITCRA SQGIRSWLAW YQQKPGKAPK
 61 LLIYAASSLQ SGVPSRFSGS GSGTDFTLTI SSLQPEDFAT YYCQQANSFP PTFGGGTKVE
121 IKRTVAAPSV FIFPPSDEQL KSGTASVVCL LNNFYPREAK VQWKVDNALQ SGNSQESVTE
181 QDSKDSTYSL SSTLTLSKAD YEKHKVYACE VTHQGLSSPV TKSFNRG
```

Figure 3S The amino acid sequence (SEQ ID NO:133) of H16-9.33 VH. Underlined is a portion of the heavy chain constant region.

```
  1 EVQLLESGPG LVKPSQTLSL TCAISGDSVS SNSAAWNWIR QSPSRGLEWL GRTYYRSKYY
 61 NAYPVSVKSR ITINPDTSKN QFSLQLNSVT PEDTAVYYCA REAGGWFDPW GQGTLVTVSS
121 AST
```

Figure 3T The amino acid sequence (SEQ ID NO:134) of H16-9.33 VL. Underlined is a portion of the light chain constant region.

```
  1 LLGLLLLWFP GSRCDIQMTQ SPSSVSASVG DRVTITCRAN QGIRSWLAWY QQKPGKAPKL
 61 LIYAASSLQS GVPSRFSGSG SGTDFTLTIS SLQPEDFATY YCQQANSFPP TFGGGTKVEI
121 KRTVAAPSVF IFPPSDEQLK SGTASVVCLL NNFYPREAKV QWKVDNALQS GNSQESVTEQ
181 DSKDSTYSLS STLTLSKADY EKHKVYACEV THQGLSSPVT KSFNR
```

Figure 3U The amino acid sequence (SEQ ID NO:135) of H16-1.68 VH. Underlined is a portion of the heavy chain constant region.

```
  1 EVHLVESGGG VVQPGRSLRL SCAASGFTFR SYGMHWVRQA PGKGLEWVAV IWYDGSNKYY
 61 ADSVKGRFTI SRDNSKNTLY LQMNSLRAED MAMYYCARSR ITIFGVVHYG MDVWGQGTTV
121 TVSSASTKGP SVFPLAPSSK ST
```

Figure 3V The amino acid sequence (SEQ ID NO:136) of H16-1.68 VL. Underlined is a portion of the light chain constant region.

```
  1 TQLTQSPSSL SASVGDRVTI TCRASQNINS YLNWYQQKPG KAPKLLIYAA SSLQSGVPSR
 61 FSGSGSGTDF TLTISSLQPE DFTTYYCQQS YSSAPTFGGG TKLEIKRTVA APSVFIFPPS
121 DEQLKSGTAS VVCLLNNFYP REAKVQWKVD NALQSG
```

Figure 3W The amino acid sequence (SEQ ID NO:137) of Ha16-1(1)11 VH. Underlined is a portion of the heavy chain constant region.

```
  1  GPGLVKPSET LSLTCTVSGG SISSYYWSWI RQPPGKGLEW IGYIYYSGST NYNPSLKSRV
 61  TISVDTSKNQ FSLKLSSVTA ADTAVYYCAR AVSYYYYGMD VWGQGTTVTV SSASTKGPSV
121  FPLAPSSKST
```

Figure 3X The amino acid sequence (SEQ ID NO:138) of Ha16-1(1)11 VL. Underlined is a portion of the light chain constant region.

```
  1  VPAQLLGLLL LWLRGARCDI QMTQSPSSLS ASVGDRVTIT CRTIQNINSY LNWYQQRPGK
 61  APKLLIYATS SLQSGVPSRF SGSGSGTDFT LTISSLQPED FATYYCQQTY STLFTFGPGT
121  KVDIKRTVAA PSVFIFPPSD EQLKSGTASV VCLLNNFYPR EAKVQWKVDN ALQSGNSQES
181  VTEQDSKDST YSLSSTLTLS KADYEKHKVY ACEVTHQGLS SPVTKSFNRG EWLE
```

Figure 3Y The amino acid sequence (SEQ ID NO:139) of Ha16-1(3,5)18 heavy chain. Underlined is the leader sequence. Double-underlined is the heavy chain variable region. Dashed underline shows the human IgG1 constant region.

```
  1  MDLLHKNMKH LWFFLLLVAA PRWVLSQVQL QESGPGLVKP SETLSLTCTV
 51  PGGSIRSYFW SWIRQPAGKG LEWIGRFYFS GSTNYNPSLK SRVTMSVDTS
101  KNQFSLKLSS VTAADTAVYY CARDYGDHYY YYGMDVWGQG TTVTVSSAST
151  KGPSVFPLAP SSKSTSGGTA ALGCLVKDYF PEPVTVSWNS GALTSGVHTF
201  PAVLQSSGLY SLSSVVTVPS SSLGTQTYIC NVNHKPSNTK VDKRVEPKSC
251  DKTHTCPPCP APELLGGPSV FLFPPKPKDT LMISRTPEVT CVVVDVSHED
301  PEVKFNWYVD GVEVHNAKTK PREEQYNSTY RVVSVLTVLH QDWLNGKEYK
351  CKVSNKALPA PIEKTISKAK GQPREPQVYT LPPSREEMTK NQVSLTCLVK
401  GFYPSDIAVE WESNGQPENN YKTTPPVLDS DGSFFLYSKL TVDKSRWQQG
451  NVFSCSVMHE ALHNHYTQKS LSLSPGK
```

Figure 3Z The amino acid sequence (SEQ ID NO:140) of Ha16-1(3,5)18 light chain. Double underlined is the light chain variable region. Dashed underline shows the human Ig lambda constant region.

```
  1  QSVLTQPPSV SAAPGQKVTI SCSGSSSNIG NNYVSWYQQF PGTAPKFLIY
 51  DNNKRSSGIP DRFSGSKSGT SATLGITGLQ TGDEADYYCG TWDSSLSAVI
101  FGGGTKLTVL GQPKAAPSVT LFPPSSEELQ ANKATLVCLI SDFYPGAVTV
151  AWKADSSPVK AGVETTTPSK QSNNKYAASS YLSLTPEQWK SHRSYSCQVT
201  HEGSTVEKTV APTECS
```

Figure 3AA The amino acid sequence (SEQ ID.NO:141) of Ha16-1(2,4)4 VH.

```
  1  GFTFSSYGMH WVRQAPGKGL EWVAIIWYDE SNKYYADSVK GRFTISRDNS KNTLYLQMNS
 61  LRAEDTAVYY CARAYSGSYG YSYYGM
```

Figure 3AB The amino acid sequence (SEQ ID NO:142) of Ha16-1(2,4)4 VL. Underlined is a portion of the light chain constant region.

```
  1  QDRQPASPGS GDKLGDKYAC WYQQKPGQSP VLVIYQDSKR PSGIPERFSG SNSGNTATLT
 61  ISGTQAMDEA DYYCQAWDNR TAVFGGGTKL TVLGQPKAAP SVTLFPPSSE ELQANKATLV
121  CLISDFYPGA VTVAWKADSS PVKAGVETTT PSKQSNNKYA ASSYLSLTPE QWKSHRSYSC
181  Q
```

Figure 3AC The amino acid sequence (SEQ ID NO:143) of Ha16-1(3,5)56 VH.

```
  1  RCRLVESGAE VKKPGESLKI SCKGSGYRFT SYWIGWVRQM PGKGLEWMGI IYPGDSDTRY
 61  SPSFQGQVTI SADKSISTAY LQWRSLKASD TAMYYCARKD YYYYVMDVWG QGTTVTVSSA
121  STKGPSVFPL APS
```

Figure 3AD The amino acid sequence (SEQ ID NO:144) of Ha16-1(3,5)56 VL. Underlined is a portion of the light chain constant region.

```
  1  DTISCTGTSS DVGNYNYVSW YQQHPGKAPK LMIYAVNKRP SGVSNRFSGS KSGNTASLTI
 61  SGLQAEDEAD YYCSSYTSSR NLVVFGGGTK LTVLGQPKAA PSVTLFPPSS EELQANKATL
121  VCLISDFYPG AVTVAWKADS SPVKAGVETT TPSKQSNNKY AASSYLSLTP EQWKSHRSYS
181  CQVTHEGSTV EKTVAPT
```

Figure 3AE The amino acid sequence (SEQ ID NO:145) of H16-7.8 VH. Double-underlined is the leader sequence. Underlined is a portion of the light chain constant region.

```
  1  MKHLWFFLLL VAAPRWVLSQ VQLQESGPGL VKPSQTLSLT CTVSGGSISS GGYYWSWIRQ
 61  HPGKGLEWIG IIYYSGSTYY NPSLKSRVTI SVDTSKNQFS LKLNSVTAAD TAVFYCARVA
121  IVTTIPGGMD VWGQGTTVTV SSASTKGPSV FPLAPCSRST SESTAALGCL VKDYFPEPVT
181  VSWNSGALTS GVHTFPAVLQ SSGLYSLSSV VTVPSSNFGT QTYTCNVDHK PSNTKVDKTV
241  ERKCCVECPP CPAPPVAGPS VFLFPPKPKD TLMISRTPEV TCVVVDVSHE DPEVQFNWYV
301  DGVEVHNAKT KPREEQFNST FRVVSVLTVV HQDWLNGKEY KCKVSNKGLP APIEKTISKT
361  KGQPREPQVY TLPPSREEMT KNQVSLTCLV KGFYPSDIAV EWESNGQPEN NYKTTPPMLD
421  SDGSFFLYSK LTVDKSRWQQ GNVFSCSVMH EALH
```

Figure 3AF The amino acid sequence (SEQ ID NO:146) of H16-7.8 VL. Double-underlined is the leader sequence. Underlined is a portion of the light chain constant region.

```
  1  MLPSQLIGFL LLWVPASRGE IVLTQSPDFQ SVTPKEKVTI TCRASQSIGI SLHWYQQKPD
 61  QSPKLLIKYA SQSFSGVPSR FSGSGSGTDF TLTINSLEAE DAATYYCHQS RSFPWTFGQG
121  TKVEIKRTVA APSVFIFPPS DEQLKSGTAS VVCLLNNFYP REAKVQWKVD NALQSGNSQE
181  SVTEQDSKDS TYSLSSTLTL SKADYEKHKV YACEVTHQG
```

Figure 3AG  The amino acid sequence (SEQ ID NO:147) of H16-1.93 VH.  Double-underlined is the leader sequence.  Underlined is a portion of the light chain constant region.

```
  1    MDWTWSILFL VAAATGAHSQ VQLVQSGAEV KKPGASVKVS CKASGYTFTS YGISWVRQAP
 61    GQGLEWMGWI SAYNGNTYYA QKLQARVTMT TDTSTSTAYM ELRSLRSDDT AVYYCARDGY
121    SSSWSLLHYY GMDVWGQGTT VTVSSASTKG PSVFPLAPSS KSTSGGTAAL GCLVKDYFPE
181    PVTVSWNSA
```

Figure 3AH  The amino acid sequence (SEQ ID NO:148) of H16-1.93 VL.  Double-underlined is part of the leader sequence.  Underlined is a portion of the light chain constant region.

```
  1    SDTRCDIQMT QSPSSLSASV GDRITITWRS SQGIYNSLAW YQQKPGKVPK LLIYAASTLH
 61    SGVPSRFSGS GSGTDFTLTI SSLQPEDVAT YYCQKYNSAP FTFGPGTKVD IKRTVAAPSV
121    FIFPPSDEQL KSGTASVVCL LNNFYPREAK VQWKVDNALQ SGNSQESVTE QDSKDSTYSL
181    SSTLTLSKAD YEKHKVYACE VTHQGLSSPV TKSFNRG
```

Figure 3AI  The amino acid sequence (SEQ ID NO:149) of Ha16-1(3,5)27.1 VH.  Double-underlined is part of the leader sequence, and underlined is a portion of the heavy chain constant region.

```
  1    LVESGAEVKK PGESLKISCK GSGYRFTSYW IGWVRQMPGK GLEWMGIIYP
 51    GDSDTRYSPS FQGQVTISAD KSISTAYLQW SSLKASDTAM YYCARKDYYY
101    YSMDVWGQGT TVTVSSASTK GPSVFPLEPS SK
```

Figure 3AJ  The amino acid sequence (SEQ ID NO:150) of Ha16-1(3,5)27 VL.  Underlined is a portion of the light chain constant region.

```
  1    GQSALTQPAS VSGSPGQSIT ISCTGTSSDV GGYNYVSWYQ QHPGQAPKLL
 51    IYGVNIRPSG VSTRFSGSKS GNTASLTISG LQAEDEADYY CSSYTRSSIL
101    VVFAGGTKLT VLGQPKAAPS VTLFPPSSEE LQANKATLVC LISDFYPGAV
151    TVAWKADSSP VKAGVETTTP SKQSNNKYAA SSYLSLTPEQ
```

Figure 3AK  The amino acid sequence (SEQ ID NO:151) of H16-1.61 VH.  Underlined is a portion of the heavy chain constant region.

```
  1    EVQLVESGGG VVQPGRSLRL SCAASGFTFS SYGMHWVRQA PGKGLEWVAV
 51    IWYDGSNKYY ADSVKGRFTI SRDNSKNTLY LQMNSLRAED TAVYYCARSR
101    ITIFGVVHYG MDVWGQGTTV TVSSASTKGP SVFPLAPSSK ST
```

Figure 3AL  The amino acid sequence (SEQ ID NO:152) of H16-1.61 VL.  Underlined is a portion of the light chain constant region.

```
  1    DTQLTQSPSS LSASVGDRVT ITCRASQSIS SYLNWYQLKP GKAPKLLIYA
 51    ASSLESGVPS RFSGSESGTD FTLTISSLQP EDFATYYCQQ SYNSPITFGP
101    GTKVDIKRTV AAPSVFIFPP SDEQLKSGTA SVVCLLNNFY PREAKVQWKV
151    DNALQS
```

Figure 3AM The amino acid sequence (SEQ ID NO:153) of H16-1(3,5)5 VH. Double-underlined is the leader sequence, and underlined is a portion of the heavy chain constant region.

```
  1    MGSTAILALL LAVLQGVCAE VQLVQSGAEV KKPGESLKIS CKGSGYRFTS
 51    YWIGWVRQMP GKGLEWMGII YPGDSDTRYS PSFQGQVTIS ADKSISTAYL
101    QWSSLKASDT AMYYCARKDY YYYTMDVWGQ GTTVTVSSAS TKGPSVFPLA
151    PSSKSTSGGT AALGCLVKDY FPEPVTVS
```

Figure 3AN The amino acid sequence (SEQ ID NO:154) of H16-1(3,5)5 VL. Double-underlined is part of the leader sequence, and underlined is a portion of the light chain constant region.

```
  1    LGQSALTQPA SVSGSPGQSI TISCTGTSSD VGGYNYVSWY QQHPGKAPKL
 51    MIYAVSNRPS GVSNRFSGSK SGNTASLTIS GLQAEDEADY YCSSYTISRI
101    LVVFGGGTKL TVLGQPKAAP SVTLFPPSSE ELQANKATLV CLISDFYPGA
151    VTVAWKADSS PVKAGVETTT PSKQSNNKYA ASSYLSLTPE QWKSHRSYSC
201    QVTHEGSTVE KTVAPT
```

Figure 3AO The amino acid sequence (SEQ ID NO:155) of H16-7.200 VH. Double-underlined is the leader sequence, and underlined is a portion of the heavy chain constant region.

```
  1    MKHLWFFLLL VAAPRWVLSQ VQLQESGPGL VKPSQTLSLT CTVSGGSITS
 51    GDYYWSWIRQ HPGKGLEWFG FIYYSGSAYY NPSLKSRITI SVDTSKNQFS
101    LKLSSVTAAD TAVYYCARER NYGGNSFDYW GQGTLVTVSS ASTKGPSVFP
151    LAPCSRSTSE STAALGCLVK DYFPEPVTVS WNSGALTSGV HTFPAVLQSS
201    GLYSLSSVVT VPSST
```

Figure 3AP The amino acid sequence (SEQ ID NO:156) of H16-7.200 VL. Double-underlined is part of the leader sequence, and underlined is a portion of the light chain constant region.

```
  1    WISGSSGDIV MTQSPLSLPV TPGEPASISC RSSQSLLHSN GYNYLDWYLQ
 51    KPGQSPQLLI YLGSNRASGV PDRFSGSGSG TDFTLKISRV EAEDVGVYYC
101    MQALQTITFG QGTRLEIKRT VAAPSVFIFP PSDEQLKSGT ASVVCLLNNF
151    YPREAKVQWK VDNALQSGNS QESVTEQDSK DSTYSLSSTL TLSKADYEKH
201    KVYACEVTHQ XLSSPVTKSF NRG
```

Figure 3AQ The amino acid sequence (SEQ ID NO:157) of Ha16-1(3,5)42 VH. Double-underlined is the leader sequence, and underlined is a portion of the heavy chain constant region.

```
  1    MGSTAILALL LAVLQGVCAE VQLVQSGAEV KKPGESLKIS CKGSGYRFTS
 51    YWIGWVRQMP GKGLEWMGII YPGDSDTRYS PSFQGQVTIS ADKSISTAYL
101    QWSSLKASDT AMYYCARKDY YYYSMDVWGQ GTTVTVSSAS TKGPSVFPLA
151    PSSKSTSGGT AALGCLVKDY FPEPSDECRE LS
```

Figure 3AR The amino acid sequence (SEQ ID NO:158) of Ha16-1(3,5)42 VL. Double-underlined is part of the leader sequence, and underlined is a portion of the light chain constant region.

```
  1   GLGQSALTQP ASVSGSPGQS ITISCTGTSS DVGRFNYVSW YQQRPGKAPK
 51   LMIYAVNLRP SGVSNRFSGS KSGNTASLTI SGLQAEDEAG YYCSSYTSSS
101   TLLVFGGGTK LTVLGQPKAA PSVTLFPPSS EELQANKATL VCLISDFYPG
151   AVTVAWKADS SPVKAGVETT TPSKQSNNKY AASSYLSLTP EQWKSHRSYS
201   CQVTHEGSTV EKTVAPT
```

Figure 3AS The amino acid sequence (SEQ ID NO:159) of H16-9.65 VH. Double-underlined is the leader sequence, and underlined is a portion of the heavy chain constant region.

```
  1   MEFGLSWVFL VALLRGVQCQ VQLVESGGGV VQPGRSLRLS CAASGFTFSS
 51   YGMHWVRQAP GKGLEWVATI WFDGSNGYYA DSVKGRFTIS RDNSKNTLYL
101   QMNSLRAEDT AVYYCARDSS GSYDHFDYWG QGTLVIVSSA STKGPSVFPL
151   APCSRSTSES TAALGCLVKD YFPEPV
```

Figure 3AT The amino acid sequence (SEQ ID NO:160) of H16-9.65 VL. Double-underlined is part of the leader sequence, and underlined is a portion of the light chain constant region.

```
  1   DQWDIVMTQS PLSLPVTPGE PASISCRSSQ SLLHSNGYNC LDWYLQKPGQ
 51   SPQLLIYLGS NRASGVPDRF SGSGSGTDFT LKISRVEAED VGVYYCMQAL
101   QTPITFGQGT RVEIKRTVAA PSVFIFPPSD EQLKSGTASV VCLLNNFYPR
151   EAKVQWKVDN ALQSGNSQES VTEQDSKDST YSLSSTLTLS KADYEKHKVY
201   ACEVTHQGLS SPVTKSFNRG EC
```

Figure 3AU The amino acid sequence (SEQ ID NO:161) of H16-1.29 VH. Double-underlined is part of the leader sequence, and underlined is a portion of the heavy chain constant region.

```
  1   CRLVESGAEV KKPGASVKVS CKASGYTFTG YYMHWVRQAP GQGLEWMGWI
 51   NPNSGGTNYA QKFQGRVTMT RDTSISTAYM ELSRLRSDDT AVYYCARDQV
101   DIVATRYYYY YYGMDVWGQG TTVTVSSAST KGPSVFPLAP SSKST
```

Figure 3AV The amino acid sequence (SEQ ID NO:162) of H16-3.4 VH. Underlined is a portion of the heavy chain constant region.

```
  1   VESGPGLVKP SQTLSLTCTV SGGSISSGGY YWSWIRQHPG KGLEWIGYIY
 51   YSGSTYYNPS LKSRVTISVD TSKNQFSLKL SSVTAADTAV YYCARVDIVA
101   TIPLIFDYWG QGTLVTVSSA STKGPSVFPL AP
```

Figure 3AW The amino acid sequence (SEQ ID NO:163) of H16-1.92 VH. Underlined is a portion of the heavy chain constant region.

```
  1   EVLLVESGPG LVKPSETLSL TCTVSGGSIS SSSYFWGWIR QPPGKGLEWI
 51   GSIYYSGNTY YNPSLKSRVT ISVDTSKNRF SLKLSSVTAA DTAVYCCASA
101   TTVTTAFDIW GQGTMVTVSS ASTKGPSVFP LAPSS
```

Figure 3AX  The amino acid sequence (SEQ ID NO:164) of Ha16-1(3,5)19 VL.  Double-underlined is part of the leader sequence, and underlined is a portion of the light chain constant region.

```
  1  LGQSALTQPA  SVSGSPGQSI  TISCTGTSSD  VGRYNYVSWY  QQHPGQAPKL
 51  MIYGISIRPS  GVSPRFSGSK  SGNTASLTIS  GLQAEDEADY  YCSSHTSNST
101  LVVFAGGTKL  TVLGQPKAAP  SVTLFPPSSE  ELQANKATLV  CLISDFYPGA
151  VTVAWKADSS  PVKAGVETTT  PSKQSNNKYA  ASSYLSLTPE  QWKSHRSYSC
201  QVTHEGSTVE  KTVAPT
```

Figure 3AY  The amino acid sequence (SEQ ID NO:175) of Ha16-1(3,5)19 VH.  Double-underlined is part of the leader sequence, and underlined is a portion of the light chain constant region.

```
  1     MGSTAILALL  LAVLQGVCAE  VQLVQSGAEV  KKPGESLKIS  CKGSGYRFTS
 51     YWIGWVRQMP  GKGLEWMGII  YPGDSDTRYS  PSFQGQVTIS  ADKSISTAYL
101     QWSSLKASDT  AMYYCARKDY  YYYAMDVWGQ  GTTVTVSSAS  TKGPSVFPLA
151     PSSKST
```

Figure 3AZ  The amino acid sequence (SEQ ID NO:176) of Ha16-1.80 VL.  Double-underlined is part of the leader sequence, and underlined is a portion of the light chain constant region.

```
  1     QLLGLLLLWL  RGARCDIQMT  QSPSSLSASV  GDRVTITCRT  SHDISNYLNW
 51     YQQKPGKAPK  LLIYAASSLQ  SGVPSRFSGS  RSGTDFTLTI  SSLQPEDFAT
101     YYCQQTYSTL  FTFGPGTKVD  IKRTVAAPSV  FIFPPSDEQL  KSGTASVVCL
151     LNNFYPREAK  VQWKVDNALQ  SGNSQESVTE  QDSKDSTYSL  SSTLTLSKAD
201     YEKHKVYACE  VTHQGLSSPV  TKSFNR
```

Figure 3AAA  The amino acid sequence (SEQ ID NO:177) of Ha16-1.80 VH.  Double-underlined is part of the leader sequence, and underlined is a portion of the light chain constant region.

```
  1  MKHLWFFLLL  VAAPRWVLSQ  VQLQESGPGL  VKPSETLSLT  CTVSGGSISS
 51  YYWSWIRQPP  GKGLEWIGYV  YFSGSTNYNP  SLKSRVTISV  DTSKNQFSLK
101  LSSVTAADTA  VYYCARATRD  YYYYGMDVWG  QGTTVTVSSA  STKGPSVFPL
151  APSSKSTSGG  TAALGCLVKD  YFPEPVTVSW  ELS
```

Figure 4

Figure 4A Alignment of H16-7.213 Heavy Chain Variable Region to human germline VH1-2/D3-9/JH4

```
<-------------------------------FWR1-------------------------------
H16-7.213    1                                      CTGGGGCCTCAGTG-A-GGTCTCCTGCAAGGCTTCTGGAT    38
VH1-2        1  CAGGTGCAGCTGGTGCAGTCTGGGGCTGAGGTGAAGAAGC...........A.-.............................    79
D3-9
JH4

<----CDR1---->                         <-------------FWR2-------------->
H16-7.213   39 ACACCTTCACC GGCTACTATATGCAC TGGGTGCGACAGGCCCCTGGACAAGGGCTTGAGTGGATGGGA TGGATCAACCCT  118
VH1-2       80 ...........                                                                          159
D3-9
JH4

<-----CDR2-----
H16-7.213  119 AACAGTGGTGGCACAAACTATGCACAGAAGTTTCAGGGC AGAGTCACCATGACCAGGACACGTCCATCAG-CACAGCCT  197
VH1-2      160                                                         .G.                         238
D3-9
JH4

-----> <-----------FWR3-----------
H16-7.213  198 ACATGGAGCTGAGCAGGCTGAGATCTGACGACACGGCCGTGTATTACTGTGCGCGA GAATTACGATATTTGGCTGGTTA  277
VH1-2      239 ..........................................A...........                              296
D3-9         3                                                           .A....               24
JH4

H16-7.213  278 TTATCCTCCCTTGACTACTGGGGCCAGGGAACCCTGGTCACCGTCTCCTCAG  329
VH1-2
D3-9        25 ....
JH4          2 -----.A.T..........A......................
```

Figure 4B Alignment of H16-9.69 Heavy Chain Variable Region to human germline VH1-8/D3-10/JH4

```
             <------------------------------------FWR1----------------------------------->
H16_9.69VH   1   ----------------------------------------------CTGGGGCCTCAGTG-A-GGTCTCCTGCAAGGCTTCTGGAT
VH1-8        1   CAGGTGCAGCTGGTGCAGTCTGGGGCTGAGGTGAAGAAGC.........A.-....................                79
D3-10        -   --------------------------------------------------------------------------------
JH4          -   --------------------------------------------------------------------------------

<----CDR1---->                                 <-------FWR2------->
H16_9.69VH   39  ACACCTTCACC -AGTTATGATATCCAC   TGGGTGCGACAGGCCACTGGACAAGGGCTTGAGTGGATGGGA   TGGATGAACCC   117
VH1-8        80  ...........  ...........A.    .....................................     ...........   158
D3-10            --------------------------------------------------------------------------------
JH4              --------------------------------------------------------------------------------

<---------CDR2---------->                                                     <-
H16_9.69VH   118 TAACAGTGGTAACACAGTCTATGCACAGAAGTTCCAGGGC   AGAGTCACCATGACCAGAGAACACCTCCATAAGCACAGCCT   197
VH1-8        159 ..............G.........................   ........................................   238
D3-10            --------------------------------------------------------------------------------
JH4              --------------------------------------------------------------------------------

------------------------FWR3----------------------->
H16_9.69VH   198 ACATGGAGCTGAGCAGCCTGAGATCTGAGGACACGGCCGTGTATTACTGTGCGAGA   ACAGTATTACTATGGCCCTTTGAC   277
VH1-8        239 .......................................................   ------------------------   294
D3-10        1   -------------------------------------------------------   ........................   12
JH4          5   -------------------------------------------------------   ........................   11

H16_9.69VH   278 TACTGGGGCCAGGGAACCCTGGTCACCGTCTCCTCAG   314
VH1-8            ------------------------------------
D3-10            ------------------------------------
JH4          12  ..........A.........................
```

Figure 4C Alignment of H16-1.52 Heavy Chain Variable Region to human germline VH3-23/6-19/JH4

```
                                    <------------------------------------FWR1-------------------------------------
H16-1.52HC    1                              AGTCTGGGGGAGGCTTGGTACAGCCTGGGGGGTCCCTGAGACTCTCCTGTGCAGCCTCTGGATT    64
VH3-23        1     GAGGTGCAGCTGTTGG..................................................................    80
D6-19
JH4

<------CDR1------>  <------------------------------------FWR2-----------------------
H16-1.52HC   65     CACCTTTAGC  AGCTATGCCATGAGC  TGGGTCCGCCAGGCTCCAGGGAAGGGCTGGAGTGGGTCTCA  GCTATTAGTGGTA   144
VH3-23            ..........  ...............  ........................................  ...........   160
D6-19
JH4

-----CDR2------->  <---------------------------------------------
H16-1.52HC  145     GTGATGGTAGCCATACGACTACGCAGACTCCGTGAAGGGC  CGGTTCACCATCTCCAGAGACAATTCCAAGAACACGCTGTAT   224
VH3-23      161     ...G....................................  .........................................   240
D6-19
JH4

--FWR3---------------------------------------------->
H16-1.52HC  225     CTGCAAATGAACAGCCTGAGAGCCGAGGACACGGCCGTGTATATTACTGTGCGAAA  GATGGTTATAGCAGTGGCTGGAACTA   304
VH3-23      241     .......................................................                                296
D6-19         1                                                             ........G.........T......    21
JH4           1                                                                                      .     4

H16-1.52HC  305     CTTTGACTACTGGGGCCAGGGAACCCTGGTCACCGTCTCCTCAG   348
VH3-23
D6-19        22     ............                                    33
JH4           5     ....A.......................................    48
```

Figure 4D Alignment of Ha16-1(1)23 Heavy Chain Variable Region to human germline VH3-33/D3-10/JH6

Figure 4E Alignment of H16-9.44 Heavy Chain Variable Region to human germline VH4-4/D3-22/JH4

```
                    <-------------------------------------FWR1------------------------------------->
H16-9.44HC    1                                                         CCTGTCCCTCACCTGCACTGTCTCTGGTGG    30
VH4-4         1     CAGGTGCAGCTGCAGGAGTCGGGCCCAGGACTGGTGAAGCCTTCGGAGAC..........................         80
D3-22
JH4
                    <----><---------CDR1--------->  <-------------FWR2------------->
H16-9.44HC   31     CTCCATCAG----T  AGT----TACTACTGGAGC  TGGATCCGGCAGTCCGCCGGGAAGGGACTGGAGTGGATTGGG    C  98
VH4-4        81     .................C................................................................ V   148
D3-22
JH4
                                <----------CDR2----------> <-
H16-9.44HC   99     GTATCTATACCGGTGTGAGCACCAACTACAACCCCTCCCTCAAGAGT CGAGTCACCATGTCAGTAGACACGTCCAAGAAC  178
VH4-4       149     ............A...G.................................  ..............................  228
D3-22
JH4
                    ------------------FWR3-----------------------------> 
H16-9.44HC  179     AGTTCTCCCCTGAAGCTGAGCTCTGTGACCGCCGCGGACACGGCCGTGTATTACTGTGCGAGA  GATTACTATGATAGTAG  258
VH4-4       229     .............................................................                       293
D3-22         3                                                                    ..................    18
JH4
H16-9.44HC  259     TGGTTATTACCCCTTTGACTACTGGGGCCAGGGAACCCTGGTCACCGTCTCCTCAG   314
VH4-4
D3-22        19     .....                                                       24
JH4           5              ...........A...........................                    
```

Figure 4F Alignment of H16-1.67 Heavy Chain Variable Region to human germline VH4-31/D3-10/JH6

```
H16-1.67HC    5  ------------GGAGTCTGGGCCAGGACTGGTGAAGCCTTCACAGACCCTGTCCCTCACCTGCACTGTCTCTGGTGG    70
VH4-31        1  CAGGTGCAGCTGCA......G...........................................................
D3-10
JH6
              <-------->  <-----CDR1------>  <------FWR2----->
H16-1.67HC   71  CTCCATCAAC  AGTTTTGGTTACTACTGGAGC  TGGATCCGCCAGTATCCAGGAAAGGGCCTGGAGTGGATTGGG  TTCCTCT  150
VH4-31       81  ..........  .........G...GG.......  ......................C.C........G......  ..A.A..  160
D3-10
JH6
              <------CDR2------>  <-
H16-1.67HC  151  ATTTCACTGGGAGCACCTACTACAACCCGTCCCTCAAGAGT  CGAGTTACCATATCAGTAGACACGTCTAAGAGCCAGTTC  230
VH4-31      161  ....A..G.................................  ..........................A..........  240
D3-10
JH6

----FWR3------->
H16-1.67HC  231  TCCCTGAAGCTGAGCTCTGTGACTGCCGCGGACACGGCCGTGTATTACTGTGCGAGA  GCAGGTACTATGGTTCGGGAGC  310
VH4-31      241  ........................................................  ......................  298
D3-10         5  ..........................................................                        21
JH6

H16-1.67HC  311  CCACTACTACGGTATGGACGTCTGGGGCCAAGGGACCACGGTCACCGTCTCCTCAG  366
VH4-31
D3-10
JH6          10  ..........................G............................  63
```

Figure 4G Alignment of Ha16-1(3,5)36 Heavy Chain Variable Region to human germline VH4-39/D6-19/JH4

```
                              <------------------------FWR1-------------------------
Ha16-1(3,5)36    2 AGGTGCAGCTGGTGGAGTCTGGGCCCAGGACTGGTGAAGCCTTCGGAGACCCTGTCCCTCACCTGCACTGTCTCTGGTGGC    81
VH4-39           5 -----..............CA......G............................................... ..    81
D6-19              ---------------------------------------------------------------------------------
JH4                ---------------------------------------------------------------------------------

<--------| <-------------CDR1----------> <---------------------FWR2
Ha16-1(3,5)36   82 TCCATCAGC   AGTAGTAGTTATTACTGGGGC  TGGATCCGGCCAGCCCCCAGGGAAGGGGCTGGAGTGGATTGGG   AGTATGTA  161
VH4-39          82 .........   .....................  ...........................................   ....C...  161
D6-19              -----------------------------------------------------------------------------------------
JH4                -----------------------------------------------------------------------------------------

-----| <------------CDR2------------>                                        |
Ha16-1(3,5)36  162 TTATAGTGGGAGCACCTACTACAACCCGTCCCTCAAGAGT    CGAGTCATCATATCCGTAGACACGTCCAAGAACCAGTTCT   241
VH4-39         162 ........................................    .........................................   241
D6-19                                                          ....T....C...............................
JH4                --------------------------------------------------------------------------------------

<------------------FWR3-------------------| >
Ha16-1(3,5)36  242 CCCTGAAGCTGAGCTCTGTGACCGCCGCAGACACGGCTGTGTATTACTGTGCGAGA   CATTATATAACAGTGGCTGGTATC   321
VH4-39         242 .......................................................                              299
D6-19            4 -------------------------------------------------------   ...............G........    20
JH4              5 -------------------------------------------------------                                  5

Ha16-1(3,5)36  322 TTTGACTACTGGGGCCAGGGAACCCTGGTCACCGTCTCCTCAG   364
VH4-39             -------------------------------------------
D6-19              -------------------------------------------
JH4              6 ..........A................................    48
```

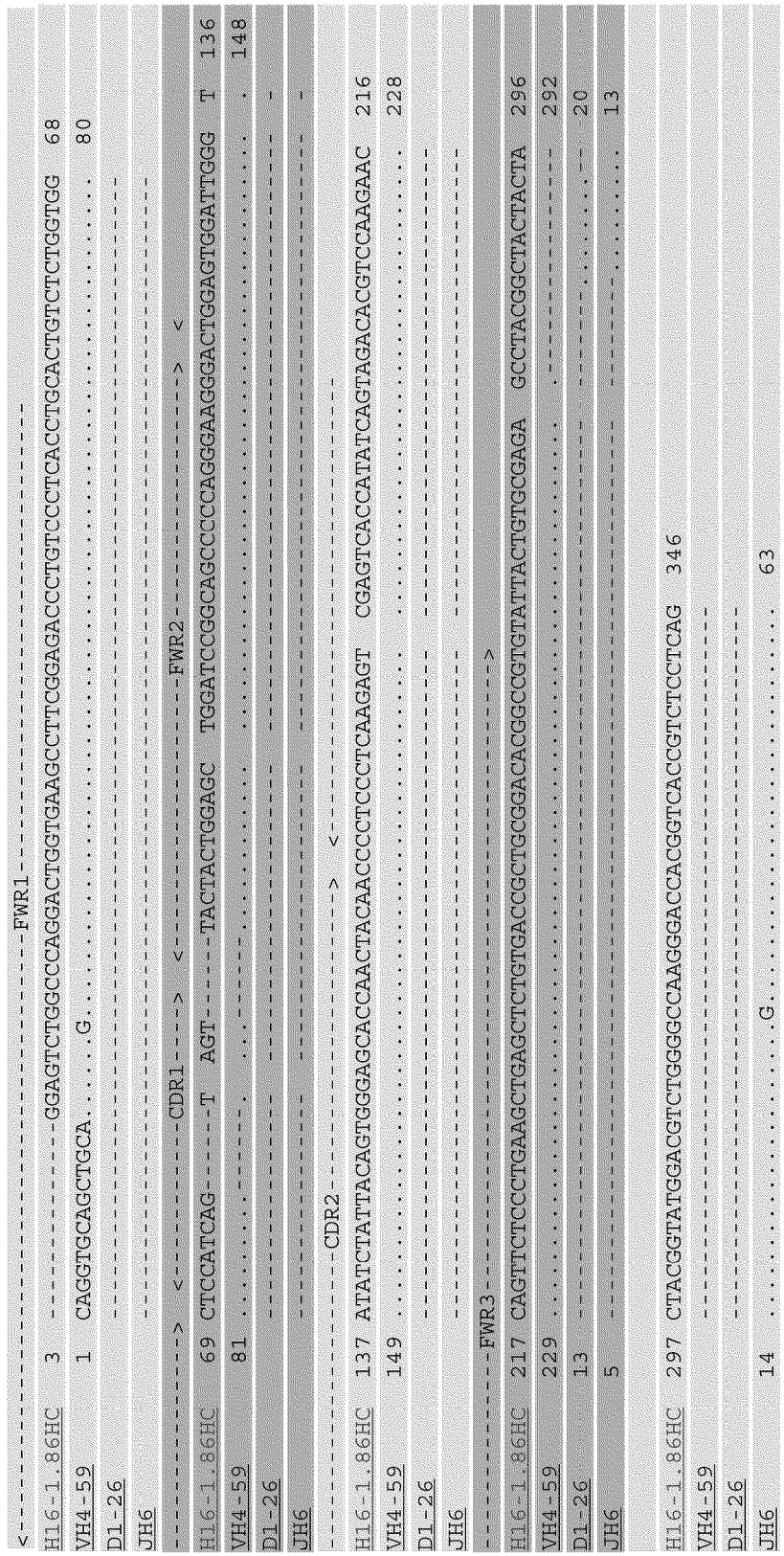
Figure 4H Alignment of H16-1.86 Heavy Chain Variable Region to human germline VH4-59/D1-26/JH6

Figure 4I Alignment of H16-9.10 Heavy Chain Variable Region to human germline VH6-1/D6-19/JH5

```
          <----------------------------------FWR1------------------------------------
H16-9.10     8  ------------------------AGTCTGGTCCAGGACTGGTGAAGCCCTCGGCAGACCCCTCACTCTGTGCCATCTCCGGGGA   71
VH6-1        1  CAGGTACAGCTGCAGC....A..........................................................   80
D6-19
JH5

<--------------->   <-------------CDR1------------->   <-------FWR2---
H16-9.10    72  CAGTGTCTCT   AGCAACAGTGCTGCTTGGAAC    TGGATCAGGCAGTCCCCATCGAGAGGCCTTGAGTGGCTGGGA   AGGACAT  151
VH6-1       81  ..........   ....................    ...........................................   .......  160
D6-19
JH5

<--------CDR2---------->   <------------
H16-9.10   152  ACTACAGGTCCAAGTGGTATAATGCTATGCAGTATCTGTGAAAAGT   CGAATGACCATCAACCCAGACACATCCAAGAAC   231
VH6-1      161  .............A................................   ......A.........................   240
D6-19
JH5

---FWR3-------------------------------------------------------------------->   <---
H16-9.10   232  CAGTTCTCCCTGCAGCTGAACTCTGTGACTCCCGAGGACACGGCTGTGTATTACTGTGCAAGA   GAGGCGGGGGGCTGGTT   311
VH6-1      241  ...............................................................                       305
D6-19       13  .....................................................................   ......-   19
JH5          5  ........                                                                               10

H16-9.10   312  CGACCCCTGGGGCCAGGGAACCCTGGTCACCGTCTCCTCAG   352
VH6-1
D6-19
JH5         11  ........T.........A.....................   51
```

Figure 4J Alignment of H16-9.33 Heavy Chain Variable Region to human germline VH6-1/D6-19/JH5

Figure 4K Alignment of Ha16-1(1)11 Heavy Chain Variable Region to human germline VH4-59/D4-23/JH6

```
                        <--------------------------------------FWR1-------------------------------------->
Ha16-1(1)11VH    3   -AGGTGCAGCTGGTGGAGTCTGGGCCAGGACTGGTGAAGCCTTCGGAGACCCTGTCCCTCACCTGCACTGTCTCTGGTGG   80
VH4-59           1   .................CA.......G.....................................................   81
D4-23
JH6

<-----CDR1----->  <-----------FWR2----------->
Ha16-1(1)11VH   82   CTCCATCAG----T AGT----TACTACTGGAGC TGGATCCGGCAGCCCCCAGGGAAGGGACTGGAGTGGATTGGG T  149
VH4-59          81   .........     .   .              ..............................................    148
D4-23
JH6                                                                                            <---

<------------CDR2-----------
Ha16-1(1)11VH  150   ATATCTATTACAGTGGGAGCACCAACTACAACCCCTCCCTCAAGAGT  CGAGTCACCATATCAGTAGACACGTCCAAGAAC   229
VH4-59         149   ...............................................  ...............................   228
D4-23
JH6

<------------FWR3------------>
Ha16-1(1)11VH  230   CAGTTCTCCCTGAAGCTGAGCTCTGTGACCGCTGCGGACACGGCCGTGTATTACTGTGCCAGA  GCGGTGTCCTACTACTA   309
VH4-59         229   ...............................................................                    292
D4-23            3                                                                   ............      3
JH6              5                                                                                ..    13

Ha16-1(1)11VH  310   CTACGGTATGGACGTCTGGGGCCAAGGGACCACGGTCACCGTCTCCTCAG   359
VH4-59
D4-23            4   ..........                                           10
JH6             14   ......G..............................                63
```

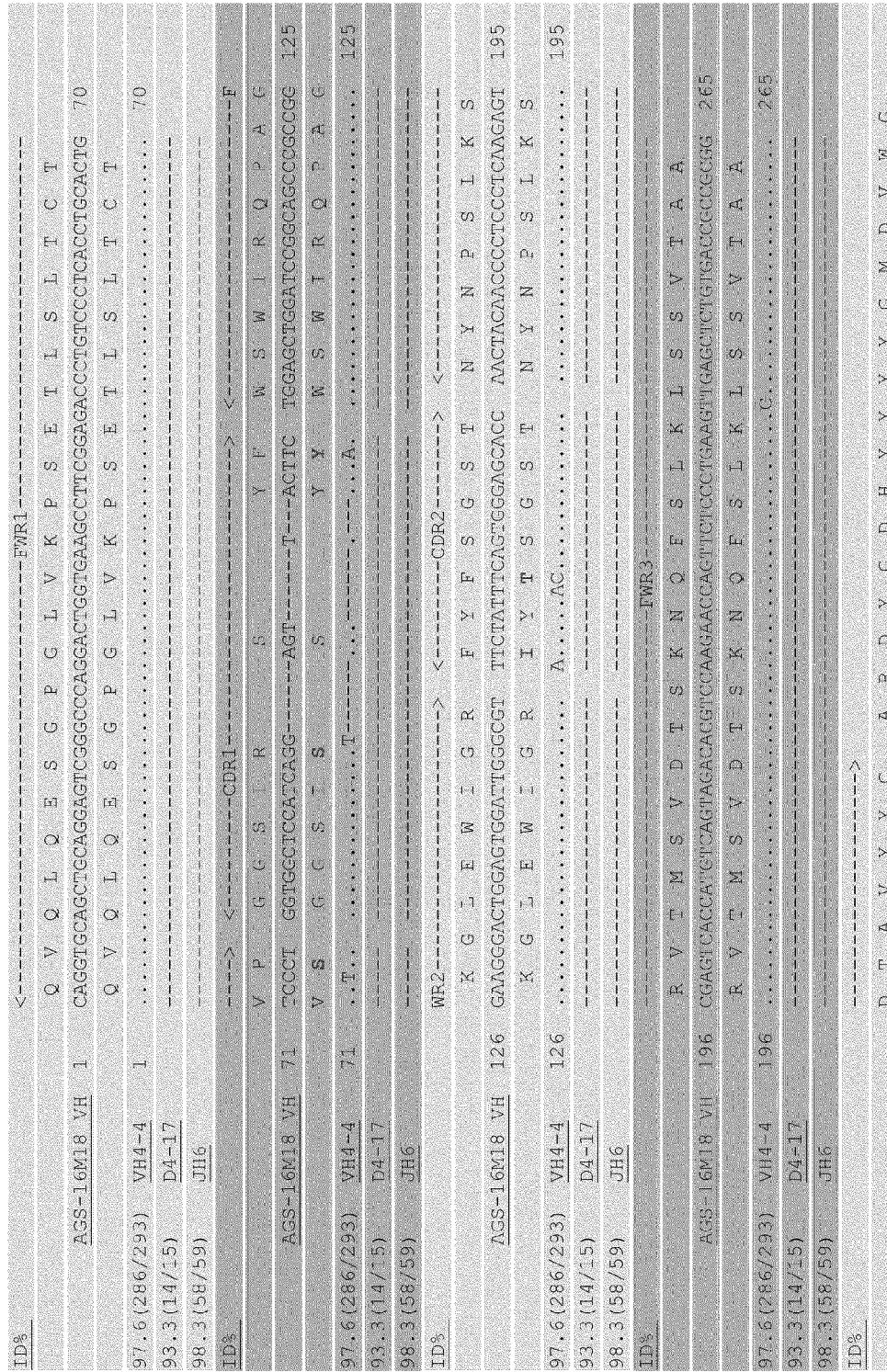
Figure 4L Alignment of Ha16-1(3,5)18 Heavy Chain Variable Region to human germline VH4-4/D4-17/JH6

Figure 4L-2

| | | | |
|---|---|---|---|
| AGS-16M18 VH | 266 | ACACGGCCGTGTATTACTGT GCGAGAGACTACGGTGTGACCACTACTACTACTACGGTATGGACGTCTGGGG | 335 |
| | | D  T  A  V  Y  Y  C   A  R | |
| 97.6(286/293) VH4-4 | 266 | ................... ---------------------------------------------------- | 293 |
| 93.3(14/15) D4-17 | 2 | ------------------- -----------------------T.------------------------- | 16 |
| 98.3(58/59) JH6 | 4 | ------------------- ----------------......................... | 34 |

ID%

| | | | |
|---|---|---|---|
| AGS-16M18 VH | 336 | CCAAGGGACCACGGTCACCGTCTCCTCA | 363 |
| | | Q  G  T  T  V  T  V  S  S | |
| 97.6(286/293) VH4-4 | | ---------------------------- | |
| 93.3(14/15) D4-17 | | ---------------------------- | |
| 98.3(58/59) JH6 | 35 | G........................... | 62 |

Figure 4M Alignment of Ha16-1(2,4)4 Heavy Chain Variable Region to human germline VH3-33/D1-26/JH6

```
                <-------------------------------------FWR1-------------------------------------
Ha16-1(2,4)4   1   --GGTGCAGCTGGTGGAGTCTGGGGGAGGCGTGGTCCAGCCTGGGAGGTCCCTGAGACTCTCCTGTGCAGCCGTCTGGATT    78
VH3-33         1   CA.............................................................................    80
D1-26
JH6

------><----CDR1----><--------FWR2--------
Ha16-1(2,4)4  79   CACCTTCAGT  AGTTATGGCATGCAC  TGGGTCCGCCAGGCTCCAGGCAAGGGGCTGGAGTGGGTGGCA  ATTATATGGTATG  158
VH3-33        81   ..........  ...............  ..........................................  G............  160
D1-26
JH6

<---------CDR2--------->
Ha16-1(2,4)4 159   ATGAAAGTAATAAATACTATGCAGAGACTCCGTGAAGGGC   CGATTCACCATCTCCAGAGACAATTCCAAGAACACGCTGTAT  238
VH3-33       161   ...G....................................   ..........................................  240
D1-26
JH6

<----FWR3------
Ha16-1(2,4)4 239   CTGCAAATGAACAGCCTGAGAGCCGAGGACACGGCTGTGTATTACTGTGCGAGA  GCTTATAGTGGGAGCTACGGGTACTC  318
VH3-33       241   ......................................................                             295
D1-26          3                                                         .....................A.   17
JH6            6                                                         ......A                   10

Ha16-1(2,4)4 319   CTACTACGGTATGGACGTCTGGGGCCAAGGGACCACGGTCACCGTCTCCTCAG   371
VH3-33
D1-26
JH6           11   ..................G...........                         63
```

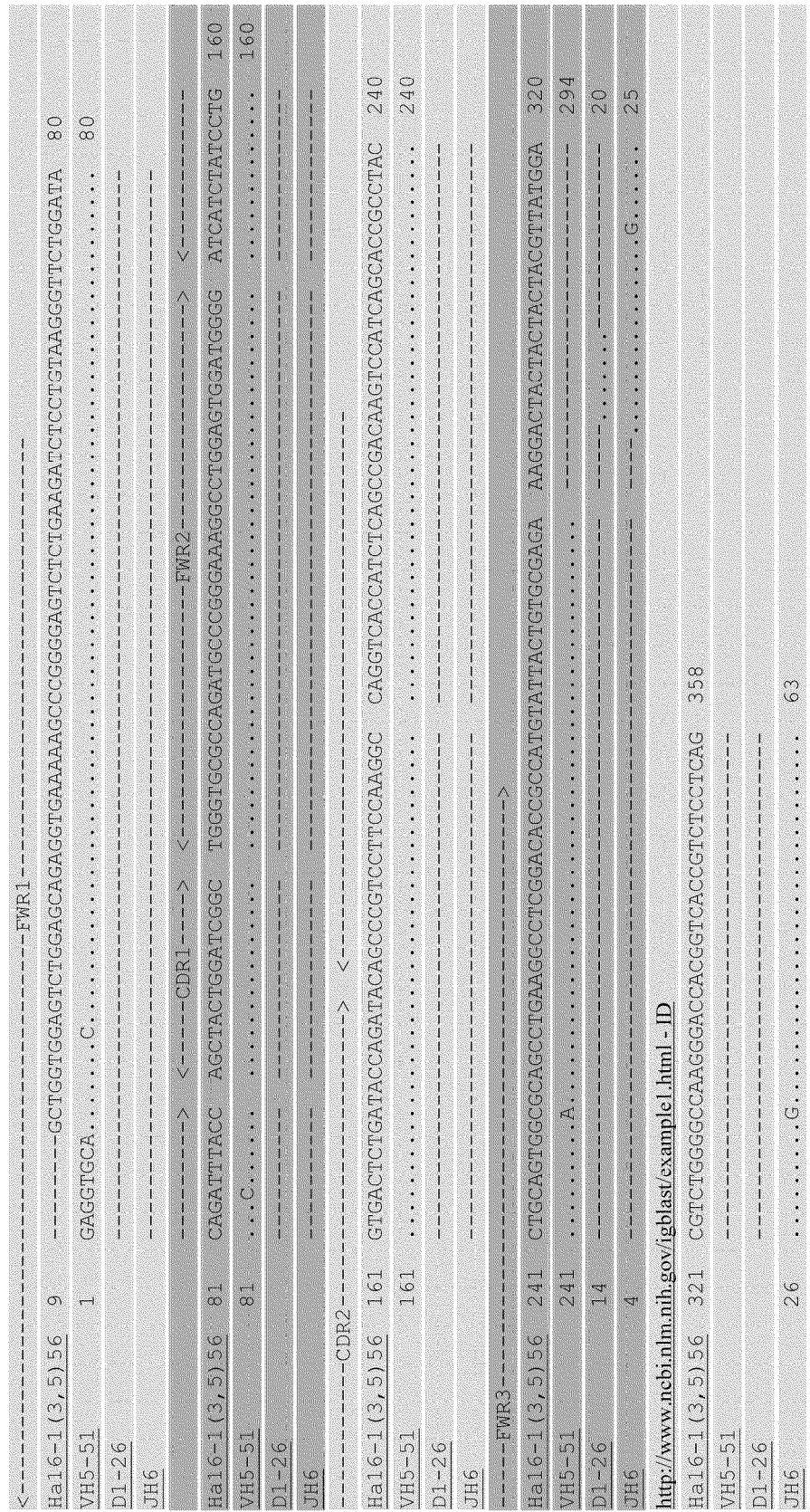
Figure 4N Alignment of Ha16-1(3,5)56 Heavy Chain Variable Region to human germline VH5-51/D1-26/JH6

Figure 4O Alignment of H16-7.8 Heavy Chain Variable Region to human germline VH4-31/D5-12/JH6

```
                                <-----------------------FWR1---------------------------
H16-7.8    1    CAGGTGCAGCTGCAGGAGTCGGGCCCAGGACTGGTGAAGCCTTCACAGACCCTGTCCTCACCTGCACTGTCTGGTGG    80
VH4-31     1    ..........................................................T..............    80
D5-12
JH6
                ---->  <------------CDR1------>  <-----------------------FWR2-----------------
H16-7.8    81   CTCCATCAGC   AGTGGTGGTTACTACTGGAGC   TGGATCCGCCAGCACCCAGGGAAGGGCCTGAGTGGATTGGG   ATCATCT   160
VH4-31     81   ..........   ......................   ........................................   TA.....   160
D5-12
JH6
                -------------->  <-------------------CDR2--------------------->  <-------------
H16-7.8    161  ATTACAGTGGAGCACCTACTACAACCCGTCCCTCAAGAGT   CGAGTTACCATATCAGTAGACACGTCTAAGAACCAGTTC   240
VH4-31     161  ........................................   ........................................   240
D5-12
JH6
                ------------FWR3----------------------------------------------------->
H16-7.8    241  TCCCTGAAGCTGAACTCTGTGACTGCCGGGACACGGCCGTGTTTTACTGTGCGAGA   GTGGCTATAGTGACTACGATCCC   320
VH4-31     241  ........................G...............................A   ........................   298
D5-12      1    ..........A...............................G............   ....................   20
JH6
H16-7.8    321  GGGCGGTATGGACGTCTGGGGCCAAGGGACCACGGTCACCGTCTCCTCA   369
VH4-31
D5-12
JH6        17   ...........G.....................................   62
```

Figure 4P Alignment of H16-1.68 Heavy Chain Variable Region to human germline VH3-33/D3-3/JH6

```
                      |-------------------------------FWR1-------------------------------|
H16-1.68    1   GAGGTGCAGCTGGTGGAGTCTGGGGGAGGCGTGGTCCAGCCTGGGAGGTCCCTGAGACTCTCCTGTGCAGCGTCTGGATT    80
VH3-33      2   -...............................................................................    80
D3-3            -------------------------------------------------------------------------------
JH6             -------------------------------------------------------------------------------

|<------CDR1------>|            |<--------------FWR2---------------
H16-1.68   81   CACCTTCAGT AGCTATGGCATGCAC TGGGTCCGCCAGGCTCCAGGCAAGGGGCTGGAGTGGGTGGCA GTTATATGGTATG   160
VH3-33     81   ................ ..............  ................................... ............   160
D3-3            ------------------------------- ----------------------------------- ------------
JH6             ------------------------------- ----------------------------------- ------------ http://www.ncbi.nlm.nih.gov/igblast/example1.html - ID

----------->    <-------------------------CDR2----------------------
H16-1.68  161   ATGGAAGTAATAAATACTATGCAGACTCCGTGAAGGGC CGATTCACCATCTCCAGAGACAATTCCAAGAACACGCTGTAT   240
VH3-33    161   ...................................... ........................................   240
D3-3            -------------------------------------- ----------------------------------------
JH6             -------------------------------------- ----------------------------------------

|-----FWR3-----
H16-1.68  241   CTGCAAATGAACAGCCTGAGAGCCGAGGACACGGCTGTATTACTGTGCGAGG TCCAGAATTACGATTTTTGGAGTGGT   320
VH3-33    241   ....................................................
D3-3        3   .....................................................                              22
JH6             -----------------------------------------------------

H16-1.68  321   TCACTACGGTATGGACGTCTGGGGCCAAGGGACCACGGTCACCGTCTCCTCAG   373
VH3-33          -----------------------------------------------------
D3-3       23   ---                                                      23
JH6        13   ....G................................................   63
```

Figure 4Q Alignment of H16-1.93 Heavy Chain Variable Region to human germline VH1-18/D6-13/JH6

```
         <---------------------------FWR1--------------------------->
H16-1.93   1  CAGGTTCAGCTGGTGCAGTCTGGAGCTGAGGTGAAGAAGCCTGGGGCCTCAGTGAAGGTCTCCTGCAAGGCTTCTGGTTA  80
VH1-18     1  ................................................................................  80
D6-13         --------------------------------------------------------------------------------
JH6           --------------------------------------------------------------------------------

<----------CDR1----------->  <--------------FWR2-------------->
H16-1.93  81  CACCTTTACC AGCTATGGTATCAGC TGGGTGCGACAGGCCCCTGGACAAGGGCTTGAGTGGATGGGA TGGATCAGCGCTT  160
VH1-18    81  .......... ............... .................................................  ............  160
D6-13         ------------------------------------------------------------------------------------
JH6           ------------------------------------------------------------------------------------

<--------CDR2-------->
H16-1.93 161  ACAATGGTAACACATACTATGCACAGAAGCTCCAGGCC AGAGTCACCATGACCACAGACACATCCACGAGCACAGCCTAC  240
VH1-18   161  ..................A..................G ........................................  240
D6-13         ------------------------------------------------------------------------------------
JH6           ------------------------------------------------------------------------------------

<----FWR3---->
H16-1.93 241  ATGGAGCTGAGGAGCCTGAGATCTGAGGACACGGCCGTGTATTACTGTGCGAGA  GATGGGTATAGCAGCAGCTGGTCCCT  320
VH1-18   241  ......................................................  ...........................  296
D6-13      1  ------------------------------------------------------  ........................ G  19
JH6           ------------------------------------------------------  ---------------------------

H16-1.93 321  CCTGCACTACTACGGTATGGACGTCTGGGGCCAAGGGACCACGGTCACCGTCTCCTCA  378
VH1-18        ---------------------------------------------------------
D6-13     10  ---------------------------------------------------------
JH6            ...............G.........................................  62
```

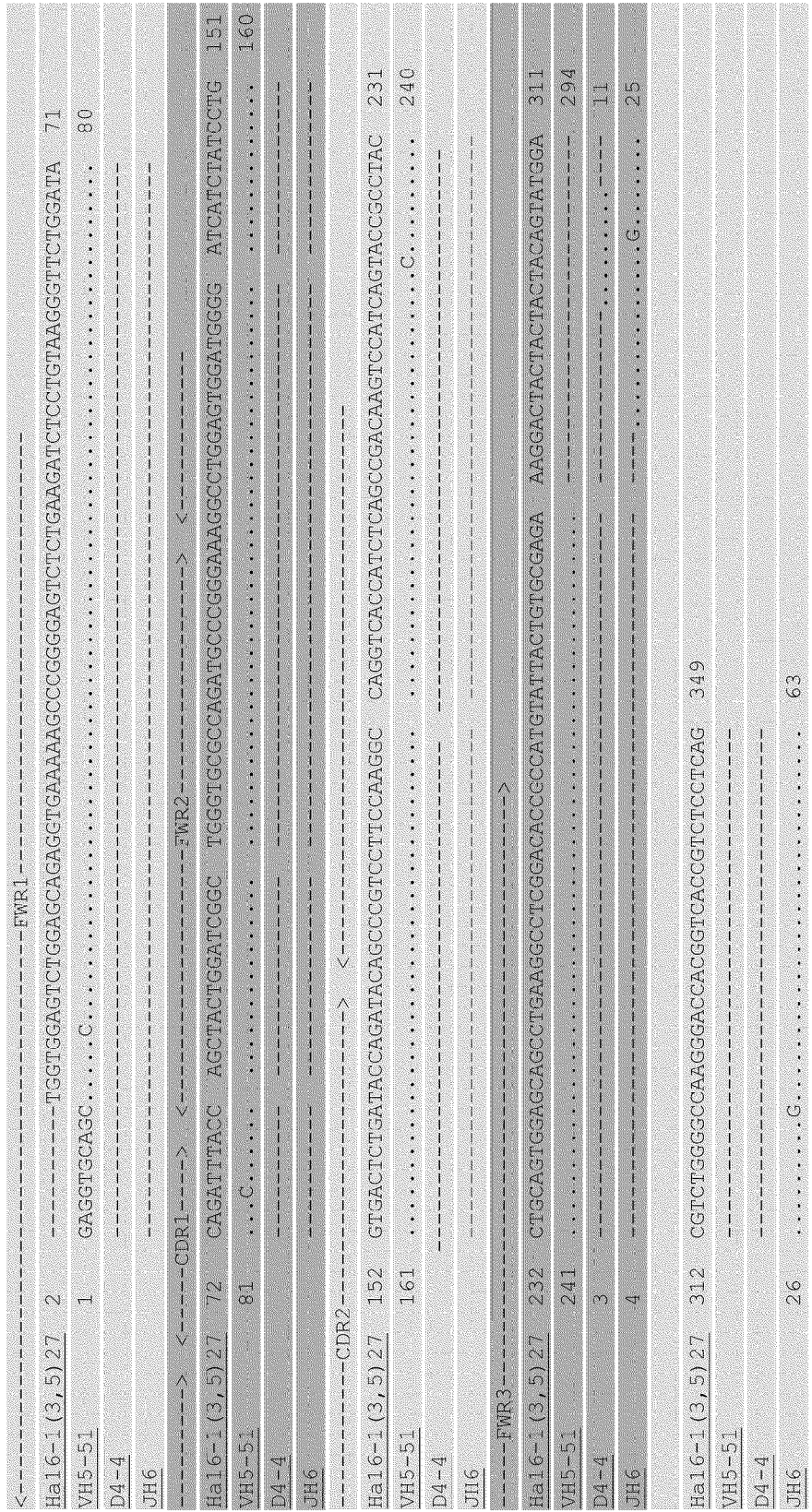
Figure 4R Alignment of Ha16-1(3,5)27 Heavy Chain Variable Region to human germline VH5-51/D4-4/JH6

Figure 4S Alignment of Ha16-1.61 Heavy Chain Variable Region to human germline VH3-33/D3-3/JH6

```
                  <------------------------------------FWR1------------------------------------
H16-1.61   221   GAGGTGCAGCTGGTGGAGTCTGGGGGAGGCGTGGTCCAGCCTGGGAGGTCCCTGAGACTCTCCTGTGCAGCGTCTGGATT   300
VH3-33       2   ...-............................................................................    80
D3-3
JH6

<----CDR1---->   <-----------------FWR2----------------->
H16-1.61   301   CACCTTCAGT  AGCTATGGCATGCAC  TGGGTCCGCCAGGCTCCAGGCAAGGGGCTGGAGTGGGTGGCA  GTTATATGGTATG   380
VH3-33      81   ..........  ...............  .........................................  .............   160
D3-3
JH6

<----------------------CDR2----------------------->
H16-1.61   381   ATGGAAGTAATAAATACTATGCAGACTCCGTGAAGGGC  CGATTCACCATCTCCAGAGACAATTCCAAGAACACGCTGTAT   460
VH3-33     161   ......................................  ..........................................   240
D3-3
JH6

<--------FWR3-------->
H16-1.61   461   CTGCAAATGAACAGCCTGAGAGCCGAGGACACGGCTGTGTATTACTGTGCGAGG  TCCAGAATTACGATTTTGGAGTGGT   540
VH3-33     241   ......................................................  ........................   293
D3-3         3   ---...................                                                              22
JH6

H16-1.61   541   TCACTACGGTATGGACGTCTGGGGCCAAGGGACCACGGTCACCGTCTCCTCAG   593
VH3-33
D3-3        23   ...................                                    23
JH6         13   ...-..G.............................                   63
```

Figure 4T Alignment of Ha16-1(3,5)5 Heavy Chain Variable Region to human germline VH5-51/D3-10/JH6

```
                        <-----FWR1-----
Ha16-1(3,5)5  118  GAGGTGCAACTAGTGCAGTCTGGAGCAGAGGTGAAAAGCCCGGGGAGTCTCTGAAGATCTCCTGTAAGGGTTCTGGATA  197
VH5-51          1  ............G..G...............................................................   80
D3-10
JH6

<------CDR1------>      <-----------FWR2----------->
Ha16-1(3,5)5  198  CAGGTTTACC  AGCTACTGGAT CGGC  TGGGTGCGCCAGATGCCCGGGAAAGGCCTGGAGTGGATGGGG  ATCATCTATCCTG  277
VH5-51         81  ..........C............................................................           160
D3-10
JH6

<------CDR2------>
Ha16-1(3,5)5  278  GTGACTCTGATACCAGATACAGCCCGTCCTTCCAAGGC  CAGGTCACCATCTCAGCCGACACAGTCCATCAGCACCGCCTAC  357
VH5-51        161  ....................................................................................  240
D3-10
JH6

-----FWR3-----
Ha16-1(3,5)5  358  CTGCAGTGGAGCAGCCTGAAGGCCTGCATGTGTGGACA  AAGGACTACTACTACTACACTATGGA  437
VH5-51        241  ...............................................................  294
D3-10           6  ......................GG........            12
JH6             4  ......................GG........            25

Ha16-1(3,5)5  438  CGTCTGGGGCCAAGGGACCACGGTCACCGTCTCCTCAGCCTCCACCAAGGGCCCATCGGTCTTCCCCCTGGCACCCTCCT  517
VH5-51
D3-10
JH6            26  ..........G..........................           63

Ha16-1(3,5)5  518  CCAAGAGCACCTCTGGGGGCACAGCGGCCCTGGGCTGCCTGGTCAAGGACTACTTCCCCGAACGGTGAC  587
VH5-51
D3-10
JH6
```

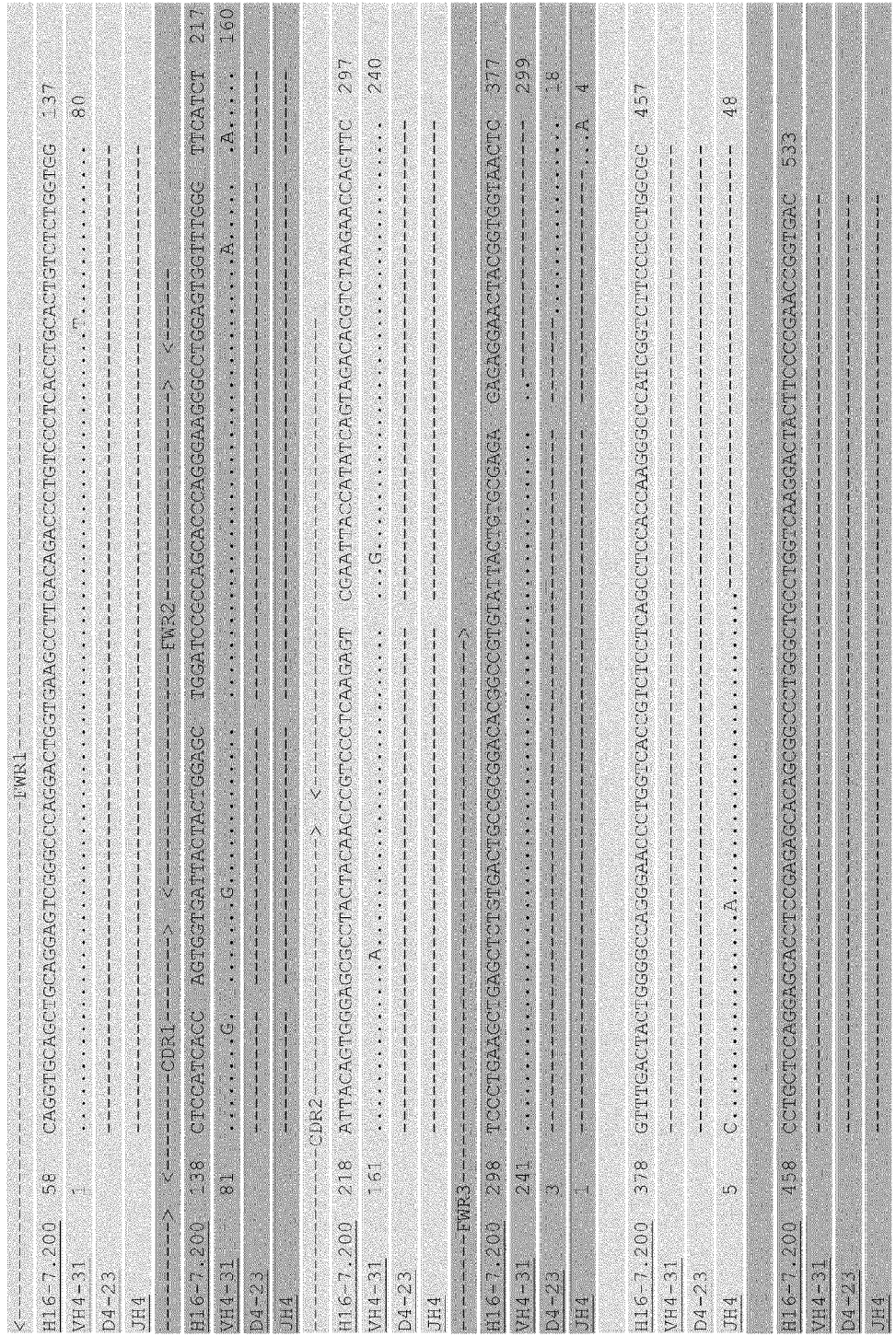
Figure 4U Alignment of H16-7.200 Heavy Chain Variable Region to human germline VH4-31/D4-23/JH4

Figure 4V Alignment of Ha16-1(3,5)42 Heavy Chain Variable Region to human germline VH5-51/D4-11/JH6

```
                  <------------------------------FWR1------------------------------->  <------CDR1------->
Ha16-(3,5)42  115 GAGGTGCAGCTGGTGCAGTCTGGAGCAGAGGTGAAAAAGCCCGGGGAGTCTCTGAAGATCTCCTGTAAGGGTTCTGGATA 194
VH5-51          1 ................................................................................  80
D4-11
JH6

<----CDR1---->    <---------------------FWR2--------------------->    <------
Ha16-(3,5)42  195 CAGTTTACC AGCTACTGGATCGGC TGGGTGCGCCAGATGCCCGGGAAAGGCCTGGAGTGGATGGGC ATCATCTATCCTG 274
VH5-51         81 .........C......................................................... ............ 160
D4-11
JH6

----------CDR2----------->
Ha16-(3,5)42  275 GTGACTCTGATACCAGATACAGCCCGTCCTTCCAAGGC CAGGTCACCATCTCAGCGACAAGTCCATCAGCACCGCCTAC 354
VH5-51        161 ......................................                                          240
D4-11
JH6

<----------------------------FWR3---------------------------->
Ha16-(3,5)42  355 CTGCAGTGGAGTAGCCTGAAGGCCTGAGGACACCGCCATGTATTACTGTGCGAGA AAGGAC ACTACTACTACAGTATGGA 434
VH5-51        241 ...........................C............................                         294
D4-11           3                                                          ....... ...............  11
JH6             4                                                                  ........G.......  25

Ha16-(3,5)42  435 CGTCTGGGGCCAAGGGACCACGGTCTCCTCAGCCTCCAGCCGTCTTCCTCTTCCCCCCTGGCACCCTCCT 514
VH5-51
D4-11          26 ....G................                                                 63
JH6

Ha16-(3,5)42  515 CCAAGGAGCACCTCTGGGGGCACAGCGGC 542
VH5-51
D4-11
JH6
```

Figure 4W Alignment of H16-9.65 Heavy Chain Variable Region to human germline VH3-33/D1-26/JH4

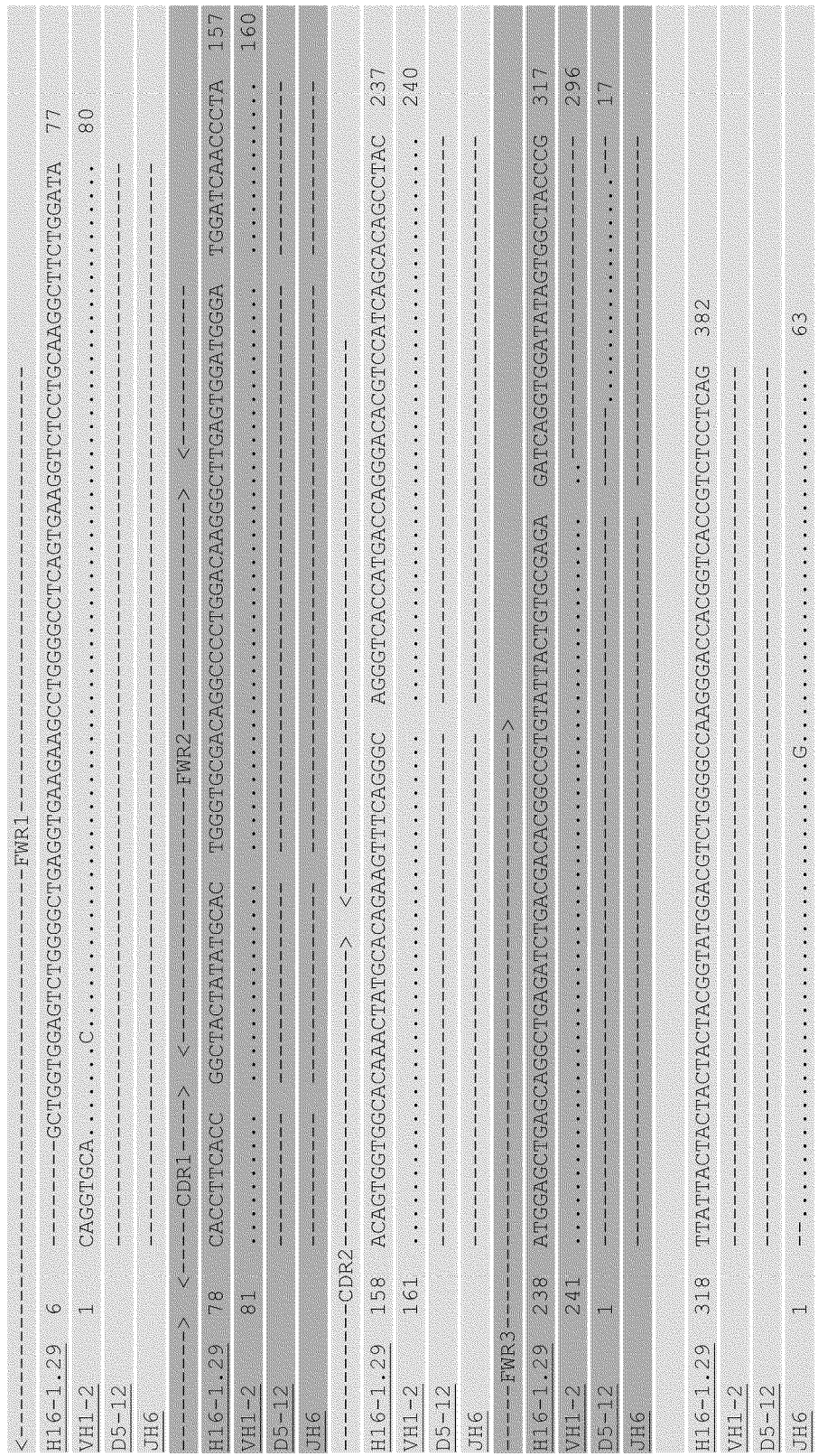
Figure 4X Alignment of H16-1.29 Heavy Chain Variable Region to human germline VH1-2/D5-12/JH6

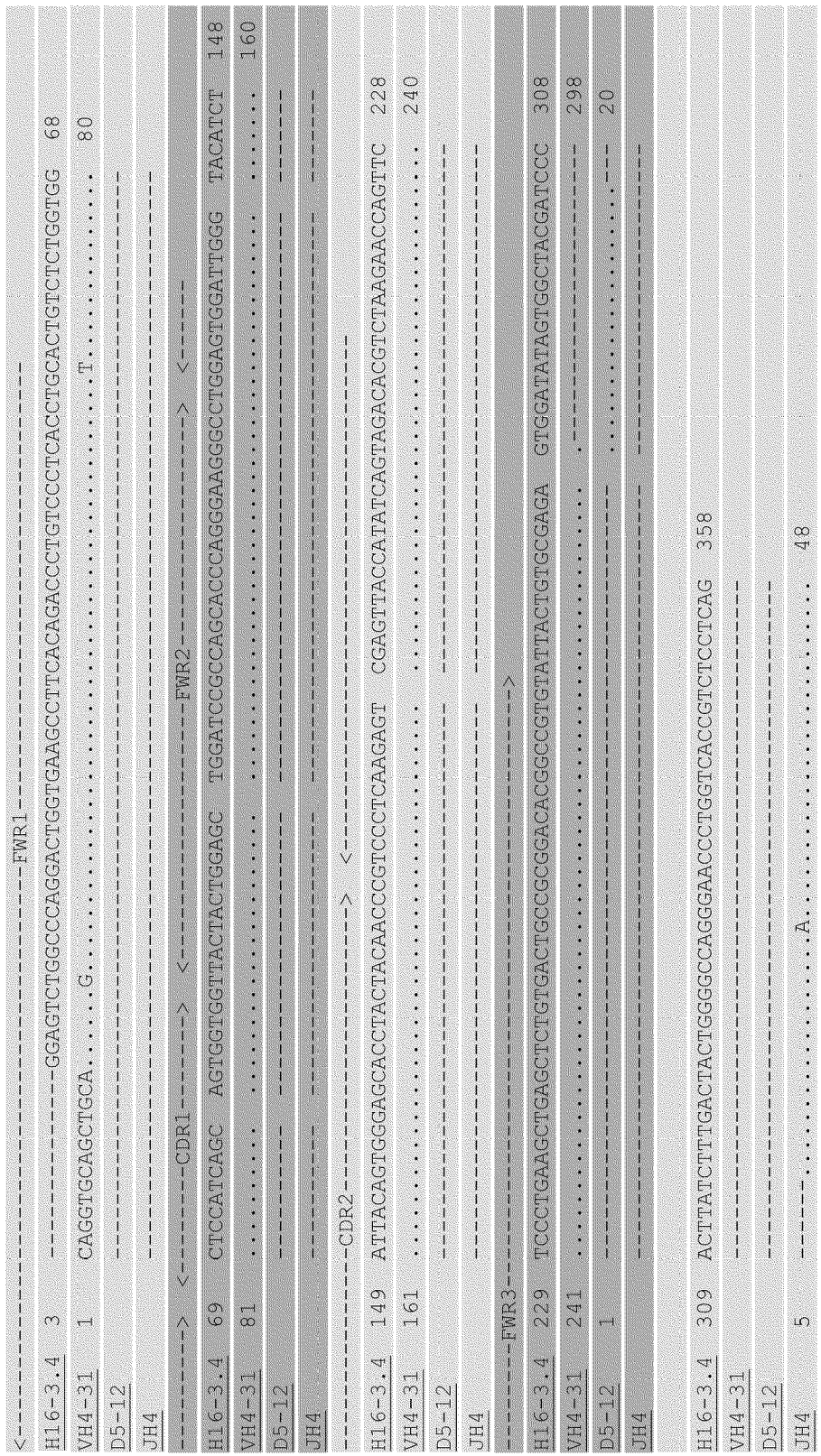

Figure 4Z Alignment of H16-1.92 Heavy Chain Variable Region to human germline VH4-39/D4-11/JH3

```
                       -----FWR1---------------------------------------------------------------------------->  <-----CDR1------->
H16-1.92     2    AGGTGCTGCTGGTGGAGTCTGGGCCCAGGACTGGTGAAGCCTTCGGAGACCCTGTCCCTCACCTGCACTGTCTCTGGTGGC   81     TCCATCAGC     AGTAGTAGTTACTTCTGGGGC
VH4-39       15   ---------------------.G.................-----------------------------------------    81     ---------     .....................
D4-11        -    --------------------------------------------------------------------------------           ---------     .....................
JH3          -    --------------------------------------------------------------------------------           ---------     .....................

<------CDR1-------->  <-----------------------FWR2------------------>                  <------CDR2---------
H16-1.92     82   TGGATCCGCCAGCCCCCAGGGAAGGGCTGGAGTGGATTGGG   AGTATCTA   161
VH4-39       82   ..........A.............................                  161
D4-11        -    -----------------------------------------   --------
JH3          -    -----------------------------------------   --------

---------------CDR2-------->  <---------------------------FWR3--------------------------->
H16-1.92     162  TTATAGTGGAAACACCTACTACAACCCGTCCCTCAAGAGT   CGAGTCACCATATCCGTAGACACGTCCAAGAACCGTTCT   241
VH4-39       162  ...........G.G..........................   ........................A...............  241
D4-11        -    -----------------------------------------   ----------------------------------------
JH3          -    -----------------------------------------   ----------------------------------------

<-----------------------------------FWR3---------------------->
H16-1.92     242  CCCTGAAGCTGAGCTCTGTGACCGCCGCAGACACGGCTGTGTATTGCTGTGCGAGC   GCCACTACAGTAACTACAGCTTTT   321
VH4-39       242  .......................................A...............                             296
D4-11        3    -------------------------------------------------------   .....A..................   16
JH3          4    -------------------------------------------------------   ........................   9

H16-1.92     322  GATATCTGGGGCCAAGGGACAATGGTCACCGTCTCTTCAGCCTCCACCAAGGGCCCAT   379
VH4-39       -    ---------------------------------------------------------
D4-11        -    ---------------------------------------------------------
JH3          10   ........G................................................   49
```

Figure 5

Figure 5A Alignment of H16-7.213 Light Chain Variable Region to human germline VK-O2/JK4

```
                    <--------------------------------------FWR1-------------------------------------->
H16-7.213LC   45  GACATCCAGATGACCCAGTCTCCATCCTCCCTGTCTGCATCTGTAGGAGACAGAGTCACCATCACTTGC  CGGGCAAGTCA  124
O2             1  ....................................................................  ...........   80
JK4
                       <----------CDR1---------->                    <-------FWR2-------->              <-----CDR2
H16-7.213LC  125  GAGCATTAGCAGCTATTTAAAT  TGGTTTCAGCAGAAACCAGGGAAAGCCCCTAAGCTCCTGATCTAT  GCTGCATCCAGTT  204
O2            81  ........A.............  ....................................A.........  .............   16
JK4
                  ------>                    <---------FWR3--------------------------------------------
H16-7.213LC  205  TGCAAAGT  GGGGTCCCCATCAAGGTTCAGTGGCAGTGGATCTGGGACAGATTTCACTCTCACCATCAGCAGTCTGCAACCT  284
O2           161  ........  .....................................G............................................  240
JK4
                  ----------------------------  
H16-7.213LC  285  GAAGATTTTGCTACTTACTACTCCTGT  CAACAGAGTTACAGTTTCCCGCTCACTTTCGGCGGAGGGACCAAGGTGGAGATCAA  364
O2           241  ........A........A........  ..........................................................  279
JK4            1  ...........................  ..........................................................   36
H16-7.213LC  365  ACGAACTGTGGCTGCACCATCTGTCTTCATCTTCCCGCCATCTGATGAGCAGTTGAAATCTGGAACTGCCTCTGTTGT  444
O2
JK4           37  ....                                                                             38
```

Figure 5B Alignment of H16-9.69 Light Chain Variable Region to human germline VK-B3/JK1

```
                   <------------------------FWR1------------------------>  <----
H16-9.69LC   24    GACATCGTGATGACCCAGTCTCCAGACTCCCTGGCTGTGTCTCTGGGCGAGAGGGCCACCATCAACTGC   AAGTCCAGCCA   103
B3            1    ..............................................................................   ...........    80
JK1

-------CDR1--------->   <-----------FWR2----------->
H16-9.69LC  104    GAGTGTTTTATACAGCTCCAAGAATAAGAACTACTTAGCT   TGGTACCAGCAGAAACCAGGACAGCCTCCTAAGCTGCTCA   183
B3           81    .............C..........................   ........................................    160
JK1

---CDR2---->   <------------FWR3------------
H16-9.69LC  184    TTTAC   TGGGCATCTACCCGGGAATCC   GGGGTCCCTGACCGATTCAGTGGCAGCGGGTCTGGGACAGATTTCACTCTCACC   263
B3          161    .....   ......................   ................................................    240
JK1

H16-9.69LC  264    ATCAGCAGCCTGCAGGCTGAAGATGTGGCAGTTTATTACTGT   CAGCAATATTATAGTACTCCTCCGTTGACGTTCGGCCA   343
B3          241    ..........................................   ......................................    305
JK1           1    ..........................................   ...............                           15

H16-9.69LC  344    AGGGACCAAGGTGGAAATCAAACGAACTGTGGCTGCACCATCTGTCTTCATCTTCCCGCCATCTGATGAGCAGTTGAAAT   423
B3
JK1          16    ...............                                                                         38
```

Figure 5C Alignment of H16-1.52 Light Chain Variable Region to human germline B3/JK2

```
                     <-------------FWR1-------------><----
H16-1.52LC    22  GACATCGTGATGACCCAGTCTCCAGACTCCCTGGCTGTCTCTGTGGGCGAGAGGGCCACCATCAACTGC  AAGTCCAGCCA  101
B3             1  ................................................................    ...........   80
JK2

-------------CDR1-------------><-------FWR2-------
H16-1.52LC   102  GAGTGTTTTATACAGCTCCAACAATAAGAACTACTTAGCT  TGGTACCAGCAGAAACCAGGACAGCCTCCCAAGCTGCTCA  181
B3            81  ........................................  .................................T......  160
JK2

---><-----CDR2------>
H16-1.52LC   182  TTTTAC  TGGGCATCTACCCGGGAATCC  GGGGTCCCTGACCGATTCAGTGGCAGCGGGTCTGGGACAGATTTCACTCTCACC  261
B3           161  ......  ....................  ...............................................   240
JK2

<------FWR3------
H16-1.52LC   262  ATCAGCAGCCTGCAGGCTGAAGATGTGGCAGTTTATTACTGT  CAGGAATATTATAGTACCATGTGCAGTTTTTGGCCAGGG  341
B3           241  .........................................  .......................C..............   299
JK2            1                                              ..................A..C.........   19

H16-1.52LC   342  GACCAAGCTGGAGATCAAACGAACTGTGGCTGCACCATCTGTCTTCATCTTCCCGCCATCTGATGAGCAGTTGAAATCTG  421
B3
JK2           20  ...............................................................................   39
```

Figure 5D Alignment of Ha16-1(1)23 Light Chain Variable Region to human germline V1-20/JL2

```
                  <-----------------------------FWR1-------------------------->  <--
Ha16-1(1)23LC  40 CAGGCAGGGCTGACTCAGCCACCCTCGGTGTCCAAGGGCTTGAGACAGACCGCCACACTCACCTGC ACTGGGAACAGCAA 119
V1-20           1 ................................................................. .............. 80
JL2
                  -------CDR1-----------> <---------------FWR2---------------->     <---
Ha16-1(1)23LC 120 CAATGTTGGCACCAAGGAGCAGCT TGGCTGCAGCAGCACCAGGGCCACCCTCCCAAACTCCTTTCCTAC AGGAATAACA 199
V1-20          81 ...T..........A......... ........................................... .A........ 160
JL2
                  --DR2------>                                     <----------FWR3-----
Ha16-1(1)23LC 200 ACCGGCCCTCA GGGATCTCAGAGAGATTATCTGCATCCACGTCAGGAAACACAGCCTCCCTGACCATTACTGACTCCAG 279
V1-20         161 ........... ..........C.................G..................................... 240
JL2
                  --------------------------------->
Ha16-1(1)23LC 280 CCTGAGGACGAGGCTGACTATTACTGC TCAGCATGGGACACAGCCTCAGTGCTGTGGTATTCGGCGAGGGACCAAGCT 359
V1-20         241 ..........................T ............................................. 294
JL2             1                              .................................... 27
Ha16-1(1)23LC 360 GACCGTCCTAG 370
V1-20
JL2            28 ........... 38
```

Figure 5E Alignment of H16-9.44 Light Chain Variable Region to human germline L1/JK3

```
                              <------------------------------FWR1----------------------------->
H16-9.44LC    43  GACATCCAGATGACCCAGTCTCCATCCTCACTGTCTGCATCTGTAGGAGACAGAGTCACCATCAGTTGT  CGGGCGAGTCA  122
L1             1  ..................................................................  .......C...   80
JK3

<---------CDR1------->                                          <------CDR2
H16-9.44LC   123  GGGCATTAGCAATTATTTAGCC  TGGTTTCAGCAGAAACCAGGGAAAGCCCCTAAGTCCCTGATCTAT  GCTGCATCCAGTT  202
L1            81  ......................  ..................................................  .............  160
JK3

<-----------------------------FWR3---
H16-9.44LC   203  TGGAAAAT  GGGGTCCCATCAAAGTTCAGCGGCAGTGGATCTGGGACAGATTTCACTCTCACCATCAGCAGCCTGCAGCCT  282
L1           161  ..C...G.  ..........................................................................  240
JK3

--->
H16-9.44LC   283  GAAGATTTTGCAACTTATTACTGC  CAACAGTATAATAGTTCCCATTCACTTTCGGCCCTGGGACCAAAGTGGATATCAG  362
L1           241  ........................  ..........................................................  280
JK3            1  ........................                                                           36
                                                                                            .A

H16-9.44LC   363  ACGAACTGTGGCTGCACCATCTGTCTTCATCTTCCCGCCATCTGATGAGCAGTTGAAATCTGGAACTGCCTCTGTTGTGT  442
L1
JK3           37  .................                                                                38
```

Figure 5F Alignment of H16-1.67 Light Chain Variable Region to human germline O2/JK1

```
                  <-------------------------------FWR1----------------------------->
H16-1.67LC    48  GACATCCAGATGACCCAGTCTCCATCCTCCCTGTCTGCATCTGTAGGAGACAGAGTCACCATCACTTGC  CGGGCAAGTCA  127
O2             1  ...................................................................  ...........   80
JK1

<------CDR1-------->                       <-------FWR2--------       <---CDR2
H16-1.67LC   128  GAGTATTAGTAACTATTTAAAT  TGGTATCAGCAGAAACCAGGGAAAGCCCCTAAGCTCCTGATCTAT  GCTGCATCCAGTT  207
O2            81  .......C...C.G........  ...................................................  .............  160
JK1

----->                                                <-------------------FWR3---
H16-1.67LC   208  TGCAAAGT  GGGGTCCCATCAAGGTTCAGTGGCAGTGGATCTGGGACAGATTTCACTCTCACCATCAGCAGTCTGCAACCT  287
O2           161  ........  ..................................................................................  240
JK1

------------------------------------------>
H16-1.67LC   288  GAAGATTTTGCAACTTACTACTGT  CAACAGATTTACAGTACCCCTCCGAGTGACGTTCGGCCAAGGGACCAAGGTGGA  367
O2           241  ........................  .....G...............................................  287
JK1            1  ...........................................................................  30

H16-1.67LC   368  AATCAAACGAACTGTGGCTGCACCATCTGTCTTCATCTTCCCGCCATCTGATGAGCAGTTGAAATCTGGAACTGCCTCTG  447
JK1           31  ........                                                                         38
```

Figure 5G Alignment of Ha16-1(3,5)36 Light Chain Variable Region to human germline V1-16/JL2

```
                    <------------------------------FWR1------------------------->  <---
Ha16-1(3,5)36   42  CAGTCTGTACTGACTCAGCCACCTCAGCCGTCTGGGACCCCCGGGCAGAGGGCCACCATCTCTTGT  TCTGGAAGCAGCAC  121
V1-16            1  .................G...............................................  ......T.......   80
JL2

----CDR1------------------------>  <----------------FWR2------
Ha16-1(3,5)36  122  CAATATCGG---AA---GTACTATTGTAAAC    TGGTACCAGCAGTCCCAGGAACGGCCCCCAAACTCCTCATCTAT  AGTA  195
V1-16           81  .........C..........................................C.....................  ....  154
JL2

----CDR2------->  <-----------------------------------FWR3-------
Ha16-1(3,5)36  196  ATAATCAGGCGGCCCTCA    GGGGTCCCTGACCGATTCTCTGGCTCCAAGTCTGGCACCTCAGCCTCCCTGGCCATCAGTGGG  275
V1-16          155  ..................  ...........................................................  234
JL2

Ha16-1(3,5)36  276  CTCCAGTCTGAGGATGAGGCTGATTATTACTGT  GCAGCATGGGATGCCAGCCTGAATGTCGGTATTCGGCGGAGGAC  355
V1-16          235  .................................  .........................A.................  296
JL2              4  ............................................................................   21

Ha16-1(3,5)36  356  CAAGCTGACCGTCCTAG  372
V1-16
JL2             22  .................   38
```

Figure 5H Alignment of H16-1.86 Light Chain Variable Region to human germline O2/JK1

```
H16-1.86LC    46  GACATCCAGATGACCCAGTCTCCATCCTCCCTGTCTGCATCTGTAGGAGACAGAGTCACCATCACTTGC    125
O2             1  ..................................................................    80
JK1

<----CDR1---->                              <----FWR2----
H16-1.86LC   126  GAGCATTAGCAGCTATTTAAAT  TGGTATCAGCAGAAACCAGGGAAAGCCCCTAACCTCCTGATCTAT  205
O2            81  ......................  ...........G..........................G......  160
JK1

<-----CDR2----->
H16-1.86LC   206  TGCAAAGT  GGGGTCTCCATCAAGGTTCAGTGGCAGTGGATCTGGGACAGATTTCACTCTCACCATCAGCAGTCTGCAACCT  285
O2           161  ........  ..........................................................................  240
JK1

<----FWR3
H16-1.86LC   286  GAAGATTTGCAACTTACTACTGT  CAACAGACTTACAGTTCCCCTCCGTGACGTTCGGCCAAGGGACCAAGGTGGAAAT  365
O2           241  .......................  ..............G........A................................  287
JK1            1  ................................................  33

H16-1.86LC   366  CAAACGAACTGTGGCTGCACCATCTGTCTTCATCTTCCCGCCATCTGATGAGCAGTTGAAATCTGAACTGCCTCTGTTG  445
O2
JK1           34  ..............  38
```

Figure 5I Alignment of H16-9.10 Light Chain Variable Region to human germline L5/JK4

Figure 5J Alignment of H16-9.33 Light Chain Variable Region to human germline L5/JK4

```
                     <-------------------------------FWR1----------------------------->  <----
H16-9.33LC   45  GACATCCAGATGACCCAGTCTCCATCTTCCGTGTCTGCATCTGTAGGAGACAGAGTCACCATCACTTGT   CGGGCGAATCA   124
L5            1  ....................................................................   .......G...    80
JK4

-----CDR1-----------> <---------------FWR2---------------->              <----CDR2
H16-9.33LC  125  GGGTATTAGGAGTTGGTTAGCC   TGGTATCAGCAGAAACCAGGGAAAGCCCCAAAGCTCCTGATCTAT   GCTGCATCCAGTT   204
L5           81  .........C..C........                             ........T.........   ............    160
JK4

----->                                                       <------------------FWR3
H16-9.33LC  205  TGCAAAGT   GGGGTCCCATCAAGGTTCAGCGGCAGTGGATCTGGGACAGATTTCACTCTCACCATCAGCAGCCTGCAGCCT   284
L5          161  ........                                                     .............................    240
JK4

H16-9.33LC  285  GAAGATTTTGCAACTTACTATTGT   CAACAGGCTAATACAGTTTCCCTCCCACTTTCGGCGGAGGGACCAAGGTGGAGATCAA   364
L5          241  ........................                                                          ........    287
JK4           4                                                                                      ..........    36

H16-9.33LC  365  ACGAACTGTGGCTGCACCAACTCTGTCTTCATCTTCCCGCCATCTGATGAGCAGTTGAAATCTGGAACTGCCTCTGTTGTGT   444
L5
JK4          37  .                                                                                    38
```

Figure 5K Alignment of Ha16-1(1)11 Light Chain Variable Region to human germline O2/JK3

Figure 5L Alignment of Ha16-1(3,5)18 Light Chain Variable Region to human germline V1-19/JL2

Figure 5M Alignment of Ha16-1(2,4)4 Light Chain Variable Region to human germline V2-1/JL2

```
Ha16-1(2,4)4 VL    1  <-------------------------FWR1-----------------------><-------
                      ---TATGTGTGACTCAGCCACCCTCAGTGTCCGTGTCCCAGAGACAGCAGCCATCACCTGC  TCTGGAGATAAATT  77
V2-1           1      ---TCC.....A..........................................  ..............  80
JL2

Ha16-1(2,4)4 VL   78  -CDR1-------><-----------------FWR2---------------------><------CDR2----
                      GGGGATAAATATGCTTGC  TGGTATCAGCAGAAGCCAGGCCAGTCCCCTGTGCTGGTCATCTAT  CAAGATAGCAAGCGGC  157
V2-1          81      ..................  ........................................  ................  160
JL2

Ha16-1(2,4)4 VL  158  ----><------------------------------FWR3-----------------------------
                      CCTCA  GGGATCCCTGAGCGATTCTCTGGCTCCAACTCTGGGAACACAGCCACTCTGACCATCAGCGGGACCCAGGCTATG  237
V2-1         161      .....  ......................................................................  240
JL2

Ha16-1(2,4)4 VL  238  ----->
                      GATGAGGCTGACTATTACTGT  CAGGGCGTGGACAACAGAACTGCGGTATTCGGCGGAGGGACCAAGCTGACCGTCCTAG  316
V2-1         241      .....................  G....C........................................G.........  284
JL2            1      .....................  ................................T..................  38
```

Figure 5N Alignment of Ha16-1(3,5)56 Light Chain Variable Region to human germline V1-4/JL2

```
                   <--------------------FWR1------------------------>   <-----
Ha16-1(3,5)56  5   --------CTGACTCAGCCTGCCTCCGTGTCTGGGTCTCCTGGACAGTCGATCACCATCCTGC  ACTGGAACCAGCAG  75
V1-4           1   CAGTCTGCC...................................................  ..............  80
JL2                ---

----CDR1------->
Ha16-1(3,5)56  76  TGACGTTGGTAATTATAACTATGTCTCC  TGGTACCAACAACACCCAGGCAAAGCCCCCAAACTCATGATTTAT  GCGGTCA  155
V1-4           81  ..........GG................  ...........G................................  ..A....  160
JL2                ---

--CDR2------>                                      <--------FWR3------
Ha16-1(3,5)56  156 ATAATCGGCCCTCA  GGGGTTTCTAATCGCTTCTCTGGCTCCCAAGTCTGGCAACACGGCCTCCCTGACCATCTCTGGGCTC  235
V1-4           161 G.............  ...............................................................  240
JL2

Ha16-1(3,5)56  236 CAGGCTGAGGACGAGGCTGATTATTACTGC  AGCTCATATACAAGCAGGAATCTTGTAGTTTTCGGCGGCCGGACCAA  315
V1-4           241 ..............................  .....G..A.....................................  290
JL2            1   ---                             A                                              24

Ha16-1(3,5)56  316 GCTGACCGTCCTAG  329
V1-4               ---
JL2            25  ..............  38
```

Figure 5O Alignment of H16-7.8 Light Chain Variable Region to human germline A26/JK1

```
                    <-----------------------------FWR1-----------------------------><---
H16-7.8    100  GAAATTGTGCTGACTCAGTCTCCAGACTTTCAGTCTGTGACTCCAAAGGAGAAAGTCACCATCACCTGC  CGGGCCAGTCA   179
A26          1  ..................................................................  ...........    80
JK1

---CDR1---------------><-----------------------------FWR2-----------------><------CDR2
H16-7.8    180  GAGCATTGTGTATTAGCTTACAC  TGTACCAGCAGAAACCAGATCAGTCTCCAAAGCTCCTCCATCAAG  TATGCTTCCCAGT   259
A26         81  .......G...............  .................................................  .............   160
JK1

<------------------------------------FWR3------------------------------------------
H16-7.8    260  CCTTCTCA  GGGGTCCCCCTCGAGGTTCAGTGGCAGTGGATCTGGGACAGATTTCACCCTCACCATCAATAGCCTGGAAGCT   339
A26        161  ........  .........................................................................   240
JK1

-------------------------->
H16-7.8    340  GAAGATGCTGCAACGTATTACTGT  CATCAGAGTAGGAGTTTCCCGTGGACGTTCGGCCAAGGGACCAAGGTGGAAATCAA   419
A26        241  ........................  ...T.........................................................   281
JK1          1  ..........................................................   36

H16-7.8    420  ACGAACTGTGGCTGCACCAACTCTGTCTTCATCTTCCCGCCATCTGATGAGCAGTTGAAATCTGAACTGCCTCTGTTGT   499
A26
JK1         37  ...............................................   38

H16-7.8    500  GCCTGCTGAATAACTTCTATCCCAGAGAGGCCAAAGTACAGTGGAAGGTGGA   551
A26
JK1
```

Figure 5P Alignment of H16-1.68 Light Chain Variable Region to human germline O2/JK4

```
                        <------------------------FWR1------------------------>                              <------
H16-1.68     10  ------------------TGACGCAGTCTCCATCCCTGTCTGCATCTGTTGGAGACAGAGTCACCATCACTTGC  CGGGCAAGTCA   79
O2           11  ------------------......................A.................................  ...........   80
JK4                                ......C....................................................
                        <------CDR1------>         <------------------------FWR2------------------------>         <------CDR2
H16-1.68     80  GAACATTAACAGCTATTTAAAT  TGGTATCAGCAGAAACCAGGGAAAGCCCCTAAGCTCCTGATCTAT  GCTGCATCCAGTT  159
O2           81  .G.....G..............  ..............................................  .............  160
JK4
                      ------>           <------------------------------------FWR3
H16-1.68    160  TGCAAAGT  GGGGTCCCATCAAGGTTCAGTGGCAGTGGATCTGGGACAGATTTCACTCTCACCATCAGCAGTCTACAACCT  239
O2          161  ........  ...................................................G..........................  240
JK4
                  ---------------------------------->
H16-1.68    240  GAAGATTTTACAACTTACTACTGT  CAGCAGAGTTACAGTTCCGCCCCCCACTTTCGGCGGAGGGACCAAGCTGGAGATCAA  319
O2          241  .........G..............                                                            279
JK4                                        ......A..........................A..................G......    36
H16-1.68    320  ACGAACTGTGGCTGCACCAACTCTGTCTTCATCTTCCCGCCATCTGATGAGCAGTTGAAATCTGGAACTGCCTCTGTTGT  399
O2
JK4              ..........                                                                             37
H16-1.68    400  GCCTGCTGAATAACTTCTATCCCAGAGAGGCCAAAGTACAGTGGAAGGTGGA  451
O2
JK4                                                                   38
```

Figure 5Q Alignment of H16-1.93 Light Chain Variable Region to human germline A20/JK3

```
            <-------------------------FWR1---------------------------->  <-
H16-1.93  16  GACATCCAGATGACCCAGTCTCCATCCTCCCTGTCTGCATCTGTAGGAGACAGAATCACCATCACTTGG  CGGTCGAGTCA  95
A20        1  ....................................................................  ....G......  80
JK3           ---------------------------------------------------------------------  -----------

-------CDR1--------->  <-------------------------FWR2---------------------->  <------CDR2
H16-1.93  96  GGGCATTTACAATTCTTTAGCC  TGGTATCAGCAGAAACCAGGGAAAGTTCCTAAGCTCCTGATCTAT  GCTGCATCCACTT  175
A20       81  ........AG.....A......  .............................................  .............  160
JK3           ----------------------  ---------------------------------------------  -------------

------>  <---------------------------------------FWR3-----------------------------------
H16-1.93 176  TGCACTCA  GGGGTCCCATCTCGGTTCAGTGGCAGTGGATCTGGGACAGATTTCACTCTCACCATCAGCAGCCTGCAGCCT  255
A20      161  ....A...  .............................................................................  240
JK3           --------  -----------------------------------------------------------------------------

H16-1.93 256  GAAGATGTTGCAACTTATTACTGT  CAAAAATATAACAGTGCCCCATTCACTTTCGGCCCTGGGACCAAAGTGGATATCAA  335
A20      241  ........................  ......G.....................................................  284
JK3        1  ------------------------  ............................................................  36

H16-1.93 336  ACGAACTGTGGCTGCACCAACTCTGTCTTCATCTTCCCGCCATCTGATGAGCAGTTGAAATCTGGAACTGCCTCTGTTGT  415
A20           -------------------------------------------------------------------------------
JK3       37  ...                                                                              38

H16-1.93 416  GCCTGCTGAATAACTTCTATCCCAGAGAGGCCAAAGTACAGTGGAAGGTGGATA  469
A20           -----------------------------------------------------
JK3           -----------------------------------------------------
```

Figure 5R Alignment of Ha16-1(3,5)27 Light Chain Variable Region to human germline V1-4/JL2

```
                  <-----------------------------FWR1--------------------------->  <----
Ha16-1(3,5)27   4 CAGTCTGCCCTGACTCAACCTGCCCCGTGTCTCCTGGGTCTCCTGGACAGTCGATCACCATCTCCTGC ACTGGAACCAGCAG  83
V1-4            1 ..................G...............................................  ..............  80
JL2             1 -----------------------------------------------------------------------------------

-----CDR1------------>   <-------------FWR2----------------->  <----
Ha16-1(3,5)27  84 TGACGTTGTGGTTATAATTATGTCTCC TGGTACCAACAGC-ACCCAGGCCCCCAAACTCCTGATTTAT GGGGTC 162
V1-4           81 .........C................. ............-.A........................A ..A... 159
JL2             1 -----------------------------------------------------------------------------

-------FWR3--------------------------------------------------
Ha16-1(3,5)27 163 AATATTCGGCCCTCA GGGGTTTCTACTGCCTTCTCTCTGGCTCCAAGTCTGGCAACACGGCCTCCCTGACCATCTCTGGGCT 242
V1-4          160 ..G..A......... ............A................................................... 239
JL2             1 -------------------------------------------------------------------------------

Ha16-1(3,5)27 243 CCAGGCTGAGGACGAGGCCGATTATTATTGT AGTTCATATACAAGAAGCAGCATTCTTGTGTTTCGCCGGAGGACCA 322
V1-4          240 ...............T......C..C..... ..................C............................ 292
JL2             1 ...........................................A..G...........................  23

Ha16-1(3,5)27 323 AACTGACCGTCCTAG 337
V1-4          ---------------
JL2            24 ..G............  38
```

Figure 5S Alignment of H16-1.61 Light Chain Variable Region to human germline O12/JK3

```
H16-1.61    11  <------------------------FWR1-------------------------->   <---
                ------TGACTCAGTCTCCATCCTCCCTGTCTGCATCTGTAGGAGACAGAGTCACCATCACTTGC    CGGGCAAGTCA   80
O12          1  GACATCCAGA....C.............................................    ...........   80
JK3             ------------------------------------------------------------    -----------

H16-1.61    81  ----CDR1-------->                                                 <--------FWR2---------->   <----CDR2
                GAGCATTAGCAGCTATTAAAT  TGGTATCAGCTGAAACCAGGGAAAGCCCCTAAGCTCCTGATCTAT   GCTGCATCCAGTT   160
O12         81  ....................A  ........................................      ............   160
JK3             ---------------------  ----------------------------------------      ------------

H16-1.61   161  <                     <---------------------------------FWR3---------
                TAGAAAGT   GGGGTCCCATCAAGGTTCAGTGGCAGTGGATCTGGGACAGATTTCACTCTCACCATCAGCAGTCTGCAACCT   240
O12        161  .GC.....   ........................G......................................................   240
JK3             --------   ----------------------------------------------------------------------------

H16-1.61   241  ------------------------------------------------->
                GAAGATTTTGCAACTTACTACTGT   CAACAGAGTTACAATTCCCCAATCACCACTTTCGGCCCTGGGACCAAAGTGGATATCAA   320
O12        241  .......................                                                                 277
JK3          3  ------------------------   ..................................................        36

H16-1.61   321  ACGAACTGTGGCTGCACCATCTGTCTTCATCTTCCCGCCATCTGATGAGCAGTTGAAATCTGGAACTGCCTCTGTTGTGT   400
O12             --------------------------------------------------------------------------------
JK3         37  ........                                                                           38

H16-1.61   401  GCCTGCTGAATAACTTCTATCCCAGAGAGGCCAAAGTACAGTGGAAGGTGGATA   454
O12             -----------------------------------------------------
JK3             -----------------------------------------------------
```

Figure 5T Alignment of Ha16-1(3,5)5 Light Chain Variable Region to human germline V1-4/JL2

| | | |
|---|---|---|
| Ha16-1(3,5)5 | 7 | CAGTCTGCCCTGACTCAGCCTGCCTCCGTGTCTGGGTCTCCTGGACAGTCGATCACCATCTCCTGC ACTGGAACCAGCAG 86 |
| V1-4 | 1 | ................................................................ ................ 80 |
| JL2 | | |
| Ha16-1(3,5)5 | 87 | TGACGTTGGTGGTTATAACTATGTCTCC TGGTACCAACAACACCCAGGCAAAGCCCCCAAACTCATGATTTAT GCGGTCA 166 |
| V1-4 | 81 | ...........G.................... .................................... A...... 160 |
| JL2 | | |
| Ha16-1(3,5)5 | 167 | GTAATCGGCCCCTCA GGGGTTTCTAATCGGCTTCTCTGGCTCCAAGTCTGGCAACACGGCCTCCCTGACCATCTCTGGGCTC 246 |
| V1-4 | 161 | ............... ................................................................ 240 |
| JL2 | | |
| Ha16-1(3,5)5 | 247 | CAGGCTGAGGACGAGGCTGATTATTACTGC AGCTCATATACAACATCAGCAGGATTCTTGTGGTTTTCGGCGGAGGGACCAA 326 |
| V1-4 | 241 | ............................... ......G.................A...........A.......... 290 |
| JL2 | 1 | | |
| Ha16-1(3,5)5 | 327 | GCTGACCGTCCTAG 340 |
| V1-4 | | |
| JL2 | 25 | ............. 38 |

Figure 5U Alignment of H16-7.200 Light Chain Variable Region to human germline A19/JK5

Figure 5V Alignment of Ha16-1(3,5)42 Light Chain Variable Region to human germline V1-4/JL2

```
                    <-----------------------FWR1------------------------>  <--
Ha16-1(3,5)42   10  CAGTCTGCCCTGACTCAGCCTGCCCTCCGTGTCTGGGTCTCCTGGACAGTCGATCACCATCTCCTGC  ACTGGAACCAGCAG  89
V1-4             1  ..................................................................  ..............  80
JL2                 ------------------------------------------------------------------  --------------

-------CDR1------->  <----------------FWR2-------------->  <---
Ha16-1(3,5)42   90  TGACGTTGGTGTTTTAACTATGTCTCC  TGGTACCAACAGGCCCAGGCAAAGCCCCAAACTCATGATTTAT  GCGGTCA  169
V1-4            81  .........G...A.............  ..........................A...............  ...A...  160
JL2                 ---------------------------  ------------------------------------------  -------

--CDR2------->  <---------------------FWR3---------------------->
Ha16-1(3,5)42  170  ATATTCGGCCCTCA  GGGGTTTCTAATGCTTCTCTGGCTCCAAGTCTGGCAACACGGCCTCCCTGACCATCTCTGGGCTC  249
V1-4           161  G..A..........  ..................................................................  240
JL2                 --------------  ------------------------------------------------------------------

Ha16-1(3,5)42  250  CAGGCTGAGGACGAGGCTGGTTATTACTGC  AGCTCATATACAAGCAGCAGCACTCTTCTGGTTTTCGGCGGAGGGACCAA  329
V1-4           241  .............................A  ..............................A..................  296
JL2              3  ------------------------------  ..................................................  24

Ha16-1(3,5)42  330  GCTGACCGGTCCT  341
V1-4                -------------
JL2             25  .............  36
```

Figure 5W Alignment of H16-9.65 Light Chain Variable Region to human germline A19/JK5

Figure 5X Alignment of Ha16-1(3,5)19 Light Chain Variable Region to human germline V1-4/JL2

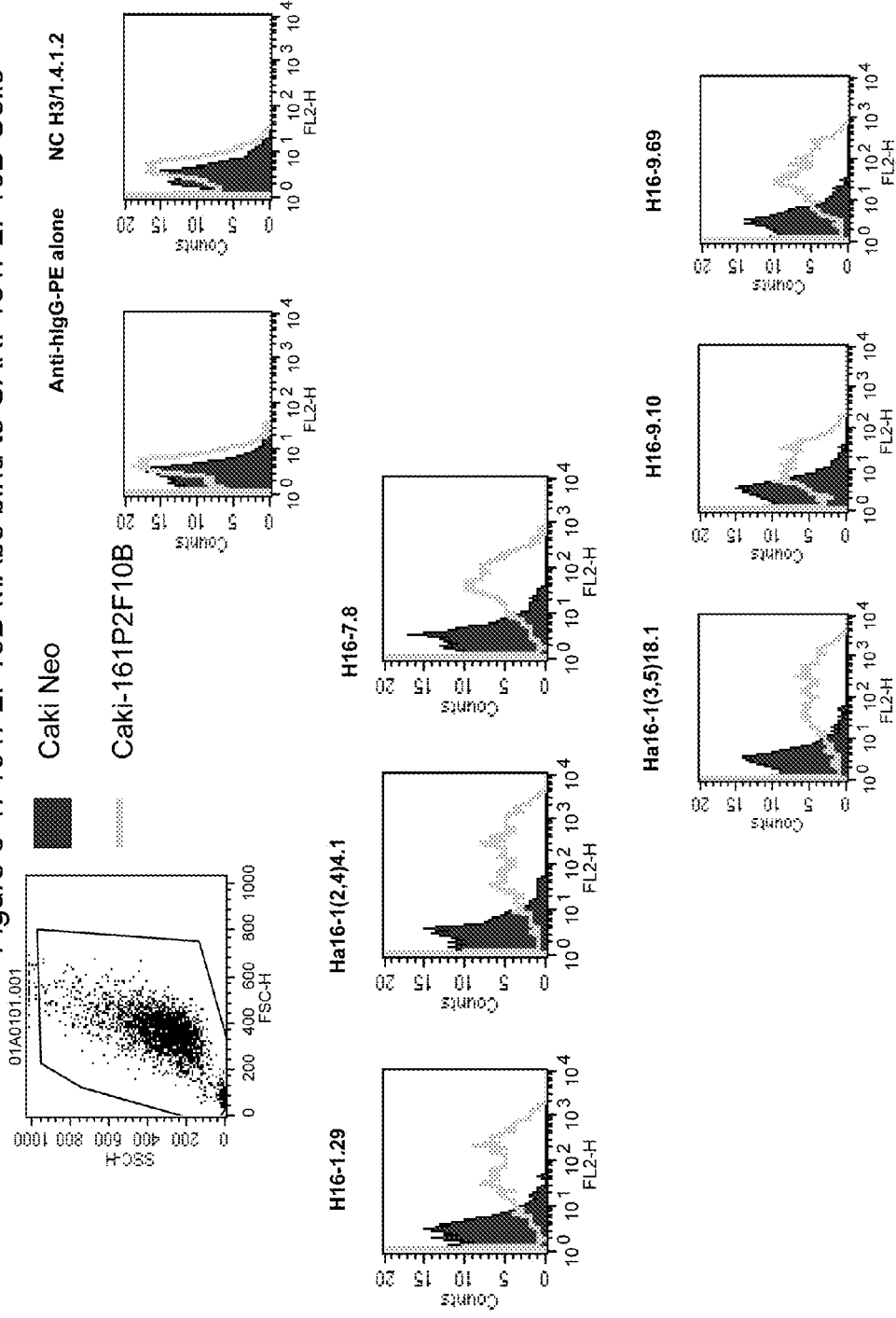

Figure 6-2
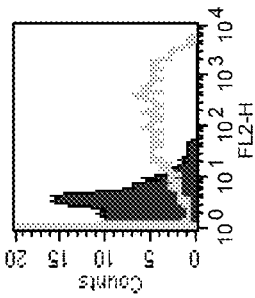
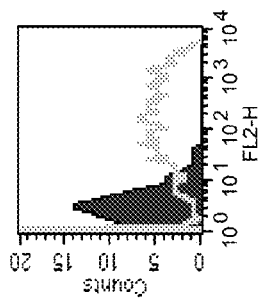
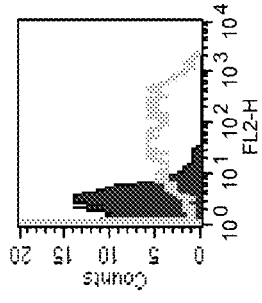
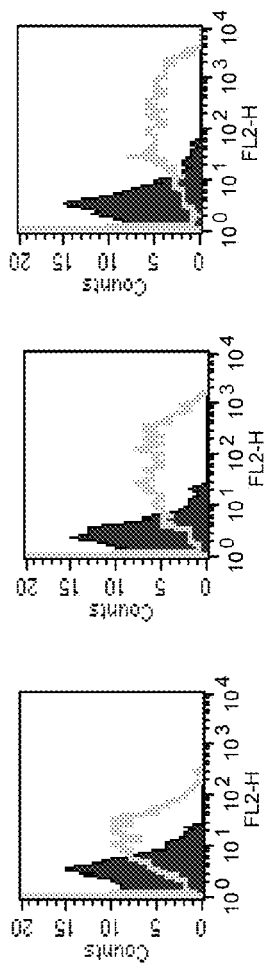
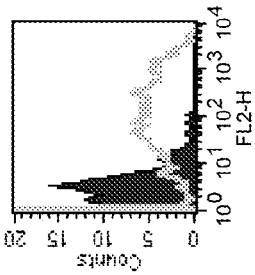
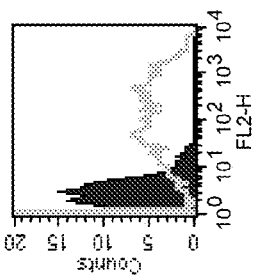
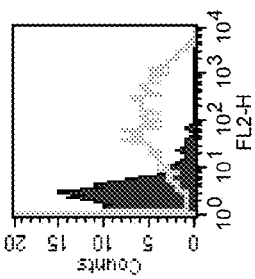

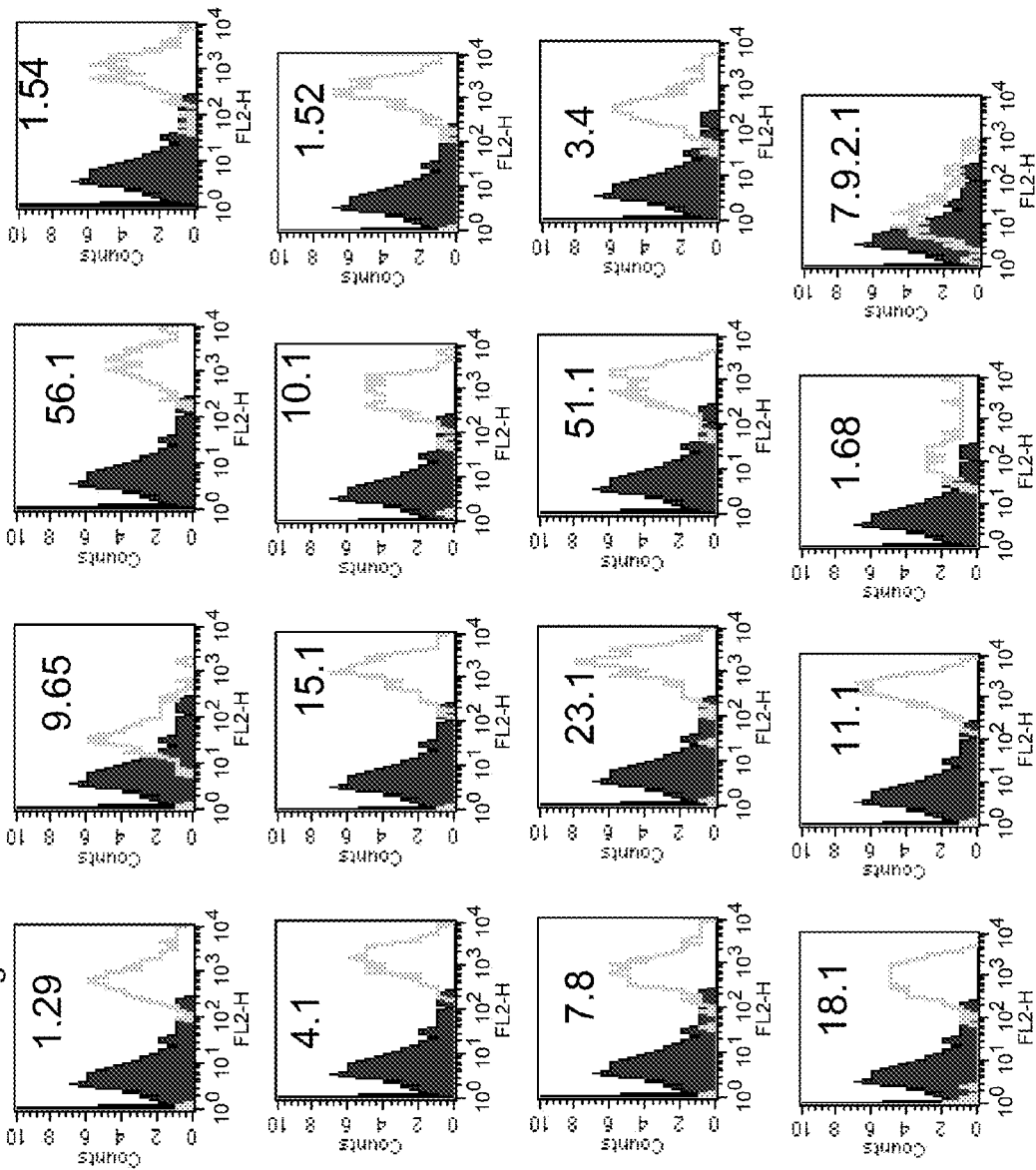
Figure 7-1: 161P2F10B MAbs bind to 161P2F10B on UG-K3 cells

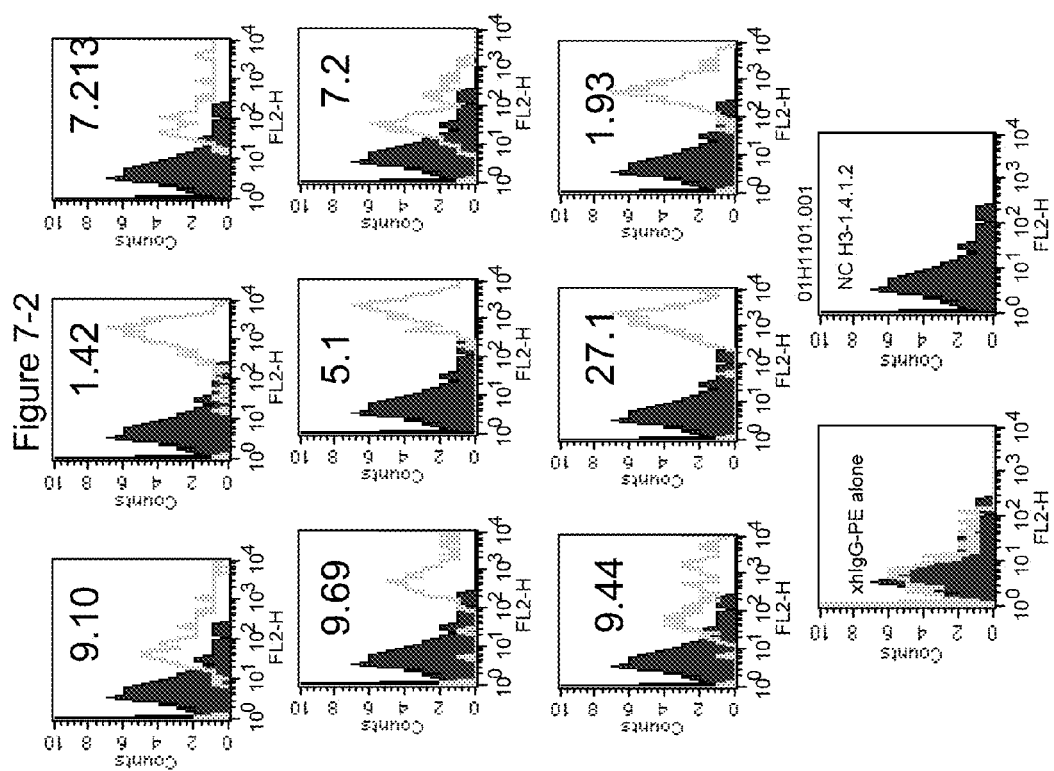

Figure 8: 161P2F10B MAbs epitope grouping on UG-K3 cells

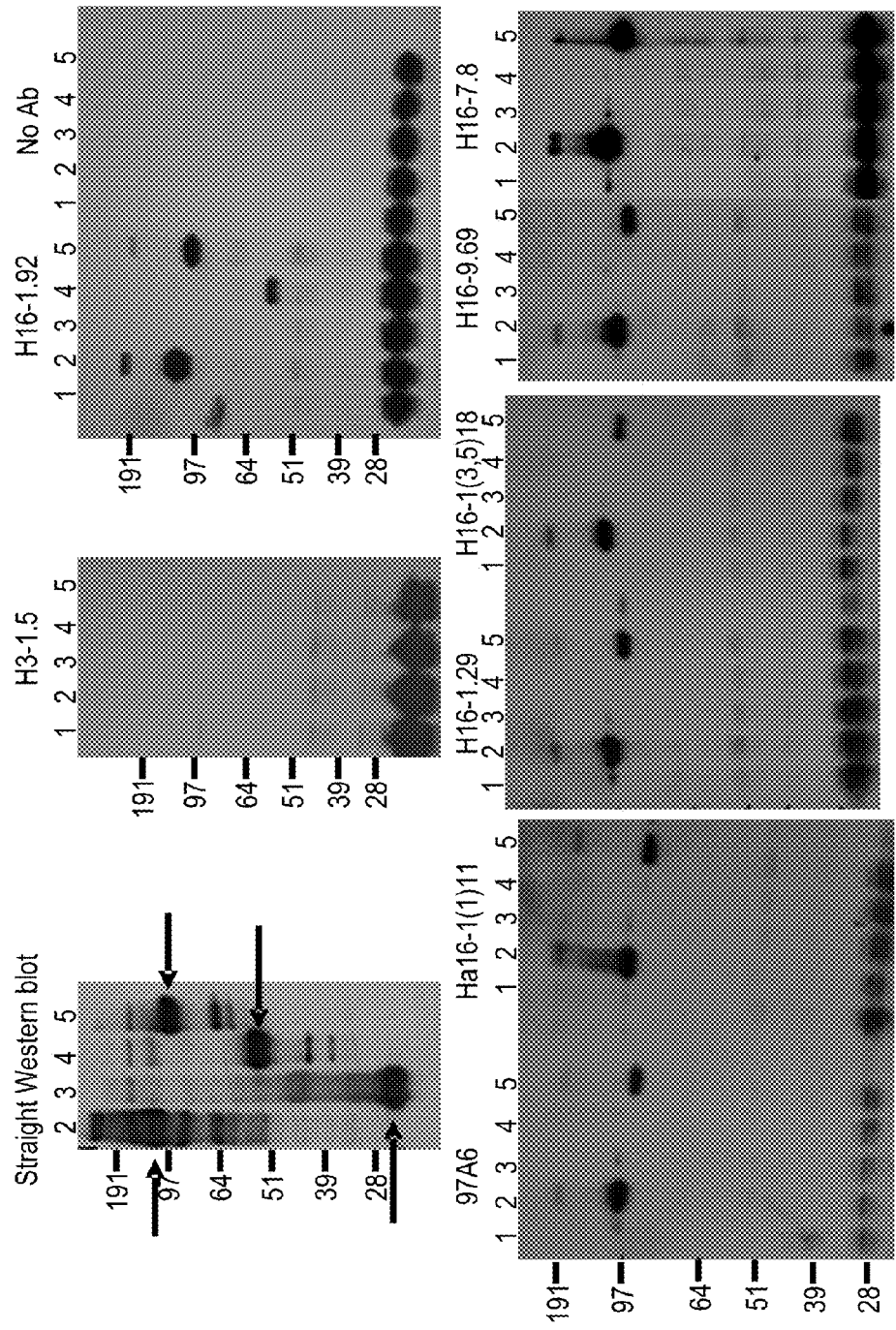
Figure 9: Domain mapping of 161P2F10B MAbs by immunoprecipitation

Figure 10: 161P2F10b MAb domain mapping
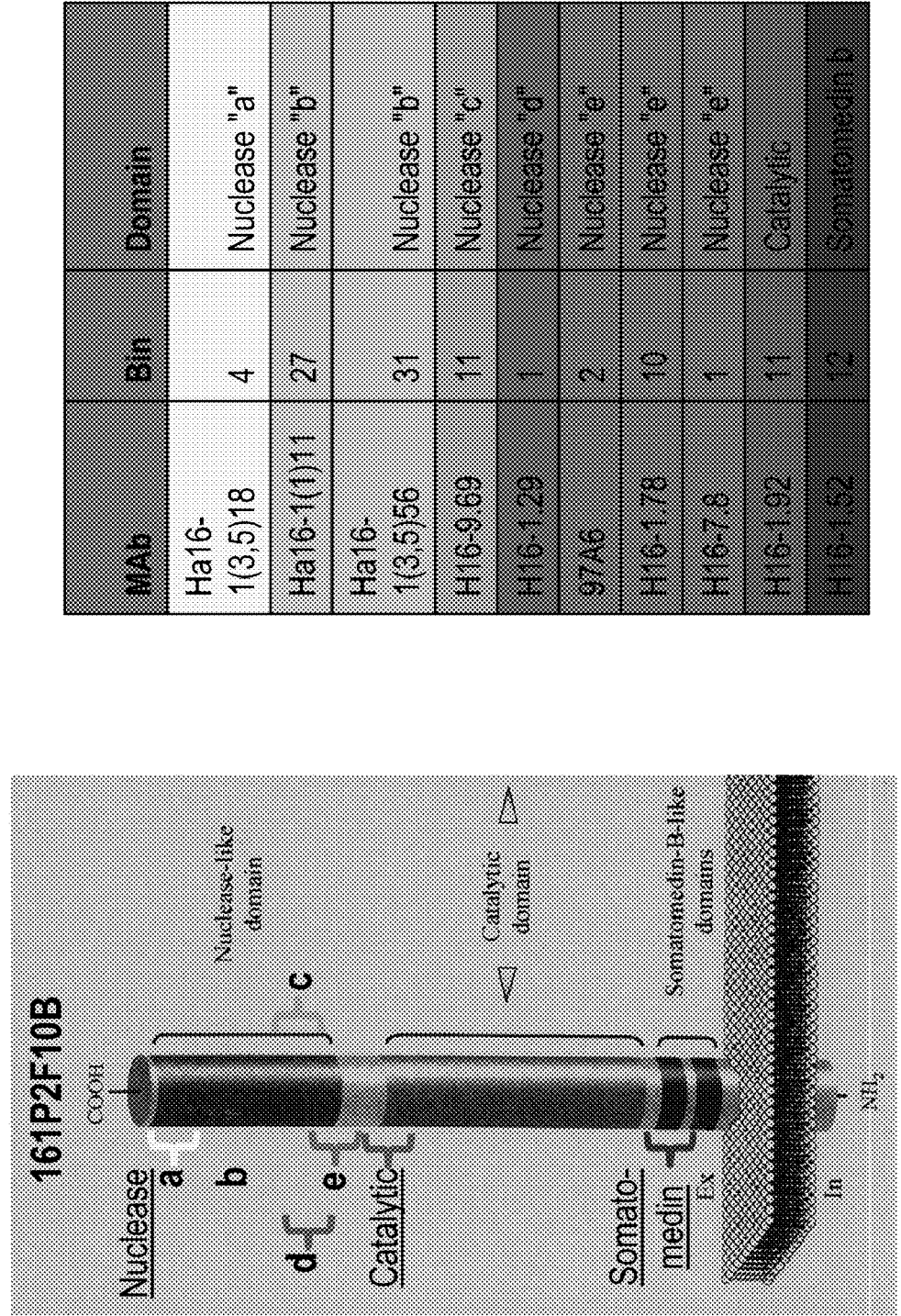

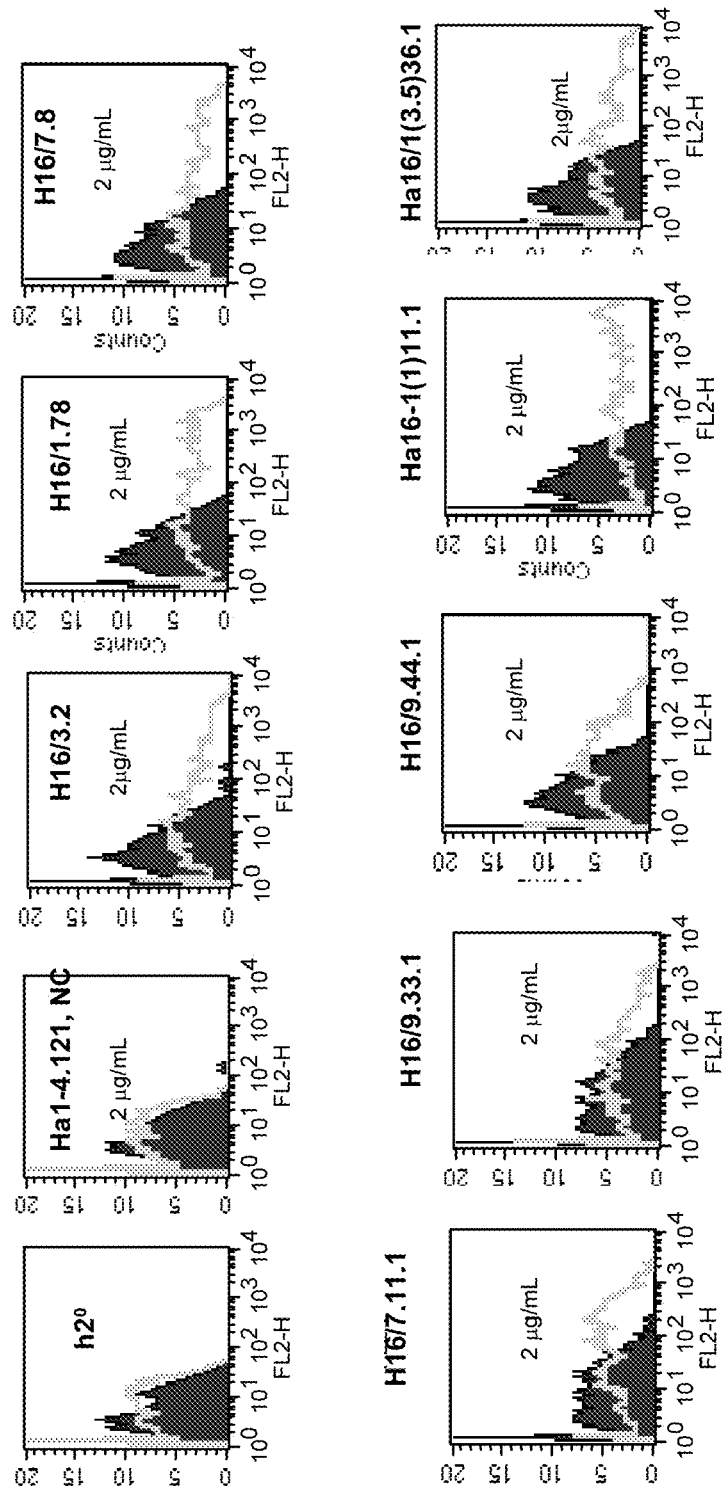
Figure 11: Cross-reactivity of 161P2F10B human MAbs to mouse 161P2F10B on 293T-161P2F10B / neo cells

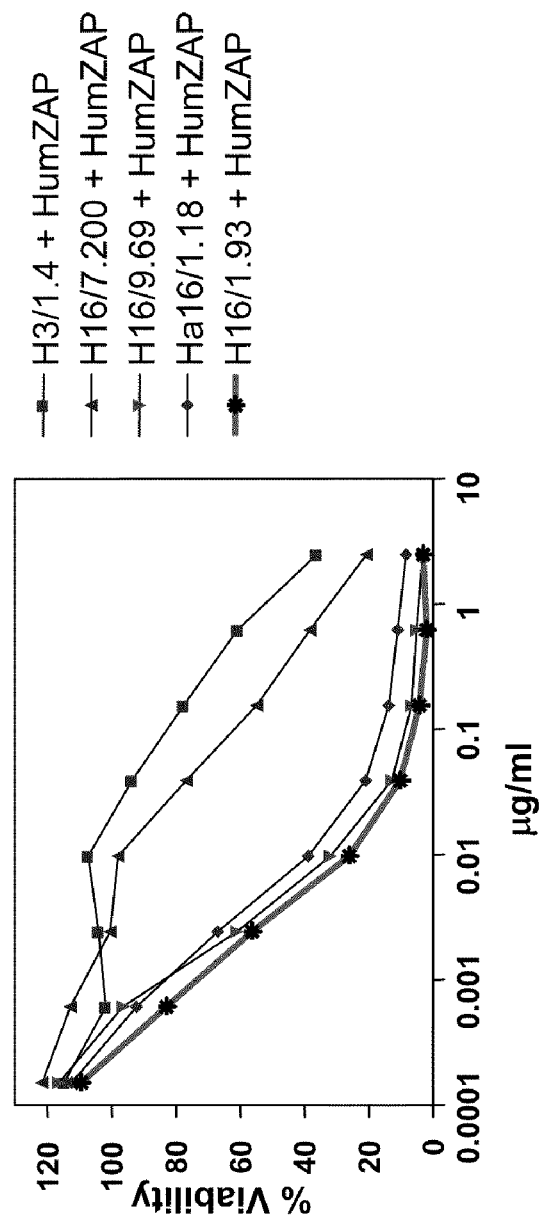
Figure 12: Saporin-Mediated Secondary Killing of KU-812 Cells

Figure 14: 161P2F10B MAbs inhibit the growth of UG-K3 cells in SCID mice

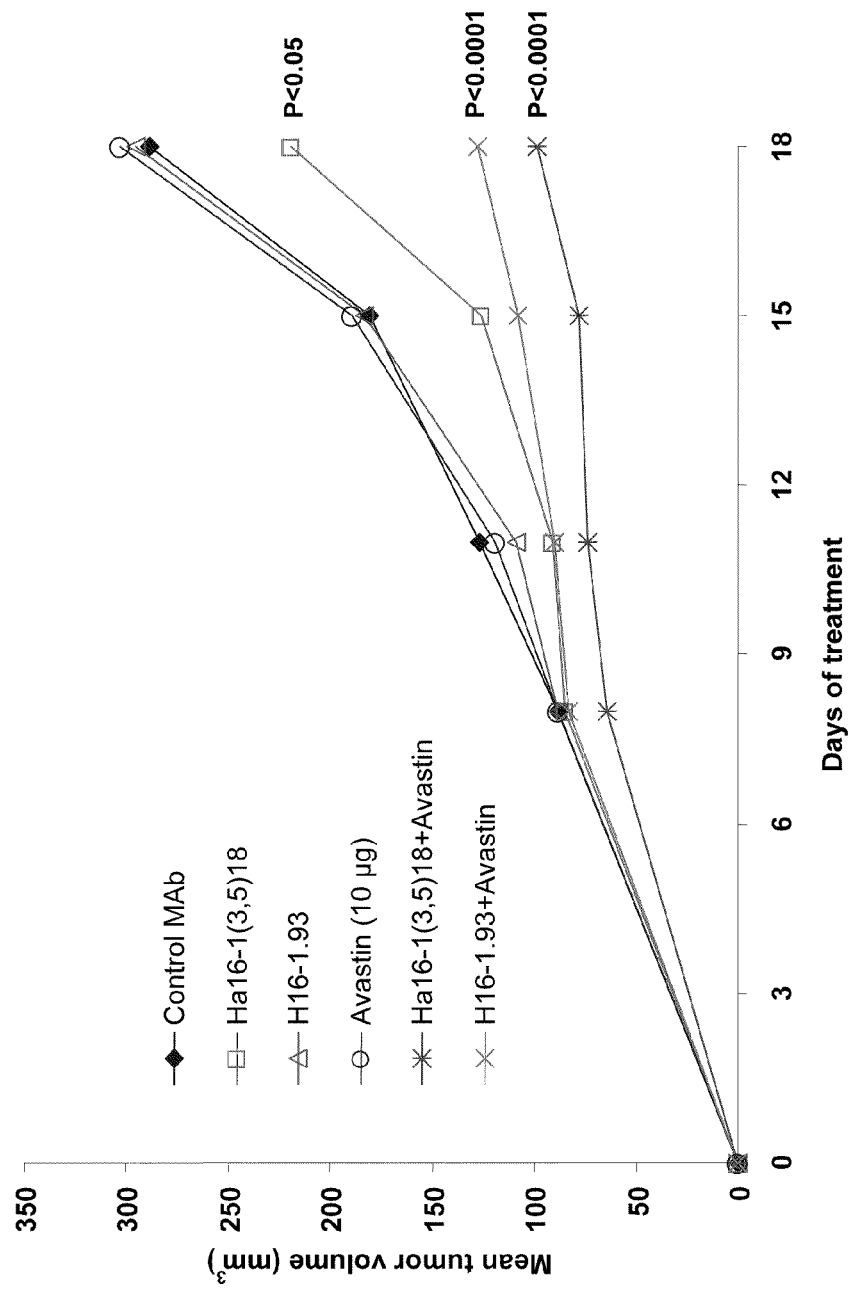
Figure 20: Combination of 161P2F10B MAbs with Avastin® inhibits the growth of human kidney cancer xenograft UG-K3 subcutaneously implanted in SCID mice

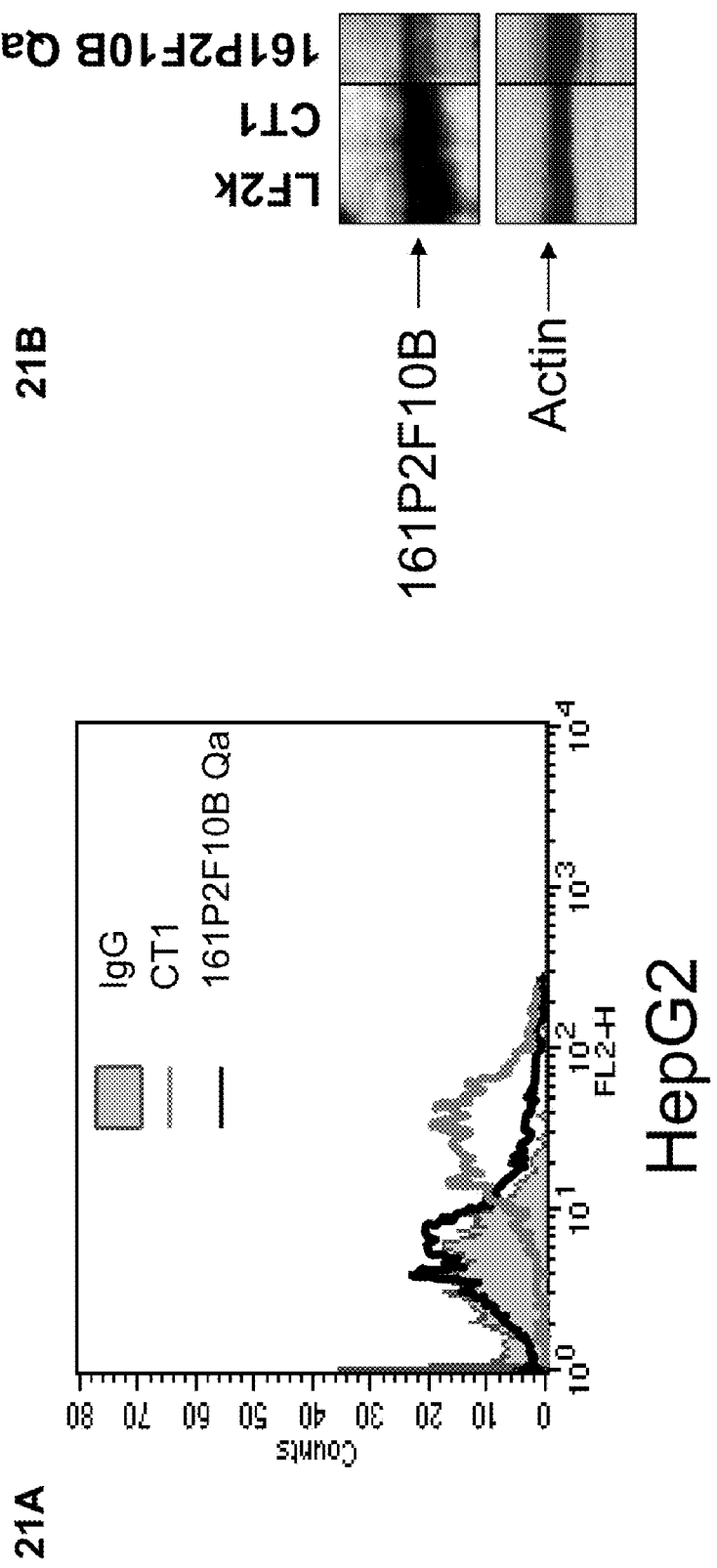
Figure 21: 161P2F10B silencing by RNAi in HepG2 cells

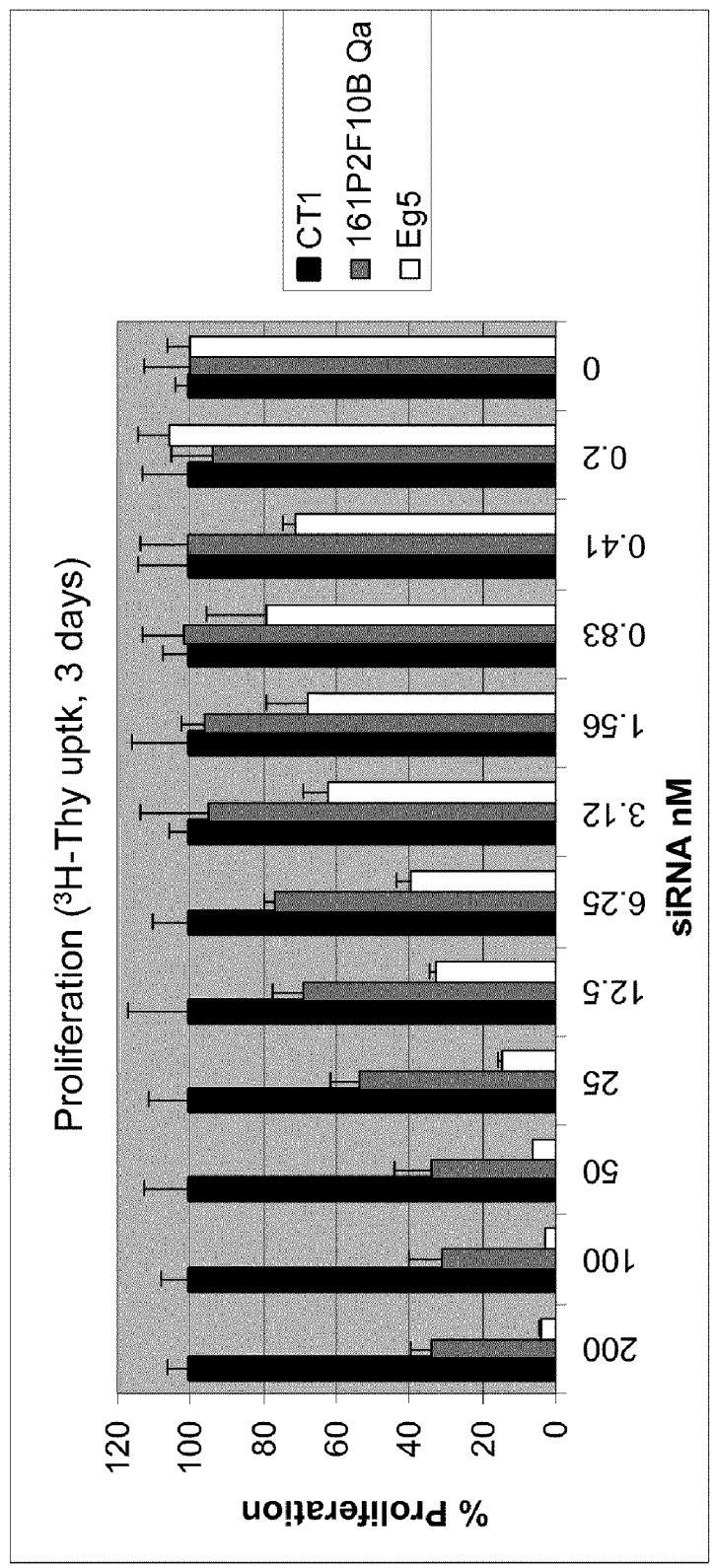
Figure 22A: 161P2F10B RNAi silencing and cell proliferation/colony growth

FIGURE 22B
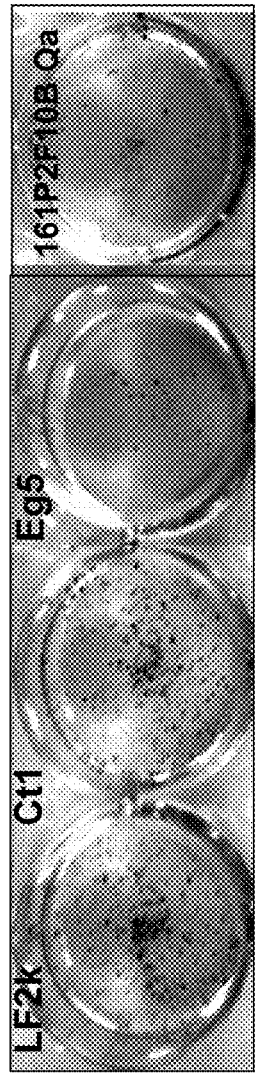
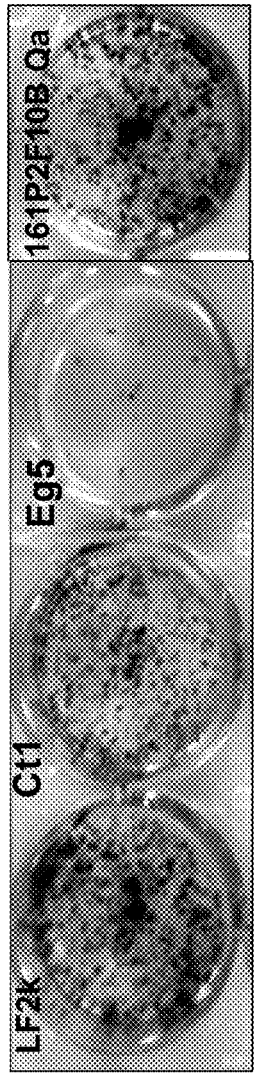

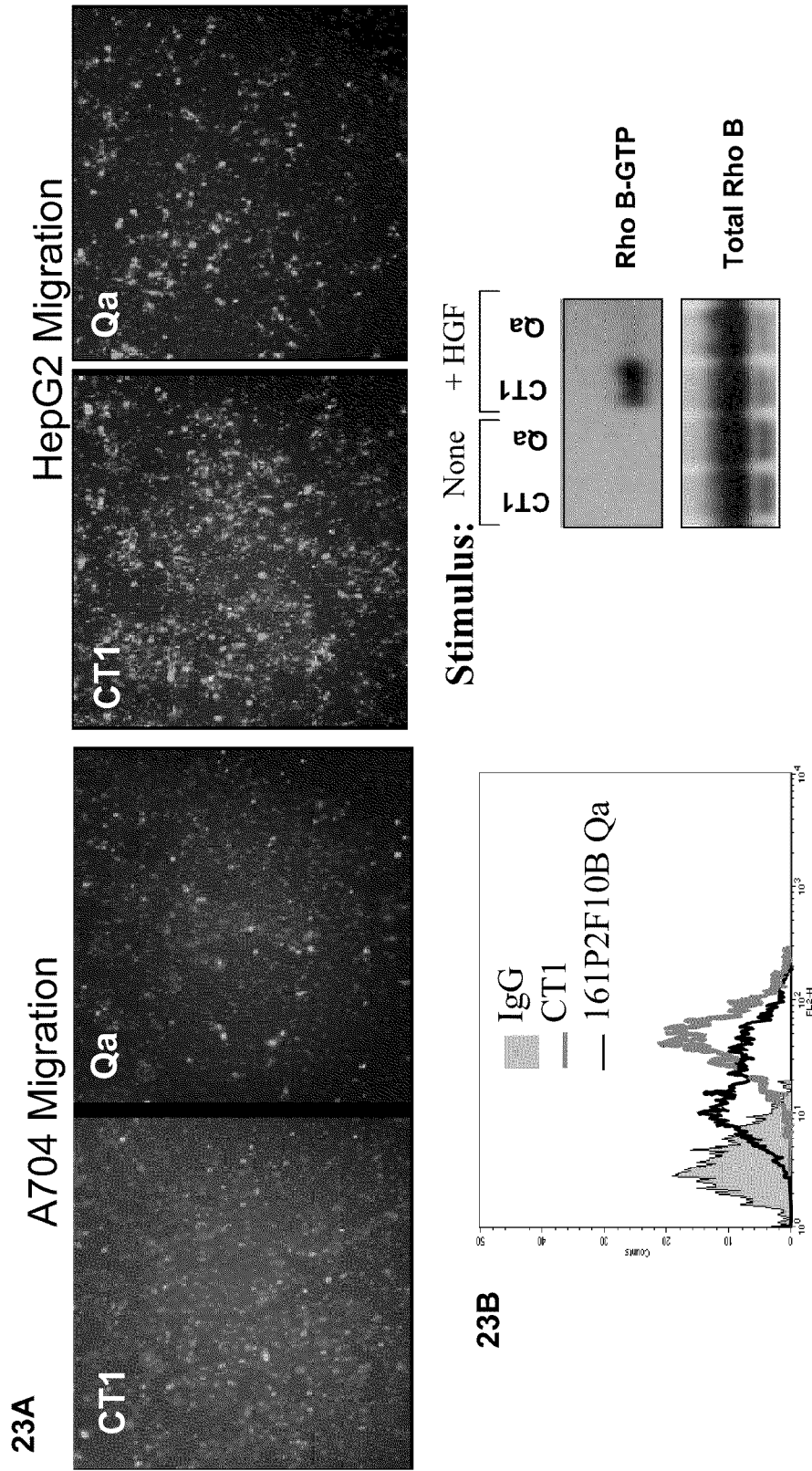
Figure 23: 161P2F10B RNAi silencing and cell migration / Rho pathway regulation

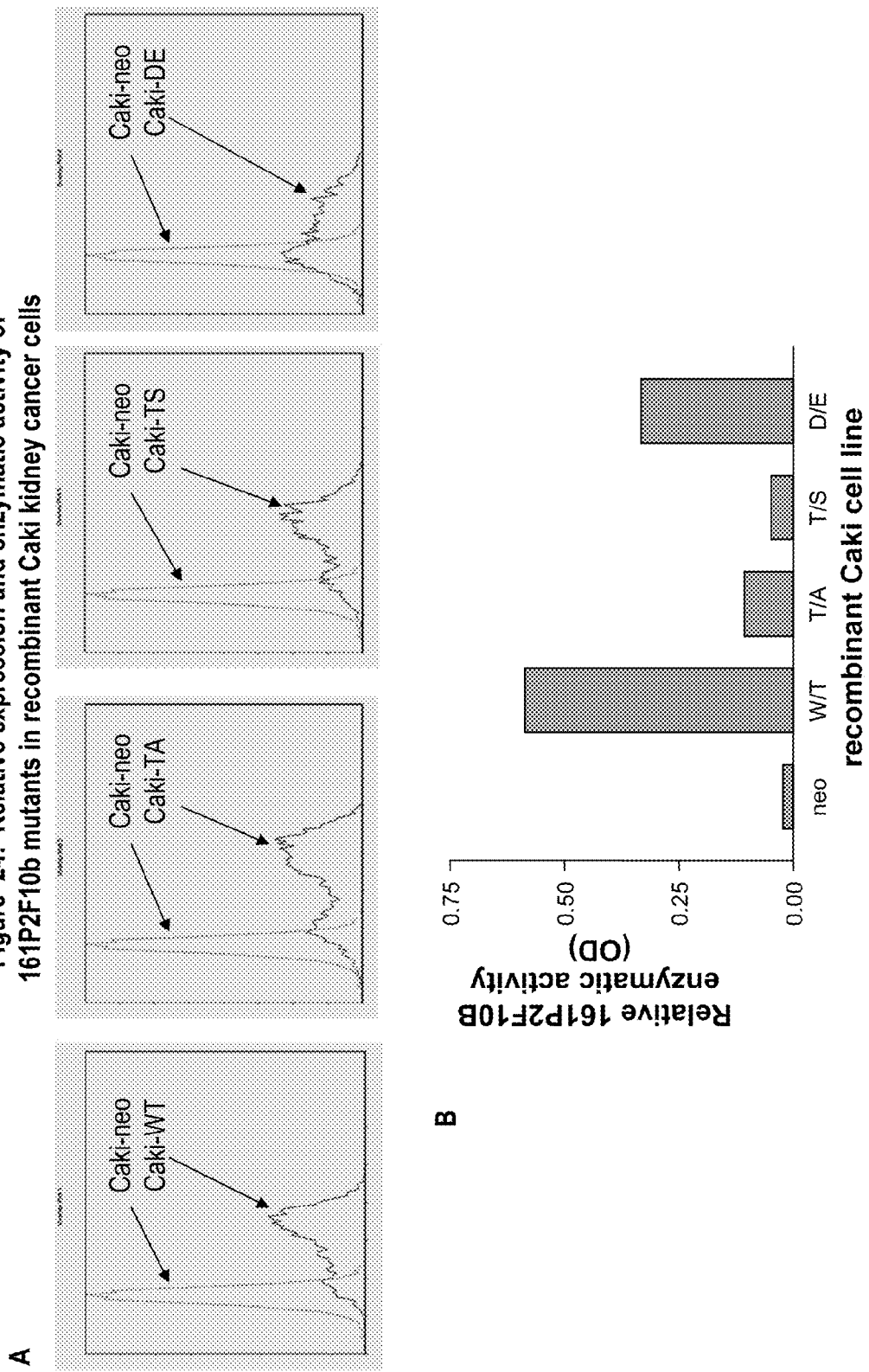
Figure 24: Relative expression and enzymatic activity of 161P2F10b mutants in recombinant Caki kidney cancer cells

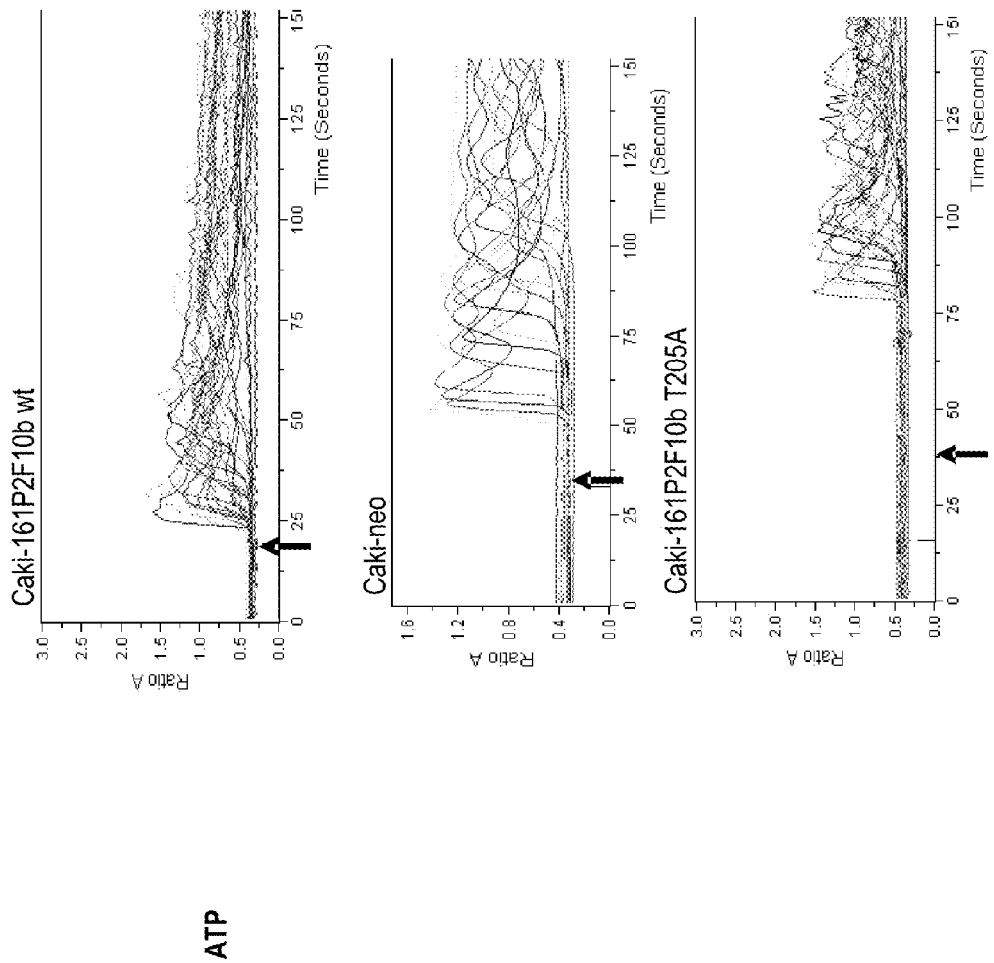
Figure 25-1: Over-expression of 161P2F10B suppresses ATP-induced intracellular Ca2+ oscillations in Cak-1 cells

ATPγS

AMP

Adenosine

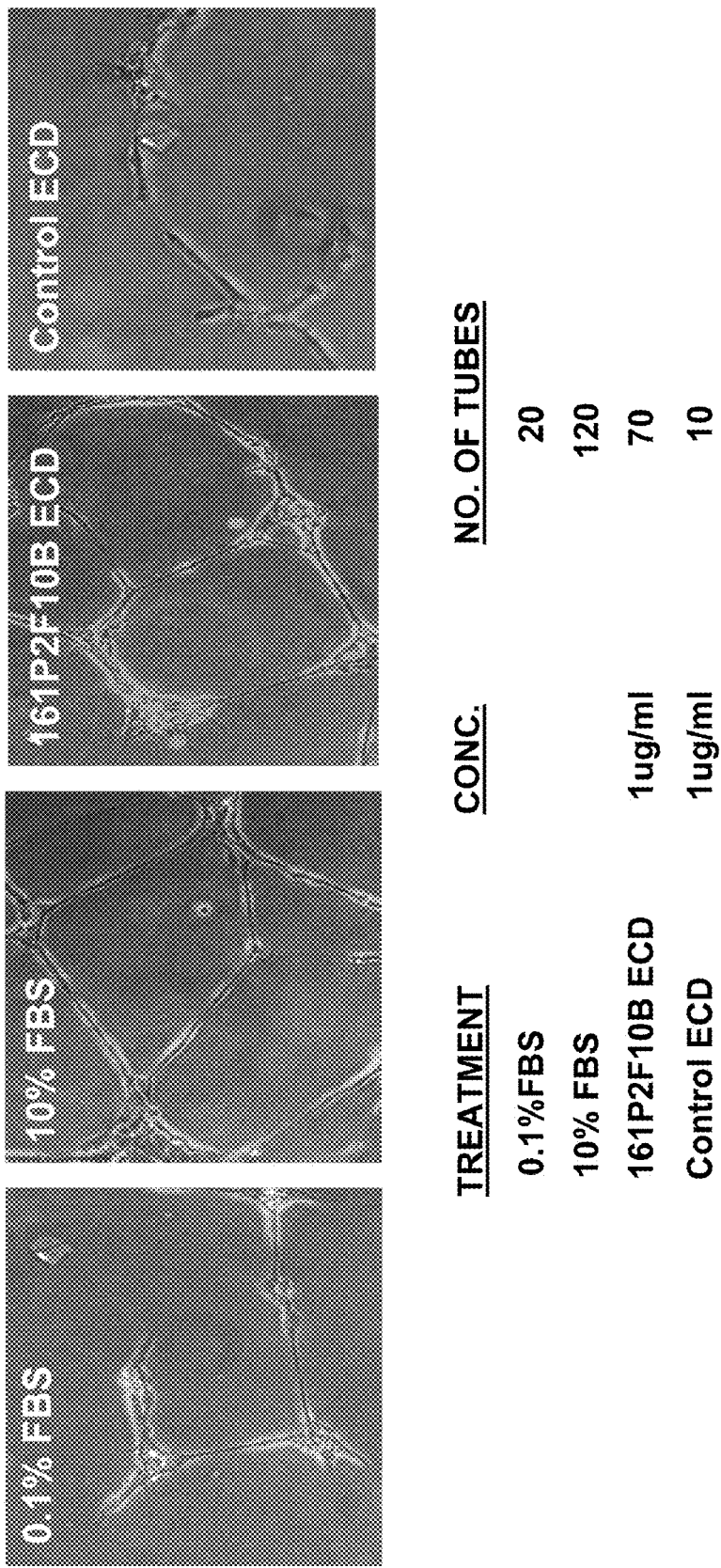
Figure 26. 161P2F10B ECD Induces HUVEC Tube Formation

Figure 27. Requirement of 161P2F10B Phosphodiesterase Activity for HUVEC Tube Formation

| TREATMENT | CONC. | TUBE NO. | |
|---|---|---|---|
| 0.1%FBS | | 20 | ← Control |
| 10%FBS | | 124 | |
| VEGF | 50ng/ml | 91 | |
| 161P2F10B WT ECD | 0.1ug/ml | 42 | ⎤ |
| | 1ug/ml | 70 | ⎬ Wild type |
| | 5ug/ml | 85 | ⎦ |
| 161P2F10B D80E ECD | 0.1ug/ml | 31 | ⎤ |
| | 1ug/ml | 44 | ⎬ Non-catalytic mutant |
| | 5ug/ml | 55 | ⎦ |
| 161P2F10B T205A ECD | 0.1ug/ml | 21 | ⎤ |
| | 1ug/ml | 13 | ⎬ Catalytic mutant |
| | 5ug/ml | 20 | ⎦ |
| Control ECD | 0.1ug/ml | 7 | |
| | 1ug/ml | 10 | |
| | 5ug/ml | 10 | |

Figure 28. 161P2F10B MAbs Inhibit HUVEC tube formation

| Treatment | | Number of tubes | % inhibition |
|---|---|---|---|
| FBS | 0.1% | 16 ± 3 | |
| FBS | 5% | 97 ± 7 | |
| 161P2F10B ECD | 1 µg/ml | 58 ± 2 | |
| H16-9.10 | 20 µg/ml | 29 ± 4 | 69 |
| H16-9.44 | 20 µg/ml | 31 ± 4 | 64 |
| H16-9.69 | 20 µg/ml | 36 ± 3 | 52 |
| H16-7.8 | 20 µg/ml | 44 ± 2 | 33 |
| Ha16-1(2,4)4 | 20 µg/ml | 21 ± 2 | 67 |
| Ha16-1(3,5)18 | 20 µg/ml | 28 ± 2 | 47 |
| Ha16-1(3,5)27 | 20 µg/ml | 25 ± 3 | 56 |
| Ha16-1(3,5)56 | 20 µg/ml | 22 ± 2 | 64 |

| Treatment | | Number of tubes | % inhibition |
|---|---|---|---|
| FBS | 0.1% | 18 ± 2 | |
| FBS | 5% | 103 ± 7 | |
| 161P2F10B ECD | 1 µg/ml | 63 ± 2 | |
| H16-1.80 | 20 µg/ml | 34 ± 3 | 65 |
| H16-1.93 | 20 µg/ml | 32 ± 2 | 69 |
| H16-3.4 | 20 µg/ml | 28 ± 2 | 78 |
| Ha16-1(3,5)18 | 20 µg/ml | 40 ± 2 | 51 |
| Ha16-1(1)15 | 20 µg/ml | 62 ± 2 | 0 |

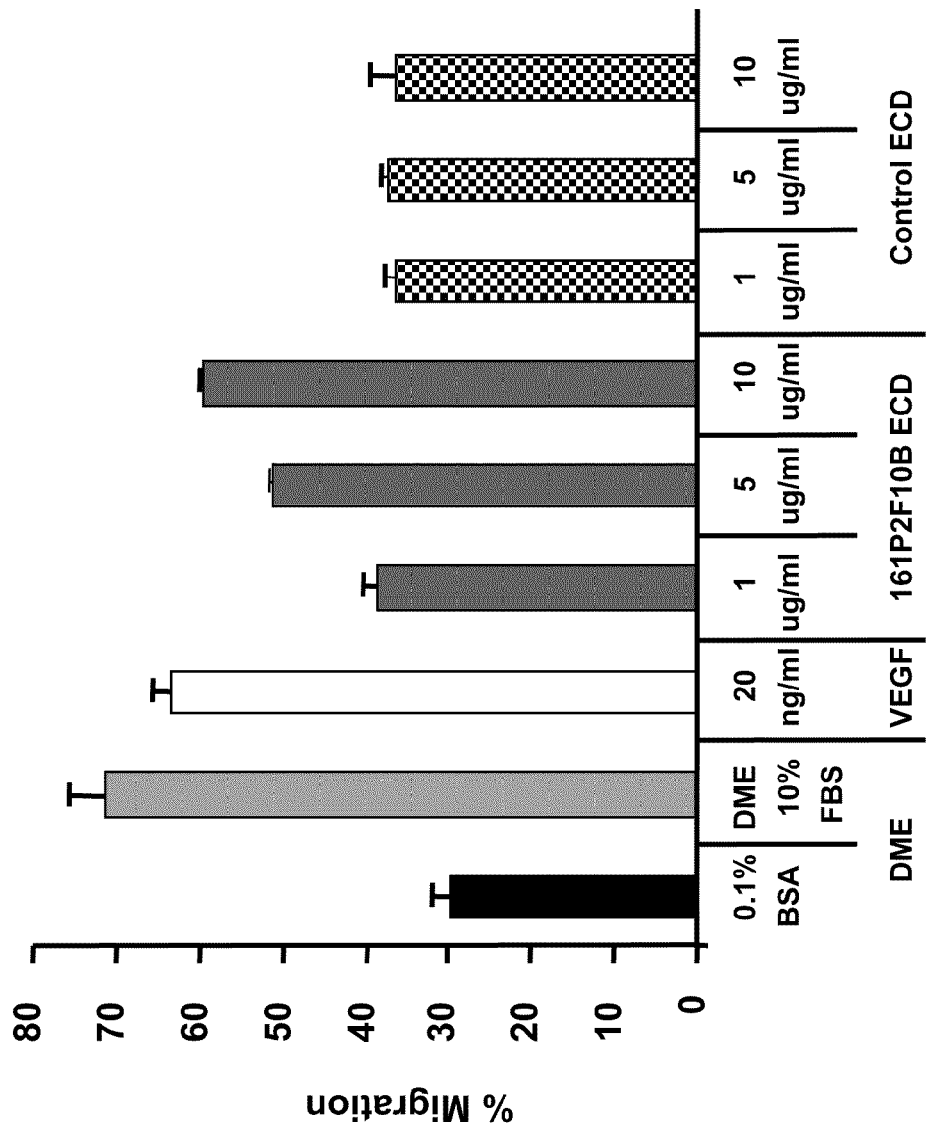
Figure 29. 161P2F10B ECD induces migration of HUVEC

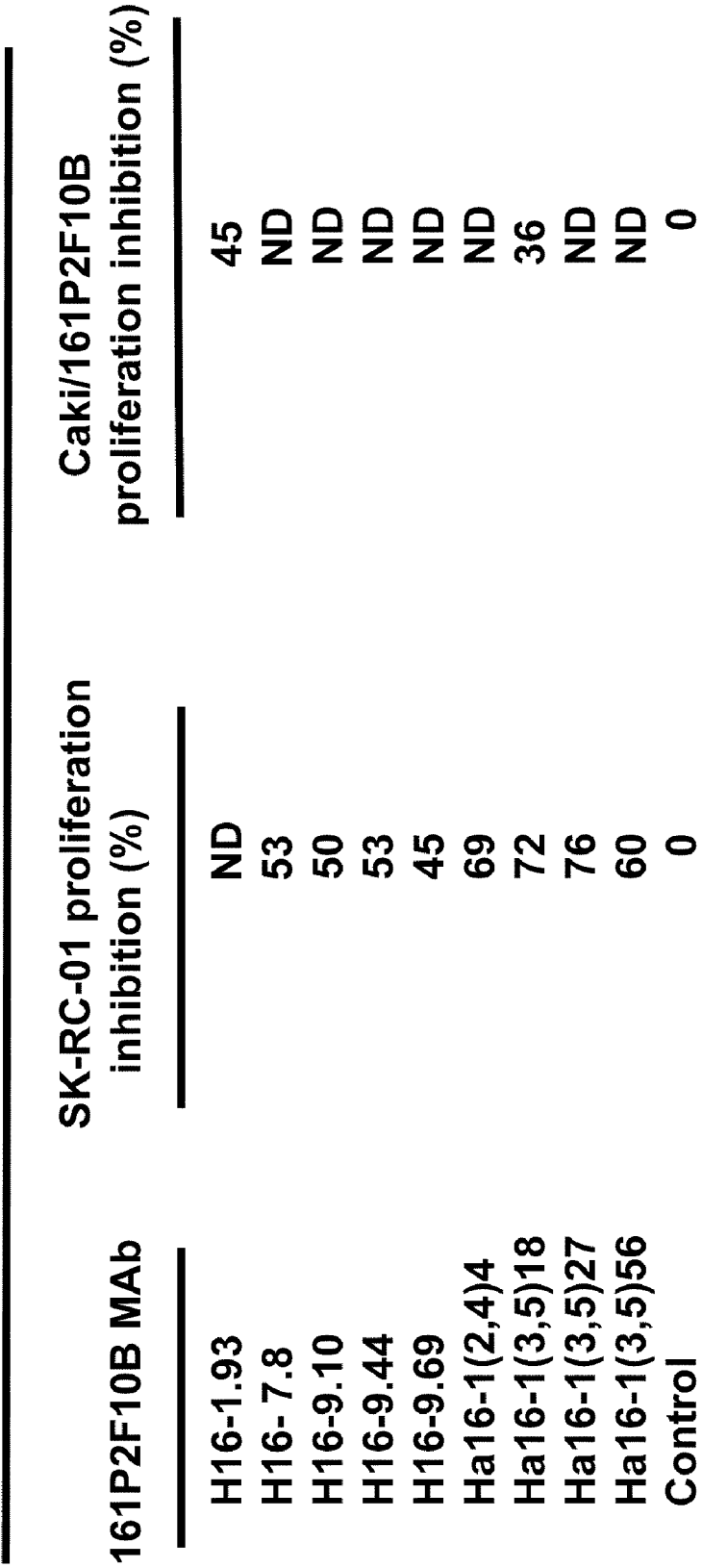
Figure 30. 161P2F10B MAbs inhibit proliferation of SK-RC-01 renal clear cell cancer and Caki/161P2F10B renal cancer
| 161P2F10B MAb | SK-RC-01 proliferation inhibition (%) | Caki/161P2F10B proliferation inhibition (%) |
|---|---|---|
| H16-1.93 | ND | 45 |
| H16-7.8 | 53 | ND |
| H16-9.10 | 50 | ND |
| H16-9.44 | 53 | ND |
| H16-9.69 | 45 | ND |
| Ha16-1(2,4)4 | 69 | ND |
| Ha16-1(3,5)18 | 72 | 36 |
| Ha16-1(3,5)27 | 76 | ND |
| Ha16-1(3,5)56 | 60 | ND |
| Control | 0 | 0 |

Figure 31. Effect of 161P2F10B MAbs on Kidney Cancer Cell Proliferation, Survival and Apoptosis

| MAb | Epitope | Proliferation inhibition (%) | Survival inhibition (%) | Apoptosis induction |
|---|---|---|---|---|
| Ha16-1(2,4)4 | 1 | 51 | 32 | 77 |
| Ha16-1(3,5)18 | 4 | 40 | 29 | 28 |
| Ha16-1(3,5)27 | 31 | 46 | 24 | 72 |
| Ha16-1(3,5)36 | 1 | 30 | 29 | 30 |
| Ha16-1(3,5)56 | 31 | 43 | 27 | 22 |
| Ha16-1(3,5)51 | 32 | 0 | 6 | 4 |
| M225 (anti-EGFR) | | 56 | 32 | 43 |

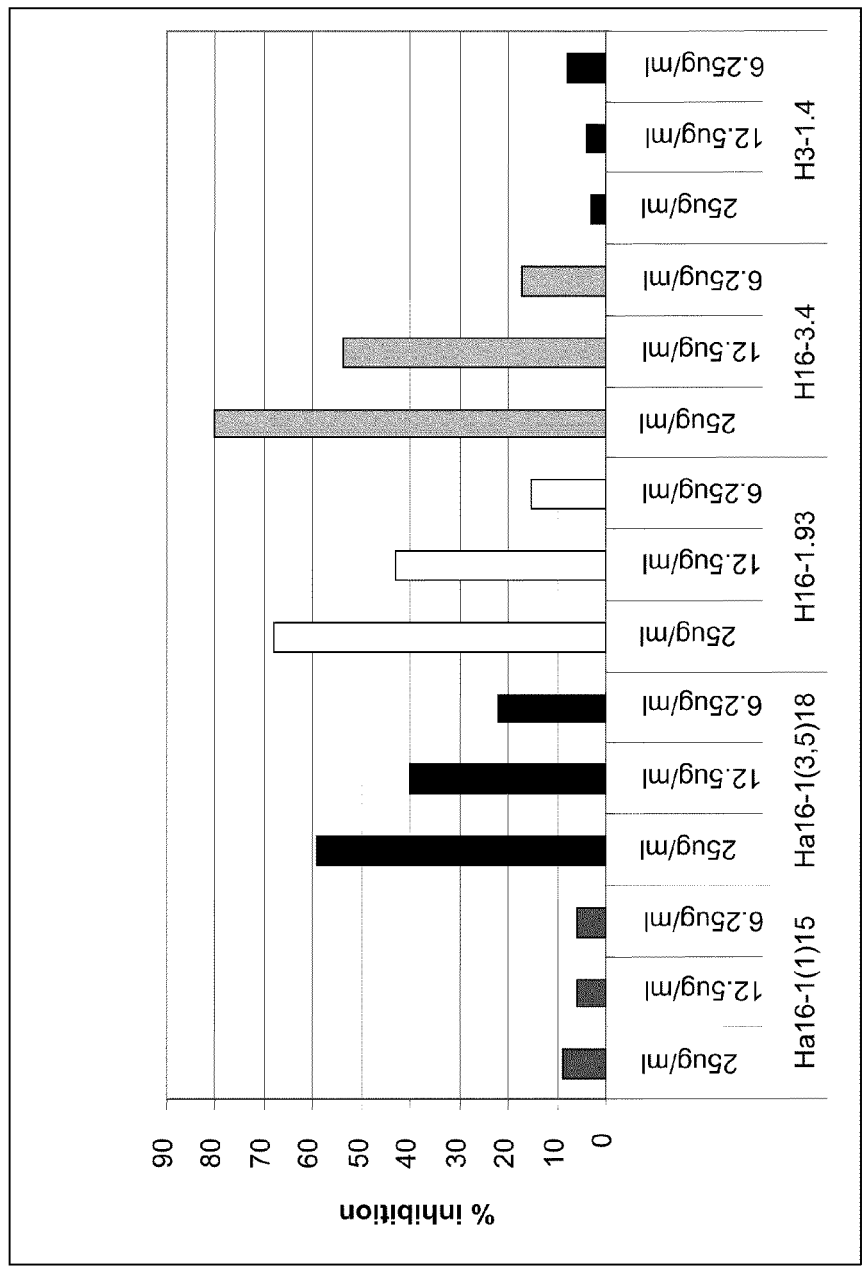
Figure 32. 161P2F10B MAbs dose-dependently inhibit HUVEC tube formation

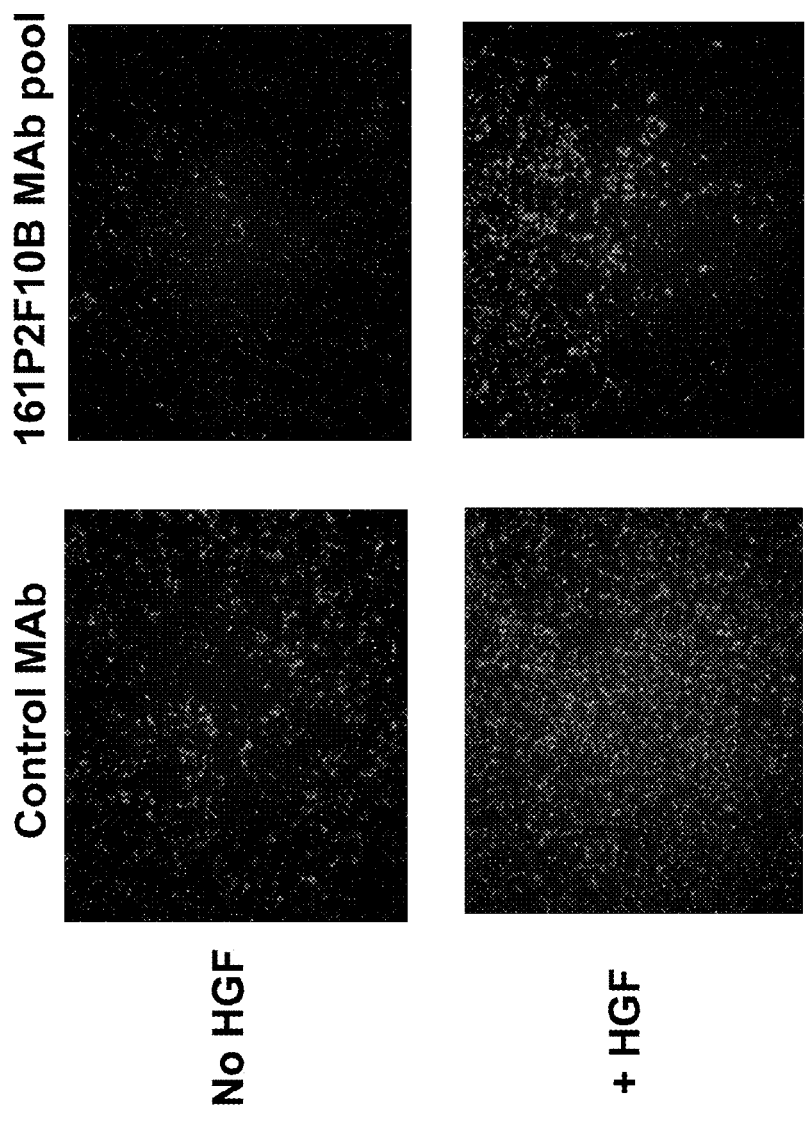
Figure 33A: 161P2F10B MAbs inhibit HepG2 liver cancer cell migration

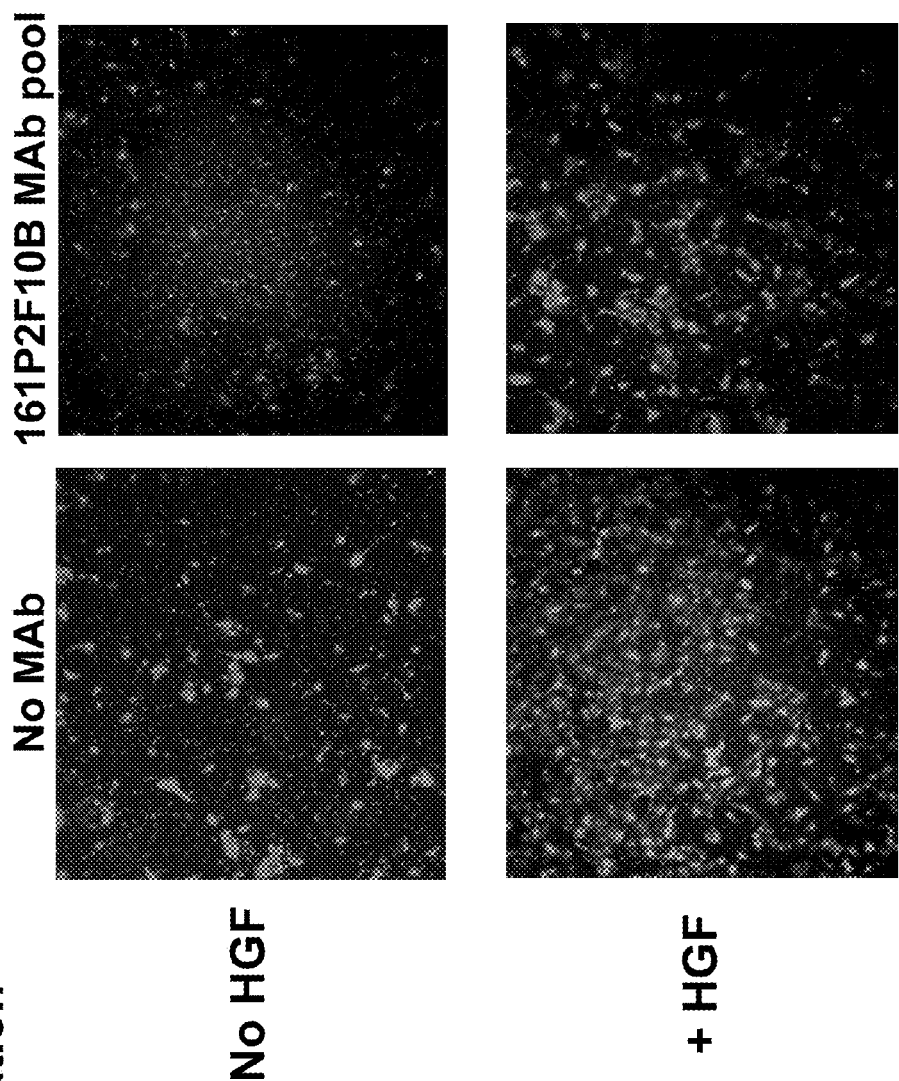
Figure 34A: 161PSF10B MAbs inhibit A-704 renal clear cell migration

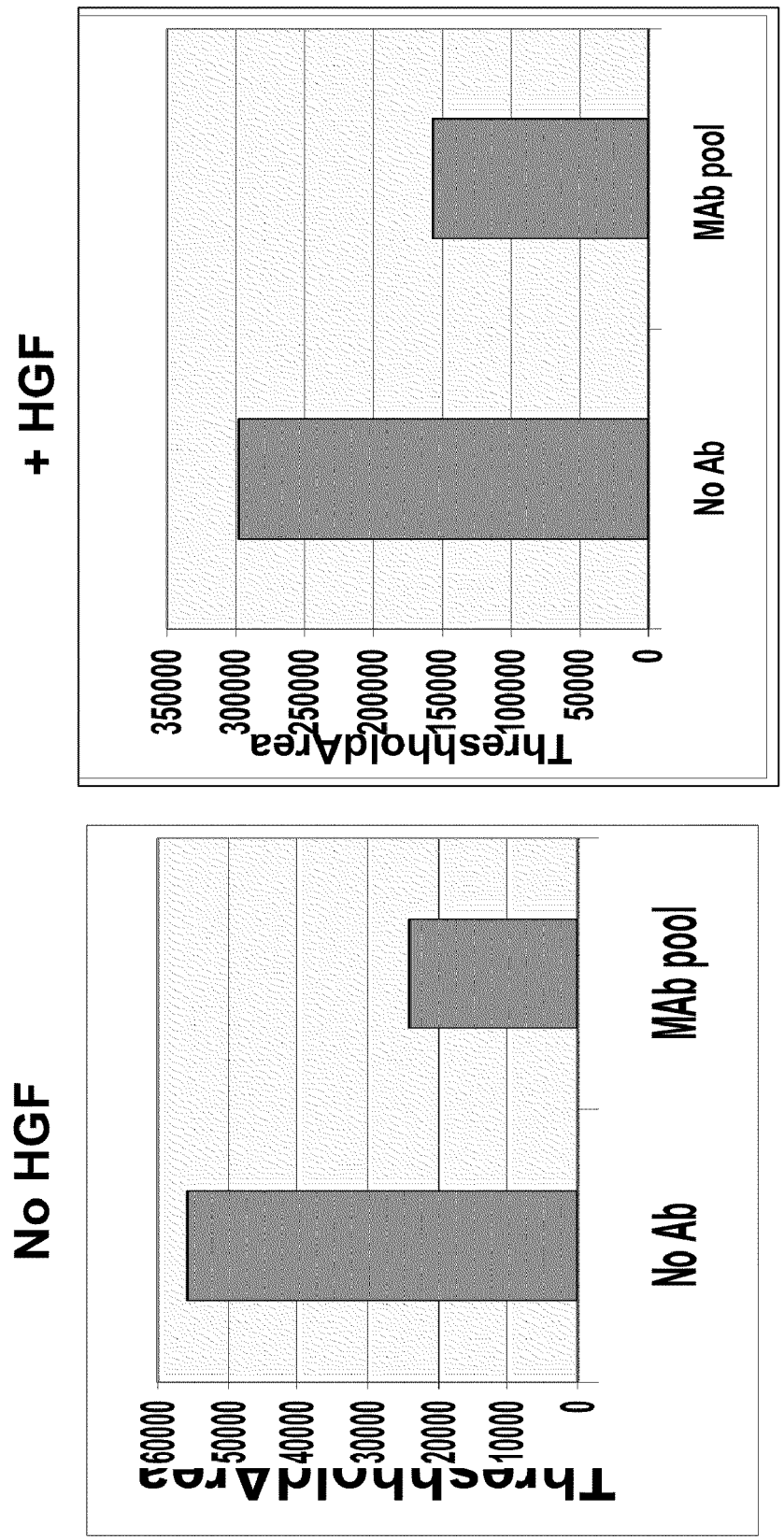

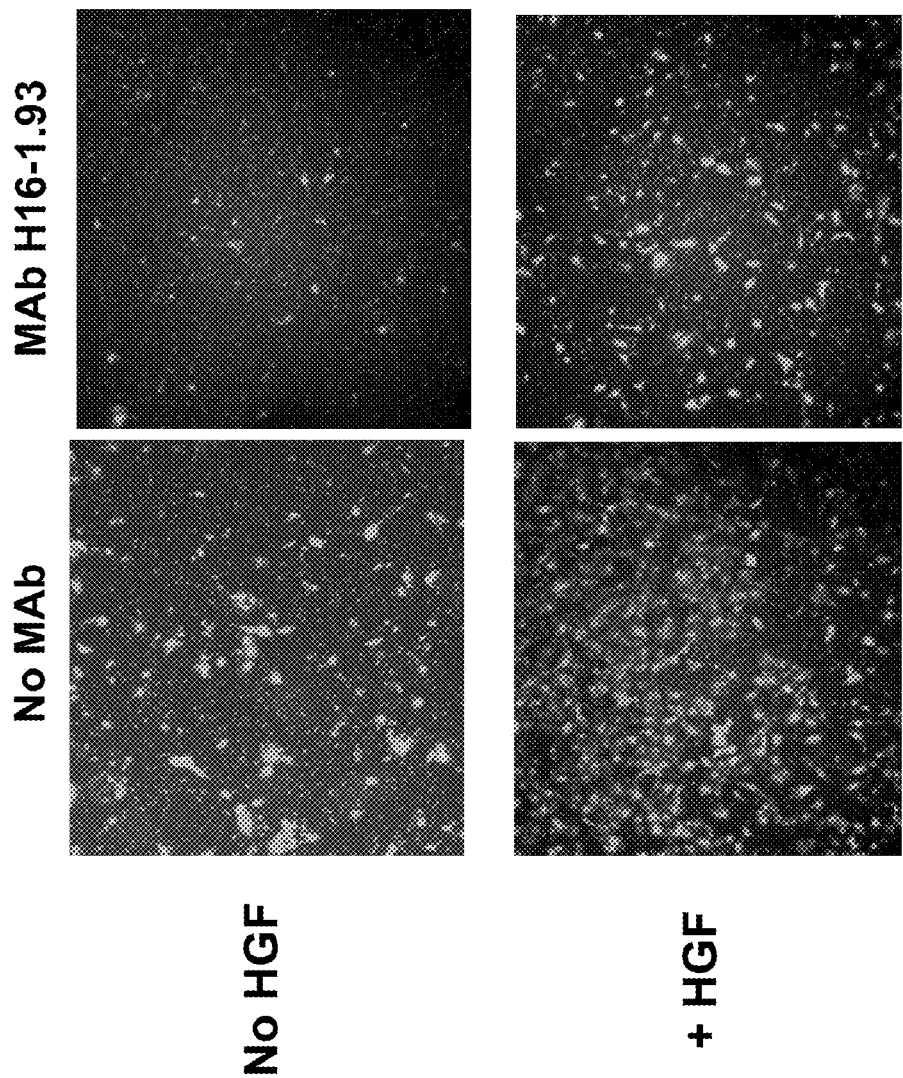
Figure 35A: 161P2F10B MAb inhibits A-704 renal clear cell invasion

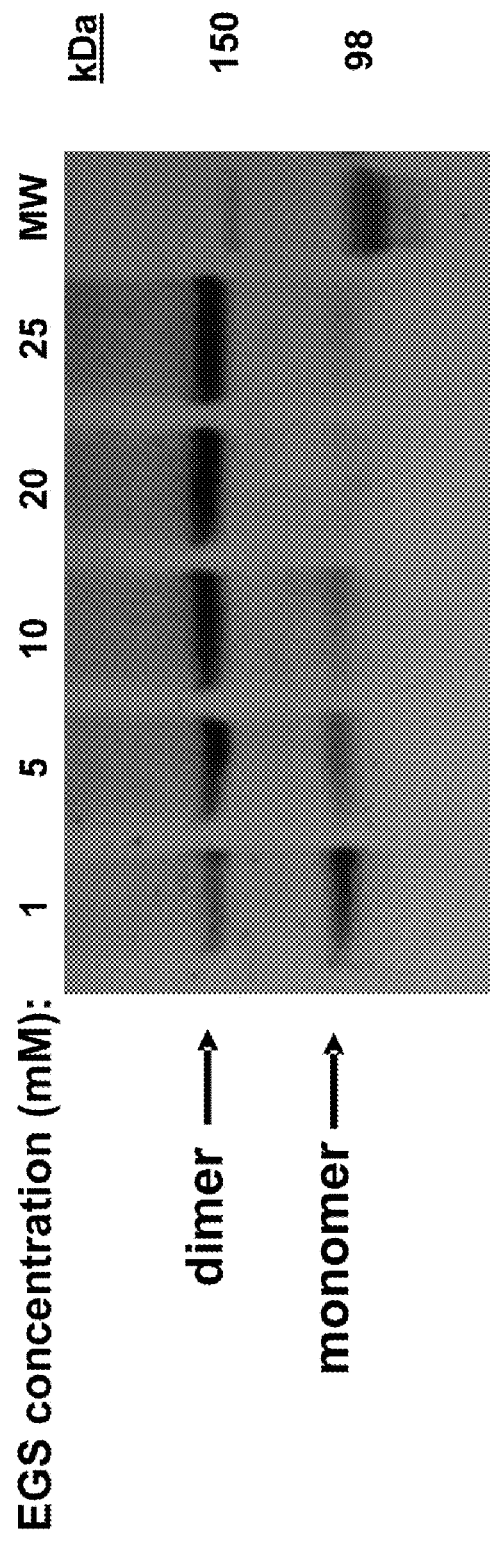
Figure 36. 161P2F10B dimerization on KU-812 cells

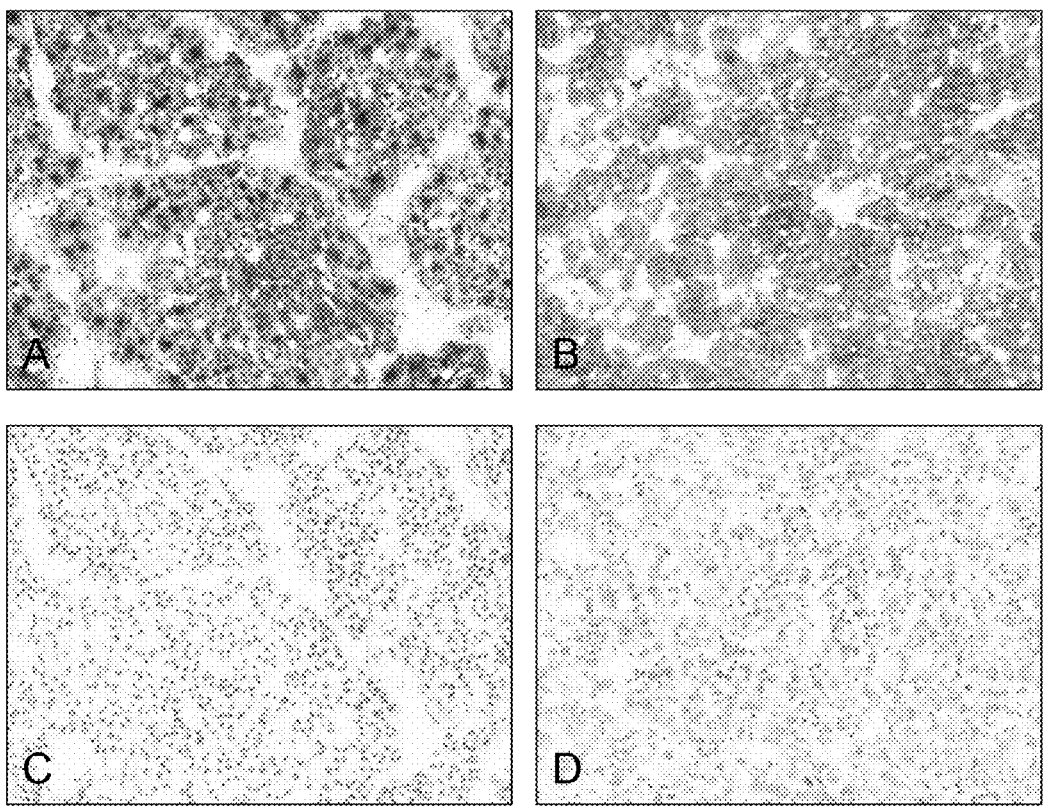
Figure 37: Detection of 161P2F10B in Liver Cancer by IHC

ANTIBODIES AND RELATED MOLECULES THAT BIND TO 161P2F10B PROTEINS

CROSS-REFERENCE TO RELATED APPLICATIONS

This patent application is a continuation-in-part of U.S. patent application Ser. No. 12/433,760 filed Apr. 30, 2009, now U.S. Pat. No. 7,811,565, which is a continuation of U.S. patent application Ser. No. 12/196,039, filed Aug. 21, 2008, now abandoned, which is a division of U.S. patent application Ser. No. 11/396,178, filed Mar. 31, 2006, now U.S. Pat. No. 7,427,399, which claims the benefit of priority from U.S. Provisional Patent Application No. 60/667,588, filed Mar. 31, 2005 and U.S. Provisional Patent Application No. 60/700,975, filed Jul. 20, 2005. The contents of each application listed in this paragraph are fully incorporated by reference herein.

STATEMENT OF RIGHTS TO INVENTIONS MADE UNDER FEDERALLY SPONSORED RESEARCH

Not applicable.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 511582006223Seqlist.txt | Jun. 6, 2012 | 311517 bytes |

FIELD OF THE INVENTION

The invention described herein relates to antibodies, as well as binding fragments thereof and molecules engineered therefrom, that bind proteins, termed 161P2F10B. The invention further relates to diagnostic, prognostic, prophylactic and therapeutic methods and compositions useful in the treatment of cancers that express 161P2F10B.

BACKGROUND OF THE INVENTION

Cancer is the second leading cause of human death next to coronary disease. Worldwide, millions of people die from cancer every year. In the United States alone, as reported by the American Cancer Society, cancer causes the death of well over a half-million people annually, with over 1.2 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. In particular, carcinomas of the lung, prostate, breast, colon, pancreas, ovary, and bladder represent the primary causes of cancer death. These and virtually all other carcinomas share a common lethal feature. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Furthermore, many cancer patients experience a recurrence.

Worldwide, prostate cancer is the fourth most prevalent cancer in men. In North America and Northern Europe, it is by far the most common cancer in males and is the second leading cause of cancer death in men. In the United States alone, well over 30,000 men die annually of this disease—second only to lung cancer. Despite the magnitude of these figures, there is still no effective treatment for metastatic prostate cancer. Surgical prostatectomy, radiation therapy, hormone ablation therapy, surgical castration and chemotherapy continue to be the main treatment modalities. Unfortunately, these treatments are ineffective for many and are often associated with undesirable consequences.

On the diagnostic front, the lack of a prostate tumor marker that can accurately detect early-stage, localized tumors remains a significant limitation in the diagnosis and management of this disease. Although the serum prostate specific antigen (PSA) assay has been a very useful tool, however its specificity and general utility is widely regarded as lacking in several important respects.

Progress in identifying additional specific markers for prostate cancer has been improved by the generation of prostate cancer xenografts that can recapitulate different stages of the disease in mice. The LAPC (Los Angeles Prostate Cancer) xenografts are prostate cancer xenografts that have survived passage in severe combined immune deficient (SCID) mice and have exhibited the capacity to mimic the transition from androgen dependence to androgen independence (Klein et al., 1997, Nat. Med. 3:402). More recently identified prostate cancer markers include PCTA-1 (Su et al., 1996, Proc. Natl. Acad. Sci. USA 93: 7252), prostate-specific membrane (PSM) antigen (Pinto et al., Clin Cancer Res 1996 Sep. 2 (9): 1445-51), STEAP (Hubert, et al., Proc Natl Acad Sci USA. 1999 Dec. 7; 96(25): 14523-8) and prostate stem cell antigen (161P2F10B) (Reiter et al., 1998, Proc. Natl. Acad. Sci. USA 95: 1735).

While previously identified markers such as PSA, PSM, PCTA and 161P2F10B have facilitated efforts to diagnose and treat prostate cancer, there is need for the identification of additional markers and therapeutic targets for prostate and related cancers in order to further improve diagnosis and therapy.

Renal cell carcinoma (RCC) accounts for approximately 3 percent of adult malignancies. Once adenomas reach a diameter of 2 to 3 cm, malignant potential exists. In the adult, the two principal malignant renal tumors are renal cell adenocarcinoma and transitional cell carcinoma of the renal pelvis or ureter. The incidence of renal cell adenocarcinoma is estimated at more than 29,000 cases in the United States, and more than 11,600 patients died of this disease in 1998. Transitional cell carcinoma is less frequent, with an incidence of approximately 500 cases per year in the United States.

Surgery has been the primary therapy for renal cell adenocarcinoma for many decades. Until recently, metastatic disease has been refractory to any systemic therapy. With recent developments in systemic therapies, particularly immunotherapies, metastatic renal cell carcinoma may be approached aggressively in appropriate patients with a possibility of durable responses. Nevertheless, there is a remaining need for effective therapies for these patients.

Of all new cases of cancer in the United States, bladder cancer represents approximately 5 percent in men (fifth most common neoplasm) and 3 percent in women (eighth most common neoplasm). The incidence is increasing slowly, concurrent with an increasing older population. In 1998, there was an estimated 54,500 cases, including 39,500 in men and 15,000 in women. The age-adjusted incidence in the United States is 32 per 100,000 for men and eight per 100,000 in women. The historic male/female ratio of 3:1 may be decreasing related to smoking patterns in women. There were an estimated 11,000 deaths from bladder cancer in 1998 (7,800 in men and 3,900 in women). Bladder cancer incidence and mortality strongly increase with age and will be an increasing problem as the population becomes more elderly.

Most bladder cancers recur in the bladder. Bladder cancer is managed with a combination of transurethral resection of the bladder (TUR) and intravesical chemotherapy or immunotherapy. The multifocal and recurrent nature of bladder cancer points out the limitations of TUR. Most muscle-invasive cancers are not cured by TUR alone. Radical cystectomy and urinary diversion is the most effective means to eliminate the cancer but carry an undeniable impact on urinary and sexual function. There continues to be a significant need for treatment modalities that are beneficial for bladder cancer patients.

An estimated 130,200 cases of colorectal cancer occurred in 2000 in the United States, including 93,800 cases of colon cancer and 36,400 of rectal cancer. Colorectal cancers are the third most common cancers in men and women. Incidence rates declined significantly during 1992-1996 (−2.1% per year). Research suggests that these declines have been due to increased screening and polyp removal, preventing progression of polyps to invasive cancers. There were an estimated 56,300 deaths (47,700 from colon cancer, 8,600 from rectal cancer) in 2000, accounting for about 11% of all U.S. cancer deaths.

At present, surgery is the most common form of therapy for colorectal cancer, and for cancers that have not spread, it is frequently curative. Chemotherapy, or chemotherapy plus radiation, is given before or after surgery to most patients whose cancer has deeply perforated the bowel wall or has spread to the lymph nodes. A permanent colostomy (creation of an abdominal opening for elimination of body wastes) is occasionally needed for colon cancer and is infrequently required for rectal cancer. There continues to be a need for effective diagnostic and treatment modalities for colorectal cancer.

There were an estimated 164,100 new cases of lung and bronchial cancer in 2000, accounting for 14% of all U.S. cancer diagnoses. The incidence rate of lung and bronchial cancer is declining significantly in men, from a high of 86.5 per 100,000 in 1984 to 70.0 in 1996. In the 1990s, the rate of increase among women began to slow. In 1996, the incidence rate in women was 42.3 per 100,000.

Lung and bronchial cancer caused an estimated 156,900 deaths in 2000, accounting for 28% of all cancer deaths. During 1992-1996, mortality from lung cancer declined significantly among men (−1.7% per year) while rates for women were still significantly increasing (0.9% per year). Since 1987, more women have died each year of lung cancer than breast cancer, which, for over 40 years, was the major cause of cancer death in women. Decreasing lung cancer incidence and mortality rates most likely resulted from decreased smoking rates over the previous 30 years; however, decreasing smoking patterns among women lag behind those of men. Of concern, although the declines in adult tobacco use have slowed, tobacco use in youth is increasing again.

Treatment options for lung and bronchial cancer are determined by the type and stage of the cancer and include surgery, radiation therapy, and chemotherapy. For many localized cancers, surgery is usually the treatment of choice. Because the disease has usually spread by the time it is discovered, radiation therapy and chemotherapy are often needed in combination with surgery. Chemotherapy alone or combined with radiation is the treatment of choice for small cell lung cancer; on this regimen, a large percentage of patients experience remission, which in some cases is long lasting. There is however, an ongoing need for effective treatment and diagnostic approaches for lung and bronchial cancers.

An estimated 182,800 new invasive cases of breast cancer were expected to occur among women in the United States during 2000. Additionally, about 1,400 new cases of breast cancer were expected to be diagnosed in men in 2000. After increasing about 4% per year in the 1980s, breast cancer incidence rates in women have leveled off in the 1990s to about 110.6 cases per 100,000.

In the U.S. alone, there were an estimated 41,200 deaths (40,800 women, 400 men) in 2000 due to breast cancer. Breast cancer ranks second among cancer deaths in women. According to the most recent data, mortality rates declined significantly during 1992-1996 with the largest decreases in younger women, both white and black. These decreases were probably the result of earlier detection and improved treatment.

Taking into account the medical circumstances and the patient's preferences, treatment of breast cancer may involve lumpectomy (local removal of the tumor) and removal of the lymph nodes under the arm; mastectomy (surgical removal of the breast) and removal of the lymph nodes under the arm; radiation therapy; chemotherapy; or hormone therapy. Often, two or more methods are used in combination. Numerous studies have shown that, for early stage disease, long-term survival rates after lumpectomy plus radiotherapy are similar to survival rates after modified radical mastectomy. Significant advances in reconstruction techniques provide several options for breast reconstruction after mastectomy. Recently, such reconstruction has been done at the same time as the mastectomy.

Local excision of ductal carcinoma in situ (DCIS) with adequate amounts of surrounding normal breast tissue may prevent the local recurrence of the DCIS. Radiation to the breast and/or tamoxifen may reduce the chance of DCIS occurring in the remaining breast tissue. This is important because DCIS, if left untreated, may develop into invasive breast cancer. Nevertheless, there are serious side effects or sequelae to these treatments. There is, therefore, a need for efficacious breast cancer treatments.

There were an estimated 23,100 new cases of ovarian cancer in the United States in 2000. It accounts for 4% of all cancers among women and ranks second among gynecologic cancers. During 1992-1996, ovarian cancer incidence rates were significantly declining Consequent to ovarian cancer, there were an estimated 14,000 deaths in 2000. Ovarian cancer causes more deaths than any other cancer of the female reproductive system.

Surgery, radiation therapy, and chemotherapy are treatment options for ovarian cancer. Surgery usually includes the removal of one or both ovaries, the fallopian tubes (salpingo-oophorectomy), and the uterus (hysterectomy). In some very early tumors, only the involved ovary will be removed, especially in young women who wish to have children. In advanced disease, an attempt is made to remove all intra-abdominal disease to enhance the effect of chemotherapy.

There continues to be an important need for effective treatment options for ovarian cancer.

There were an estimated 28,300 new cases of pancreatic cancer in the United States in 2000. Over the past 20 years, rates of pancreatic cancer have declined in men. Rates among women have remained approximately constant but may be beginning to decline. Pancreatic cancer caused an estimated 28,200 deaths in 2000 in the United States. Over the past 20 years, there has been a slight but significant decrease in mortality rates among men (about −0.9% per year) while rates have increased slightly among women.

Surgery, radiation therapy, and chemotherapy are treatment options for pancreatic cancer. These treatment options can extend survival and/or relieve symptoms in many patients but are not likely to produce a cure for most. There is a significant need for additional therapeutic and diagnostic options for cancers. These include the use of antibodies, vaccines, and small molecules as treatment modalities. Additionally, there is also a need to use these modilities as research tools to diagnose, detect, monitor, and further the state of the art in all areas of cancer treatment and studies.

The therapeutic utility of monoclonal antibodies (mAbs) (G. Kohler and C. Milstein, Nature 256:495-497 (1975)) is being realized. Monoclonal antibodies have now been approved as therapies in transplantation, cancer, infectious disease, cardiovascular disease and inflammation. Different isotypes have different effector functions. Such differences in function are reflected in distinct 3-dimensional structures for the various immunoglobulin isotypes (P. M. Alzari et al., Annual Rev. Immunol., 6:555-580 (1988)).

Because mice are convenient for immunization and recognize most human antigens as foreign, mAbs against human targets with therapeutic potential have typically been of murine origin. However, murine mAbs have inherent disadvantages as human therapeutics. They require more frequent dosing as mAbs have a shorter circulating half-life in humans than human antibodies. More critically, the repeated administration of murine antibodies to the human immune system causes the human immune system to respond by recognizing the mouse protein as a foreign and generating a human anti-mouse antibody (HAMA) response. Such a HAMA response may result in allergic reaction and the rapid clearing of the murine antibody from the system thereby rendering the treatment by murine antibody useless. To avoid such affects, attempts to create human immune systems within mice have been attempted.

Initial attempts hoped to create transgenic mice capable of responding to antigens with antibodies having human sequences (See Bruggemann et al., Proc. Nat'l. Acad. Sci. USA 86:6709-6713 (1989)), but were limited by the amount of DNA that could be stably maintained by available cloning vehicles. The use of yeast artificial chromosome (YAC) cloning vectors led the way to introducing large germline fragments of human Ig locus into transgenic mammals. Essentially a majority of the human V, D, and J region genes arranged with the same spacing found in the human genome and the human constant regions were introduced into mice using YACs. One such transgenic mouse strain is known as XenoMouse® mice and is commercially available from Abgenix, Inc. (Fremont Calif.).

SUMMARY OF THE INVENTION

The invention provides antibodies as well as binding fragments thereof and molecules engineered therefrom, that bind to 161P2F10B proteins and polypeptide fragments of 161P2F10B proteins. The invention comprises polyclonal and monoclonal antibodies, murine and other mammalian antibodies, chimeric antibodies, humanized and fully human antibodies, and antibodies labeled with a detectable marker or therapeutic agent. In certain embodiments, there is a proviso that the entire nucleic acid sequence of FIG. 3 is not encoded and/or the entire amino acid sequence of FIG. 2 is not prepared. In certain embodiments, the entire nucleic acid sequence of FIG. 3 is encoded and/or the entire amino acid sequence of FIG. 2 is prepared, either of which are in respective human unit dose forms.

The invention further provides methods for detecting the presence and status of 161P2F10B polynucleotides and proteins in various biological samples, as well as methods for identifying cells that express 161P2F10B. An embodiment of this invention provides methods for monitoring 161P2F10B gene products in a tissue or hematology sample having or suspected of having some form of growth dysregulation such as cancer.

The invention further provides various immunogenic or therapeutic compositions and strategies for treating cancers that express 161P2F10B such as cancers of tissues listed in Table I, including therapies aimed at inhibiting the transcription, translation, processing or function of 161P2F10B as well as cancer vaccines. In one aspect, the invention provides compositions, and methods comprising them, for treating a cancer that expresses 161P2F10B in a human subject wherein the composition comprises a carrier suitable for human use and a human unit dose of one or more than one agent that inhibits the production or function of 161P2F10B. Preferably, the carrier is a uniquely human carrier. In another aspect of the invention, the agent is a moiety that is immunoreactive with 161P2F10B protein. Non-limiting examples of such moieties include, but are not limited to, antibodies (such as single chain, monoclonal, polyclonal, humanized, chimeric, or human antibodies), functional equivalents thereof (whether naturally occurring or synthetic), and combinations thereof. The antibodies can be conjugated to a diagnostic or therapeutic moiety. In another aspect, the agent is a small molecule as defined herein.

BRIEF DESCRIPTION OF THE FIGURES

FIG. 1. FIG. 1A. The cDNA and amino acid sequence of 161P2F10B variant 1 (also called "161P2F10B v.1" or "161P2F10B variant 1") is shown in FIG. 1A. The start methionine is underlined. The open reading frame extends from nucleic acid 44-2671 including the stop codon.

FIG. 1B. The cDNA and amino acid sequence of 161P2F10B variant 2 (also called "161P2F10B v.2") is shown in FIG. 1B. The codon for the start methionine is underlined. The open reading frame extends from nucleic acid 44-2671 including the stop codon.

FIG. 1C. The cDNA and amino acid sequence of 161P2F10B variant 3 (also called "161P2F10B v.3") is shown in FIG. 1C. The codon for the start methionine is underlined. The open reading frame extends from nucleic acid 44-2671 including the stop codon.

FIG. 1D. The cDNA and amino acid sequence of 161P2F10B variant 4 (also called "161P2F10B v.4") is shown in FIG. 1D. The codon for the start methionine is underlined. The open reading frame extends from nucleic acid 44-2671 including the stop codon.

FIG. 1E. The cDNA and amino acid sequence of 161P2F10B variant 5 (also called "161P2F10B v.5") is shown in FIG. 1E. The codon for the start methionine is underlined. The open reading frame extends from nucleic acid 44-2671 including the stop codon.

FIG. 1F. The cDNA and amino acid sequence of 161P2F10B variant 6 (also called "161P2F10B v.6") is shown in FIG. 1F. The codon for the start methionine is underlined. The open reading frame extends from nucleic acid 84-2711 including the stop codon.

FIG. 1G. The cDNA and amino acid sequence of 161P2F10B variant 7 (also called "161P2F10B v.7") is shown in FIG. 1G. The codon for the start methionine is underlined. The open reading frame extends from nucleic acid 276-2801 including the stop codon.

FIG. 2A The cDNA and amino acid sequence of H16-7.213 VH. Underlined is a portion of the heavy chain constant region.

FIG. 2B The cDNA and amino acid sequence of H16-7.213 VL. Underlined is a portion of the light chain constant region.

FIG. 2C The cDNA and amino acid sequence of H16-9.69 VH. Double-underlined is the leader sequence, and underlined is a portion of the heavy chain constant region.

FIG. 2D The cDNA and amino acid sequence of H16-9.69 VL. Double-underlined is the leader sequence, and underlined is a portion of the heavy chain constant region.

FIG. 2E The cDNA and amino acid sequence of H16-1.52 VH. Underlined is a portion of the heavy chain constant region.

FIG. 2F The cDNA and amino acid sequence of H16-1.52 VL. Underlined is a portion of the light chain constant region.

FIG. 2G The cDNA and amino acid sequence of Ha16-1(1)23 VH. Underlined is a portion of the heavy chain constant region.

FIG. 2H The cDNA and amino acid sequence of Ha16-1(1)23 VL. Underlined is a portion of the light chain constant region.

FIG. 2I The cDNA and amino acid sequence of Ha16-9.44 VH. Underlined is a portion of the heavy chain constant region.

FIG. 2J The cDNA and amino acid sequence of H16-9.44 VL. Underlined is a portion of the light chain constant region.

FIG. 2K The cDNA and amino acid sequence of H16-1.67 VH.

FIG. 2L The cDNA and amino acid sequence of H16-1.67 VL. Underlined is the light chain constant region.

FIG. 2M The cDNA and amino acid sequence of Ha16-1(3,5)36 VH. Underlined is a portion of the heavy chain constant region.

FIG. 2N The cDNA and amino acid sequence of Ha16-1(3,5)36 VL. Underlined is a portion of the light chain constant region.

FIG. 2O The cDNA and amino acid sequence of H16-1.86 VH. Underlined is a portion of the heavy chain constant region.

FIG. 2P The cDNA and amino acid sequence of H16-1.86 VL. Underlined is a portion of the light chain constant region.

FIG. 2Q The cDNA and amino acid sequence of Ha16-9.10 VH. Underlined is a portion of the heavy chain constant region.

FIG. 2R The cDNA and amino acid sequence of H16-9.10 VL. Underlined is a portion of the light chain constant region.

FIG. 2S The cDNA and amino acid sequence of H16-9.33 VH. Underlined is a portion of the heavy chain constant region.

FIG. 2T The cDNA and amino acid sequence of H16-9.33 VL. Underlined is a portion of the light chain constant region.

FIG. 2U The cDNA and amino acid sequence of H16-1.68 VH. Underlined is a portion of the heavy chain constant region.

FIG. 2V The cDNA and amino acid sequence of H16-1.68 VL. Underlined is a portion of the light chain constant region.

FIG. 2W The cDNA and amino acid sequence of Ha16-1(1)11 VH. Underlined is a portion of the heavy chain constant region.

FIG. 2X The cDNA and amino acid sequence of Ha16-1(1)11 VL. Underlined is a portion of the light chain constant region.

FIG. 2Y The cDNA and amino acid sequence of Ha16-1(3,5)18 VH. Underlined is the leader sequence and double-underlined is the heavy chain variable region. Dashed underline shows the human IgG1 constant region.

FIG. 2Z The cDNA and amino acid sequence of Ha16-1(3,5)18 VL. Double-underlined is the light chain variable region. Dashed underline shows the human Ig lambda constant region.

FIG. 2AA The cDNA and amino acid sequence of Ha16-1(2,4)4 VH.

FIG. 2AB The cDNA and amino acid sequence of Ha16-1(2,4)4 VL. Underlined is a portion of the light chain constant region.

FIG. 2AC The cDNA and amino acid sequence of Ha16-1(3,5)56 VH. Underlined is a portion of the heavy chain constant region.

FIG. 2AD The cDNA and amino acid sequence of Ha16-1(3,5)56 VL. Underlined is a portion of the light chain constant region.

FIG. 2AE The cDNA and amino acid sequence of H16-1.93 VH. Double-underlined is the leader sequence, and underlined is a portion of the heavy chain constant region.

FIG. 2AF The cDNA and amino acid sequence of H16-1.93 VL. Double-underlined is the leader sequence, and underlined is a portion of the light chain constant region.

FIG. 2AG The cDNA and amino acid sequence of H16-7.8 VH. Double-underlined is the leader sequence, and underlined is a portion of the heavy chain constant region.

FIG. 2AH The cDNA and amino acid sequence of H16-7.8 VL. Double-underlined is the leader sequence, and underlined is a portion of the light chain constant region.

FIG. 2AI The cDNA and amino acid sequence of Ha16-1(3,5)27.1 VH. Underlined is a portion of the heavy chain constant region.

FIG. 2AJ The cDNA and amino acid sequence of Ha16-1(3,5)27 VL. Underlined is a portion of the light chain constant region.

FIG. 2AK The cDNA and amino acid sequence of H16-1.61 VH. Underlined is a portion of the heavy chain constant region.

FIG. 2AL The cDNA and amino acid sequence of H16-1.61 VL. Underlined is a portion of the light chain constant region.

FIG. 2AM The cDNA and amino acid sequence of Ha16-1(3,5)5 VH. Double-underlined is the leader sequence, and underlined is a portion of the heavy chain constant region.

FIG. 2AN The cDNA and amino acid sequence of H16-1(3,5)5 VL. Double-underlined is part of the leader sequence, and underlined is a portion of the light chain constant region.

FIG. 2AO The cDNA and amino acid sequence of H16-7.200 VH. Double-underlined is the leader sequence, and underlined is a portion of the heavy chain constant region.

FIG. 2AP The cDNA and amino acid sequence of H16-7.200 VL. Double-underlined is part of the leader sequence, and underlined is a portion of the light chain constant region.

FIG. 2AQ The cDNA and amino acid sequence of Ha16-1(3,5)42 VH. Double-underlined is the leader sequence, and underlined is a portion of the heavy chain constant region.

FIG. 2AR The cDNA and amino acid sequence of Ha16-1 (3,5)42 VL. Double-underlined is part of the leader sequence, and underlined is a portion of the light chain constant region.

FIG. 2AS The cDNA and amino acid sequence of H16-9.65 VH. Double-underlined is the leader sequence, and underlined is a portion of the heavy chain constant region.

FIG. 2AT The cDNA and amino acid sequence of H16-9.65 VL. Double-underlined is part of the leader sequence, and underlined is a portion of the light chain constant region.

FIG. 2AU The cDNA and amino acid sequence of H16-1.29 VH. Underlined is a portion of the heavy chain constant region.

FIG. 2AV The cDNA and amino acid sequence of H16-3.4 VH. Underlined is a portion of the heavy chain constant region.

FIG. 2AW The cDNA and amino acid sequence of H16-1.92 VH. Underlined is a portion of the heavy chain constant region.

FIG. 2AX The cDNA and amino acid sequence of Ha16-1(3,5)19 VL. Double-underlined is part of the leader sequence, and underlined is a portion of the light chain constant region.

FIG. 2AY The cDNA and amino acid sequence of Ha16-1(3,5)19 VH. Double-underlined is part of the leader sequence, and underlined is a portion of the light chain constant region.

FIG. 2AZ The cDNA and amino acid sequence of Ha 16-1.80 VH. Double-underlined is part of the leader sequence, and underlined is a portion of the light chain constant region.

FIG. 2AAA The cDNA and amino acid sequence of Ha16-1.80 VL. Double-underlined is part of the leader sequence, and underlined is a portion of the light chain constant region.

FIG. 3A The amino acid sequence of H16-7.213 VH. Underlined is a portion of the heavy chain constant region.

FIG. 3B The amino acid sequence of H16-7.213 VL. Underlined is a portion of the light chain constant region.

FIG. 3C The amino acid sequence of H16-9.69 VH. Underlined is a portion of the heavy chain constant region.

FIG. 3D The amino acid sequence of H16-9.69 VL. Underlined is a portion of the light chain constant region.

FIG. 3E The amino acid sequence of H16-1.52 VH. Underlined is a portion of the heavy chain constant region.

FIG. 3F The amino acid sequence of H16-1.52 VL. Underlined is a portion of the light chain constant region.

FIG. 3G The amino acid sequence of Ha 16-1(1)23 VH. Underlined is a portion of the heavy chain constant region.

FIG. 3H The amino acid sequence of Ha 16-1(1)23 VL. Underlined is a portion of the light chain constant region.

FIG. 3I The amino acid sequence of H16-9.44 VH. Underlined is a portion of the heavy chain constant region.

FIG. 3J The amino acid sequence of H16-9.44 VL. Underlined is a portion of the light chain constant region.

FIG. 3K The amino acid sequence of H16-1.67 VH. Underlined is a portion of the heavy chain constant region.

FIG. 3L The amino acid sequence of H16-1.67 VL. Underlined is the light chain constant region.

FIG. 3M The amino acid sequence of Ha 16-1(3,5)36 VH. Underlined is a portion of the heavy chain constant region.

FIG. 3N The amino acid sequence of Ha16-1(3,5)36 VL. Underlined is a portion of the light chain constant region.

FIG. 3O The amino acid sequence of H16-1.86 VH. Underlined is a portion of the heavy chain constant region.

FIG. 3P The amino acid sequence of H16-1.86 VL. Underlined is a portion of the light chain constant region.

FIG. 3Q The amino acid sequence of H16-9.10 VH. Underlined is a portion of the heavy chain constant region.

FIG. 3R The amino acid sequence of H16-9.10 VL. Underlined is a portion of the light chain constant region.

FIG. 3S The amino acid sequence of H16-9.33 VH. Underlined is a portion of the heavy chain constant region.

FIG. 3T The amino acid sequence of H16-9.33 VL. Underlined is a portion of the light chain constant region.

FIG. 3U The amino acid sequence of H16-1.68 VH. Underlined is a portion of the heavy chain constant region.

FIG. 3V The amino acid sequence of H16-1.68 VL. Underlined is a portion of the light chain constant region.

FIG. 3W The amino acid sequence of Ha16-1(1)11 VH. Underlined is a portion of the heavy chain constant region.

FIG. 3X The amino acid sequence of Ha16-1(1)11 VL. Underlined is a portion of the light chain constant region.

FIG. 3Y The amino acid sequence of Ha16-1(3,5)18 VH. Underlined is the leader sequence. Double-underlined is the heavy chain variable region. Dashed underline shows the human IgG1 constant region.

FIG. 3Z The amino acid sequence of Ha16-1(3,5)18 VL. Double-underlined is the light chain variable region. Dashed underline shows the human Ig lambda constant region.

FIG. 3AA The amino acid sequence of Ha 16-1(2,4)4 VH.

FIG. 3AB The amino acid sequence of Ha16-1(2,4)4 VL. Underlined is a portion of the light chain constant region.

FIG. 3AC The amino acid sequence of Ha16-1(3,5)56 VH.

FIG. 3AD The amino acid sequence of Ha16-1(3,5)56 VL. Underlined is a portion of the light chain constant region.

FIG. 3AE The amino acid sequence of H16-7.8 VH. Double-underlined is the leader sequence. Underlined is a portion of the heavy chain constant region.

FIG. 3AF The amino acid sequence of H16-7.8 VL. Double-underlined is the leader sequence. Underlined is a portion of the light chain constant region.

FIG. 3AG The amino acid sequence of H16-1.93 VH. Double-underlined is the leader sequence. Underlined is a portion of the heavy chain constant region.

FIG. 3AH The amino acid sequence of H16-1.93 VL. Double-underlined is part of the leader sequence. Underlined is a portion of the light chain constant region.

FIG. 3AI The amino acid sequence of Ha16-1(3,5)27.1 VH. Double-underlined is part of the leader sequence, and underlined is a portion of the heavy chain constant region.

FIG. 3AJ The amino acid sequence of Ha16-1(3,5)27 VL. Underlined is a portion of the light chain constant region.

FIG. 3AK The amino acid sequence of H16-1.61 VH. Underlined is a portion of the heavy chain constant region.

FIG. 3AL The amino acid sequence of H16-1.61 VL. Underlined is a portion of the light chain constant region.

FIG. 3AM The amino acid sequence of H16-1(3,5)5 VH. Double-underlined is the leader sequence, and underlined is a portion of the heavy chain constant region.

FIG. 3AN The amino acid sequence of H16-1(3,5)5 VL. Double-underlined is part of the leader sequence, and underlined is a portion of the light chain constant region.

FIG. 3AO The amino acid sequence of H16-7.200 VH. Double-underlined is the leader sequence, and underlined is a portion of the heavy chain constant region.

FIG. 3AP The amino acid sequence of H16-7.200 VL. Double-underlined is part of the leader sequence, and underlined is a portion of the light chain constant region.

FIG. 3AQ The amino acid sequence of Ha16-1(3,5)42 VH. Double-underlined is the leader sequence, and underlined is a portion of the heavy chain constant region.

FIG. 3AR The amino acid sequence of Ha16-1(3,5)42 VL. Double-underlined is part of the leader sequence, and underlined is a portion of the light chain constant region.

FIG. 3AS The amino acid sequence of H16-9.65 VH. Double-underlined is the leader sequence, and underlined is a portion of the heavy chain constant region.

FIG. 3AT The amino acid sequence of H16-9.65 VL. Double-underlined is part of the leader sequence, and underlined is a portion of the light chain constant region.

FIG. 3AU The amino acid sequence of H16-1.29 VH. Double-underlined is part of the leader sequence, and underlined is a portion of the heavy chain constant region.

FIG. 3AV The amino acid sequence of H16-3.4 VH. Underlined is a portion of the heavy chain constant region.

FIG. 3AW The amino acid sequence of H16-1.92 VH. Underlined is a portion of the heavy chain constant region.

FIG. 3AX The amino acid sequence of Ha16-1(3,5)19 VL. Double-underlined is part of the leader sequence, and underlined is a portion of the light chain constant region.

FIG. 3AY The amino acid sequence of Ha16-1(3,5)19 VH. Double-underlined is part of the leader sequence, and underlined is a portion of the light chain constant region.

FIG. 3AZ The amino acid sequence of Ha16-1.80 VL. Double-underlined is part of the leader sequence, and underlined is a portion of the light chain constant region.

FIG. 3AAA The amino acid sequence of Ha16-1.80 VH. Double-underlined is part of the leader sequence, and underlined is a portion of the light chain constant region.

FIG. 4A Alignment of H16-7.213 Heavy Chain Variable Region to human germline VH1-2/D3-9/JH4

FIG. 4B Alignment of H16-9.69 Heavy Chain Variable Region to human germline VH1-8/D3-10/JH4

FIG. 4C Alignment of H16-1.52 Heavy Chain Variable Region to human germline VH3-23/6-19/JH4

FIG. 4D Alignment of Ha16-1(1)23 Heavy Chain Variable Region to human germline VH3-33/D3-10/JH6

FIG. 4E Alignment of H16-9.44 Heavy Chain Variable Region to human germline VH4-4/D3-22/JH4

Figure 4J:
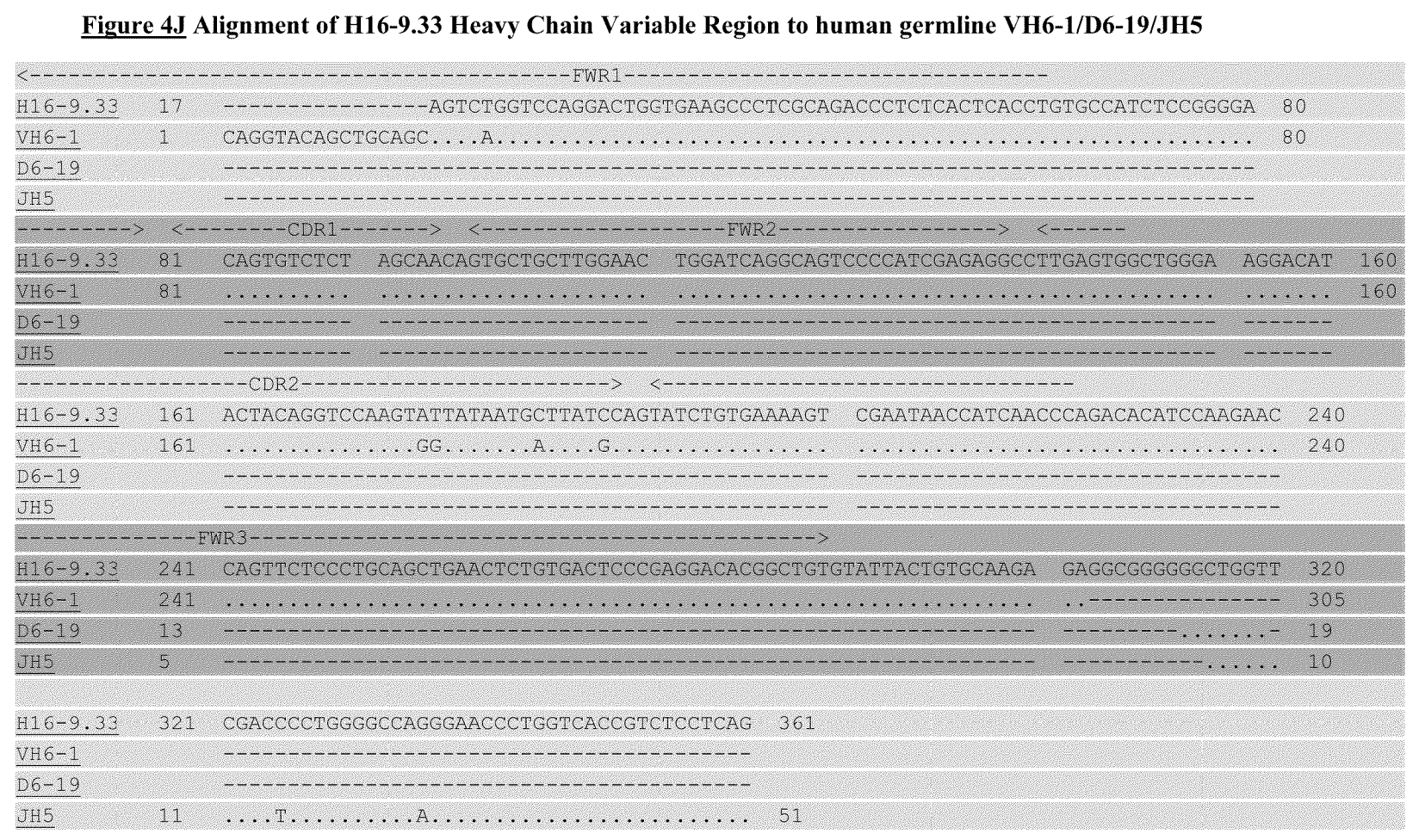
Figure 4W:
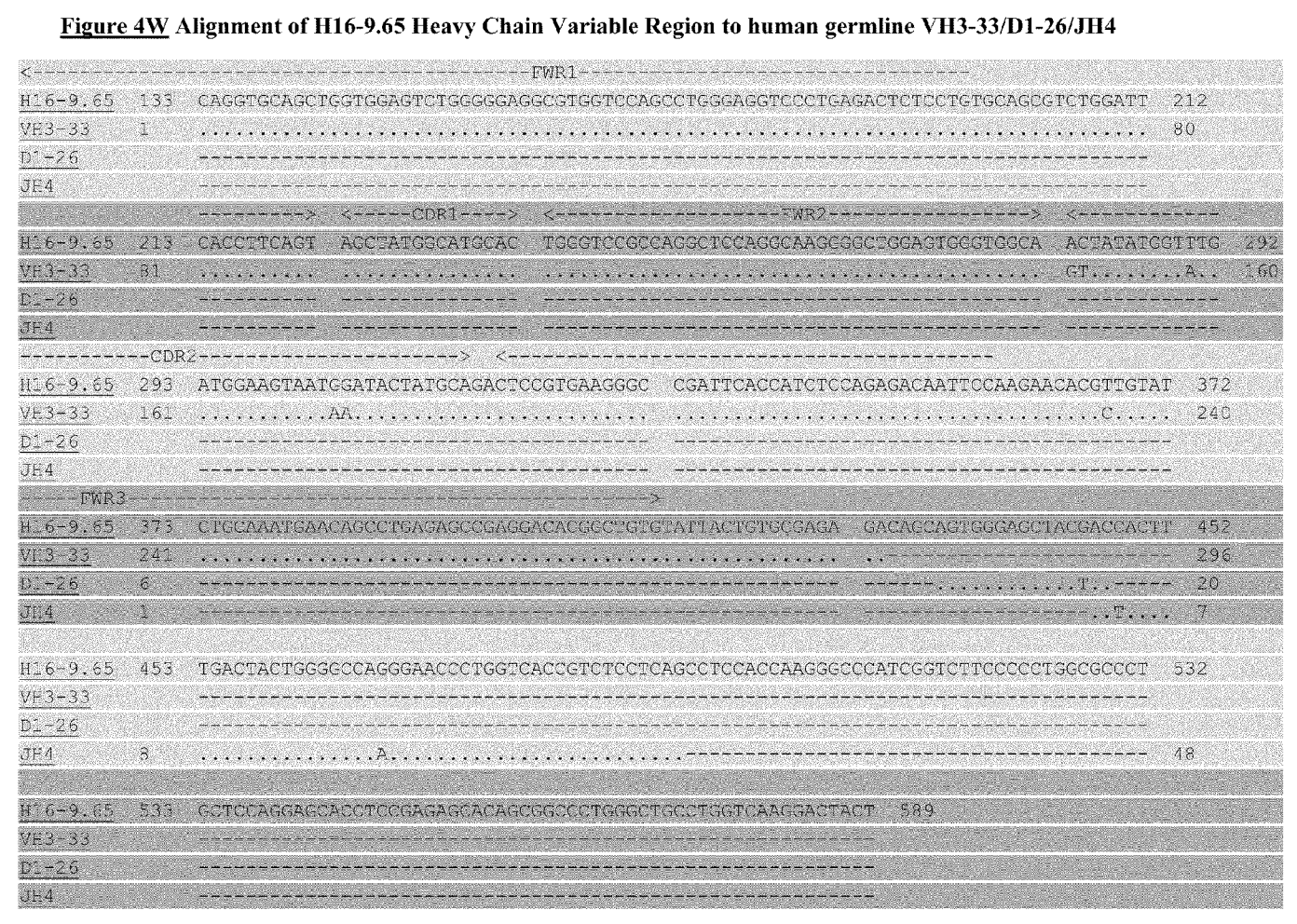
Figures 2, 25:
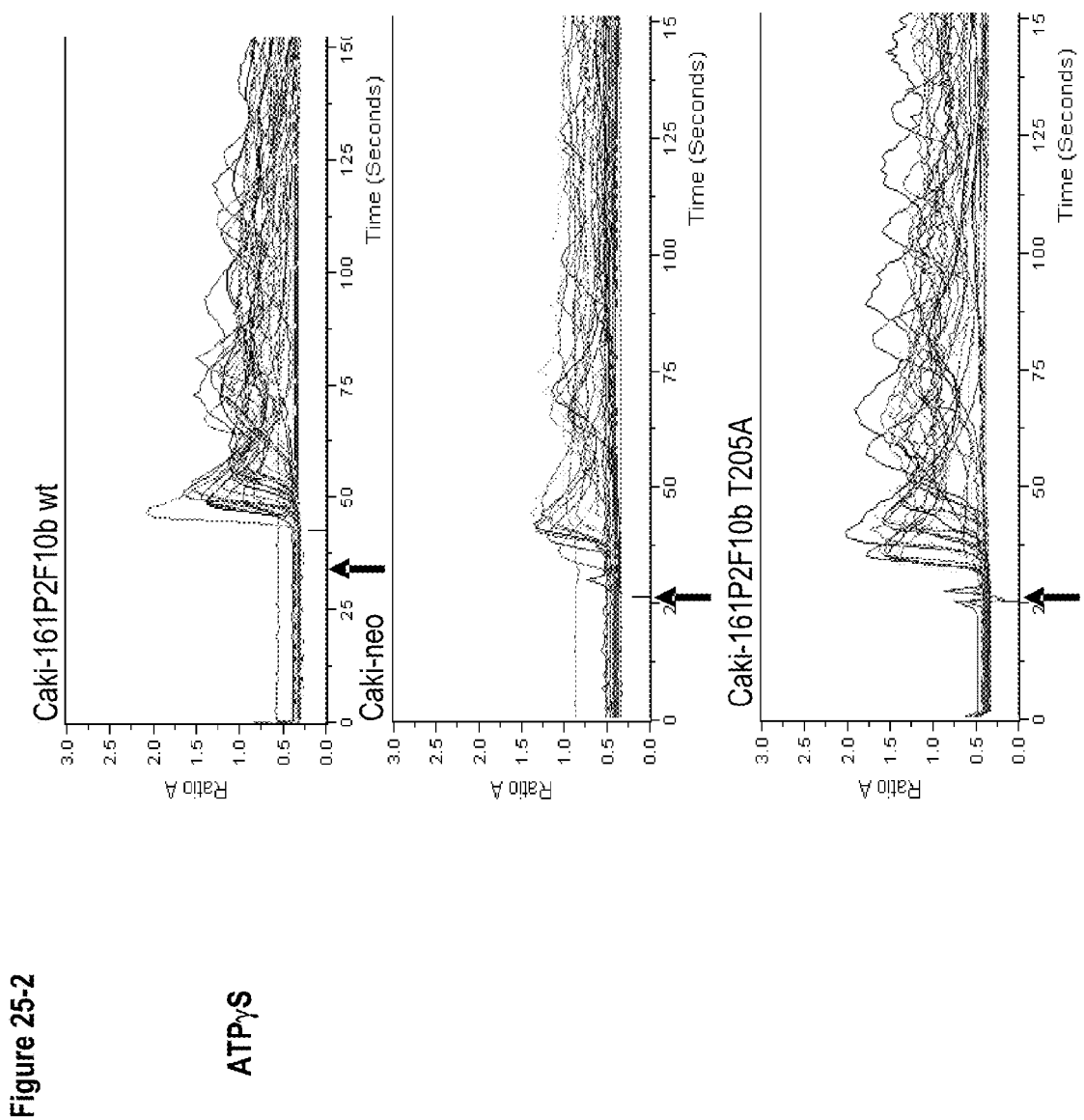
FIG. 2. Nucleic Acid and Amino Acid sequences of 161P2F10b antibodies.
Figures 3, 25:
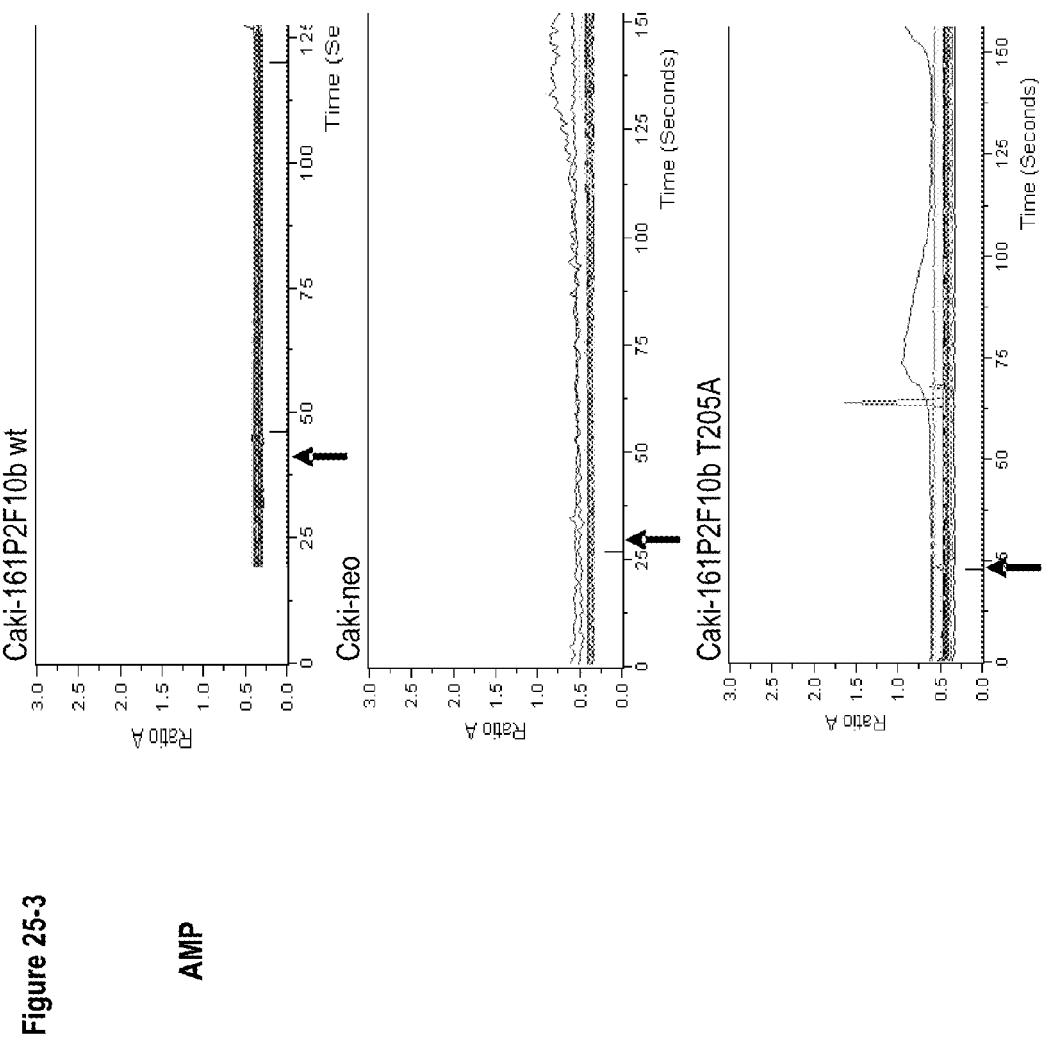
Figures 4, 25:
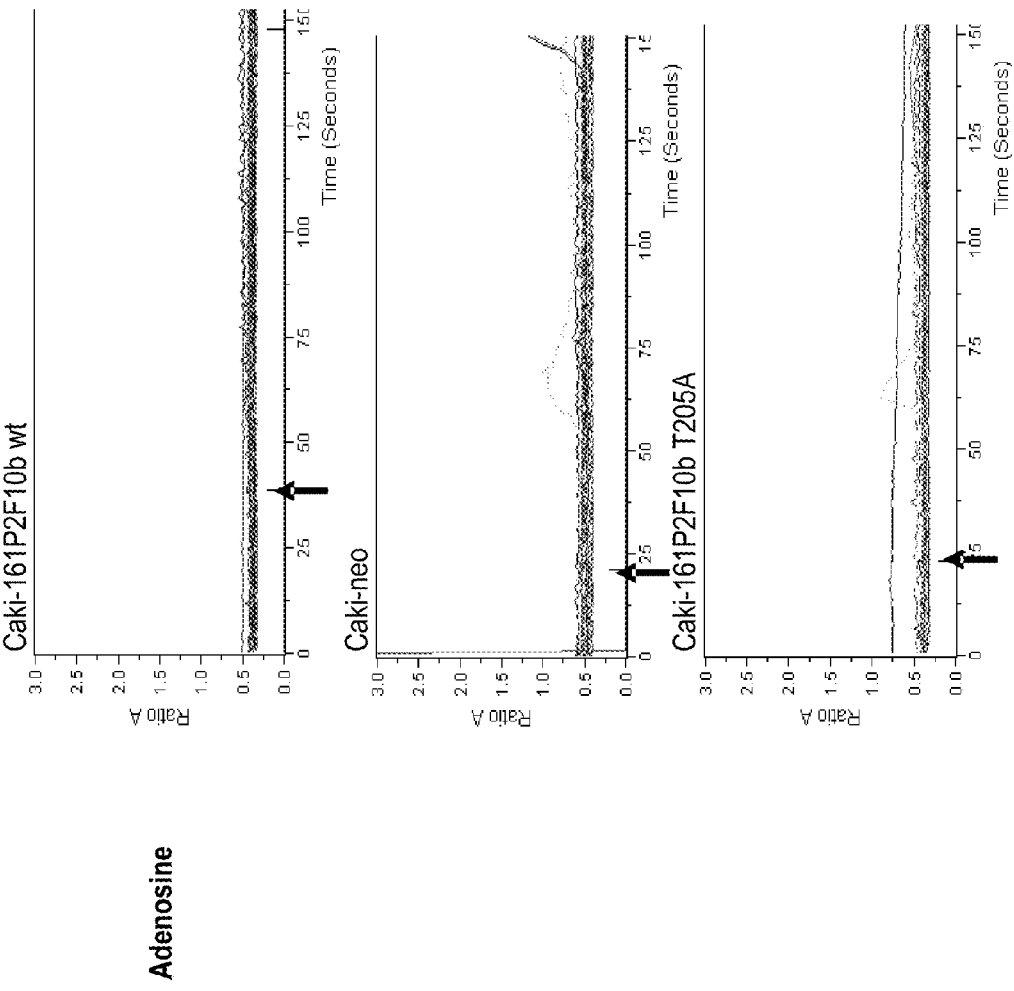
FIG. 4. Alignment of 161P2F10B antibodies Heavy Chain Variable Region to germline V-D-J. Sequences.

FIG. 4F Alignment of H16-1.67 Heavy Chain Variable Region to human germline VH4-31/D3-10/JH6

FIG. 4G Alignment of Ha16-1(3,5)36 Heavy Chain Variable Region to human germline VH4-39/D6-19/JH4

FIG. 4H Alignment of H16-1.86 Heavy Chain Variable Region to human germline VH4-59/D1-26/JH6

FIG. 4I Alignment of H16-9.10 Heavy Chain Variable Region to human germline VH6-1/D6-19/JH5

FIG. 4J Alignment of H16-9.33 Heavy Chain Variable Region to human germline VH6-1/D6-19/JH5

FIG. 4K Alignment of Ha16-1(1)11 Heavy Chain Variable Region to human germline VH4-59/D4-23/JH6

FIG. 4L Alignment of Ha16-1(3,5)18 Heavy Chain Variable Region to human germline VH4-4/D4-17/JH6

FIG. 4M Alignment of Ha16-1(2,4)4 Heavy Chain Variable Region to human germline VH3-33/D1-26/JH6

FIG. 4N Alignment of Ha16-1(3,5)56 Heavy Chain Variable Region to human germline VH5-51/D1-26/JH6

FIG. 4O Alignment of H16-7.8 Heavy Chain Variable Region to human germline VH4-31/D5-12/JH6

FIG. 4P Alignment of H16-1.68 Heavy Chain Variable Region to human germline VH3-33/D3-3/JH6

FIG. 4Q Alignment of H16-1.93 Heavy Chain Variable Region to human germline VH1-18/D6-13/JH6

FIG. 4R Alignment of Ha16-1(3,5)27 Heavy Chain Variable Region to human germline VH5-51/D4-4/JH6

FIG. 4S Alignment of H16-1.61 Heavy Chain Variable Region to human germline VH3-33/D3-3/JH6

FIG. 4T Alignment of Ha16-1(3,5)5 Heavy Chain Variable Region to human germline VH5-51/D3-10/JH6

FIG. 4U Alignment of H16-7.200 Heavy Chain Variable Region to human germline VH4-31/D4-23/JH4

FIG. 4V Alignment of Ha16-1(3,5)42 Heavy Chain Variable Region to human germline VH5-51/D4-11/JH6

FIG. 4W Alignment of H16-9.65 Heavy Chain Variable Region to human germline VH3-33/D1-26/JH4

FIG. 4X Alignment of H16-1.29 Heavy Chain Variable Region to human germline VH1-2/D5-12/JH6

FIG. 4Y Alignment of H16-3.4 Heavy Chain Variable Region to human germline VH4-31/D5-12/JH4

FIG. 4Z Alignment of H16-1.92 Heavy Chain Variable Region to human germline VH4-39/D4-11/JH3

FIG. 5. Alignment of 161P2F10B antibodies Light Chain Variable Region to germline V-D-J. Sequences. FIG. 5A Alignment of H16-7.213 Light Chain Variable Region to human germline VK-O2/JK4.

FIG. 5B Alignment of H16-9.69 Light Chain Variable Region to human germline VK-B3/JK1.

FIG. 5C Alignment of H16-1.52 Light Chain Variable Region to human germline B3/JK2.

FIG. 5D Alignment of Ha16-1(1)23 Light Chain Variable Region to human germline V1-20/JL2.

FIG. 5E Alignment of H16-9.44 Light Chain Variable Region to human germline L1/JK3.

FIG. 5F Alignment of H16-1.67 Light Chain Variable Region to human germline O2/JK1.

FIG. 5G Alignment of Ha16-1(3,5)36 Light Chain Variable Region to human germline V1-16/JL2.

FIG. 5H Alignment of H16-1.86 Light Chain Variable Region to human germline O2/JK1.

Figure 5I:
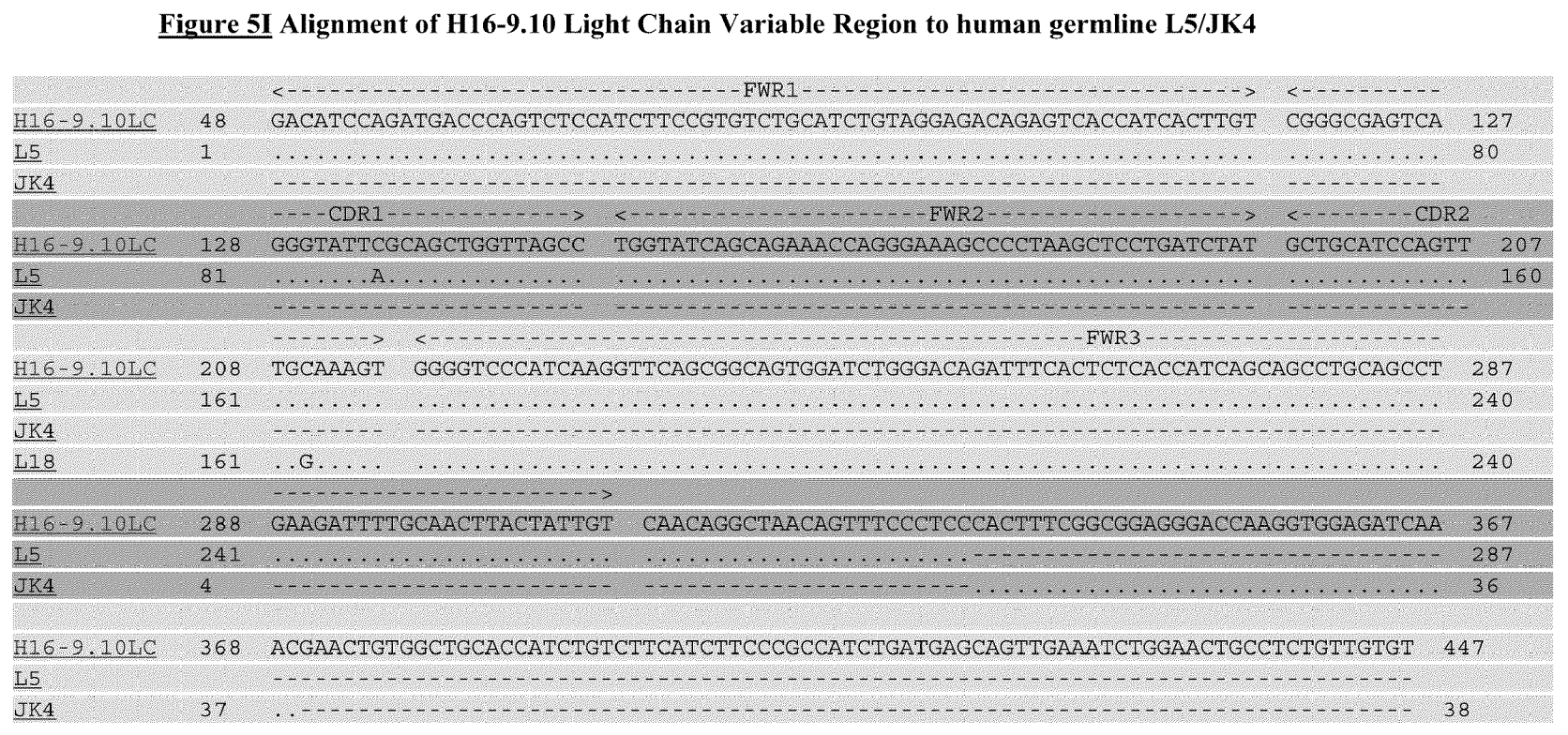

FIG. 5I Alignment of H16-9.10 Light Chain Variable Region to human germline L5/JK4.

FIG. 5J Alignment of H16-9.33 Light Chain Variable Region to human germline L5/JK4.

FIG. 5K Alignment of Ha16-1(1)11 Light Chain Variable Region to human germline O2/JK3.

FIG. 5L Alignment of Ha16-1(3,5)18 Light Chain Variable Region to human germline V1-19/JL2.

FIG. 5M Alignment of Ha16-1(2,4)4 Light Chain Variable Region to human germline V2-1/JL2.

FIG. 5N Alignment of Ha16-1(3,5)56 Light Chain Variable Region to human germline V1-4/JL2.

FIG. 5O Alignment of H16-7.8 Light Chain Variable Region to human germline A26/JK1.

FIG. 5P Alignment of H16-1.68 Light Chain Variable Region to human germline O2/JK4.

FIG. 5Q Alignment of H16-1.93 Light Chain Variable Region to human germline A20/JK3.

FIG. 5R Alignment of Ha16-1(3,5)27 Light Chain Variable Region to human germline V1-4/JL2.

FIG. 5S Alignment of H16-1.61 Light Chain Variable Region to human germline O12/JK3.

FIG. 5T Alignment of Ha16-1(3,5)5 Light Chain Variable Region to human germline V1-4/JL2.

Figure 5U:
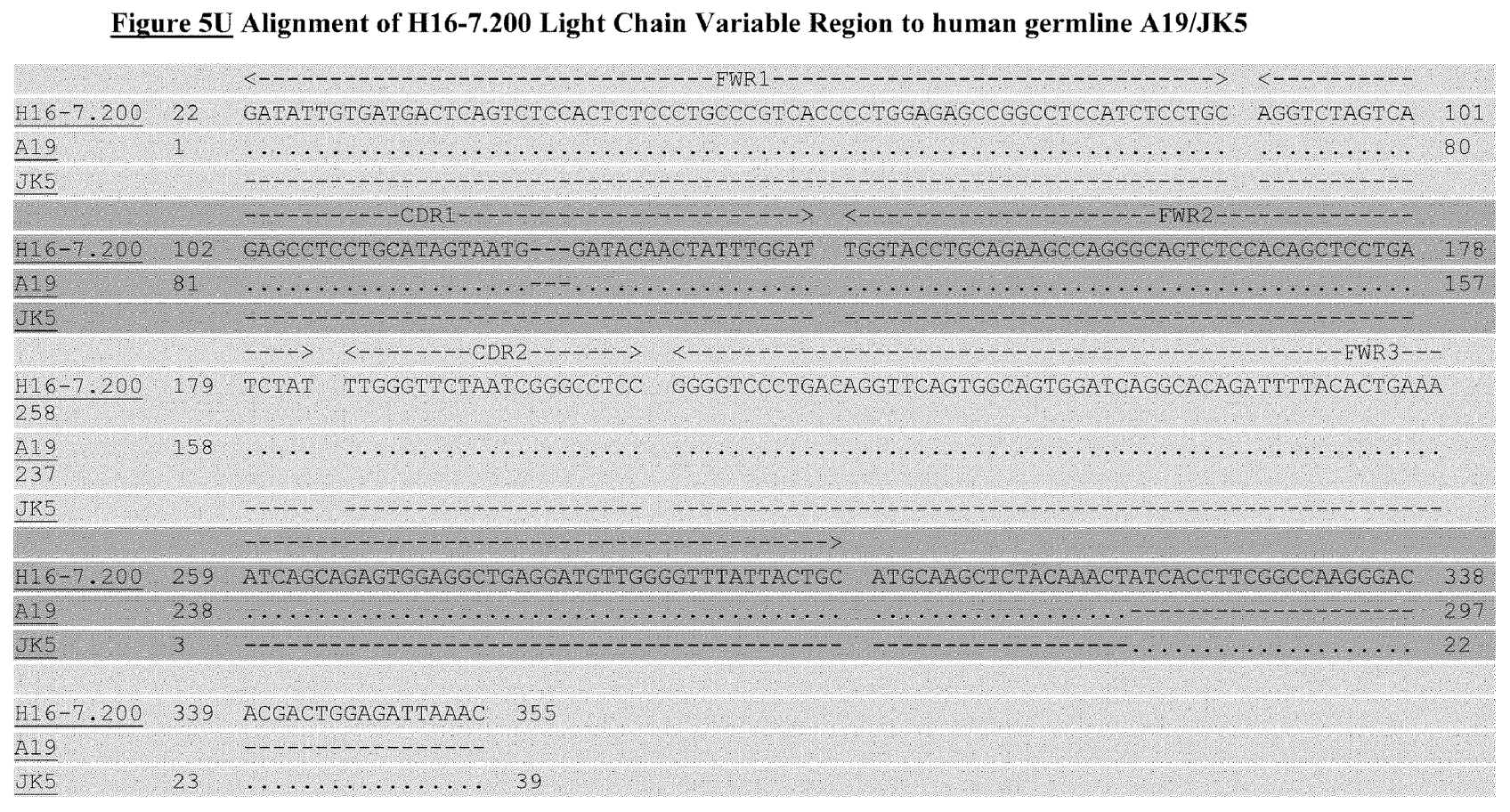

FIG. 5U Alignment of H16-7.200 Light Chain Variable Region to human germline A19/JK5.

FIG. 5V Alignment of Ha16-1(3,5)42 Light Chain Variable Region to human germline V1-4/JL2.

FIG. 5W Alignment of H16-9.65 Light Chain Variable Region to human germline A19/JK5.

Figure 5X:
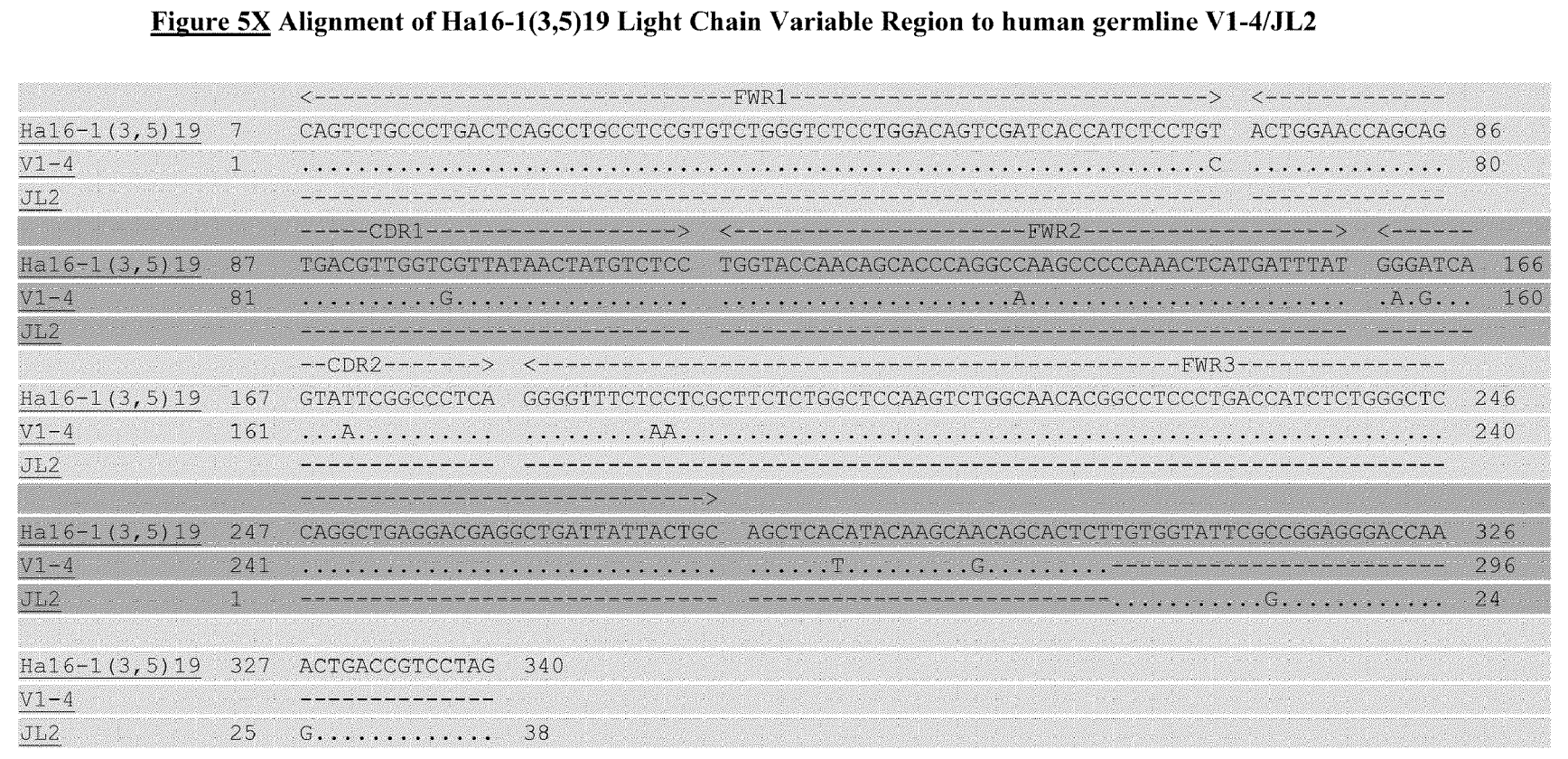

FIG. 5X Alignment of Ha16-1(3,5)19 Light Chain Variable Region to human germline V1-4/JL2.

Figures 3, 6:
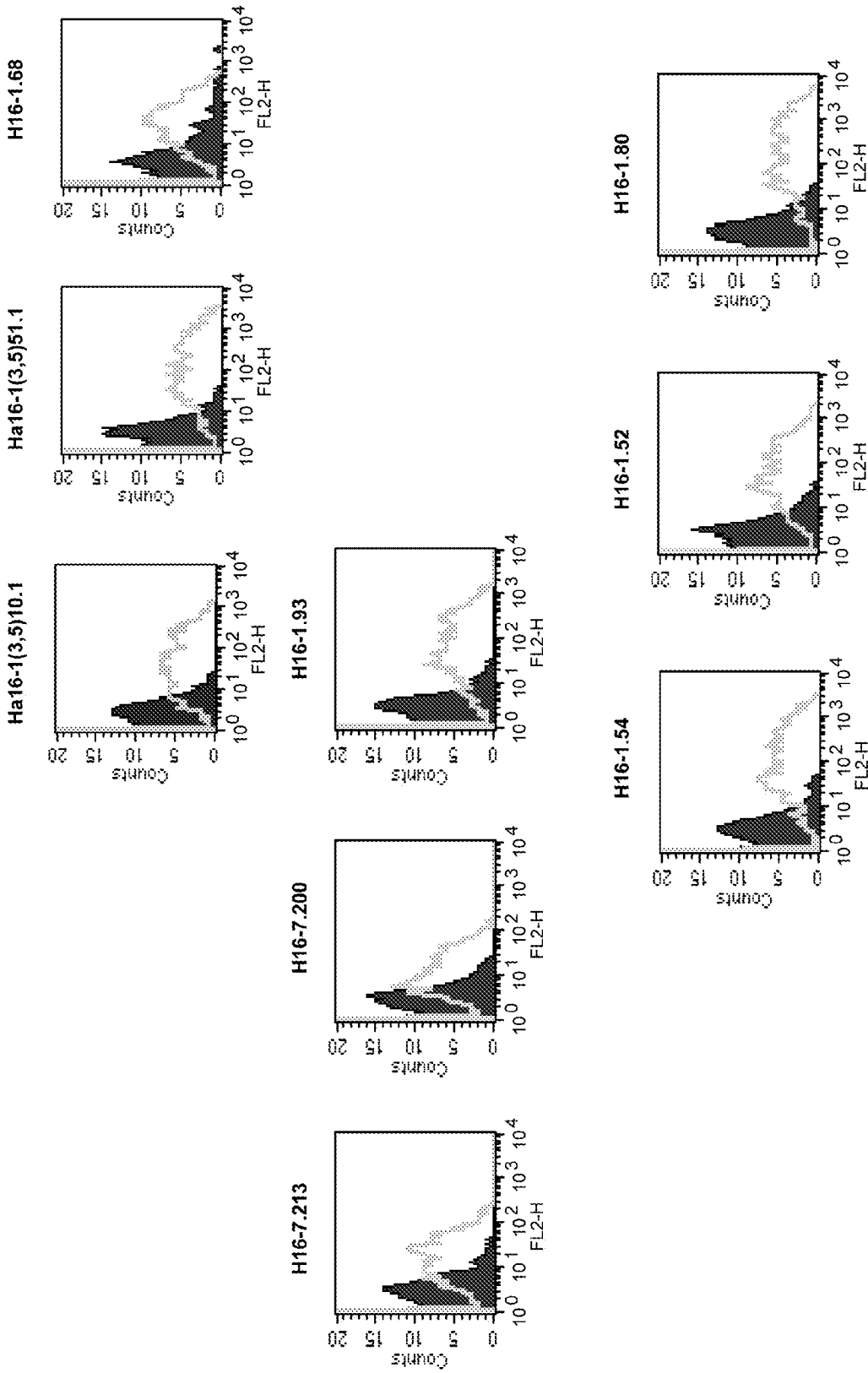
FIG. 3. Amino Acid sequences of 161P2F10B antibodies.

FIG. 6. 161P2F10B MAbs bind to CAKI-161P2F10B cells by FACS. FACS analysis was performed by using CAKI-neo as a negative control. The results show that 161P2F10B mAbs specifically bind to human 161P2F10B on CAKI-161P2F10B cells.

FIG. 7. 161P2F10B MAbs bind to UG-K3 cells by FACS. FACS analysis was performed by using CAKI-neo as a negative control. The results show that 161P2F10B mAbs specifically bind to human 161P2F10B on UG-K3 cells.

Figure 8:
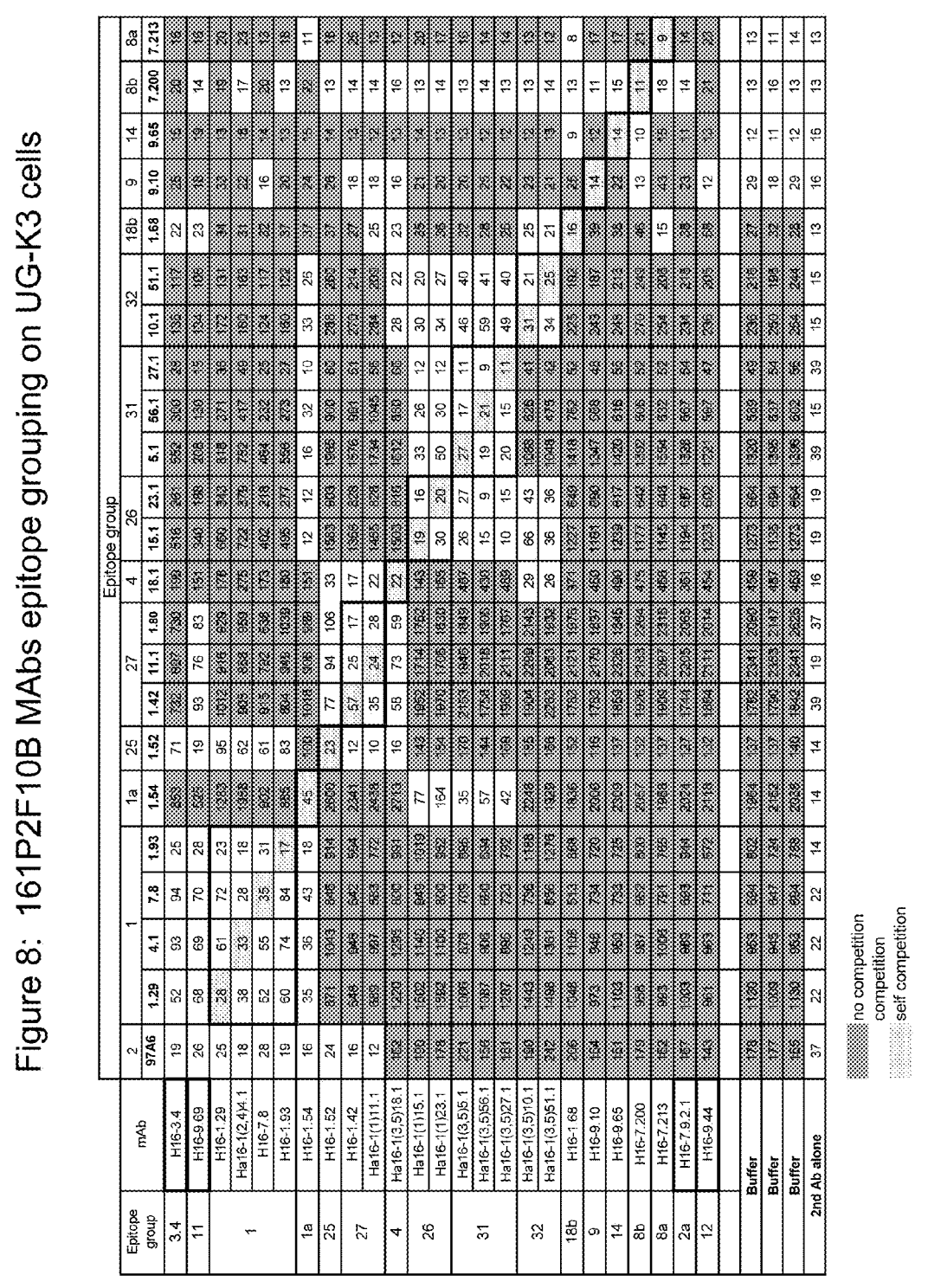

FIG. 8. 161P2F10B MAb Epitope grouping using UG-K3 cells. Binding of each of biotinylated 161P2F10B MAbs on the UG-K3 cells were competed with excess amount of each of antibodies, biotinylated antibodies were detected by streptavidin-PE. The cells were analyzed using FACScan. MFI values from FACS were used for data analysis. A shown in the table, cells are highlighted to indicate self-competition (100% competition), the MFI value in these cells are background control for each biotinylated antibody. Additionally, cells with no color indicate that the two antibodies compete each other (low MFI), cells highlighted in gray (high MFI) indicate that the two antibodies bind to two distinct epitopes. The results show the antibodies that have the same binding pattern bind to the same epitope among the antibodies and that there are 16 epitope groups within the antibodies tested.

FIG. 9. Domain mapping of 161P2F10B MAbs by immunoprecipitation. Tag5 expression constructs encoding either the full extracellular domain (ECD) of 161P2F10B (amino acids 46-875), the somatomedin-b-like domain (amino acids 46-157), the catalytic domain (amino acids 158-558), or the catalytic and nuclease domain (amino acids 158-875) were transfected into 293T cells and cellular lysates were made. These lysates were then used for immunoprecipitation with the indicated 161P2F10B MAbs or H3-1.5 control MAb (10 μg of MAb and 100-200 μg of cell lysate). Western blotting of the immunoprecipitates was then carried out using an anti-His polyclonal Ab that recognizes the His epitope tag present on each recombinant protein. The specific molecular weight band of each recombinant protein was identified by straight Western blotting of the lysates (upper right blot) and is indicated by an arrow. MAbs that bind to the full length ECD and to the somatomedin-b-like domain map to the somatomedin-b-like domain. MAbs that bind to the full length ECD and the catalytic domain, but not the catalytic+nuclease domain, map to the catalytic domain. MAbs that bind the full length ECD and to the catalytic+nuclease domain, but not to the catalytic domain, map to the nuclease domain. The lanes shown in the figure represent: lane 1. Vector, lane 2. pTag5 161P2F10b WT full length ECD, lane 3. pTag5 161P2F10b (46-157) somatomedin-b-like domain, lane 4. pTtag5 161P2F10b (158-558) catalytic domain, and lane 5. pTag5 161P2F10b (158-875) catalytic+nuclease domain. The results show that this technique enables mapping of MAbs to 161P2F10B to distinct regions of the extracellular domain.

FIG. 10. 161P2F10B MAb domain mapping. Presented on the right is a summary table of selected 161P2F10B MAbs, their relative affinity as determined by BiaCore analysis on the full length ECD (amino acids 46-875), their epitope group as determined by a FACS based MAb competition assay, and their epitope domain as determined by immunoprecipitation assay using cell lysates containing either the full length ECD, the somatomedin-b-like domain (amino acids 46-157), the catalytic domain (amino acids 158-558), or the catalytic and nuclease domain (amino acids 158-875). Presented on the left is a schematic of the 161P2F10B protein and assignment of the MAbs groups. The presence of MAbs within a group was inferred by a BiaCore competition assay in which the ability of MAbs to bind simultaneously to the 161P2F10B protein is analyzed. Inability to bind simultaneously suggests the MAbs share the same or an overlapping epitope. Simultaneous binding suggests that the MAbs employed belong in different epitope groups and recognize distinct or non-overlapping regions. The location of MAb groups within each domain in the schematic is arbitrary; however, placement of Nuclease groups c, d, e, and the catalytic group in close and overlapping proximity to each other has been inferred from BiaCore competition data in which MAbs present in different groups compete with MAbs analyzed from a larger panel. These results show that 161P2F10B MAbs map to distinct regions of the extracellular domain.

FIG. 11. Cross reactivity of human MAbs on mouse 161P2F10B. 293T-mouse 161P2F10B and 293T-neo cells were used to test cross-reactivity of human mAbs with mouse 161P2F10B by FACS. 50 ul of MAbs at 2 ug/ml were incubated with 293T-mouse 161P2F10B or 293T-neo cells (50, 000 cells/100 μl). Antibodies bound on the cells were detected using anti-hIgG-PE and analyzed on FACS. Data were analyzed using CellQuest Pro software. The solid purple line is data from negative control cells. The green line is from 161P2F10B-positive cells. These results show that human 161P2F10B MAbs bind to mouse 161P2F10B protein on the cell surface.

FIG. 12. MAbs to 161P2F10B mediate saporin dependent killing in KU-812 cells. KU-812 cells are a CML cell line that expresses high levels of endogenous 161P2F10B. KU-812 cells (3000 cells/well) were seeded into a 96 well plate on day 1. The following day an equal volume of medium containing 2× concentration of the indicated primary antibody together with a 2-fold excess of anti-human (Hum-Zap) polyclonal antibody conjugated with saporin toxin (Advanced Targeting Systems, San Diego, Calif.) was added to each well. The cells were allowed to incubate for 5 days at 37 degrees C. At the end of the incubation period, MTS (Promega) was added to each well and incubation continued for an additional 4 hours. The optical density at 450 nM was then determined The results in show that 161P2F10B MAbs HA16-9.69, HA16-1.18 and HA16-1.93 mediated saporin dependent cytotoxicity in KU-812 cells while a control, nonspecific human IgG1 (H3-1.4) and another 161P2F10B MAb (HA16-7.200) had no effect.

Figure 13:
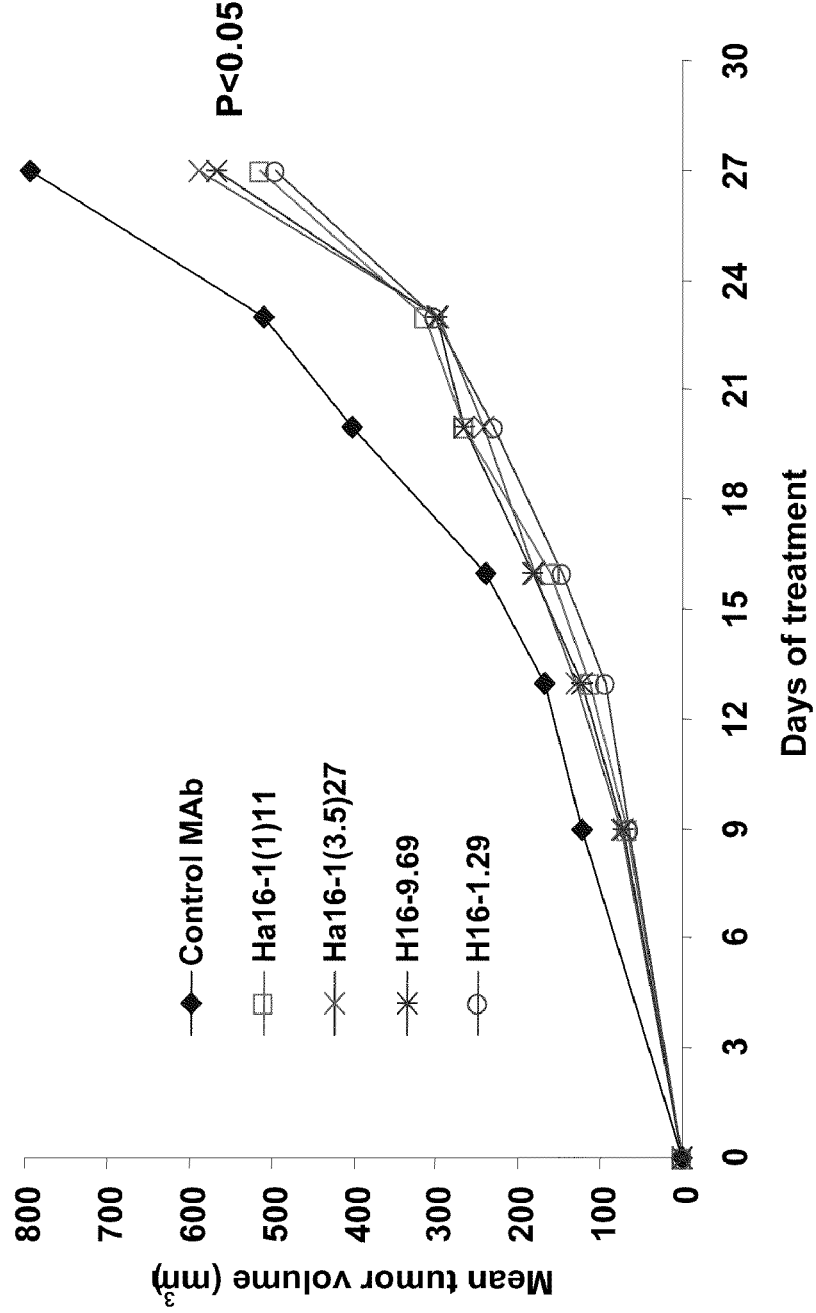

FIG. 13. 161P2F10B MAbs inhibit the growth of renal cell carcinoma. Human renal cancer UG-K3 tumor cells ($2.0 \times 10^6$ cells) were injected subcutaneously into male SCID mice. The mice were randomized into groups (n=10 in each group) and treatment initiated intraperitoneally (i.p.) on day 0 with treatment MAbs or isotype MAb control as indicated. Animals were treated twice weekly for a total of 8 doses at 750 μg/dose until study day 27. Tumor growth was monitored using caliper measurements every 3 to 4 days as indicated. The results show 161P2F10B MAbs H16-1.29.1.1, Ha16-1 (3,5)27.1, H16-9.69 and Ha16-1(1)11 statistically and significantly inhibited the growth of human renal cancer xenograft UG-K3 implanted subcutaneously in SCID mice ($p<0.05$).

Figure 14:
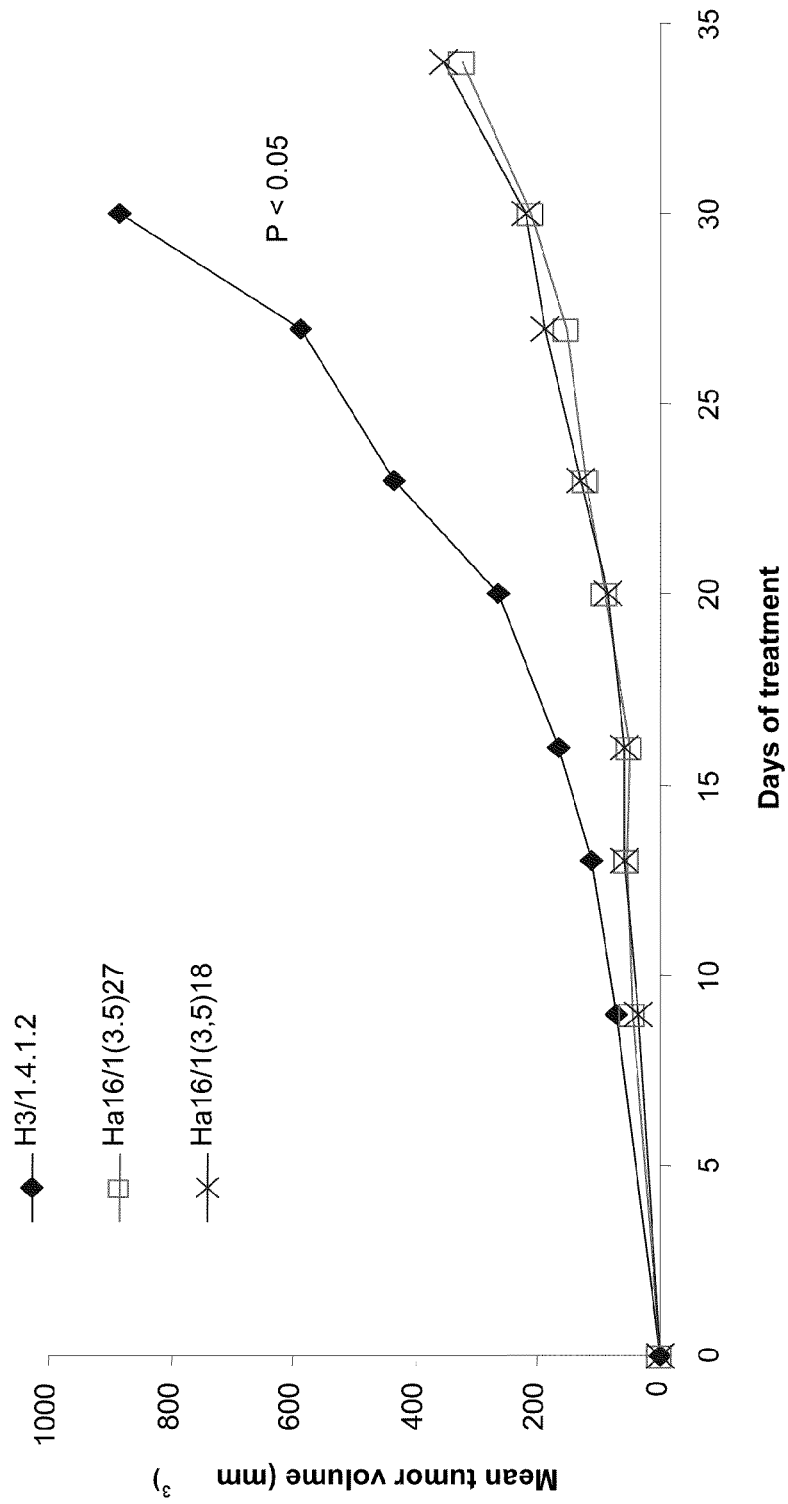

FIG. 14. 161P2F10B MAbs inhibit the growth of UG-K3 cells in SCID mice. Human renal cancer UG-K3 tumor cells ($2.0 \times 10^6$ cells) were injected subcutaneously into male SCID mice. The mice were randomized into groups (n=10 mice in each group) and treatment initiated intraperitoneally (i.p.) on Day 0 with treatment MAbs or isotype MAb control as indicated. Animals were treated twice weekly for a total of 6 doses until study day 20. Tumor growth was monitored using caliper measurements every 3 to 4 days as indicated. The results show 161P2F10B MAbs Ha16-11(3,5)27 and Ha16-1(3,5)18 statistically and significantly inhibited the growth of human renal cancer xenograft UG-K3 implanted subcutaneously in SCID mice ($P<0.05$).

Figure 15:
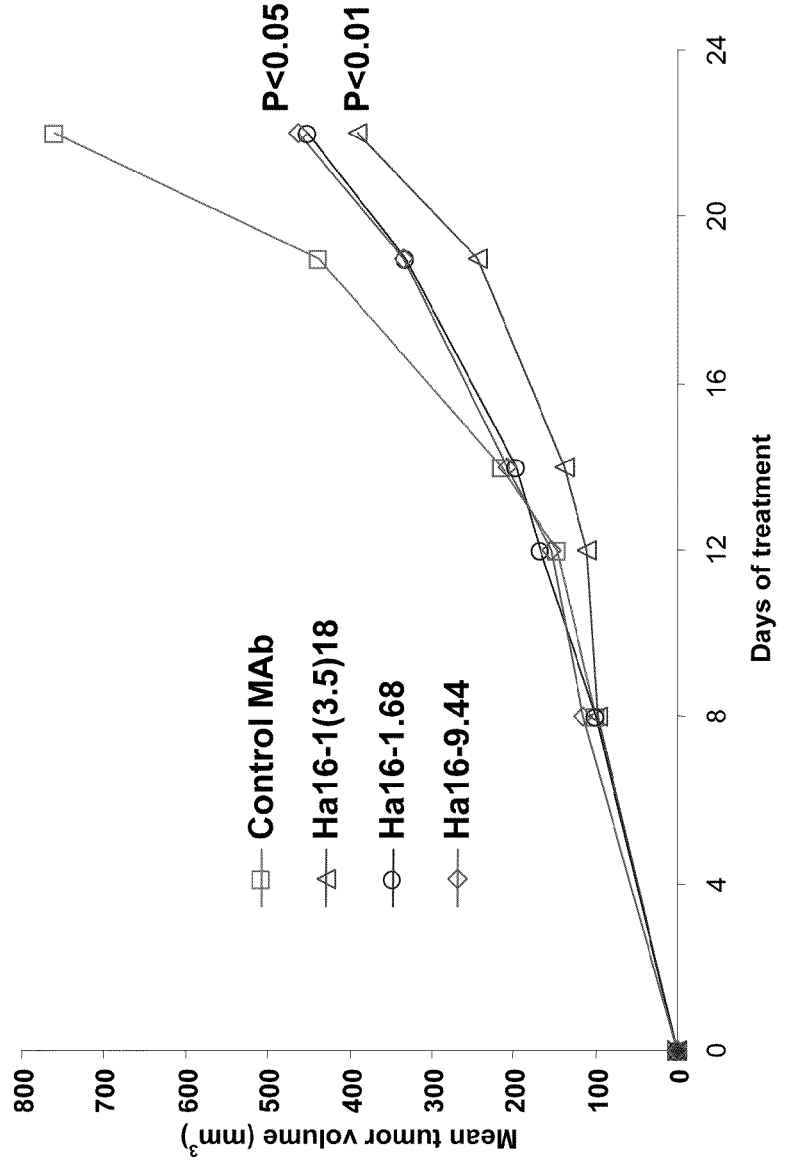

FIG. 15. 161P2F10B MAbs inhibit human renal cancer xenograft. Human renal cancer RXF-393 tumor cells ($2.0 \times 10^6$ cells) were injected subcutaneously into male SCID mice.

The mice were randomized into groups (n=10 in each group) and treatment initiated intraperitoneally (i.p.) on day 0 with treatment MAbs or isotype MAb control as indicated. Animals were treated twice weekly for a total of 7 doses at 400 μg/dose until study day 22. Tumor growth was monitored using caliper measurements every 3 to 4 days as indicated. The results show 161P2F10B MAbs Ha16-1(3,5)18 (P<0.01), H16-1.68 (P<0.05) and H16-9.44 (P<0.05) statistically and significantly inhibited the growth of human renal cancer xenograft RXF-393 implanted subcutaneously in SCID mice.

Figure 16:
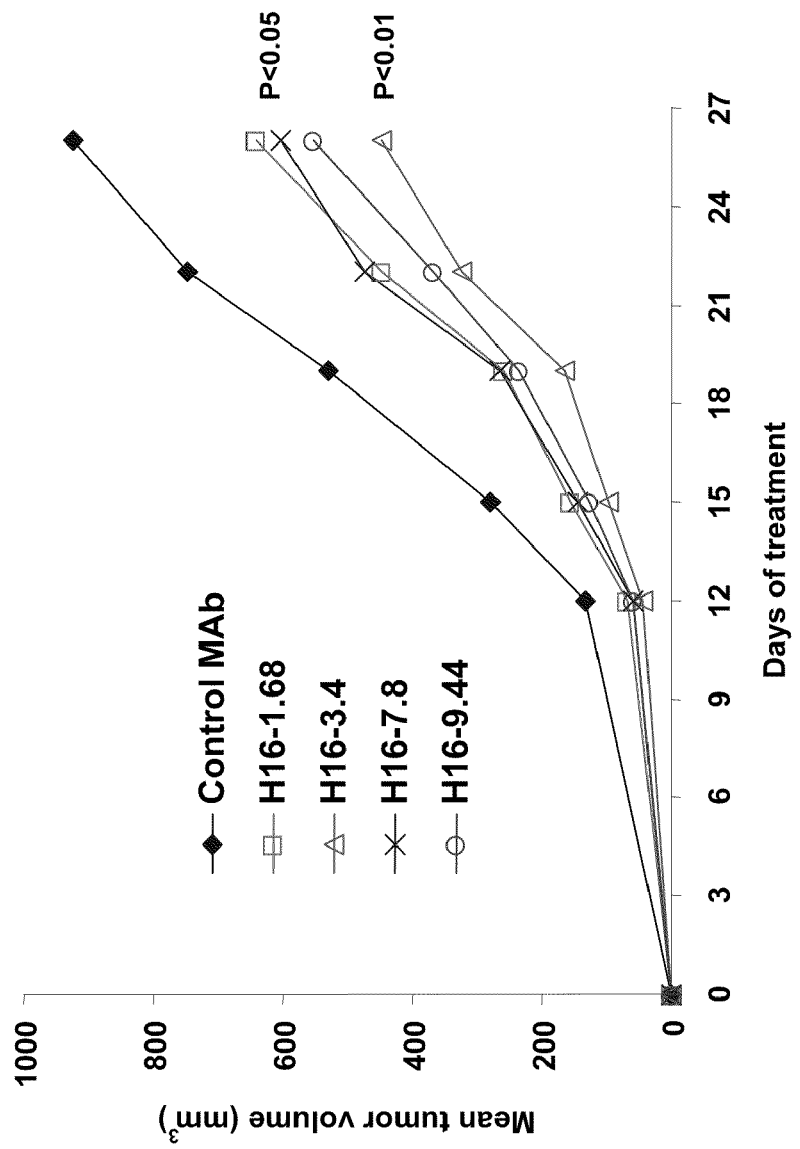

FIG. 16. 161P2F10B MAbs inhibit the growth of human renal cancer SKRC-01 in SCID mice. Human renal cancer SKRC-01 tumor cells ($2.5 \times 10^6$ cells) were injected subcutaneously into male SCID mice. The mice were randomized into groups (n=10 in each group) and treatment initiated intraperitoneally (i.p.) on day 0 with treatment MAbs or isotype MAb control as indicated. Animals were treated twice weekly for a total of 7 doses at 250 μg/dose until study day 22. Tumor growth was monitored using caliper measurements every 3 to 4 days as indicated. The results show 161P2F10B MAbs H16-1.68 (P<0.05), H16-7.8 (P<0.05), H16-9.44 (P<0.05) and H16-3.4 (P<0.01) statistically and significantly inhibited the growth of human renal cancer xenograft SKRC-01 implanted subcutaneously in SCID mice.

Figure 17:
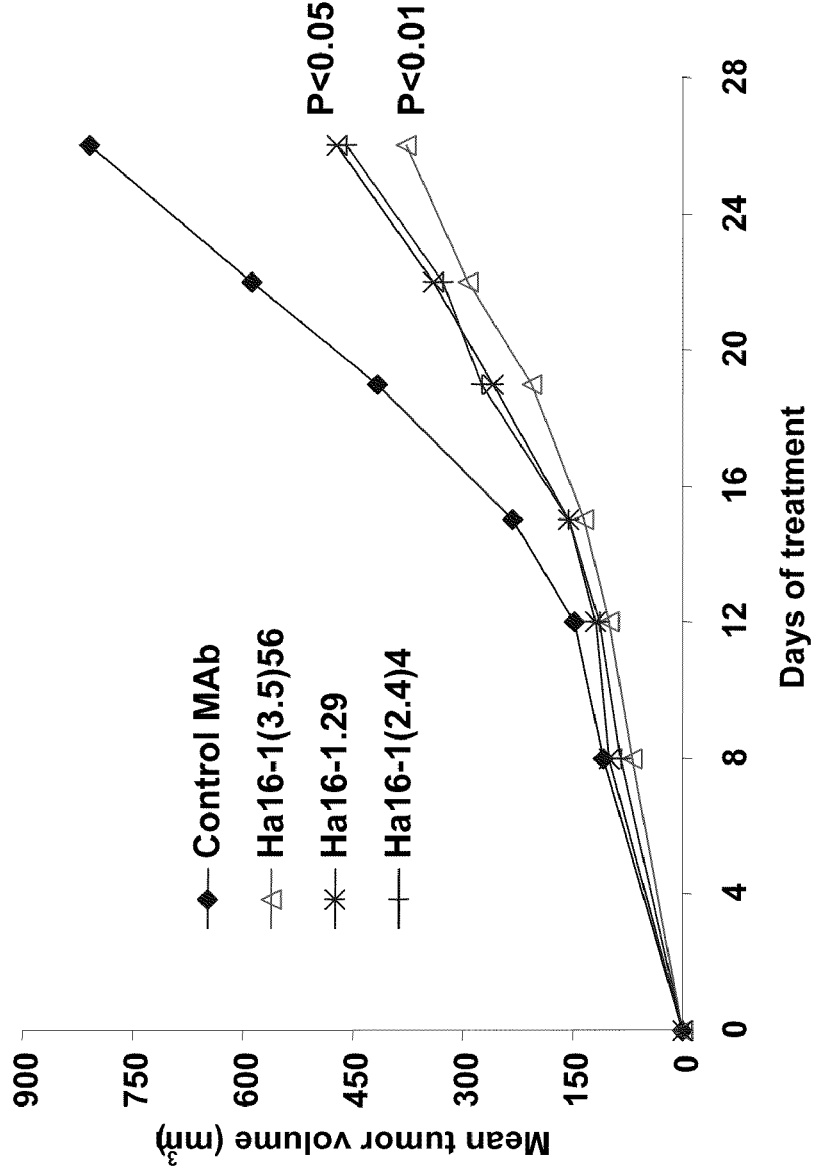

FIG. 17. 161P2F10B MAbs inhibit the growth of human renal cancer UG-K3 in SCID mice. Human renal cancer UG-K3 tumor cells ($2.0 \times 10^6$ cells) were injected subcutaneously into male SCID mice. The mice were randomized into groups (n=10 in each group) and treatment initiated intraperitoneally (i.p.) on day 0 with treatment MAbs or isotype MAb control as indicated. Animals were treated twice weekly for a total of 6 doses at 750 μg/dose until study day 19. Tumor growth was monitored using caliper measurements every 3 to 4 days as indicated. The results show 161P2F10B MAbs H16-1.29.1.1 (P<0.05), Ha16-1(3,5)56 (P<0.01) and Ha16-1(2,4)4 (P<0.05) statistically and significantly inhibited the growth of human renal cancer xenograft UG-K3 implanted subcutaneously in SCID mice.

Figure 18:
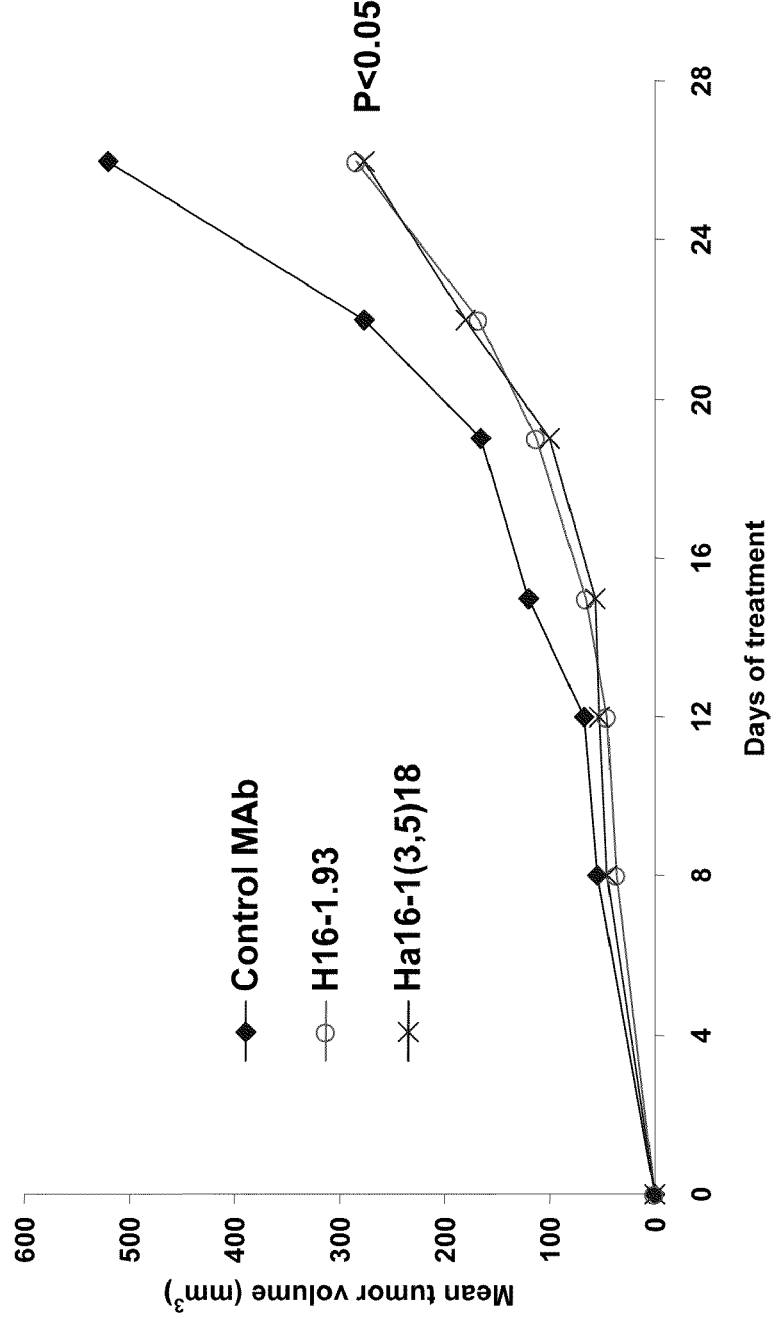

FIG. 18. 161P2F10B MAbs inhibit the growth of human renal cancer UG-K3 in SCID mice. Human renal cancer UG-K3 tumor cells ($2.0 \times 10^6$ cells) were injected subcutaneously into male SCID mice. The mice were randomized into groups (n=10 in each group) and treatment initiated intraperitoneally (i.p.) on day 0 with treatment MAbs or isotype MAb control as indicated. Animals were treated twice weekly for a total of 7 doses at 500 μg/dose until study day 22. Tumor growth was monitored using caliper measurements every 3 to 4 days as indicated. The results show 161P2F10B MAbs H16-1.93 and Ha16-1(3,5)18 statistically and significantly inhibited the growth of human renal cancer xenograft UG-K3 implanted subcutaneously in SCID mice (P<0.05).

Figure 19:
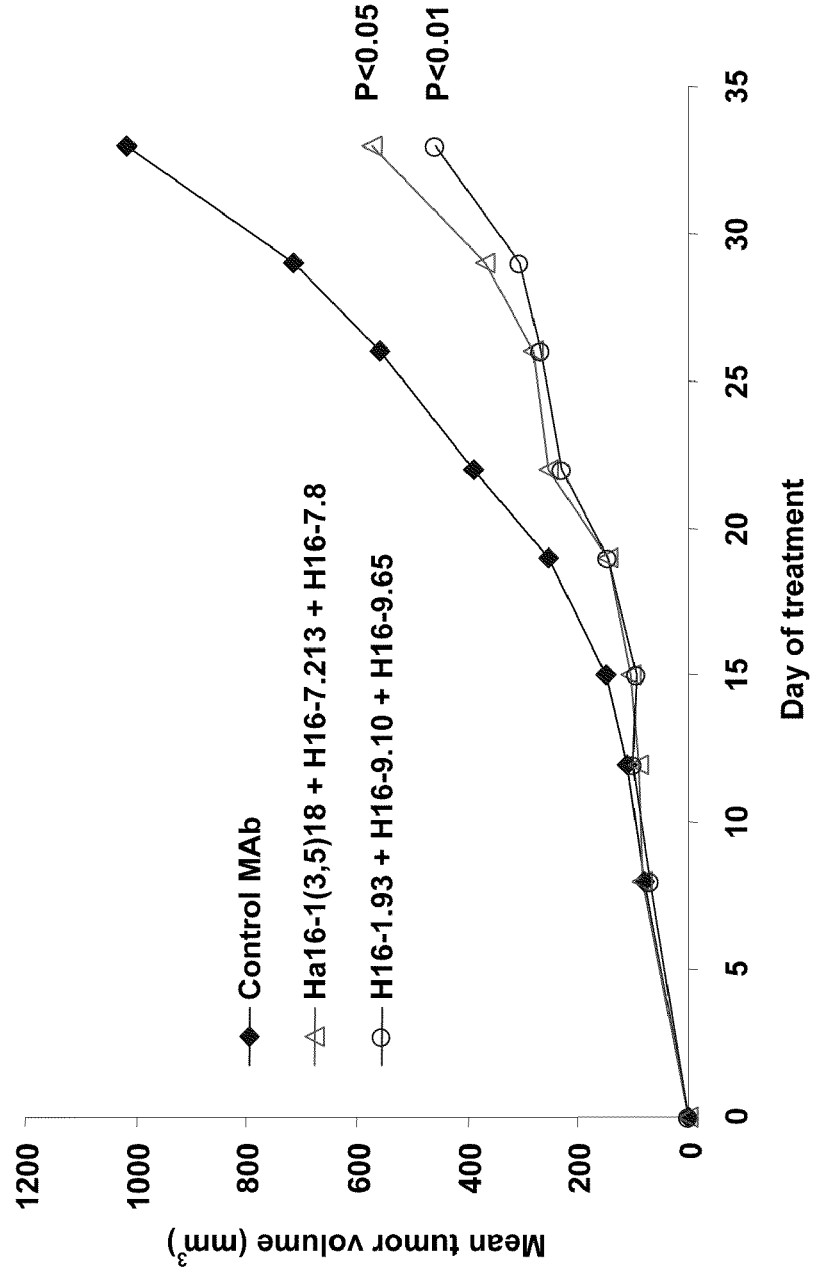

FIG. 19. Combined 161P2F10B MAbs inhibit the growth of human renal cancer Ug-K3 in SCID mice. Human renal cancer UG-K3 tumor cells ($2.0 \times 10^6$ cells) were injected subcutaneously into male SCID mice. The mice were randomized into groups (n=10 in each group) and treatment initiated intraperitoneally (i.p.) on day 0 as indicated. For 161P2F10B MAb treatment, three MAbs at 200 μg each were pooled together at each dosing. Animals were treated twice weekly for a total of 7 doses until study day 27. Tumor growth was monitored using caliper measurements every 3 to 4 days as indicated. The results show that combination treatment with a cocktail of 161P2F10B MAbs statistically and significantly inhibited the growth of human renal cancer xenograft UG-K3 implanted subcutaneously in SCID mice (P<0.05).

FIG. 20. Combination of 161P2F10B MAbs with Avastin® (bevacizumab). Human renal cancer UG-K3 tumor cells ($2.0 \times 10^6$ cells) were injected subcutaneously into male SCID mice. The mice were randomized into groups (n=10 in each group) and treatment initiated intraperitoneally (i.p.) on Day 0 with treatment MAbs, Avastin® (bevacizumab), or isotype MAb control as indicated. Animals were treated twice weekly for a total of 6 doses until study day 18. Tumor growth was monitored using caliper measurements every 3 to 4 days as indicated. The results show 161P2F10B MAbs H16-1.93 and Ha16-1(3,5)18.1, when combined with Avastin, statistically and significantly inhibited the growth of human renal cancer xenograft UG-K3 implanted subcutaneously in SCID mice (p<0.01).

FIG. 21. Validation of the 161P2F10B Qa siRNA duplex in HepG2 cells. $2 \times 10^5$ cells were plated in 6 well plates in DMEM plus 10% FBS O.N. and subsequently treated with 20 nM of each indicated siRNA duplex (CT1 or 161P2F10B Qa) complexed with 1 μg/ml Lipofectamine 2000 (Invitrogen) for 72 h at 37° C. Then, cells were harvested with 10 mM EDTA and cell surface stained with 1/100 final dilution of PE conjugated anti-161P2F10B, 97A6 MAb from Immunotech Cat#PNIM3575 (open grey and open black profiles) or control IgG (solid grey profile) and analyzed by FACS (21A). In addition, replicate cells were lysed and equal amounts of each cell lysate were analyzed by SDS-PAGE, transferred to PVDF membranes and Western blotted with a mixture of specific 161P2F10B MAbs (H16-1.52, H16-1.68 and H16-1.92) at 1 μg/ml each (top) or anti-actin MAb, Sigma Cat#A5060 (bottom). The data indicate that 161P2F10B antigen levels are down-regulated on the cell surface and as total protein, specifically by the 161P2F10B Qa siRNA duplex in HepG2 cells.

FIG. 22. RNAi silencing of 161P2F10B inhibits cell growth. Cells endogenously expressing the 161P2F10B antigen (HepG2) or not expressing 161P2F10B (UMUC3) were treated with the indicated siRNA duplexes and concentrations. Cells were prepared as stated in FIG. 22 and replated for a standard $^3$H-Thymidine incorporation assay (22A) or a colony growth assay (22B). Briefly, for the $^3$H-Thymidine incorporation assay, 2000 cells were replated in triplicate in DMEM plus 10% FBS, and $^3$H-Thymidine was added for 6 hours after which samples were harvested and incorporation of radioactivity was counted. Data are normalized to control CT1 siRNA treated cells at each oligo concentration. For the colony growth assay, 400 cells were replated in 12 well plates and allowed to grow for 14 days after which colonies were fixed with methanol and stained with crystal violet before the photographs were taken. Expression of 161P2F10B is indicated in the adjacent FACS charts showing expression of 161P2F10B in HepG2 cells (thick black line) by not in UMUC3 (thick black line). These data indicate that silencing 161P2F10B on the cell surface of HepG2 cells, but not on 161P2F10B-deficient UMUC3 cells, inhibits cell growth and proliferation.

FIG. 23. 161P2F10B silencing with RNAi inhibits cell migration and the Rho signal transduction pathway. $2 \times 10^5$ cells were plated in replicate 6-well plates in DMEM plus 10% FBS O.N. and subsequently treated with 10 nM of each indicated siRNA duplex complexed with 1 μg/ml Lipofectamine 2000 for 72 h at 37° C. Cells were harvested with 10 mM EDTA and replated in DMEM containing 0.1% FBS into the top chamber of collagen I pre-coated Boyden migration chambers (8 μm pore size). Ten (10) percent FBS containing DMEM media was used as chemoattractant in the lower chamber. Cells were allowed to migrate for 18 hours, then stained with Calcein AM and photographed at 4× magnification (23A). In parallel, replicate cells were cell surface stained to measure the 161P2F10B silencing level (23B, left panel). Replicate cells were also separately starved in DMEM plus 0.1% FBS O.N. and subsequently stimulated (or not) with 20 ng/ml HGF for 15 mM before whole cell lysates were prepared. Equivalent amounts of each cell lysate were incubated with Rhotekin-agarose beads to "pull down" the GTP-bound Rho proteins (Rho in active conformation) following manufacturer's (Upstate Biotechnology) specifications. Active Rho pull downs or total whole cell lysate (to control protein loading) were analyzed by SDS-PAGE, transferred to PVDF membranes and Western blotted with a specific RhoB antibody. Overall, the data indicate that 161P2F10B cell surface silencing reduces the ability of the cells to migrate, correlating with a significant down regulation in Rho B activation.

FIG. 24. Relative expression and enzymatic activity of 161P2F10b mutants in recombinant Caki kidney cancer cells. Caki kidney cancer cells were infected with retrovirus containing either wildtype 161P2F10B cDNA, or point mutant cDNAs encoding either a threonine to serine mutation (T/S) at amino acid 205, a threonine to alanine mutation (T/A) at amino acid 205, or a aspartic acid to glutamic acid mutation (D/E) at amino acid 80. Stably expressing cell lines were analyzed for 161P2F10B expression by flow cytometry with 97A6 (CD203c) MAb (25A) and for enzymatic activity with p-nTMP substrate (25B). The results show that mutation of threonine 205 to aspartic acid or alanine abolishes the ability to cleave the substrate, demonstrating that threonine 205 is critical to the enzymatic activity of 161P2F10B.

FIG. 25. Over-expression of 161P2F10B suppresses ATP-induced intracellular Ca2+ oscillations in Caki-1 cells. Fura-2-loaded Caki-1 cells overexpressing either wild-type (wt) 161P2F10B, a catalytically inactive mutant (T205A), or only a control neomycin resistance gene (neo), were tested for their intracellular Ca2+ mobilization response over time to the purine ligands ATP, ATPγ-S (non-hydrolysable ATP analog), AMP, and adenosine using single cell fluorescent microscopic imaging. 5,000 cells of each cell line were plated on collagen coated multi-chambered glass slides and allowed to adhere overnight. After mounting the slides in the microscopic imaging system and initiating image acquisition (alternating 340 nm and 38 nM excitation), the reaction was started by adding the indicated compound (arrow) to a final concentration of 100 μM. Shown in each panel are approximately 15-30 340/380 nm fluorescence ratio traces representing individual cells in a microscopic field. The variation between panels in initiation of the Ca2+ response upon ligand addition was due to variations in the time necessary for the ligand to diffuse to the location of the cells within the field. ATP induced Ca2+ oscillatory waves in both Cak1-neo and Caki-1-161P2F10B catalytically inactive mutant cells. However, the response in Caki-1-161P2F10B wt cells was that of an initial Ca2+ flux that gradually decayed over time with minimal oscillatory waves of lower frequency and longer duration. The non-hydrolysable ATP analog ATPγS induced oscillatory Ca2+ waves in all cell lines. Adenosine and AMP did not induce Ca2+ response in any of the lines, suggesting that the ATP-mediated response is due to signaling through P2Y purinergic ATP receptors and not through receptors for adenosine or AMP, potential metabolites of ATP. Taken together these data suggest that it is the removal of ATP in the extracellular medium by 161P2F10B mediated-enzymatic cleavage that causes the suppressive effect. This assay enables the screening of compounds, drugs, antibodies, and proteins that would disrupt the pyrophosphatase/phosphodiesterase activity of 161P2F10B and alter the ATP and other purine nucleotide-mediated Ca2+ responses in 161P2F10B-expressing cells and tissues.

FIG. 26. 161P2F10B ECD induces HUVEC tube formation. Primary human umbilical vein endothelial cells (HUVEC) were seeded in endothelial growth media (EGM) onto 200 μl of semi-solid Matrigel® in the presence of 0.1% FBS alone, 10% FBS alone, 0.1% FBS+161P2F10B ECD (1 ug/ml) or 0.1% FBS+control ECD (1 ug/ml). The cells were allowed to form tube networks for 7 hours and then photographed. The closed tube networks were quantitated in each well. The results indicate that the extracellular domain (ECD) of 161P2F10B induces the formation of tube networks in primary endothelial cells when plated on Matrigel®.

FIG. 27. Requirement of 161P2F10B phosphodiesterase activity for HUVEC tube formation. Primary human umbilical vein endothelial cells (HUVEC) were seeded in endothelial growth media (EGM) onto 200 μl of semi-solid Matrigel® in the presence of 0.1% FBS alone, 10% FBS alone, 0.1% FBS+VEGF (50 ng/ml), 0.1% FBS+wild-type 161P2F10B WT ECD (0.1, 1 or 5 μg/ml), 0.1% FBS+non-catalytic mutant 161P2F10B D80E ECD (DE) (0.1, 1 or 5 μg/ml), or 0.1% FBS+catalytic mutant 161P2F10B T205A ECD (TA) (0.1, 1 or 5 μg/ml). The cells were allowed to form tube networks for 7 hours and then photographed. The closed tube networks were quantitated in each well. The results show that the phosphodiesterase activity of 161P2F10B is critical for the activity of the ECD in inducing the formation of tube networks in primary endothelial cells when plated on Matrigel®. Further, the RGD domain of the 161P2F10B ECD is also partially critical for the formation of tube networks in primary endothelial cells when plated on Matrigel®.

FIG. 28. 161P2F10B MAbs inhibit HUVEC tube formation. Primary human umbilical vein endothelial cells (HUVEC) were seeded in endothelial growth media (EGM) onto 200 μl of semi-solid Matrigel® in the presence of 0.1% FBS alone, 5% FBS alone, or 0.1% FBS+161P2F10B ECD (1 ug/ml) with or without MAbs to 161P2F10B (20 ug/ml). The cells were allowed to form tube networks for 18 hours and then photographed. The closed tube networks were quantitated in each well. Percent inhibition was calculated based on the control wells representing 100% tube formation. The results indicate that MAbs to 161P2F10B inhibit the formation of tube networks in primary endothelial cells when plated on Matrigel®.

FIG. 29. 161P2F10B ECD induces migration of HUVEC. Primary human umbilical vein endothelial cells (HUVEC) were grown in endothelial growth media (EGM) and labeled with the fluorescent dye Calcien AM. The cells were incubated with 0.1% BSA, 10% FBS, 0.1% BSA+VEGF (20 ng/ml), 0.1% BSA+161P2F10B ECD (1, 5 or 10 ug/ml) or 0.1% BSA+control ECD (1, 5 or 10 ug/ml) and then seeded onto the upper insert of Boyden chambers. The cells were allowed to migrate through the chambers for 20 hours and then quantitated using microscopy and MetaMorph software. The results show that the ECD of 161P2F10B induces the migration of endothelial cells in a dose-dependent manner.

FIG. 30. 161P2F10B MAbs inhibit proliferation of SK-RC-01 (renal clear cell) cancer cells. SK-RC-01 cells were incubated with 20 μg/ml MAbs and then grown for 3-5 days in culture with 10% FBS. A 6-hour pulse of $^3$H-Thymidine was added to the cultures and the cells were then processed for incorporation of $^3$H-Thymidine. The level of inhibition indicated was calculated using the control MAb as the maximum total counts incorporated. The results show that the MAbs to 161P2F10B inhibit the proliferation of SK-RC-01 renal clear cell cancer cells (45-76%) relative to control MAb.

FIG. 31. Effect of 161P2F10B MAbs on kidney cancer cell proliferation, survival and apoptosis. RFX-393 renal cancer cells were incubated with 20 ug/ml MAbs as indicated (or 5 ug/ml EGFR MAb M225) and then grown for 6 days in culture with 10% FBS. A 6-hour pulse of $^3$H-Thymidine was added to the cultures and the cells were then processed for incorporation of $^3$H-Thymidine. The level of inhibition indicated was calculated using the control MAb as the maximum total counts incorporated. For the survival assay (MTS), a small amount of the Solution Reagent from the kit was added directly to cell culture wells, followed by incubation for 1-4 hours, then recording absorbance at 490 nm with a 96-well plate reader. The quantity of colored formazan product as measured by the amount of 490 nm absorbance is directly proportional to the mitochondrial activity and/or the number of living cells in culture. The % inhibition was calculated relative to a control MAb. For the apoptosis assay, the same cell lysates prepared for the MTS assay were used in a nucleosome release assay (cell death ELISA). The level of apoptosis is recorded as the % induction relative to control MAb. The more potent MAbs affect all three assays to the highest degrees. The results indicate that the MAbs to 161P2F10B inhibit proliferation of RXF-393 renal cancer clear cells, reduce their cell survival capacity and induce the apoptotic program.

FIG. 32. 161P2F10B MAbs dose-dependently inhibit HUVEC tube formation. Primary human umbilical vein endothelial cells (HUVEC) were seeded in endothelial growth media (EGM) onto 200 µl of semi-solid Matrigel® in the presence of 0.1% FBS alone, 5% FBS alone, or 0.1% FBS+161P2F10B ECD (1 µg/ml) with or without MAbs to 161P2F10B (at the indicated concentrations). The cells were allowed to form tube networks for 18 hours and then photographed. The closed tube networks were quantitated in each well. Percent inhibition was calculated based on the control wells representing 100% tube formation. The results indicate that MAbs to 161P2F10B dose-dependently inhibit the formation of tube networks in primary endothelial cells when plated on Matrigel®.

Figure 33B:
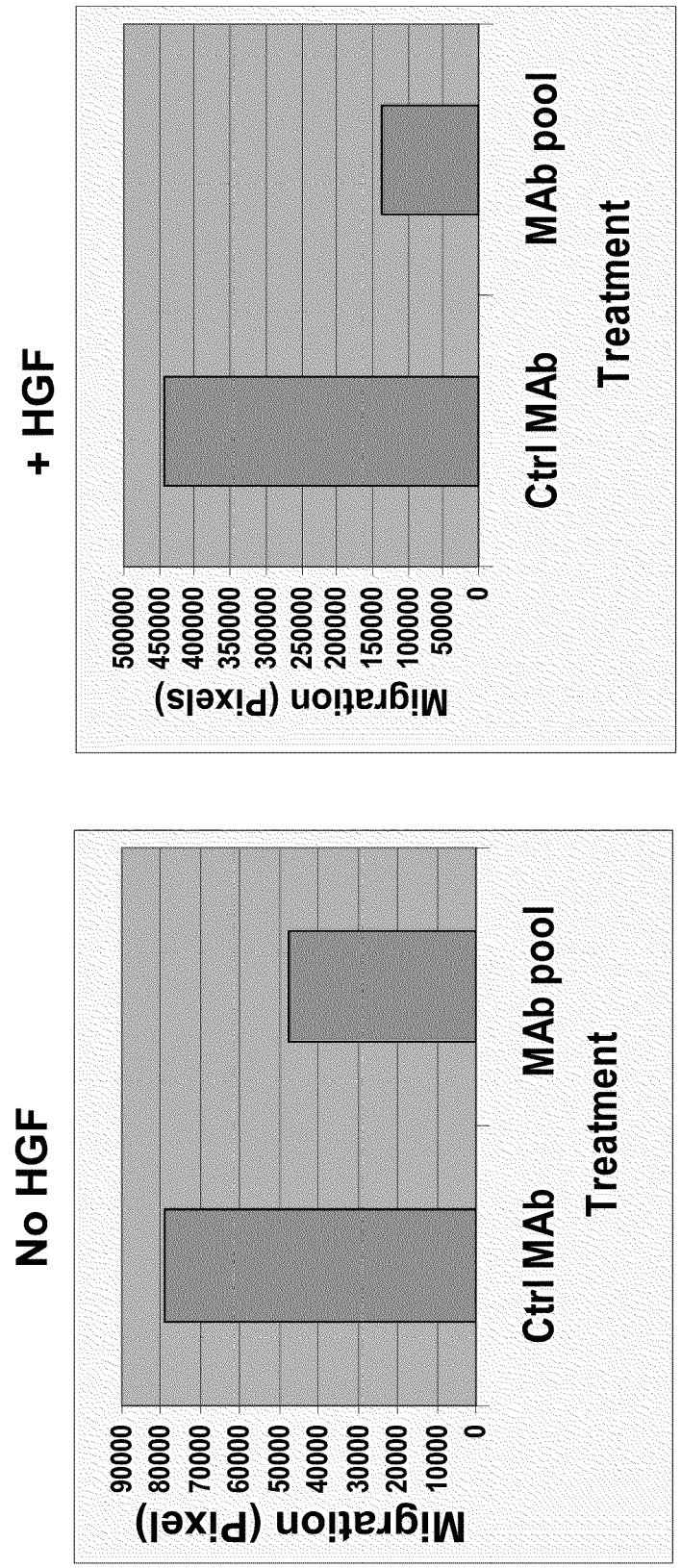

FIG. 33A-B. 161P2F10B MAbs inhibit HepG2 liver cancer cell migration. HepG2 liver cancer cells were grown in 10% FBS, labeled with Calcien AM fluorescent dye, and $2\times10^4$ cells were incubated with either control MAb or a pool of 161P2F10B MAbs (25 µg/ml each) and seeded onto the upper inserts of Boyden chambers in the absence or presence of 8 ng/ml Hepatocyte Growth Factor (HGF). The cells were allowed to migrate through the chambers for 24 hours and were then photographed and quantitated using the MetaMorph software. The results show that MAbs to 161P2F10B inhibit the migration of HepG2 cells, and that treatment of the cells with Hepatocyte Growth Factor potentiates the cell migration which is sensitive to inhibition with MAbs to 161P2F10B.

FIG. 34A-B. 161P2F10B MAbs inhibit A-704 renal clear cell migration. A-704 (renal clear cell) cancer cells were grown in 10% FBS, labeled with Calcein AM fluorescent dye, and $2\times10^4$ cells were incubated with either control MAb or a pool of 161P2F10B MAbs (25 ug/ml each) and seeded onto the upper inserts of Boyden chambers in the absence or presence of 8 ng/ml Hepatocyte Growth Factor (HGF). The cells were allowed to migrate through the chambers for 24 hours and were then photographed and quantitated using the MetaMorph software. The results indicate that MAbs to 161P2F10B inhibit the migration of A-704 cells, and that treatment of the cells with Hepatocyte Growth Factor potentiates the cell migration which is sensitive to inhibition with MAbs to 161P2F10B.

Figure 35B:
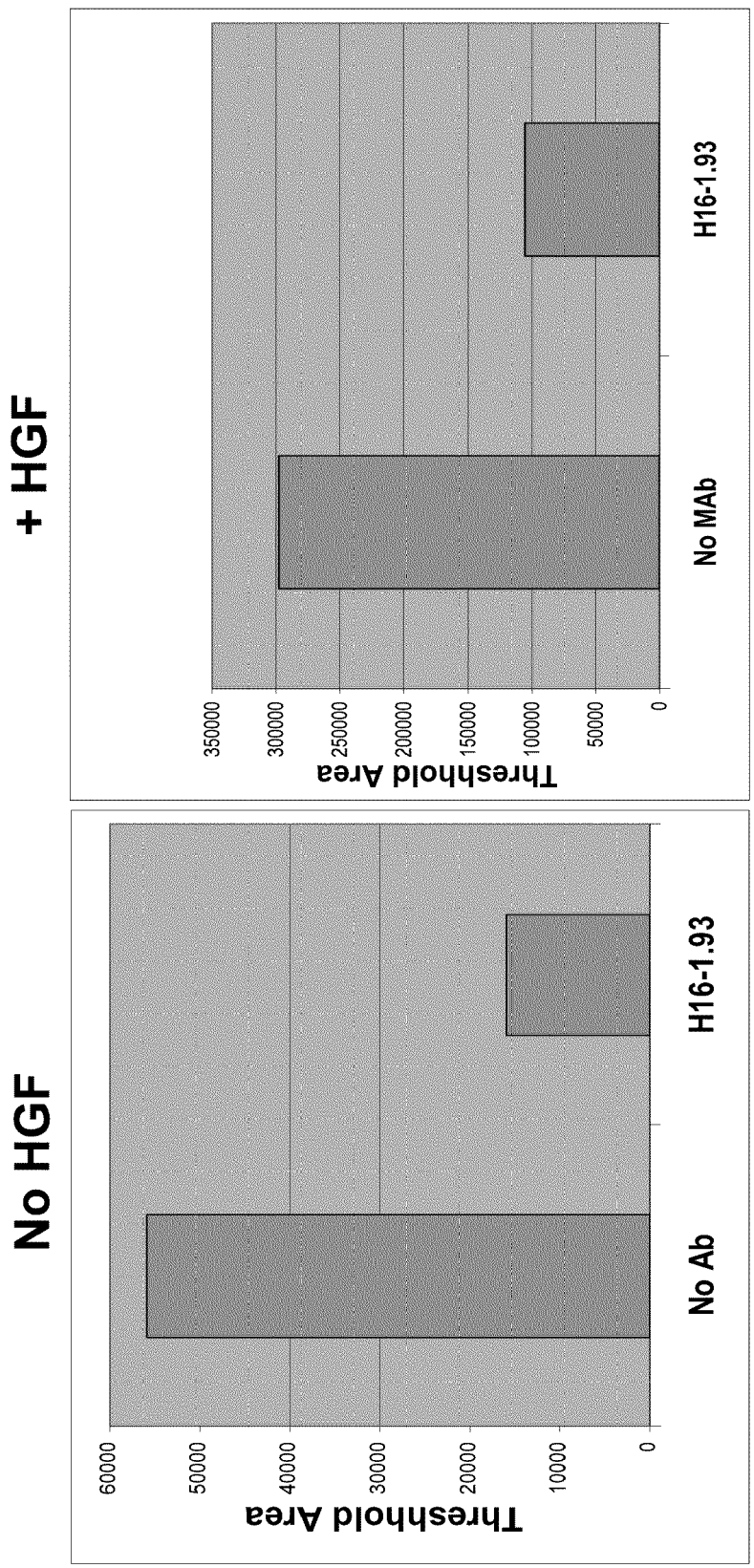

FIG. 35A-B. 161P2F10B MAbs inhibit A-704 renal clear cell invasion. A-704 (renal clear cell) cancer cells were grown in 10% FBS, labeled with Calcein AM fluorescent dye, and $2\times10^4$ cells were incubated with either control MAb or a pool of 161P2F10B MAbs (25 ug/ml each) and seeded onto the upper inserts of Boyden chambers coated with Matrigel® in the absence or presence of 67 ng/ml Hepatocyte Growth Factor (HGF). The cells were allowed to invade through the chambers for 44 hours and were then photographed and quantitated using the MetaMorph software. The results show that HGF stimulates the invasion of A-704 cells, and that the MAbs to 161P2F10B (H16-1.93) inhibits the cell invasion in both the HGF treated cells and the untreated cells. The results demonstrate that MAbs to 161P2F10B inhibit the invasion of A-704 cells through Matrigel®, and that treatment of the cells with Hepatocyte Growth Factor potentiates the cell invasion which is sensitive to inhibition with MAbs to 161P2F10B.

FIG. 36. 161P2F10B dimerization on KU-812 cells. KU-812 cells ($2\times10^5$) were incubated with increasing concentrations of ethylene glycol bis[succinimidylsuccinate] (EGS) in PBS as indicated for 30 minutes at room temperature. The cells were lysed in RIPA buffer (1% NP-40), subjected to 4-12% gradient non-reducing SDS-PAGE, and then Western blotted for 161P2F10B using a 1 ug/ml MAb mixture (H16-1.52, H16-1.68 and H16-1.92). The results indicate that 161P2F10B is dimeric on the cell surface, and that this property may be required for full enzymatic activity and other functional activities of 161P2F10B when expressed on the surface of tumor cells.

FIG. 37. Detection of 161P2F10B protein in cancer patient specimens by IHC. Briefly, frozen tissues were cut into 6 micron sections and mounted on glass slides. The sections were dried for 2 hours at room temperature, fixed for 8 minutes in acetone and subsequently allowed to dry. Sections were then incubated in 161P2F10B antibody, M16-41(3)50, for 3 hours at room temperature. The slides were washed three times in buffer and further incubated with DAKO EnVision+™ peroxidase-conjugated goat anti-mouse immunoglobulin secondary antibody (DAKO Corporation, Carpenteria, Calif.) for 1 hour. The sections were then washed in buffer, developed using a DAB kit (SIGMA Chemicals), counterstained using hematoxylin, and analyzed by bright field microscopy. The results show expression of 161P2F10B in the tumor cells of hepatocellular carcinoma (37A and 37B) as indicated by the brown coloration of the cells. Serial sections with no incubation in M16-41(3)50 had no staining (37C and 37D). These results indicate that 161P2F10B is expressed in human liver cancers and that antibodies directed to this antigen are useful as diagnostic reagents.

Figure 38:
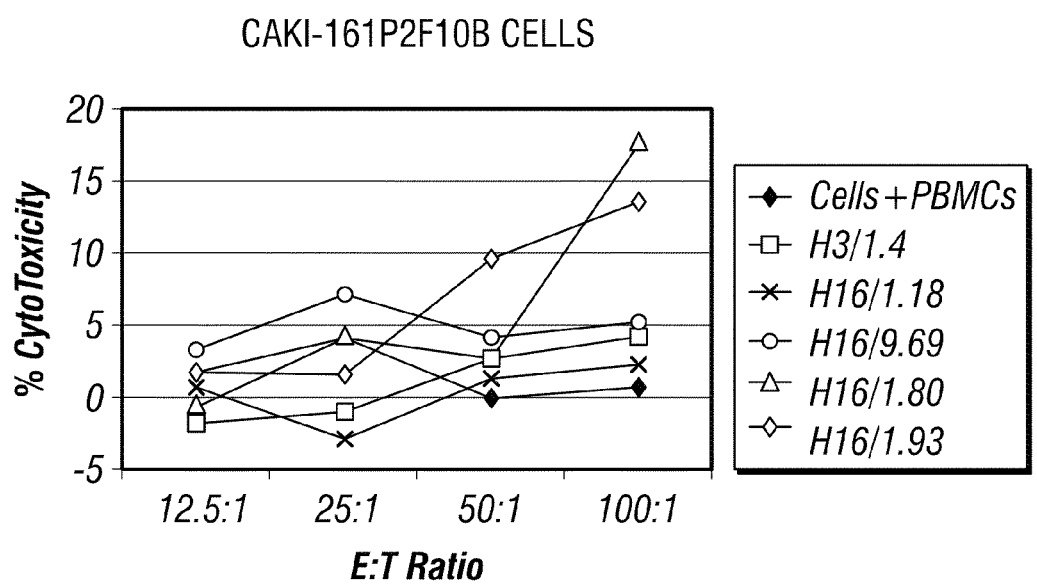

FIG. 38. 161P2F10B Mabs demonstrate that antibody dependent cell killing increases when the effector to target cell ratio is increased.

DETAILED DESCRIPTION OF THE INVENTION

Outline of Sections

I.) Definitions
II.) 161P2F10B Polynucleotides
    II.A.) Uses of 161P2F10B Polynucleotides
        II.A.1.) Monitoring of Genetic Abnormalities
        II.A.2.) Antisense Embodiments
        II.A.3.) Primers and Primer Pairs
        II.A.4.) Isolation of 161P2F10B-Encoding Nucleic Acid Molecules
        II.A.5.) Recombinant Nucleic Acid Molecules and Host-Vector Systems III.) 161P2F10B-related Proteins
  III.A.) Motif-bearing Protein Embodiments
  III.B.) Expression of 161P2F10B-related Proteins
  III.C.) Modifications of 161P2F10B-related Proteins
  III.D.) Uses of 161P2F10B-related Proteins
IV.) 161P2F10B Antibodies
V.) 161P2F10B Cellular Immune Responses
VI.) 161P2F10B Transgenic Animals
VII.) Methods for the Detection of 161P2F10B
VIII.) Methods for Monitoring the Status of 161P2F10B-related Genes and Their Products
IX.) Identification of Molecules That Interact With 161P2F10B
X.) Therapeutic Methods and Compositions
  X.A.) Anti-Cancer Vaccines
  X.B.) 161P2F10B as a Target for Antibody-Based Therapy
  X.C.) 161P2F10B as a Target for Cellular Immune Responses
    X.C.1. Minigene Vaccines
    X.C.2. Combinations of CTL Peptides with Helper Peptides
    X.C.3. Combinations of CTL Peptides with T Cell Priming Agents
    X.C.4. Vaccine Compositions Comprising DC Pulsed with CTL and/or HTL Peptides
  X.D.) Adoptive Immunotherapy
  X.E.) Administration of Vaccines for Therapeutic or Prophylactic Purposes
XI.) Diagnostic and Prognostic Embodiments of 161P2F10B.
XII.) Inhibition of 161P2F10B Protein Function
  XII.A.) Inhibition of 161P2F10B With Intracellular Antibodies
  XII.B.) Inhibition of 161P2F10B with Recombinant Proteins
  XII.C.) Inhibition of 161P2F10B Transcription or Translation
  XII.D.) General Considerations for Therapeutic Strategies
XIII.) Identification, Characterization and Use of Modulators of 161P2F10B
XIV.) RNAi and Therapeutic use of small interfering RNA (siRNAs)
XV.) KITS/Articles of Manufacture

I.) DEFINITIONS

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

The terms "advanced cancer", "locally advanced cancer", "advanced disease" and "locally advanced disease" mean cancers that have extended through the relevant tissue capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease, and these patients have substantially less favorable outcomes compared to patients having clinically localized (organ-confined) cancer.

"Altering the native glycosylation pattern" is intended for purposes herein to mean deleting one or more carbohydrate moieties found in native sequence 161P2F10B (either by removing the underlying glycosylation site or by deleting the glycosylation by chemical and/or enzymatic means), and/or adding one or more glycosylation sites that are not present in the native sequence 161P2F10B. In addition, the phrase includes qualitative changes in the glycosylation of the native proteins, involving a change in the nature and proportions of the various carbohydrate moieties present.

The term "analog" refers to a molecule which is structurally similar or shares similar or corresponding attributes with another molecule (e.g. a 161P2F10B-related protein). For example, an analog of a 161P2F10B protein can be specifically bound by an antibody or T cell that specifically binds to 161P2F10B.

The term "antibody" is used in the broadest sense unless clearly indicated otherwise. Therefore, an "antibody" can be naturally occurring or man-made such as monoclonal antibodies produced by conventional hybridoma technology. Anti-161P2F10B antibodies comprise monoclonal and polyclonal antibodies as well as fragments containing the antigen-binding domain and/or one or more complementarity determining regions of these antibodies. As used herein, the term "antibody" refers to any form of antibody or fragment thereof that specifically binds 161P2F10B and/or exhibits the desired biological activity and specifically covers monoclonal antibodies (including full length monoclonal antibodies), polyclonal antibodies, multispecific antibodies (e.g., bispecific antibodies), and antibody fragments so long as they specifically bind 161P2F10B and/or exhibit the desired biological activity. Any specific antibody can be used in the methods and compositions provided herein. Thus, in one embodiment the term "antibody" encompasses a molecule comprising at least one variable region from a light chain immunoglobulin molecule and at least one variable region from a heavy chain molecule that in combination form a specific binding site for the target antigen. In one embodiment, the antibody is an IgG antibody. For example, the antibody is a IgG1, IgG2, IgG3, or IgG4 antibody. The antibodies useful in the present methods and compositions can be generated in cell culture, in phage, or in various animals, including but not limited to cows, rabbits, goats, mice, rats, hamsters, guinea pigs, sheep, dogs, cats, monkeys, chimpanzees, apes. Therefore, in one embodiment, an antibody of the present invention is a mammalian antibody. Phage techniques can be used to isolate an initial antibody or to generate variants with altered specificity or avidity characteristics. Such techniques are routine and well known in the art. In one embodiment, the antibody is produced by recombinant means known in the art. For example, a recombinant antibody can be produced by transfecting a host cell with a vector comprising a DNA sequence encoding the antibody. One or more vectors can be used to transfect the DNA sequence expressing at least one VL and one VH region in the host cell. Exemplary descriptions of recombinant means of antibody generation and production include Delves, ANTIBODY PRODUCTION: ESSENTIAL TECHNIQUES (Wiley, 1997); Shephard, et al., MONOCLONAL ANTI- BODIES (Oxford University Press, 2000); Goding, MONOCLONAL ANTIBODIES: PRINCIPLES AND PRACTICE (Academic Press, 1993); CURRENT PROTOCOLS IN IMMUNOLOGY (John Wiley & Sons, most recent edition). An antibody of the present invention can be modified by recombinant means to increase greater efficacy of the antibody in mediating the desired function. Thus, it is within the scope of the invention that antibodies can be modified by substitutions using recombinant means. Typically, the substitutions will be conservative substitutions. For example, at least one amino acid in the constant region of the antibody can be replaced with a different residue. See, e.g., U.S. Pat. No. 5,624,821, U.S. Pat. No. 6,194,551, Application No. WO 9958572; and Angal, et al., Mol. Immunol. 30: 105-08 (1993). The modification in amino acids includes deletions, additions, substitutions of amino acids. In some cases, such changes are made to reduce undesired activities, e.g., complement-dependent cytotoxicity. Frequently, the antibodies are labeled by joining, either covalently or non-covalently, a substance which provides for a detectable signal. A wide variety of labels and conjugation techniques are known and are reported extensively in both the scientific and patent literature. These antibodies can be screened for binding to normal or defective 161P2F10B. See e.g., ANTIBODY ENGINEERING: A PRACTICAL APPROACH (Oxford University Press, 1996). Suitable antibodies with the desired biologic activities can be identified the following in vitro assays including but not limited to: proliferation, migration, adhesion, soft agar growth, angiogenesis, cell-cell communication, apoptosis, transport, signal transduction, and the following in vivo assays such as the inhibition of tumor growth. The antibodies provided herein can also be useful in diagnostic applications. As capture or non-neutralizing antibodies, they can be screened for the ability to bind to the specific antigen without inhibiting the receptor-binding or biological activity of the antigen. As neutralizing antibodies, the antibodies can be useful in competitive binding assays. They can also be used to quantify the 161P2F10B or its receptor.

An "antibody fragment" is defined as at least a portion of the variable region of the immunoglobulin molecule that binds to its target, i.e., the antigen-binding region. In one embodiment it specifically covers single anti-161P2F10B antibodies and clones thereof (including agonist, antagonist and neutralizing antibodies) and anti-161P2F10B antibody compositions with polyepitopic specificity. The antibody of the present methods and compositions can be monoclonal or polyclonal. An antibody can be in the form of an antigen binding antibody fragment including a Fab fragment, $F(ab')_2$ fragment, a single chain variable region, and the like. Fragments of intact molecules can be generated using methods well known in the art and include enzymatic digestion and recombinant means.

As used herein, any form of the "antigen" can be used to generate an antibody that is specific for 161P2F10B. Thus, the eliciting antigen may be a single epitope, multiple epitopes, or the entire protein alone or in combination with one or more immunogenicity enhancing agents known in the art. The eliciting antigen may be an isolated full-length protein, a cell surface protein (e.g., immunizing with cells transfected with at least a portion of the antigen), or a soluble protein (e.g., immunizing with only the extracellular domain portion of the protein). The antigen may be produced in a genetically modified cell. The DNA encoding the antigen may genomic or non-genomic (e.g., cDNA) and encodes at least a portion of the extracellular domain. As used herein, the term "portion" refers to the minimal number of amino acids or nucleic acids, as appropriate, to constitute an immunogenic epitope of the antigen of interest. Any genetic vectors suitable for transformation of the cells of interest may be employed, including but not limited to adenoviral vectors, plasmids, and non-viral vectors, such as cationic lipids. In one embodiment, the antibody of the methods and compositions herein specifically bind at least a portion of the extracellular domain of the 161P2F10B of interest.

The antibodies or antigen binding fragments thereof provided herein may be conjugated to a "bioactive agent." As used herein, the term "bioactive agent" refers to any synthetic or naturally occurring compound that binds the antigen and/or enhances or mediates a desired biological effect to enhance cell-killing toxins.

In one embodiment, the binding fragments useful in the present invention are biologically active fragments. As used herein, the term "biologically active" refers to an antibody or antibody fragment that is capable of binding the desired the antigenic epitope and directly or indirectly exerting a biologic effect. Direct effects include, but are not limited to the modulation, stimulation, and/or inhibition of a growth signal, the modulation, stimulation, and/or inhibition of an anti-apoptotic signal, the modulation, stimulation, and/or inhibition of an apoptotic or necrotic signal, modulation, stimulation, and/ or inhibition the ADCC cascade, and modulation, stimulation, and/or inhibition the CDC cascade.

"Bispecific" antibodies are also useful in the present methods and compositions. As used herein, the term "bispecific antibody" refers to an antibody, typically a monoclonal antibody, having binding specificities for at least two different antigenic epitopes. In one embodiment, the epitopes are from the same antigen. In another embodiment, the epitopes are from two different antigens. Methods for making bispecific antibodies are known in the art. For example, bispecific antibodies can be produced recombinantly using the co-expression of two immunoglobulin heavy chain/light chain pairs. See, e.g., Milstein et al., Nature 305:537-39 (1983). Alternatively, bispecific antibodies can be prepared using chemical linkage. See, e.g., Brennan, et al., Science 229:81 (1985). Bispecific antibodies include bispecific antibody fragments. See, e.g., Hollinger, et al., Proc. Natl. Acad. Sci. U.S.A. 90:6444-48 (1993), Gruber, et al., J. Immunol. 152:5368 (1994).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they specifically bind the target antigen and/or exhibit the desired biological activity (U.S. Pat. No. 4,816,567; and Morrison et al., Proc. Natl. Acad. Sci. USA 81: 6851-6855 (1984)).

The term "Chemotherapeutic Agent" refers to all chemical compounds that are effective in inhibiting tumor growth. Non-limiting examples of chemotherapeutic agents include alkylating agents; for example, nitrogen mustards, ethyleneimine compounds and alkyl sulphonates; antimetabolites; for example, folic acid, purine or pyrimidine antagonists; mitotic inhibitors; for example, vinca alkaloids and derivatives of podophyllotoxin, cytotoxic antibiotics, compounds that damage or interfere with DNA expression, and growth factor receptor antagonists. In addition, chemotherapeutic agents include cytotoxic agents (as defined herein), antibodies, biological molecules and small molecules.

The term "codon optimized sequences" refers to nucleotide sequences that have been optimized for a particular host species by replacing any codons having a usage frequency of less than about 20%. Nucleotide sequences that have been optimized for expression in a given host species by elimination of spurious polyadenylation sequences, elimination of exon/intron splicing signals, elimination of transposon-like repeats and/or optimization of GC content in addition to codon optimization are referred to herein as an "expression enhanced sequences."

A "combinatorial library" is a collection of diverse chemical compounds generated by either chemical synthesis or biological synthesis by combining a number of chemical "building blocks" such as reagents. For example, a linear combinatorial chemical library, such as a polypeptide (e.g., mutein) library, is formed by combining a set of chemical building blocks called amino acids in every possible way for a given compound length (i.e., the number of amino acids in a polypeptide compound). Numerous chemical compounds are synthesized through such combinatorial mixing of chemical building blocks (Gallop et al., J. Med. Chem. 37(9): 1233-1251 (1994)).

Preparation and screening of combinatorial libraries is well known to those of skill in the art. Such combinatorial chemical libraries include, but are not limited to, peptide libraries (see, e.g., U.S. Pat. No. 5,010,175, Furka, Pept. Prot. Res. 37:487-493 (1991), Houghton et al., Nature, 354:84-88 (1991)), peptoids (PCT Publication No WO 91/19735), encoded peptides (PCT Publication WO 93/20242), random bio-oligomers (PCT Publication WO 92/00091), benzodiazepines (U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with a Beta-D-Glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbarnates (Cho, et al., Science 261: 1303 (1993)), and/or peptidyl phosphonates (Campbell et al., J. Org. Chem. 59:658 (1994)). See, generally, Gordon et al., J. Med. Chem. 37:1385 (1994), nucleic acid libraries (see, e.g., Stratagene, Corp.), peptide nucleic acid libraries (see, e.g., U.S. Pat. No. 5,539,083), antibody libraries (see, e.g., Vaughn et al., Nature Biotechnology 14(3): 309-314 (1996), and PCT/US96/10287), carbohydrate libraries (see, e.g., Liang et al., Science 274:1520-1522 (1996), and U.S. Pat. No. 5,593,853), and small organic molecule libraries (see, e.g., benzodiazepines, Baum, C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514; and the like).

Devices for the preparation of combinatorial libraries are commercially available (see, e.g., 357 NIPS, 390 NIPS, Advanced Chem Tech, Louisville Ky.; Symphony, Rainin, Woburn, Mass.; 433A, Applied Biosystems, Foster City, Calif.; 9050, Plus, Millipore, Bedford, NIA). A number of well-known robotic systems have also been developed for solution phase chemistries. These systems include automated workstations such as the automated synthesis apparatus developed by Takeda Chemical Industries, LTD. (Osaka, Japan) and many robotic systems utilizing robotic arms (Zymate H, Zymark Corporation, Hopkinton, Mass.; Orca, Hewlett-Packard, Palo Alto, Calif.), which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J.; Asinex, Moscow, RU; Tripos, Inc., St. Louis, Mo.; ChemStar, Ltd, Moscow, RU; 3D Pharmaceuticals, Exton, Pa.; Martek Biosciences, Columbia, Md.; etc.).

As used herein, the term "conservative substitution" refers to substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson, et al., MOLECULAR BIOLOGY OF THE GENE, The Benjamin/Cummings Pub. Co., p. 224 (4th Edition 1987)). Such exemplary substitutions are preferably made in accordance with those set forth in Table(s) III(a-b). For example, such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments (see, e.g. Table III(a) herein; pages 13-15 "Biochemistry" 2nd ED. Lubert Stryer ed (Stanford University); Henikoff et al., PNAS 1992 Vol 89 10915-10919; Lei et al., J Biol Chem 1995 May 19; 270(20):11882-6). Other substitutions are also permissible and may be determined empirically or in accord with known conservative substitutions.

The term "cytotoxic agent" refers to a substance that inhibits or prevents the expression activity of cells, function of cells and/or causes destruction of cells. The term is intended to include radioactive isotopes, chemotherapeutic agents, and toxins such as small molecule toxins or enzymatically active toxins of bacterial, fungal, plant or animal origin, including fragments and/or variants thereof. Examples of cytotoxic agents include, but are not limited to auristatins, auristatin e, auromycins, maytansinoids, yttrium, bismuth, ricin, ricin A-chain, combrestatin, duocarmycins, dolostatins, doxorubicin, daunorubicin, taxol, cisplatin, cc1065, ethidium bromide, mitomycin, etoposide, tenoposide, vincristine, vinblastine, colchicine, dihydroxy anthracin dione, actinomycin, diphtheria toxin, *Pseudomonas* exotoxin (PE) A, PE40, abrin, abrin A chain, modeccin A chain, alpha-sarcin, gelonin, mitogellin, retstrictocin, phenomycin, enomycin, curicin, crotin, calicheamicin, Sapaonaria officinalis inhibitor, and glucocorticoid and other chemotherapeutic agents, as well as radioisotopes such as $At^{211}$, $I^{131}$, $I^{125}$, $Y^{90}$, $Re^{186}$, $Re^{188}$, $Sm^{153}$, $Bi^{212}$ or $^{213}$, $P^{32}$ and radioactive isotopes of Lu including $Lu^{177}$. Antibodies may also be conjugated to an anti-cancer pro-drug activating enzyme capable of converting the pro-drug to its active form.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Hollinger et al., Proc. Natl. Acad. Sci. USA 90:6444-48 (1993).

The "gene product" is used herein to indicate a peptide/protein or mRNA. For example, a "gene product of the invention" is sometimes referred to herein as a "cancer amino acid sequence", "cancer protein", "protein of a cancer listed in Table I", a "cancer mRNA", "mRNA of a cancer listed in Table I", etc. In one embodiment, the cancer protein is encoded by a nucleic acid of FIG. 1. The cancer protein can be a fragment, or alternatively, be the full-length protein encoded by nucleic acids of FIG. 1. In one embodiment, a cancer amino acid sequence is used to determine sequence identity or similarity. In another embodiment, the sequences are naturally occurring allelic variants of a protein encoded by a nucleic acid of FIG. 1. In another embodiment, the sequences are sequence variants as further described herein.

"Heteroconjugate" antibodies are useful in the present methods and compositions. As used herein, the term "heteroconjugate antibody" refers to two covalently joined antibodies. Such antibodies can be prepared using known methods in synthetic protein chemistry, including using crosslinking agents. See, e.g., U.S. Pat. No. 4,676,980.

"High throughput screening" assays for the presence, absence, quantification, or other properties of particular nucleic acids or protein products are well known to those of skill in the art. Similarly, binding assays and reporter gene assays are similarly well known. Thus, e.g., U.S. Pat. No. 5,559,410 discloses high throughput screening methods for proteins; U.S. Pat. No. 5,585,639 discloses high throughput screening methods for nucleic acid binding (i.e., in arrays); while U.S. Pat. Nos. 5,576,220 and 5,541,061 disclose high throughput methods of screening for ligand/antibody binding.

In addition, high throughput screening systems are commercially available (see, e.g., Amersham Biosciences, Piscataway, N.J.; Zymark Corp., Hopkinton, Mass.; Air Technical Industries, Mentor, Ohio; Beckman Instruments, Inc. Fullerton, Calif.; Precision Systems, Inc., Natick, Mass.; etc.). These systems typically automate entire procedures, including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, e.g., Zymark Corp. provides technical bulletins describing screening systems for detecting the modulation of gene transcription, ligand binding, and the like.

The term "homolog" refers to a molecule which exhibits homology to another molecule, by for example, having sequences of chemical residues that are the same or similar at corresponding positions.

In one embodiment, the antibody provided herein is a "human antibody." As used herein, the term "human antibody" refers to an antibody in which essentially the entire sequences of the light chain and heavy chain sequences, including the complementary determining regions (CDRs), are from human genes. In one embodiment, human monoclonal antibodies are prepared by the trioma technique, the human B-cell technique (see, e.g., Kozbor, et al., Immunol. Today 4: 72 (1983), EBV transformation technique (see, e.g., Cole et al. MONOCLONAL ANTIBODIES AND CANCER THERAPY 77-96 (1985)), or using phage display (see, e.g., Marks et al., J. Mol. Biol. 222:581 (1991)). In a specific embodiment, the human antibody is generated in a transgenic mouse. Techniques for making such partially to fully human antibodies are known in the art and any such techniques can be used. According to one particularly preferred embodiment, fully human antibody sequences are made in a transgenic mouse engineered to express human heavy and light chain antibody genes. An exemplary description of preparing transgenic mice that produce human antibodies found in Application No. WO 02/43478 and U.S. Pat. No. 6,657,103 (Abgenix) and its progeny. B cells from transgenic mice that produce the desired antibody can then be fused to make hybridoma cell lines for continuous production of the antibody. See, e.g., U.S. Pat. Nos. 5,569,825; 5,625,126; 5,633,425; 5,661,016; and 5,545,806; and Jakobovits, Adv. Drug Del. Rev. 31:33-42 (1998); Green, et al., J. Exp. Med. 188: 483-95 (1998).

"Human Leukocyte Antigen" or "HLA" is a human class I or class II Major Histocompatibility Complex (MHC) protein (see, e.g., Stites, et al., IMMUNOLOGY, 8TH ED., Lange Publishing, Los Altos, Calif. (1994).

As used herein, the term "humanized antibody" refers to forms of antibodies that contain sequences from non-human (e.g., murine) antibodies as well as human antibodies. Such antibodies are chimeric antibodies which contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. See e.g., Cabilly U.S. Pat. No. 4,816,567; Queen et al. (1989) Proc. Nat'l Acad. Sci. USA 86:10029-10033; and ANTIBODY ENGINEERING: A PRACTICAL APPROACH (Oxford University Press 1996).

The terms "hybridize", "hybridizing", "hybridizes" and the like, used in the context of polynucleotides, are meant to refer to conventional hybridization conditions, preferably such as hybridization in 50% formamide/6×SSC/0.1% SDS/100 μg/ml ssDNA, in which temperatures for hybridization are above 37 degrees C. and temperatures for washing in 0.1×SSC/0.1% SDS are above 55 degrees C.

The phrases "isolated" or "biologically pure" refer to material which is substantially or essentially free from components which normally accompany the material as it is found in its native state. Thus, isolated peptides in accordance with the invention preferably do not contain materials normally associated with the peptides in their in situ environment. For example, a polynucleotide is said to be "isolated" when it is substantially separated from contaminant polynucleotides that correspond or are complementary to genes other than the 161P2F10B genes or that encode polypeptides other than 161P2F10B gene product or fragments thereof. A skilled artisan can readily employ nucleic acid isolation procedures to obtain an isolated 161P2F10B polynucleotide. A protein is said to be "isolated," for example, when physical, mechanical or chemical methods are employed to remove the 161P2F10B proteins from cellular constituents that are normally associated with the protein. A skilled artisan can readily employ standard purification methods to obtain an isolated 161P2F10B protein. Alternatively, an isolated protein can be prepared by chemical means.

Suitable "labels" include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. In addition, the antibodies provided herein can be useful as the antigen-binding component of fluorobodies. See e.g., Zeytun et al., Nat. Biotechnol. 21:1473-79 (2003).

The term "mammal" refers to any organism classified as a mammal, including mice, rats, rabbits, dogs, cats, cows, horses and humans. In one embodiment of the invention, the mammal is a mouse. In another embodiment of the invention, the mammal is a human.

The terms "metastatic cancer" and "metastatic disease" mean cancers that have spread to regional lymph nodes or to distant sites, and are meant to include stage D disease under the AUA system and stage T×N×M+under the TNM system.

The term "modulator" or "test compound" or "drug candidate" or grammatical equivalents as used herein describe any molecule, e.g., protein, oligopeptide, small organic molecule, polysaccharide, polynucleotide, etc., to be tested for the capacity to directly or indirectly alter the cancer phenotype or the expression of a cancer sequence, e.g., a nucleic acid or protein sequences, or effects of cancer sequences (e.g., signaling, gene expression, protein interaction, etc.) In one aspect, a modulator will neutralize the effect of a cancer protein of the invention. By "neutralize" is meant that an activity of a protein is inhibited or blocked, along with the consequent effect on the cell. In another aspect, a modulator will neutralize the effect of a gene, and its corresponding protein, of the invention by normalizing levels of said protein. In preferred embodiments, modulators alter expression profiles, or expression profile nucleic acids or proteins provided herein, or downstream effector pathways. In one embodiment, the modulator suppresses a cancer phenotype, e.g. to a normal tissue fingerprint. In another embodiment, a modulator induced a cancer phenotype. Generally, a plurality of assay mixtures is run in parallel with different agent concentrations to obtain a differential response to the various concentrations. Typically, one of these concentrations serves as a negative control, i.e., at zero concentration or below the level of detection.

Modulators, drug candidates or test compounds encompass numerous chemical classes, though typically they are organic molecules, preferably small organic compounds having a molecular weight of more than 100 and less than about 2,500 Daltons. Preferred small molecules are less than 2000, or less than 1500 or less than 1000 or less than 500 D. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Modulators also comprise biomolecules such as peptides, saccharides, fatty acids, steroids, purines, pyrimidines, derivatives, structural analogs or combinations thereof. Particularly preferred are peptides. One class of modulators are peptides, for example of from about five to about 35 amino acids, with from about five to about 20 amino acids being preferred, and from about 7 to about 15 being particularly preferred. Preferably, the cancer modulatory protein is soluble, includes a non-transmembrane region, and/or, has an N-terminal Cys to aid in solubility. In one embodiment, the C-terminus of the fragment is kept as a free acid and the N-terminus is a free amine to aid in coupling, i.e., to cysteine. In one embodiment, a cancer protein of the invention is conjugated to an immunogenic agent as discussed herein. In one embodiment, the cancer protein is conjugated to BSA. The peptides of the invention, e.g., of preferred lengths, can be linked to each other or to other amino acids to create a longer peptide/protein. The modulatory peptides can be digests of naturally occurring proteins as is outlined above, random peptides, or "biased" random peptides. In a preferred embodiment, peptide/protein-based modulators are antibodies, and fragments thereof, as defined herein.

Modulators of cancer can also be nucleic acids. Nucleic acid modulating agents can be naturally occurring nucleic acids, random nucleic acids, or "biased" random nucleic acids. For example, digests of prokaryotic or eukaryotic genomes can be used in an approach analogous to that outlined above for proteins.

The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. In one embodiment, the polyclonal antibody contains a plurality of monoclonal antibodies with different epitope specificities, affinities, or avidities within a single antigen that contains multiple antigenic epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256: 495 (1975), or may be made by recombinant DNA methods (see, e.g., U.S. Pat. No. 4,816,567). The "monoclonal antibodies" may also be isolated from phage antibody libraries using the techniques described in Clackson et al., Nature 352: 624-628 (1991) and Marks et al., J. Mol. Biol. 222: 581-597 (1991), for example. These monoclonal antibodies will usually bind with at least a Kd of about 1 µM, more usually at least about 300 nM, typically at least about 30 nM, preferably at least about 10 nM, more preferably at least about 3 nM or better, usually determined by ELISA.

A "motif", as in biological motif of a 161P2F10B-related protein, refers to any pattern of amino acids forming part of the primary sequence of a protein, that is associated with a particular function (e.g. protein-protein interaction, protein-DNA interaction, etc) or modification (e.g. that is phosphorylated, glycosylated or amidated), or localization (e.g. secretory sequence, nuclear localization sequence, etc.) or a sequence that is correlated with being immunogenic, either humorally or cellularly. A motif can be either contiguous or capable of being aligned to certain positions that are generally correlated with a certain function or property. In the context of HLA motifs, "motif" refers to the pattern of residues in a peptide of defined length, usually a peptide of from about 8 to about 13 amino acids for a class I HLA motif and from about 6 to about 25 amino acids for a class II HLA motif, which is recognized by a particular HLA molecule. Peptide motifs for HLA binding are typically different for each protein encoded by each human HLA allele and differ in the pattern of the primary and secondary anchor residues. Frequently occurring motifs are set forth in Table V.

A "pharmaceutical excipient" comprises a material such as an adjuvant, a carrier, pH-adjusting and buffering agents, tonicity adjusting agents, wetting agents, preservative, and the like.

"Pharmaceutically acceptable" refers to a non-toxic, inert, and/or composition that is physiologically compatible with humans or other mammals.

The term "polynucleotide" means a polymeric form of nucleotides of at least 10 bases or base pairs in length, either ribonucleotides or deoxynucleotides or a modified form of either type of nucleotide, and is meant to include single and double stranded forms of DNA and/or RNA. In the art, this term if often used interchangeably with "oligonucleotide". A polynucleotide can comprise a nucleotide sequence disclosed herein wherein thymidine (T), as shown for example in FIG. 1, can also be uracil (U); this definition pertains to the differences between the chemical structures of DNA and RNA, in particular the observation that one of the four major bases in RNA is uracil (U) instead of thymidine (T).

The term "polypeptide" means a polymer of at least about 4, 5, 6, 7, or 8 amino acids. Throughout the specification, standard three letter or single letter designations for amino acids are used. In the art, this term is often used interchangeably with "peptide" or "protein".

An HLA "primary anchor residue" is an amino acid at a specific position along a peptide sequence which is understood to provide a contact point between the immunogenic peptide and the HLA molecule. One to three, usually two, primary anchor residues within a peptide of defined length generally defines a "motif" for an immunogenic peptide. These residues are understood to fit in close contact with peptide binding groove of an HLA molecule, with their side chains buried in specific pockets of the binding groove. In one embodiment, for example, the primary anchor residues for an HLA class I molecule are located at position 2 (from the amino terminal position) and at the carboxyl terminal position of a 8, 9, 10, 11, or 12 residue peptide epitope in accordance with the invention. Alternatively, in another embodiment, the primary anchor residues of a peptide binds an HLA class II molecule are spaced relative to each other, rather than to the termini of a peptide, where the peptide is generally of at least 9 amino acids in length. The primary anchor positions for each motif and supermotif are set forth in Table IV(a). For example, analog peptides can be created by altering the presence or absence of particular residues in the primary and/or secondary anchor positions shown in Table IV. Such analogs are used to modulate the binding affinity and/or population coverage of a peptide comprising a particular HLA motif or supermotif.

"Radioisotopes" include, but are not limited to the following (non-limiting exemplary uses are also set forth in Table IV(I)).

By "randomized" or grammatical equivalents as herein applied to nucleic acids and proteins is meant that each nucleic acid and peptide consists of essentially random nucleotides and amino acids, respectively. These random peptides (or nucleic acids, discussed herein) can incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, a library is "fully randomized," with no sequence preferences or constants at any position. In another embodiment, the library is a "biased random" library. That is, some positions within the sequence either are held constant, or are selected from a limited number of possibilities. For example, the nucleotides or amino acid residues are randomized within a defined class, e.g., of hydrophobic amino acids, hydrophilic residues, sterically biased (either small or large) residues, towards the creation of nucleic acid binding domains, the creation of cysteines, for cross-linking, prolines for SH-3 domains, serines, threonines, tyrosines or histidines for phosphorylation sites, etc., or to purines, etc.

A "recombinant" DNA or RNA molecule is a DNA or RNA molecule that has been subjected to molecular manipulation in vitro.

As used herein, the term "single-chain Fv" or "scFv" or "single chain" antibody refers to antibody fragments comprising the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv, see Pluckthun, THE PHARMACOLOGY OF MONOCLONAL ANTIBODIES, vol. 113, Rosenburg and Moore eds. Springer-Verlag, New York, pp. 269-315 (1994).

Non-limiting examples of "small molecules" include compounds that bind or interact with 161P2F10B, ligands including hormones, neuropeptides, chemokines, odorants, phospholipids, and functional equivalents thereof that bind and preferably inhibit 161P2F10B protein function. Such non-limiting small molecules preferably have a molecular weight of less than about 10 kDa, more preferably below about 9, about 8, about 7, about 6, about 5 or about 4 kDa. In certain embodiments, small molecules physically associate with, or bind, 161P2F10B protein; are not found in naturally occurring metabolic pathways; and/or are more soluble in aqueous than non-aqueous solutions.

As used herein, the term "specific" refers to the selective binding of the antibody to the target antigen epitope. Antibodies can be tested for specificity of binding by comparing binding to appropriate antigen to binding to irrelevant antigen or antigen mixture under a given set of conditions. If the antibody binds to the appropriate antigen at least 2, 5, 7, and preferably 10 times more than to irrelevant antigen or antigen mixture then it is considered to be specific. In one embodiment, a specific antibody is one that only binds the 161P2F10B antigen, but does not bind to the irrelevent antigen. In another embodiment, a specific antibody is one that binds human 161P2F10B antigen but does not bind a non-human 161P2F10B antigen with 70%, 75%, 80%, 85%, 90%, 91%, 92%, 93%, 94%, 95%, 96%, 97%, 98%, 99% or greater amino acid homology with the 161P2F10B antigen. In another embodiment, a specific antibody is one that binds human 161P2F10B antigen and binds murine 161P2F10B antigen, but with a higher degree of binding the human antigen. In another embodiment, a specific antibody is one that binds human 161P2F10B antigen and binds primate 161P2F10B antigen, but with a higher degree of binding the human antigen. In another embodiment, the specific antibody binds to human 161P2F10B antigen and any non-human 161P2F10B antigen, but with a higher degree of binding the human antigen or any combination thereof.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, are identified by, but not limited to, those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium. citrate) and 50% formamide at 55° C., followed by a high-stringency wash consisting of 0.1×SSC containing EDTA at 55° C. "Moderately stringent conditions" are described by, but not limited to, those in Sambrook et al., Molecular Cloning: A Laboratory Manual, New York: Cold Spring Harbor Press, 1989, and include the use of washing solution and hybridization conditions (e.g., temperature, ionic strength and % SDS) less stringent than those described above. An example of moderately stringent conditions is overnight incubation at 65° C. in a solution comprising: 1% bovine serum albumin, 0.5M sodium phosphate pH7.5, 1.25 mM EDTA, and 7% SDS 5×SSC (150 mM NaCl, 15 mM trisodium citrate), followed by washing the filters in 2×SSC/1% SDS at 50° C. and 0.2×SSC/0.1% SDS at 50° C. The skilled artisan will recognize how to adjust the temperature, ionic strength, etc. as necessary to accommodate factors such as probe length and the like.

An HLA "supermotif" is a peptide binding specificity shared by HLA molecules encoded by two or more HLA alleles. Overall phenotypic frequencies of HLA-supertypes in different ethnic populations are set forth in Table IV (f). The non-limiting constituents of various supertypes are as follows:

A2: A*0201, A*0202, A*0203, A*0204, A*0205, A*0206, A*6802, A*6901, A*0207

A3: A3, A11, A31, A*3301, A*6801, A*0301, A*1101, A*3101

B7: B7, B*3501-03, B*51, B*5301, B*5401, B*5501, B*5502, B*5601, B*6701, B*7801, B*0702, B*5101, B*5602

B44: B*3701, B*4402, B*4403, B*60 (B*4001), B61 (B*4006)

A1: A*0102, A*2604, A*3601, A*4301, A*8001

A24: A*24, A*30, A*2403, A*2404, A*3002, A*3003

B27: B*1401-02, B*1503, B*1509, B*1510, B*1518, B*3801-02, B*3901, B*3902, B*3903-04, B*4801-02, B*7301, B*2701-08

B58: B*1516, B*1517, B*5701, B*5702, B58

B62: B*4601, B52, B*1501 (B62), B*1502 (B75), B*1513 (B77)

Calculated population coverage afforded by different HLA-supertype combinations are set forth in Table IV(g).

As used herein "to treat" or "therapeutic" and grammatically related terms, refer to any improvement of any consequence of disease, such as prolonged survival, less morbidity, and/or a lessening of side effects which are the byproducts of an alternative therapeutic modality; as is readily appreciated in the art, full eradication of disease is a preferred out albeit not a requirement for a treatment act.

A "transgenic animal" (e.g., a mouse or rat) is an animal having cells that contain a transgene, which transgene was introduced into the animal or an ancestor of the animal at a prenatal, e.g., an embryonic stage. A "transgene" is a DNA that is integrated into the genome of a cell from which a transgenic animal develops.

As used herein, an HLA or cellular immune response "vaccine" is a composition that contains or encodes one or more peptides of the invention. There are numerous embodiments of such vaccines, such as a cocktail of one or more individual peptides; one or more peptides of the invention comprised by a polyepitopic peptide; or nucleic acids that encode such individual peptides or polypeptides, e.g., a minigene that encodes a polyepitopic peptide. The "one or more peptides" can include any whole unit integer from 1-150 or more, e.g., at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, or 150 or more peptides of the invention. The peptides or polypeptides can optionally be modified, such as by lipidation, addition of targeting or other sequences. HLA class I peptides of the invention can be admixed with, or linked to, HLA class II peptides, to facilitate activation of both cytotoxic T lymphocytes and helper T lymphocytes. HLA vaccines can also comprise peptide-pulsed antigen presenting cells, e.g., dendritic cells.

The term "variant" refers to a molecule that exhibits a variation from a described type or norm, such as a protein that has one or more different amino acid residues in the corresponding position(s) of a specifically described protein (e.g. the 161P2F10B protein shown in FIG. 1.) An analog is an example of a variant protein. Splice isoforms and single nucleotides polymorphisms (SNPs) are further examples of variants.

The "161P2F10B-related proteins" of the invention include those specifically identified herein, as well as allelic variants, conservative substitution variants, analogs and homologs that can be isolated/generated and characterized without undue experimentation following the methods outlined herein or readily available in the art. Fusion proteins that combine parts of different 161P2F10B proteins or fragments thereof, as well as fusion proteins of a 161P2F10B protein and a heterologous polypeptide are also included. Such 161P2F10B proteins are collectively referred to as the 161P2F10B-related proteins, the proteins of the invention, or 161P2F10B. The term "161P2F10B-related protein" refers to a polypeptide fragment or a 161P2F10B protein sequence of 4, 5, 6, 7, 8, 9, 10, 11, 12, 13, 14, 15, 16, 17, 18, 19, 20, 21, 22, 23, 24, 25, or more than 25 amino acids; or, at least 30, 35, 40, 45, 50, 55, 60, 65, 70, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 330, 335, 339 or more amino acids.

II.) 161P2F10B POLYNUCLEOTIDES

One aspect of the invention provides polynucleotides corresponding or complementary to all or part of a 161P2F10B gene, mRNA, and/or coding sequence, preferably in isolated form, including polynucleotides encoding a 161P2F10B-related protein and fragments thereof, DNA, RNA, DNA/RNA hybrid, and related molecules, polynucleotides or oligonucleotides complementary to a 161P2F10B gene or mRNA sequence or a part thereof, and polynucleotides or oligonucleotides that hybridize to a 161P2F10B gene, mRNA, or to a 161P2F10B encoding polynucleotide (collectively, "161P2F10B polynucleotides"). In all instances when referred to in this section, T can also be U in FIG. 1.

Embodiments of a 161P2F10B polynucleotide include: a 161P2F10B polynucleotide having the sequence shown in FIG. 1, the nucleotide sequence of 161P2F10B as shown in FIG. 1 wherein T is U; at least 10 contiguous nucleotides of a polynucleotide having the sequence as shown in FIG. 1; or, at least 10 contiguous nucleotides of a polynucleotide having the sequence as shown in FIG. 1 where T is U.

Polynucleotides encoding relatively long portions of a 161P2F10B protein are also within the scope of the invention. For example, polynucleotides encoding from about amino acid 1 (or 20 or 30 or 40 etc.) to about amino acid 20, (or 30, or 40 or 50 etc.) of the 161P2F10B protein "or variant" shown in FIG. 1 or FIG. 3 can be generated by a variety of techniques well known in the art. These polynucleotide fragments can include any portion of the 161P2F10B sequence as shown in FIG. 1.

II.A.) Uses of 161P2F10B Polynucleotides

II.A.1. Monitoring of Genetic Abnormalities

The polynucleotides of the preceding paragraphs have a number of different specific uses. The human 161P2F10B gene maps to the chromosomal location set forth in the Example entitled "Chromosomal Mapping of 161P2F10B." For example, because the 161P2F10B gene maps to this chromosome, polynucleotides that encode different regions of the 161P2F10B proteins are used to characterize cytogenetic abnormalities of this chromosomal locale, such as abnormalities that are identified as being associated with various cancers. In certain genes, a variety of chromosomal abnormalities including rearrangements have been identified as frequent cytogenetic abnormalities in a number of different cancers (see e.g. Krajinovic et al., Mutat. Res. 382(3-4): 81-83 (1998); Johansson et al., Blood 86(10): 3905-3914 (1995) and Finger et al., P.N.A.S. 85(23): 9158-9162 (1988)). Thus, polynucleotides encoding specific regions of the 161P2F10B proteins provide new tools that can be used to delineate, with greater precision than previously possible, cytogenetic abnormalities in the chromosomal region that encodes 161P2F10B that may contribute to the malignant phenotype. In this context, these polynucleotides satisfy a need in the art for expanding the sensitivity of chromosomal screening in order to identify more subtle and less common chromosomal abnormalities (see e.g. Evans et al., Am. J. Obstet. Gynecol 171(4): 1055-1057 (1994)).

Furthermore, as 161P2F10B was shown to be highly expressed in prostate and other cancers, 161P2F10B polynucleotides are used in methods assessing the status of 161P2F10B gene products in normal versus cancerous tissues. Typically, polynucleotides that encode specific regions of the 161P2F10B proteins are used to assess the presence of perturbations (such as deletions, insertions, point mutations, or alterations resulting in a loss of an antigen etc.) in specific regions of the 161P2F10B gene, such as regions containing one or more motifs. Exemplary assays include both RT-PCR assays as well as single-strand conformation polymorphism (SSCP) analysis (see, e.g., Marrogi et al., J. Cutan. Pathol. 26(8): 369-378 (1999), both of which utilize polynucleotides encoding specific regions of a protein to examine these regions within the protein.

II.A.2. Antisense Embodiments

Other specifically contemplated nucleic acid related embodiments of the invention disclosed herein are genomic DNA, cDNAs, ribozymes, and antisense molecules, as well as nucleic acid molecules based on an alternative backbone, or including alternative bases, whether derived from natural sources or synthesized, and include molecules capable of inhibiting the RNA or protein expression of 161P2F10B. For example, antisense molecules can be RNAs or other molecules, including peptide nucleic acids (PNAs) or non-nucleic acid molecules such as phosphorothioate derivatives that specifically bind DNA or RNA in a base pair-dependent manner. A skilled artisan can readily obtain these classes of nucleic acid molecules using the 161P2F10B polynucleotides and polynucleotide sequences disclosed herein.

Antisense technology entails the administration of exogenous oligonucleotides that bind to a target polynucleotide located within the cells. The term "antisense" refers to the fact that such oligonucleotides are complementary to their intracellular targets, e.g., 161P2F10B. See for example, Jack Cohen, Oligodeoxynucleotides, Antisense Inhibitors of Gene Expression, CRC Press, 1989; and Synthesis 1:1-5 (1988). The 161P2F10B antisense oligonucleotides of the present invention include derivatives such as S-oligonucleotides (phosphorothioate derivatives or S-oligos, see, Jack Cohen, supra), which exhibit enhanced cancer cell growth inhibitory action. S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention can be prepared by treatment of the corresponding O-oligos with 3H-1,2-benzodithiol-3-one-1,1-dioxide, which is a sulfur transfer reagent. See, e.g., Iyer, R. P. et al., J. Org. Chem. 55:4693-4698 (1990); and Iyer, R. P. et al., J. Am. Chem. Soc. 112:1253-1254 (1990). Additional 161P2F10B antisense oligonucleotides of the present invention include morpholino antisense oligonucleotides known in the art (see, e.g., Partridge et al., 1996, Antisense & Nucleic Acid Drug Development 6: 169-175).

The 161P2F10B antisense oligonucleotides of the present invention typically can be RNA or DNA that is complementary to and stably hybridizes with the first 100 5' codons or last 100 3' codons of a 161P2F10B genomic sequence or the corresponding mRNA. Absolute complementarity is not required, although high degrees of complementarity are preferred. Use of an oligonucleotide complementary to this region allows for the selective hybridization to 161P2F10B mRNA and not to mRNA specifying other regulatory subunits of protein kinase. In one embodiment, 161P2F10B antisense oligonucleotides of the present invention are 15 to 30-mer fragments of the antisense DNA molecule that have a sequence that hybridizes to 161P2F10B mRNA. Optionally, 161P2F10B antisense oligonucleotide is a 30-mer oligonucleotide that is complementary to a region in the first 10 5' codons or last 10 3' codons of 161P2F10B. Alternatively, the antisense molecules are modified to employ ribozymes in the inhibition of 161P2F10B expression, see, e.g., L. A. Couture & D. T. Stinchcomb; Trends Genet. 12: 510-515 (1996).

II.A.3. Primers and Primer Pairs

Further specific embodiments of these nucleotides of the invention include primers and primer pairs, which allow the specific amplification of polynucleotides of the invention or of any specific parts thereof, and probes that selectively or specifically hybridize to nucleic acid molecules of the invention or to any part thereof. Probes can be labeled with a detectable marker, such as, for example, a radioisotope, fluorescent compound, bioluminescent compound, a chemiluminescent compound, metal chelator or enzyme. Such probes and primers are used to detect the presence of a 161P2F10B polynucleotide in a sample and as a means for detecting a cell expressing a 161P2F10B protein.

Examples of such probes include polypeptides comprising all or part of the human 161P2F10B cDNA sequence shown in FIG. 1. Examples of primer pairs capable of specifically amplifying 161P2F10B mRNAs are also described in the Examples. As will be understood by the skilled artisan, a great many different primers and probes can be prepared based on the sequences provided herein and used effectively to amplify and/or detect a 161P2F10B mRNA.

The 161P2F10B polynucleotides of the invention are useful for a variety of purposes, including but not limited to their use as probes and primers for the amplification and/or detection of the 161P2F10B gene(s), mRNA(s), or fragments thereof; as reagents for the diagnosis and/or prognosis of prostate cancer and other cancers; as coding sequences capable of directing the expression of 161P2F10B polypeptides; as tools for modulating or inhibiting the expression of the 161P2F10B gene(s) and/or translation of the 161P2F10B transcript(s); and as therapeutic agents.

The present invention includes the use of any probe as described herein to identify and isolate a 161P2F10B or 161P2F10B related nucleic acid sequence from a naturally occurring source, such as humans or other mammals, as well as the isolated nucleic acid sequence per se, which would comprise all or most of the sequences found in the probe used.

II.A.4. Isolation of 161P2F10B-Encoding Nucleic Acid Molecules

The 161P2F10B cDNA sequences described herein enable the isolation of other polynucleotides encoding 161P2F10B gene product(s), as well as the isolation of polynucleotides encoding 161P2F10B gene product homologs, alternatively spliced isoforms, allelic variants, and mutant forms of a 161P2F10B gene product as well as polynucleotides that encode analogs of 161P2F10B-related proteins. Various molecular cloning methods that can be employed to isolate full length cDNAs encoding a 161P2F10B gene are well known (see, for example, Sambrook, J. et al., Molecular Cloning: A Laboratory Manual, 2d edition, Cold Spring Harbor Press, New York, 1989; Current Protocols in Molecular Biology. Ausubel et al., Eds., Wiley and Sons, 1995). For example, lambda phage cloning methodologies can be conveniently employed, using commercially available cloning systems (e.g., Lambda ZAP Express, Stratagene). Phage clones containing 161P2F10B gene cDNAs can be identified by probing with a labeled 161P2F10B cDNA or a fragment thereof. For example, in one embodiment, a 161P2F10B cDNA (e.g., FIG. 1) or a portion thereof can be synthesized and used as a probe to retrieve overlapping and full-length cDNAs corresponding to a 161P2F10B gene. A 161P2F10B gene itself can be isolated by screening genomic DNA libraries, bacterial artificial chromosome libraries (BACs), yeast artificial chromosome libraries (YACs), and the like, with 161P2F10B DNA probes or primers.

II.A.5. Recombinant Nucleic Acid Molecules and Host-Vector Systems

The invention also provides recombinant DNA or RNA molecules containing a 161P2F10B polynucleotide, a fragment, analog or homologue thereof, including but not limited to phages, plasmids, phagemids, cosmids, YACs, BACs, as well as various viral and non-viral vectors well known in the art, and cells transformed or transfected with such recombinant DNA or RNA molecules. Methods for generating such molecules are well known (see, for example, Sambrook et al., 1989, supra).

The invention further provides a host-vector system comprising a recombinant DNA molecule containing a 161P2F10B polynucleotide, fragment, analog or homologue thereof within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 or HighFive cell). Examples of suitable mammalian cells include various prostate cancer cell lines such as DU145 and TsuPr1, other transfectable or transducible prostate cancer cell lines, primary cells (PrEC), as well as a number of mammalian cells routinely used for the expression of recombinant proteins (e.g., COS, CHO, 293, 293T cells). More particularly, a polynucleotide comprising the coding sequence of 161P2F10B or a fragment, analog or homolog thereof can be used to generate 161P2F10B proteins or fragments thereof using any number of host-vector systems routinely used and widely known in the art.

A wide range of host-vector systems suitable for the expression of 161P2F10B proteins or fragments thereof are available, see for example, Sambrook et al., 1989, supra; Current Protocols in Molecular Biology, 1995, supra). Preferred vectors for mammalian expression include but are not limited to pcDNA 3.1 myc-His-tag (Invitrogen) and the retroviral vector pSR tkneo (Muller et al., 1991, MCB 11:1785). Using these expression vectors, 161P2F10B can be expressed in several prostate cancer and non-prostate cell lines, including for example 293, 293T, rat-1, NIH 3T3 and TsuPr1. The host-vector systems of the invention are useful for the production of a 161P2F10B protein or fragment thereof. Such host-vector systems can be employed to study the functional properties of 161P2F10B and 161P2F10B mutations or analogs.

Recombinant human 161P2F10B protein or an analog or homolog or fragment thereof can be produced by mammalian cells transfected with a construct encoding a 161P2F10B-related nucleotide. For example, 293T cells can be transfected with an expression plasmid encoding 161P2F10B or fragment, analog or homolog thereof, a 161P2F10B-related protein is expressed in the 293T cells, and the recombinant 161P2F10B protein is isolated using standard purification methods (e.g., affinity purification using anti-161P2F10B antibodies). In another embodiment, a 161P2F10B coding sequence is subcloned into the retroviral vector pSRαMSVt-kneo and used to infect various mammalian cell lines, such as NIH 3T3, TsuPr1, 293 and rat-1 in order to establish 161P2F10B expressing cell lines. Various other expression systems well known in the art can also be employed. Expression constructs encoding a leader peptide joined in frame to a 161P2F10B coding sequence can be used for the generation of a secreted form of recombinant 161P2F10B protein.

As discussed herein, redundancy in the genetic code permits variation in 161P2F10B gene sequences. In particular, it is known in the art that specific host species often have specific codon preferences, and thus one can adapt the disclosed sequence as preferred for a desired host. For example, preferred analog codon sequences typically have rare codons (i.e., codons having a usage frequency of less than about 20% in known sequences of the desired host) replaced with higher frequency codons. Codon preferences for a specific species are calculated, for example, by utilizing codon usage tables available on the INTERNET such as at URL dna.affrc.go.jp/~nakamura/codon.html.

Additional sequence modifications are known to enhance protein expression in a cellular host. These include elimination of sequences encoding spurious polyadenylation signals, exon/intron splice site signals, transposon-like repeats, and/or other such well-characterized sequences that are deleterious to gene expression. The GC content of the sequence is adjusted to levels average for a given cellular host, as calculated by reference to known genes expressed in the host cell. Where possible, the sequence is modified to avoid predicted hairpin secondary mRNA structures. Other useful modifications include the addition of a translational initiation consensus sequence at the start of the open reading frame, as described in Kozak, Mol. Cell. Biol., 9:5073-5080 (1989). Skilled artisans understand that the general rule that eukaryotic ribosomes initiate translation exclusively at the 5' proximal AUG codon is abrogated only under rare conditions (see, e.g., Kozak PNAS 92(7): 2662-2666, (1995) and Kozak NAR 15(20): 8125-8148 (1987)).

III.) 161P2F10B-RELATED PROTEINS

Another aspect of the present invention provides 161P2F10B-related proteins. Specific embodiments of 161P2F10B proteins comprise a polypeptide having all or part of the amino acid sequence of human 161P2F10B as shown in FIG. 1, preferably FIG. 1A. Alternatively, embodiments of 161P2F10B proteins comprise variant, homolog or analog polypeptides that have alterations in the amino acid sequence of 161P2F10B shown in FIG. 1.

Embodiments of a 161P2F10B polypeptide include: a 161P2F10B polypeptide having a sequence shown in FIG. 1, a peptide encoded by a polynucleotide sequence of a 161P2F10B as shown in FIG. 1 wherein T is U; at least 10 contiguous nucleotides encoding a polypeptide having the sequence as shown in FIG. 1; or, at least 10 contiguous peptides encoded by a polynucleotide having the sequence as shown in FIG. 1 where T is U.

Amino acid abbreviations are provided in Table II. Conservative amino acid substitutions can frequently be made in a protein without altering either the conformation or the function of the protein. Proteins of the invention can comprise 1, 2, 3, 4, 5, 6, 7, 8, 9, 10, 11, 12, 13, 14, 15 conservative substitutions.

Embodiments of the invention disclosed herein include a wide variety of art-accepted variants or analogs of 161P2F10B proteins such as polypeptides having amino acid insertions, deletions and substitutions. 161P2F10B variants can be made using methods known in the art such as site-directed mutagenesis, alanine scanning, and PCR mutagenesis. Site-directed mutagenesis (Carter et al., Nucl. Acids Res., 13:4331 (1986); Zoller et al., Nucl. Acids Res., 10:6487 (1987)), cassette mutagenesis (Wells et al., Gene, 34:315 (1985)), restriction selection mutagenesis (Wells et al., Philos. Trans. R. Soc. London SerA, 317:415 (1986)) or other known techniques can be performed on the cloned DNA to produce the 161P2F10B variant DNA.

Scanning amino acid analysis can also be employed to identify one or more amino acids along a contiguous sequence that is involved in a specific biological activity such as a protein-protein interaction. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions (Creighton, The Proteins, (W.H. Freeman & Co., N.Y.); Chothia, J. Mol. Biol., 150:1 (1976)). If alanine substitution does not yield adequate amounts of variant, an isosteric amino acid can be used.

As defined herein, 161P2F10B variants, analogs or homologs, have the distinguishing attribute of having at least one epitope that is "cross reactive" with a 161P2F10B protein having an amino acid sequence of FIG. 1. As used in this sentence, "cross reactive" means that an antibody or T cell that specifically binds to a 161P2F10B variant also specifically binds to a 161P2F10B protein having an amino acid sequence set forth in FIG. 1. A polypeptide ceases to be a variant of a protein shown in FIG. 1, when it no longer contains any epitope capable of being recognized by an antibody or T cell that specifically binds to the starting 161P2F10B protein. Those skilled in the art understand that antibodies that recognize proteins bind to epitopes of varying size, and a grouping of the order of about four or five amino acids, contiguous or not, is regarded as a typical number of amino acids in a minimal epitope. See, e.g., Nair et al., J. Immunol. 2000 165(12): 6949-6955; Hebbes et al., Mol Immunol (1989) 26(9):865-73; Schwartz et al., J Immunol (1985) 135(4):2598-608.

Other classes of 161P2F10B-related protein variants share 70%, 75%, 80%, 85%, 90%, 95% or more similarity with an amino acid sequence of FIG. 1, or a fragment thereof. Another specific class of 161P2F10B protein variants or analogs comprises one or more of the 161P2F10B biological motifs described herein or presently known in the art. Thus, encompassed by the present invention are analogs of 161P2F10B fragments (nucleic or amino acid) that have altered functional (e.g. immunogenic) properties relative to the starting fragment. It is to be appreciated that motifs now or which become part of the art are to be applied to the nucleic or amino acid sequences of FIG. 1.

As discussed herein, embodiments of the claimed invention include polypeptides containing less than the full amino acid sequence of a 161P2F10B protein shown in FIG. 1. For example, representative embodiments of the invention comprise peptides/proteins having any 4, 5, 6, 7, 8, 9, 10, 11, 12, 13, 14, 15 or more contiguous amino acids of a 161P2F10B protein shown in FIG. 1.

161P2F10B-related proteins are generated using standard peptide synthesis technology or using chemical cleavage methods well known in the art. Alternatively, recombinant methods can be used to generate nucleic acid molecules that encode a 161P2F10B-related protein. In one embodiment, nucleic acid molecules provide a means to generate defined fragments of a 161P2F10B protein (or variants, homologs or analogs thereof).

III.A.) Motif-Bearing Protein Embodiments

Additional illustrative embodiments of the invention disclosed herein include 161P2F10B polypeptides comprising the amino acid residues of one or more of the biological motifs contained within a 161P2F10B polypeptide sequence set forth in FIG. 1. Various motifs are known in the art, and a protein can be evaluated for the presence of such motifs by a number of publicly available Internet sites such as BIMAS.

Motif bearing subsequences of all 161P2F10B variant proteins have previously been disclosed.

Table IV(h) sets forth several frequently occurring motifs based on pfam searches (see URL address pfam.wustl.edu/). The columns of Table IV(h) list (1) motif name abbreviation, (2) percent identity found amongst the different member of the motif family, (3) motif name or description and (4) most common function; location information is included if the motif is relevant for location.

Polypeptides comprising one or more of the 161P2F10B motifs discussed above are useful in elucidating the specific characteristics of a malignant phenotype in view of the observation that the 161P2F10B motifs discussed above are associated with growth dysregulation and because 161P2F10B is overexpressed in certain cancers (See, e.g., Table I). Casein kinase II, cAMP and camp-dependent protein kinase, and Protein Kinase C, for example, are enzymes known to be associated with the development of the malignant phenotype (see e.g. Chen et al., Lab Invest., 78(2): 165-174 (1998); Gaiddon et al., Endocrinology 136(10): 4331-4338 (1995); Hall et al., Nucleic Acids Research 24(6): 1119-1126 (1996); Peterziel et al., Oncogene 18(46): 6322-6329 (1999) and O'Brian, Oncol. Rep. 5(2): 305-309 (1998)). Moreover, both glycosylation and myristoylation are protein modifications also associated with cancer and cancer progression (see e.g. Dennis et al., Biochem. Biophys. Acta 1473(1):21-34 (1999); Raju et al., Exp. Cell Res. 235(1): 145-154 (1997)). Amidation is another protein modification also associated with cancer and cancer progression (see e.g. Treston et al., J. Natl. Cancer Inst. Monogr. (13): 169-175 (1992)).

In another embodiment, proteins of the invention comprise one or more of the immunoreactive epitopes identified in accordance with art-accepted methods, such as the peptides previously disclosed. CTL epitopes can be determined using specific algorithms to identify peptides within a 161P2F10B protein that are capable of optimally binding to specified HLA alleles (e.g., Table IV; Epimatrix™ and Epimer™, Brown University, URL brown.edu/Research/TB-HIV_Lab/ epimatrix/epimatrix.html; and BIMAS, URL bimas.dcrt.nih. gov/.) Moreover, processes for identifying peptides that have sufficient binding affinity for HLA molecules and which are correlated with being immunogenic epitopes, are well known in the art, and are carried out without undue experimentation. In addition, processes for identifying peptides that are immunogenic epitopes, are well known in the art, and are carried out without undue experimentation either in vitro or in vivo.

Also known in the art are principles for creating analogs of such epitopes in order to modulate immunogenicity. For example, one begins with an epitope that bears a CTL or HTL motif (see, e.g., the HLA Class I and HLA Class II motifs/ supermotifs of Table IV). The epitope is analoged by substituting out an amino acid at one of the specified positions, and replacing it with another amino acid specified for that position. For example, on the basis of residues defined in Table IV, one can substitute out a deleterious residue in favor of any other residue, such as a preferred residue; substitute a less-preferred residue with a preferred residue; or substitute an originally-occurring preferred residue with another preferred residue. Substitutions can occur at primary anchor positions or at other positions in a peptide; see, e.g., Table IV.

A variety of references reflect the art regarding the identification and generation of epitopes in a protein of interest as well as analogs thereof. See, for example, WO 97/33602 to Chesnut et al.; Sette, Immunogenetics 1999 50(3-4): 201-212; Sette et al., J. Immunol. 2001 166(2): 1389-1397; Sidney et al., Hum. Immunol. 1997 58(1): 12-20; Kondo et al., Immunogenetics 1997 45(4): 249-258; Sidney et al., J. Immunol. 1996 157(8): 3480-90; and Falk et al., Nature 351: 290-6 (1991); Hunt et al., Science 255:1261-3 (1992); Parker et al., J. Immunol. 149:3580-7 (1992); Parker et al., J. Immunol. 152:163-75 (1994)); Kast et al., 1994 152(8): 3904-12; Borras-Cuesta et al., Hum. Immunol. 2000 61(3): 266-278; Alexander et al., J. Immunol. 2000 164(3); 164(3): 1625-1633; Alexander et al., PMID: 7895164, UI: 95202582; O'Sullivan et al., J. Immunol. 1991 147(8): 2663-2669; Alexander et al., Immunity 1994 1(9): 751-761 and Alexander et al., Immunol. Res. 1998 18(2): 79-92.

Related embodiments of the invention include polypeptides comprising combinations of the different motifs set forth in Table(s) IV(a), IV(b), IV(c), IV(d), and IV(h), and/or, one or more of the predicted CTL epitopes of previously disclosed, and/or, one or more of the T cell binding motifs known in the art. Preferred embodiments contain no insertions, deletions or substitutions either within the motifs or within the intervening sequences of the polypeptides. In addition, embodiments which include a number of either N-terminal and/or C-terminal amino acid residues on either side of these motifs may be desirable (to, for example, include a greater portion of the polypeptide architecture in which the motif is located). Typically, the number of N-terminal and/or C-terminal amino acid residues on either side of a motif is between about 1 to about 100 amino acid residues, preferably 5 to about 50 amino acid residues.

161P2F10B-related proteins are embodied in many forms, preferably in isolated form. A purified 161P2F10B protein molecule will be substantially free of other proteins or molecules that impair the binding of 161P2F10B to antibody, T cell or other ligand. The nature and degree of isolation and purification will depend on the intended use. Embodiments of a 161P2F10B-related proteins include purified 161P2F10B-related proteins and functional, soluble 161P2F10B-related proteins. In one embodiment, a functional, soluble 161P2F10B protein or fragment thereof retains the ability to be bound by antibody, T cell or other ligand.

The invention also provides 161P2F10B proteins comprising biologically active fragments of a 161P2F10B amino acid sequence shown in FIG. 1. Such proteins exhibit properties of the starting 161P2F10B protein, such as the ability to elicit the generation of antibodies that specifically bind an epitope associated with the starting 161P2F10B protein; to be bound by such antibodies; to elicit the activation of HTL or CTL; and/or, to be recognized by HTL or CTL that also specifically bind to the starting protein.

161P2F10B-related polypeptides that contain particularly interesting structures can be predicted and/or identified using various analytical techniques well known in the art, including, for example, the methods of Chou-Fasman, Garnier-Robson, Kyte-Doolittle, Eisenberg, Karplus-Schultz or Jameson-Wolf analysis, or based on immunogenicity. Fragments that contain such structures are particularly useful in generating subunit-specific anti-161P2F10B antibodies or T cells or in identifying cellular factors that bind to 161P2F10B. For example, hydrophilicity profiles can be generated, and immunogenic peptide fragments identified, using the method of Hopp, T. P. and Woods, K. R., 1981, Proc. Natl. Acad. Sci. U.S.A. 78:3824-3828. Hydropathicity profiles can be generated, and immunogenic peptide fragments identified, using the method of Kyte, J. and Doolittle, R. F., 1982, J. Mol. Biol. 157:105-132. Percent (%) Accessible Residues profiles can be generated, and immunogenic peptide fragments identified, using the method of Janin J., 1979, Nature 277:491-492. Average Flexibility profiles can be generated, and immunogenic peptide fragments identified, using the method of Bhaskaran R., Ponnuswamy P. K., 1988, Int. J. Pept. Protein Res. 32:242-255. Beta-turn profiles can be generated, and immunogenic peptide fragments identified, using the method of Deleage, G., Roux B., 1987, Protein Engineering 1:289-294.

CTL epitopes can be determined using specific algorithms to identify peptides within a 161P2F10B protein that are capable of optimally binding to specified HLA alleles such as BIMAS and SYFPEITHI. Illustrating this, peptide epitopes from 161P2F10B that are presented in the context of human MHC Class I molecules, e.g., HLA-A1, A2, A3, A11, A24, B7 and B35 were predicted. Specifically, the complete amino acid sequence of the 161P2F10B protein and relevant portions of other variants, i.e., for HLA Class I predictions 9 flanking residues on either side of a point mutation or exon junction, and for HLA Class II predictions 14 flanking residues on either side of a point mutation or exon junction corresponding to that variant, were entered into the HLA Peptide Motif Search algorithm found in the Bioinformatics and Molecular Analysis Section.

The HLA peptide motif search algorithm was developed by Dr. Ken Parker based on binding of specific peptide sequences in the groove of HLA Class 1 molecules, in particular HLA-A2 (see, e.g., Falk et al., Nature 351: 290-6 (1991); Hunt et al., Science 255:1261-3 (1992); Parker et al., J. Immunol. 149:3580-7 (1992); Parker et al., J. Immunol. 152:163-75 (1994)). This algorithm allows location and ranking of 8-mer, 9-mer, and 10-mer peptides from a complete protein sequence for predicted binding to HLA-A2 as well as numerous other HLA Class I molecules. Many HLA class I binding peptides are 8-, 9-, 10 or 11-mers. For example, for Class I HLA-A2, the epitopes preferably contain a leucine (L) or methionine (M) at position 2 and a valine (V) or leucine (L) at the C-terminus (see, e.g., Parker et al., J. Immunol. 149: 3580-7 (1992)). Selected results of 161P2F10B predicted binding peptides have been shown. The binding score corresponds to the estimated half time of dissociation of complexes containing the peptide at 37° C. at pH 6.5. Peptides with the highest binding score are predicted to be the most tightly bound to HLA Class I on the cell surface for the greatest period of time and thus represent the best immunogenic targets for T-cell recognition.

Actual binding of peptides to an HLA allele can be evaluated by stabilization of HLA expression on the antigen-processing defective cell line T2 (see, e.g., Xue et al., Prostate 30:73-8 (1997) and Peshwa et al., Prostate 36:129-38 (1998)) Immunogenicity of specific peptides can be evaluated in vitro by stimulation of CD8+ cytotoxic T lymphocytes (CTL) in the presence of antigen presenting cells such as dendritic cells.

It is to be appreciated that every epitope predicted by the BIMAS site, Epimer™ and Epimatrix™ sites, or specified by the HLA class I or class II motifs available in the art or which become part of the art such as set forth in Table IV are to be "applied" to a 161P2F10B protein in accordance with the invention. As used in this context "applied" means that a 161P2F10B protein is evaluated, e.g., visually or by computer-based patterns finding methods, as appreciated by those of skill in the relevant art. Every subsequence of a 161P2F10B protein of 8, 9, 10, or 11 amino acid residues that bears an HLA Class I motif, or a subsequence of 9 or more amino acid residues that bear an HLA Class II motif are within the scope of the invention.

III.B.) Expression of 161P2F10B-Related Proteins

In an embodiment described in the examples that follow, 161P2F10B can be conveniently expressed in cells (such as 293T cells) transfected with a commercially available expression vector such as a CMV-driven expression vector encoding 161P2F10B with a C-terminal 6×His and MYC tag (pcDNA3.1/mycHIS, Invitrogen or Tag5, GenHunter Corporation, Nashville Tenn.). The Tag5 vector provides an IgGK secretion signal that can be used to facilitate the production of a secreted 161P2F10B protein in transfected cells. The secreted HIS-tagged 161P2F10B in the culture media can be purified, e.g., using a nickel column using standard techniques.

III.C.) Modifications of 161P2F10B-Related Proteins

Modifications of 161P2F10B-related proteins such as covalent modifications are included within the scope of this invention. One type of covalent modification includes reacting targeted amino acid residues of a 161P2F10B polypeptide with an organic derivatizing agent that is capable of reacting with selected side chains or the N- or C-terminal residues of a 161P2F10B protein. Another type of covalent modification of a 161P2F10B polypeptide included within the scope of this invention comprises altering the native glycosylation pattern of a protein of the invention. Another type of covalent modification of 161P2F10B comprises linking a 161P2F10B polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The 161P2F10B-related proteins of the present invention can also be modified to form a chimeric molecule comprising 161P2F10B fused to another, heterologous polypeptide or amino acid sequence. Such a chimeric molecule can be synthesized chemically or recombinantly. A chimeric molecule can have a protein of the invention fused to another tumor-associated antigen or fragment thereof. Alternatively, a protein in accordance with the invention can comprise a fusion of fragments of a 161P2F10B sequence (amino or nucleic acid) such that a molecule is created that is not, through its length, directly homologous to the amino or nucleic acid sequences shown in FIG. 1. Such a chimeric molecule can comprise multiples of the same subsequence of 161P2F10B. A chimeric molecule can comprise a fusion of a 161P2F10B-related protein with a polyhistidine epitope tag, which provides an epitope to which immobilized nickel can selectively bind, with cytokines or with growth factors. The epitope tag is generally placed at the amino- or carboxyl-terminus of a 161P2F10B protein. In an alternative embodiment, the chimeric molecule can comprise a fusion of a 161P2F10B-related protein with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a 161P2F10B polypeptide in place of at least one variable region within an Ig molecule. In a preferred embodiment, the immunoglobulin fusion includes the hinge, CH2 and CH3, or the hinge, CHI, CH2 and CH3 regions of an IgGI molecule. For the production of immunoglobulin fusions see, e.g., U.S. Pat. No. 5,428, 130 issued Jun. 27, 1995.

III.D.) Uses of 161P2F10B-Related Proteins

The proteins of the invention have a number of different specific uses. As 161P2F10B is highly expressed in prostate and other cancers, 161P2F10B-related proteins are used in methods that assess the status of 161P2F10B gene products in normal versus cancerous tissues, thereby elucidating the malignant phenotype. Typically, polypeptides from specific regions of a 161P2F10B protein are used to assess the presence of perturbations (such as deletions, insertions, point mutations etc.) in those regions (such as regions containing one or more motifs). Exemplary assays utilize antibodies or T cells targeting 161P2F10B-related proteins comprising the amino acid residues of one or more of the biological motifs contained within a 161P2F10B polypeptide sequence in order to evaluate the characteristics of this region in normal versus cancerous tissues or to elicit an immune response to the epitope. Alternatively, 161P2F10B-related proteins that contain the amino acid residues of one or more of the biological motifs in a 161P2F10B protein are used to screen for factors that interact with that region of 161P2F10B.

161P2F10B protein fragments/subsequences are particularly useful in generating and characterizing domain-specific antibodies (e.g., antibodies recognizing an extracellular or intracellular epitope of a 161P2F10B protein), for identifying agents or cellular factors that bind to 161P2F10B or a particular structural domain thereof, and in various therapeutic and diagnostic contexts, including but not limited to diagnostic assays, cancer vaccines and methods of preparing such vaccines.

Proteins encoded by the 161P2F10B genes, or by analogs, homologs or fragments thereof, have a variety of uses, including but not limited to generating antibodies and in methods for identifying ligands and other agents and cellular constituents that bind to a 161P2F10B gene product. Antibodies raised against a 161P2F10B protein or fragment thereof are useful in diagnostic and prognostic assays, and imaging methodologies in the management of human cancers characterized by expression of 161P2F10B protein, such as those listed in Table I. Such antibodies can be expressed intracellularly and used in methods of treating patients with such cancers. 161P2F10B-related nucleic acids or proteins are also used in generating HTL or CTL responses.

Various immunological assays useful for the detection of 161P2F10B proteins are used, including but not limited to various types of radioimmunoassays, enzyme-linked immunosorbent assays (ELISA), enzyme-linked immunofluorescent assays (ELIFA), immunocytochemical methods, and the like. Antibodies can be labeled and used as immunological imaging reagents capable of detecting 161P2F10B-expressing cells (e.g., in radioscintigraphic imaging methods). 161P2F10B proteins are also particularly useful in generating cancer vaccines, as further described herein.

IV.) 161P2F10B ANTIBODIES

Another aspect of the invention provides antibodies that bind to 161P2F10B-related proteins. Preferred antibodies specifically bind to a 161P2F10B-related protein and do not bind (or bind weakly) to peptides or proteins that are not 161P2F10B-related proteins under physiological conditions. In this context, examples of physiological conditions include: 1) phosphate buffered saline; 2) Tris-buffered saline containing 25 mM Tris and 150 mM NaCl; or normal saline (0.9% NaCl); 4) animal serum such as human serum; or, 5) a combination of any of 1) through 4); these reactions preferably taking place at pH 7.5, alternatively in a range of pH 7.0 to 8.0, or alternatively in a range of pH 6.5 to 8.5; also, these reactions taking place at a temperature between 4° C. to 37° C. For example, antibodies that bind 161P2F10B can bind 161P2F10B-related proteins such as the homologs or analogs thereof.

161P2F10B antibodies of the invention are particularly useful in cancer (see, e.g., Table I) diagnostic and prognostic assays, and imaging methodologies. Similarly, such antibodies are useful in the treatment, diagnosis, and/or prognosis of prostate and other cancers, to the extent 161P2F10B is also expressed or overexpressed in these other cancers. Moreover, intracellularly expressed antibodies (e.g., single chain antibodies) are therapeutically useful in treating cancers in which the expression of 161P2F10B is involved, such as advanced or metastatic prostate cancers or other advanced or metastatic cancers.

The invention also provides various immunological assays useful for the detection and quantification of 161P2F10B and mutant 161P2F10B-related proteins. Such assays can comprise one or more 161P2F10B antibodies capable of recognizing and binding a 161P2F10B-related protein, as appropriate. These assays are performed within various immunological assay formats well known in the art, including but not limited to various types of radioimmunoassays, enzyme-linked immunosorbent assays (ELISA), enzyme-linked immunofluorescent assays (ELIFA), and the like.

Immunological non-antibody assays of the invention also comprise T cell immunogenicity assays (inhibitory or stimulatory) as well as major histocompatibility complex (MHC) binding assays.

In addition, immunological imaging methods capable of detecting kidney cancer and other cancers expressing 161P2F10B are also provided by the invention, including but not limited to radioscintigraphic imaging methods using labeled 161P2F10B antibodies. Such assays are clinically useful in the detection, monitoring, and prognosis of 161P2F10B expressing cancers such as kidney cancer.

161P2F10B antibodies are also used in methods for purifying a 161P2F10B-related protein and for isolating 161P2F10B homologues and related molecules. For example, a method of purifying a 161P2F10B-related protein comprises incubating a 161P2F10B antibody, which has been coupled to a solid matrix, with a lysate or other solution containing a 161P2F10B-related protein under conditions that permit the 161P2F10B antibody to bind to the 161P2F10B-related protein; washing the solid matrix to eliminate impurities; and eluting the 161P2F10B-related protein from the coupled antibody. Other uses of 161P2F10B antibodies in accordance with the invention include generating anti-idiotypic antibodies that mimic a 161P2F10B protein.

Various methods for the preparation of antibodies are well known in the art. For example, antibodies can be prepared by immunizing a suitable mammalian host using a 161P2F10B-related protein, peptide, or fragment, in isolated or immunoconjugated form (Antibodies: A Laboratory Manual, CSH Press, Eds., Harlow, and Lane (1988); Harlow, Antibodies, Cold Spring Harbor Press, NY (1989)). In addition, fusion proteins of 161P2F10B can also be used, such as a 161P2F10B GST-fusion protein. In a particular embodiment, a GST fusion protein comprising all or most of the amino acid sequence of FIG. 1 is produced, then used as an immunogen to generate appropriate antibodies. In another embodiment, a 161P2F10B-related protein is synthesized and used as an immunogen.

In addition, naked DNA immunization techniques known in the art are used (with or without purified 161P2F10B-related protein or 161P2F10B expressing cells) to generate an immune response to the encoded immunogen (for review, see Donnelly et al., 1997, Ann. Rev. Immunol. 15: 617-648).

The amino acid sequence of a 161P2F10B protein as shown in FIG. 1 can be analyzed to select specific regions of the 161P2F10B protein for generating antibodies. For example, hydrophobicity and hydrophilicity analyses of a 161P2F10B amino acid sequence are used to identify hydrophilic regions in the 161P2F10B structure. Regions of a 161P2F10B protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis. Hydrophilicity profiles can be generated using the method of Hopp, T. P. and Woods, K. R., 1981, Proc. Natl. Acad. Sci. U.S.A. 78:3824-

3828. Hydropathicity profiles can be generated using the method of Kyte, J. and Doolittle, R. F., 1982, J. Mol. Biol. 157:105-132. Percent (%) Accessible Residues profiles can be generated using the method of Janin J., 1979, Nature 277:491-492. Average Flexibility profiles can be generated using the method of Bhaskaran R., Ponnuswamy P. K., 1988, Int. J. Pept. Protein Res. 32:242-255. Beta-turn profiles can be generated using the method of Deleage, G., Roux B., 1987, Protein Engineering 1:289-294. Thus, each region identified by any of these programs or methods is within the scope of the present invention. Preferred methods for the generation of 161P2F10B antibodies are further illustrated by way of the examples provided herein. Methods for preparing a protein or polypeptide for use as an immunogen are well known in the art. Also well known in the art are methods for preparing immunogenic conjugates of a protein with a carrier, such as BSA, KLH or other carrier protein. In some circumstances, direct conjugation using, for example, carbodiimide reagents are used; in other instances linking reagents such as those supplied by Pierce Chemical Co., Rockford, Ill., are effective. Administration of a 161P2F10B immunogen is often conducted by injection over a suitable time period and with use of a suitable adjuvant, as is understood in the art. During the immunization schedule, titers of antibodies can be taken to determine adequacy of antibody formation.

161P2F10B monoclonal antibodies can be produced by various means well known in the art. For example, immortalized cell lines that secrete a desired monoclonal antibody are prepared using the standard hybridoma technology of Kohler and Milstein or modifications that immortalize antibody-producing B cells, as is generally known Immortalized cell lines that secrete the desired antibodies are screened by immunoassay in which the antigen is a 161P2F10B-related protein. When the appropriate immortalized cell culture is identified, the cells can be expanded and antibodies produced either from in vitro cultures or from ascites fluid.

The antibodies or fragments of the invention can also be produced, by recombinant means. Regions that bind specifically to the desired regions of a 161P2F10B protein can also be produced in the context of chimeric or complementarity-determining region (CDR) grafted antibodies of multiple species origin. Humanized or human 161P2F10B antibodies can also be produced, and are preferred for use in therapeutic contexts. Methods for humanizing murine and other non-human antibodies, by substituting one or more of the non-human antibody CDRs for corresponding human antibody sequences, are well known (see for example, Jones et al., 1986, Nature 321: 522-525; Riechmann et al., 1988, Nature 332: 323-327; Verhoeyen et al., 1988, Science 239: 1534-1536). See also, Carter et al., 1993, Proc. Natl. Acad. Sci. USA 89: 4285 and Sims et al., 1993, J. Immunol. 151: 2296.

Methods for producing fully human monoclonal antibodies include phage display and transgenic methods (for review, see Vaughan et al., 1998, Nature Biotechnology 16: 535-539). Fully human 161P2F10B monoclonal antibodies can be generated using cloning technologies employing large human Ig gene combinatorial libraries (i.e., phage display) (Griffiths and Hoogenboom, Building an in vitro immune system: human antibodies from phage display libraries. In: Protein Engineering of Antibody Molecules for Prophylactic and Therapeutic Applications in Man, Clark, M. (Ed.), Nottingham Academic, pp 45-64 (1993); Burton and Barbas, Human Antibodies from combinatorial libraries. Id., pp 65-82). Fully human 161P2F10B monoclonal antibodies can also be produced using transgenic mice engineered to contain human immunoglobulin gene loci as described in PCT Patent Application WO98/24893, Kucherlapati and Jakobovits et al., published Dec. 3, 1997 (see also, Jakobovits, 1998, Exp. Opin. Invest. Drugs 7(4): 607-614; U.S. Pat. Nos. 6,162,963 issued 19 Dec. 2000; 6,150,584 issued 12 Nov. 2000; and, 6,114598 issued 5 Sep. 2000). This method avoids the in vitro manipulation required with phage display technology and efficiently produces high affinity authentic human antibodies.

Reactivity of 161P2F10B antibodies with a 161P2F10B-related protein can be established by a number of well known means, including Western blot, immunoprecipitation, ELISA, and FACS analyses using, as appropriate, 161P2F10B-related proteins, 161P2F10B-expressing cells or extracts thereof. A 161P2F10B antibody or fragment thereof can be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. Further, bi-specific antibodies specific for two or more 161P2F10B epitopes are generated using methods generally known in the art. Homodimeric antibodies can also be generated by cross-linking techniques known in the art (e.g., Wolff et al., Cancer Res. 53: 2560-2565).

In one embodiment, the invention provides for monoclonal antibodies identified as Ha16-1(3,5)18, Ha16-1(1)11, H16-1.93, H16-9.69 were sent (via Federal Express) to the American Type Culture Collection (ATCC), P.O. Box 1549, Manassas, Va. 20108 on Mar. 28, 2006 and assigned Accession numbers PTA-7452 and PTA-7450 and PTA-7449 and PTA-7451 respectively.

V.) 161P2F10B CELLULAR IMMUNE RESPONSES

The mechanism by which T cells recognize antigens has been delineated. Efficacious peptide epitope vaccine compositions of the invention induce a therapeutic or prophylactic immune responses in very broad segments of the world-wide population. For an understanding of the value and efficacy of compositions of the invention that induce cellular immune responses, a brief review of immunology-related technology is provided.

A complex of an HLA molecule and a peptidic antigen acts as the ligand recognized by HLA-restricted T cells (Buus, S. et al., Cell 47:1071, 1986; Babbitt, B. P. et al., Nature 317: 359, 1985; Townsend, A. and Bodmer, H., Annu. Rev. Immunol. 7:601, 1989; Germain, R. N., Annu. Rev. Immunol. 11:403, 1993). Through the study of single amino acid substituted antigen analogs and the sequencing of endogenously bound, naturally processed peptides, critical residues that correspond to motifs required for specific binding to HLA antigen molecules have been identified and are set forth in Table IV (see also, e.g., Southwood, et al., J. Immunol. 160: 3363, 1998; Rammensee, et al., Immunogenetics 41:178, 1995; Rammensee et al., SYFPEITHI, access via World Wide Web at URL (134.2.96.221/scripts.hlaserver.dll/home.htm); Sette, A. and Sidney, J. Curr. Opin. Immunol. 10:478, 1998; Engelhard, V. H., Curr. Opin. Immunol. 6:13, 1994; Sette, A. and Grey, H. M., Curr. Opin. Immunol. 4:79, 1992; Sinigaglia, F. and Hammer, J. Curr. Biol. 6:52, 1994; Ruppert et al., Cell 74:929-937, 1993; Kondo et al., J. Immunol. 155: 4307-4312, 1995; Sidney et al., J. Immunol. 157:3480-3490, 1996; Sidney et al., Human Immunol. 45:79-93, 1996; Sette, A. and Sidney, J. Immunogenetics 1999 November; 50(3-4): 201-12, Review).

Furthermore, x-ray crystallographic analyses of HLA-peptide complexes have revealed pockets within the peptide binding cleft/groove of HLA molecules which accommodate, in an allele-specific mode, residues borne by peptide ligands; these residues in turn determine the HLA binding capacity of the peptides in which they are present. (See, e.g., Madden, D. R. Annu. Rev. Immunol. 13:587, 1995; Smith, et al., Immunity 4:203, 1996; Fremont et al., Immunity 8:305, 1998; Stern et al., Structure 2:245, 1994; Jones, E. Y. Curr. Opin. Immunol. 9:75, 1997; Brown, J. H. et al., Nature 364:33, 1993; Guo, H. C. et al., Proc. Natl. Acad. Sci. USA 90:8053, 1993; Guo, H. C. et al., Nature 360:364, 1992; Silver, M. L. et al., Nature 360:367, 1992; Matsumura, M. et al., Science 257:927, 1992; Madden et al., Cell 70:1035, 1992; Fremont, D. H. et al., Science 257:919, 1992; Saper, M. A., Bjorkman, P. J. and Wiley, D.C., J. Mol. Biol. 219:277, 1991.)

Accordingly, the definition of class I and class II allele-specific HLA binding motifs, or class I or class II supermotifs allows identification of regions within a protein that are correlated with binding to particular HLA antigen(s).

Thus, by a process of HLA motif identification, candidates for epitope-based vaccines have been identified; such candidates can be further evaluated by HLA-peptide binding assays to determine binding affinity and/or the time period of association of the epitope and its corresponding HLA molecule. Additional confirmatory work can be performed to select, amongst these vaccine candidates, epitopes with preferred characteristics in terms of population coverage, and/or immunogenicity.

Various strategies can be utilized to evaluate cellular immunogenicity, including:

1) Evaluation of primary T cell cultures from normal individuals (see, e.g., Wentworth, P. A. et al., Mol. Immunol. 32:603, 1995; Celis, E. et al., Proc. Natl. Acad. Sci. USA 91:2105, 1994; Tsai, V. et al., J. Immunol. 158:1796, 1997; Kawashima, I. et al., Human Immunol. 59:1, 1998). This procedure involves the stimulation of peripheral blood lymphocytes (PBL) from normal subjects with a test peptide in the presence of antigen presenting cells in vitro over a period of several weeks. T cells specific for the peptide become activated during this time and are detected using, e.g., a lymphokine- or 51Cr-release assay involving peptide sensitized target cells.

2) Immunization of HLA transgenic mice (see, e.g., Wentworth, P. A. et al., J. Immunol. 26:97, 1996; Wentworth, P. A. et al., Int. Immunol. 8:651, 1996; Alexander, J. et al., J. Immunol. 159:4753, 1997). For example, in such methods peptides in incomplete Freund's adjuvant are administered subcutaneously to HLA transgenic mice. Several weeks following immunization, splenocytes are removed and cultured in vitro in the presence of test peptide for approximately one week. Peptide-specific T cells are detected using, e.g., a 51Cr-release assay involving peptide sensitized target cells and target cells expressing endogenously generated antigen.

3) Demonstration of recall T cell responses from immune individuals who have been either effectively vaccinated and/or from chronically ill patients (see, e.g., Rehermann, B. et al., J. Exp. Med. 181:1047, 1995; Doolan, D. L. et al., Immunity 7:97, 1997; Bertoni, R. et al., J. Clin. Invest. 100:503, 1997; Threlkeld, S. C. et al., J. Immunol. 159:1648, 1997; Diepolder, H. M. et al., J. Virol. 71:6011, 1997). Accordingly, recall responses are detected by culturing PBL from subjects that have been exposed to the antigen due to disease and thus have generated an immune response "naturally", or from patients who were vaccinated against the antigen. PBL from subjects are cultured in vitro for 1-2 weeks in the presence of test peptide plus antigen presenting cells (APC) to allow activation of "memory" T cells, as compared to "naive" T cells. At the end of the culture period, T cell activity is detected using assays including $^{51}$Cr release involving peptide-sensitized targets, T cell proliferation, or lymphokine release.

VI.) 161P2F10B TRANSGENIC ANIMALS

Nucleic acids that encode a 161P2F10B-related protein can also be used to generate either transgenic animals or "knock out" animals that, in turn, are useful in the development and screening of therapeutically useful reagents. In accordance with established techniques, cDNA encoding 161P2F10B can be used to clone genomic DNA that encodes 161P2F10B. The cloned genomic sequences can then be used to generate transgenic animals containing cells that express DNA that encode 161P2F10B. Methods for generating transgenic animals, particularly animals such as mice or rats, have become conventional in the art and are described, for example, in U.S. Pat. Nos. 4,736,866 issued 12 Apr. 1988, and 4,870,009 issued 26 Sep. 1989. Typically, particular cells would be targeted for 161P2F10B transgene incorporation with tissue-specific enhancers.

Transgenic animals that include a copy of a transgene encoding 161P2F10B can be used to examine the effect of increased expression of DNA that encodes 161P2F10B. Such animals can be used as tester animals for reagents thought to confer protection from, for example, pathological conditions associated with its overexpression. In accordance with this aspect of the invention, an animal is treated with a reagent and a reduced incidence of a pathological condition, compared to untreated animals that bear the transgene, would indicate a potential therapeutic intervention for the pathological condition.

Alternatively, non-human homologues of 161P2F10B can be used to construct a 161P2F10B "knock out" animal that has a defective or altered gene encoding 161P2F10B as a result of homologous recombination between the endogenous gene encoding 161P2F10B and altered genomic DNA encoding 161P2F10B introduced into an embryonic cell of the animal. For example, cDNA that encodes 161P2F10B can be used to clone genomic DNA encoding 161P2F10B in accordance with established techniques. A portion of the genomic DNA encoding 161P2F10B can be deleted or replaced with another gene, such as a gene encoding a selectable marker that can be used to monitor integration. Typically, several kilobases of unaltered flanking DNA (both at the 5' and 3' ends) are included in the vector (see, e.g., Thomas and Capecchi, Cell, 51:503 (1987) for a description of homologous recombination vectors). The vector is introduced into an embryonic stem cell line (e.g., by electroporation) and cells in which the introduced DNA has homologously recombined with the endogenous DNA are selected (see, e.g., Li et al., Cell, 69:915 (1992)). The selected cells are then injected into a blastocyst of an animal (e.g., a mouse or rat) to form aggregation chimeras (see, e.g., Bradley, in Teratocarcinomas and Embryonic Stem Cells: A Practical Approach, E. J. Robertson, ed. (IRL, Oxford, 1987), pp. 113-152). A chimeric embryo can then be implanted into a suitable pseudopregnant female foster animal, and the embryo brought to term to create a "knock out" animal. Progeny harboring the homologously recombined DNA in their germ cells can be identified by standard techniques and used to breed animals in which all cells of the animal contain the homologously recombined DNA. Knock out animals can be characterized, for example, for their ability to defend against certain pathological conditions or for their development of pathological conditions due to absence of a 161P2F10B polypeptide.

VII.) METHODS FOR THE DETECTION OF 161P2F10B

Another aspect of the present invention relates to methods for detecting 161P2F10B polynucleotides and 161P2F10B-related proteins, as well as methods for identifying a cell that expresses 161P2F10B. The expression profile of 161P2F10B makes it a diagnostic marker for metastasized disease. Accordingly, the status of 161P2F10B gene products provides information useful for predicting a variety of factors including susceptibility to advanced stage disease, rate of progression, and/or tumor aggressiveness. As discussed in detail herein, the status of 161P2F10B gene products in patient samples can be analyzed by a variety protocols that are well known in the art including immunohistochemical analysis, the variety of Northern blotting techniques including in situ hybridization, RT-PCR analysis (for example on laser capture micro-dissected samples), Western blot analysis and tissue array analysis.

More particularly, the invention provides assays for the detection of 161P2F10B polynucleotides in a biological sample, such as serum, bone, prostate, and other tissues, urine, semen, cell preparations, and the like. Detectable 161P2F10B polynucleotides include, for example, a 161P2F10B gene or fragment thereof, 161P2F10B mRNA, alternative splice variant 161P2F10B mRNAs, and recombinant DNA or RNA molecules that contain a 161P2F10B polynucleotide. A number of methods for amplifying and/or detecting the presence of 161P2F10B polynucleotides are well known in the art and can be employed in the practice of this aspect of the invention.

In one embodiment, a method for detecting a 161P2F10B mRNA in a biological sample comprises producing cDNA from the sample by reverse transcription using at least one primer; amplifying the cDNA so produced using a 161P2F10B polynucleotides as sense and antisense primers to amplify 161P2F10B cDNAs therein; and detecting the presence of the amplified 161P2F10B cDNA. Optionally, the sequence of the amplified 161P2F10B cDNA can be determined.

In another embodiment, a method of detecting a 161P2F10B gene in a biological sample comprises first isolating genomic DNA from the sample; amplifying the isolated genomic DNA using 161P2F10B polynucleotides as sense and antisense primers; and detecting the presence of the amplified 161P2F10B gene. Any number of appropriate sense and antisense probe combinations can be designed from a 161P2F10B nucleotide sequence (see, e.g., FIG. 1) and used for this purpose.

The invention also provides assays for detecting the presence of a 161P2F10B protein in a tissue or other biological sample such as serum, semen, bone, prostate, urine, cell preparations, and the like. Methods for detecting a 161P2F10B-related protein are also well known and include, for example, immunoprecipitation, immunohistochemical analysis, Western blot analysis, molecular binding assays, ELISA, ELIFA and the like. For example, a method of detecting the presence of a 161P2F10B-related protein in a biological sample comprises first contacting the sample with a 161P2F10B antibody, a 161P2F10B-reactive fragment thereof, or a recombinant protein containing an antigen-binding region of a 161P2F10B antibody; and then detecting the binding of 161P2F10B-related protein in the sample.

Methods for identifying a cell that expresses 161P2F10B are also within the scope of the invention. In one embodiment, an assay for identifying a cell that expresses a 161P2F10B gene comprises detecting the presence of 161P2F10B mRNA in the cell. Methods for the detection of particular mRNAs in cells are well known and include, for example, hybridization assays using complementary DNA probes (such as in situ hybridization using labeled 161P2F10B riboprobes, Northern blot and related techniques) and various nucleic acid amplification assays (such as RT-PCR using complementary primers specific for 161P2F10B, and other amplification type detection methods, such as, for example, branched DNA, SISBA, TMA and the like). Alternatively, an assay for identifying a cell that expresses a 161P2F10B gene comprises detecting the presence of 161P2F10B-related protein in the cell or secreted by the cell. Various methods for the detection of proteins are well known in the art and are employed for the detection of 161P2F10B-related proteins and cells that express 161P2F10B-related proteins.

161P2F10B expression analysis is also useful as a tool for identifying and evaluating agents that modulate 161P2F10B gene expression. For example, 161P2F10B expression is significantly upregulated in kidney cancer, and is expressed in cancers of the tissues listed in Table I. Identification of a molecule or biological agent that inhibits 161P2F10B expression or over-expression in cancer cells is of therapeutic value. For example, such an agent can be identified by using a screen that quantifies 161P2F10B expression by RT-PCR, nucleic acid hybridization or antibody binding.

VIII.) METHODS FOR MONITORING THE STATUS OF 161P2F10B-RELATED GENES AND THEIR PRODUCTS

Oncogenesis is known to be a multistep process where cellular growth becomes progressively dysregulated and cells progress from a normal physiological state to precancerous and then cancerous states (see, e.g., Alers et al., Lab Invest. 77(5): 437-438 (1997) and Isaacs et al., Cancer Surv. 23: 19-32 (1995)). In this context, examining a biological sample for evidence of dysregulated cell growth (such as aberrant 161P2F10B expression in cancers) allows for early detection of such aberrant physiology, before a pathologic state such as cancer has progressed to a stage that therapeutic options are more limited and or the prognosis is worse. In such examinations, the status of 161P2F10B in a biological sample of interest can be compared, for example, to the status of 161P2F10B in a corresponding normal sample (e.g. a sample from that individual or alternatively another individual that is not affected by a pathology). An alteration in the status of 161P2F10B in the biological sample (as compared to the normal sample) provides evidence of dysregulated cellular growth. In addition to using a biological sample that is not affected by a pathology as a normal sample, one can also use a predetermined normative value such as a predetermined normal level of mRNA expression (see, e.g., Grever et al., J. Comp. Neurol. 1996 Dec. 9; 376(2): 306-14 and U.S. Pat. No. 5,837,501) to compare 161P2F10B status in a sample.

The term "status" in this context is used according to its art accepted meaning and refers to the condition or state of a gene and its products. Typically, skilled artisans use a number of parameters to evaluate the condition or state of a gene and its products. These include, but are not limited to the location of expressed gene products (including the location of 161P2F10B expressing cells) as well as the level, and biological activity of expressed gene products (such as 161P2F10B mRNA, polynucleotides and polypeptides).

Typically, an alteration in the status of 161P2F10B comprises a change in the location of 161P2F10B and/or 161P2F10B expressing cells and/or an increase in 161P2F10B mRNA and/or protein expression.

161P2F10B status in a sample can be analyzed by a number of means well known in the art, including without limitation, immunohistochemical analysis, in situ hybridization, RT-PCR analysis on laser capture micro-dissected samples, Western blot analysis, and tissue array analysis. Typical protocols for evaluating the status of a 161P2F10B gene and gene products are found, for example in Ausubel et al. eds., 1995, Current Protocols In Molecular Biology, Units 2 (Northern Blotting), 4 (Southern Blotting), 15 (Immunoblotting) and 18 (PCR Analysis). Thus, the status of 161P2F10B in a biological sample is evaluated by various methods utilized by skilled artisans including, but not limited to genomic Southern analysis (to examine, for example perturbations in a 161P2F10B gene), Northern analysis and/or PCR analysis of 161P2F10B mRNA (to examine, for example alterations in the polynucleotide sequences or expression levels of 161P2F10B mRNAs), and, Western and/or immunohistochemical analysis (to examine, for example alterations in polypeptide sequences, alterations in polypeptide localization within a sample, alterations in expression levels of 161P2F10B proteins and/or associations of 161P2F10B proteins with polypeptide binding partners). Detectable 161P2F10B polynucleotides include, for example, a 161P2F10B gene or fragment thereof, 161P2F10B mRNA, alternative splice variants, 161P2F10B mRNAs, and recombinant DNA or RNA molecules containing a 161P2F10B polynucleotide.

The expression profile of 161P2F10B makes it a diagnostic marker for local and/or metastasized disease, and provides information on the growth or oncogenic potential of a biological sample. In particular, the status of 161P2F10B provides information useful for predicting susceptibility to particular disease stages, progression, and/or tumor aggressiveness.

The invention provides methods and assays for determining 161P2F10B status and diagnosing cancers that express 161P2F10B, such as cancers of the tissues listed in Table I. For example, because 161P2F10B mRNA is so highly expressed in kidney and other cancers relative to normal kidney tissue, assays that evaluate the levels of 161P2F10B mRNA transcripts or proteins in a biological sample can be used to diagnose a disease associated with 161P2F10B dysregulation, and can provide prognostic information useful in defining appropriate therapeutic options.

The expression status of 161P2F10B provides information including the presence, stage and location of dysplastic, precancerous and cancerous cells, predicting susceptibility to various stages of disease, and/or for gauging tumor aggressiveness. Moreover, the expression profile makes it useful as an imaging reagent for metastasized disease. Consequently, an aspect of the invention is directed to the various molecular prognostic and diagnostic methods for examining the status of 161P2F10B in biological samples such as those from individuals suffering from, or suspected of suffering from a pathology characterized by dysregulated cellular growth, such as cancer.

As described above, the status of 161P2F10B in a biological sample can be examined by a number of well-known procedures in the art. For example, the status of 161P2F10B in a biological sample taken from a specific location in the body can be examined by evaluating the sample for the presence or absence of 161P2F10B expressing cells (e.g. those that express 161P2F10B mRNAs or proteins). This examination can provide evidence of dysregulated cellular growth, for example, when 161P2F10B-expressing cells are found in a biological sample that does not normally contain such cells (such as a lymph node), because such alterations in the status of 161P2F10B in a biological sample are often associated with dysregulated cellular growth. Specifically, one indicator of dysregulated cellular growth is the metastases of cancer cells from an organ of origin (such as the prostate) to a different area of the body (such as a lymph node). In this context, evidence of dysregulated cellular growth is important for example because occult lymph node metastases can be detected in a substantial proportion of patients with prostate cancer, and such metastases are associated with known predictors of disease progression (see, e.g., Murphy et al., Prostate 42(4): 315-317 (2000); Su et al., Semin Surg. Oncol. 18(1): 17-28 (2000) and Freeman et al., J Urol 1995 August 154(2 Pt 1):474-8).

In one aspect, the invention provides methods for monitoring 161P2F10B gene products by determining the status of 161P2F10B gene products expressed by cells from an individual suspected of having a disease associated with dysregulated cell growth (such as hyperplasia or cancer) and then comparing the status so determined to the status of 161P2F10B gene products in a corresponding normal sample. The presence of aberrant 161P2F10B gene products in the test sample relative to the normal sample provides an indication of the presence of dysregulated cell growth within the cells of the individual.

In another aspect, the invention provides assays useful in determining the presence of cancer in an individual, comprising detecting a significant increase in 161P2F10B mRNA or protein expression in a test cell or tissue sample relative to expression levels in the corresponding normal cell or tissue. The presence of 161P2F10B mRNA can, for example, be evaluated in tissues including but not limited to those listed in Table I. The presence of significant 161P2F10B expression in any of these tissues is useful to indicate the emergence, presence and/or severity of a cancer, since the corresponding normal tissues do not express 161P2F10B mRNA or express it at lower levels.

In a related embodiment, 161P2F10B status is determined at the protein level rather than at the nucleic acid level. For example, such a method comprises determining the level of 161P2F10B protein expressed by cells in a test tissue sample and comparing the level so determined to the level of 161P2F10B expressed in a corresponding normal sample. In one embodiment, the presence of 161P2F10B protein is evaluated, for example, using immunohistochemical methods. 161P2F10B antibodies or binding partners capable of detecting 161P2F10B protein expression are used in a variety of assay formats well known in the art for this purpose.

In a further embodiment, one can evaluate the status of 161P2F10B nucleotide and amino acid sequences in a biological sample in order to identify perturbations in the structure of these molecules. These perturbations can include insertions, deletions, substitutions and the like. Such evaluations are useful because perturbations in the nucleotide and amino acid sequences are observed in a large number of proteins associated with a growth dysregulated phenotype (see, e.g., Marrogi et al., 1999, J. Cutan. Pathol. 26(8):369-378). For example, a mutation in the sequence of 161P2F10B may be indicative of the presence or promotion of a tumor. Such assays therefore have diagnostic and predictive value where a mutation in 161P2F10B indicates a potential loss of function or increase in tumor growth.

A wide variety of assays for observing perturbations in nucleotide and amino acid sequences are well known in the art. For example, the size and structure of nucleic acid or amino acid sequences of 161P2F10B gene products are observed by the Northern, Southern, Western, PCR and DNA sequencing protocols discussed herein. In addition, other methods for observing perturbations in nucleotide and amino acid sequences such as single strand conformation polymorphism analysis are well known in the art (see, e.g., U.S. Pat. Nos. 5,382,510 issued 7 Sep. 1999, and 5,952,170 issued 17 Jan. 1995).

Additionally, one can examine the methylation status of a 161P2F10B gene in a biological sample. Aberrant demethylation and/or hypermethylation of CpG islands in gene 5' regulatory regions frequently occurs in immortalized and transformed cells, and can result in altered expression of various genes. For example, promoter hypermethylation of the pi-class glutathione S-transferase (a protein expressed in normal prostate but not expressed in >90% of prostate carcinomas) appears to permanently silence transcription of this gene and is the most frequently detected genomic alteration in prostate carcinomas (De Marzo et al., Am. J. Pathol. 155(6): 1985-1992 (1999)). In addition, this alteration is present in at least 70% of cases of high-grade prostatic intraepithelial neoplasia (PIN) (Brooks et al., Cancer Epidemiol. Biomarkers Prev., 1998, 7:531-536). In another example, expression of the LAGE-I tumor specific gene (which is not expressed in normal prostate but is expressed in 25-50% of prostate cancers) is induced by deoxy-azacytidine in lymphoblastoid cells, suggesting that tumoral expression is due to demethylation (Lethe et al., Int. J. Cancer 76(6): 903-908 (1998)). A variety of assays for examining methylation status of a gene are well known in the art. For example, one can utilize, in Southern hybridization approaches, methylation-sensitive restriction enzymes that cannot cleave sequences that contain methylated CpG sites to assess the methylation status of CpG islands. In addition, MSP (methylation specific PCR) can rapidly profile the methylation status of all the CpG sites present in a CpG island of a given gene. This procedure involves initial modification of DNA by sodium bisulfite (which will convert all unmethylated cytosines to uracil) followed by amplification using primers specific for methylated versus unmethylated DNA. Protocols involving methylation interference can also be found for example in Current Protocols In Molecular Biology, Unit 12, Frederick M. Ausubel et al. eds., 1995.

Gene amplification is an additional method for assessing the status of 161P2F10B. Gene amplification is measured in a sample directly, for example, by conventional Southern blotting or Northern blotting to quantitate the transcription of mRNA (Thomas, 1980, Proc. Natl. Acad. Sci. USA, 77:5201 5205), dot blotting (DNA analysis), or in situ hybridization, using an appropriately labeled probe, based on the sequences provided herein. Alternatively, antibodies are employed that recognize specific duplexes, including DNA duplexes, RNA duplexes, and DNA RNA hybrid duplexes or DNA protein duplexes. The antibodies in turn are labeled and the assay carried out where the duplex is bound to a surface, so that upon the formation of duplex on the surface, the presence of antibody bound to the duplex can be detected.

Biopsied tissue or peripheral blood can be conveniently assayed for the presence of cancer cells using for example, Northern, dot blot or RT-PCR analysis to detect 161P2F10B expression. The presence of RT-PCR amplifiable 161P2F10B mRNA provides an indication of the presence of cancer. RT-PCR assays are well known in the art. RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik et al., 1997, Urol. Res. 25:373-384; Ghossein et al., 1995, J. Clin. Oncol. 13:1195-2000; Heston et al., 1995, Clin. Chem. 41:1687-1688).

A further aspect of the invention is an assessment of the susceptibility that an individual has for developing cancer. In one embodiment, a method for predicting susceptibility to cancer comprises detecting 161P2F10B mRNA or 161P2F10B protein in a tissue sample, its presence indicating susceptibility to cancer, wherein the degree of 161P2F10B mRNA expression correlates to the degree of susceptibility. In a specific embodiment, the presence of 161P2F10B in prostate or other tissue is examined, with the presence of 161P2F10B in the sample providing an indication of prostate cancer susceptibility (or the emergence or existence of a prostate tumor). Similarly, one can evaluate the integrity 161P2F10B nucleotide and amino acid sequences in a biological sample, in order to identify perturbations in the structure of these molecules such as insertions, deletions, substitutions and the like. The presence of one or more perturbations in 161P2F10B gene products in the sample is an indication of cancer susceptibility (or the emergence or existence of a tumor).

The invention also comprises methods for gauging tumor aggressiveness. In one embodiment, a method for gauging aggressiveness of a tumor comprises determining the level of 161P2F10B mRNA or 161P2F10B protein expressed by tumor cells, comparing the level so determined to the level of 161P2F10B mRNA or 161P2F10B protein expressed in a corresponding normal tissue taken from the same individual or a normal tissue reference sample, wherein the degree of 161P2F10B mRNA or 161P2F10B protein expression in the tumor sample relative to the normal sample indicates the degree of aggressiveness. In a specific embodiment, aggressiveness of a tumor is evaluated by determining the extent to which 161P2F10B is expressed in the tumor cells, with higher expression levels indicating more aggressive tumors. Another embodiment is the evaluation of the integrity of 161P2F10B nucleotide and amino acid sequences in a biological sample, in order to identify perturbations in the structure of these molecules such as insertions, deletions, substitutions and the like. The presence of one or more perturbations indicates more aggressive tumors.

Another embodiment of the invention is directed to methods for observing the progression of a malignancy in an individual over time. In one embodiment, methods for observing the progression of a malignancy in an individual over time comprise determining the level of 161P2F10B mRNA or 161P2F10B protein expressed by cells in a sample of the tumor, comparing the level so determined to the level of 161P2F10B mRNA or 161P2F10B protein expressed in an equivalent tissue sample taken from the same individual at a different time, wherein the degree of 161P2F10B mRNA or 161P2F10B protein expression in the tumor sample over time provides information on the progression of the cancer. In a specific embodiment, the progression of a cancer is evaluated by determining 161P2F10B expression in the tumor cells over time, where increased expression over time indicates a progression of the cancer. Also, one can evaluate the integrity 161P2F10B nucleotide and amino acid sequences in a biological sample in order to identify perturbations in the structure of these molecules such as insertions, deletions, substitutions and the like, where the presence of one or more perturbations indicates a progression of the cancer.

The above diagnostic approaches can be combined with any one of a wide variety of prognostic and diagnostic protocols known in the art. For example, another embodiment of the invention is directed to methods for observing a coincidence between the expression of 161P2F10B gene and 161P2F10B gene products (or perturbations in 161P2F10B gene and 161P2F10B gene products) and a factor that is associated with malignancy, as a means for diagnosing and prognosticating the status of a tissue sample. A wide variety of factors associated with malignancy can be utilized, such as the expression of genes associated with malignancy as well as gross cytological observations (see, e.g., Bocking et al., 1984, Anal. Quant. Cytol. 6(2):74-88; Epstein, 1995, Hum. Pathol. 26(2):223-9; Thorson et al., 1998, Mod. Pathol. 11(6):543-51; Baisden et al., 1999, Am. J. Surg. Pathol. 23(8):918-24). Methods for observing a coincidence between the expression of 161P2F10B gene and 161P2F10B gene products (or perturbations in 161P2F10B gene and 161P2F10B gene products) and another factor that is associated with malignancy are useful, for example, because the presence of a set of specific factors that coincide with disease provides information crucial for diagnosing and prognosticating the status of a tissue sample.

Methods for detecting and quantifying the expression of 161P2F10B mRNA or protein are described herein, and standard nucleic acid and protein detection and quantification technologies are well known in the art. Standard methods for the detection and quantification of 161P2F10B mRNA include in situ hybridization using labeled 161P2F10B riboprobes, Northern blot and related techniques using 161P2F10B polynucleotide probes, RT-PCR analysis using primers specific for 161P2F10B, and other amplification type detection methods, such as, for example, branched DNA, SISBA, TMA and the like. In a specific embodiment, semi-quantitative RT-PCR is used to detect and quantify 161P2F10B mRNA expression. Any number of primers capable of amplifying 161P2F10B can be used for this purpose, including but not limited to the various primer sets specifically described herein. In a specific embodiment, polyclonal or monoclonal antibodies specifically reactive with the wild-type 161P2F10B protein can be used in an immunohistochemical assay of biopsied tissue.

IX.) IDENTIFICATION OF MOLECULES THAT INTERACT WITH 161P2F10B

The 161P2F10B protein and nucleic acid sequences disclosed herein allow a skilled artisan to identify proteins, small molecules and other agents that interact with 161P2F10B, as well as pathways activated by 161P2F10B via any one of a variety of art accepted protocols. For example, one can utilize one of the so-called interaction trap systems (also referred to as the "two-hybrid assay"). In such systems, molecules interact and reconstitute a transcription factor which directs expression of a reporter gene, whereupon the expression of the reporter gene is assayed. Other systems identify protein-protein interactions in vivo through reconstitution of a eukaryotic transcriptional activator, see, e.g., U.S. Pat. Nos. 5,955,280 issued 21 Sep. 1999, 5,925,523 issued 20 Jul. 1999, 5,846,722 issued 8 Dec. 1998 and 6,004,746 issued 21 Dec. 1999. Algorithms are also available in the art for genome-based predictions of protein function (see, e.g., Marcotte, et al., Nature 402: 4 Nov. 1999, 83-86).

Alternatively one can screen peptide libraries to identify molecules that interact with 161P2F10B protein sequences. In such methods, peptides that bind to 161P2F10B are identified by screening libraries that encode a random or controlled collection of amino acids. Peptides encoded by the libraries are expressed as fusion proteins of bacteriophage coat proteins, the bacteriophage particles are then screened against the 161P2F10B protein(s).

Accordingly, peptides having a wide variety of uses, such as therapeutic, prognostic or diagnostic reagents, are thus identified without any prior information on the structure of the expected ligand or receptor molecule. Typical peptide libraries and screening methods that can be used to identify molecules that interact with 161P2F10B protein sequences are disclosed for example in U.S. Pat. Nos. 5,723,286 issued 3 Mar. 1998 and 5,733,731 issued 31 Mar. 1998.

Alternatively, cell lines that express 161P2F10B are used to identify protein-protein interactions mediated by 161P2F10B. Such interactions can be examined using immunoprecipitation techniques (see, e.g., Hamilton B. J., et al. Biochem. Biophys. Res. Commun. 1999, 261:646-51). 161P2F10B protein can be immunoprecipitated from 161P2F10B-expressing cell lines using anti-161P2F10B antibodies. Alternatively, antibodies against His-tag can be used in a cell line engineered to express fusions of 161P2F10B and a His-tag (vectors mentioned above). The immunoprecipitated complex can be examined for protein association by procedures such as Western blotting, $^{35}$S-methionine labeling of proteins, protein microsequencing, silver staining and two-dimensional gel electrophoresis.

Small molecules and ligands that interact with 161P2F10B can be identified through related embodiments of such screening assays. For example, small molecules can be identified that interfere with protein function, including molecules that interfere with 161P2F10B's ability to mediate phosphorylation and de-phosphorylation, interaction with DNA or RNA molecules as an indication of regulation of cell cycles, second messenger signaling or tumorigenesis. Similarly, small molecules that modulate 161P2F10B-related ion channel, protein pump, or cell communication functions are identified and used to treat patients that have a cancer that expresses 161P2F10B (see, e.g., Hille, B., Ionic Channels of Excitable Membranes 2nd Ed., Sinauer Assoc., Sunderland, Mass., 1992). Moreover, ligands that regulate 161P2F10B function can be identified based on their ability to bind 161P2F10B and activate a reporter construct. Typical methods are discussed for example in U.S. Pat. No. 5,928,868 issued 27 Jul. 1999, and include methods for forming hybrid ligands in which at least one ligand is a small molecule. In an illustrative embodiment, cells engineered to express a fusion protein of 161P2F10B and a DNA-binding protein are used to co-express a fusion protein of a hybrid ligand/small molecule and a cDNA library transcriptional activator protein. The cells further contain a reporter gene, the expression of which is conditioned on the proximity of the first and second fusion proteins to each other, an event that occurs only if the hybrid ligand binds to target sites on both hybrid proteins. Those cells that express the reporter gene are selected and the unknown small molecule or the unknown ligand is identified. This method provides a means of identifying modulators, which activate or inhibit 161P2F10B.

An embodiment of this invention comprises a method of screening for a molecule that interacts with a 161P2F10B amino acid sequence shown in FIG. 1, comprising the steps of contacting a population of molecules with a 161P2F10B amino acid sequence, allowing the population of molecules and the 161P2F10B amino acid sequence to interact under conditions that facilitate an interaction, determining the presence of a molecule that interacts with the 161P2F10B amino acid sequence, and then separating molecules that do not interact with the 161P2F10B amino acid sequence from molecules that do. In a specific embodiment, the method further comprises purifying, characterizing and identifying a molecule that interacts with the 161P2F10B amino acid sequence. The identified molecule can be used to modulate a function performed by 161P2F10B. In a preferred embodiment, the 161P2F10B amino acid sequence is contacted with a library of peptides.

X.) THERAPEUTIC METHODS AND COMPOSITIONS

The identification of 161P2F10B as a protein that is normally expressed in a restricted set of tissues, but which is also expressed in cancers such as those listed in Table I, opens a number of therapeutic approaches to the treatment of such cancers.

Of note, targeted antitumor therapies have been useful even when the targeted protein is expressed on normal tissues, even vital normal organ tissues. A vital organ is one that is necessary to sustain life, such as the heart or colon. A non-vital organ is one that can be removed whereupon the individual is still able to survive. Examples of non-vital organs are ovary, breast, and prostate.

For example, Herceptin® is an FDA approved pharmaceutical that consists of an antibody which is immunoreactive with the protein variously known as HER2, HER2/neu, and erb-b-2. It is marketed by Genentech and has been a commercially successful antitumor agent. Herceptin® sales reached almost $400 million in 2002. Herceptin® is a treatment for HER2 positive metastatic breast cancer. However, the expression of HER2 is not limited to such tumors. The same protein is expressed in a number of normal tissues. In particular, it is known that HER2/neu is present in normal kidney and heart, thus these tissues are present in all human recipients of Herceptin. The presence of HER2/neu in normal kidney is also confirmed by Latif, Z., et al., B. J. U. International (2002) 89:5-9. As shown in this article (which evaluated whether renal cell carcinoma should be a preferred indication for anti-HER2 antibodies such as Herceptin) both protein and mRNA are produced in benign renal tissues. Notably, HER2/neu protein was strongly overexpressed in benign renal tissue.

Despite the fact that HER2/neu is expressed in such vital tissues as heart and kidney, Herceptin is a very useful, FDA approved, and commercially successful drug. The effect of Herceptin on cardiac tissue, i.e., "cardiotoxicity," has merely been a side effect to treatment. When patients were treated with Herceptin alone, significant cardiotoxicity occurred in a very low percentage of patients. To minimize cardiotoxicity there is a more stringent entry requirement for the treatment with HER2/neu. Factors such as predisposition to heart condition are evaluated before treatment can occur.

Of particular note, although kidney tissue is indicated to exhibit normal expression, possibly even higher expression than cardiac tissue, kidney has no appreciable Herceptin side effect whatsoever. Moreover, of the diverse array of normal tissues in which HER2 is expressed, there is very little occurrence of any side effect. Only cardiac tissue has manifested any appreciable side effect at all. A tissue such as kidney, where HER2/neu expression is especially notable, has not been the basis for any side effect.

Furthermore, favorable therapeutic effects have been found for antitumor therapies that target epidermal growth factor receptor (EGFR); Erbitux (ImClone). EGFR is also expressed in numerous normal tissues. There have been very limited side effects in normal tissues following use of anti-EGFR therapeutics. A general side effect that occurs with the EGFR treatment is a severe skin rash observed in 100% of the patients undergoing treatment.

Thus, expression of a target protein in normal tissue, even vital normal tissue, does not defeat the utility of a targeting agent for the protein as a therapeutic for certain tumors in which the protein is also overexpressed. For example, expression in vital organs is not in and of itself detrimental. In addition, organs regarded as dispensible, such as the prostate and ovary, can be removed without affecting mortality. Finally, some vital organs are not affected by normal organ expression because of an immunoprivilege. Immunoprivileged organs are organs that are protected from blood by a blood-organ barrier and thus are not accessible to immunotherapy. Examples of immunoprivileged organs are the brain and testis.

Accordingly, therapeutic approaches that inhibit the activity of a 161P2F10B protein are useful for patients suffering from a cancer that expresses 161P2F10B. These therapeutic approaches generally fall into three classes. The first class modulates 161P2F10B function as it relates to tumor cell growth leading to inhibition or retardation of tumor cell growth or inducing its killing. The second class comprises various methods for inhibiting the binding or association of a 161P2F10B protein with its binding partner or with other proteins. The third class comprises a variety of methods for inhibiting the transcription of a 161P2F10B gene or translation of 161P2F10B mRNA.

X.A.) Anti-Cancer Vaccines

The invention provides cancer vaccines comprising a 161P2F10B-related protein or 161P2F10B-related nucleic acid. In view of the expression of 161P2F10B, cancer vaccines prevent and/or treat 161P2F10B-expressing cancers with minimal or no effects on non-target tissues. The use of a tumor antigen in a vaccine that generates cell-mediated humoral immune responses as anti-cancer therapy is well known in the art and has been employed in prostate cancer using human PSMA and rodent PAP immunogens (Hodge et al., 1995, Int. J. Cancer 63:231-237; Fong et al., 1997, J. Immunol. 159:3113-3117).

Such methods can be readily practiced by employing a 161P2F10B-related protein, or a 161P2F10B-encoding nucleic acid molecule and recombinant vectors capable of expressing and presenting the 161P2F10B immunogen (which typically comprises a number of T-cell epitopes or antibody). Skilled artisans understand that a wide variety of vaccine systems for delivery of immunoreactive epitopes are known in the art (see, e.g., Heryln et al., Ann Med 1999 February 31(1):66-78; Maruyama et al., Cancer Immunol Immunother 2000 June 49(3):123-32) Briefly, such methods of generating an immune response (e.g. cell-mediated and/or humoral) in a mammal, comprise the steps of: exposing the mammal's immune system to an immunoreactive epitope (e.g. an epitope present in a 161P2F10B protein shown in FIG. 1 or analog or homolog thereof) so that the mammal generates an immune response that is specific for that epitope (e.g. generates antibodies that specifically recognize that epitope).

The entire 161P2F10B protein, immunogenic regions or epitopes thereof can be combined and delivered by various means. Such vaccine compositions can include, for example, lipopeptides (e.g., Vitiello, A. et al., J. Clin. Invest. 95:341, 1995), peptide compositions encapsulated in poly(DL-lactide-co-glycolide) ("PLG") microspheres (see, e.g., Eldridge, et al., Molec. Immunol. 28:287-294, 1991: Alonso et al., Vaccine 12:299-306, 1994; Jones et al., Vaccine 13:675-681, 1995), peptide compositions contained in immune stimulating complexes (ISCOMS) (see, e.g., Takahashi et al., Nature 344:873-875, 1990; Hu et al., Clin Exp Immunol. 113:235-243, 1998), multiple antigen peptide systems (MAPs) (see e.g., Tam, J. P., Proc. Natl. Acad. Sci. U.S.A. 85:5409-5413, 1988; Tam, J. P., J. Immunol. Methods 196:17-32, 1996), peptides formulated as multivalent peptides; peptides for use in ballistic delivery systems, typically crystallized peptides, viral delivery vectors (Perkus, M. E. et al., In: Concepts in vaccine development, Kaufmann, S. H. E., ed., p. 379, 1996; Chakrabarti, S. et al., Nature 320:535, 1986; Hu, S. L. et al., Nature 320:537, 1986; Kieny, M.-P. et al., AIDS Bio/Technology 4:790, 1986; Top, F. H. et al., J. Infect. Dis. 124:148, 1971; Chanda, P. K. et al., Virology 175:535, 1990), particles of viral or synthetic origin (e.g., Kofler, N. et al., J. Immunol. Methods. 192:25, 1996; Eldridge, J. H. et al., Sem. Hematol. 30:16, 1993; Falo, L. D., Jr. et al., Nature Med. 7:649, 1995), adjuvants (Warren, H. S., Vogel, F. R., and Chedid, L. A. Annu. Rev. Immunol. 4:369, 1986; Gupta, R. K. et al., Vaccine 11:293, 1993), liposomes (Reddy, R. et al., J. Immunol. 148:1585, 1992; Rock, K. L., Immunol. Today 17:131, 1996), or, naked or particle absorbed cDNA (Ulmer, J. B. et al., Science 259:1745, 1993; Robinson, H. L., Hunt, L. A., and Webster, R. G., Vaccine 11:957, 1993; Shiver, J. W. et al., In: Concepts in vaccine development, Kaufmann, S. H. E., ed., p. 423, 1996; Cease, K. B., and Berzofsky, J. A., Annu. Rev. Immunol. 12:923, 1994 and Eldridge, J. H. et al., Sem. Hematol. 30:16, 1993). Toxin-targeted delivery technologies, also known as receptor mediated targeting, such as those of Avant Immunotherapeutics, Inc. (Needham, Mass.) may also be used.

In patients with 161P2F10B-associated cancer, the vaccine and antibody compositions of the invention can also be used in conjunction with other treatments used for cancer, e.g., surgery, chemotherapy, drug therapies, radiation therapies, etc. including use in combination with immune adjuvants such as IL-2, IL-12, GM-CSF, and the like.

Cellular Vaccines:

CTL epitopes can be determined using specific algorithms to identify peptides within 161P2F10B protein that bind corresponding HLA alleles (e.g., Brown University, BIMAS, and SYFPEITHI. In a preferred embodiment, a 161P2F10B immunogen contains one or more amino acid sequences identified using techniques well known in the art, such as the sequences shown in Tables previously disclosed or a peptide of 8, 9, 10 or 11 amino acids specified by an HLA Class I motif/supermotif (e.g., Table IV (A), Table IV (D), or Table IV (E)) and/or a peptide of at least 9 amino acids that comprises an HLA Class II motif/supermotif (e.g., Table IV (B) or Table IV (C)). As is appreciated in the art, the HLA Class I binding groove is essentially closed ended so that peptides of only a particular size range can fit into the groove and be bound, generally HLA Class I epitopes are 8, 9, 10, or 11 amino acids long. In contrast, the HLA Class II binding groove is essentially open ended; therefore a peptide of about 9 or more amino acids can be bound by an HLA Class II molecule. Due to the binding groove differences between HLA Class I and II, HLA Class I motifs are length specific, i.e., position two of a Class I motif is the second amino acid in an amino to carboxyl direction of the peptide. The amino acid positions in a Class II motif are relative only to each other, not the overall peptide, i.e., additional amino acids can be attached to the amino and/or carboxyl termini of a motif-bearing sequence. HLA Class II epitopes are often 9, 10, 11, 12, 13, 14, 15, 16, 17, 18, 19, 20, 21, 22, 23, 24, or 25 amino acids long, or longer than 25 amino acids.

A wide variety of methods for generating an immune response in a mammal are known in the art (for example as the first step in the generation of hybridomas). Methods of generating an immune response in a mammal comprise exposing the mammal's immune system to an immunogenic epitope on a protein (e.g. a 161P2F10B protein) so that an immune response is generated. A typical embodiment consists of a method for generating an immune response to 161P2F10B in a host, by contacting the host with a sufficient amount of at least one 161P2F10B B cell or cytotoxic T-cell epitope or analog thereof; and at least one periodic interval thereafter re-contacting the host with the 161P2F10B B cell or cytotoxic T-cell epitope or analog thereof. A specific embodiment consists of a method of generating an immune response against a 161P2F10B-related protein or a man-made multiepitopic peptide comprising: administering 161P2F10B immunogen (e.g. a 161P2F10B protein or a peptide fragment thereof, a 161P2F10B fusion protein or analog etc.) in a vaccine preparation to a human or another mammal. Typically, such vaccine preparations further contain a suitable adjuvant (see, e.g., U.S. Pat. No. 6,146,635) or a universal helper epitope such as a PADRE™ peptide (Epimmune Inc., San Diego, Calif.; see, e.g., Alexander et al., J. Immunol. 2000 164(3); 164(3): 1625-1633; Alexander et al., Immunity 1994 1(9): 751-761 and Alexander et al., Immunol. Res. 1998 18(2): 79-92). An alternative method comprises generating an immune response in an individual against a 161P2F10B immunogen by: administering in vivo to muscle or skin of the individual's body a DNA molecule that comprises a DNA sequence that encodes a 161P2F10B immunogen, the DNA sequence operatively linked to regulatory sequences which control the expression of the DNA sequence; wherein the DNA molecule is taken up by cells, the DNA sequence is expressed in the cells and an immune response is generated against the immunogen (see, e.g., U.S. Pat. No. 5,962,428). Optionally a genetic vaccine facilitator such as anionic lipids; saponins; lectins; estrogenic compounds; hydroxylated lower alkyls; dimethyl sulfoxide; and urea is also administered. In addition, an antiidiotypic antibody can be administered that mimics 161P2F10B, in order to generate a response to the target antigen.

Nucleic Acid Vaccines:

Vaccine compositions of the invention include nucleic acid-mediated modalities. DNA or RNA that encode protein(s) of the invention can be administered to a patient. Genetic immunization methods can be employed to generate prophylactic or therapeutic humoral and cellular immune responses directed against cancer cells expressing 161P2F10B. Constructs comprising DNA encoding a 161P2F10B-related protein/immunogen and appropriate regulatory sequences can be injected directly into muscle or skin of an individual, such that the cells of the muscle or skin take-up the construct and express the encoded 161P2F10B protein/immunogen. Alternatively, a vaccine comprises a 161P2F10B-related protein. Expression of the 161P2F10B-related protein immunogen results in the generation of prophylactic or therapeutic humoral and cellular immunity against cells that bear a 161P2F10B protein. Various prophylactic and therapeutic genetic immunization techniques known in the art can be used. Nucleic acid-based delivery is described, for instance, in Wolff et. al., Science 247:1465 (1990) as well as U.S. Pat. Nos. 5,580,859; 5,589,466; 5,804, 566; 5,739,118; 5,736,524; 5,679,647; WO 98/04720. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687).

For therapeutic or prophylactic immunization purposes, proteins of the invention can be expressed via viral or bacterial vectors. Various viral gene delivery systems that can be used in the practice of the invention include, but are not limited to, vaccinia, fowlpox, canarypox, adenovirus, influenza, poliovirus, adeno-associated virus, lentivirus, and sindbis virus (see, e.g., Restifo, 1996, Curr. Opin. Immunol.

8:658-663; Tsang et al. J. Natl. Cancer Inst. 87:982-990 (1995)). Non-viral delivery systems can also be employed by introducing naked DNA encoding a 161P2F10B-related protein into the patient (e.g., intramuscularly or intradermally) to induce an anti-tumor response.

Vaccinia virus is used, for example, as a vector to express nucleotide sequences that encode the peptides of the invention. Upon introduction into a host, the recombinant vaccinia virus expresses the protein immunogenic peptide, and thereby elicits a host immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 351:456-460 (1991). A wide variety of other vectors useful for therapeutic administration or immunization of the peptides of the invention, e.g. adeno and adeno-associated virus vectors, retroviral vectors, Salmonella typhi vectors, detoxified anthrax toxin vectors, and the like, will be apparent to those skilled in the art from the description herein.

Thus, gene delivery systems are used to deliver a 161P2F10B-related nucleic acid molecule. In one embodiment, the full-length human 161P2F10B cDNA is employed. In another embodiment, 161P2F10B nucleic acid molecules encoding specific cytotoxic T lymphocyte (CTL) and/or antibody epitopes are employed.

Ex Vivo Vaccines

Various ex vivo strategies can also be employed to generate an immune response. One approach involves the use of antigen presenting cells (APCs) such as dendritic cells (DC) to present 161P2F10B antigen to a patient's immune system. Dendritic cells express MHC class I and II molecules, B7 co-stimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa et al., 1996, Prostate 28:65-69; Murphy et al., 1996, Prostate 29:371-380). Thus, dendritic cells can be used to present 161P2F10B peptides to T cells in the context of MHC class I or II molecules. In one embodiment, autologous dendritic cells are pulsed with 161P2F10B peptides capable of binding to MHC class I and/or class II molecules. In another embodiment, dendritic cells are pulsed with the complete 161P2F10B protein. Yet another embodiment involves engineering the overexpression of a 161P2F10B gene in dendritic cells using various implementing vectors known in the art, such as adenovirus (Arthur et al., 1997, Cancer Gene Ther. 4:17-25), retrovirus (Henderson et al., 1996, Cancer Res. 56:3763-3770), lentivirus, adeno-associated virus, DNA transfection (Ribas et al., 1997, Cancer Res. 57:2865-2869), or tumor-derived RNA transfection (Ashley et al., 1997, J. Exp. Med. 186:1177-1182). Cells that express 161P2F10B can also be engineered to express immune modulators, such as GM-CSF, and used as immunizing agents.

X.B.) 161P2F10B as a Target for Antibody-Based Therapy

161P2F10B is an attractive target for antibody-based therapeutic strategies. A number of antibody strategies are known in the art for targeting both extracellular and intracellular molecules (see, e.g., complement and ADCC mediated killing as well as the use of intrabodies). Because 161P2F10B is expressed by cancer cells of various lineages relative to corresponding normal cells, systemic administration of 161P2F10B-immunoreactive compositions are prepared that exhibit excellent sensitivity without toxic, non-specific and/or non-target effects caused by binding of the immunoreactive composition to non-target organs and tissues. Antibodies specifically reactive with domains of 161P2F10B are useful to treat 161P2F10B-expressing cancers systemically, either as conjugates with a toxin or therapeutic agent, or as naked antibodies capable of inhibiting cell proliferation or function.

161P2F10B antibodies can be introduced into a patient such that the antibody binds to 161P2F10B and modulates a function, such as an interaction with a binding partner, and consequently mediates destruction of the tumor cells and/or inhibits the growth of the tumor cells. Mechanisms by which such antibodies exert a therapeutic effect can include complement-mediated cytolysis, antibody-dependent cellular cytotoxicity, modulation of the physiological function of 161P2F10B, inhibition of ligand binding or signal transduction pathways, modulation of tumor cell differentiation, alteration of tumor angiogenesis factor profiles, and/or apoptosis.

Those skilled in the art understand that antibodies can be used to specifically target and bind immunogenic molecules such as an immunogenic region of a 161P2F10B sequence shown in FIG. 1. In addition, skilled artisans understand that it is routine to conjugate antibodies to cytotoxic agents (see, e.g., Slevers et al. Blood 93:11 3678-3684 (Jun. 1, 1999)). When cytotoxic and/or therapeutic agents are delivered directly to cells, such as by conjugating them to antibodies specific for a molecule expressed by that cell (e.g. 161P2F10B), the cytotoxic agent will exert its known biological effect (i.e. cytotoxicity) on those cells.

A wide variety of compositions and methods for using antibody-cytotoxic agent conjugates to kill cells are known in the art. In the context of cancers, typical methods entail administering to an animal having a tumor a biologically effective amount of a conjugate comprising a selected cytotoxic and/or therapeutic agent linked to a targeting agent (e.g. an anti-161P2F10B antibody) that binds to a marker (e.g. 161P2F10B) expressed, accessible to binding or localized on the cell surfaces. A typical embodiment is a method of delivering a cytotoxic and/or therapeutic agent to a cell expressing 161P2F10B, comprising conjugating the cytotoxic agent to an antibody that immunospecifically binds to a 161P2F10B epitope, and, exposing the cell to the antibody-agent conjugate. Another illustrative embodiment is a method of treating an individual suspected of suffering from metastasized cancer, comprising a step of administering parenterally to said individual a pharmaceutical composition comprising a therapeutically effective amount of an antibody conjugated to a cytotoxic and/or therapeutic agent.

Cancer immunotherapy using anti-161P2F10B antibodies can be done in accordance with various approaches that have been successfully employed in the treatment of other types of cancer, including but not limited to colon cancer (Arlen et al., 1998, Crit. Rev. Immunol. 18:133-138), multiple myeloma (Ozaki et al., 1997, Blood 90:3179-3186, Tsunenari et al., 1997, Blood 90:2437-2444), gastric cancer (Kasprzyk et al., 1992, Cancer Res. 52:2771-2776), B-cell lymphoma (Funakoshi et al., 1996, J. Immunother. Emphasis Tumor Immunol. 19:93-101), leukemia (Zhong et al., 1996, Leuk. Res. 20:581-589), colorectal cancer (Moun et al., 1994, Cancer Res. 54:6160-6166; Velders et al., 1995, Cancer Res. 55:4398-4403), and breast cancer (Shepard et al., 1991, J. Clin. Immunol. 11:117-127). Some therapeutic approaches involve conjugation of naked antibody to a toxin or radioisotope, such as the conjugation of $Y^{91}$ or $I^{131}$ to anti-CD20 antibodies (e.g., Zevalin™, IDEC Pharmaceuticals Corp. or Bexxar™, Coulter Pharmaceuticals) respectively, while others involve co-administration of antibodies and other therapeutic agents, such as Herceptin™ (trastuzu MAb) with paclitaxel (Genentech, Inc.). The antibodies can be conjugated to a therapeutic agent. To treat kidney cancer, for example, 161P2F10B antibodies can be administered in conjunction with radiation, chemotherapy or hormone ablation. Also, antibodies can be conjugated to a toxin such as calicheamicin (e.g., Mylotarg™, Wyeth-Ayerst, Madison, N.J., a recombinant humanized IgG$_4$ kappa antibody conjugated to antitumor antibiotic calicheamicin) or a maytansinoid (e.g., taxane-based Tumor-Activated Prodrug, TAP, platform, ImmunoGen, Cambridge, Mass., also see e.g., U.S. Pat. No. 5,416,064) or Auristatin E (Nat. Biotechnol. 2003 July; 21(7):778-84. (Seattle Genetics)).

Although 161P2F10B antibody therapy is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well. Fan et al. (Cancer Res. 53:4637-4642, 1993), Prewett et al. (International J. of Onco. 9:217-224, 1996), and Hancock et al. (Cancer Res. 51:4575-4580, 1991) describe the use of various antibodies together with chemotherapeutic agents.

Although 161P2F10B antibody therapy is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well.

Cancer patients can be evaluated for the presence and level of 161P2F10B expression, preferably using immunohistochemical assessments of tumor tissue, quantitative 161P2F10B imaging, or other techniques that reliably indicate the presence and degree of 161P2F10B expression Immunohistochemical analysis of tumor biopsies or surgical specimens is preferred for this purpose. Methods for immunohistochemical analysis of tumor tissues are well known in the art.

Anti-161P2F10B monoclonal antibodies that treat prostate and other cancers include those that initiate a potent immune response against the tumor or those that are directly cytotoxic. In this regard, anti-161P2F10B monoclonal antibodies (MAbs) can elicit tumor cell lysis by either complement-mediated or antibody-dependent cell cytotoxicity (ADCC) mechanisms, both of which require an intact Fc portion of the immunoglobulin molecule for interaction with effector cell Fc receptor sites on complement proteins. In addition, anti-161P2F10B MAbs that exert a direct biological effect on tumor growth are useful to treat cancers that express 161P2F10B. Mechanisms by which directly cytotoxic MAbs act include: inhibition of cell growth, modulation of cellular differentiation, modulation of tumor angiogenesis factor profiles, and the induction of apoptosis. The mechanism(s) by which a particular anti-161P2F10B MAb exerts an anti-tumor effect is evaluated using any number of in vitro assays that evaluate cell death such as ADCC, ADMMC, complement-mediated cell lysis, and so forth, as is generally known in the art.

In some patients, the use of murine or other non-human monoclonal antibodies, or human/mouse chimeric MAbs can induce moderate to strong immune responses against the non-human antibody. This can result in clearance of the antibody from circulation and reduced efficacy. In the most severe cases, such an immune response can lead to the extensive formation of immune complexes which, potentially, can cause renal failure. Accordingly, preferred monoclonal antibodies used in the therapeutic methods of the invention are those that are either fully human or humanized and that bind specifically to the target 161P2F10B antigen with high affinity but exhibit low or no antigenicity in the patient.

Therapeutic methods of the invention contemplate the administration of single anti-161P2F10B MAbs as well as combinations, or cocktails, of different MAbs (i.e. 161P2F10B MAbs or Mabs that bind another protein). Such MAb cocktails can have certain advantages inasmuch as they contain MAbs that target different epitopes, exploit different effector mechanisms or combine directly cytotoxic MAbs with MAbs that rely on immune effector functionality. Such MAbs in combination can exhibit synergistic therapeutic effects. In addition, 161P2F10B MAbs can be administered concomitantly with other therapeutic modalities, including but not limited to various chemotherapeutic and biologic agents, androgen-blockers, immune modulators (e.g., IL-2, GM-CSF), surgery or radiation. The 161P2F10B MAbs are administered in their "naked" or unconjugated form, or can have a therapeutic agent(s) conjugated to them.

161P2F10B Mab formulations are administered via any route capable of delivering the antibodies to a tumor cell. Routes of administration include, but are not limited to, intravenous, intraperitoneal, intramuscular, intratumor, intradermal, and the like. Treatment generally involves repeated administration of the 161P2F10B Mab preparation, via an acceptable route of administration such as intravenous injection (IV), typically at a dose in the range, including but not limited to, 0.1, 0.2, 0.3, 0.4, 0.5, 0.6, 0.7, 0.8, 0.9, 1, 2, 3, 4, 5, 6, 7, 8, 9, 10, 15, 20, or 25 mg/kg body weight. In general, doses in the range of 10-1000 mg MAb per week are effective and well tolerated.

Based on clinical experience with the Herceptin® (Trastuzumab) in the treatment of metastatic breast cancer, an initial loading dose of approximately 4 mg/kg patient body weight IV, followed by weekly doses of about 2 mg/kg IV of the MAb preparation represents an acceptable dosing regimen. Preferably, the initial loading dose is administered as a 90-minute or longer infusion. The periodic maintenance dose is administered as a 30 minute or longer infusion, provided the initial dose was well tolerated. As appreciated by those of skill in the art, various factors can influence the ideal dose regimen in a particular case. Such factors include, for example, the binding affinity and half life of the MAbs used, the degree of 161P2F10B expression in the patient, the extent of circulating shed 161P2F10B antigen, the desired steady-state antibody concentration level, frequency of treatment, and the influence of chemotherapeutic or other agents used in combination with the treatment method of the invention, as well as the health status of a particular patient.

Optionally, patients should be evaluated for the levels of 161P2F10B in a given sample (e.g. the levels of circulating 161P2F10B antigen and/or 161P2F10B expressing cells) in order to assist in the determination of the most effective dosing regimen, etc. Such evaluations are also used for monitoring purposes throughout therapy, and are useful to gauge therapeutic success in combination with the evaluation of other parameters (for example, urine cytology and/or ImmunoCyt levels in bladder cancer therapy, or by analogy, serum PSA levels in prostate cancer therapy).

Anti-idiotypic anti-161P2F10B antibodies can also be used in anti-cancer therapy as a vaccine for inducing an immune response to cells expressing a 161P2F10B-related protein. In particular, the generation of anti-idiotypic antibodies is well known in the art; this methodology can readily be adapted to generate anti-idiotypic anti-161P2F10B antibodies that mimic an epitope on a 161P2F10B-related protein (see, for example, Wagner et al., 1997, Hybridoma 16: 33-40; Foon et al., 1995, J. Clin. Invest. 96:334-342; Herlyn et al., 1996, Cancer Immunol. Immunother. 43:65-76). Such anti-idiotypic antibody can be used in cancer vaccine strategies.

An object of the present invention is to provide 161P2F10B Mabs, which inhibit or retard the growth of tumor cells expressing 161P2F10B. A further object of this invention is to provide methods to inhibit angiogenesis and other biological functions and thereby reduce tumor growth in mammals, preferably humans, using such 161P2F10B Mabs, and in particular using such 161P2F10B Mabs combined with other drugs or immunologically active treatments, including but not limited to: Avastin® (bevacizumab), Sutent® (sunitinib malate), Nexavar® (Sorafinib tosylate), Taxotere® (docetaxel), Interleukin-2 (a.k.a. Proleukin®, IL-2, or Aldesleukin), or Interferon Alpha (Interferon-Alpha-2a, or Interferon-Alpha-2b) and others in the art known to treat renal and other cancers.

In one embodiment, there is synergy when tumors, including human tumors, are treated with 161P2F10B antibodies in conjunction with chemotherapeutic agents or radiation or combinations thereof. In other words, the inhibition of tumor growth by a 161P2F10B antibody is enhanced more than expected when combined with chemotherapeutic agents or radiation or combinations thereof. Synergy may be shown, for example, by greater inhibition of tumor growth with combined treatment than would be expected from a treatment of only 161P2F10B antibodies or the additive effect of treatment with a 161P2F10B antibody and a chemotherapeutic agent or radiation. Preferably, synergy is demonstrated by remission of the cancer where remission is not expected from treatment either from a naked 161P2F10B antibody or with treatment using an additive combination of a 161P2F10B antibody and a chemotherapeutic agent or radiation.

The method for inhibiting growth of tumor cells using a 161P2F10B antibody and a combination of chemotherapy or radiation or both comprises administering the 161P2F10B antibody before, during, or after commencing chemotherapy or radiation therapy, as well as any combination thereof (i.e. before and during, before and after, during and after, or before, during, and after commencing the chemotherapy and/or radiation therapy). For example, the 161P2F10B antibody is typically administered between 1 and 60 days, preferably between 3 and 40 days, more preferably between 5 and 12 days before commencing radiation therapy and/or chemotherapy. However, depending on the treatment protocol and the specific patient needs, the method is performed in a manner that will provide the most efficacious treatment and ultimately prolong the life of the patient.

The administration of chemotherapeutic agents can be accomplished in a variety of ways including systemically by the parenteral and enteral routes. In one embodiment, the 161P2F10B antibody and the chemotherapeutic agent are administered as separate molecules. In another embodiment, the 161P2F10B antibody is attached, for example, by conjugation, to a chemotherapeutic agent. (See the Example entitled "Human Clinical Trials for the Treatment and Diagnosis of Human Carcinomas through use of 161P2F10B Mabs"). Particular examples of chemotherapeutic agents or chemotherapy include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin, paclitaxel (taxol), docetaxel (taxotere), aldesleukin, asparaginase, busulfan, carboplatin, cladribine, dacarbazine, floxuridine, fludarabine, hydroxyurea, ifosfamide, interferon alpha, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil, taxol and combinations thereof.

The source of radiation, used in combination with a 161P2F10B Mab, can be either external or internal to the patient being treated. When the source is external to the patient, the therapy is known as external beam radiation therapy (EBRT). When the source of radiation is internal to the patient, the treatment is called brachytherapy (BT).

The above described therapeutic regimens may be further combined with additional cancer treating agents and/or regimes, for example additional chemotherapy, cancer vaccines, signal transduction inhibitors, agents useful in treating abnormal cell growth or cancer, antibodies (e.g. Anti-CTLA-4 antibodies as described in WO/2005/092380 (Pfizer)) or other ligands that inhibit tumor growth by binding to IGF-1R, and cytokines.

When the mammal is subjected to additional chemotherapy, chemotherapeutic agents described above may be used. Additionally, growth factor inhibitors, biological response modifiers, anti-hormonal therapy, selective estrogen receptor modulators (SERMs), angiogenesis inhibitors, and anti-androgens may be used. For example, anti-hormones, for example anti-estrogens such as Nolvadex (tamoxifen) or, anti-androgens such as Casodex (4'-cyano-3-(4-fluorophenylsulphonyl)-2-hydroxy-2-methyl-3-'-(trifluoromethyl) propionanilide) may be used.

In certain embodiments of the invention, the above described methods are combined with a cancer vaccine. Useful vaccines may be, without limitation, those comprised of cancer-associated antigens (e.g. BAGE, carcinoembryonic antigen (CEA), EBV, GAGE, gp100 (including gp100:209-217 and gp100:280-288, among others), HBV, HER-2/neu, HPV, HCV, MAGE, mammaglobin, MART-1/Melan-A, Mucin-1, NY-ESO-1, proteinase-3, PSA, RAGE, TRP-1, TRP-2, Tyrosinase (e.g., Tyrosinase: 368-376), WT-1), GM-CSF DNA and cell-based vaccines, dendritic cell vaccines, recombinant viral (e.g. vaccinia virus) vaccines, and heat shock protein (HSP) vaccines. Useful vaccines also include tumor vaccines, such as those formed of melanoma cells, and can be autologous or allogeneic. The vaccines may be, e.g., peptide, DNA or cell-based. These various agents can be combined such that a combination comprising, inter alia, gp100 peptides, Tyrosinase and MART-1 can be administered with the antibody.

Vaccines may be administered prior to, or subsequent to, stem cell transplantation, and when chemotherapy is part of the regimen, a vaccine may be administered prior to chemotherapy. In certain embodiments, the antibody of the invention may also be administered prior to chemotherapy. Vaccine may also be administered after stem cell transplantation and in certain embodiments concomitantly with the antibody.

The above described treatments may also be used with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors, such as VEGF receptors and molecules that can inhibit VEGF; and erbB2 receptor inhibitors, such as organic molecules or antibodies that bind to the erbB2 receptor.

EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein. EGFR-inhibiting agents include, but are not limited to, the monoclonal antibodies ERBITUX (ImClone Systems Incorporated of New York, N.Y.), and ABX-EGF (Abgenix Inc. of Fremont, Calif.), the compounds ZD-1839 (AstraZeneca), BIBX-1382 (Boehringer Ingelheim), MDX-447 (Medarex Inc. of Annandale, New. Jersey), and OLX-103 (Merck & Co. of Whitehouse Station, N.J.), VRCTC-310 (Ventech Research) and EGF fusion toxin (Seragen Inc. of Hopkinton, Mass.). These and other EGFR-inhibiting agents can be used in the present invention.

VEGF inhibitors, for example SU-5416 and SU-6668 (Sugen Inc. of South San Francisco, Calif.), can also be employed in combination with the antibody. VEGF inhibitors are described for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998). Other examples of some specific VEGF inhibitors useful in the present invention are IM862 (Cytran Inc. of Kirkland, Wash.); IMC-1C11 Imclone antibody and angiozyme, a synthetic ribozyme from Ribozyme (Boulder, Colo.) and Chiron (Emeryville, Calif.).

ErbB2 receptor inhibitors, such as GW-282974 (Glaxo Wellcome), and the monoclonal antibodies AR-209 (Aronex Pharmaceuticals Inc. of The Woodlands, Tex.) and 2B-1 (Chiron), can furthermore be combined with the antibody, for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999). ErbB2 receptor inhibitors useful in the present invention are also described in EP1029853 (published Aug. 23, 2000) and in WO 00/44728, (published Aug. 3, 2000). The erbB2 receptor inhibitor compounds and substance described in the aforementioned PCT applications, U.S. patents, and U.S. provisional applications, as well as other compounds and substances that inhibit the erbB2 receptor, can be used with the antibody in accordance with the present invention.

The present treatment regimens may also be combined with antibodies or other ligands that inhibit tumor growth by binding to IGF-1R (insulin-like growth factor 1 receptor). Specific anti-IGF-1R antibodies that can be used in the present invention include those described in PCT application PCT/US01/51113, filed Dec. 20, 2001 and published as WO02/053596.

The treatment regimens described herein may be combined with anti-angiogenesis agents, such as MMP-2 (matrix-metalloproteinase 2) inhibitors, MMP-9 (matrix-metalloproteinase 9) inhibitors, and COX-II (cyclooxygenase II) inhibitors, can be used in conjunction with the antibody in the method of the invention. Examples of useful COX-II inhibitors include CELEBREX (celecoxib), valdecoxib, and rofecoxib.

X.C.) 161P2F10B as a Target for Cellular Immune Responses

Vaccines and methods of preparing vaccines that contain an immunogenically effective amount of one or more HLA-binding peptides as described herein are further embodiments of the invention. Furthermore, vaccines in accordance with the invention encompass compositions of one or more of the claimed peptides. A peptide can be present in a vaccine individually. Alternatively, the peptide can exist as a homopolymer comprising multiple copies of the same peptide, or as a heteropolymer of various peptides. Polymers have the advantage of increased immunological reaction and, where different peptide epitopes are used to make up the polymer, the additional ability to induce antibodies and/or CTLs that react with different antigenic determinants of the pathogenic organism or tumor-related peptide targeted for an immune response. The composition can be a naturally occurring region of an antigen or can be prepared, e.g., recombinantly or by chemical synthesis.

Carriers that can be used with vaccines of the invention are well known in the art, and include, e.g., thyroglobulin, albumins such as human serum albumin, tetanus toxoid, polyamino acids such as poly L-lysine, poly L-glutamic acid, influenza, hepatitis B virus core protein, and the like. The vaccines can contain a physiologically tolerable (i.e., acceptable) diluent such as water, or saline, preferably phosphate buffered saline. The vaccines also typically include an adjuvant. Adjuvants such as incomplete Freund's adjuvant, aluminum phosphate, aluminum hydroxide, or alum are examples of materials well known in the art. Additionally, as disclosed herein, CTL responses can be primed by conjugating peptides of the invention to lipids, such as tripalmitoyl-S-glycerylcysteinlyseryl-serine ($P_3CSS$). Moreover, an adjuvant such as a synthetic cytosine-phosphorothiolated-guanine-containing (CpG) oligonucleotides has been found to increase CTL responses 10- to 100-fold (see, e.g. Davila and Celis, J. Immunol. 165:539-547 (2000)).

Upon immunization with a peptide composition in accordance with the invention, via injection, aerosol, oral, transdermal, transmucosal, intrapleural, intrathecal, or other suitable routes, the immune system of the host responds to the vaccine by producing large amounts of CTLs and/or HTLs specific for the desired antigen. Consequently, the host becomes at least partially immune to later development of cells that express or overexpress 161P2F10B antigen, or derives at least some therapeutic benefit when the antigen was tumor-associated.

In some embodiments, it may be desirable to combine the class I peptide components with components that induce or facilitate neutralizing antibody and or helper T cell responses directed to the target antigen. A preferred embodiment of such a composition comprises class I and class II epitopes in accordance with the invention. An alternative embodiment of such a composition comprises a class I and/or class II epitope in accordance with the invention, along with a cross reactive HTL epitope such as PADRE™ (Epimmune, San Diego, Calif.) molecule (described e.g., in U.S. Pat. No. 5,736,142).

A vaccine of the invention can also include antigen-presenting cells (APC), such as dendritic cells (DC), as a vehicle to present peptides of the invention. Vaccine compositions can be created in vitro, following dendritic cell mobilization and harvesting, whereby loading of dendritic cells occurs in vitro. For example, dendritic cells are transfected, e.g., with a minigene in accordance with the invention, or are pulsed with peptides. The dendritic cell can then be administered to a patient to elicit immune responses in vivo. Vaccine compositions, either DNA- or peptide-based, can also be administered in vivo in combination with dendritic cell mobilization whereby loading of dendritic cells occurs in vivo.

Preferably, the following principles are utilized when selecting an array of epitopes for inclusion in a polyepitopic composition for use in a vaccine, or for selecting discrete epitopes to be included in a vaccine and/or to be encoded by nucleic acids such as a minigene. It is preferred that each of the following principles be balanced in order to make the selection. The multiple epitopes to be incorporated in a given vaccine composition may be, but need not be, contiguous in sequence in the native antigen from which the epitopes are derived.

1.) Epitopes are selected which, upon administration, mimic immune responses that have been observed to be correlated with tumor clearance. For HLA Class I this includes 3-4 epitopes that come from at least one tumor associated antigen (TAA). For HLA Class II a similar rationale is employed; again 3-4 epitopes are selected from at least one TAA (see, e.g., Rosenberg et al., Science 278:1447-1450). Epitopes from one TAA may be used in combination with epitopes from one or more additional TAAs to produce a vaccine that targets tumors with varying expression patterns of frequently-expressed TAAs.

2.) Epitopes are selected that have the requisite binding affinity established to be correlated with immunogenicity: for HLA Class I an $IC_{50}$ of 500 nM or less, often 200 nM or less; and for Class II an $IC_{50}$ of 1000 nM or less.

3.) Sufficient supermotif bearing-peptides, or a sufficient array of allele-specific motif-bearing peptides, are selected to give broad population coverage. For example, it is preferable to have at least 80% population coverage. A Monte Carlo analysis, a statistical evaluation known in the art, can be employed to assess the breadth, or redundancy of, population coverage.

4.) When selecting epitopes from cancer-related antigens it is often useful to select analogs because the patient may have developed tolerance to the native epitope.

5.) Of particular relevance are epitopes referred to as "nested epitopes." Nested epitopes occur where at least two epitopes overlap in a given peptide sequence. A nested peptide sequence can comprise B cell, HLA class I and/or HLA class II epitopes. When providing nested epitopes, a general objective is to provide the greatest number of epitopes per sequence. Thus, an aspect is to avoid providing a peptide that is any longer than the amino terminus of the amino terminal epitope and the carboxyl terminus of the carboxyl terminal epitope in the peptide. When providing a multi-epitopic sequence, such as a sequence comprising nested epitopes, it is generally important to screen the sequence in order to insure that it does not have pathological or other deleterious biological properties.

6.) If a polyepitopic protein is created, or when creating a minigene, an objective is to generate the smallest peptide that encompasses the epitopes of interest. This principle is similar, if not the same as that employed when selecting a peptide comprising nested epitopes. However, with an artificial polyepitopic peptide, the size minimization objective is balanced against the need to integrate any spacer sequences between epitopes in the polyepitopic protein. Spacer amino acid residues can, for example, be introduced to avoid junctional epitopes (an epitope recognized by the immune system, not present in the target antigen, and only created by the man-made juxtaposition of epitopes), or to facilitate cleavage between epitopes and thereby enhance epitope presentation. Junctional epitopes are generally to be avoided because the recipient may generate an immune response to that non-native epitope. Of particular concern is a junctional epitope that is a "dominant epitope." A dominant epitope may lead to such a zealous response that immune responses to other epitopes are diminished or suppressed.

7.) Where the sequences of multiple variants of the same target protein are present, potential peptide epitopes can also be selected on the basis of their conservancy. For example, a criterion for conservancy may define that the entire sequence of an HLA class I binding peptide or the entire 9-mer core of a class II binding peptide be conserved in a designated percentage of the sequences evaluated for a specific protein antigen.

X.C.1. Minigene Vaccines

A number of different approaches are available which allow simultaneous delivery of multiple epitopes. Nucleic acids encoding the peptides of the invention are a particularly useful embodiment of the invention. Epitopes for inclusion in a minigene are preferably selected according to the guidelines set forth in the previous section. A preferred means of administering nucleic acids encoding the peptides of the invention uses minigene constructs encoding a peptide comprising one or multiple epitopes of the invention.

The use of multi-epitope minigenes is described below and in, Ishioka et al., J. Immunol. 162:3915-3925, 1999; An, L. and Whitton, J. L., J. Virol. 71:2292, 1997; Thomson, S. A. et al., J. Immunol. 157:822, 1996; Whitton, J. L. et al., J. Virol. 67:348, 1993; Hanke, R. et al., Vaccine 16:426, 1998. For example, a multi-epitope DNA plasmid encoding supermotif- and/or motif-bearing epitopes derived 161P2F10B, the PADRE™ universal helper T cell epitope or multiple HTL epitopes from 161P2F10B, and an endoplasmic reticulum-translocating signal sequence can be engineered. A vaccine may also comprise epitopes that are derived from other TAAs.

The immunogenicity of a multi-epitopic minigene can be confirmed in transgenic mice to evaluate the magnitude of CTL induction responses against the epitopes tested. Further, the immunogenicity of DNA-encoded epitopes in vivo can be correlated with the in vitro responses of specific CTL lines against target cells transfected with the DNA plasmid. Thus, these experiments can show that the minigene serves to both: 1.) generate a CTL response and 2.) that the induced CTLs recognized cells expressing the encoded epitopes.

For example, to create a DNA sequence encoding the selected epitopes (minigene) for expression in human cells, the amino acid sequences of the epitopes may be reverse translated. A human codon usage table can be used to guide the codon choice for each amino acid. These epitope-encoding DNA sequences may be directly adjoined, so that when translated, a continuous polypeptide sequence is created. To optimize expression and/or immunogenicity, additional elements can be incorporated into the minigene design. Examples of amino acid sequences that can be reverse translated and included in the minigene sequence include: HLA class I epitopes, HLA class II epitopes, antibody epitopes, a ubiquitination signal sequence, and/or an endoplasmic reticulum targeting signal. In addition, HLA presentation of CTL and HTL epitopes may be improved by including synthetic (e.g. poly-alanine) or naturally-occurring flanking sequences adjacent to the CTL or HTL epitopes; these larger peptides comprising the epitope(s) are within the scope of the invention.

The minigene sequence may be converted to DNA by assembling oligonucleotides that encode the plus and minus strands of the minigene. Overlapping oligonucleotides (30-100 bases long) may be synthesized, phosphorylated, purified and annealed under appropriate conditions using well known techniques. The ends of the oligonucleotides can be joined, for example, using T4 DNA ligase. This synthetic minigene, encoding the epitope polypeptide, can then be cloned into a desired expression vector.

Standard regulatory sequences well known to those of skill in the art are preferably included in the vector to ensure expression in the target cells. Several vector elements are desirable: a promoter with a down-stream cloning site for minigene insertion; a polyadenylation signal for efficient transcription termination; an *E. coli* origin of replication; and an *E. coli* selectable marker (e.g., ampicillin or kanamycin resistance). Numerous promoters can be used for this purpose, e.g., the human cytomegalovirus (hCMV) promoter. See, e.g., U.S. Pat. Nos. 5,580,859 and 5,589,466 for other suitable promoter sequences.

Additional vector modifications may be desired to optimize minigene expression and immunogenicity. In some cases, introns are required for efficient gene expression, and one or more synthetic or naturally-occurring introns could be incorporated into the transcribed region of the minigene. The inclusion of mRNA stabilization sequences and sequences for replication in mammalian cells may also be considered for increasing minigene expression.

Once an expression vector is selected, the minigene is cloned into the polylinker region downstream of the promoter. This plasmid is transformed into an appropriate *E. coli* strain, and DNA is prepared using standard techniques. The orientation and DNA sequence of the minigene, as well as all other elements included in the vector, are confirmed using restriction mapping and DNA sequence analysis. Bacterial cells harboring the correct plasmid can be stored as a master cell bank and a working cell bank.

In addition, immunostimulatory sequences (ISSs or CpGs) appear to play a role in the immunogenicity of DNA vaccines. These sequences may be included in the vector, outside the minigene coding sequence, if desired to enhance immunogenicity.

In some embodiments, a bi-cistronic expression vector which allows production of both the minigene-encoded epitopes and a second protein (included to enhance or decrease immunogenicity) can be used. Examples of proteins or polypeptides that could beneficially enhance the immune response if co-expressed include cytokines (e.g., IL-2, IL-12, GM-CSF), cytokine-inducing molecules (e.g., LeIF), costimulatory molecules, or for HTL responses, pan-DR binding proteins (PADRE™, Epimmune, San Diego, Calif.). Helper (HTL) epitopes can be joined to intracellular targeting signals and expressed separately from expressed CTL epitopes; this allows direction of the HTL epitopes to a cell compartment different than that of the CTL epitopes. If required, this could facilitate more efficient entry of HTL epitopes into the HLA class II pathway, thereby improving HTL induction. In contrast to HTL or CTL induction, specifically decreasing the immune response by co-expression of immunosuppressive molecules (e.g. TGF-β) may be beneficial in certain diseases.

Therapeutic quantities of plasmid DNA can be produced for example, by fermentation in *E. coli*, followed by purification. Aliquots from the working cell bank are used to inoculate growth medium, and grown to saturation in shaker flasks or a bioreactor according to well-known techniques. Plasmid DNA can be purified using standard bioseparation technologies such as solid phase anion-exchange resins supplied by QIAGEN, Inc. (Valencia, Calif.). If required, supercoiled DNA can be isolated from the open circular and linear forms using gel electrophoresis or other methods.

Purified plasmid DNA can be prepared for injection using a variety of formulations. The simplest of these is reconstitution of lyophilized DNA in sterile phosphate-buffer saline (PBS). This approach, known as "naked DNA," is currently being used for intramuscular (IM) administration in clinical trials. To maximize the immunotherapeutic effects of minigene DNA vaccines, an alternative method for formulating purified plasmid DNA may be desirable. A variety of methods have been described, and new techniques may become available. Cationic lipids, glycolipids, and fusogenic liposomes can also be used in the formulation (see, e.g., as described by WO 93/24640; Mannino & Gould-Fogerite, BioTechniques 6(7): 682 (1988); U.S. Pat. No. 5,279,833; WO 91/06309; and Felgner, et al., Proc. Nat'l Acad. Sci. USA 84:7413 (1987). In addition, peptides and compounds referred to collectively as protective, interactive, non-condensing compounds (PINC) could also be complexed to purified plasmid DNA to influence variables such as stability, intramuscular dispersion, or trafficking to specific organs or cell types.

Target cell sensitization can be used as a functional assay for expression and HLA class I presentation of minigene-encoded CTL epitopes. For example, the plasmid DNA is introduced into a mammalian cell line that is suitable as a target for standard CTL chromium release assays. The transfection method used will be dependent on the final formulation. Electroporation can be used for "naked" DNA, whereas cationic lipids allow direct in vitro transfection. A plasmid expressing green fluorescent protein (GFP) can be co-transfected to allow enrichment of transfected cells using fluorescence activated cell sorting (FACS). These cells are then chromium-51 ($^{51}$Cr) labeled and used as target cells for epitope-specific CTL lines; cytolysis, detected by $^{51}$Cr release, indicates both production of, and HLA presentation of, minigene-encoded CTL epitopes. Expression of HTL epitopes may be evaluated in an analogous manner using assays to assess HTL activity.

In vivo immunogenicity is a second approach for functional testing of minigene DNA formulations. Transgenic mice expressing appropriate human HLA proteins are immunized with the DNA product. The dose and route of administration are formulation dependent (e.g., IM for DNA in PBS, intraperitoneal (i.p.) for lipid-complexed DNA). Twenty-one days after immunization, splenocytes are harvested and restimulated for one week in the presence of peptides encoding each epitope being tested. Thereafter, for CTL effector cells, assays are conducted for cytolysis of peptide-loaded, $^{51}$Cr-labeled target cells using standard techniques. Lysis of target cells that were sensitized by HLA loaded with peptide epitopes, corresponding to minigene-encoded epitopes, demonstrates DNA vaccine function for in vivo induction of CTLs. Immunogenicity of HTL epitopes is confirmed in transgenic mice in an analogous manner.

Alternatively, the nucleic acids can be administered using ballistic delivery as described, for instance, in U.S. Pat. No. 5,204,253. Using this technique, particles comprised solely of DNA are administered. In a further alternative embodiment, DNA can be adhered to particles, such as gold particles.

Minigenes can also be delivered using other bacterial or viral delivery systems well known in the art, e.g., an expression construct encoding epitopes of the invention can be incorporated into a viral vector such as vaccinia.

X.C.2. Combinations of CTL Peptides with Helper Peptides

Vaccine compositions comprising CTL peptides of the invention can be modified, e.g., analoged, to provide desired attributes, such as improved serum half life, broadened population coverage or enhanced immunogenicity.

For instance, the ability of a peptide to induce CTL activity can be enhanced by linking the peptide to a sequence which contains at least one epitope that is capable of inducing a T helper cell response. Although a CTL peptide can be directly linked to a T helper peptide, often CTL epitope/HTL epitope conjugates are linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer. When present, the spacer will usually be at least one or two residues, more usually three to six residues and sometimes 10 or more residues. The CTL peptide epitope can be linked to the T helper peptide epitope either directly or via a spacer either at the amino or carboxy terminus of the CTL peptide. The amino terminus of either the immunogenic peptide or the T helper peptide may be acylated.

HTL peptide epitopes can also be modified to alter their biological properties. For example, they can be modified to include D-amino acids to increase their resistance to proteases and thus extend their serum half life, or they can be conjugated to other molecules such as lipids, proteins, carbohydrates, and the like to increase their biological activity. For example, a T helper peptide can be conjugated to one or more palmitic acid chains at either the amino or carboxyl termini.

X.C.3. Combinations of CTL Peptides with T Cell Priming Agents

In some embodiments it may be desirable to include in the pharmaceutical compositions of the invention at least one component which primes B lymphocytes or T lymphocytes. Lipids have been identified as agents capable of priming CTL in vivo. For example, palmitic acid residues can be attached to the $\epsilon$- and $\alpha$-amino groups of a lysine residue and then linked, e.g., via one or more linking residues such as Gly, Gly-Gly-, Ser, Ser-Ser, or the like, to an immunogenic peptide. The lipidated peptide can then be administered either directly in a micelle or particle, incorporated into a liposome, or emulsified in an adjuvant, e.g., incomplete Freund's adjuvant. In a preferred embodiment, a particularly effective immunogenic composition comprises palmitic acid attached to $\epsilon$- and $\alpha$-amino groups of Lys, which is attached via linkage, e.g., Ser-Ser, to the amino terminus of the immunogenic peptide.

As another example of lipid priming of CTL responses, *E. coli* lipoproteins, such as tripalmitoyl-S-glycerylcysteinly-seryl-serine ($P_3CSS$) can be used to prime virus specific CTL when covalently attached to an appropriate peptide (see, e.g., Deres, et al., Nature 342:561, 1989). Peptides of the invention can be coupled to $P_3CSS$, for example, and the lipopeptide administered to an individual to prime specifically an immune response to the target antigen. Moreover, because the induction of neutralizing antibodies can also be primed with P3CSS-conjugated epitopes, two such compositions can be combined to more effectively elicit both humoral and cell-mediated responses.

X.C.4. Vaccine Compositions Comprising DC Pulsed with CTL and/or HTL Peptides

An embodiment of a vaccine composition in accordance with the invention comprises ex vivo administration of a cocktail of epitope-bearing peptides to PBMC, or isolated DC therefrom, from the patient's blood. A pharmaceutical to facilitate harvesting of DC can be used, such as Progenipoietin™ (Pharmacia-Monsanto, St. Louis, Mo.) or GM-CSF/IL-4. After pulsing the DC with peptides and prior to reinfusion into patients, the DC are washed to remove unbound peptides. In this embodiment, a vaccine comprises peptide-pulsed DCs which present the pulsed peptide epitopes complexed with HLA molecules on their surfaces.

The DC can be pulsed ex vivo with a cocktail of peptides, some of which stimulate CTL responses to 161P2F10B. Optionally, a helper T cell (HTL) peptide, such as a natural or artificial loosely restricted HLA Class II peptide, can be included to facilitate the CTL response. Thus, a vaccine in accordance with the invention is used to treat a cancer which expresses or overexpresses 161P2F10B.

X.D.) Adoptive Immunotherapy

Antigenic 161P2F10B-related peptides are used to elicit a CTL and/or HTL response ex vivo, as well. The resulting CTL or HTL cells, can be used to treat tumors in patients that do not respond to other conventional forms of therapy, or will not respond to a therapeutic vaccine peptide or nucleic acid in accordance with the invention. Ex vivo CTL or HTL responses to a particular antigen are induced by incubating in tissue culture the patient's, or genetically compatible, CTL or HTL precursor cells together with a source of antigen-presenting cells (APC), such as dendritic cells, and the appropriate immunogenic peptide. After an appropriate incubation time (typically about 7-28 days), in which the precursor cells are activated and expanded into effector cells, the cells are infused back into the patient, where they will destroy (CTL) or facilitate destruction (HTL) of their specific target cell (e.g., a tumor cell). Transfected dendritic cells may also be used as antigen presenting cells.

X.E.) Administration of Vaccines for Therapeutic or Prophylactic Purposes

Pharmaceutical and vaccine compositions of the invention are typically used to treat and/or prevent a cancer that expresses or overexpresses 161P2F10B. In therapeutic applications, peptide and/or nucleic acid compositions are administered to a patient in an amount sufficient to elicit an effective B cell, CTL and/or HTL response to the antigen and to cure or at least partially arrest or slow symptoms and/or complications. An amount adequate to accomplish this is defined as "therapeutically effective dose." Amounts effective for this use will depend on, e.g., the particular composition administered, the manner of administration, the stage and severity of the disease being treated, the weight and general state of health of the patient, and the judgment of the prescribing physician.

For pharmaceutical compositions, the immunogenic peptides of the invention, or DNA encoding them, are generally administered to an individual already bearing a tumor that expresses 161P2F10B. The peptides or DNA encoding them can be administered individually or as fusions of one or more peptide sequences. Patients can be treated with the immunogenic peptides separately or in conjunction with other treatments, such as surgery, as appropriate.

For therapeutic use, administration should generally begin at the first diagnosis of 161P2F10B-associated cancer. This is followed by boosting doses until at least symptoms are substantially abated and for a period thereafter. The embodiment of the vaccine composition (i.e., including, but not limited to embodiments such as peptide cocktails, polyepitopic polypeptides, minigenes, or TAA-specific CTLs or pulsed dendritic cells) delivered to the patient may vary according to the stage of the disease or the patient's health status. For example, in a patient with a tumor that expresses 161P2F10B, a vaccine comprising 161P2F10B-specific CTL may be more efficacious in killing tumor cells in patient with advanced disease than alternative embodiments.

It is generally important to provide an amount of the peptide epitope delivered by a mode of administration sufficient to stimulate effectively a cytotoxic T cell response; compositions which stimulate helper T cell responses can also be given in accordance with this embodiment of the invention.

The dosage for an initial therapeutic immunization generally occurs in a unit dosage range where the lower value is about 1, 5, 50, 500, or 1,000 µg and the higher value is about 10,000; 20,000; 30,000; or 50,000 µg. Dosage values for a human typically range from about 500 µg to about 50,000 µg per 70 kilogram patient. Boosting dosages of between about 1.0 µg to about 50,000 µg of peptide pursuant to a boosting regimen over weeks to months may be administered depending upon the patient's response and condition as determined by measuring the specific activity of CTL and HTL obtained from the patient's blood. Administration should continue until at least clinical symptoms or laboratory tests indicate that the neoplasia, has been eliminated or reduced and for a period thereafter. The dosages, routes of administration, and dose schedules are adjusted in accordance with methodologies known in the art.

In certain embodiments, the peptides and compositions of the present invention are employed in serious disease states, that is, life-threatening or potentially life threatening situations. In such cases, as a result of the minimal amounts of extraneous substances and the relative nontoxic nature of the peptides in preferred compositions of the invention, it is possible and may be felt desirable by the treating physician to administer substantial excesses of these peptide compositions relative to these stated dosage amounts.

The vaccine compositions of the invention can also be used purely as prophylactic agents. Generally the dosage for an initial prophylactic immunization generally occurs in a unit dosage range where the lower value is about 1, 5, 50, 500, or 1000 µg and the higher value is about 10,000; 20,000; 30,000; or 50,000 µg. Dosage values for a human typically range from about 500 µg to about 50,000 µg per 70 kilogram patient. This is followed by boosting dosages of between about 1.0 µg to about 50,000 µg of peptide administered at defined intervals from about four weeks to six months after the initial administration of vaccine. The immunogenicity of the vaccine can be assessed by measuring the specific activity of CTL and HTL obtained from a sample of the patient's blood.

The pharmaceutical compositions for therapeutic treatment are intended for parenteral, topical, oral, nasal, intrathecal, or local (e.g. as a cream or topical ointment) administration. Preferably, the pharmaceutical compositions are administered parentally, e.g., intravenously, subcutaneously, intradermally, or intramuscularly. Thus, the invention provides compositions for parenteral administration which comprise a solution of the immunogenic peptides dissolved or suspended in an acceptable carrier, preferably an aqueous carrier.

A variety of aqueous carriers may be used, e.g., water, buffered water, 0.8% saline, 0.3% glycine, hyaluronic acid and the like. These compositions may be sterilized by conventional, well-known sterilization techniques, or may be sterile filtered. The resulting aqueous solutions may be packaged for use as is, or lyophilized, the lyophilized preparation being combined with a sterile solution prior to administration.

The compositions may contain pharmaceutically acceptable auxiliary substances as required to approximate physiological conditions, such as pH-adjusting and buffering agents, tonicity adjusting agents, wetting agents, preservatives, and the like, for example, sodium acetate, sodium lactate, sodium chloride, potassium chloride, calcium chloride, sorbitan monolaurate, triethanolamine oleate, etc.

The concentration of peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

A human unit dose form of a composition is typically included in a pharmaceutical composition that comprises a human unit dose of an acceptable carrier, in one embodiment an aqueous carrier, and is administered in a volume/quantity that is known by those of skill in the art to be used for administration of such compositions to humans (see, e.g., Remington's Pharmaceutical Sciences, 17th Edition, A. Gennaro, Editor, Mack Publishing Co., Easton, Pa., 1985). For example a peptide dose for initial immunization can be from about 1 to about 50,000 µg, generally 100-5,000 µg, for a 70 kg patient. For example, for nucleic acids an initial immunization may be performed using an expression vector in the form of naked nucleic acid administered IM (or SC or ID) in the amounts of 0.5-5 mg at multiple sites. The nucleic acid (0.1 to 1000 µg) can also be administered using a gene gun. Following an incubation period of 3-4 weeks, a booster dose is then administered. The booster can be recombinant fowlpox virus administered at a dose of $5\text{-}10^7$ to $5\times10^9$ pfu.

For antibodies, a treatment generally involves repeated administration of the anti-161P2F10B antibody preparation, via an acceptable route of administration such as intravenous injection (IV), typically at a dose in the range of about 0.1 to about 10 mg/kg body weight. In general, doses in the range of 10-500 mg MAb per week are effective and well tolerated. Moreover, an initial loading dose of approximately 4 mg/kg patient body weight IV, followed by weekly doses of about 2 mg/kg IV of the anti-161P2F10B MAb preparation represents an acceptable dosing regimen. As appreciated by those of skill in the art, various factors can influence the ideal dose in a particular case. Such factors include, for example, half life of a composition, the binding affinity of an Ab, the immunogenicity of a substance, the degree of 161P2F10B expression in the patient, the extent of circulating shed 161P2F10B antigen, the desired steady-state concentration level, frequency of treatment, and the influence of chemotherapeutic or other agents used in combination with the treatment method of the invention, as well as the health status of a particular patient. Non-limiting preferred human unit doses are, for example, 500 µg-1 mg, 1 mg-50 mg, 50 mg-100 mg, 100 mg-200 mg, 200 mg-300 mg, 400 mg-500 mg, 500 mg-600 mg, 600 mg-700 mg, 700 mg-800 mg, 800 mg-900 mg, 900 mg-1 g, or 1 mg-700 mg. In certain embodiments, the dose is in a range of 2-5 mg/kg body weight, e.g., with follow on weekly doses of 1-3 mg/kg; 0.5 mg, 1, 2, 3, 4, 5, 6, 7, 8, 9, 10 mg/kg body weight followed, e.g., in two, three or four weeks by weekly doses; 0.5-10 mg/kg body weight, e.g., followed in two, three or four weeks by weekly doses; 225, 250, 275, 300, 325, 350, 375, 400 mg m$^2$ of body area weekly; 1-600 mg m$^2$ of body area weekly; 225-400 mg m$^2$ of body area weekly; these does can be followed by weekly doses for 2, 3, 4, 5, 6, 7, 8, 9, 19, 11, 12 or more weeks.

In one embodiment, human unit dose forms of polynucleotides comprise a suitable dosage range or effective amount that provides any therapeutic effect. As appreciated by one of ordinary skill in the art a therapeutic effect depends on a number of factors, including the sequence of the polynucleotide, molecular weight of the polynucleotide and route of administration. Dosages are generally selected by the physician or other health care professional in accordance with a variety of parameters known in the art, such as severity of symptoms, history of the patient and the like. Generally, for a polynucleotide of about 20 bases, a dosage range may be selected from, for example, an independently selected lower limit such as about 0.1, 0.25, 0.5, 1, 2, 5, 10, 20, 30, 40, 50, 60, 70, 80, 90, 100, 200, 300, 400 or 500 mg/kg up to an independently selected upper limit, greater than the lower limit, of about 60, 80, 100, 200, 300, 400, 500, 750, 1000, 1500, 2000, 3000, 4000, 5000, 6000, 7000, 8000, 9000 or 10,000 mg/kg. For example, a dose may be about any of the following: 0.1 to 100 mg/kg, 0.1 to 50 mg/kg, 0.1 to 25 mg/kg, 0.1 to 10 mg/kg, 1 to 500 mg/kg, 100 to 400 mg/kg, 200 to 300 mg/kg, 1 to 100 mg/kg, 100 to 200 mg/kg, 300 to 400 mg/kg, 400 to 500 mg/kg, 500 to 1000 mg/kg, 500 to 5000 mg/kg, or 500 to 10,000 mg/kg. Generally, parenteral routes of administration may require higher doses of polynucleotide compared to more direct application to the nucleotide to diseased tissue, as do polynucleotides of increasing length.

In one embodiment, human unit dose forms of T-cells comprise a suitable dosage range or effective amount that provides any therapeutic effect. As appreciated by one of ordinary skill in the art, a therapeutic effect depends on a number of factors. Dosages are generally selected by the physician or other health care professional in accordance with a variety of parameters known in the art, such as severity of symptoms, history of the patient and the like. A dose may be about $10^4$ cells to about $10^6$ cells, about $10^6$ cells to about $10^8$ cells, about $10^8$ to about $10^{11}$ cells, or about $10^8$ to about $5 \times 10^{10}$ cells. A dose may also about $10^6$ cells/m$^2$ to about $10^{10}$ cells/m$^2$, or about $10^6$ cells/m$^2$ to about $10^8$ cells/m$^2$.

Proteins(s) of the invention, and/or nucleic acids encoding the protein(s), can also be administered via liposomes, which may also serve to: 1) target the proteins(s) to a particular tissue, such as lymphoid tissue; 2) to target selectively to diseases cells; or, 3) to increase the half-life of the peptide composition. Liposomes include emulsions, foams, micelles, insoluble monolayers, liquid crystals, phospholipid dispersions, lamellar layers and the like. In these preparations, the peptide to be delivered is incorporated as part of a liposome, alone or in conjunction with a molecule which binds to a receptor prevalent among lymphoid cells (such as monoclonal antibodies which bind to the CD45 antigen) or with other therapeutic or immunogenic compositions. Thus, liposomes either filled or decorated with a desired peptide of the invention can be directed to the site of lymphoid cells, where the liposomes then deliver the peptide compositions. Liposomes for use in accordance with the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka, et al., Ann. Rev. Biophys. Bioeng. 9:467 (1980), and U.S. Pat. Nos. 4,235,871, 4,501,728, 4,837,028, and 5,019,369.

For targeting cells of the immune system, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more peptides of the invention, and more preferably at a concentration of 25%-75%.

For aerosol administration, immunogenic peptides are preferably supplied in finely divided form along with a surfactant and propellant. Typical percentages of peptides are about 0.01%-20% by weight, preferably about 1%-10%. The surfactant must, of course, be nontoxic, and preferably soluble in the propellant. Representative of such agents are the esters or partial esters of fatty acids containing from about 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute about 0.1%-20% by weight of the composition, preferably about 0.25-5%. The balance of the composition is ordinarily propellant. A carrier can also be included, as desired, as with, e.g., lecithin for intranasal delivery.

XI.) DIAGNOSTIC AND PROGNOSTIC EMBODIMENTS OF 161P2F10B

As disclosed herein, 161P2F10B polynucleotides, polypeptides, reactive cytotoxic T cells (CTL), reactive helper T cells (HTL) and anti-polypeptide antibodies are used in well known diagnostic, prognostic and therapeutic assays that examine conditions associated with dysregulated cell growth such as cancer, in particular the cancers listed in Table I (see, e.g., both its specific pattern of tissue expression as well as its overexpression in certain cancers as described for example in the Example entitled "Expression analysis of 161P2F10B in normal tissues, and patient specimens").

161P2F10B can be analogized to a prostate associated antigen PSA, the archetypal marker that has been used by medical practitioners for years to identify and monitor the presence of prostate cancer (see, e.g., Merrill et al., J. Urol. 163(2): 503-5120 (2000); Polascik et al., J. Urol. Aug; 162 (2):293-306 (1999) and Fortier et al., J. Nat. Cancer Inst. 91(19): 1635-1640 (1999)). A variety of other diagnostic markers are also used in similar contexts including p53 and K-ras (see, e.g., Tulchinsky et al., Int J Mol Med 1999 Jul. 4(1):99-102 and Minimoto et al., Cancer Detect Prev 2000; 24(1):1-12). Therefore, this disclosure of 161P2F10B polynucleotides and polypeptides (as well as 161P2F10B polynucleotide probes and anti-161P2F10B antibodies used to identify the presence of these molecules) and their properties allows skilled artisans to utilize these molecules in methods that are analogous to those used, for example, in a variety of diagnostic assays directed to examining conditions associated with cancer.

Typical embodiments of diagnostic methods which utilize the 161P2F10B polynucleotides, polypeptides, reactive T cells and antibodies are analogous to those methods from well-established diagnostic assays, which employ, (e.g., PSA polynucleotides, polypeptides, reactive T cells and antibodies.) For example, just as PSA polynucleotides are used as probes (for example in Northern analysis, see, e.g., Sharief et al., Biochem. Mol. Biol. Int. 33(3):567-74 (1994)) and primers (for example in PCR analysis, see, e.g., Okegawa et al., J. Urol. 163(4): 1189-1190 (2000)) to observe the presence and/or the level of PSA mRNAs in methods of monitoring PSA overexpression or the metastasis of prostate cancers, the 161P2F10B polynucleotides described herein can be utilized in the same way to detect 161P2F10B overexpression or the metastasis of kidney and other cancers expressing this gene. Alternatively, just as PSA polypeptides are used to generate antibodies specific for PSA which can then be used to observe the presence and/or the level of PSA proteins in methods to monitor PSA protein overexpression (see, e.g., Stephan et al., Urology 55(4):560-3 (2000)) or the metastasis of prostate cells (see, e.g., Alanen et al., Pathol. Res. Pract. 192(3):233-7 (1996)), the 161P2F10B polypeptides described herein can be utilized to generate antibodies for use in detecting 161P2F10B overexpression or the metastasis of kidney cells and cells of other cancers expressing this gene.

Specifically, because metastases involves the movement of cancer cells from an organ of origin (such as the lung or prostate gland etc.) to a different area of the body (such as a lymph node), assays which examine a biological sample for the presence of cells expressing 161P2F10B polynucleotides and/or polypeptides can be used to provide evidence of metastasis. For example, when a biological sample from tissue that does not normally contain 161P2F10B-expressing cells is found to contain 161P2F10B-expressing cells this finding is indicative of metastasis.

Alternatively 161P2F10B polynucleotides and/or polypeptides can be used to provide evidence of cancer, for example, when cells in a biological sample that do not normally express 161P2F10B or express 161P2F10B at a different level are found to express 161P2F10B or have an increased expression of 161P2F10B (see, e.g., the 161P2F10B expression in the cancers listed in Table I and in patient samples etc. shown in the accompanying Figures). In such assays, artisans may further wish to generate supplementary evidence of metastasis by testing the biological sample for the presence of a second tissue restricted marker (in addition to 161P2F10B).

The use of immunohistochemistry to identify the presence of a 161P2F10B polypeptide within a tissue section can indicate an altered state of certain cells within that tissue. It is well understood in the art that the ability of an antibody to localize to a polypeptide that is expressed in cancer cells is a way of diagnosing presence of disease, disease stage, progression and/or tumor aggressiveness. Such an antibody can also detect an altered distribution of the polypeptide within the cancer cells, as compared to corresponding non-malignant tissue.

The 161P2F10B polypeptide and immunogenic compositions are also useful in view of the phenomena of altered subcellular protein localization in disease states. Alteration of cells from normal to diseased state causes changes in cellular morphology and is often associated with changes in subcellular protein localization/distribution. For example, cell membrane proteins that are expressed in a polarized manner in normal cells can be altered in disease, resulting in distribution of the protein in a non-polar manner over the whole cell surface.

The phenomenon of altered subcellular protein localization in a disease state has been demonstrated with MUC1 and Her2 protein expression by use of immunohistochemical means. Normal epithelial cells have a typical apical distribution of MUC1, in addition to some supranuclear localization of the glycoprotein, whereas malignant lesions often demonstrate an apolar staining pattern (Diaz et al, The Breast Journal, 7; 40-45 (2001); Zhang et al, Clinical Cancer Research, 4; 2669-2676 (1998): Cao, et al, The Journal of Histochemistry and Cytochemistry, 45: 1547-1557 (1997)). In addition, normal breast epithelium is either negative for Her2 protein or exhibits only a basolateral distribution whereas malignant cells can express the protein over the whole cell surface (De Potter, et al, International Journal of Cancer, 44; 969-974 (1989): McCormick, et al, 117; 935-943 (2002)). Alternatively, distribution of the protein may be altered from a surface only localization to include diffuse cytoplasmic expression in the diseased state. Such an example can be seen with MUC1 (Diaz, et al, The Breast Journal, 7: 40-45 (2001)).

Alteration in the localization/distribution of a protein in the cell, as detected by immunohistochemical methods, can also provide valuable information concerning the favorability of certain treatment modalities. This last point is illustrated by a situation where a protein may be intracellular in normal tissue, but cell surface in malignant cells; the cell surface location makes the cells favorably amenable to antibody-based diagnostic and treatment regimens. When such an alteration of protein localization occurs for 161P2F10B, the 161P2F10B protein and immune responses related thereto are very useful. Use of the 161P2F10B compositions allows those skilled in the art to make important diagnostic and therapeutic decisions.

Immunohistochemical reagents specific to 161P2F10B are also useful to detect metastases of tumors expressing 161P2F10B when the polypeptide appears in tissues where 161P2F10B is not normally produced.

Thus, 161P2F10B polypeptides and antibodies resulting from immune responses thereto are useful in a variety of important contexts such as diagnostic, prognostic, preventative and/or therapeutic purposes known to those skilled in the art.

Additionally, 161P2F10B-related proteins or polynucleotides of the invention can be used to treat a pathologic condition characterized by the over-expression of 161P2F10B. For example, the amino acid or nucleic acid sequence of FIG. 1, or fragments of either, can be used to generate an immune response to a 161P2F10B antigen. Antibodies or other molecules that react with 161P2F10B can be used to modulate the function of this molecule, and thereby provide a therapeutic benefit.

XI.A.) Inhibition of 161P2F10B Protein Function

The invention includes various methods and compositions for inhibiting the binding of 161P2F10B to its binding partner or its association with other protein(s) as well as methods for inhibiting 161P2F10B function.

XI.B.) Inhibition of 161P2F10B with Intracellular Antibodies

In one approach, a recombinant vector that encodes single chain antibodies that specifically bind to 161P2F10B are introduced into 161P2F10B expressing cells via gene transfer technologies. Accordingly, the encoded single chain anti-161P2F10B antibody is expressed intracellularly, binds to 161P2F10B protein, and thereby inhibits its function. Methods for engineering such intracellular single chain antibodies are well known. Such intracellular antibodies, also known as "intrabodies", are specifically targeted to a particular compartment within the cell, providing control over where the inhibitory activity of the treatment is focused. This technology has been successfully applied in the art (for review, see Richardson and Marasco, 1995, TIBTECH vol. 13). Intrabodies have been shown to virtually eliminate the expression of otherwise abundant cell surface receptors (see, e.g., Richardson et al., 1995, Proc. Natl. Acad. Sci. USA 92: 3137-3141; Beerli et al., 1994, J. Biol. Chem. 289: 23931-23936; Deshane et al., 1994, Gene Ther. 1: 332-337).

Single chain antibodies comprise the variable domains of the heavy and light chain joined by a flexible linker polypeptide, and are expressed as a single polypeptide. Optionally, single chain antibodies are expressed as a single chain variable region fragment joined to the light chain constant region.

Well-known intracellular trafficking signals are engineered into recombinant polynucleotide vectors encoding such single chain antibodies in order to target precisely the intrabody to the desired intracellular compartment. For example, intrabodies targeted to the endoplasmic reticulum (ER) are engineered to incorporate a leader peptide and, optionally, a C-terminal ER retention signal, such as the KDEL amino acid motif. Intrabodies intended to exert activity in the nucleus are engineered to include a nuclear localization signal. Lipid moieties are joined to intrabodies in order to tether the intrabody to the cytosolic side of the plasma membrane. Intrabodies can also be targeted to exert function in the cytosol. For example, cytosolic intrabodies are used to sequester factors within the cytosol, thereby preventing them from being transported to their natural cellular destination.

In one embodiment, intrabodies are used to capture 161P2F10B in the nucleus, thereby preventing its activity within the nucleus. Nuclear targeting signals are engineered into such 161P2F10B intrabodies in order to achieve the desired targeting. Such 161P2F10B intrabodies are designed to bind specifically to a particular 161P2F10B domain. In another embodiment, cytosolic intrabodies that specifically bind to a 161P2F10B protein are used to prevent 161P2F10B from gaining access to the nucleus, thereby preventing it from exerting any biological activity within the nucleus (e.g., preventing 161P2F10B from forming transcription complexes with other factors).

XI.C.) Inhibition of 161P2F10B with Recombinant Proteins

In another approach, recombinant molecules bind to 161P2F10B and thereby inhibit 161P2F10B function. For example, these recombinant molecules prevent or inhibit 161P2F10B from accessing/binding to its binding partner(s) or associating with other protein(s). Such recombinant molecules can, for example, contain the reactive part(s) of a 161P2F10B specific antibody molecule. In a particular embodiment, the 161P2F10B binding domain of a 161P2F10B binding partner is engineered into a dimeric fusion protein, whereby the fusion protein comprises two 161P2F10B ligand binding domains linked to the Fc portion of a human IgG, such as human $IgG_1$. Such IgG portion can contain, for example, the $CH_2$ and $CH_3$ domains and the hinge region, but not the $CH_1$ domain. Such dimeric fusion proteins are administered in soluble form to patients suffering from a cancer associated with the expression of 161P2F10B, whereby the dimeric fusion protein specifically binds to 161P2F10B and blocks 161P2F10B interaction with a binding partner. Such dimeric fusion proteins are further combined into multimeric proteins using known antibody linking technologies.

XI.D.) Inhibition of 161P2F10B Transcription or Translation

The present invention also comprises various methods and compositions for inhibiting the transcription of the 161P2F10B gene Similarly, the invention also provides methods and compositions for inhibiting the translation of 161P2F10B mRNA into protein.

In one approach, a method of inhibiting the transcription of the 161P2F10B gene comprises contacting the 161P2F10B gene with a 161P2F10B antisense polynucleotide. In another approach, a method of inhibiting 161P2F10B mRNA translation comprises contacting a 161P2F10B mRNA with an antisense polynucleotide. In another approach, a 161P2F10B specific ribozyme is used to cleave a 161P2F10B message, thereby inhibiting translation. Such antisense and ribozyme based methods can also be directed to the regulatory regions of the 161P2F10B gene, such as 161P2F10B promoter and/or enhancer elements. Similarly, proteins capable of inhibiting a 161P2F10B gene transcription factor are used to inhibit 161P2F10B mRNA transcription. The various polynucleotides and compositions useful in the aforementioned methods have been described above. The use of antisense and ribozyme molecules to inhibit transcription and translation is well known in the art.

Other factors that inhibit the transcription of 161P2F10B by interfering with 161P2F10B transcriptional activation are also useful to treat cancers expressing 161P2F10B. Similarly, factors that interfere with 161P2F10B processing are useful to treat cancers that express 161P2F10B. Cancer treatment methods utilizing such factors are also within the scope of the invention.

XI.E.) General Considerations for Therapeutic Strategies

Gene transfer and gene therapy technologies can be used to deliver therapeutic polynucleotide molecules to tumor cells synthesizing 161P2F10B (i.e., antisense, ribozyme, polynucleotides encoding intrabodies and other 161P2F10B inhibitory molecules). A number of gene therapy approaches are known in the art. Recombinant vectors encoding 161P2F10B antisense polynucleotides, ribozymes, factors capable of interfering with 161P2F10B transcription, and so forth, can be delivered to target tumor cells using such gene therapy approaches.

The above therapeutic approaches can be combined with any one of a wide variety of surgical, chemotherapy or radiation therapy regimens. The therapeutic approaches of the invention can enable the use of reduced dosages of chemotherapy (or other therapies) and/or less frequent administration, an advantage for all patients and particularly for those that do not tolerate the toxicity of the chemotherapeutic agent well.

The anti-tumor activity of a particular composition (e.g., antisense, ribozyme, intrabody), or a combination of such compositions, can be evaluated using various in vitro and in vivo assay systems. In vitro assays that evaluate therapeutic activity include cell growth assays, soft agar assays and other assays indicative of tumor promoting activity, binding assays capable of determining the extent to which a therapeutic composition will inhibit the binding of 161P2F10B to a binding partner, etc.

In vivo, the effect of a 161P2F10B therapeutic composition can be evaluated in a suitable animal model. For example, xenogenic kidney cancer models can be used, wherein human prostate cancer explants or passaged xenograft tissues are introduced into immune compromised animals, such as nude or SCID mice (Klein et al., 1997, Nature Medicine 3: 402-408). For example, PCT Patent Application WO98/16628 and U.S. Pat. No. 6,107,540 describe various xenograft models of human prostate cancer capable of recapitulating the development of primary tumors, micrometastasis, and the formation of osteoblastic metastases characteristic of late stage disease. Efficacy can be predicted using assays that measure inhibition of tumor formation, tumor regression or metastasis, and the like.

In vivo assays that evaluate the promotion of apoptosis are useful in evaluating therapeutic compositions. In one embodiment, xenografts from tumor bearing mice treated with the therapeutic composition can be examined for the presence of apoptotic foci and compared to untreated control xenograft-bearing mice. The extent to which apoptotic foci are found in the tumors of the treated mice provides an indication of the therapeutic efficacy of the composition.

The therapeutic compositions used in the practice of the foregoing methods can be formulated into pharmaceutical compositions comprising a carrier suitable for the desired delivery method. Suitable carriers include any material that when combined with the therapeutic composition retains the anti-tumor function of the therapeutic composition and is generally non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences 16th Edition, A. Osal., Ed., 1980).

Therapeutic formulations can be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations can be lyophilized and stored as sterile powders, preferably under vacuum, and then reconstituted in bacteriostatic water (containing for example, benzyl alcohol preservative) or in sterile water prior to injection.

Dosages and administration protocols for the treatment of cancers using the foregoing methods will vary with the method and the target cancer, and will generally depend on a number of other factors appreciated in the art.

XII.) IDENTIFICATION, CHARACTERIZATION AND USE OF MODULATORS OF 161P2F10B

Methods to Identify and Use Modulators

In one embodiment, screening is performed to identify modulators that induce or suppress a particular expression profile, suppress or induce specific pathways, preferably generating the associated phenotype thereby. In another embodiment, having identified differentially expressed genes important in a particular state; screens are performed to identify modulators that alter expression of individual genes, either increase or decrease. In another embodiment, screening is performed to identify modulators that alter a biological function of the expression product of a differentially expressed gene. Again, having identified the importance of a gene in a particular state, screens are performed to identify agents that bind and/or modulate the biological activity of the gene product.

In addition, screens are done for genes that are induced in response to a candidate agent. After identifying a modulator (one that suppresses a cancer expression pattern leading to a normal expression pattern, or a modulator of a cancer gene that leads to expression of the gene as in normal tissue) a screen is performed to identify genes that are specifically modulated in response to the agent. Comparing expression profiles between normal tissue and agent-treated cancer tissue reveals genes that are not expressed in normal tissue or cancer tissue, but are expressed in agent treated tissue, and vice versa. These agent-specific sequences are identified and used by methods described herein for cancer genes or proteins. In particular these sequences and the proteins they encode are used in marking or identifying agent-treated cells. In addition, antibodies are raised against the agent-induced proteins and used to target novel therapeutics to the treated cancer tissue sample.

Modulator-Related Identification and Screening Assays:
Gene Expression-Related Assays Proteins, nucleic acids, and antibodies of the invention are used in screening assays. The cancer-associated proteins, antibodies, nucleic acids, modified proteins and cells containing these sequences are used in screening assays, such as evaluating the effect of drug candidates on a "gene expression profile," expression profile of polypeptides or alteration of biological function. In one embodiment, the expression profiles are used, preferably in conjunction with high throughput screening techniques to allow monitoring for expression profile genes after treatment with a candidate agent (e.g., Davis, G F, et al, J Biol Screen 7:69 (2002); Zlokarnik, et al., Science 279:84-8 (1998); Heid, Genome Res 6:986-94, 1996).

The cancer proteins, antibodies, nucleic acids, modified proteins and cells containing the native or modified cancer proteins or genes are used in screening assays. That is, the present invention comprises methods for screening for compositions which modulate the cancer phenotype or a physiological function of a cancer protein of the invention. This is done on a gene itself or by evaluating the effect of drug candidates on a "gene expression profile" or biological function. In one embodiment, expression profiles are used, preferably in conjunction with high throughput screening techniques to allow monitoring after treatment with a candidate agent, see Zlokarnik, supra.

A variety of assays are executed directed to the genes and proteins of the invention. Assays are run on an individual nucleic acid or protein level. That is, having identified a particular gene as up regulated in cancer, test compounds are screened for the ability to modulate gene expression or for binding to the cancer protein of the invention. "Modulation" in this context includes an increase or a decrease in gene expression. The preferred amount of modulation will depend on the original change of the gene expression in normal versus tissue undergoing cancer, with changes of at least 10%, preferably 50%, more preferably 100-300%, and in some embodiments 300-1000% or greater. Thus, if a gene exhibits a 4-fold increase in cancer tissue compared to normal tissue, a decrease of about four-fold is often desired; similarly, a 10-fold decrease in cancer tissue compared to normal tissue a target value of a 10-fold increase in expression by the test compound is often desired. Modulators that exacerbate the type of gene expression seen in cancer are also useful, e.g., as an upregulated target in further analyses.

The amount of gene expression is monitored using nucleic acid probes and the quantification of gene expression levels, or, alternatively, a gene product itself is monitored, e.g., through the use of antibodies to the cancer protein and standard immunoassays. Proteomics and separation techniques also allow for quantification of expression.

Expression Monitoring to Identify Compounds that Modify Gene Expression

In one embodiment, gene expression monitoring, i.e., an expression profile, is monitored simultaneously for a number of entities. Such profiles will typically involve one or more of the genes of FIG. 1. In this embodiment, e.g., cancer nucleic acid probes are attached to biochips to detect and quantify cancer sequences in a particular cell. Alternatively, PCR can be used. Thus, a series, e.g., wells of a microtiter plate, can be used with dispensed primers in desired wells. A PCR reaction can then be performed and analyzed for each well.

Expression monitoring is performed to identify compounds that modify the expression of one or more cancer-associated sequences, e.g., a polynucleotide sequence set out in FIG. 1. Generally, a test modulator is added to the cells prior to analysis. Moreover, screens are also provided to identify agents that modulate cancer, modulate cancer proteins of the invention, bind to a cancer protein of the invention, or interfere with the binding of a cancer protein of the invention and an antibody or other binding partner.

In one embodiment, high throughput screening methods involve providing a library containing a large number of potential therapeutic compounds (candidate compounds). Such "combinatorial chemical libraries" are then screened in one or more assays to identify those library members (particular chemical species or subclasses) that display a desired characteristic activity. The compounds thus identified can serve as conventional "lead compounds," as compounds for screening, or as therapeutics.

In certain embodiments, combinatorial libraries of potential modulators are screened for an ability to bind to a cancer polypeptide or to modulate activity. Conventionally, new chemical entities with useful properties are generated by identifying a chemical compound (called a "lead compound") with some desirable property or activity, e.g., inhibiting activity, creating variants of the lead compound, and evaluating the property and activity of those variant compounds. Often, high throughput screening (HTS) methods are employed for such an analysis.

As noted above, gene expression monitoring is conveniently used to test candidate modulators (e.g., protein, nucleic acid or small molecule). After the candidate agent has been added and the cells allowed to incubate for a period, the sample containing a target sequence to be analyzed is, e.g., added to a biochip.

If required, the target sequence is prepared using known techniques. For example, a sample is treated to lyse the cells, using known lysis buffers, electroporation, etc., with purification and/or amplification such as PCR performed as appropriate. For example, an in vitro transcription with labels covalently attached to the nucleotides is performed. Generally, the nucleic acids are labeled with biotin-FITC or PE, or with cy3 or cy5.

The target sequence can be labeled with, e.g., a fluorescent, a chemiluminescent, a chemical, or a radioactive signal, to provide a means of detecting the target sequence's specific binding to a probe. The label also can be an enzyme, such as alkaline phosphatase or horseradish peroxidase, which when provided with an appropriate substrate produces a product that is detected. Alternatively, the label is a labeled compound or small molecule, such as an enzyme inhibitor, that binds but is not catalyzed or altered by the enzyme. The label also can be a moiety or compound, such as, an epitope tag or biotin which specifically binds to streptavidin. For the example of biotin, the streptavidin is labeled as described above, thereby, providing a detectable signal for the bound target sequence. Unbound labeled streptavidin is typically removed prior to analysis.

As will be appreciated by those in the art, these assays can be direct hybridization assays or can comprise "sandwich assays", which include the use of multiple probes, as is generally outlined in U.S. Pat. Nos. 5,681,702; 5,597,909; 5,545,730; 5,594,117; 5,591,584; 5,571,670; 5,580,731; 5,571,670; 5,591,584; 5,624,802; 5,635,352; 5,594,118; 5,359,100; 5,124,246; and 5,681,697. In this embodiment, in general, the target nucleic acid is prepared as outlined above, and then added to the biochip comprising a plurality of nucleic acid probes, under conditions that allow the formation of a hybridization complex.

A variety of hybridization conditions are used in the present invention, including high, moderate and low stringency conditions as outlined above. The assays are generally run under stringency conditions which allow formation of the label probe hybridization complex only in the presence of target. Stringency can be controlled by altering a step parameter that is a thermodynamic variable, including, but not limited to, temperature, formamide concentration, salt concentration, chaotropic salt concentration pH, organic solvent concentration, etc. These parameters may also be used to control non-specific binding, as is generally outlined in U.S. Pat. No. 5,681,697. Thus, it can be desirable to perform certain steps at higher stringency conditions to reduce non-specific binding.

The reactions outlined herein can be accomplished in a variety of ways. Components of the reaction can be added simultaneously, or sequentially, in different orders, with preferred embodiments outlined below. In addition, the reaction may include a variety of other reagents. These include salts, buffers, neutral proteins, e.g. albumin, detergents, etc. which can be used to facilitate optimal hybridization and detection, and/or reduce nonspecific or background interactions. Reagents that otherwise improve the efficiency of the assay, such as protease inhibitors, nuclease inhibitors, anti-microbial agents, etc., may also be used as appropriate, depending on the sample preparation methods and purity of the target. The assay data are analyzed to determine the expression levels of individual genes, and changes in expression levels as between states, forming a gene expression profile.

Biological Activity-Related Assays

The invention provides methods to identify or screen for a compound that modulates the activity of a cancer-related gene or protein of the invention. The methods comprise adding a test compound, as defined above, to a cell comprising a cancer protein of the invention. The cells contain a recombinant nucleic acid that encodes a cancer protein of the invention. In another embodiment, a library of candidate agents is tested on a plurality of cells.

In one aspect, the assays are evaluated in the presence or absence or previous or subsequent exposure of physiological signals, e.g. hormones, antibodies, peptides, antigens, cytokines, growth factors, action potentials, pharmacological agents including chemotherapeutics, radiation, carcinogenics, or other cells (i.e., cell-cell contacts). In another example, the determinations are made at different stages of the cell cycle process. In this way, compounds that modulate genes or proteins of the invention are identified. Compounds with pharmacological activity are able to enhance or interfere with the activity of the cancer protein of the invention. Once identified, similar structures are evaluated to identify critical structural features of the compound.

In one embodiment, a method of modulating (e.g., inhibiting) cancer cell division is provided; the method comprises administration of a cancer modulator. In another embodiment, a method of modulating (e.g., inhibiting) cancer is provided; the method comprises administration of a cancer modulator. In a further embodiment, methods of treating cells or individuals with cancer are provided; the method comprises administration of a cancer modulator.

In one embodiment, a method for modulating the status of a cell that expresses a gene of the invention is provided. As used herein status comprises such art-accepted parameters such as growth, proliferation, survival, function, apoptosis, senescence, location, enzymatic activity, signal transduction, etc. of a cell. In one embodiment, a cancer inhibitor is an antibody as discussed above. In another embodiment, the cancer inhibitor is an antisense molecule. A variety of cell growth, proliferation, and metastasis assays are known to those of skill in the art, as described herein.

High Throughput Screening to Identify Modulators

The assays to identify suitable modulators are amenable to high throughput screening. Preferred assays thus detect enhancement or inhibition of cancer gene transcription, inhibition or enhancement of polypeptide expression, and inhibition or enhancement of polypeptide activity.

In one embodiment, modulators evaluated in high throughput screening methods are proteins, often naturally occurring proteins or fragments of naturally occurring proteins. Thus, e.g., cellular extracts containing proteins, or random or directed digests of proteinaceous cellular extracts, are used. In this way, libraries of proteins are made for screening in the methods of the invention. Particularly preferred in this embodiment are libraries of bacterial, fungal, viral, and mammalian proteins, with the latter being preferred, and human proteins being especially preferred. Particularly useful test compound will be directed to the class of proteins to which the target belongs, e.g., substrates for enzymes, or ligands and receptors.

Use of Soft Agar Growth and Colony Formation to Identify and Characterize Modulators Normal cells require a solid substrate to attach and grow. When cells are transformed, they lose this phenotype and grow detached from the substrate. For example, transformed cells can grow in stirred suspension culture or suspended in semi-solid media, such as semi-solid or soft agar. The transformed cells, when transfected with tumor suppressor genes, can regenerate normal phenotype and once again require a solid substrate to attach to and grow. Soft agar growth or colony formation in assays are used to identify modulators of cancer sequences, which when expressed in host cells, inhibit abnormal cellular proliferation and transformation. A modulator reduces or eliminates the host cells' ability to grow suspended in solid or semisolid media, such as agar.

Techniques for soft agar growth or colony formation in suspension assays are described in Freshney, Culture of Animal Cells a Manual of Basic Technique (3rd ed., 1994). See also, the methods section of Garkavtsev et al. (1996), supra.

Evaluation of Contact Inhibition and Growth Density Limitation to Identify and Characterize Modulators Normal cells typically grow in a flat and organized pattern in cell culture until they touch other cells. When the cells touch one another, they are contact inhibited and stop growing. Transformed cells, however, are not contact inhibited and continue to grow to high densities in disorganized foci. Thus, transformed cells grow to a higher saturation density than corresponding normal cells. This is detected morphologically by the formation of a disoriented monolayer of cells or cells in foci. Alternatively, labeling index with (3H)-thymidine at saturation density is used to measure density limitation of growth, similarly an MTT or Alamar blue assay will reveal proliferation capacity of cells and the ability of modulators to affect same. See Freshney (1994), supra. Transformed cells, when transfected with tumor suppressor genes, can regenerate a normal phenotype and become contact inhibited and would grow to a lower density.

In this assay, labeling index with 3H-thymidine at saturation density is a preferred method of measuring density limitation of growth. Transformed host cells are transfected with a cancer-associated sequence and are grown for 24 hours at saturation density in non-limiting medium conditions. The percentage of cells labeling with ($^3$H)-thymidine is determined by incorporated cpm.

Contact independent growth is used to identify modulators of cancer sequences, which had led to abnormal cellular proliferation and transformation. A modulator reduces or eliminates contact independent growth, and returns the cells to a normal phenotype.

Evaluation of Growth Factor or Serum Dependence to Identify and Characterize Modulators Transformed cells have lower serum dependence than their normal counterparts (see, e.g., Temin, J. Natl. Cancer Inst. 37:167-175 (1966); Eagle et al., J. Exp. Med. 131:836-879 (1970)); Freshney, supra. This is in part due to release of various growth factors by the transformed cells. The degree of growth factor or serum dependence of transformed host cells can be compared with that of control. For example, growth factor or serum dependence of a cell is monitored in methods to identify and characterize compounds that modulate cancer-associated sequences of the invention.

Use of Tumor-Specific Marker Levels to Identify and Characterize Modulators

Tumor cells release an increased amount of certain factors (hereinafter "tumor specific markers") than their normal counterparts. For example, plasminogen activator (PA) is released from human glioma at a higher level than from normal brain cells (see, e.g., Gullino, Angiogenesis, Tumor Vascularization, and Potential Interference with Tumor Growth, in Biological Responses in Cancer, pp. 178-184 (Mihich (ed.) 1985)). Similarly, Tumor Angiogenesis Factor (TAF) is released at a higher level in tumor cells than their normal counterparts. See, e.g., Folkman, Angiogenesis and Cancer, Sem. Cancer Biol. (1992)), while bFGF is released from endothelial tumors (Ensoli, B et al.).

Various techniques which measure the release of these factors are described in Freshney (1994), supra. Also, see, Unkless et al., J. Biol. Chem. 249:4295-4305 (1974); Strickland & Beers, J. Biol. Chem. 251:5694-5702 (1976); Whur et al., Br. J. Cancer 42:305 312 (1980); Gullino, Angiogenesis, Tumor Vascularization, and Potential Interference with Tumor Growth, in Biological Responses in Cancer, pp. 178-184 (Mihich (ed.) 1985); Freshney, Anticancer Res. 5:111-130 (1985). For example, tumor specific marker levels are monitored in methods to identify and characterize compounds that modulate cancer-associated sequences of the invention.

Invasiveness into Matrigel to Identify and Characterize Modulators

The degree of invasiveness into Matrigel or an extracellular matrix constituent can be used as an assay to identify and characterize compounds that modulate cancer associated sequences. Tumor cells exhibit a positive correlation between malignancy and invasiveness of cells into Matrigel or some other extracellular matrix constituent. In this assay, tumorigenic cells are typically used as host cells. Expression of a tumor suppressor gene in these host cells would decrease invasiveness of the host cells. Techniques described in Cancer Res. 1999; 59:6010; Freshney (1994), supra, can be used. Briefly, the level of invasion of host cells is measured by using filters coated with Matrigel or some other extracellular matrix constituent. Penetration into the gel, or through to the distal side of the filter, is rated as invasiveness, and rated histologically by number of cells and distance moved, or by prelabeling the cells with $^{125}$I and counting the radioactivity on the distal side of the filter or bottom of the dish. See, e.g., Freshney (1984), supra.

Evaluation of Tumor Growth In Vivo to Identify and Characterize Modulators

Effects of cancer-associated sequences on cell growth are tested in transgenic or immune-suppressed organisms. Transgenic organisms are prepared in a variety of art-accepted ways. For example, knock-out transgenic organisms, e.g., mammals such as mice, are made, in which a cancer gene is disrupted or in which a cancer gene is inserted. Knock-out transgenic mice are made by insertion of a marker gene or other heterologous gene into the endogenous cancer gene site in the mouse genome via homologous recombination. Such mice can also be made by substituting the endogenous cancer gene with a mutated version of the cancer gene, or by mutating the endogenous cancer gene, e.g., by exposure to carcinogens.

To prepare transgenic chimeric animals, e.g., mice, a DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells some of which are derived from the mutant cell line. Therefore, by breeding the chimeric mice it is possible to obtain a new line of mice containing the introduced genetic lesion (see, e.g., Capecchi et al., Science 244:1288 (1989)). Chimeric mice can be derived according to U.S. Pat. No. 6,365,797, issued 2 Apr. 2002; U.S. Pat. No. 6,107,540 issued 22 Aug. 2000; Hogan et al., Manipulating the Mouse Embryo: A laboratory Manual, Cold Spring Harbor Laboratory (1988) and Teratocarcinomas and Embryonic Stem Cells: A Practical Approach, Robertson, ed., IRL Press, Washington, D.C., (1987).

Alternatively, various immune-suppressed or immune-deficient host animals can be used. For example, a genetically athymic "nude" mouse (see, e.g., Giovanella et al., J. Natl. Cancer Inst. 52:921 (1974)), a SCID mouse, a thymectornized mouse, or an irradiated mouse (see, e.g., Bradley et al., Br. J. Cancer 38:263 (1978); Selby et al., Br. J. Cancer 41:52 (1980)) can be used as a host. Transplantable tumor cells (typically about $10^6$ cells) injected into isogenic hosts produce invasive tumors in a high proportion of cases, while normal cells of similar origin will not. In hosts which developed invasive tumors, cells expressing cancer-associated sequences are injected subcutaneously or orthotopically. Mice are then separated into groups, including control groups and treated experimental groups) e.g. treated with a modulator). After a suitable length of time, preferably 4-8 weeks, tumor growth is measured (e.g., by volume or by its two largest dimensions, or weight) and compared to the control. Tumors that have statistically significant reduction (using, e.g., Student's T test) are said to have inhibited growth.

In Vitro Assays to Identify and Characterize Modulators

Assays to identify compounds with modulating activity can be performed in vitro. For example, a cancer polypeptide is first contacted with a potential modulator and incubated for a suitable amount of time, e.g., from 0.5 to 48 hours. In one embodiment, the cancer polypeptide levels are determined in vitro by measuring the level of protein or mRNA. The level of protein is measured using immunoassays such as Western blotting, ELISA and the like with an antibody that selectively binds to the cancer polypeptide or a fragment thereof. For measurement of mRNA, amplification, e.g., using PCR, LCR, or hybridization assays, e.g., Northern hybridization, RNAse protection, dot blotting, are preferred. The level of protein or mRNA is detected using directly or indirectly labeled detection agents, e.g., fluorescently or radioactively labeled nucleic acids, radioactively or enzymatically labeled antibodies, and the like, as described herein.

Alternatively, a reporter gene system can be devised using a cancer protein promoter operably linked to a reporter gene such as luciferase, green fluorescent protein, CAT, or P-gal. The reporter construct is typically transfected into a cell. After treatment with a potential modulator, the amount of reporter gene transcription, translation, or activity is measured according to standard techniques known to those of skill in the art (Davis G F, supra; Gonzalez, J. & Negulescu, P. Curr. Opin. Biotechnol. 1998: 9:624).

As outlined above, in vitro screens are done on individual genes and gene products. That is, having identified a particular differentially expressed gene as important in a particular state, screening of modulators of the expression of the gene or the gene product itself is performed.

In one embodiment, screening for modulators of expression of specific gene(s) is performed. Typically, the expression of only one or a few genes is evaluated. In another embodiment, screens are designed to first find compounds that bind to differentially expressed proteins. These compounds are then evaluated for the ability to modulate differentially expressed activity. Moreover, once initial candidate compounds are identified, variants can be further screened to better evaluate structure activity relationships.

Binding Assays to Identify and Characterize Modulators

In binding assays in accordance with the invention, a purified or isolated gene product of the invention is generally used. For example, antibodies are generated to a protein of the invention, and immunoassays are run to determine the amount and/or location of protein. Alternatively, cells comprising the cancer proteins are used in the assays.

Thus, the methods comprise combining a cancer protein of the invention and a candidate compound such as a ligand, and determining the binding of the compound to the cancer protein of the invention. Preferred embodiments utilize the human cancer protein; animal models of human disease of can also be developed and used. Also, other analogous mammalian proteins also can be used as appreciated by those of skill in the art. Moreover, in some embodiments variant or derivative cancer proteins are used.

Generally, the cancer protein of the invention, or the ligand, is non-diffusibly bound to an insoluble support. The support can, e.g., be one having isolated sample receiving areas (a microtiter plate, an array, etc.). The insoluble supports can be made of any composition to which the compositions can be bound, is readily separated from soluble material, and is otherwise compatible with the overall method of screening. The surface of such supports can be solid or porous and of any convenient shape.

Examples of suitable insoluble supports include microtiter plates, arrays, membranes and beads. These are typically made of glass, plastic (e.g., polystyrene), polysaccharide, nylon, nitrocellulose, or Teflon™, etc. Microtiter plates and arrays are especially convenient because a large number of assays can be carried out simultaneously, using small amounts of reagents and samples. The particular manner of binding of the composition to the support is not crucial so long as it is compatible with the reagents and overall methods of the invention, maintains the activity of the composition and is nondiffusable. Preferred methods of binding include the use of antibodies which do not sterically block either the ligand binding site or activation sequence when attaching the protein to the support, direct binding to "sticky" or ionic supports, chemical crosslinking, the synthesis of the protein or agent on the surface, etc. Following binding of the protein or ligand/binding agent to the support, excess unbound material is removed by washing. The sample receiving areas may then be blocked through incubation with bovine serum albumin (BSA), casein or other innocuous protein or other moiety.

Once a cancer protein of the invention is bound to the support, and a test compound is added to the assay. Alternatively, the candidate binding agent is bound to the support and the cancer protein of the invention is then added. Binding agents include specific antibodies, non-natural binding agents identified in screens of chemical libraries, peptide analogs, etc.

Of particular interest are assays to identify agents that have a low toxicity for human cells. A wide variety of assays can be used for this purpose, including proliferation assays, cAMP assays, labeled in vitro protein-protein binding assays, electrophoretic mobility shift assays, immunoassays for protein binding, functional assays (phosphorylation assays, etc.) and the like.

A determination of binding of the test compound (ligand, binding agent, modulator, etc.) to a cancer protein of the invention can be done in a number of ways. The test compound can be labeled, and binding determined directly, e.g., by attaching all or a portion of the cancer protein of the invention to a solid support, adding a labeled candidate compound (e.g., a fluorescent label), washing off excess reagent, and determining whether the label is present on the solid support. Various blocking and washing steps can be utilized as appropriate.

In certain embodiments, only one of the components is labeled, e.g., a protein of the invention or ligands labeled. Alternatively, more than one component is labeled with different labels, e.g., $I^{125}$ for the proteins and a fluorophor for the compound. Proximity reagents, e.g., quenching or energy transfer reagents are also useful.

Competitive Binding to Identify and Characterize Modulators

In one embodiment, the binding of the "test compound" is determined by competitive binding assay with a "competitor." The competitor is a binding moiety that binds to the target molecule (e.g., a cancer protein of the invention). Competitors include compounds such as antibodies, peptides, binding partners, ligands, etc. Under certain circumstances, the competitive binding between the test compound and the competitor displaces the test compound. In one embodiment, the test compound is labeled. Either the test compound, the competitor, or both, is added to the protein for a time sufficient to allow binding. Incubations are performed at a temperature that facilitates optimal activity, typically between four and 40° C. Incubation periods are typically optimized, e.g., to facilitate rapid high throughput screening; typically between zero and one hour will be sufficient. Excess reagent is generally removed or washed away. The second component is then added, and the presence or absence of the labeled component is followed, to indicate binding.

In one embodiment, the competitor is added first, followed by the test compound. Displacement of the competitor is an indication that the test compound is binding to the cancer protein and thus is capable of binding to, and potentially modulating, the activity of the cancer protein. In this embodiment, either component can be labeled. Thus, e.g., if the competitor is labeled, the presence of label in the post-test compound wash solution indicates displacement by the test compound. Alternatively, if the test compound is labeled, the presence of the label on the support indicates displacement.

In an alternative embodiment, the test compound is added first, with incubation and washing, followed by the competitor. The absence of binding by the competitor indicates that the test compound binds to the cancer protein with higher affinity than the competitor. Thus, if the test compound is labeled, the presence of the label on the support, coupled with a lack of competitor binding, indicates that the test compound binds to and thus potentially modulates the cancer protein of the invention.

Accordingly, the competitive binding methods comprise differential screening to identity agents that are capable of modulating the activity of the cancer proteins of the invention. In this embodiment, the methods comprise combining a cancer protein and a competitor in a first sample. A second sample comprises a test compound, the cancer protein, and a competitor. The binding of the competitor is determined for both samples, and a change, or difference in binding between the two samples indicates the presence of an agent capable of binding to the cancer protein and potentially modulating its activity. That is, if the binding of the competitor is different in the second sample relative to the first sample, the agent is capable of binding to the cancer protein.

Alternatively, differential screening is used to identify drug candidates that bind to the native cancer protein, but cannot bind to modified cancer proteins. For example the structure of the cancer protein is modeled and used in rational drug design to synthesize agents that interact with that site, agents which generally do not bind to site-modified proteins. Moreover, such drug candidates that affect the activity of a native cancer protein are also identified by screening drugs for the ability to either enhance or reduce the activity of such proteins.

Positive controls and negative controls can be used in the assays. Preferably control and test samples are performed in at least triplicate to obtain statistically significant results. Incubation of all samples occurs for a time sufficient to allow for the binding of the agent to the protein. Following incubation, samples are washed free of non-specifically bound material and the amount of bound, generally labeled agent determined. For example, where a radiolabel is employed, the samples can be counted in a scintillation counter to determine the amount of bound compound.

A variety of other reagents can be included in the screening assays. These include reagents like salts, neutral proteins, e.g. albumin, detergents, etc. which are used to facilitate optimal protein-protein binding and/or reduce non-specific or background interactions. Also reagents that otherwise improve the efficiency of the assay, such as protease inhibitors, nuclease inhibitors, anti-microbial agents, etc., can be used. The mixture of components is added in an order that provides for the requisite binding.

Use of Polynucleotides to Down-Regulate or Inhibit a Protein of the Invention.

Polynucleotide modulators of cancer can be introduced into a cell containing the target nucleotide sequence by formation of a conjugate with a ligand-binding molecule, as described in WO 91/04753. Suitable ligand-binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell. Alternatively, a polynucleotide modulator of cancer can be introduced into a cell containing the target nucleic acid sequence, e.g., by formation of a polynucleotide-lipid complex, as described in WO 90/10448. It is understood that the use of antisense molecules or knock out and knock in models may also be used in screening assays as discussed above, in addition to methods of treatment.

Inhibitory and Antisense Nucleotides

In certain embodiments, the activity of a cancer-associated protein is down-regulated, or entirely inhibited, by the use of antisense polynucleotide or inhibitory small nuclear RNA (snRNA), i.e., a nucleic acid complementary to, and which can preferably hybridize specifically to, a coding mRNA nucleic acid sequence, e.g., a cancer protein of the invention, mRNA, or a subsequence thereof. Binding of the antisense polynucleotide to the mRNA reduces the translation and/or stability of the mRNA.

In the context of this invention, antisense polynucleotides can comprise naturally occurring nucleotides, or synthetic species formed from naturally occurring subunits or their close homologs. Antisense polynucleotides may also have altered sugar moieties or inter-sugar linkages. Exemplary among these are the phosphorothioate and other sulfur containing species which are known for use in the art. Analogs are comprised by this invention so long as they function effectively to hybridize with nucleotides of the invention. See, e.g., Isis Pharmaceuticals, Carlsbad, Calif.; Sequitor, Inc., Natick, Mass.

Such antisense polynucleotides can readily be synthesized using recombinant means, or can be synthesized in vitro. Equipment for such synthesis is sold by several vendors, including Applied Biosystems. The preparation of other oligonucleotides such as phosphorothioates and alkylated derivatives is also well known to those of skill in the art.

Antisense molecules as used herein include antisense or sense oligonucleotides. Sense oligonucleotides can, e.g., be employed to block transcription by binding to the anti-sense strand. The antisense and sense oligonucleotide comprise a single stranded nucleic acid sequence (either RNA or DNA) capable of binding to target mRNA (sense) or DNA (antisense) sequences for cancer molecules. Antisense or sense oligonucleotides, according to the present invention, comprise a fragment generally at least about 12 nucleotides, preferably from about 12 to 30 nucleotides. The ability to derive an antisense or a sense oligonucleotide, based upon a cDNA sequence encoding a given protein is described in, e.g., Stein &Cohen (Cancer Res. 48:2659 (1988 and van der Krol et al. (BioTechniques 6:958 (1988)).

Ribozymes

In addition to antisense polynucleotides, ribozymes can be used to target and inhibit transcription of cancer-associated nucleotide sequences. A ribozyme is an RNA molecule that catalytically cleaves other RNA molecules. Different kinds of ribozymes have been described, including group I ribozymes, hammerhead ribozymes, hairpin ribozymes, RNase P, and axhead ribozymes (see, e.g., Castanotto et al., Adv. in Pharmacology 25: 289-317 (1994) for a general review of the properties of different ribozymes).

The general features of hairpin ribozymes are described, e.g., in Hampel et al., Nucl. Acids Res. 18:299-304 (1990); European Patent Publication No. 0360257; U.S. Pat. No. 5,254,678. Methods of preparing are well known to those of skill in the art (see, e.g., WO 94/26877; Ojwang et al., Proc. Natl. Acad. Sci. USA 90:6340-6344 (1993); Yamada et al., Human Gene Therapy 1:39-45 (1994); Leavitt et al., Proc. Natl. Acad. Sci. USA 92:699-703 (1995); Leavitt et al., Human Gene Therapy 5: 1151-120 (1994); and Yamada et al., Virology 205: 121-126 (1994)).

Use of Modulators in Phenotypic Screening

In one embodiment, a test compound is administered to a population of cancer cells, which have an associated cancer expression profile. By "administration" or "contacting" herein is meant that the modulator is added to the cells in such a manner as to allow the modulator to act upon the cell, whether by uptake and intracellular action, or by action at the cell surface. In some embodiments, a nucleic acid encoding a proteinaceous agent (i.e., a peptide) is put into a viral construct such as an adenoviral or retroviral construct, and added to the cell, such that expression of the peptide agent is accomplished, e.g., PCT US97/01019. Regulatable gene therapy systems can also be used. Once the modulator has been administered to the cells, the cells are washed if desired and are allowed to incubate under preferably physiological conditions for some period. The cells are then harvested and a new gene expression profile is generated. Thus, e.g., cancer tissue is screened for agents that modulate, e.g., induce or suppress, the cancer phenotype. A change in at least one gene, preferably many, of the expression profile indicates that the agent has an effect on cancer activity. Similarly, altering a biological function or a signaling pathway is indicative of modulator activity. By defining such a signature for the cancer phenotype, screens for new drugs that alter the phenotype are devised. With this approach, the drug target need not be known and need not be represented in the original gene/protein expression screening platform, nor does the level of transcript for the target protein need to change. The modulator inhibiting function will serve as a surrogate marker As outlined above, screens are done to assess genes or gene products. That is, having identified a particular differentially expressed gene as important in a particular state, screening of modulators of either the expression of the gene or the gene product itself is performed.

Use of Modulators to Affect Peptides of the Invention

Measurements of cancer polypeptide activity, or of the cancer phenotype are performed using a variety of assays. For example, the effects of modulators upon the function of a cancer polypeptide(s) are measured by examining parameters described above. A physiological change that affects activity is used to assess the influence of a test compound on the polypeptides of this invention. When the functional outcomes are determined using intact cells or animals, a variety of effects can be assesses such as, in the case of a cancer associated with solid tumors, tumor growth, tumor metastasis, neovascularization, hormone release, transcriptional changes to both known and uncharacterized genetic markers (e.g., by Northern blots), changes in cell metabolism such as cell growth or pH changes, and changes in intracellular second messengers such as cGNIP.

Methods of Identifying Characterizing Cancer-Associated Sequences

Expression of various gene sequences is correlated with cancer. Accordingly, disorders based on mutant or variant cancer genes are determined. In one embodiment, the invention provides methods for identifying cells containing variant cancer genes, e.g., determining the presence of, all or part, the sequence of at least one endogenous cancer gene in a cell. This is accomplished using any number of sequencing techniques. The invention comprises methods of identifying the cancer genotype of an individual, e.g., determining all or part of the sequence of at least one gene of the invention in the individual. This is generally done in at least one tissue of the individual, e.g., a tissue set forth in Table I, and may include the evaluation of a number of tissues or different samples of the same tissue. The method may include comparing the sequence of the sequenced gene to a known cancer gene, i.e., a wild-type gene to determine the presence of family members, homologies, mutations or variants. The sequence of all or part of the gene can then be compared to the sequence of a known cancer gene to determine if any differences exist. This is done using any number of known homology programs, such as BLAST, Bestfit, etc. The presence of a difference in the sequence between the cancer gene of the patient and the known cancer gene correlates with a disease state or a propensity for a disease state, as outlined herein.

In a preferred embodiment, the cancer genes are used as probes to determine the number of copies of the cancer gene in the genome. The cancer genes are used as probes to determine the chromosomal localization of the cancer genes. Information such as chromosomal localization finds use in providing a diagnosis or prognosis in particular when chromosomal abnormalities such as translocations, and the like are identified in the cancer gene locus.

XIII.) RNAI AND THERAPEUTIC USE OF SMALL INTERFERING RNA (SIRNAS)

The present invention is also directed towards siRNA oligonucleotides, particularly double stranded RNAs encompassing at least a fragment of the 161P2F10B coding region or 5" UTR regions, or complement, or any antisense oligonucleotide specific to the 161P2F10B sequence. In one embodiment such oligonucleotides are used to elucidate a function of 161P2F10B, or are used to screen for or evaluate modulators of 161P2F10B function or expression. In another embodiment, gene expression of 161P2F10B is reduced by using siRNA transfection and results in significantly diminished proliferative capacity of transformed cancer cells that endogenously express the antigen; cells treated with specific 161P2F10B siRNAs show reduced survival as measured, e.g., by a metabolic readout of cell viability, correlating to the reduced proliferative capacity. Thus, 161P2F10B siRNA compositions comprise siRNA (double stranded RNA) that correspond to the nucleic acid ORF sequence of the 161P2F10B protein or subsequences thereof; these subsequences are generally 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more than 35 contiguous RNA nucleotides in length and contain sequences that are complementary and non-complementary to at least a portion of the mRNA coding sequence In a preferred embodiment, the subsequences are 19-25 nucleotides in length, most preferably 21-23 nucleotides in length.

RNA interference is a novel approach to silencing genes in vitro and in vivo, thus small double stranded RNAs (siRNAs) are valuable therapeutic agents. The power of siRNAs to silence specific gene activities has now been brought to animal models of disease and is used in humans as well. For example, hydrodynamic infusion of a solution of siRNA into a mouse with a siRNA against a particular target has been proven to be therapeutically effective.

The pioneering work by Song et al. indicates that one type of entirely natural nucleic acid, small interfering RNAs (siRNAs), served as therapeutic agents even without further chemical modification (Song, E., et al. "RNA interference targeting Fas protects mice from fulminant hepatitis" Nat. Med. 9(3): 347-51 (2003)). This work provided the first in vivo evidence that infusion of siRNAs into an animal could alleviate disease. In that case, the authors gave mice injections of siRNA designed to silence the FAS protein (a cell death receptor that when over-activated during inflammatory response induces hepatocytes and other cells to die). The next day, the animals were given an antibody specific to Fas. Control mice died of acute liver failure within a few days, while over 80% of the siRNA-treated mice remained free from serious disease and survived. About 80% to 90% of their liver cells incorporated the naked siRNA oligonucleotides. Furthermore, the RNA molecules functioned for 10 days before losing effect after 3 weeks.

For use in human therapy, siRNA is delivered by efficient systems that induce long-lasting RNAi activity. A major caveat for clinical use is delivering siRNAs to the appropriate cells. Hepatocytes seem to be particularly receptive to exogenous RNA. Today, targets located in the liver are attractive because liver is an organ that can be readily targeted by nucleic acid molecules and viral vectors. However, other tissue and organs targets are preferred as well.

Formulations of siRNAs with compounds that promote transit across cell membranes are used to improve administration of siRNAs in therapy. Chemically modified synthetic siRNA, that are resistant to nucleases and have serum stability have concomitant enhanced duration of RNAi effects, are an additional embodiment.

Thus, siRNA technology is a therapeutic for human malignancy by delivery of siRNA molecules directed to 161P2F10B to individuals with the cancers, such as those listed in Table 1. Such administration of siRNAs leads to reduced growth of cancer cells expressing 161P2F10B, and provides an anti-tumor therapy, lessening the morbidity and/or mortality associated with malignancy.

The effectiveness of this modality of gene product knockdown is significant when measured in vitro or in vivo. Effectiveness in vitro is readily demonstrable through application of siRNAs to cells in culture (as described above) or to aliquots of cancer patient biopsies when in vitro methods are used to detect the reduced expression of 161P2F10B protein.

XIV.) KITS/ARTICLES OF MANUFACTURE

For use in the laboratory, prognostic, prophylactic, diagnostic and therapeutic applications described herein, kits are within the scope of the invention. Such kits can comprise a carrier, package, or container that is compartmentalized to receive one or more containers such as vials, tubes, and the like, each of the container(s) comprising one of the separate elements to be used in the method, along with a label or insert comprising instructions for use, such as a use described herein. For example, the container(s) can comprise a probe that is or can be detectably labeled. Such probe can be an antibody or polynucleotide specific for a protein or a gene or message of the invention, respectively. Where the method utilizes nucleic acid hybridization to detect the target nucleic acid, the kit can also have containers containing nucleotide(s) for amplification of the target nucleic acid sequence. Kits can comprise a container comprising a reporter, such as a biotin-binding protein, such as avidin or streptavidin, bound to a reporter molecule, such as an enzymatic, fluorescent, or radioisotope label; such a reporter can be used with, e.g., a nucleic acid or antibody. The kit can include all or part of the amino acid sequences in FIG. 1, FIG. 2, or FIG. 3 or analogs thereof, or a nucleic acid molecule that encodes such amino acid sequences.

The kit of the invention will typically comprise the container described above and one or more other containers associated therewith that comprise materials desirable from a commercial and user standpoint, including buffers, diluents, filters, needles, syringes; carrier, package, container, vial and/or tube labels listing contents and/or instructions for use, and package inserts with instructions for use.

A label can be present on or with the container to indicate that the composition is used for a specific therapy or non-therapeutic application, such as a prognostic, prophylactic, diagnostic or laboratory application, and can also indicate directions for either in vivo or in vitro use, such as those described herein. Directions and or other information can also be included on an insert(s) or label(s) which is included with or on the kit. The label can be on or associated with the container. A label a can be on a container when letters, numbers or other characters forming the label are molded or etched into the container itself; a label can be associated with a container when it is present within a receptacle or carrier that also holds the container, e.g., as a package insert. The label can indicate that the composition is used for diagnosing, treating, prophylaxing or prognosing a condition, such as a neoplasia of a tissue set forth in Table I.

The terms "kit" and "article of manufacture" can be used as synonyms.

In another embodiment of the invention, an article(s) of manufacture containing compositions, such as amino acid sequence(s), small molecule(s), nucleic acid sequence(s), and/or antibody(s), e.g., materials useful for the diagnosis, prognosis, prophylaxis and/or treatment of neoplasias of tissues such as those set forth in Table I is provided. The article of manufacture typically comprises at least one container and at least one label. Suitable containers include, for example, bottles, vials, syringes, and test tubes. The containers can be formed from a variety of materials such as glass, metal or plastic. The container can hold amino acid sequence(s), small molecule(s), nucleic acid sequence(s), cell population(s) and/or antibody(s). In one embodiment, the container holds a polynucleotide for use in examining the mRNA expression profile of a cell, together with reagents used for this purpose. In another embodiment a container comprises an antibody, binding fragment thereof or specific binding protein for use in evaluating protein expression of 161P2F10B in cells and tissues, or for relevant laboratory, prognostic, diagnostic, prophylactic and therapeutic purposes; indications and/or directions for such uses can be included on or with such container, as can reagents and other compositions or tools used for these purposes. In another embodiment, a container comprises materials for eliciting a cellular or humoral immune response, together with associated indications and/or directions. In another embodiment, a container comprises materials for adoptive immunotherapy, such as cytotoxic T cells (CTL) or helper T cells (HTL), together with associated indications and/or directions; reagents and other compositions or tools used for such purpose can also be included.

The container can alternatively hold a composition that is effective for treating, diagnosis, prognosing or prophylaxing a condition and can have a sterile access port (for example the container can be an intravenous solution bag or a vial having a stopper pierceable by a hypodermic injection needle). The active agents in the composition can be an antibody capable of specifically binding 161P2F10B and modulating the function of 161P2F10B.

The article of manufacture can further comprise a second container comprising a pharmaceutically-acceptable buffer, such as phosphate-buffered saline, Ringer's solution and/or dextrose solution. It can further include other materials desirable from a commercial and user standpoint, including other buffers, diluents, filters, stirrers, needles, syringes, and/or package inserts with indications and/or instructions for use.

EXAMPLES

Various aspects of the invention are further described and illustrated by way of the several examples that follow, none of which is intended to limit the scope of the invention.

Example 1

Expression Analysis of 161P2F10B Variants in Normal Tissues and Patient Specimens To compare expression of 161P2F10B and 161P2F10B variants in normal versus patient cancer tissues, RT-PCR experiments were performed using normal and patient cancer tissues. First strand cDNA was generated from normal stomach, normal brain, normal heart, normal liver, normal skeletal muscle, normal testis, normal prostate, normal bladder, normal kidney, normal colon, normal lung, normal pancreas, and a pool of cancer specimens from prostate cancer patients, bladder cancer patients, kidney cancer patients, colon cancer patients, lung cancer patients, pancreas cancer patients, a pool of prostate cancer xenografts (LAPC-4AD, LAPC-4AI, LAPC-9AD and LAPC-9AI), and a pool of 2 patient prostate metastasis to lymph node. Normalization was performed by PCR using primers to actin. Semi-quantitative PCR, using primers to 161P2F10B, was performed at 26 and 30 cycles of amplification. Samples were run on an agarose gel, and PCR products were quantitated using the AlphaImager software.

Expression of 161P2F10B in a panel of kidney cancer clear cell carcinoma, kidney cancer papillary carcinoma, and in uterus patient cancer specimens has been shown previously. First strand cDNA was prepared from the patient specimens. Normalization was performed by PCR using primers to actin. Semi-quantitative PCR, using primers to 161P2F10B, was performed at 26 and 30 cycles of amplification. Samples were run on an agarose gel, and PCR products were quantitated using the AlphaImager software. Expression was recorded as absent, low, medium or strong. Results show expression of 161P2F10B in 94.7% of clear cell renal carcinoma, 62.5% of papillary renal cell carcinoma, and in 61.5% of uterus cancer.

The restricted expression of 161P2F10B in normal tissues and the upregulation detected in kidney cancer, in kidney cancer metastasis, as well as in prostate, bladder, colon, lung, pancreas, bone, lymphoma, uterus, breast, and ovary cancers, suggest that 161P2F10B is a therapeutic target and a diagnostic marker for human cancers.

Example 2

Splice Variants of 161P2F10B

Transcript variants are variants of mature mRNA from the same gene, which arise by alternative transcription or alternative splicing. Alternative transcripts are transcripts from the same gene but start transcription at different points. Splice variants are mRNA variants spliced differently from the same transcript. In eukaryotes, when a multi-exon gene is transcribed from genomic DNA, the initial RNA is spliced to produce functional mRNA, which has only exons and is used for translation into an amino acid sequence. Accordingly, a given gene can have zero to many alternative transcripts and each transcript can have zero to many splice variants. Each transcript variant has a unique exon makeup, and can have different coding and/or non-coding (5' or 3' end) portions, from the original transcript. Transcript variants can code for similar or different proteins with the same or a similar function or can encode proteins with different functions, and can be expressed in the same tissue at the same time, or in different tissues at the same time, or in the same tissue at different times, or in different tissues at different times. Proteins encoded by transcript variants can have similar or different cellular or extracellular localizations, e.g., secreted versus intracellular.

Transcript variants are identified by a variety of art-accepted methods. For example, alternative transcripts and splice variants are identified by full-length cloning experiment, or by use of full-length transcript and EST sequences. First, all human ESTs were grouped into clusters which show direct or indirect identity with each other. Second, ESTs in the same cluster were further grouped into sub-clusters and assembled into a consensus sequence. The original gene sequence is compared to the consensus sequence(s) or other full-length sequences. Each consensus sequence is a potential splice variant for that gene. Even when a variant is identified that is not a full-length clone, that portion of the variant is very useful for antigen generation and for further cloning of the full-length splice variant, using techniques known in the art.

Moreover, computer programs are available in the art that identify transcript variants based on genomic sequences. Genomic-based transcript variant identification programs include FgenesH (A. Salamov and V. Solovyev, "Ab initio gene finding in *Drosophila* genomic DNA," Genome Research. 2000 April; 10(4):516-22); Grail and GenScan. For a general discussion of splice variant identification protocols see., e.g., Southan, C., A genomic perspective on human proteases, FEBS Lett. 2001 Jun. 8; 498(2-3):214-8; de Souza, S. J., et al., Identification of human chromosome 22 transcribed sequences with ORF expressed sequence tags, Proc. Natl. Acad Sci USA. 2000 Nov. 7; 97(23):12690-3.

To further confirm the parameters of a transcript variant, a variety of techniques are available in the art, such as full-length cloning, proteomic validation, PCR-based validation, and 5' RACE validation, etc. (see e.g., Proteomic Validation: Brennan, S. O., et al., Albumin banks peninsula: a new termination variant characterized by electrospray mass spectrometry, Biochem Biophys Acta. 1999 Aug. 17; 1433(1-2): 321-6; Ferranti P, et al., Differential splicing of pre-messenger RNA produces multiple forms of mature caprine alpha(s1)-casein, Eur J. Biochem. 1997 Oct. 1; 249(1):1-7. For PCR-based Validation: Wellmann S, et al., Specific reverse transcription-PCR quantification of vascular endothelial growth factor (VEGF) splice variants by LightCycler technology, Clin Chem. 2001 April; 47(4):654-60; Jia, H. P., et al., Discovery of new human beta-defensins using a genomics-based approach, Gene. 2001 Jan. 24; 263(1-2): 211-8. For PCR-based and 5' RACE Validation: Brigle, K. E., et al., Organization of the murine reduced folate carrier gene and identification of variant splice forms, Biochem Biophys Acta. 1997 Aug. 7; 1353(2): 191-8).

It is known in the art that genomic regions are modulated in cancers. When the genomic region to which a gene maps is modulated in a particular cancer, the alternative transcripts or splice variants of the gene are modulated as well. Disclosed herein is that 161P2F10B has a particular expression profile related to cancer. Alternative transcripts and splice variants of 161P2F10B are also involved in cancers in the same or different tissues, thus serving as tumor-associated markers/antigens.

161P2F10B amino acid and nucleic acid sequences are set forth on a variant by variant basis in FIG. 1.

Example 3

Single Nucleotide Polymorphisms of 161P2F10B

A Single Nucleotide Polymorphism (SNP) is a single base pair variation in a nucleotide sequence at a specific location. At any given point of the genome, there are four possible nucleotide base pairs: A/T, C/G, G/C and T/A. Genotype refers to the specific base pair sequence of one or more locations in the genome of an individual. Haplotype refers to the base pair sequence of more than one location on the same DNA molecule (or the same chromosome in higher organisms), often in the context of one gene or in the context of several tightly linked genes. SNPs that occur on a cDNA are called cSNPs. These cSNPs may change amino acids of the protein encoded by the gene and thus change the functions of the protein. Some SNPs cause inherited diseases; others contribute to quantitative variations in phenotype and reactions to environmental factors including diet and drugs among individuals. Therefore, SNPs and/or combinations of alleles (called haplotypes) have many applications, including diagnosis of inherited diseases, determination of drug reactions and dosage, identification of genes responsible for diseases, and analysis of the genetic relationship between individuals (P. Nowotny, J. M. Kwon and A. M. Goate, "SNP analysis to dissect human traits," Curr. Opin. Neurobiol. 2001 October; 11(5):637-641; M. Pirmohamed and B. K. Park, "Genetic susceptibility to adverse drug reactions," Trends Pharmacol. Sci. 2001 June; 22(6):298-305; J. H. Riley, C. J. Allan, E. Lai and A. Roses, "The use of single nucleotide polymorphisms in the isolation of common disease genes," Pharmacogenomics. 2000 February; 1(1):39-47; R. Judson, J. C. Stephens and A. Windemuth, "The predictive power of haplotypes in clinical response," Pharmacogenomics. 2000 feb; 1(1):15-26).

SNPs are identified by a variety of art-accepted methods (P. Bean, "The promising voyage of SNP target discovery," Am. Clin. Lab. 2001 October-November; 20(9):18-20; K. M. Weiss, "In search of human variation," Genome Res. 1998 July; 8(7):691-697; M. M. She, "Enabling large-scale pharmacogenetic studies by high-throughput mutation detection and genotyping technologies," Clin. Chem. 2001 February; 47(2):164-172). For example, SNPs are identified by sequencing DNA fragments that show polymorphism by gel-based methods such as restriction fragment length polymorphism (RFLP) and denaturing gradient gel electrophoresis (DGGE). They can also be discovered by direct sequencing of DNA samples pooled from different individuals or by comparing sequences from different DNA samples. With the rapid accumulation of sequence data in public and private databases, one can discover SNPs by comparing sequences using computer programs (Z. Gu, L. Hillier and P. Y. Kwok, "Single nucleotide polymorphism hunting in cyberspace," Hum. Mutat. 1998; 12(4):221-225). SNPs can be verified and genotype or haplotype of an individual can be determined by a variety of methods including direct sequencing and high throughput microarrays (P. Y. Kwok, "Methods for genotyping single nucleotide polymorphisms," Annu. Rev. Genomics Hum. Genet. 2001; 2:235-258; M. Kokoris, K. Dix, K. Moynihan, J. Mathis, B. Erwin, P. Grass, B. Hines and A. Duesterhoeft, "High-throughput SNP genotyping with the Masscode system," Mol. Diagn. 2000 December; 5(4):329-340).

Using the methods described above, four SNPs were identified in the original transcript, 161P2F10B v.1, at positions 408 (A/G), 2502 (A/G), 2663 (A/C) and 3233 (A/C). The transcripts or proteins with alternative alleles were designated as variants 161P2F10B v.2, v.3, v.4, and v.5, respectively. These alleles of the SNPs, though discussed separately, can occur in different combinations (haplotypes) and in any one of the transcript variants (such as 161P2F10B v.7) that contains the sequence context of the SNPs.

161P2F10B amino acid and nucleic acid sequences are set forth on a variant by variant basis in FIG. 1.

Example 4

Production of Recombinant 161P2F10B in Prokaryotic Systems

To express recombinant 161P2F10B and 161P2F10B variants in prokaryotic cells, the full or partial length 161P2F10B and 161P2F10B variant cDNA sequences are cloned into any one of a variety of expression vectors known in the art. One or more of the following regions of 161P2F10B variants are expressed: the full length sequence presented in FIG. 1, or any 8, 9, 10, 11, 12, 13, 14, 15, 16, 17, 18, 19, 20, 21, 22, 23, 24, 25, 26, 27, 28, 29, 30 or more contiguous amino acids from 161P2F10B, variants, or analogs thereof.

In Vitro Transcription and Translation Constructs:

pCRII: To generate 161P2F10B sense and anti-sense RNA probes for RNA in situ investigations, pCRII constructs (Invitrogen, Carlsbad Calif.) are generated encoding either all or fragments of the 161P2F10B cDNA. The pCRII vector has Sp6 and T7 promoters flanking the insert to drive the transcription of 161P2F10B RNA for use as probes in RNA in situ hybridization experiments. These probes are used to analyze the cell and tissue expression of 161P2F10B at the RNA level. Transcribed 161P2F10B RNA representing the cDNA amino acid coding region of the 161P2F10B gene is used in in vitro translation systems such as the TnT™ Coupled Reticulolysate System (Promega, Corp., Madison, Wis.) to synthesize 161P2F10B protein.

Bacterial Constructs:

pGEX Constructs: To generate recombinant 161P2F10B proteins in bacteria that are fused to the Glutathione S-transferase (GST) protein, all or parts of the 161P2F10B cDNA protein coding sequence are cloned into the pGEX family of GST-fusion vectors (Amersham Pharmacia Biotech, Piscataway, N.J.). These constructs allow controlled expression of recombinant 161P2F10B protein sequences with GST fused at the amino-terminus and a six histidine epitope (6×His) at the carboxyl-terminus. The GST and 6× His tags permit purification of the recombinant fusion protein from induced bacteria with the appropriate affinity matrix and allow recognition of the fusion protein with anti-GST and anti-His antibodies. The 6× His tag is generated by adding 6 histidine codons to the cloning primer at the 3' end, e.g., of the open reading frame (ORF). A proteolytic cleavage site, such as the PreScission™ recognition site in pGEX-6P-1, may be employed such that it permits cleavage of the GST tag from 161P2F10B-related protein. The ampicillin resistance gene and pBR322 origin permits selection and maintenance of the pGEX plasmids in E. coli.

pMAL Constructs: To generate, in bacteria, recombinant 161P2F10B proteins that are fused to maltose-binding protein (MBP), all or parts of the 161P2F10B cDNA protein coding sequence are fused to the MBP gene by cloning into the pMAL-c2X and pMAL-p2X vectors (New England Biolabs, Beverly, Mass.). These constructs allow controlled expression of recombinant 161P2F10B protein sequences with MBP fused at the amino-terminus and a 6×His epitope tag at the carboxyl-terminus The MBP and 6×His tags permit purification of the recombinant protein from induced bacteria with the appropriate affinity matrix and allow recognition of the fusion protein with anti-MBP and anti-His antibodies. The 6×His epitope tag is generated by adding 6 histidine codons to the 3' cloning primer. A Factor Xa recognition site permits cleavage of the pMAL tag from 161P2F10B. The pMAL-c2X and pMAL-p2X vectors are optimized to express the recombinant protein in the cytoplasm or periplasm respectively. Periplasm expression enhances folding of proteins with disulfide bonds.

pET Constructs: To express 161P2F10B in bacterial cells, all or parts of the 161P2F10B cDNA protein coding sequence are cloned into the pET family of vectors (Novagen, Madison, Wis.). These vectors allow tightly controlled expression of recombinant 161P2F10B protein in bacteria with and without fusion to proteins that enhance solubility, such as NusA and thioredoxin (Trx), and epitope tags, such as 6× His and S-Tag™ that aid purification and detection of the recombinant protein. For example, constructs are made utilizing pET NusA fusion system 43.1 such that regions of the 161P2F10B protein are expressed as amino-terminal fusions to NusA.

Yeast Constructs:

pESC Constructs: To express 161P2F10B in the yeast species Saccharomyces cerevisiae for generation of recombinant protein and functional studies, all or parts of the 161P2F10B cDNA protein coding sequence are cloned into the pESC family of vectors each of which contain 1 of 4 selectable markers, HIS3, TRP1, LEU2, and URA3 (Stratagene, La Jolla, Calif.). These vectors allow controlled expression from the same plasmid of up to 2 different genes or cloned sequences containing either Flag™ or Myc epitope tags in the same yeast cell. This system is useful to confirm proteinprotein interactions of 161P2F10B. In addition, expression in yeast yields similar post-translational modifications, such as glycosylations and phosphorylations that are found when expressed in eukaryotic cells.

pESP Constructs: To express 161P2F10B in the yeast species Saccharomyces pombe, all or parts of the 161P2F10B cDNA protein coding sequence are cloned into the pESP family of vectors. These vectors allow controlled high level of expression of a 161P2F10B protein sequence that is fused at either the amino terminus or at the carboxyl terminus to GST which aids purification of the recombinant protein. A Flag™ epitope tag allows detection of the recombinant protein with anti-Flag™ antibody.

Example 5

Production of Recombinant 161P2F10B in Higher Eukaryotic Systems

A. Mammalian Constructs:

To express recombinant 161P2F10B in eukaryotic cells, the full or partial length 161P2F10B cDNA sequences, or variants thereof, can be cloned into any one of a variety of expression vectors known in the art. One or more of the following regions of 161P2F10B are expressed in these constructs, amino acids 1 to 875, or any 8, 9, 10, 11, 12, 13, 14, 15, 16, 17, 18, 19, 20, 21, 22, 23, 24, 25, 26, 27, 28, 29, 30 or more contiguous amino acids from 161P2F10B v.1, 161P2F10B variants, or analogs thereof.

The constructs can be transfected into any one of a wide variety of mammalian cells such as 293T cells. Transfected 293T cell lysates can be probed with the anti-161P2F10B polyclonal serum, described herein.

pcDNA4/HisMax Constructs: To express 161P2F10B in mammalian cells, a 161P2F10B ORF, or portions thereof, of 161P2F10B are cloned into pcDNA4/HisMax Version A (Invitrogen, Carlsbad, Calif.). Protein expression is driven from the cytomegalovirus (CMV) promoter and the SP16 translational enhancer. The recombinant protein has Xpress™ and six histidine (6× His) epitopes fused to the amino-terminus The pcDNA4/HisMax vector also contains the bovine growth hormone (BGH) polyadenylation signal and transcription termination sequence to enhance mRNA stability along with the SV40 origin for episomal replication and simple vector rescue in cell lines expressing the large T antigen. The Zeocin resistance gene allows for selection of mammalian cells expressing the protein and the ampicillin resistance gene and ColE1 origin permits selection and maintenance of the plasmid in E. coli.

pcDNA3.1/MycHis Constructs: To express 161P2F10B in mammalian cells, a 161P2F10B ORF, or portions thereof, of 161P2F10B with a consensus Kozak translation initiation site was cloned into pcDNA3.1/MycHis Version A (Invitrogen, Carlsbad, Calif.). Protein expression is driven from the cytomegalovirus (CMV) promoter. The recombinant proteins have the myc epitope and 6× His epitope fused to the carboxyl-terminus. The pcDNA3.1/MycHis vector also contains the bovine growth hormone (BGH) polyadenylation signal and transcription termination sequence to enhance mRNA stability, along with the SV40 origin for episomal replication and simple vector rescue in cell lines expressing the large T antigen. The Neomycin resistance gene can be used, as it allows for selection of mammalian cells expressing the protein and the ampicillin resistance gene and ColE1 origin permits selection and maintenance of the plasmid in E. coli.

pcDNA3.1/CT-GFP-TOPO Construct: To express 161P2F10B in mammalian cells and to allow detection of the recombinant proteins using fluorescence, a 161P2F10B ORF, or portions thereof, with a consensus Kozak translation initiation site are cloned into pcDNA3.1/CT-GFP-TOPO (Invitrogen, CA). Protein expression is driven from the cytomegalovirus (CMV) promoter. The recombinant proteins have the Green Fluorescent Protein (GFP) fused to the carboxyl-terminus facilitating non-invasive, in vivo detection and cell biology studies. The pcDNA3.1CT-GFP-TOPO vector also contains the bovine growth hormone (BGH) polyadenylation signal and transcription termination sequence to enhance mRNA stability along with the SV40 origin for episomal replication and simple vector rescue in cell lines expressing the large T antigen. The Neomycin resistance gene allows for selection of mammalian cells that express the protein and the ampicillin resistance gene and ColE1 origin permits selection and maintenance of the plasmid in E. coli. Additional constructs with an amino-terminal GFP fusion are made in pcDNA3.1/NT-GFP-TOPO spanning the entire length of a 161P2F10B protein.

PAPtag: A 161P2F10B ORF, or portions thereof, is cloned into pAPtag-5 (GenHunter Corp. Nashville, Tenn.). This construct generates an alkaline phosphatase fusion at the carboxyl-terminus of a 161P2F10B protein while fusing the IgGκ signal sequence to the amino-terminus Constructs are also generated in which alkaline phosphatase with an amino-terminal IgGκ signal sequence is fused to the amino-terminus of a 161P2F10B protein. The resulting recombinant 161P2F10B proteins are optimized for secretion into the media of transfected mammalian cells and can be used to identify proteins such as ligands or receptors that interact with 161P2F10B proteins. Protein expression is driven from the CMV promoter and the recombinant proteins also contain myc and 6× His epitopes fused at the carboxyl-terminus that facilitates detection and purification. The Zeocin resistance gene present in the vector allows for selection of mammalian cells expressing the recombinant protein and the ampicillin resistance gene permits selection of the plasmid in E. coli.

ptag5: A 161P2F10B ORF, or portions thereof, was cloned into pTag-5. This vector is similar to pAPtag but without the alkaline phosphatase fusion. This construct generates 161P2F10B protein with an amino-terminal IgGκ signal sequence and myc and 6× His epitope tags at the carboxyl-terminus that facilitate detection and affinity purification. The resulting recombinant 161P2F10B protein is optimized for secretion into the media of transfected mammalian cells, and is used as immunogen or ligand to identify proteins such as ligands or receptors that interact with the 161P2F10B proteins. Protein expression is driven from the CMV promoter. The Zeocin resistance gene present in the vector allows for selection of mammalian cells expressing the protein, and the ampicillin resistance gene permits selection of the plasmid in E. coli.

PsecFc: A 161P2F10B ORF, or portions thereof, was cloned into psecFc. The psecFc vector was assembled by cloning the human immunoglobulin G1 (IgG) Fc (hinge, CH2, CH3 regions) into pSecTag2 (Invitrogen, California). This construct generates an IgG1 Fc fusion at the carboxyl-terminus of the 161P2F10B proteins, while fusing the IgGK signal sequence to N-terminus. 161P2F10B fusions utilizing the murine IgG1 Fc region are also used. The resulting recombinant 161P2F10B proteins are optimized for secretion into the media of transfected mammalian cells, and can be used as immunogens or to identify proteins such as ligands or receptors that interact with 161P2F10B protein. Protein expression is driven from the CMV promoter. The hygromycin resistance gene present in the vector allows for selection of mammalian cells that express the recombinant protein, and the ampicillin resistance gene permits selection of the plasmid in E. coli.

pSRα Constructs: To generate mammalian cell lines that express 161P2F10B constitutively, 161P2F10B ORF, or portions thereof, of 161P2F10B were cloned into pSRα constructs. Amphotropic and ecotropic retroviruses were generated by transfection of pSRα constructs into the 293T-10A1 packaging line or co-transfection of pSRα and a helper plasmid (containing deleted packaging sequences) into the 293 cells, respectively. The retrovirus is used to infect a variety of mammalian cell lines, resulting in the integration of the cloned gene, 161P2F10B, into the host cell-lines. Protein expression is driven from a long terminal repeat (LTR). The Neomycin resistance gene present in the vector allows for selection of mammalian cells that express the protein, and the ampicillin resistance gene and ColE1 origin permit selection and maintenance of the plasmid in E. coli. The retroviral vectors can thereafter be used for infection and generation of various cell lines using, for example, PC3, NIH 3T3, TsuPr1, 293 or rat-1 cells.

Additional pSRα constructs are made that fuse an epitope tag such as the FLAG™ tag to the carboxyl-terminus of 161P2F10B sequences to allow detection using anti-Flag antibodies. For example, the FLAG™ sequence 5' GAT TAC AAG GAT GAC GAC GAT AAG 3' (SEQ ID NO: 165) is added to cloning primer at the 3' end of the ORF. Additional pSRα constructs are made to produce both amino-terminal and carboxyl-terminal GFP and myc/6× His fusion proteins of the full-length 161P2F10B proteins.

Additional Viral Vectors: Additional constructs are made for viral-mediated delivery and expression of 161P2F10B. High virus titer leading to high level expression of 161P2F10B is achieved in viral delivery systems such as adenoviral vectors and herpes amplicon vectors. A 161P2F10B coding sequences or fragments thereof are amplified by PCR and subcloned into the AdEasy shuttle vector (Stratagene). Recombination and virus packaging are performed according to the manufacturer's instructions to generate adenoviral vectors. Alternatively, 161P2F10B coding sequences or fragments thereof are cloned into the HSV-1 vector (Imgenex) to generate herpes viral vectors. The viral vectors are thereafter used for infection of various cell lines such as PC3, NIH 3T3, 293 or rat-1 cells.

Regulated Expression Systems: To control expression of 161P2F10B in mammalian cells, coding sequences of 161P2F10B, or portions thereof, are cloned into regulated mammalian expression systems such as the T-Rex System (Invitrogen), the GeneSwitch System (Invitrogen) and the tightly-regulated Ecdysone System (Sratagene). These systems allow the study of the temporal and concentration dependent effects of recombinant 161P2F10B. These vectors are thereafter used to control expression of 161P2F10B in various cell lines such as PC3, NIH 3T3, 293 or rat-1 cells.

B. Baculovirus Expression Systems

To generate recombinant 161P2F10B proteins in a baculovirus expression system, 161P2F10B ORF, or portions thereof, are cloned into the baculovirus transfer vector pBlue- Bac 4.5 (Invitrogen), which provides a His-tag at the N-terminus. Specifically, pBlueBac-161P2F10B is co-transfected with helper plasmid pBac-N-Blue (Invitrogen) into SF9 (*Spodoptera frugiperda*) insect cells to generate recombinant baculovirus (see Invitrogen instruction manual for details). Baculovirus is then collected from cell supernatant and purified by plaque assay.

Recombinant 161P2F10B protein is then generated by infection of HighFive insect cells (Invitrogen) with purified baculovirus. Recombinant 161P2F10B protein can be detected using anti-161P2F10B or anti-His-tag antibody. 161P2F10B protein can be purified and used in various cell-based assays or as immunogen to generate polyclonal and monoclonal antibodies specific for 161P2F10B.

Expression Vectors for 161P2F10B Orthologs

Mouse and monkey orthologs of 161P2F10B were cloned into pcDNA3.1/MycHis Version A (Invitrogen, Carlsbad, Calif.). Protein expression is driven from the cytomegalovirus (CMV) promoter. The recombinant proteins have the myc epitope and 6× His epitope fused to the carboxyl-terminus. These vectors allow expression of 161P2F10B orthologs to assay cross-reactivity of monoclonal anti-human 161P2F10B antibodies.

Mouse and monkey orthologs of 161P2F10B were also cloned into pSRα constructs. The pSRα constructs allow for the generation of mammalian cell lines that express 161P2F10B orthologs constitutively. Protein expression is driven from the cytomegalovirus (CMV) promoter. The recombinant proteins have the myc epitope and 6× His epitope fused to the carboxyl-terminus These vectors allow expression of 161P2F10B orthologs to assay cross-reactivity of monoclonal anti-human 161P2F10B antibodies and to study functional activity of 161P2F10B orthologs. Amphotropic and ecotropic retroviruses were generated by transfection of pSRα constructs into the 293T-10A1 packaging line or co-transfection of pSRα and a helper plasmid (containing deleted packaging sequences) into the 293 cells, respectively. The retrovirus is used to infect a variety of mammalian cell lines, resulting in the integration of the cloned gene, 161P2F10B ortholog, into the host cell-lines.

Example 6

Antigenicity Profiles and Secondary Structure

Amino acid profiles of 161P2F10B and 161P2F10B variants were found accessing the ProtScale website on the World Wide Web at on the ExPasy molecular biology server.

These profiles: Hydrophilicity, (Hopp T. P., Woods K. R., 1981. Proc. Natl. Acad. Sci. U.S.A. 78:3824-3828); Hydropathicity, (Kyte J., Doolittle R. F., 1982. J. Mol. Biol. 157: 105-132); Percentage Accessible Residues (Janin J., 1979 Nature 277:491-492); Average Flexibility, (Bhaskaran R., and Ponnuswamy P. K., 1988. Int. J. Pept. Protein Res. 32:242-255); Beta-turn (Deleage, G., Roux B. 1987 Protein Engineering 1:289-294); and optionally others available in the art, such as on the ProtScale website, were used to identify antigenic regions of each of the 161P2F10B variant proteins. Each of the above amino acid profiles of 161P2F10B variants were generated using the following ProtScale parameters for analysis: 1) A window size of 9; 2) 100% weight of the window edges compared to the window center; and, 3) amino acid profile values normalized to lie between 0 and 1.

Hydrophilicity, Hydropathicity, and Percentage Accessible Residues profiles were used to determine stretches of hydrophilic amino acids (i.e., values greater than 0.5 on the Hydrophilicity and Percentage Accessible Residues profile, and values less than 0.5 on the Hydropathicity profile). Such regions are likely to be exposed to the aqueous environment, be present on the surface of the protein, and thus available for immune recognition, such as by antibodies.

Average Flexibility and Beta-turn profiles determine stretches of amino acids (i.e., values greater than 0.5 on the Beta-turn profile and the Average Flexibility profile) that are not constrained in secondary structures such as beta sheets and alpha helices. Such regions are also more likely to be exposed on the protein and thus accessible to immune recognition, such as by antibodies.

Antigenic sequences of the 161P2F10B variant proteins indicated, e.g., by the profiles described above are used to prepare immunogens, either peptides or nucleic acids that encode them, to generate therapeutic and diagnostic anti-161P2F10B antibodies. The immunogen can be any 5, 6, 7, 8, 9, 10, 11, 12, 13, 14, 15, 16, 17, 18, 19, 20, 21, 22, 23, 24, 25, 30, 35, 40, 45, 50 or more than 50 contiguous amino acids, or the corresponding nucleic acids that encode them, from the 161P2F10B protein variants listed in FIG. 1 of which the amino acid profiles can be inferred because the variant contains sequence that is the same as a variant depicted. In particular, peptide immunogens of the invention can comprise, a peptide region of at least 5 amino acids of FIG. 1 in any whole number increment that includes an amino acid position having a value greater than 0.5 in the Hydrophilicity profile; a peptide region of at least 5 amino acids of FIG. 1 in any whole number increment that includes an amino acid position having a value less than 0.5 in the Hydropathicity profile; a peptide region of at least 5 amino acids of FIG. 1 in any whole number increment that includes an amino acid position having a value greater than 0.5 in the Percent Accessible Residues profiles; a peptide region of at least 5 amino acids of FIG. 1 in any whole number increment that includes an amino acid position having a value greater than 0.5 in the Average Flexibility profiles; and, a peptide region of at least 5 amino acids of FIG. 1 in any whole number increment that includes an amino acid position having a value greater than 0.5 in the Beta-turn profile. Peptide immunogens of the invention can also comprise nucleic acids that encode any of the forgoing.

All immunogens of the invention, peptide or nucleic acid, can be embodied in human unit dose form, or comprised by a composition that includes a pharmaceutical excipient compatible with human physiology.

The secondary structure of 161P2F10B and 161P2F10B variants, namely the predicted presence and location of alpha helices, extended strands, and random coils, is predicted from the primary amino acid sequence using the HNN—Hierarchical Neural Network method (NPS@: Network Protein Sequence Analysis TIBS 2000 March Vol. 25, No 3 [291]: 147-150 Combet C., Blanchet C., Geourjon C. and Deléage G., accessed from the ExPasy molecular biology server located on the World Wide Web. The analysis indicates that 161P2F10B variant 1 is composed of 31.31% alpha helix, 11.31% extended strand, and 57.37% random coil.

Analysis for the potential presence of transmembrane domains in the 161P2F10B variant proteins was carried out using a variety of transmembrane prediction algorithms accessed from the ExPasy molecular biology server located on the World Wide Web.

Example 7

Generation of 161P2F10B Polyclonal Antibodies

Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. In addition to immunizing with a full length 161P2F10B protein variant, computer algorithms are employed in design of immunogens that, based on amino acid sequence analysis contain characteristics of being antigenic and available for recognition by the immune system of the immunized host (see the Example entitled "Antigenicity Profiles and Secondary Structure"). Such regions would be predicted to be hydrophilic, flexible, in beta-turn conformations, and be exposed on the surface of the protein.

For example, recombinant bacterial fusion proteins or peptides containing hydrophilic, flexible, beta-turn regions of 161P2F10B protein variants are used as antigens to generate polyclonal antibodies in New Zealand White rabbits or monoclonal antibodies as described in the Example entitled "Generation of 161P2F10B Monoclonal Antibodies (MAbs)". For example, in 161P2F10B variant 1, such regions include, but are not limited to, amino acids 43-93, 100-134, 211-246, 567-492, 500-517 and amino acids 810-870.

Other recombinant bacterial fusion proteins that may be employed include maltose binding protein, LacZ, thioredoxin, NusA, or an immunoglobulin constant region (see the section entitled "Production of 161P2F10B in Prokaryotic Systems" and Current Protocols In Molecular Biology, Volume 2, Unit 16, Frederick M. Ausubul et al. eds., 1995; Linsley, P.S., Brady, W., Urnes, M., Grosmaire, L., Damle, N., and Ledbetter, L. (1991) J. Exp. Med. 174, 561-566).

In addition to bacterial derived fusion proteins, mammalian expressed protein antigens are also used. These antigens are expressed from mammalian expression vectors such as the Tag5 and Fc-fusion vectors (see the section entitled "Production of Recombinant 161P2F10B in Eukaryotic Systems"), and retain post-translational modifications such as glycosylations found in native protein. In one embodiment, amino acids 45-875, are cloned into the Tag5 mammalian secretion vector. The recombinant protein was purified by metal chelate chromatography from tissue culture supernatants of 293T cells stably expressing the recombinant vector. The purified Tag5 161P2F10B protein was then used as immunogen.

During the immunization protocol, it is useful to mix or emulsify the antigen in adjuvants that enhance the immune response of the host animal. Examples of adjuvants include, but are not limited to, complete Freund's adjuvant (CFA) and MPL-TDM adjuvant (monophosphoryl Lipid A, synthetic trehalose dicorynomycolate).

In a typical protocol, rabbits are initially immunized subcutaneously with up to 200 μg, typically 100-200 μg, of fusion protein or peptide conjugated to KLH mixed in complete Freund's adjuvant (CFA). Rabbits are then injected subcutaneously every two weeks with up to 200 μg, typically 100-200 μg, of the immunogen in incomplete Freund's adjuvant (IFA). Test bleeds are taken approximately 7-10 days following each immunization and used to monitor the titer of the antiserum by ELISA.

To test reactivity and specificity of immune serum, such as rabbit serum derived from immunization with Tag5 161P2F10B encoding amino acids 58-538, the respective full-length 161P2F10B variant cDNA is cloned into pcDNA 3.1 myc-his expression vector (Invitrogen, see the Example entitled "Production of Recombinant 161P2F10B in Eukaryotic Systems"). After transfection of the constructs into 293T cells, cell lysates are probed with the anti-variant serum and with anti-His antibody (Santa Cruz Biotechnologies) to determine specific reactivity to denatured variant protein using the Western blot technique. In addition, the immune serum is tested by fluorescence microscopy, flow cytometry and immunoprecipitation against 293T and other recombinant 161P2F10B variant-expressing cells to determine specific recognition of native protein. Western blot, immunoprecipitation, fluorescent microscopy, and flow cytometric techniques using cells that endogenously express 161P2F10B are also carried out to test reactivity and specificity.

Anti-serum from the Tag5 161P2F10B immunized rabbit is affinity purified by passage over a column of GST protein covalently coupled to AffiGel matrix (BioRad). The antiserum is then affinity purified by passage over a column composed of a MBP-161P2F10B fusion protein covalently coupled to Affigel matrix. The serum is then further purified by protein G affinity chromatography to isolate the IgG fraction. Sera from other His-tagged antigens and peptide immunized rabbits as well as fusion partner depleted sera are affinity purified by passage over a column matrix composed of the original protein immunogen or free peptide.

Example 8

Generation of 161P2F10B Monoclonal Antibodies (MAbs)

In one embodiment, therapeutic Monoclonal Antibodies ("MAbs") to 161P2F10B and 161P2F10B variants comprise those that react with epitopes specific for each protein or specific to sequences in common between the variants that would bind, internalize, disrupt or modulate the biological function of 161P2F10B or 161P2F10B variants, for example, those that would disrupt the interaction with ligands, substrates, and binding partners Immunogens for generation of such MAbs include those designed to encode or contain the extracellular domain or the entire 161P2F10B protein sequence, regions predicted to contain functional motifs, and regions of the 161P2F10B protein variants predicted to be antigenic from computer analysis of the amino acid sequence. Immunogens include peptides and recombinant proteins such as tag5-161P2F10B a mammalian expressed purified His tagged protein. In addition, cells engineered through retroviral transduction to express high levels of 161P2F10B variant 1, such as RAT1-161P2F10B are used to immunize mice.

To generate MAbs to 161P2F10B, mice are first immunized in the foot pad (FP) with, typically, 5-50 μg of protein immunogen or between $10^6$ and $10^7$ 161P2F10B-expressing cells mixed in a suitable adjuvant. Examples of suitable adjuvants for FP immunizations are TiterMax (Sigma) for the initial FP injection and alum gel for subsequent immunizations. Following an initial injection, mice are immunized twice a week until the time they are sacrificed. Upon sacrifice, lymph nodes are removed and their B-cells are harvested for electro-cell fusion.

In the course of the immunizations test bleeds are taken to monitor the titer and specificity of the immune response. In most cases, once appropriate reactivity and specificity are obtained as determined by ELISA, Western blotting, immunoprecipitation, fluorescence microscopy or flow cytometric analyses, fusion and hybridoma generation are then carried out using electrocell fusion (BTX, ECM2000).

In one embodiment, the invention provides for monoclonal antibodies designated: Ha16-1(3,5)18, Ha16-1(2,4)4, Ha16-1(3,5)56, Ha16-1(1)11, H16-1.68, H16-1.93, H16-7.8, H16-9.10, H16-9.44, H16-9.69, Ha16-1(1)23, Ha16-1(3,5)36, H16-1.52, H16-1.67, H16-1.86, H16-7.213, H16-9.33, Ha16-1(3,5)27.1, H16-1.61.1, H16-1(3,5)5, H16-7.200, Ha16-1(3,5)42, H16-9.65, H16-1.29.1.1, H16-3.4, H16-1.92.1.1, Ha16-1(3,5)19, and H16-1.80.

The antibodies listed above were shown to react and bind with cell surface 161P2F10B by flow cytometry or immobilized 161P2F10B by ELISA.

MAbs to 161P2F10B were generated using XenoMouse Technology® wherein the murine heavy and kappa light chain loci have been inactivated and a majority of the human heavy and kappa light chain immunoglobulin loci have been inserted. MAbs designated Ha16-1(3,5)18, Ha16-1(2,4)4, Ha16-1(3,5)56, Ha16-1(1)11, Ha16-1(1)23, Ha16-1(3,5)36, Ha16-1(3,5)27.1, Ha16-1(3,5)42, and Ha16-1(3,5)19 were generated from immunization of human gamma 1 producing XenoMice with RAT1-161P2F10B cells. MAbs designated H16-1.68, H16-1.93, H16-1.52, H16-1.67, H16-1.86, H16-1.61.1, H16-1(3,5)5, H16-1.29.1.1, H16-1.80, and H16-1.92.1.1 were generated from immunization of human gamma 1 producing XenoMice with purified tag5-161P2F10B. MAbs designated H16-7.8, H16-9.10, H16-9.44, H16-9.69, H16-7.213, H16-9.33, and H16-7.200 were generated from immunization with human gamma 2 producing XenoMice with tag5-161P2F10B.

The 161P2F10B MAbs Ha16-1(3,5)18, Ha16-1(2,4)4, Ha16-1(3,5)56, Ha16-1(1)11, H16-1.68, H16-1.93, H16-7.8, H16-9.10, H16-9.44, H16-9.69, Ha16-1(1)23, Ha16-1(3,5)36, H16-1.52, H16-1.67, H16-1.86, H16-7.213, H16-9.33, Ha16-1(3,5)27.1, H16-1.61.1, H16-1(3,5)5, H16-7.200, Ha16-1(3,5)42, H16-9.65, H16-1.29.1.1, H16-3.4, H16-1.92.1.1, and Ha16-1(3,5)19 specifically bind to recombinant 161P2F10B expressing cells and endogenous cell surface 161P2F10B expressed in cancer xenograft cells (FIG. 6 and FIG. 7).

The antibodies designated Ha16-1(3,5)18, Ha16-1(1)11, H16-1.93, H16-9.69 were sent (via Federal Express) to the American Type Culture Collection (ATCC), P.O. Box 1549, Manassas, Va. 20108 on 28 Mar. 2006 and assigned Accession numbers PTA-7452, PTA-7450, PTA-7449, PTA-7451, respectively.

DNA coding sequences for 161P2F10B MAbs Ha16-1(3,5)18, Ha16-1(2,4)4, Ha16-1(3,5)56, Ha16-1(1)11, H16-1.68, H16-1.93, H16-7.8, H16-9.10, H16-9.44, H16-9.69, Ha16-1(1)23, Ha16-1(3,5)36, H16-1.52, H16-1.67, H16-1.86, H16-7.213, H16-9.33, Ha16-1(3,5)27.1, H16-1.61.1, H16-1(3,5)5, H16-7.200, Ha16-1(3,5)42, H16-9.65, H16-1.29.1.1, H16-3.4, H16-1.92.1.1, Ha16-1(3,5)19, and H16-1.80 were determined after isolating mRNA from the respective hybridoma cells with Trizol reagent (Life Technologies, Gibco BRL).

Total RNA was purified and quantified. First strand cDNAs was generated from total RNA with oligo (dT)12-18 priming using the Gibco BRL Superscript Preamplification system. First strand cDNA was amplified using human immunoglobulin variable heavy chain primers, and human immunoglobulin variable light chain primers. PCR products were cloned into the pCRScript vector (Stratagene). Several clones were sequenced and the variable heavy and light chain regions determined.

The nucleic acid and amino acid sequences of the variable heavy and light chain regions are listed in FIG. 2 and FIG. 3. Alignment of 161P2F10B antibodies to germline V-D-J Sequences is set forth in FIG. 4A-FIG. 4Z and FIG. 5A-FIG. 5X.

Example 9

Screening, Identification, and Characterization of 161P2F10B MAbs

Antibodies generated using the procedures set forth in the example entitled "Generation of 161P2F10B Monoclonal Antibodies (MAbs)" were screened, identified, and characterized using a combination of assays including ELISA, FACS, affinity ranking by Surface Plasmon Resonance (BIAcore) ("SPR"), epitope grouping, affinity to recombiant 161P2F10B, and 161P2F10B expressed on the cell surface.

161P2F10B Human MAb Screening by FACS.

Primary hybridoma screening for MAbs to 161P2F10B is performed by FACS analysis. The protocol is as follows: 50 µl/well of hybridoma supernatant (neat) or purified antibodies (in serial dilutions) are added to 96-well FACS plates and mixed with 161P2F10B-expressing cells (endogenous or recombinant, 50,000 cells/well). The mixture is incubated at 4° C. for two hours. At the end of incubation, the cells are washed with FACS Buffer and incubated with 100 µl of detection antibody (anti-hIgG-PE) for 45 minutes at 4° C. At the end of incubation, the cells are washed with FACS Buffer, fixed with Formaldehyde and analyzed using FACScan. Data are analyzed using CellQuest Pro software.

Positive hybridomas identified from primary screens are transferred to 24-well plates and supernatants collected for confirmatory screens. Confirmatory screens included FACS analysis on Caki-161P2F10B/Caki-neo, HepG2 (human liver cancer cell line), KU812 (human promyeolcytic cell line), SKRC-01 (human renal tumor cell line), and ELISA using Tag5-161P2F10B.

B. 161P2F10B human MAb screening by ELISA.

161P2F10B MAbs were screened by ELISA to determine antibody isotype. The protocol used is as follows, ELISA plates were coated with Tag5-161P2F10B-ECD or anti-hIgG antibody. Several sets of testing antibodies were added on the plates and incubated for 1 hour. After washing the plates to wash out unbound antibodies, bound antibodies were detected by the following HRP conjugated detection antibodies: anti-hIgG1, anti-hIgG2, anti-hIgK, and anti-hIgL.

C. 161P2F10B human MAb screening by SPR.

SPR allows identification and real time characterization of the kinetics and affinity of protein-protein interactions and therefore is a useful technique in the selection and characterization of MAbs to target antigens of interest. SPR analysis is employed to screen and characterize hybridoma supernatants and purified MAbs to 161P2F10B. Hybridoma screening for MAbs to 161P2F10B by SPR biosensor (BIAcore 3000) are performed as follows: 50 µl/well of hybridoma supernatant (neat) diluted to 1.5-2 µg/ml with the running buffer (HBS-P, 10 ug/ml BSA) are added to 96-well plates (BIAcore) and MAbs (20 µl) are captured on goat-anti-human Fcγ pAbs covalently immobilized on the surface of the CM5 sensor chip. Three (3) MAbs containing hybridoma supernatants are tested per run (cycle) on channels 2, 3 and 4 of the flow cell, where channel 1 is reserved as reference for non-specific binding. Prior to measuring antigen binding to captured MAbs in each individual channel, 60 µl of running buffer is injected over the chip surface at the flowrate of 20 µl/min to serve as reference for drift in captured MAb baseline. Sixty microliters (60 µl) of the purified recombinant 161P2F10B at 150 nM is then injected over the chip surface at the same flowrate of 20 µl/min to measure antigen binding. Each cycle of antigen binding to MAbs are followed by surface regeneration with injection of 100 mM phosphoric acid (for 1 min) to strip the surface of any captured MAb.

Data analysis is performed using BiaEvaluation 4.1 and CLAMP software (Myszka and Morton, 1998). After subtracting the references and normalizing the response to the level of captured MAb, data is fit globally using a 1:1 binding model.

The affinities are calculated from the association and dissociation rate constants. As is apparent to one of ordinary skill in the art, slow dissociation rates generally indicate higher overall affinity for MAbs. The preliminary affinity data and dissociation rates are used as a basis of the selection criteria for therapeutic MAbs to 161P2F10B.

D. Epitope Grouping by FACS

161P2F10B antibodies were grouped according to epitope by evaluating their binding pattern on UG-K3 (human renal cancer cell line), or KU812 cells. In brief, a small amount of each of the antibodies was biotinylated; then each of the biotinylated antibodies were incubated with KU812 in the presence of excess (100×) amount of non-biotinylated antibodies at 4° C. for 1 hour. One of ordinary skill in the art will understand that during the incubation, an excess amount of antibodies will compete with biotinylated antibodies if they bind to the same epitope. At the end of incubation, cells were washed and incubated with Streptavidin-PE for 45 min at 4° C. After washing off the unbound streptavidin-PE, the cells were analyzed using FACS. MFI values were obtained using CellQuest Pro software and were used for data analysis. As shown in FIG. 8, twenty-five (25) 161P2F10B MAbs were epitope grouped using UG-K3 cells. Cells are highlighted to indicate self-competition (100% competition), the MFI value in these cells are background control for each biotinylated antibody. Additionally, cells with no color indicate that the two antibodies compete each other (low MFI), cells highlighted in gray (high MFI) indicate that the two antibodies bind to two distinct epitopes. The results show the antibodies that have the same binding pattern bind to the same epitope among the antibodies and that there are 16 epitope groups within the antibodies tested.

E. Domain Mapping of 161P2F10B MAbs

In order to identify regions of the 161P2F10B protein that contain the binding epitope of MAbs several constructs were created encoding portions of the 161P2F10B extracellular domain and used in immunoprecipitation experiments. Tag5 expression constructs encoding either the full extracellular domain (ECD) of 161P2F10B (amino acids 46-875), the somatomedin-b-like domain (amino acids 46-157), the catalytic domain (amino acids 158-558), or the catalytic and nuclease domain (amino acids 158-875) were transfected into 293T cells and cellular lysates were made. These lysates were then used for immunoprecipitation with the indicated 161P2F10B MAbs or control MAb. Western blotting of the immunoprecipitates was then performed using an anti-His polyclonal polyclonal MAb that recognizes the His epitope tag present on each recombinant protein. The specific molecular weight band of each recombinant protein was identified by straight Western blotting of the lysates. The domain containing the binding epitope of each MAb is determined through identification of the pattern of recombinant proteins immunoprecipitated by each MAb. MAbs that bind to the full length ECD and to the somatomedin-b-like domain map to the somatomedin-b-like domain. MAbs that bind to the full length ECD and the catalytic domain, but not the catalytic+nuclease domain, map to the catalytic domain. MAbs that bind the full length ECD and to the catalytic+nuclease domain, but not to the catalytic domain, map to the nuclease domain. Such analysis is presented in FIG. 9. Such data when combined with SPR competition data is useful in grouping together MAbs that bind to similar or overlapping epitopes as presented in FIG. 10.

F. Affinity Determination by FACS

A panel of 33 human 161P2F10B MAbs were tested for their binding affinity to 161P2F10B on several cell lines (HepG2, KU812, SKRC-01, and RXF393) which express 161P2F10B. Briefly, twenty-three (23) serial 1:2 dilutions of purified antibodies were incubated with 161P2F10B expressing cells (50,000 cells per well) overnight at 4° C. at a final concentration of 167 nM to 0.01 pM. At the end of the incubation, cells were washed and incubated with anti-hIgG-PE detection antibody for 45 min at 4° C. After washing the unbound detection antibodies, the cells were analyzed by FACS. MFI values of each point were obtained using CellQuest Pro software and were used for the affinity calculation using Graphpad Prism software and the one site binding (hyperbola) equation. A summary of affinity values of thirteen (13) antibodies are set forth in Table VI.

G. Affinity Determination by SPR

Panels of purified anti-human 161P2F10B MAbs were tested for their binding affinity to the purified recombinant 161P2F10B by SPR. Briefly, each purified human MAb is captured onto a CM5 sensor chip surface. On average approximately 150 RUs of each MAb is captured in every cycle. A series of 5-6 dilutions of recombinant 161P2F10B ranging from 1 nM to 100 nM is injected over such surface to generate binding curves (sensograms) that are globally fit to a 1:1 interaction model using CLAMP software (Myszka and Morton, 1998). The affinity of several 161P2F10B MAbs, expressed as $K_D$, defined by dissociation rate constant and association rate constant using the equation $K_D = k_{diss}/k_{assoc}$ is shown in Table VII. The affinity data and dissociation rates along with the affinity analysis by FACS (See, part F, above) were part of the selection criteria for MAbs to 161P2F10B.

H. Cross Reactivity with Mouse 161P2F10B

MAbs were screened and characterized for their ability to react with mouse 161P2F10B orthology. This property is useful to understand the consequences of MAb engagement of 161P2F10B on cells and tissues when using mouse animal models. The mouse 161P2F10B gene was cloned then transiently transfected into 293T cells. To test cross-reactivity of 161P2F10B MAbs with mouse 161P2F10B, the antibodies were incubated with 293-T cells expressing murine 161P2F10B or 293T cells expressing the-neo gene only as a negative control and Ku812 cells were used as positive controls for MAb binding to human 161P2F10B. Specific recognition was determined using anti-hIgG-PE secondary detection antibody. A representative histogram depicting species cross-reactivity and binding to human 161P2F10B is presented in FIG. 11. The results show eight (8) antibodies cross-react with mouse 161P2F10B.

I. Cross Reactivity with Monkey 161P2F10B

161P2F10B MAbs are screened and characterized for their ability to react with 161P2F10B of monkey origin. This property is useful to understand the expression of 161P2F10B on tissues from different monkey species for toxicological purposes. The cynomolgous monkey 161P2F10B gene was cloned and sequenced. The homology to human 161P2F10B is 100%. Cross-reactivity of all 161P2F10B MAbs with monkey tissues expressing 161P2F10B is equivalent to that of cells and tissues of human origin expressing 161P2F10B.

Example 10

Antibody Immune Mediated Cytotoxicity

ADCC (Antibody-Dependent Cellular Cytotoxicity) is an immune mediated lytic attack on cells bound with an antibody targeted to a specific cell surface antigen Immune cells recognize the Fc portion of the antibody through binding to Fcã receptors on the surface of leukocytes, monocytes, and NK cells triggering a lytic attack that result in cell death. Briefly, Caki cells engineered to express the target antigen 161P2F10B are incubated in vitro with 51chromium for 1 hr. After washing with fresh medium, the labeled cells are incubated with 2.5 mg/ml human MAbs directed to 16P2F10B and freshly isolated peripheral blood mono nuclear cells at different effector to target cell ratios (E:T Ratio). After 4 hours at 37 C, the cells are gently centrifuged and the supernatant containing 51Cr released from the dead cells is counted in a Beta counter.

The results demonstrate that antibody dependent cell killing increased when the effector to target (E:T) cell ratio was increased. At E:T ratios of 50:1 or greater, HA16-1.80 and HA16-1.93 demonstrated specific killing of Caki-AGS-16 cells while Ha16-9.69, which has a g-2 isotype, showed no activity in the assay. The specificity of the assay was determined by showing that an irrelevant IgG1 Control MAb (H3-1.4) and incubation of target cells and effector cells in the absence of antibody (Cells+PBMCs) did not cause cell killing.

Example 11

Antibody Mediated Secondary Killing

MAbs to 161P2F10B mediate saporin dependent killing in KU-812 cells. KU-812 cells are a CML cell line that expresses high levels of endogenous 161P2F10B. KU-812 cells (3000 cells/well) were seeded into a 96 well plate on day 1. The following day an equal volume of medium containing 2× concentration of the indicated primary antibody together with a 2-fold excess of anti-human (Hum-Zap) polyclonal antibody conjugated with saporin toxin (Advanced Targeting Systems, San Diego, Calif.) was added to each well. The cells were allowed to incubate for 5 days at 37 degrees C. At the end of the incubation period, MTS (Promega) was added to each well and incubation continued for an additional 4 hours. The optical density at 450 nM was then determined.

The results in FIG. 12 show that 161P2F10B MAbs HA16-9.69, HA16-1.18 and HA16-1.93 mediated saporin dependent cytotoxicity in KU-812 cells while a control, nonspecific human IgG1 (H3-1.4) and another 161P2F10B MAb (HA16-7.200) had no effect. These results indicate that drugs or cytotoxic proteins can selectively be delivered to KU-812 and other 161P2F10B expressing cells using an appropriate 161P2F10B MAb.

Example 12

Generation of F(Ab')2 Fragments

Generation of F(Ab')2 fragments of MAbs is useful to study the effects of MAb molecules that retain their bivalent anitgen binding site but lack the immune effector Fc domain in in vitro and in vivo therapeutic models. Generally, the protocol is as follows, 20 mgs of MAb in 20 mM sodium acetate buffer pH 4.5 is incubated with and without immobilized pepsin (Pierce. Rockford Ill.) for the indicated times. Intact MAb and digested Fc fragments are removed by protein A chromatography. The reagent can be used to treat animals bearing 161P2F10B expressing tumors. The antitumor activity observed with this antibody fragment can distinguish intrinsic biologic activity from activity mediated by immune dependent mechanisms.

Example 13

Expression of Human MAbs using Recombinant DNA Methods

To express 161P2F10B MAbs recombinantly in transfected cells, 161P2F10B MAb variable heavy and light chain sequences are cloned upstream of the human heavy chain IgG1 and light chain Igκ constant regions respectively. The complete 161P2F10B MAb human heavy chain and light chain cassettes are cloned downstream of the CMV promoter/enhancer in a cloning vector. A polyadenylation site is included downstream of the MAb coding sequence. The recombinant 161P2F10B MAb expressing constructs are transfected into 293T, Cos and CHO cells. The 161P2F10B MAbs secreted from recombinant cells are evaluated for binding to cell surface 161P2F10B.

Example 14

In Vivo Assay for 161P2F10B Tumor Growth Promotion

The effect of the 161P2F10B protein on tumor cell growth is evaluated in vivo by evaluating tumor development and growth of cells expressing or lacking 161P2F10B. For example, SCID mice are injected subcutaneously on each flank with $1 \times 10^6$ of kidney cancer cell lines (e.g. UG-K3) containing tkNeo empty vector or 161P2F10B. At least two strategies may be used: (1) Constitutive 161P2F10B expression under regulation of a promoter such as a constitutive promoter obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), or from heterologous mammalian promoters, e.g., the actin promoter or an immunoglobulin promoter, provided such promoters are compatible with the host cell systems, and (2) Regulated expression under control of an inducible vector system, such as ecdysone, tetracycline, etc., provided such promoters are compatible with the host cell systems. Tumor volume is then monitored by caliper measurement at the appearance of palpable tumors and followed over time to determine if 161P2F10B-expressing cells grow at a faster rate and whether tumors produced by 161P2F10B-expressing cells demonstrate characteristics of altered aggressiveness (e.g. enhanced metastasis, vascularization, reduced responsiveness to chemotherapeutic drugs).

Additionally, mice can be implanted with $1 \times 10^5$ of the same cells orthotopically to determine if 161P2F10B has an effect on local growth in the kidney, and whether 161P2F10B affects the ability of the cells to metastasize (Mild T et al, Oncol Res. 2001; 12:209; Fu X et al, Int J. Cancer. 1991, 49:938). The effect of 161P2F10B on tumor formation and growth may be assessed by injecting kidney or liver tumor cells intratibially.

The assay is also useful to determine the 161P2F10B inhibitory effect of candidate therapeutic compositions, such as for example, 161P2F10B intrabodies, 161P2F10B antisense molecules and ribozymes.

Example 15

161P2F10B Monoclonal Antibody-mediated Inhibition of Tumors In Vivo

The significant expression of 161P2F10B on the cell surface of tumor tissues, together with its restrictive expression in normal tissues makes 161P2F10B a good target for antibody therapy. Similarly, 161P2F10B is a target for T cell-based immunotherapy. Thus, the therapeutic efficacy of 161P2F10B MAbs in human kidney cancer xenograft mouse models and human liver cancer xenograft mouse models is evaluated by using cell lines such as RXF-393 and HepG2, as well as human renal clear cell xenograft models such as UG-K3.

Antibody efficacy on tumor growth and metastasis formation is studied, e.g., in a mouse orthotopic kidney or liver cancer xenograft models. The antibodies can be unconjugated, as discussed in this Example, or can be conjugated to a therapeutic modality, as appreciated in the art. 161P2F10B MAbs inhibit formation of both renal and hepatic cancer xenografts. 161P2F10B MAbs also retard the growth of established orthotopic tumors and prolonged survival of tumor-bearing mice. These results indicate the utility of 161P2F10B MAbs in the treatment of local and advanced stages of kidney and liver cancer and those cancers set forth in Table I.

Administration of the 161P2F10B MAbs led to retardation of established orthotopic tumor growth and inhibition of metastasis to distant sites, resulting in a significant prolongation in the survival of tumor-bearing mice. These studies indicate that 161P2F10B is an attractive target for immunotherapy and demonstrate the therapeutic potential of 161P2F10B MAbs for the treatment of local and metastatic kidney and liver cancer. This example demonstrates that unconjugated 161P2F10B MAbs are effective to inhibit the growth of human kidney tumor xenografts grown in SCID mice; accordingly a combination of such efficacious MAbs is also effective.

Tumor inhibition using multiple 161P2F10B MAbs
Materials and Methods
161P2F10B Monoclonal Antibodies:

Monoclonal antibodies were raised against 161P2F10B as described in the Example entitled "Generation of 161P2F10B Monoclonal Antibodies (MAbs)." The MAbs are characterized by ELISA, Western blot, FACS, and immunoprecipitation for their capacity to bind 161P2F10B. Epitope mapping data for the 161P2F10B MAbs, as determined by ELISA and Western analysis, recognize epitopes on the 161P2F10B protein Immunohistochemical analysis of normal and cancer tissues and cells with these antibodies is performed.

The MAbs are purified from ascites or hybridoma tissue culture supernatants by Protein-G or Protein-A Sepharose chromatography, dialyzed against PBS, filter sterilized, and stored at $-20°$ C. Protein determinations are performed by a Bradford assay (Bio-Rad, Hercules, Calif.). A therapeutic MAb or a cocktail comprising a mixture of individual MAbs is prepared and used for the treatment of mice receiving subcutaneous or orthotopic injections of UG-K3 and RXF-393 tumor xenografts.

Cell Lines and Xenografts

The kidney cancer cell line RXF-393 and SKRC01 as well as the liver cancer cell line HepG2 (American Type Culture Collection) are maintained in RPMI and DMEM respectively, supplemented with L-glutamine and 10% FBS.

The UG-K3 xenograft is passaged in 6- to 8-week-old male ICR-severe combined immunodeficient (SCID) mice (Taconic Farms) by s.c. trocar implant (Craft, N., et al., Nat. Med. 1999, 5:280). Single-cell suspensions of UG-K3 tumor cells are prepared as described in Craft, et al. Other cell lines are used as well.

Xenograft Mouse Models.

Subcutaneous (s.c.) tumors are generated by injection of $1 \times 10^6$ cancer cells mixed at a 1:1 dilution with Matrigel (Collaborative Research) in the right flank of male SCID mice. To test antibody efficacy on tumor formation, i.e. antibody injections are started on the same day as tumor-cell injections. As a control, mice are injected with either purified mouse IgG (ICN) or PBS; or a purified MAb that recognizes an irrelevant antigen not expressed in human cells. In preliminary studies, no difference is found between mouse IgG or PBS on tumor growth. Tumor sizes are determined by caliper measurements, and the tumor volume is calculated as length× width×height. Mice with subcutaneous tumors greater than 1.5 cm in diameter are sacrificed.

Orthotopic injections are performed under anesthesia by using ketamine/xylazine. For kidney orthotopic studies, an incision is made through the abdomen to expose the kidney and UG-K3 or RXF-393 tumor cells ($2 \times 10^6$) mixed with Matrigel are injected into the kidney capsule in a 10-µl volume. To monitor tumor growth, mice are palpated. The mice are segregated into groups for the appropriate treatments, with 161P2F10B or control MAbs being injected i.p.

161P2F10B MAbs Inhibit Growth of 161P2F10B-Expressing Xenograft Tumors

The effect of 161P2F10B MAbs on tumor formation is tested by using UG-K3 and RXF-393 orthotopic models. As compared with the s.c. tumor model, the orthotopic model, which requires injection of tumor cells directly in the mouse kidney, results in a local tumor growth, development of metastasis in distal sites, deterioration of mouse health, and subsequent death. These features make the orthotopic model more representative of human disease progression and allowed us to follow the therapeutic effect of MAbs on clinically relevant end points.

Accordingly, tumor cells are injected into the mouse kidney, and 2 days later, the mice are segregated into two groups and treated with either: a) 250-1000 µg, of 161P2F10B MAb, or b) control antibody three times per week for two to five weeks.

A major advantage of the orthotopic cancer models is the ability to study the development of metastases. Formation of metastasis in mice bearing established orthotopic tumors is studies by IHC analysis on tissue sections.

Another advantage of xenograft cancer models is the ability to study neovascularization and angiogenesis. Tumor growth is partly dependent on new blood vessel development. Although the capillary system and developing blood network is of host origin, the initiation and architecture of the neovasculature is regulated by the xenograft tumor (Davidoff et al., Clin Cancer Res. (2001) 7:2870; Solesvik et al., Eur J Cancer Clin Oncol. (1984) 20:1295). The effect of antibody and small molecule on neovascularization is studied in accordance with procedures known in the art, such as by IHC analysis of tumor tissues and their surrounding microenvironment.

Mice bearing established orthotopic tumors are administered injections of either 161P2F10B MAb or control antibody over a 4-week period. Mice in both groups are allowed to establish a high tumor burden, to ensure a high frequency of metastasis formation in mouse lungs. Mice then are killed and their bladders, livers, bone and lungs are analyzed for the presence of tumor cells by IHC analysis. These studies demonstrate a broad anti-tumor efficacy of anti-161P2F10B antibodies on initiation and progression of kidney cancer in xenograft mouse models. Anti-161P2F10B antibodies inhibit tumor formation of tumors as well as retarding the growth of already established tumors and prolong the survival of treated mice. Moreover, 161P2F10B MAbs demonstrate a dramatic inhibitory effect on the spread of local kidney tumor to distal sites, even in the presence of a large tumor burden. Thus, 161P2F10B MAbs are efficacious on major clinically relevant end points (tumor growth), prolongation of survival, and health.

Effect of 161P2F10B Mabs on the Growth of Human Renal Cell Carcinoma in Mice

The following protocol was used. Patient-derived clear cell renal cancer UG-K3 cells ($2.0 \times 10^6$ cells) were injected subcutaneously into male SCID mice. The mice were randomized into groups (n=10 in each group) and treatment initiated intraperitoneally (i.p.) on day 0 with treatment MAbs or isotype MAb control as indicated. Animals were treated twice weekly for a total of 8 doses at 750 µg/dose until study day 27. Tumor growth was monitored using caliper measurements every 3 to 4 days as indicated. The results show 161P2F10B MAbs H16-1.29.1.1, Ha16-1(3,5)27.1, H16-9.69 and Ha16-1(1)11 statistically and significantly inhibited the growth of human renal cancer xenograft UG-K3 implanted subcutaneously in SCID mice (p<0.05). (FIG. 13).

In another experiment, human renal cancer UG-K3 tumor cells ($2.0 \times 10^6$ cells) were injected subcutaneously into male SCID mice. The mice were randomized into groups (n=10 mice in each group) and treatment initiated intraperitoneally (i.p.) on Day 0 with treatment MAbs or isotype MAb control as indicated. Animals were treated twice weekly for a total of 6 doses until study day 20. Tumor growth was monitored using caliper measurements every 3 to 4 days as indicated. The results show 161P2F10B MAbs Ha16-11(3,5)27 and Ha16-1(3,5)18 statistically and significantly inhibited the growth of human renal cancer xenograft UG-K3 implanted subcutaneously in SCID mice (P<0.05). (FIG. 14).

In another experiment, human renal cancer RXF-393 tumor cells ($2.0 \times 10^6$ cells) were injected subcutaneously into male SCID mice. The mice were randomized into groups (n=10 in each group) and treatment initiated intraperitoneally (i.p.) on day 0 with treatment MAbs or isotype MAb control as indicated Animals were treated twice weekly for a total of 7 doses at 400 µg/dose until study day 22. Tumor growth was monitored using caliper measurements every 3 to 4 days as indicated. The results show 161P2F10B MAbs Ha16-1(3,5)18 (P<0.01), H16-1.68 (P<0.05) and H16-9.44 (P<0.05) statistically and significantly inhibited the growth of human renal cancer xenograft RXF-393 implanted subcutaneously in SCID mice. (FIG. 15).

In another experiment, human renal cancer SKRC-01 tumor cells ($2.5 \times 10^6$ cells) were injected subcutaneously into male SCID mice. The mice were randomized into groups (n=10 in each group) and treatment initiated intraperitoneally (i.p.) on day 0 with treatment MAbs or isotype MAb control as indicated. Animals were treated twice weekly for a total of 7 doses at 250 µg/dose until study day 22. Tumor growth was monitored using caliper measurements every 3 to 4 days as indicated. The results show 161P2F10B MAbs H16-1.68 (P<0.05), H16-7.8 (P<0.05), H16-9.44 (P<0.05) and H16-3.4 (P<0.01) statistically and significantly inhibited the growth of human renal cancer xenograft SKRC-01 implanted subcutaneously in SCID mice. (FIG. 16).

In another experiment, human renal cancer UG-K3 tumor cells ($2.0 \times 10^6$ cells) were injected subcutaneously into male SCID mice. The mice were randomized into groups (n=10 in each group) and treatment initiated intraperitoneally (i.p.) on day 0 with treatment MAbs or isotype MAb control as indicated. Animals were treated twice weekly for a total of 6 doses at 750 µg/dose until study day 19. Tumor growth was monitored using caliper measurements every 3 to 4 days as indicated. The results show 161P2F10B MAbs H16-1.29.1.1 (P<0.05), Ha16-1(3,5)56 (P<0.01) and Ha16-1(2,4)4 (P<0.05) statistically and significantly inhibited the growth of human renal cancer xenograft UG-K3 implanted subcutaneously in SCID mice. (FIG. 17).

In another experiment, human renal cancer UG-K3 tumor cells ($2.0 \times 10^6$ cells) were injected subcutaneously into male SCID mice. The mice were randomized into groups (n=10 in each group) and treatment initiated intraperitoneally (i.p.) on day 0 with treatment MAbs or isotype MAb control as indicated. Animals were treated twice weekly for a total of 7 doses at 500 µg/dose until study day 22. Tumor growth was monitored using caliper measurements every 3 to 4 days as indicated. The results show 161P2F10B MAbs H16-1.93 and Ha16-1(3,5)18 statistically and significantly inhibited the growth of human renal cancer xenograft UG-K3 implanted subcutaneously in SCID mice (P<0.05). (FIG. 18).

Effect of a Cocktail of 161P2F10B MAbs on the Growth of Human Renal Cancer in Mice In this experiment, human renal cancer UG-K3 tumor cells ($2.0 \times 10^6$ cells) were injected subcutaneously into male SCID mice. The mice were randomized into groups (n=10 in each group) and treatment initiated intraperitoneally (i.p.) on day 0 as indicated. For 161P2F10B MAb treatment, three MAbs at 200 µg each were pooled together at each dosing. Animals were treated twice weekly for a total of 7 doses until study day 27. Tumor growth was monitored using caliper measurements every 3 to 4 days as indicated. The results show that combination treatment with a cocktail of 161P2F10B MAbs statistically and significantly inhibited the growth of human renal cancer xenograft UG-K3 implanted subcutaneously in SCID mice (P<0.05). (FIG. 19).

Effect of a Combination Treatment of 161P2F10B Mabs and Avastin® (Bevacizumab) on the Growth of Human Renal Cancer Xenografts in Mice In this experiment, human renal cancer UG-K3 tumor cells ($2.0 \times 10^6$ cells) were injected subcutaneously into male SCID mice. The mice were randomized into groups (n=10 mice in each group) and treatment initiated intraperitoneally (i.p.) on Day 0 with treatment MAbs, Avastin, or isotype MAb control as indicated. Animals were treated twice weekly for a total of 6 doses until study day 18. Tumor growth was monitored using caliper measurements every 3 to 4 days as indicated.

The results show 161P2F10B MAbs H16-1.93 and Ha16-1(3,5)18.1, when combined with Avastin® (bevacizumab), statistically and significantly inhibited the growth of human renal cancer xenograft UG-K3 implanted subcutaneously in SCID mice (p<0.01). (FIG. 20).

The results of these experiments show that 161P2F10B MAbs can be used for therapeutic and diagnostic purposes to treat and manage cancers set forth in Table I.

Example 16

Therapeutic and Diagnostic use of Anti-161P2F10B Antibodies in Humans.

Anti-161P2F10B monoclonal antibodies are safely and effectively used for diagnostic, prophylactic, prognostic and/or therapeutic purposes in humans. Western blot and immunohistochemical analysis of cancer tissues and cancer xenografts with anti-161P2F10B MAb show strong extensive staining in carcinoma but significantly lower or undetectable levels in normal tissues. Detection of 161P2F10B in carcinoma and in metastatic disease demonstrates the usefulness of the MAb as a diagnostic and/or prognostic indicator. Anti-161P2F10B antibodies are therefore used in diagnostic applications such as immunohistochemistry of kidney biopsy specimens to detect cancer from suspect patients.

As determined by flow cytometry, anti-161P2F10B MAb specifically binds to carcinoma cells. Thus, anti-161P2F10B antibodies are used in diagnostic whole body imaging applications, such as radioimmunoscintigraphy and radioimmunotherapy, (see, e.g., Potamianos S., et. al. Anticancer Res 20(2A):925-948 (2000)) for the detection of localized and metastatic cancers that exhibit expression of 161P2F10B. Shedding or release of an extracellular domain of 161P2F10B into the extracellular milieu, such as that seen for alkaline phosphodiesterase B 10 (Meerson, N. R., Hepatology 27:563-568 (1998)), allows diagnostic detection of 161P2F10B by anti-161P2F10B antibodies in serum and/or urine samples from suspect patients.

Anti-161P2F10B antibodies that specifically bind 161P2F10B are used in therapeutic applications for the treatment of cancers that express 161P2F10B. Anti-161P2F10B antibodies are used as an unconjugated modality and as conjugated form in which the antibodies are attached to one of various therapeutic or imaging modalities well known in the art, such as a prodrugs, enzymes or radioisotopes. In preclinical studies, unconjugated and conjugated anti-161P2F10B antibodies are tested for efficacy of tumor prevention and growth inhibition in the SCID mouse cancer xenograft models, e.g., kidney cancer models, (see, e.g., the Example entitled "161P2F10B Monoclonal Antibody-mediated Inhibition of Tumors In Vivo"). Either conjugated and unconjugated anti-161P2F10B antibodies are used as a therapeutic modality in human clinical trials either alone or in combination with other treatments as described in following Examples.

Example 17

Human Clinical Trials for the Treatment and Diagnosis of Human Carcinomas Through Use of 161P2F10B MAbs Antibodies are used in accordance with the present invention which recognize an epitope on 161P2F10B, and are used in the treatment of certain tumors, preferably those listed in Table I. In connection with each of these indications, three clinical approaches are successfully pursued.

I.) Adjunctive therapy: In adjunctive therapy, patients are treated with 161P2F10B MAbs (either naked or conjugated to an agent) in combination with a chemotherapeutic or antineoplastic agent and/or radiation therapy or a combination thereof. Primary cancer targets, such as those listed in Table I, are treated under standard protocols by the addition of 161P2F10B MAbs to standard first and second line therapy. Protocol designs address effectiveness as assessed by the following examples, including but not limited to, reduction in tumor mass of primary or metastatic lesions, increased progression free survival, overall survival, improvement of patients health, disease stabilization, as well as the ability to reduce usual doses of standard chemotherapy and other biologic agents. These dosage reductions allow additional and/or prolonged therapy by reducing dose-related toxicity of the chemotherapeutic or biologic agent. 161P2F10B MAbs are utilized in several adjunctive clinical trials in combination with the chemotherapeutic or anti-neoplastic agents.

II.) Monotherapy: In connection with the use of the 161P2F10B MAbs (either naked or conjugated) in monotherapy of tumors, the antibodies are administered to patients without a chemotherapeutic or anti-neoplastic agent. In one embodiment, monotherapy is conducted clinically in end-stage cancer patients with extensive metastatic disease. Protocol designs address effectiveness as assessed by the following examples, including but not limited to, reduction in tumor mass of primary or metastatic lesions, increased progression free survival, overall survival, improvement of patients health, disease stabilization, as well as the ability to reduce usual doses of standard chemotherapy and other biologic agents.

III.) Imaging Agent: Through binding a radionuclide (e.g., iodine or yttrium ($I^{131}$, $Y^{90}$) to 161P2F10B MAbs, the radiolabeled antibodies are utilized as a diagnostic and/or imaging agent. In such a role, the labeled antibodies localize to both solid tumors, as well as, metastatic lesions of cells expressing 161P2F10B. In connection with the use of the 161P2F10B MAbs as imaging agents, the antibodies are used as an adjunct to surgical treatment of solid tumors, as both a pre-surgical screen as well as a post-operative follow-up to determine what tumor remains and/or returns. In one embodiment, a ($^{111}$In)-161P2F10B antibody is used as an imaging agent in a Phase I human clinical trial in patients having a carcinoma that expresses 161P2F10B (by analogy see, e.g., Divgi et al. J. Natl. Cancer Inst. 83:97-104 (1991)). Patients are followed with standard anterior and posterior gamma camera. The results indicate that primary lesions and metastatic lesions are identified.

Dosage

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the antibody and the particular therapeutic or prophylactic effect to be achieved, and (b) the limitations inherent in the art of compounding such an active compound for the treatment of sensitivity in individuals.

An exemplary, non limiting range for a therapeutically effective amount of an antibody administered in combination according to the invention is at least 1 mg/kg, at least 5 mg/kg, at least 10 mg/kg, more than 10 mg/kg, or at least 15 mg/kg, for example 1-21 mg/kg, or for example 5-21 mg/kg, or for example 5-18 mg/kg, or for example 10-18 mg/kg, or for example 15 mg/kg. The high dose embodiment of the invention relates to a dosage of more than 10 mg/kg. It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Clinical Development Plan (CDP)

The CDP follows and develops treatments of 161P2F10B MAbs in connection with adjunctive therapy, monotherapy, and/or as an imaging agent. Trials initially demonstrate safety and thereafter confirm efficacy in repeat doses. Trials are open label comparing standard chemotherapy with standard therapy plus 161P2F10B MAbs. As will be appreciated, one non-limiting criteria that can be utilized in connection with enrollment of patients is 161P2F10B expression levels in their tumors as determined by biopsy.

As with any protein or antibody infusion-based therapeutic, safety concerns are related primarily to (i) cytokine release syndrome, i.e., hypotension, fever, shaking, chills; (ii) the development of an immunogenic response to the material (i.e., development of human antibodies by the patient to the antibody therapeutic, or HAHA response); and, (iii) toxicity to normal cells that express 161P2F10B. Standard tests and follow-up are utilized to monitor each of these safety concerns. 161P2F10B MAbs are found to be safe upon human administration.

Example 18

161P2F10B Functional Studies

A. RNA Interference (RNAi)

RNAi is a post-transcriptional gene silencing mechanism activated by double-stranded RNA (dsRNA) which induces specific mRNA degradation leading to changes in protein expression and subsequently in gene function. The RNAi technology has been used successfully in mammalian cells to silence the intended genes. In mammalian cells, these dsRNAs (called short interfering RNA or siRNA) activate the RNAi pathway, leading to the degradation of target sequence specific mRNAs. See, Elbashir S. M., et al., *Duplexes of 21-nucleotide RNAs Mediate RNA interference in Cultured Mammalian Cells*, Nature 411(6836):494-8 (2001).

Accordingly, RNAi was used to investigate the function of the 161P2F10B antigen. To generate specific siRNAs for 161P2F10B, algorithms were used to predict oligonucleotides that exhibit the critical molecular parameters (G:C content, melting temperature, etc.) and have the ability to significantly reduce the expression levels of the 161P2F10B protein when introduced into cells. In accordance with this Example, 161P2F10B siRNA compositions used correspond to the nucleic acid ORF, 5' or 3' untranslated sequences of the 161P2F10B protein or subsequences thereof. Thus, siRNA subsequences used in this manner are generally 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more than 35 contiguous RNA nucleotides in length. These siRNA sequences are complementary and non-complementary to at least a portion of the mRNA coding or non-coding sequence. In a preferred embodiment, the subsequences are 19-25 nucleotides in length, most preferably 21-23 nucleotides in length. In preferred embodiments, these siRNA achieve a substantial knockdown of 161P2F10B antigen in cells expressing the protein and have the potential of reversing a phenotype found in a particular disease by mimicking the inhibition of the 161P2F10B target. Therefore, correlating gene knockdown with functional cellular phenotype is critical to draw valid conclusions and rule out toxicity or other non specific effects.

To validate our approach, the level of 161P2F10B silencing upon RNAi transfection was assessed in HepG2 liver cancer cells both by cell surface staining using a fluorescence activated cell sorter (FACS) and by Western blotting (WB). The following samples were prepared: LF2k (cells treated with the transfection reagent LF2k only), control siRNA duplex CT1 and 161P2F10B specific duplex Qa (the sequences are disclosed below). Mammalian siRNA transfections: The day before siRNA transfection, cell lines were plated in media (RPMI 1640 with 10% FBS w/o antibiotics) at $2 \times 10^3$ cells/well in 80 μl (96 well plate format). In parallel with the 161P2F10B specific siRNA oligo, the following sequences were included in every experiment as controls: a) Mock transfected cells with Lipofectamine 2000 (Invitrogen, Carlsbad, Calif.) and annealing buffer (LF2k); b) CT1 non-specific siRNA (targeted sequence: 5'-AATTCTCCGAACGTGT-CACGT-3') (SEQ ID NO: 166); c) Eg5 specific siRNA (targeted sequence: 5'-AACTGAAGACCTGAAGACAATAA-3') (SEQ ID NO: 167) and 161P2F10B specific siRNA Qa (targeted sequence 5'-AACCTCATGGCTGGAAGAAAA-3') (SEQ ID NO:168). The siRNAs were used at the indicated concentrations and 1 μg/ml Lipofectamine 2000 final concentration.

The procedure was as follows: The siRNAs were first diluted in OPTIMEM (serum-free transfection media, Invitrogen) at 0.1 μM (10-fold concentrated) and incubated 5-10 min RT. Lipofectamine 2000 was diluted at 10 μg/ml (10-fold concentrated) for the total number transfections and incubated 5-10 minutes at room temperature (RT). Appropriate amounts of diluted 10-fold concentrated Lipofectamine 2000 were mixed 1:1 with diluted 10-fold concentrated siRNA and incubated at RT for 20-30" (5-fold concentrated transfection solution). Twenty (20) μl of the 5-fold concentrated transfection solutions were added to the respective samples and incubated at 37° C. for 96 hours before analysis. In every case, the cells were incubated for 72 h prior to the analysis by FACS with the 161P2F10B specific PE-labelled MAb 97A6 (Beckman-Coulter) or by WB. The 161P2F10B siRNA duplex Qa efficiently down-regulated the targeted gene as detected both by FACS and by WB (FIG. 21).

Another embodiment of the invention is a method to analyze the role of 161P2F10B in cell proliferation. Loss of cell proliferation control is a hallmark of cancerous cells; therefore, the role of specific 161P2F10B protein silencing in cell proliferation assays was addressed. Incorporation of the labeled precursor (i.e. $^3$H-Thymidine) into DNA is directly proportional to the amount of cell divisions occurring in the culture. HepG2 cells were treated with different concentrations (ranging from 200 nM to 20 pM) of control siRNA duplexes (negative control CT1 and positive control Eg5) as well as the 161P2F10B siRNA duplex Qa, and their impact on cell proliferation was assessed by the $^3$H-Thymidime incorporation assay. The data shown in FIG. 22A indicate that the cell surface levels of 161P2F10B (FIG. 21) correlate with cell proliferation, since reduction of the 161P2F10B protein levels corresponded to an impact on the ability of the cells to synthesize DNA under these conditions.

Another method used to measure cell proliferation is the clonogenic/colony forming assay. In this assay, a defined number of cells are plated onto the appropriate matrix and the number and size of the colonies formed after a period of growth following siRNA treatment is assessed. 161P2F10B positive HepG2 cells or 161P2F10B negative UMUC3 cells were treated with LF2k of the following siRNA duplexes: CT1, Eg5 and 161P2F10B Qa. As shown in FIG. 22B, the 161P2F10B Qa duplex reduced both the number and the size of the colonies formed only in the endogenously 161P2F10B expressing cells and had no effect in the UMUC3 negative cells, correlating with the effect on cell proliferation previously observed. Overall, the data indicate that cell proliferation and growth, which are key hallmarks of the cancer phenotype, are regulated by expression of the 161P2F10B in cancer cells.

Cell migration plays a central role in a wide variety of biological phenomena. In the adult organism, cell migration remains prominent in both normal physiological and pathological conditions. In metastasis, tumor cells migrate from the initial tumor mass to localize in other areas of the body. Cell migration is evaluated by several different methods, of which, the most widely accepted is the Boyden chamber assay. This assay uses a hollow plastic transwell chamber with a porous membrane (membranes can be coated with an extra cellular matrix if necessary). This chamber is suspended over a larger well which may contain media plus chemoattractants. Cells are placed inside the chamber and allowed to migrate through the pores to the other side of the membrane; migratory cells are then stained and counted. The potential role of 161P2F10B in regulating cell migration was addressed. The selected 161P2F10B Qa duplex was tested in two cell lines endogenously expressing 161P2F10B (HepG2 and A-704) in the Boyden chamber migration assay. As shown in FIG. 23, 161P2F10B silencing with oligo Qa significantly reduced the level of cell migration on collagen I coated inserts relative to control oligo CT1 in both A-704 (renal clear cell cancer) and HepG2 (liver cancer) systems.

To further support the role of 161P2F10B in cell migration, we sought to investigate the molecular mechanism underlying this phenotype. One of the major signal transduction networks driving cell motility is the Rho/Rac/Cdc42 pathway. Rho is a member of a family of small GTPases that regulates cell morphology and motility via actin cytoskeleton reorganization in response to extracellular signals. Active Rho increases the stability of actin-based structures such as stress fibers and focal adhesions. Deregulation of Rho activity has been linked to changes both in cell proliferation and cell motility by reorganizing the actin cytoskeleton and gene expression control. We assessed whether 161P2F10B expression regulates Rho activity by using the Rhotekin pull down assay which uses the Rhotekin protein that Specifically binds to and precipitates GTP-Rho, not GDP-Rho from cell lysates. specifically binds to and precipitates active GTP-Rho, but not inactive GDP-Rho from cell lysates. FIG. 23B shows that 161P2F10B silencing significantly reduces the cell surface expression of 161P2F10B on HepG2 cells and concomitantly reduces the Hepatocyte Growth Factor (HGF)-induced Rho B activation (Rho B-GTP). Together, the results in FIG. 23 indicate that 161P2F10B plays a role in cancer cell migration through activation of the Rho-family GTPases (Rho B), and is critical for the metastasis of 161P2F10B-expressing cancer cells during tumorigenesis. Specifically binds to and precipitates GTP-Rho, not GDP-Rho from cell lysates. Specifically binds to and precipitates GTP-Rho, not GDP-Rho from cell lysates.

For the 161P2F10B gene, RNAi studies facilitate the understanding of the contribution of the gene product in cancer pathways. Such active RNAi molecules have use in identifying assays to screen for MAbs that are active anti-tumor therapeutics. Further, siRNA are administered as therapeutics to cancer patients for reducing the malignant growth of several cancer types, including those listed in Table 1. When 161P2F10B plays a role in cell survival, cell proliferation, tumor genesis, or apoptosis, it is used as a target for diagnostic, prognostic, preventative and/or therapeutic purposes.

B. 161P2F10B-modulated ATP-induced Ca2+ Mobilization Assay in 161P2F10B-Expressing Cells.

161P2F10B is a cell surface pyrophosphatase/phosphodiesterase (PDE) capable of hydrolyzing the purine nucleotide ATP. Mutation of the PDE catalytic domain at amino acid 205 from threonine to alanine (T205A) eliminates the PDE activity of 161P2F10B (FIG. 24). In addition to ATP, other purine based analogs are known to be substrates for the enzymatic activity of 161P2F10B. ATP present in the extracellular milieu modulates a variety of biological responses, some of which are mediated through binding and activation of P2Y G-protein coupled receptors (GPCR) that induce signal transduction through Ca2+ mobilization from intracellular stores and through P2X ligand gated Ca2+ channels that modulate Ca2+ flux from extracellular sources (See, McLarnon, J. G. (2005) J. NeuroSci. Res. 81:349-356). Therefore the effect of ATP on calcium mobilization in cells expressing 161P2F10B was investigated. Over-expression of 161P2F10B in the Caki cell line results in noticeable differences in cytoplasmic calcium mobilization in response to treatment with purine nucleotides and purine nucleotide analogs. We employed single cell imaging to record the intracellular Ca2+ mobilization of Caki-1 cells expressing either wild type 161P2F10B (wt), 161P2F10B T205A mutant devoid of PDE activity, or control cells expressing only the neomycin resistance gene (neo) in response to the purine ligands ATP, ATPγ-S (non-hydrolysable ATP analog), AMP, and adenosine. The results are presented in FIG. 25.

The experiments were performed as follows: Caki-1-neo, or Caki-1-161P2F10B, or Caki-1-161P2F10B T205A mutant cells were plated overnight onto chambered coverslips pre-coated with collagen; cells were washed in serum-free media and loaded with fura-2 dye (3 uM in serum free media) for 30 minutes at 37° C. followed by wash and additional 30 minute incubation in serum free media at 37° C. Then media was replaced with Ringers' solution (20 mM HEPES, pH7.4, 130 mM NaCl, 5 mM KCl, 3 mM CaCl2, 2 mM MgCl2, 10 mM glucose) and cells were analyzed by ratiometric imaging of intracellular Ca2+ [Ca2+]i on an inverted microscope (Nikon 2000TS) equipped with a 20× objective, 340/380 nm excitation filters fitted to LAMBDA-10B filter wheel (Sutter), a dichroic (beam splitter) filter and emission filter (CHROMA) fitted to a filter cube for FURA-2 measurements. Ratio images were obtained by acquiring pair of images at alternate wavelengths (340/380 nm) using an ORCA-ER Hamamatsu CCD camera under the control of MetaFluor 6.2 imaging software (Molecular Devices Corp.).

All studied compounds were prepared as 400 uM stock in Ringer's solution and added to a final concentration of 100 µM into a chamber with cells. While ATP elicited a robust Ca2+ mobilization response in all three cell lines, the kinetics and pattern of this response was noticeably different between them: both Neo and the enzymatic "dead" mutant of 161P2F10B demonstrated calcium oscillations with high amplitude and frequency, while the wild-type 161P2F10B (wt) expressing cells exhibited an initial Ca2+ flux that gradually decayed over time with minimal oscillatory waves of lower frequency and longer duration. The non-hydrolysable analog of ATP, ATP☐S, induced similar "wave-like" oscillatory responses in all three cell lines. Taken together these data suggest that the pyrophosphatase/phosphodiesterase enzymatic activity of 161P2F10B mediates the suppression of Ca2+ oscillations in Caki-1 cells expressing 161P2F10B through depletion of ATP in the extracellular medium by cleavage into AMP and pyrophosphate. In addition, adenosine and adenosine monophosphate (AMP), potential metabolites of ATP, did not elicit calcium response in any of the cell lines suggesting that the response is mediated through the ATP activated P2Y family of GPCRs and not through receptors activated by adenosine or AMP.

The Ca2+ mobilization assay and monitoring of intracellular signaling pathways activated by P2Y receptors enables the screening of compounds, drugs, antibodies, and proteins that would modulate the PDE activity of 161P2F10B leading to suppression or alteration of ATP and other purine nucleotide responses in 161P2F10B-expressing cells and tissues. The significance of calcium oscillations in the 161P2F10B mutant or Neo cells versus that of the smooth sustained response in wild-type 16P2F10B is that a normal resolved calcium response correlates with an increased proliferative capacity of cells (See, Schreiber, R., 2005, J. Membrane Biol. 205:129-137). Calcium mobilization leads to activation of calmodulin and CamKII cell proliferation components, which induces the stimulation of the Ras-Raf axis of the cell growth pathway (See, Agell, N., Bachs, O., Rocamora, N., and Villalonga, P., 2002, Cellular Signaling 14:649-654). Thus, calcium is a critical element in the stimulation of the cell growth program. ATP-mediated activation of P2Y receptors leads to phospholipase C activation and downstream signal transduction events (See, Communi, D., et. al., 2000, Cellular Signaling 12: 351-360). Extracellular ATP plays a role in providing energy to extracellular ATP-dependent enzymes and transporters, is a DNA building block, and also stimulates cells to proliferate. Additionally, the PDE activity of 161P2F10B may supply tumor cells with metabolites from ATP (ADP, AMP, Adenosine, inorganic phosphate) and other purine nucleotides which are critical nutrients for tumor cell growth. Together, the results indicate that 161P2F10B provides a regulatory function for extracellular ATP that impacts the growth and survival of tumor cells.

C. Enhanced Angiogenesis (Tube Formation) of Human Umbilical Vein Endothelial Cells by Recombinant Extracellular Domain (ECD) of 161P2F10B and Modulation by MAb.

Angiogenesis is a critical event in the maintenance of tumors for their growth, nutrition and oxygenation. Growth and migration of endothelial cells is a hallmark of angiogenesis, and the stimulation of such cells requires multiple serum growth factors including vascular endothelial growth factor (VEGF). To address whether 161P2F10B facilitates angiogenesis of primary endothelium, an assay was established to detect the effect of the extracellular domain (ECD) (amino acids 46-875) of 161P2F10B on the formation of endothelial networks (tubes) when plated on Matrigel®. Human umbilical vein endothelial cells (HUVEC) or human lung microvascular endothelial cells (HMVEC) were grown in 10% FBS in media to 70% confluency (passage 2-passage 6). Cells were detached in 1:1 trypsin:PBS or 10 mM EDTA, washed and resuspended in EBM-0.1% FBS. Recombinant 161P2F10B ECD (described in Example entitled "Production of Recombinant 161P2F10B in Eukaryotic Systems") was added to the cells and then incubated on a 200 ul layer of Matrigel® for 8-16 hours at 37° C. Tube formation was quantitated by microscopy and data captured by photography. FIG. 26 shows that the 161P2F10B ECD induced the formation of endothelial tubes similarly as generated by treatment with 10% FBS, although fewer closed networks were observed using the 161P2F10B ECD, while control ECD did not generate tubes above the 0.1% FBS control. FIG. 27 shows that mutation of either the catalytic domain of 161P2F10B (T205A) which inactivates the PDE enzymatic activity 161P2F10B or the putative integrin binding RGD sequence (D80E) resulted in reduced tube formation. These data indicate that the PDE activity of 161P2F10B is required for the observed tube formation of HUVEC. Together these results indicate that the 161P2F10B protein is involved in promoting angiogenesis through its PDE activity that facilitates tumor growth, tumor cell invasion and/or activation of endothelium for tumor vascularization.

D. Enhanced Migration of Endothelial Cells by Recombinant Extracellular Domain (ECD) of 161P2F10B.

Enhanced migration is a hallmark of both angiogenesis and the cancer cell phenotype. To address the effect of the 161P2F10B protein on the migration of normal endothelial cells, HUVEC were treated with the 161P2F10B ECD and assayed in serum free conditions (0.1% BSA). The cells were grown overnight in 0.5% FBS, washed and then compared to cells treated with VEGF, 10% FBS or 161P2F10B ECD. The cells were evaluated for migration in transwells by the Boyden chamber assay. The results in FIG. 29 indicate that HUVEC cell migration was increased by the endothelial growth factor VEGF or 10% FBS (positive controls) as well as increasing concentrations of recombinant 161P2F10B ECD. These results indicate that HUVEC cells that are treated with 161P2F10B protein have an enhanced migratory capacity in low serum conditions. Accordingly, 161P2F10B expressing cells induce increased potential for migration of endothelium in vivo.

E. 161P2F10B Dimerization on KU-812 Cells.

The 161P2F10B protein contains different extracellular domains (for example, the somatomedin B-like domain) that may be involved in protein homodimerization. To investigate the potential dimeric state of 161P2F10B on the cell surface, KU-812 cells which endogenously express 161P2F10B were treated with a chemical cross-linking agent, ethylene glycol bis[succinimidylsuccinate] (EGS), at different concentrations for 30 minutes. The cells were then lysed, the cell proteins were subjected to SDS-PAGE and then Western blotted for 161P2F10B. The results in FIG. 36 indicate that with increasing concentrations of EGS treatment, the monomeric form of 161P2F10B (~100 kDa) was diminished while a new band at ~200-kDa was observed. The 200-kDa band correlates with a dimeric form of the 161P2F10B protein. The EGS agent will cross-link molecules that are within 16.1 Angstroms distance between each other to form stable dimers or multimers. The data indicate that 161P2F10B molecules on KU-812 cells are in close proximity, such that they are already dimers on the cell surface prior to chemical cross-linking. The hypothesis that 161P2F10B could randomly form dimers with other proteins is eliminated by the observation that only a dimeric molecular weight species was observed in the specific Western blot, and not other molecular weight bands. Overall, the results indicate that 161P2F10B is dimeric on the cell surface, and that this property may be required for full enzymatic activity and other functional activities of 161P2F10B when expressed on the surface of tumor cells.

Example 19

161P2F10B MAb Inhibition Studies

A. MAbs Inhibit Cell Proliferation, Survival and Apoptosis in 161P2F10B Expressing Cells.

Enhanced proliferation and entry into S-phase of tumor cells relative to normal cells are hallmarks of the cancer cell phenotype. To address the effect of modulation of 161P2F10B on the proliferation rate of cells, cancer cell lines endogenously expressing the 161P2F10B gene (renal clear cell cancer lines SK-RC-01 and RXF-393; liver cancer line HepG2; promyelocytic line KU-812) were evaluated in a 3H-thymidine incorporation assay (cell proliferation assay) in the absence or presence of MAbs to the 161P2F10B protein. The cells were grown in 10% FBS, incubated with MAb and then evaluated for proliferation after 18-96 hr post-treatment by a 3H-thymidine incorporation assay. The results in FIG. 30 show that MAbs inhibited the proliferation of cells expressing the 161P2F10B antigen; while the isotype matched control MAb did not affect cell growth. Similar results were obtained for the RXF-393, HepG2 and KU-812 cancer cells expressing 161P2F10B. Further, renal clear cell line RXF-393 cells were evaluated in an MTS survival assay (FIG. 31). The MTS assay is a colorimetric method for determining the number of viable cells in proliferation, cytotoxicity or chemosensitivity assays based on a tetrazolium compound [3-(4,5-dimethylthiazol-2-yl)-5-(3-carboxymethoxyphenyl)-2-(4-sulfophenyl)-2H-tetrazolium, inner salt; MTS(b)] and an electron coupling reagent (phenazine ethosulfate; PES). Assays were performed by adding a small amount of the Solution Reagent directly to culture wells, incubating for 1-4 hours and then recording absorbance at 490 nm with a 96-well plate reader. The quantity of colored formazan product as measured by the amount of 490 nm absorbance is directly proportional to the mitochondrial activity and/or the number of living cells in culture. As shown in FIG. 31, MAbs to 161P2F10B inhibited the survival of the RXF-393 cells, which correlated with inhibition of cell proliferation. As a further test of MAb modulation of cell viability, the cells tested in the MTS survival assay were lysed and also tested in a cell death ELISA that measures cellular apoptosis. A method to observe fragmented DNA in cells is the immunological detection of histone-complexed DNA fragments by an immunoassay (i.e. cell death detection ELISA) which measures the enrichment of histone-complexed DNA fragments (mono- and oligo-nucleosomes) in the cytoplasm of apoptotic cells. In FIG. 31, the same MAbs that inhibited both proliferation and survival also induced increased apoptosis. These results confirm that cells expressing 161P2F10B antigen are modulated by MAb to 161P2F10B protein, resulting in reduced proliferative capacity and survival in high serum conditions, and an increased apoptotic program. Accordingly, 161P2F10B expressing cancer cells with potential for growth as tumor cells in vivo may be modulated for growth by MAb to 161P2F10B.

B. MAbs Inhibit Enhanced Angiogenesis (Tube Formation) of Human Umbilical Vein Endothelial Cells Stimulated with Recombinant Extracellular Domain (ECD) of 161P2F10B.

FIG. 28 shows that incubation of HUVEC cells and ECD in the in vitro angiogenesis (tube formation) assay with 20 µg/ml MAb to 161P2F10B resulted in 33-78% inhibition of network formation, depending upon the MAb used in the assay. An isotype control MAb at the same concentration did not inhibit tube formation. Further, as shown in FIG. 32, inhibition of angiogenesis by 161P2F10B MAbs is dose-dependent. Together, these results indicate that the 161P2F10B protein is involved in promoting angiogenesis through its PDE activity that facilitates tumor growth, tumor cell invasion and/or activation of endothelium for tumor vascularization, and that MAbs to 161P2F10B inhibit such activity.

C. Inhibition of Cell Migration and Invasion by 161P2F10B Mab.

Enhanced migration and invasion are hallmarks of the cancer cell phenotype. To address the effect of MAbs to 161P2F10B on migration, HepG2 cells (liver cancer) and A-704 cells (renal clear cell cancer) which endogenously express 161P2F10B protein were evaluated in a transwell migration assay. The cells were incubated with a control MAb or a pool of three MAbs (25 ug/ml each) to 161P2F10B and allowed to migrate for 24 hours through a transwell chamber. The results in FIG. 33 indicate that the MAb pool to 161P2F10B inhibited the migration of HepG2 cells, while the control MAb did not inhibit migration. As shown in FIG. 34, inhibition of A-704 renal clear cell migration also was observed. Enhancement of migration was seen in both cell lines by treatment of the cells with 8 ng/ml Hepatocyte Growth Factor (HGF). For both cell lines, the enhanced HGF-induced migration was inhibited by the MAbs to 161P2F10B (FIGS. 33 and 34). To address the ability of the cells to invade into the extracellular matrix, A-704 cells were seeded into transwell chambers that were coated with Matrigel®. This assay is fundamentally similar to the migration assay except that the cells need to migrate through the Matrigel® in order to be scored as having moved in the assay. This is a property of tumor cells in that they express enzymes (i.e., matrix metalloproteases such as MMPs, ADAMs, etc.) that degrade the extracellular matrix proteins in the Matrigel® and facilitate cellular migration. The results in FIG. 35 demonstrate that A-704 cells possess the ability to invade and that MAb H16-1.93 exhibits an inhibitory activity on this cell phenotype. Furthermore, HGF treatment of the cells increases their capacity to invade in the Matrigel® which is inhibited by MAb H16-1.93.

Overall, the in vitro functional results and MAb inhibition studies indicate that the 161P2F10B protein has growth promoting, survival potentiating, migration and invasion enhancing, and angiogenic activities. These activities when assayed in vitro were inhibited by MAbs to 161P2F10B. Such cellular and biochemical functions are vital for the establishment and maintenance of tumors by stimulating capillary bed formation by endothelial cells (See, Ferrara, N. and Kerbel, R. S., 2005 Nature 438: 967-974). This increased angiogenesis provides a means of increased nutrition and oxygenation of growing tumors, and affords a therapeutic intervention strategy for targeting of 161P2F10B in malignancies. The 161P2F10B protein also plays a role in cell migration and invasion, particularly for cells that express the protein, and also serves as an attractant for endothelial cells and other cells expressing its ligand. The phosphodiesterase/pyrophosphatase (PDE) activity of 161P2F10B protein may be critical for altering the concentration of ATP in the tumor microenvironment to facilitate angiogenesis and provide a nutritional advantage. Cell migration and invasion are important for the metastatic potential of tumor cells, and facilitate their homing and recruitment to remote tissues. Expression of 161P2F10B protein in metastases indicates that the migratory phenotype of 161P2F10B-expressing cells imparts a strong potential for such cells to metastasize. All of the assayed functions of 161P2F10B in vitro are inhibited by MAbs.

Example 20

Detection of 161P2F10B Protein in Cancer Patient Specimens by IHC

Expression of 161P2F10B protein in tumor specimens from liver cancer patients was detected using the antibody M16-41(3)50. Briefly, frozen tissues were cut into 6 micron sections and mounted on glass slides. The sections were dried for 2 hours at room temperature, fixed for 8 minutes in acetone and subsequently allowed to dry. Sections were then incubated in 161P2F10B antibody, M16-41(3)50, for 3 hours at room temperature. The slides were washed three times in buffer and further incubated with DAKO EnVision+™ peroxidase-conjugated goat anti-mouse immunoglobulin secondary antibody (DAKO Corporation, Carpenteria, Calif.) for 1 hour. The sections were then washed in buffer, developed using a DAB kit (SIGMA Chemicals), counterstained using hematoxylin, and analyzed by bright field microscopy. The results show expression of 161P2F10B in the tumor cells of hepatocellular carcinoma (37A and 37B) as indicated by the brown coloration of the cells. Serial sections with no incubation in M16-41(3)50 had no staining (37C and 37D). These results indicate that 161P2F10B is expressed in human liver cancers and that antibodies directed to this antigen are useful as diagnostic reagents (FIG. 37).

These results indicate that 161P2F10B is a target for diagnostic, prognostic and therapeutic applications in cancer.

Example 21

161P2F10B MAb Named Ha16-1(3,5)18

In one embodiment, the invention comprises a therapeutic Monoclonal Antibody ("MAbs") to 161P2F10B and 161P2F10B variants named Ha16-1(3,5)18. Ha16-1(3,5)18 was generated from immunization of human gamma 1 producing XenoMice with RAT1-161P2F10B cells.

DNA coding sequences for 161P2F10B MAb Ha16-1(3,5)18 was determined after isolating mRNA from the respective hybridoma cells with Trizol reagent (Life Technologies, Gibco BRL).

Total RNA was purified and quantified. First strand cDNAs was generated from total RNA with oligo (dT)12-18 priming using the Gibco BRL Superscript Preamplification system. First strand cDNA was amplified using human immunoglobulin variable heavy chain primers, and human immunoglobulin variable light chain primers. PCR products were cloned into the pCRScript vector (Stratagene). Several clones were sequenced and the variable heavy and light chain regions determined.

The nucleic acid and amino acid sequences of the variable heavy and light chain regions of Ha16-1(3,5)18 are listed in FIGS. 2Y and 2Z and FIGS. 3Y and 3Z.

In a preferred embodiment, a 161P2F10B MAb of the invention comprises heavy and light chain variable regions of an antibody designated Ha16-1(3,5)18 (See, FIGS. 3Y and 3Z), or heavy and light variable regions comprising amino acid sequences that are homologous to the amino acid sequences of the heavy and light chain variable regions of Ha16-1(3,5)18, and wherein the antibodies retain the desired functional properties of the 161P2F10B MAbs of the invention. The heavy chain variable region of Ha16-1(3,5)18 consists of the amino acid sequence ranging from $27^{th}$ Q residue to the $147^{th}$ S residue of SEQ ID NO: 139, and the light chain variable region of Ha16-1(3,5)16 consists of the amino acid sequence ranging from $1^{st}$ Q residue to the $110^{th}$ L residue of SEQ ID NO: 140. As the constant region of the antibody of the invention, any subclass of constant region can be chosen. Preferably, human IgG1 constant region as the heavy chain constant region and human Ig lambda constant region as the light chain constant region can be used.

Throughout this application, various website data content, publications, patent applications and patents are referenced. (Websites are referenced by their Uniform Resource Locator, or URL, addresses on the World Wide Web.) The disclosures of each of these references are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

Tables

TABLE I

Tissues that express 161P2F10B when malignant.

Prostate
Kidney
Colon
Lung
Ovary
Breast
Lymphoma
Bone
Uterus
Pancreas
Liver

TABLE II

Amino Acid Abbreviations

| SINGLE LETTER | THREE LETTER | FULL NAME |
|---|---|---|
| F | Phe | phenylalanine |
| L | Leu | leucine |
| S | Ser | serine |
| Y | Tyr | tyrosine |
| C | Cys | cysteine |
| W | Trp | tryptophan |
| P | Pro | proline |
| H | His | histidine |
| Q | Gln | glutamine |
| R | Arg | arginine |
| I | Ile | isoleucine |
| M | Met | methionine |
| T | Thr | threonine |
| N | Asn | asparagine |
| K | Lys | lysine |
| V | Val | valine |
| A | Ala | alanine |
| D | Asp | aspartic acid |
| E | Glu | glutamic acid |
| G | Gly | glycine |

TABLE III

Amino Acid Substitution Matrix
Adapted from the GCG Software 9.0 BLOSUM62 amino acid substitution matrix (block substitution matrix). The higher the value, the more likely a substitution is found in related, natural proteins.

| A | C | D | E | F | G | H | I | K | L | M | N | P | Q | R | S | T | V | W | Y | . |
|---|---|---|---|---|---|---|---|---|---|---|---|---|---|---|---|---|---|---|---|---|
| 4 | 0 | -2 | -1 | -2 | 0 | -2 | -1 | -1 | -1 | -1 | -2 | -1 | -1 | -1 | 1 | 0 | 0 | -3 | -2 | A |
|   | 9 | -3 | -4 | -2 | -3 | -3 | -1 | -3 | -1 | -1 | -3 | -3 | -3 | -3 | -1 | -1 | -1 | -2 | -2 | C |
|   |   | 6 | 2 | -3 | -1 | -1 | -3 | -1 | -4 | -3 | 1 | -1 | 0 | -2 | 0 | -1 | -3 | -4 | -3 | D |
|   |   |   | 5 | -3 | -2 | 0 | -3 | 1 | -3 | -2 | 0 | -1 | 2 | 0 | 0 | -1 | -2 | -3 | -2 | E |
|   |   |   |   | 6 | -3 | -1 | 0 | -3 | 0 | 0 | -3 | -4 | -3 | -3 | -2 | -2 | -1 | 1 | 3 | F |

TABLE III-continued

Amino Acid Substitution Matrix
Adapted from the GCG Software 9.0 BLOSUM62 amino acid substitution matrix (block substitution matrix). The higher the value, the more likely a substitution is found in related, natural proteins.

```
A C D E F G H I K L M N P Q R S T V W Y .

6 -2 -4 -2 -4 -3  0 -2 -2 -2  0 -2 -3 -2 -3 G
          8 -3 -1 -3 -2  1 -2  0  0 -1 -2 -3 -2  2 H
             4 -3  2  1 -3 -3 -3 -3 -2 -1  3 -3 -1 I
                5 -2 -1  0 -1  1  2  0 -1 -2 -3 -2 K
                   4  2 -3 -3 -2 -2 -2 -1  1 -2 -1 L
                      5 -2 -2  0 -1 -1 -1  1 -1 -1 M
                         6 -2  0  0  1  0 -3 -4 -2 N
                            7 -1 -2 -1 -1 -2 -4 -3 P
                               5  1  0 -1 -2 -2 -1 Q
                                  5 -1 -1 -3 -3 -2 R
                                     4  1 -2 -3 -2 S
                                        5  0 -2 -2 T
                                           4 -3 -1 V
                                             11  2 W
                                                 7 Y
```

Table IV:
HLA Class I/II Motifs/Supermotifs

TABLE IV (A)

HLA Class I Supermotifs/Motifs

| | POSITION 2 (Primary Anchor) | POSITION 3 (Primary Anchor) | POSITION C Terminus (Primary Anchor) |
|---|---|---|---|
| SUPERMOTIF | | | |
| A1 | TILVMS | | FWY |
| A2 | LIVMATQ | | IVMATL |
| A3 | VSMATLI | | RK |
| A24 | YFWIVLMT | | FIYWLM |
| B7 | P | | VILFMWYA |
| B27 | RHK | | FYLWMIVA |
| B44 | ED | | FWYLIMVA |
| B58 | ATS | | FWYLIVMA |
| B62 | QLIVMP | | FWYMIVLA |
| MOTIFS | | | |
| A1 | TSM | | Y |
| A1 | | DEAS | Y |
| A2.1 | LMVQIAT | | VLIMAT |
| A3 | LMVISATFCGD | | KYRHFA |
| A11 | VTMLISAGNCDF | | KRYH |
| A24 | YFWM | | FLIW |

TABLE IV (A)-continued

HLA Class I Supermotifs/Motifs

| | POSITION 2 (Primary Anchor) | POSITION 3 (Primary Anchor) | POSITION C Terminus (Primary Anchor) |
|---|---|---|---|
| A*3101 | MVTALIS | | RK |
| A*3301 | MVALFIST | | RK |
| A*6801 | AVTMSLI | | RK |
| B*0702 | P | | LMFWYAIV |
| B*3501 | P | | LMFWYIVA |
| B51 | P | | LIVFWYAM |
| B*5301 | P | | IMFWYALV |
| B*5401 | P | | ATIVLMFWY |

Bolded residues are preferred, italicized residues are less preferred: A peptide is considered motif-bearing if it has primary anchors at each primary anchor position for a motif or supermotif as specified in the above table.

TABLE IV (B)

HLA Class II Supermotif

| 1 | 6 | 9 |
|---|---|---|
| W, F, Y, V, .I, L | A, V, I, L, P, C, S, T | A, V, I, L, C, S, T, M, Y |

TABLE IV (C)

HLA Class II Motifs

| MOTIFS | | 1° anchor 1 | 2 | 3 | 4 | 5 | 1° anchor 6 | 7 | 8 | 9 |
|---|---|---|---|---|---|---|---|---|---|---|
| DR4 | preferred | FMY*LIVW* | M | T | | I | VST*CPALIM* | MH | | MH |
| | deleterious | | | W | | | | R | | WDE |
| DR1 | preferred | MF*LIVWY* | | | PAMQ | | VMAT*SPLIC* | M | | AVM |
| | deleterious | | C | CH | FD | CWD | | GDE | D | |
| DR7 | preferred | MF*LIVWY* | M | W | A | | IVMSA*CTPL* | M | | IV |
| | deleterious | | C | | G | | | GRD | N | G |

| DR3 | MOTIFS | 1° anchor 1 | 2 | 3 | 1° anchor 4 | 5 | 1° anchor 6 |
|---|---|---|---|---|---|---|---|
| Motif a preferred | | LIVMFY | | | D | | |
| Motif b preferred | | LIVMFAY | | | DNQEST | | KRH |
| DR Supermotif | | MF*LIVWY* | | | | | VMSTA*CPLI* |

Italicized residues indicate less preferred or "tolerated" residues

TABLE IV (D)

HLA Class I Supermotifs

| SUPER-MOTIFS | POSITION: | 1 | 2 | 3 | 4 | 5 | 6 | 7 | 8 | C-terminus |
|---|---|---|---|---|---|---|---|---|---|---|
| A1 | | | 1° Anchor TI*LVMS* | | | | | | | 1° Anchor FWY |
| A2 | | | 1° Anchor LIVMATQ | | | | | | | 1° Anchor LIVMAT |
| A3 | Preferred | | 1° Anchor VSMA*TLI* | YFW (4/5) | | | YFW (3/5) | YFW (4/5) | P (4/5) | 1° Anchor RK |
| | deleterious | DE(3/5); P(5/5) | | DE (4/5) | | | | | | |
| A24 | | | 1° Anchor YF*WIVLMT* | | | | | | | 1° Anchor FIY*WLM* |
| B7 | Preferred | FWY(5/5) LIVM(3/5) | 1° Anchor P | FWY (4/5) | | | | | FWY (3/5) | 1° Anchor VILF*MWYA* |
| | deleterious | DE (3/5); P(5/5); G(4/5); A(3/5); QN(3/5) | | | | | DE (3/5) | G (4/5) | QN (4/5) | DE (4/5) | |
| B27 | | | 1° Anchor RHK | | | | | | | 1° Anchor FYL*WMIVA* |
| B44 | | | 1° Anchor ED | | | | | | | 1° Anchor FWYLIMVA |
| B58 | | | 1° Anchor ATS | | | | | | | 1° Anchor FWY*LIVMA* |
| B62 | | | 1° Anchor QL*IVMP* | | | | | | | 1° Anchor FWY*MIVLA* |

Italicized residues indicate less preferred or "tolerated" residues

TABLE IV (E)

| | HLA Class I Motifs | | | | | | | | | |
|---|---|---|---|---|---|---|---|---|---|---|
| POSITION | | 1 | 2 | 3 | 4 | 5 | 6 | 7 | 8 | 9 or C-terminus / C-terminus |
| A1 9-mer | preferred | GFYW | 1° Anchor STM | DEA | YFW | | P | DEQN | YFW | 1° Anchor Y |
| | deleterious | DE | | RHKLIVMP | A | G | A | | | |
| A1 9-mer | preferred | GRHK | ASTCLIVM | 1° Anchor DEAS | GSTC | | ASTC | LIVM | DE | 1° Anchor Y |
| | deleterious | A | RHKDEPYFW | | DE | PQN | RHK | PG | GP | |
| A1 10-mer | preferred | YFW | 1° Anchor STM | DEAQN | A | YFWQN | | PASTC | GDE | P | 1° Anchor Y |
| | deleterious | GP | | RHKGLIVM | DE | RHK | QNA | RHKYFW | RHK | A | |
| A1 10-mer | preferred | YFW | STCLIVM | 1° Anchor DEAS | A | YFW | | PG | G | YFW | 1° Anchor Y |
| | deleterious | RHK | RHKDEPYFW | | | P | G | | PRHK | QN | |
| A2.1 9-mer | preferred | YFW | 1° Anchor LMIVQAT | YFW | STC | YFW | | A | P | 1° Anchor VLIMAT |
| | deleterious | DEP | | DERKH | | | RKH | DERKH | | |
| A2.1 10-mer | preferred | AYFW | 1° Anchor LMIVQAT | LVIM | G | | G | | FYWL VIM | 1° Anchor VLIMAT |
| | deleterious | DEP | | DE | RKHA | P | | RKH | DERKH | RKH | |
| A3 | preferred | RHK | 1° Anchor LMVISATFCGD | YFW | PRHKYFW | A | YFW | | P | 1° Anchor KYRHFA |
| | deleterious | DEP | | DE | | | | | | |
| A11 | preferred | A | 1° Anchor VTLMISAGNCDF | YFW | YFW | A | YFW | YFW | P | 1° Anchor KRYH |
| | deleterious | DEP | | | | | | A | G | |
| A24 9-mer | preferred | YFWRHK | 1° Anchor YFWM | | STC | | | YFW | YFW | 1° Anchor FLIW |
| | deleterious | DEG | | DE | G | QNP | DERHK | G | AQN | |
| A24 10-mer | Preferred | | 1° Anchor YFWM | | P | YFWP | | P | | 1° Anchor FLIW |
| | Deleterious | | | GDE | QN | RHK | DE | A | QN | DEA |
| A3101 | Preferred | RHK | 1° Anchor MVTALIS | YFW | P | | YFW | YFW | AP | 1° Anchor RK |
| | Deleterious | DEP | | DE | | ADE | DE | DE | DE | |
| A3301 | Preferred | | 1° Anchor MVALFIST | YFW | | | | AYFW | | 1° Anchor RK |
| | Deleterious | GP | | DE | | | | | | |
| A6801 | Preferred | YFWSTC | 1° Anchor AVTMSLI | | | YFWLIVM | YFW | | P | 1° Anchor RK |
| | deleterious | GP | | DEG | | RHK | | | A | |
| B0702 | Preferred | RHKFWY | 1° Anchor P | RHK | | RHK | RHK | RHK | PA | 1° Anchor LMFWYAIV |
| | deleterious | DEQNP | | DEP | DE | DE | GDE | QN | DE | |
| B3501 | Preferred | FWYLIVM | 1° Anchor P | FWY | | | FWY | | 1° Anchor LMFWYIVA |
| | deleterious | AGP | | | | G | G | | | |

TABLE IV (E)-continued

HLA Class I Motifs

| POSITION | | 1 | 2 | 3 | 4 | 5 | 6 | 7 | 8 | 9 or C-terminus | C-terminus |
|---|---|---|---|---|---|---|---|---|---|---|---|
| B51 | Preferred | LIVMFWY | 1° Anchor P | FWY | | STC | FWY | | G | FWY | 1° Anchor LIVFWYA M |
| | deleterious | AGPDER HKSTC | | | | DE | G | DEQN | GDE | | |
| B5301 | preferred | LIVMFWY | 1° Anchor P | FWY | | STC | FWY | | LIVMFW Y | FWY | 1° Anchor IMFWYAL V |
| | deleterious | AGPQN | | | | | G | RHKQN | DE | | |
| B5401 | preferred | FWY | 1° Anchor P | FWYLIVM | | LIVM | | ALIVM | FWYA P | 1° Anchor ATIVLMF WY | |
| | deleterious | GPQNDE | | GDESTC | | RHKDE | DE | QNDGE | DE | | |

TABLE IV (F)

Summary of HLA-supertypes
Overall phenotypic frequencies of HLA-supertypes in different ethnic populations

| | Specificity | | Phenotypic frequency | | | | | |
|---|---|---|---|---|---|---|---|---|
| Super-type | Position 2 | C-Terminus | Cauca-sian | N.A. Black | Japa-nese | Chinese | Hispanic | Average |
| B7 | P | AILMVFWY | 43.2 | 55.1 | 57.1 | 43.0 | 49.3 | 49.5 |
| A3 | AILMVST | RK | 37.5 | 42.1 | 45.8 | 52.7 | 43.1 | 44.2 |
| A2 | AILMVT | AILMVT | 45.8 | 39.0 | 42.4 | 45.9 | 43.0 | 42.2 |
| A24 | YF(WIVLMT) | FI(YWLM) | 23.9 | 38.9 | 58.6 | 40.1 | 38.3 | 40.0 |
| B44 | E(D) | FWYLIMVA | 43.0 | 21.2 | 42.9 | 39.1 | 39.0 | 37.0 |
| A1 | TI(LVMS) | FWY | 47.1 | 16.1 | 21.8 | 14.7 | 26.3 | 25.2 |
| B27 | RHK | FYL(WMI) | 28.4 | 26.1 | 13.3 | 13.9 | 35.3 | 23.4 |
| B62 | QL(IVMP) | FWY(MIV) | 12.6 | 4.8 | 36.5 | 25.4 | 11.1 | 18.1 |
| B58 | ATS | FWY(LIV) | 10.0 | 25.1 | 1.6 | 9.0 | 5.9 | 10.3 |

TABLE IV (G)

Calculated population coverage afforded by different HLA-supertype combinations

| | Phenotypic frequency | | | | | |
|---|---|---|---|---|---|---|
| HLA-supertypes | Caucasian | N.A Blacks | Japanese | Chinese | Hispanic | Average |
| A2, A3 and B7 | 83.0 | 86.1 | 87.5 | 88.4 | 86.3 | 86.2 |
| A2, A3, B7, A24, B44 and A1 | 99.5 | 98.1 | 100.0 | 99.5 | 99.4 | 99.3 |
| A2, A3, B7, A24, B44, A1, B27, B62, and B 58 | 99.9 | 99.6 | 100.0 | 99.8 | 99.9 | 99.8 |

Motifs indicate the residues defining supertype specificites. The motifs incorporate residues determined on the basis of published data to be recognized by multiple alleles within the supertype. Residues within brackets are additional residues also predicted to be tolerated by multiple alleles within the supertype.

TABLE V

Frequently Occurring Motifs

| Name | avrg. % identity | Description | Potential Function |
|---|---|---|---|
| zf-C2H2 | 34% | Zinc finger, C2H2 type | Nucleic acid-binding protein functions as transcription factor, nuclear location probable |
| cytochrome_b_N | 68% | Cytochrome b(N-terminal)/b6/petB | membrane bound oxidase, generate superoxide |
| Ig | 19% | Immunoglobulin domain | domains are one hundred amino acids long and include a conserved intradomain disulfide bond. |
| WD40 | 18% | WD domain, G-beta repeat | tandem repeats of about 40 residues, each containing a Trp-Asp motif. Function in signal transduction and protein interaction |
| PDZ | 23% | PDZ domain | may function in targeting signaling molecules to sub-membranous sites |
| LRR | 28% | Leucine Rich Repeat | short sequence motifs involved in protein-protein interactions |
| Pkinase | 23% | Protein kinase domain | conserved catalytic core common to both serine/threonine and tyrosine protein kinases containing an ATP binding site and a catalytic site |
| PH | 16% | PH domain | pleckstrin homology involved in intracellular signaling or as constituents of the cytoskeleton |
| EGF | 34% | EGF-like domain | 30-40 amino-acid long found in the extracellular domain of membrane-bound proteins or in secreted proteins |
| Rvt | 49% | Reverse transcriptase (RNA-dependent DNA polymerase) | |
| Ank | 25% | Ank repeat | Cytoplasmic protein, associates integral membrane proteins to the cytoskeleton |
| Oxidored_q1 | 32% | NADH-Ubiquinone/plastoquinone (complex I), various chains | membrane associated. Involved in proton translocation across the membrane |
| Efhand | 24% | EF hand | calcium-binding domain, consists of a12 residue loop flanked on both sides by a 12 residue alpha-helical domain |
| Rvp | 79% | Retroviral aspartyl protease | Aspartyl or acid proteases, centered on a catalytic aspartyl residue |
| Collagen | 42% | Collagen triple helix repeat (20 copies) | extracellular structural proteins involved in formation of connective tissue. The sequence consists of the G-X-Y and the polypeptide chains forms a triple helix. |
| Fn3 | 20% | Fibronectin type III domain | Located in the extracellular ligand-binding region of receptors and is about 200 amino acid residues long with two pairs of cysteines involved in disulfide bonds |
| 7tm_1 | 19% | 7 transmembrane receptor (rhodopsin family) | seven hydrophobic transmembrane regions, with the N-terminus located extracellularly while the C-terminus is cytoplasmic. Signal through G proteins |

TABLE VI

161P2F10B MAb affinity determined by FACS using Ku812 cells.

| MAb | Epitope group | Kd (nM) FACS (KU-812) |
|---|---|---|
| hIgG1-λ | | |
| Ha16-1(2,4)4 | 1 | 0.008 |
| Ha16-1(3,5)18 | 4 | 0.047 |
| Ha16-1(1)15 | 26 | 0.013 |
| Ha16-1(3,5)30 | 28 | 0.46 |
| Ha16-1(3,5)27 | 31 | 0.014 |
| Ha16-1(3,5)56 | 31 | 0.019 |
| hIgG1-÷ | | |
| H16-1.93 | 1 | 0.09 |
| H16-1.79 | 3 | 0.06 |
| H16-1.67 | 7 | 0.02 |
| H16-1.42 | 8 | 0.02 |
| H16-1.82 | 9 | 0.01 |
| H16-1.86 | 9 | 0.02 |
| H16-1.62 | 10 | 0.04 |
| H16-1.78 | 10 | 0.03 |
| H16-1.92 | 11 | 4.73 |
| Ha16-1(1)11 | 27 | 0.004 |
| hIgG2-÷ | | |
| H16-7.8 | 1 | 0.07 |
| H16-7.79 | 6 | 7.08 |
| H16-9.10 | 9 | 0.50 |
| H16-9.69 | 11 | 0.27 |
| H16-9.44 | 12 | 1.27 |

TABLE VII

161P2F10B MAb affinity determined by SPR.

| 161P2F10B MAb | kon (M-1s-1) | koff (s-1) | Affinity - KD (nM) |
|---|---|---|---|
| Ha16-1(1)23 | 3.60E+04 | 8.80E-04 | 24 |
| Ha16-1(3,5)36 | 5.29E+04 | 4.60E-04 | 8.7 |
| H16-1.52 | 9.00E+05 | 1.20E-05 | 0.133 |
| H16-1.67 | 1.60E+04 | 7.00E-04 | 43 |
| H16-1.86 | 4.30E+04 | 6.40E-04 | 14.9 |
| H16-7.213 | 1.29E+05 | 5.09E-04 | 3.9 |
| H16-9.10 | 5.95E+04 | 4.42E-04 | 7.4 |
| H16-9.33 | 6.63E+04 | 2.57E-04 | 3.9 |
| H16-9.44 | 1.74E+05 | 1.32E-04 | 0.76 |
| H16-9.69 | 4.24E+04 | 1.86E-04 | 4 |
| Ha16-1(1)11 | 6.58E+04 | 1.43E-03 | 21.7 |
| Ha16-1(3,5)18 | 2.20E+04 | 6.20E-04 | 28 |
| Ha16-1(2,4)4 | 7.70E+04 | 1.75E-03 | 22.6 |
| Ha16-1(3,5)56 | 4.08E+04 | 5.93E-04 | 14.5 |
| H16-7.8 | 3.50E+04 | 6.30E-04 | 18 |
| H16-1.68 | 1.06E+05 | 2.44E-04 | 2.3 |
| Ha16-1(3,5)27.1 | 3.69E+04 | 1.77E-04 | 4.8 |
| H16-1(3,5)5 | 6.60E+03 | 4.76E-05 | 7.2 |
| H16-7.200 | 6.50E+04 | 5.90E-04 | 9 |
| Ha16-1(3,5)42 | 4.76E+04 | 2.05E-04 | 4.3 |
| H16-9.65 | 9.37E+04 | 4.64E-04 | 5 |
| H16-1.29.1.1 | 3.20E+04 | 8.30E-04 | 26 |
| H16-3.4 | 9.62E+04 | 9.01E-03 | 94 |
| H16-1.92.1.1 | 3.70E+04 | 3.60E-04 | 9.8 |
| Ha16-1(3,5)19 | 5.00E+04 | 8.40E-05 | 1.68 |

The invention claimed is:

1. A monoclonal antibody which specifically binds to a 161P2F10B protein (SEQ ID NO:4) and comprises the heavy chain variable region sequence of SEQ ID NO:139, from residue 27 to 147 and the light chain variable region sequence of SEQ ID NO:140, from residue 1 to 110.

2. The monoclonal antibody of claim 1, wherein the monoclonal antibody comprising a heavy chain sequence as shown from the 27th to 477th residues in SEQ. ID NO:139, and a light chain sequence comprising a sequence as shown from the 1st to 216th residues in SEQ. ID NO:140.

3. The antibody of claim 1 or 2, wherein the antibody is coupled to a detectable marker, a toxin, a therapeutic agent, or a chemotherapeutic agent.

4. A pharmaceutical composition that comprises the antibody of claim 1 or 2.

5. The pharmaceutical composition of claim 4, wherein the composition is for cancer treatment.

6. The pharmaceutical composition of claim 5, wherein the cancer is renal cancer.

7. An assay for detecting the presence of a 161P2F10B protein in a biological sample, wherein the assay comprises contacting the sample with the antibody of claim 1 or 2, and detecting binding of the antibody to 161P2F10B protein (SEQ ID NO:4) in the sample.

8. A method for detecting a 161P2F10B protein (SEQ ID NO:4) in a biological sample, the method comprising steps of:
   providing the biological sample and a control sample;
   contacting the biological sample and control sample with the antibody of claim 1 or 2 which specifically binds to the 161P2F10B protein; and
   determining the amount of a complex of the substance containing the 161P2F10B protein and the antibody present in the biological sample and the control sample.

* * * * *

SEQUENCE LISTING

<160> NUMBER OF SEQ ID NOS: 177

<210> SEQ ID NO 1
<211> LENGTH: 3858
<212> TYPE: DNA
<213> ORGANISM: Homo sapiens

<400> SEQUENCE: 1

```
ctactttatt ctgataaaac aggtctatgc agctaccagg acaatggaat ctacgttgac      60
tttagcaacg gaacaacctg ttaagaagaa cactcttaag aaatataaaa tagcttgcat     120
tgttcttctt gctttgctgg tgatcatgtc acttggatta ggcctggggc ttggactcag     180
gaaactggaa aagcaaggca gctgcaggaa gaagtgcttt gatgcatcat ttagaggact     240
ggagaactgc cggtgtgatg tggcatgtaa agaccgaggt gattgctgct gggattttga     300
agacacctgt gtggaatcaa ctcgaatatg gatgtgcaat aaatttcgtt gtggagagac     360
cagattagag gccagccttt gctcttgttc agatgactgt ttgcagaaga agattgctg     420 tgctgactat aagagtgttt gccaaggaga acctcatgg ctggaagaaa actgtgacac     480
agcccagcag tctcagtgcc cagaagggtt tgacctgcca ccagttatct tgttttctat     540
ggatggattt agagctgaat attttatacac atgggatact ttaatgccaa atatcaataa     600
actgaaaaca tgtggaattc attcaaaata catgagagct atgtatccta ccaaaacctt     660
cccaaatcat tacaccattg tcacgggctt gtatccagag tcacatggca tcattgacaa     720
taatatgtat gatgtaaatc tcaacaagaa ttttttcactt tcttcaaagg aacaaaataa     780
tccagcctgg tggcatgggc aaccaatgtg gctgacagca atgtatcaag gtttaaaagc     840
cgctacctac ttttggcccg gatcagagt ggctataaat ggctcctttc cttccatata     900
catgccttac aacggaagtg tcccatttga agagaggatt tctacactgt taaaatggct     960
ggacctgccc aaagctgaaa gacccaggtt ttataccatg tattttgaag aacctgattc    1020
ctctggacat gcaggtggac cagtcagtgc cagagtaatt aaagccttac aggtagtaga    1080
tcatgctttt gggatgttga tggaaggcct gaagcagcgg aatttgcaca actgtgtcaa    1140
tatcatcctt ctggctgacc atggaatgga ccagactat tgtaacaaga tggaatacat    1200
gactgattat tttcccagaa taaacttctt ctacatgtac gaaggcctg cccccgcat    1260 ccgagctcat aatatacctc atgactttt tagttttaat tctgaggaaa ttgttagaaa    1320
cctcagttgc cgaaaacctg atcagcatt caagcccat ttgactcctg atttgccaaa    1380
```

```
gcgactgcac tatgccaaga acgtcagaat cgacaaagtt catctctttg tggatcaaca    1440
gtggctggct gttaggagta aatcaaatac aaattgtgga ggaggcaacc atggttataa    1500
caatgagttt aggagcatgg aggctatctt tctggcacat ggacccagtt ttaaagagaa    1560
gactgaagtt gaaccatttg aaaatattga agtctataac ctaatgtgtg atcttctacg    1620
cattcaacca gcaccaaaca atggaaccca tggtagttta aaccatcttc tgaaggtgcc    1680
tttttatgag ccatcccatg cagaggaggt gtcaaagttt tctgtttgtg ctttgctaa    1740 tccattgccc acagagtctc ttgactgttt ctgccctcac ctacaaaata gtactcagct    1800
ggaacaagtg aatcagatgc taaatctcac ccaagaagaa ataacagcaa cagtgaaagt    1860
aaatttgcca tttgggaggc ctagggtact gcagaagaac gtggaccact gtctccttta    1920
ccacagggaa tatgtcagtg gatttggaaa agctatgagg atgcccatgt ggagttcata    1980
cacagtcccc cagttgggag acacatcgcc tctgcctccc actgtcccag actgtctgcg    2040
ggctgatgtc agggttcctc cttctgagag ccaaaaatgt tccttctatt tagcagacaa    2100
gaatatcacc cacggcttcc tctatcctcc tgccagcaat agaacatcag atagccaata    2160
tgatgcttta attactagca atttggtacc tatgtatgaa gaattcagaa aaatgtggga    2220
ctacttccac agtgttcttc ttataaaaca tgccacagaa agaaatggag taaatgtggt    2280
tagtggacca atatttgatt ataattatga tggccatttt gatgctccag atgaaattac    2340
caaacattta gccaacactg atgttcccat cccaacacac tactttgtgg tgctgaccag    2400
ttgtaaaaac aagagccaca caccggaaaa ctgccctggg tggctggatg tcctaccctt    2460
tatcatccct caccgaccta ccaacgtgga gagctgtcct gaaggtaaac cagaagctct    2520
ttgggttgaa gaaagattta cagctcacat tgcccgggtc cgtgatgtag aacttctcac    2580
tgggcttgac ttctatcagg ataaagtgca gcctgtctct gaaattttgc aactaaagac    2640
atatttacca acatttgaaa ccactatttta acttaataat gtctacttaa tatataattt    2700
actgtataaa gtaattttgg caaaatataa gtgattttttt ctggagaatt gtaaaataaa    2760
gttttctatt ttttccttaaa aaaaaaccg gaattccggg cttgggaggc tgaggcagga    2820
gactcgcttg aacccgggag gcagaggttg cagtgagcca agattgcgcc attgcactcc    2880
agagcctggg tgacagagca agactacatc tcaaaaaata aataaataaa ataaagtaa    2940 caataaaaat aaaagaaca gcagagagaa tgagcaagga gaaatgtcac aaactattgc    3000
aaaatactgt tacactgggt tggctctcca agaagatact ggaatctctt cagccatttg    3060
cttttcagaa gtagaaacca gcaaaccacc tctaagcgga gaacatacga ttctttatta    3120
agtagctctg ggaaggaaa gaataaaagt tgatagctcc ctgattggga aaaaatgcac    3180
aattaataaa gaatgaagat gaaagaaagc atgcttatgt tgtaacacaa aaaaaattca    3240
caaacgttgg tggaaggaaa acagtataga aaacattact ttaactaaaa gctggaaaaa    3300
ttttcagttg gatgcgact gacaaaaaga acgggatttc caggcataaa gttggcgtga    3360
gctacagagg gcaccatgtg gctcagtgga agaccccttca agattcaaag ttccatttga    3420
cagagcaaag gcacttcgca aggagaaggg tttaaattat gggtccaaaa gccaagtggt    3480
aaagcgagca atttgcagca taactgcttc tcctagacag ggctgagtgg gcaaaatacg    3540
acagtacaca cagtgactat tagccactgc cagaaacagg ctgaacagcc ctgggagaca    3600
agggaaggca ggtggtggga gttgttcatg gagagaaagg agagttttag aaccagcaca    3660
tccactggag atgctgggcc accagacccc tcccagtcaa taaagtctgg tgcctcattt    3720
gatctcagcc tcatcatgac cctggagaga ccctgatacc atctgccagt ccccgacagc    3780
```

```
ttaggcactc cttgccatca acctgacccc ccgagtggtt ctccaggctc cctgccccac    3840
ccattcaggc cggaattc                                                  3858
```

<210> SEQ ID NO 2
<211> LENGTH: 875
<212> TYPE: PRT
<213> ORGANISM: Homo sapiens

<400> SEQUENCE: 2

```
Met Glu Ser Thr Leu Thr Leu Ala Thr Glu Gln Pro Val Lys Lys Asn
1               5                   10                  15

Thr Leu Lys Lys Tyr Lys Ile Ala Cys Ile Val Leu Leu Ala Leu Leu
            20                  25                  30

Val Ile Met Ser Leu Gly Leu Gly Leu Gly Leu Gly Leu Arg Lys Leu
        35                  40                  45

Glu Lys Gln Gly Ser Cys Arg Lys Lys Cys Phe Asp Ala Ser Phe Arg
    50                  55                  60

Gly Leu Glu Asn Cys Arg Cys Asp Val Ala Cys Lys Asp Arg Gly Asp
65                  70                  75                  80

Cys Cys Trp Asp Phe Glu Asp Thr Cys Val Glu Ser Thr Arg Ile Trp
                85                  90                  95

Met Cys Asn Lys Phe Arg Cys Gly Glu Thr Arg Leu Glu Ala Ser Leu
            100                 105                 110

Cys Ser Cys Ser Asp Asp Cys Leu Gln Lys Lys Asp Cys Cys Ala Asp
        115                 120                 125

Tyr Lys Ser Val Cys Gln Gly Glu Thr Ser Trp Leu Glu Glu Asn Cys
    130                 135                 140

Asp Thr Ala Gln Gln Ser Gln Cys Pro Glu Gly Phe Asp Leu Pro Pro
145                 150                 155                 160

Val Ile Leu Phe Ser Met Asp Gly Phe Arg Ala Glu Tyr Leu Tyr Thr
                165                 170                 175

Trp Asp Thr Leu Met Pro Asn Ile Asn Lys Leu Lys Thr Cys Gly Ile
            180                 185                 190

His Ser Lys Tyr Met Arg Ala Met Tyr Pro Thr Lys Thr Phe Pro Asn
        195                 200                 205

His Tyr Thr Ile Val Thr Gly Leu Tyr Pro Glu Ser His Gly Ile Ile
    210                 215                 220

Asp Asn Asn Met Tyr Asp Val Asn Leu Asn Lys Asn Phe Ser Leu Ser
225                 230                 235                 240

Ser Lys Glu Gln Asn Asn Pro Ala Trp Trp His Gly Gln Pro Met Trp
                245                 250                 255

Leu Thr Ala Met Tyr Gln Gly Leu Lys Ala Ala Thr Tyr Phe Trp Pro
            260                 265                 270

Gly Ser Glu Val Ala Ile Asn Gly Ser Phe Pro Ser Ile Tyr Met Pro
        275                 280                 285

Tyr Asn Gly Ser Val Pro Phe Glu Glu Arg Ile Ser Thr Leu Leu Lys
    290                 295                 300

Trp Leu Asp Leu Pro Lys Ala Glu Arg Pro Arg Phe Tyr Thr Met Tyr
305                 310                 315                 320

Phe Glu Glu Pro Asp Ser Ser Gly His Ala Gly Gly Pro Val Ser Ala
                325                 330                 335

Arg Val Ile Lys Ala Leu Gln Val Val Asp His Ala Phe Gly Met Leu
            340                 345                 350

Met Glu Gly Leu Lys Gln Arg Asn Leu His Asn Cys Val Asn Ile Ile
        355                 360                 365
```

```
Leu Leu Ala Asp His Gly Met Asp Gln Thr Tyr Cys Asn Lys Met Glu
    370                 375                 380

Tyr Met Thr Asp Tyr Phe Pro Arg Ile Asn Phe Phe Tyr Met Tyr Glu
385                 390                 395                 400

Gly Pro Ala Pro Arg Ile Arg Ala His Asn Ile Pro His Asp Phe Phe
                405                 410                 415

Ser Phe Asn Ser Glu Glu Ile Val Arg Asn Leu Ser Cys Arg Lys Pro
                420                 425                 430

Asp Gln His Phe Lys Pro Tyr Leu Thr Pro Asp Leu Pro Lys Arg Leu
            435                 440                 445

His Tyr Ala Lys Asn Val Arg Ile Asp Lys Val His Leu Phe Val Asp
        450                 455                 460

Gln Gln Trp Leu Ala Val Arg Ser Lys Ser Asn Thr Asn Cys Gly Gly
465                 470                 475                 480

Gly Asn His Gly Tyr Asn Asn Glu Phe Arg Ser Met Glu Ala Ile Phe
                485                 490                 495

Leu Ala His Gly Pro Ser Phe Lys Glu Lys Thr Glu Val Glu Pro Phe
                500                 505                 510

Glu Asn Ile Glu Val Tyr Asn Leu Met Cys Asp Leu Leu Arg Ile Gln
            515                 520                 525

Pro Ala Pro Asn Asn Gly Thr His Gly Ser Leu Asn His Leu Leu Lys
530                 535                 540

Val Pro Phe Tyr Glu Pro Ser His Ala Glu Glu Val Ser Lys Phe Ser
545                 550                 555                 560

Val Cys Gly Phe Ala Asn Pro Leu Pro Thr Glu Ser Leu Asp Cys Phe
                565                 570                 575

Cys Pro His Leu Gln Asn Ser Thr Gln Leu Glu Gln Val Asn Gln Met
                580                 585                 590

Leu Asn Leu Thr Gln Glu Glu Ile Thr Ala Thr Val Lys Val Asn Leu
            595                 600                 605

Pro Phe Gly Arg Pro Arg Val Leu Gln Lys Asn Val Asp His Cys Leu
    610                 615                 620

Leu Tyr His Arg Glu Tyr Val Ser Gly Phe Gly Lys Ala Met Arg Met
625                 630                 635                 640

Pro Met Trp Ser Ser Tyr Thr Val Pro Gln Leu Gly Asp Thr Ser Pro
                645                 650                 655

Leu Pro Pro Thr Val Pro Asp Cys Leu Arg Ala Asp Val Arg Val Pro
                660                 665                 670

Pro Ser Glu Ser Gln Lys Cys Ser Phe Tyr Leu Ala Asp Lys Asn Ile
            675                 680                 685

Thr His Gly Phe Leu Tyr Pro Pro Ala Ser Asn Arg Thr Ser Asp Ser
        690                 695                 700

Gln Tyr Asp Ala Leu Ile Thr Ser Asn Leu Val Pro Met Tyr Glu Glu
705                 710                 715                 720

Phe Arg Lys Met Trp Asp Tyr Phe His Ser Val Leu Leu Ile Lys His
                725                 730                 735

Ala Thr Glu Arg Asn Gly Val Asn Val Val Ser Gly Pro Ile Phe Asp
                740                 745                 750

Tyr Asn Tyr Asp Gly His Phe Asp Ala Pro Asp Glu Ile Thr Lys His
            755                 760                 765

Leu Ala Asn Thr Asp Val Pro Ile Pro Thr His Tyr Phe Val Val Leu
    770                 775                 780

Thr Ser Cys Lys Asn Lys Ser His Thr Pro Glu Asn Cys Pro Gly Trp
```

```
                785               790               795               800
Leu Asp Val Leu Pro Phe Ile Ile Pro His Arg Pro Thr Asn Val Glu
                    805               810               815
Ser Cys Pro Glu Gly Lys Pro Glu Ala Leu Trp Val Glu Glu Arg Phe
                    820               825               830
Thr Ala His Ile Ala Arg Val Arg Asp Val Glu Leu Leu Thr Gly Leu
                    835               840               845
Asp Phe Tyr Gln Asp Lys Val Gln Pro Val Ser Glu Ile Leu Gln Leu
                    850               855               860
Lys Thr Tyr Leu Pro Thr Phe Glu Thr Thr Ile
865                 870               875

<210> SEQ ID NO 3
<211> LENGTH: 3858
<212> TYPE: DNA
<213> ORGANISM: Homo sapiens

<400> SEQUENCE: 3
ctactttatt ctgataaaac aggtctatgc agctaccagg acaatggaat ctacgttgac      60
tttagcaacg gaacaacctg ttaagaagaa cactcttaag aaatataaaa tagcttgcat     120
tgttcttctt gctttgctgg tgatcatgtc acttggatta ggcctggggc ttggactcag     180
gaaactggaa aagcaaggca gctgcaggaa gaagtgcttt gatgcatcat ttagaggact     240
ggagaactgc cggtgtgatg tggcatgtaa agaccgaggt gattgctgct gggattttga     300
agacacctgt gtggaatcaa ctcgaatatg gatgtgcaat aaatttcgtt gtggagagac     360
cagattagag gccagccttt gctcttgttc agatgactgt ttgcagagga agattgctg     420
tgctgactat aagagtgttt gccaaggaga aacctcatgg ctggaagaaa actgtgacac     480
agcccagcag tctcagtgcc agaagggtt tgacctgcca ccagttatct tgttttctat     540
ggatggattt agagctgaat atttatacac atgggatact ttaatgccaa atatcaataa     600
actgaaaaca tgtggaattc attcaaaata catgagagct atgtatccta ccaaaacctt     660
cccaaatcat tacaccattg tcacgggctt gtatccagag tcatgcca tcattgacaa     720
taatatgtat gatgtaaatc tcaacaagaa ttttcactt tcttcaaagg aacaaaataa     780
tccagcctgg tggcatgggc aaccaatgtg gctgacagca atgtatcaag gtttaaaagc     840
cgctacctac ttttggcccg gatcagaagt ggctataaat ggctccttc cttccatata     900
catgccttac aacggaagtg tcccatttga agagaggatt tctacactgt aaaatggct     960
ggacctgccc aaagctgaaa gacccaggtt ttataccatg tatttgaag aacctgattc    1020
ctctggacat gcaggtggac cagtcagtgc cagagtaatt aaagccttac aggtagtaga    1080
tcatgctttt gggatgttga tggaaggcct gaagcagcgg aatttgcaca actgtgtcaa    1140
tatcatcctt ctggctgacc atggaatgga ccagacttat gtaacaaga tggaatacat    1200
gactgattat tttcccagaa taaacttctt ctacatgtac gaagggcctg cccccgcat    1260
ccgagctcat aatatacctc atgctttt tagttttaat tctgaggaaa ttgttagaaa    1320
cctcagttgc cgaaaacctg atcagcattt caagccctat ttgactcctg atttgccaaa    1380
gcgactgcac tatgccaaga acgtcagaat cgacaaagtt catctctttg tggatcaaca    1440
gtggctggct gttaggagta atcaaatac aaattgtgga ggaggcaacc atggttataa    1500
caatgagttt aggagcatgg aggctatctt tctggcacat ggacccagtt ttaaagagaa    1560
gactgaagtt gaaccatttg aaaatattga agtctataac ctaatgtgtg atcttctacg    1620
cattcaacca gcaccaaaca atggaaccca tggtagttta aaccatcttc tgaaggtgcc    1680
```

```
ttttatgag ccatcccatg cagaggaggt gtcaaagttt tctgtttgtg gctttgctaa    1740
tccattgccc acagagtctc ttgactgttt ctgccctcac ctacaaaata gtactcagct    1800
ggaacaagtg aatcagatgc taaatctcac ccaagaagaa ataacagcaa cagtgaaagt    1860
aaatttgcca tttgggaggc ctagggtact gcagaagaac gtggaccact gtctccttta    1920
ccacagggaa tatgtcagtg gatttggaaa agctatgagg atgcccatgt ggagttcata    1980
cacagtcccc cagttgggag acacatcgcc tctgcctccc actgtcccag actgtctgcg    2040
ggctgatgtc agggttcctc cttctgagag ccaaaaatgt tccttctatt tagcagacaa    2100
gaatatcacc cacggcttcc tctatcctcc tgccagcaat agaacatcag atagccaata    2160
tgatgcttta attactagca atttggtacc tatgtatgaa gaattcagaa aaatgtggga    2220
ctacttccac agtgttcttc ttataaaaca tgccacagaa agaaatggag taaatgtggt    2280
tagtggacca atatttgatt ataattatga tggccatttt gatgctccag atgaaattac    2340
caaacattta gccaacactg atgttcccat cccaacacac tactttgtgg tgctgaccag    2400
ttgtaaaaac aagagccaca caccggaaaa ctgccctggg tggctggatg tcctacccett    2460 tatcatccct caccgaccta ccaacgtgga gagctgtcct gaaggtaaac cagaagctct    2520
ttgggttgaa gaaagattta cagctcacat tgcccgggtc cgtgatgtag aacttctcac    2580
tgggcttgac ttctatcagg ataaagtgca gcctgtctct gaaattttgc aactaaagac    2640
atatttacca acatttgaaa ccactattta acttaataat gtctacttaa tatataattt    2700
actgtataaa gtaattttgg caaaatataa gtgattttt ctggagaatt gtaaaataaa    2760
gttttctatt tttccttaaa aaaaaaccg gaattccggg cttgggaggc tgaggcagga    2820
gactcgcttg aacccgggag gcagaggttg cagtgagcca agattgcgcc attgcactcc    2880
agagcctggg tgacagagca agactacatc tcaaaaaata aataaataaa ataaagtaa    2940 caataaaaat aaaagaaca gcagagagaa tgagcaagga gaaatgtcac aaactattgc    3000
aaaatactgt tacactgggt tggctctcca agaagatact ggaatctctt cagccatttg    3060
cttttcagaa gtagaaacca gcaaaccacc tctaagcgga gaacatacga ttctttatta    3120
agtagctctg gggaaggaaa gaataaaagt tgatagctcc ctgattggga aaaaatgcac    3180
aattaataaa gaatgaagat gaaagaaagc atgcttatgt tgtaacacaa aaaaaattca    3240
caaacgttgg tggaaggaaa acagtataga aaacattact ttaactaaaa gctggaaaaa    3300
ttttcagttg ggatgcgact gacaaaaaga acgggatttc caggcataaa gttggcgtga    3360
gctacagagg gcaccatgtg gctcagtgga agacccttca agattcaaag ttccatttga    3420
cagagcaaag gcacttcgca aggagaaggg tttaaattat gggtccaaaa gccaagtggt    3480
aaagcgagca atttgcagca taactgcttc tcctagacag ggctgagtgg gcaaaatacg    3540
acagtacaca cagtgactat tagccactgc cagaaacagg ctgaacagcc ctgggagaca    3600
agggaaggca ggtggtggga gttgttcatg gagagaaagg agagttttag aaccagcaca    3660
tccactggag atgctgggcc accagacccc tcccagtcaa taaagtctgg tgcctcattt    3720
gatctcagcc tcatcatgac cctggagaga ccctgatacc atctgccagt ccccgacagc    3780
ttaggcactc cttgccatca acctgacccc ccgagtggtt ctccaggctc cctgccccac    3840
ccattcaggc cggaattc                                                 3858

<210> SEQ ID NO 4
<211> LENGTH: 875
<212> TYPE: PRT
<213> ORGANISM: Homo sapiens
```

```
<400> SEQUENCE: 4

Met Glu Ser Thr Leu Thr Leu Ala Thr Glu Gln Pro Val Lys Lys Asn
1               5                   10                  15

Thr Leu Lys Lys Tyr Lys Ile Ala Cys Ile Val Leu Leu Ala Leu Leu
            20                  25                  30

Val Ile Met Ser Leu Gly Leu Gly Leu Gly Leu Arg Lys Leu
        35                  40                  45

Glu Lys Gln Gly Ser Cys Arg Lys Cys Phe Asp Ala Ser Phe Arg
50                  55                  60

Gly Leu Glu Asn Cys Arg Cys Asp Val Ala Cys Lys Asp Arg Gly Asp
65                  70                  75                  80

Cys Cys Trp Asp Phe Glu Asp Thr Cys Val Glu Ser Thr Arg Ile Trp
                85                  90                  95

Met Cys Asn Lys Phe Arg Cys Gly Glu Thr Arg Leu Glu Ala Ser Leu
                100                 105                 110

Cys Ser Cys Ser Asp Asp Cys Leu Gln Arg Lys Asp Cys Cys Ala Asp
            115                 120                 125

Tyr Lys Ser Val Cys Gln Gly Glu Thr Ser Trp Leu Glu Glu Asn Cys
130                 135                 140

Asp Thr Ala Gln Gln Ser Gln Cys Pro Glu Gly Phe Asp Leu Pro Pro
145                 150                 155                 160

Val Ile Leu Phe Ser Met Asp Gly Phe Arg Ala Glu Tyr Leu Tyr Thr
                165                 170                 175

Trp Asp Thr Leu Met Pro Asn Ile Asn Lys Leu Lys Thr Cys Gly Ile
                180                 185                 190

His Ser Lys Tyr Met Arg Ala Met Tyr Pro Thr Lys Thr Phe Pro Asn
            195                 200                 205

His Tyr Thr Ile Val Thr Gly Leu Tyr Pro Glu Ser His Gly Ile Ile
210                 215                 220

Asp Asn Asn Met Tyr Asp Val Asn Leu Asn Lys Asn Phe Ser Leu Ser
225                 230                 235                 240

Ser Lys Glu Gln Asn Asn Pro Ala Trp Trp His Gly Gln Pro Met Trp
                245                 250                 255

Leu Thr Ala Met Tyr Gln Gly Leu Lys Ala Ala Thr Tyr Phe Trp Pro
                260                 265                 270

Gly Ser Glu Val Ala Ile Asn Gly Ser Phe Pro Ser Ile Tyr Met Pro
            275                 280                 285

Tyr Asn Gly Ser Val Pro Phe Glu Glu Arg Ile Ser Thr Leu Leu Lys
290                 295                 300

Trp Leu Asp Leu Pro Lys Ala Glu Arg Pro Arg Phe Tyr Thr Met Tyr
305                 310                 315                 320

Phe Glu Glu Pro Asp Ser Ser Gly His Ala Gly Gly Pro Val Ser Ala
                325                 330                 335

Arg Val Ile Lys Ala Leu Gln Val Val Asp His Ala Phe Gly Met Leu
                340                 345                 350

Met Glu Gly Leu Lys Gln Arg Asn Leu His Asn Cys Val Asn Ile Ile
            355                 360                 365

Leu Leu Ala Asp His Gly Met Asp Gln Thr Tyr Cys Asn Lys Met Glu
370                 375                 380

Tyr Met Thr Asp Tyr Phe Pro Arg Ile Asn Phe Phe Met Tyr Glu
385                 390                 395                 400

Gly Pro Ala Pro Arg Ile Arg Ala His Asn Ile Pro His Asp Phe Phe
                405                 410                 415
```

```
Ser Phe Asn Ser Glu Glu Ile Val Arg Asn Leu Ser Cys Arg Lys Pro
            420                 425                 430

Asp Gln His Phe Lys Pro Tyr Leu Thr Pro Asp Leu Pro Lys Arg Leu
            435                 440                 445

His Tyr Ala Lys Asn Val Arg Ile Asp Lys Val His Leu Phe Val Asp
        450                 455                 460

Gln Gln Trp Leu Ala Val Arg Ser Lys Ser Asn Thr Asn Cys Gly Gly
465                 470                 475                 480

Gly Asn His Gly Tyr Asn Asn Glu Phe Arg Ser Met Glu Ala Ile Phe
                485                 490                 495

Leu Ala His Gly Pro Ser Phe Lys Glu Lys Thr Glu Val Glu Pro Phe
            500                 505                 510

Glu Asn Ile Glu Val Tyr Asn Leu Met Cys Asp Leu Leu Arg Ile Gln
            515                 520                 525

Pro Ala Pro Asn Asn Gly Thr His Gly Ser Leu Asn His Leu Leu Lys
        530                 535                 540

Val Pro Phe Tyr Glu Pro Ser His Ala Glu Glu Val Ser Lys Phe Ser
545                 550                 555                 560

Val Cys Gly Phe Ala Asn Pro Leu Pro Thr Glu Ser Leu Asp Cys Phe
                565                 570                 575

Cys Pro His Leu Gln Asn Ser Thr Gln Leu Glu Gln Val Asn Gln Met
            580                 585                 590

Leu Asn Leu Thr Gln Glu Glu Ile Thr Ala Thr Val Lys Val Asn Leu
            595                 600                 605

Pro Phe Gly Arg Pro Arg Val Leu Gln Lys Asn Val Asp His Cys Leu
        610                 615                 620

Leu Tyr His Arg Glu Tyr Val Ser Gly Phe Gly Lys Ala Met Arg Met
625                 630                 635                 640

Pro Met Trp Ser Ser Tyr Thr Val Pro Gln Leu Gly Asp Thr Ser Pro
                645                 650                 655

Leu Pro Pro Thr Val Pro Asp Cys Leu Arg Ala Asp Val Arg Val Pro
            660                 665                 670

Pro Ser Glu Ser Gln Lys Cys Ser Phe Tyr Leu Ala Asp Lys Asn Ile
        675                 680                 685

Thr His Gly Phe Leu Tyr Pro Pro Ala Ser Asn Arg Thr Ser Asp Ser
        690                 695                 700

Gln Tyr Asp Ala Leu Ile Thr Ser Asn Leu Val Pro Met Tyr Glu Glu
705                 710                 715                 720

Phe Arg Lys Met Trp Asp Tyr Phe His Ser Val Leu Leu Ile Lys His
                725                 730                 735

Ala Thr Glu Arg Asn Gly Val Asn Val Ser Gly Pro Ile Phe Asp
            740                 745                 750

Tyr Asn Tyr Asp Gly His Phe Asp Ala Pro Asp Glu Ile Thr Lys His
        755                 760                 765

Leu Ala Asn Thr Asp Val Pro Ile Pro Thr His Tyr Phe Val Val Leu
        770                 775                 780

Thr Ser Cys Lys Asn Lys Ser His Thr Pro Glu Asn Cys Pro Gly Trp
785                 790                 795                 800

Leu Asp Val Leu Pro Phe Ile Ile Pro His Arg Pro Thr Asn Val Glu
                805                 810                 815

Ser Cys Pro Glu Gly Lys Pro Glu Ala Leu Trp Val Glu Glu Arg Phe
            820                 825                 830

Thr Ala His Ile Ala Arg Val Arg Asp Val Glu Leu Leu Thr Gly Leu
```

```
                          835                 840                 845
Asp Phe Tyr Gln Asp Lys Val Gln Pro Val Ser Glu Ile Leu Gln Leu
            850                 855                 860

Lys Thr Tyr Leu Pro Thr Phe Glu Thr Thr Ile
865                 870                 875

<210> SEQ ID NO 5
<211> LENGTH: 3858
<212> TYPE: DNA
<213> ORGANISM: Homo sapiens

<400> SEQUENCE: 5
ctactttatt ctgataaaac aggtctatgc agctaccagg acaatggaat ctacgttgac    60
tttagcaacg gaacaacctg ttaagaagaa cactcttaag aaatataaaa tagcttgcat   120
tgttcttctt gctttgctgg tgatcatgtc acttggatta ggcctggggc ttggactcag   180
gaaactggaa aagcaaggca gctgcaggaa gaagtgcttt gatgcatcat ttagaggact   240
ggagaactgc cggtgtgatg tggcatgtaa agaccgaggt gattgctgct gggattttga   300
agacacctgt gtggaatcaa ctcgaatatg gatgtgcaat aaatttcgtt gtggagagac   360
cagattagag gccagccttt gctcttgttc agatgactgt ttgcagaaga aagattgctg   420
tgctgactat aagagtgttt gccaaggaga aacctcatgg ctggaagaaa actgtgacac   480
agcccagcag tctcagtgcc agaagggtt tgacctgcca ccagttatct tgttttctat   540
ggatggattt agagctgaat atttatacac atgggatact ttaatgccaa atatcaataa   600
actgaaaaca tgtggaattc attcaaaata catgagagct atgtatccta ccaaaacctt   660
cccaaatcat tacaccattg tcacgggctt gtatccagag tcacatgcca tcattgacaa   720
taatatgtat gatgtaaatc tcaacaagaa ttttttcactt tcttcaaagg aacaaaataa   780
tccagcctgg tggcatgggc aaccaatgtg gctgacagca atgtatcaag gtttaaaagc   840
cgctacctac ttttggcccg gatcagaagt ggctataaat ggctcctttc cttccatata   900
catgccttac aacggaagtg tcccatttga agagaggatt tctacactgt taaaatggct   960
ggacctgccc aaagctgaaa gacccaggtt ttataccatg tattttgaag aacctgattc  1020
ctctggacat gcaggtggac cagtcagtgc cagagtaatt aaagccttac aggtagtaga  1080
tcatgctttt gggatgttga tggaaggcct gaagcagcgg aatttgcaca actgtgtcaa  1140
tatcatcctt ctggctgacc atggaatgga ccagactat tgtaacaaga tggaatacat  1200
gactgattat tttcccagaa taaacttctt ctacatgtac gaagggcctg ccccccgcat  1260
ccgagctcat aatatacctc atgacttttt tagttttaat tctgaggaaa ttgttagaaa  1320
cctcagttgc cgaaaacctg atcagcattt caagccctat ttgactcctg atttgccaaa  1380
gcgactgcac tatgccaaga acgtcagaat cgacaaagtt catctctttg tggatcaaca  1440
gtggctggct gttaggagta aatcaaatac aaattgtgga ggaggcaacc atggttataa  1500
caatgagttt aggagcatgg aggctatctt tctggcacat ggacccagtt ttaaagagaa  1560
gactgaagtt gaaccatttg aaaatattga agtctataac ctaatgtgtg atcttctacg  1620
cattcaacca gcaccaaaca atggaaccca tggtagttta aaccatcttc tgaaggtgcc  1680 ttttatgag ccatcccatg cagaggaggt gtcaaagttt tctgtttgtg ctttgctaa   1740 tccattgccc acagagtctc ttgactgttt ctgccctcac ctacaaaata gtactcagct  1800
ggaacaagtg aatcagatgc taaatctcac ccaagaagaa ataacagcaa cagtgaaagt  1860
aaatttgcca tttgggaggc ctagggtact gcagaagaac gtggaccact gtctccttta  1920
```

```
ccacagggaa tatgtcagtg gatttggaaa agctatgagg atgcccatgt ggagttcata    1980
cacagtcccc cagttgggag acacatcgcc tctgcctccc actgtcccag actgtctgcg    2040
ggctgatgtc agggttcctc cttctgagag ccaaaaatgt tccttctatt tagcagacaa    2100
gaatatcacc cacggcttcc tctatcctcc tgccagcaat agaacatcag atagccaata    2160
tgatgcttta attactagca atttggtacc tatgtatgaa gaattcagaa aaatgtggga    2220
ctacttccac agtgttcttc ttataaaaca tgccacagaa agaaatggag taaatgtggt    2280
tagtggacca atatttgatt ataattatga tggccatttt gatgctccag atgaaattac    2340
caaacattta gccaacactg atgttcccat cccaacacac tactttgtgg tgctgaccag    2400
ttgtaaaaac aagagccaca caccggaaaa ctgccctggg tggctggatg tcctacccct    2460
tatcatccct caccgaccta ccaacgtgga gagctgtcct ggaggtaaac cagaagctct    2520
ttggggttgaa gaaagattta cagctcacat tgcccgggtc cgtgatgtag aacttctcac    2580
tgggcttgac ttctatcagg ataaagtgca gcctgtctct gaaattttgc aactaaagac    2640
atatttacca acatttgaaa ccactatttta acttaataat gtctacttaa tatataattt    2700
actgtataaa gtaattttgg caaaatataa gtgattttt ctggagaatt gtaaaataaa    2760
gttttctatt tttccttaaa aaaaaaccg gaattccggg cttgggaggc tgaggcagga    2820
gactcgcttg aacccgggag gcagaggttg cagtgagcca agattgcgcc attgcactcc    2880
agagcctggg tgacagagca agactacatc tcaaaaaata aataaataaa ataaagtaa    2940
caataaaaat aaaagaaca gcagagagaa tgagcaagga gaaatgtcac aaactattgc    3000
aaaatactgt tacactgggt tggctctcca agaagatact ggaatctctt cagccatttg    3060
cttttcagaa gtagaaacca gcaaaccacc tctaagcgga gaacatacga ttctttatta    3120
agtagctctg gggaaggaaa gaataaaagt tgatagctcc ctgattggga aaaaatgcac    3180
aattaataaa gaatgaagat gaagaaagc atgcttatgt tgtaacacaa aaaaaattca    3240
caaacgttgg tggaaggaaa acagtataga aaacattact ttaactaaaa gctggaaaaa    3300
ttttcagttg ggatgcgact gacaaaaaga acgggatttc caggcataaa gttggcgtga    3360
gctacagagg gcaccatgtg gctcagtgga agacccttca agattcaaag ttccatttga    3420
cagagcaaag gcacttcgca aggagaaggg tttaaattat gggtccaaaa gccaagtggt    3480
aaagcgagca atttgcagca taactgcttc tcctagacag ggctgagtgg gcaaaatacg    3540
acagtacaca cagtgactat tagccactgc cagaaacagg ctgaacagcc ctgggagaca    3600
agggaaggca ggtggtggga gttgttcatg gagagaaagg agagttttag aaccagcaca    3660
tccactggag atgctgggcc accagacccc tcccagtcaa taaagtctgg tgcctcattt    3720
gatctcagcc tcatcatgac cctggagaga ccctgatacc atctgccagt ccccgacagc    3780
ttaggcactc cttgccatca acctgacccc ccgagtggtt ctccaggctc cctgccccac    3840
ccattcaggc cggaattc                                                 3858
```

<210> SEQ ID NO 6
<211> LENGTH: 875
<212> TYPE: PRT
<213> ORGANISM: Homo sapiens

<400> SEQUENCE: 6

Met Glu Ser Thr Leu Thr Leu Ala Thr Glu Gln Pro Val Lys Lys Asn
1               5                   10                  15

Thr Leu Lys Lys Tyr Lys Ile Ala Cys Ile Val Leu Leu Ala Leu Leu
            20                  25                  30

```
Val Ile Met Ser Leu Gly Leu Gly Leu Gly Leu Arg Lys Leu
        35              40              45

Glu Lys Gln Gly Ser Cys Arg Lys Cys Phe Asp Ala Ser Phe Arg
 50              55              60

Gly Leu Glu Asn Cys Arg Cys Asp Val Ala Cys Lys Asp Arg Gly Asp
 65              70              75              80

Cys Cys Trp Asp Phe Glu Asp Thr Cys Val Glu Ser Thr Arg Ile Trp
             85              90              95

Met Cys Asn Lys Phe Arg Cys Gly Glu Thr Arg Leu Glu Ala Ser Leu
            100             105             110

Cys Ser Cys Ser Asp Asp Cys Leu Gln Lys Lys Asp Cys Cys Ala Asp
        115             120             125

Tyr Lys Ser Val Cys Gln Gly Glu Thr Ser Trp Leu Glu Glu Asn Cys
    130             135             140

Asp Thr Ala Gln Gln Ser Gln Cys Pro Glu Gly Phe Asp Leu Pro Pro
145             150             155             160

Val Ile Leu Phe Ser Met Asp Gly Phe Arg Ala Glu Tyr Leu Tyr Thr
                165             170             175

Trp Asp Thr Leu Met Pro Asn Ile Asn Lys Leu Lys Thr Cys Gly Ile
            180             185             190

His Ser Lys Tyr Met Arg Ala Met Tyr Pro Thr Lys Thr Phe Pro Asn
    195             200             205

His Tyr Thr Ile Val Thr Gly Leu Tyr Pro Glu Ser His Gly Ile Ile
210             215             220

Asp Asn Asn Met Tyr Asp Val Asn Leu Asn Lys Asn Phe Ser Leu Ser
225             230             235             240

Ser Lys Glu Gln Asn Asn Pro Ala Trp Trp His Gly Gln Pro Met Trp
                245             250             255

Leu Thr Ala Met Tyr Gln Gly Leu Lys Ala Ala Thr Tyr Phe Trp Pro
            260             265             270

Gly Ser Glu Val Ala Ile Asn Gly Ser Phe Pro Ser Ile Tyr Met Pro
    275             280             285

Tyr Asn Gly Ser Val Pro Phe Glu Glu Arg Ile Ser Thr Leu Leu Lys
290             295             300

Trp Leu Asp Leu Pro Lys Ala Glu Arg Pro Arg Phe Tyr Thr Met Tyr
305             310             315             320

Phe Glu Glu Pro Asp Ser Ser Gly His Ala Gly Gly Pro Val Ser Ala
                325             330             335

Arg Val Ile Lys Ala Leu Gln Val Val Asp His Ala Phe Gly Met Leu
            340             345             350

Met Glu Gly Leu Lys Gln Arg Asn Leu His Asn Cys Val Asn Ile Ile
    355             360             365

Leu Leu Ala Asp His Gly Met Asp Gln Thr Tyr Cys Asn Lys Met Glu
370             375             380

Tyr Met Thr Asp Tyr Phe Pro Arg Ile Asn Phe Tyr Met Tyr Glu
385             390             395             400

Gly Pro Ala Pro Arg Ile Arg Ala His Asn Ile Pro His Asp Phe Phe
                405             410             415

Ser Phe Asn Ser Glu Glu Ile Val Arg Asn Leu Ser Cys Arg Lys Pro
            420             425             430

Asp Gln His Phe Lys Pro Tyr Leu Thr Pro Asp Leu Pro Lys Arg Leu
    435             440             445

His Tyr Ala Lys Asn Val Arg Ile Asp Lys Val His Leu Phe Val Asp
450             455             460
```

-continued

```
Gln Gln Trp Leu Ala Val Arg Ser Lys Ser Asn Thr Asn Cys Gly Gly
465                 470                 475                 480

Gly Asn His Gly Tyr Asn Asn Glu Phe Arg Ser Met Glu Ala Ile Phe
                485                 490                 495

Leu Ala His Gly Pro Ser Phe Lys Glu Lys Thr Glu Val Glu Pro Phe
            500                 505                 510

Glu Asn Ile Glu Val Tyr Asn Leu Met Cys Asp Leu Leu Arg Ile Gln
        515                 520                 525

Pro Ala Pro Asn Asn Gly Thr His Gly Ser Leu Asn His Leu Leu Lys
    530                 535                 540

Val Pro Phe Tyr Glu Pro Ser His Ala Glu Glu Val Ser Lys Phe Ser
545                 550                 555                 560

Val Cys Gly Phe Ala Asn Pro Leu Pro Thr Glu Ser Leu Asp Cys Phe
                565                 570                 575

Cys Pro His Leu Gln Asn Ser Thr Gln Leu Glu Gln Val Asn Gln Met
            580                 585                 590

Leu Asn Leu Thr Gln Glu Glu Ile Thr Ala Thr Val Lys Val Asn Leu
        595                 600                 605

Pro Phe Gly Arg Pro Arg Val Leu Gln Lys Asn Val Asp His Cys Leu
    610                 615                 620

Leu Tyr His Arg Glu Tyr Val Ser Gly Phe Gly Lys Ala Met Arg Met
625                 630                 635                 640

Pro Met Trp Ser Ser Tyr Thr Val Pro Gln Leu Gly Asp Thr Ser Pro
                645                 650                 655

Leu Pro Pro Thr Val Pro Asp Cys Leu Arg Ala Asp Val Arg Val Pro
            660                 665                 670

Pro Ser Glu Ser Gln Lys Cys Ser Phe Tyr Leu Ala Asp Lys Asn Ile
        675                 680                 685

Thr His Gly Phe Leu Tyr Pro Pro Ala Ser Asn Arg Thr Ser Asp Ser
    690                 695                 700

Gln Tyr Asp Ala Leu Ile Thr Ser Asn Leu Val Pro Met Tyr Glu Glu
705                 710                 715                 720

Phe Arg Lys Met Trp Asp Tyr Phe His Ser Val Leu Ile Lys His
                725                 730                 735

Ala Thr Glu Arg Asn Gly Val Asn Val Val Ser Gly Pro Ile Phe Asp
            740                 745                 750

Tyr Asn Tyr Asp Gly His Phe Asp Ala Pro Asp Glu Ile Thr Lys His
        755                 760                 765

Leu Ala Asn Thr Asp Val Pro Ile Pro Thr His Tyr Phe Val Val Leu
    770                 775                 780

Thr Ser Cys Lys Asn Lys Ser His Thr Pro Glu Asn Cys Pro Gly Trp
785                 790                 795                 800

Leu Asp Val Leu Pro Phe Ile Ile Pro His Arg Pro Thr Asn Val Glu
                805                 810                 815

Ser Cys Pro Gly Gly Lys Pro Glu Ala Leu Trp Val Glu Glu Arg Phe
            820                 825                 830

Thr Ala His Ile Ala Arg Val Arg Asp Val Glu Leu Leu Thr Gly Leu
        835                 840                 845

Asp Phe Tyr Gln Asp Lys Val Gln Pro Val Ser Glu Ile Leu Gln Leu
    850                 855                 860

Lys Thr Tyr Leu Pro Thr Phe Glu Thr Ile
865                 870                 875
```

<210> SEQ ID NO 7
<211> LENGTH: 3858
<212> TYPE: DNA
<213> ORGANISM: Homo sapiens

<400> SEQUENCE: 7

| | | | | | | |
|---|---|---|---|---|---|---|
| ctactttatt | ctgataaaac | aggtctatgc | agctaccagg | acaatggaat | ctacgttgac | 60 |
| tttagcaacg | gaacaacctg | ttaagaagaa | cactcttaag | aaatataaaa | tagcttgcat | 120 |
| tgttcttctt | gctttgctgg | tgatcatgtc | acttggatta | ggcctggggc | ttggactcag | 180 |
| gaaactggaa | aagcaaggca | gctgcaggaa | gaagtgcttt | gatgcatcat | ttagaggact | 240 |
| ggagaactgc | cggtgtgatg | tggcatgtaa | agaccgaggt | gattgctgct | gggattttga | 300 |
| agacacctgt | gtggaatcaa | ctcgaatatg | gatgtgcaat | aaatttcgtt | gtggagagac | 360 |
| cagattagag | gccagccttt | gctcttgttc | agatgactgt | ttgcagaaga | aagattgctg | 420 |
| tgctgactat | aagagtgttt | gccaaggaga | aacctcatgg | ctggaagaaa | actgtgacac | 480 |
| agcccagcag | tctcagtgcc | cagaagggtt | tgacctgcca | ccagttatct | tgttttctat | 540 |
| ggatggattt | agagctgaat | atttatacac | atgggatact | taatgccaa | atatcaataa | 600 |
| actgaaaaca | tgtggaattc | attcaaaata | catgagagct | atgtatccta | ccaaaacctt | 660 |
| cccaaatcat | tacaccattg | tcacgggctt | gtatccagag | tcacatggca | tcattgacaa | 720 |
| taatatgtat | gatgtaaatc | tcaacaagaa | tttttcactt | tcttcaaagg | aacaaaataa | 780 |
| tccagcctgg | tggcatgggc | aaccaatgtg | gctgacagca | atgtatcaag | gtttaaaagc | 840 |
| cgctaccttac | ttttggcccg | gatcagaagt | ggctataaat | ggctcctttc | cttccatata | 900 |
| catgccttac | aacggaagtg | tcccatttga | agagaggatt | tctacactgt | taaaatggct | 960 |
| ggacctgccc | aaagctgaaa | gacccaggtt | ttataccatg | tattttgaag | aacctgattc | 1020 |
| ctctggacat | gcaggtggac | cagtcagtgc | cagagtaatt | aaagccttac | aggtagtaga | 1080 |
| tcatgctttt | gggatgttga | tggaaggcct | gaagcagcgg | aatttgcaca | actgtgtcaa | 1140 |
| tatcatcctt | ctggctgacc | atggaatgga | ccagacttat | tgtaacaaga | tggaatacat | 1200 |
| gactgattat | tttcccagaa | taaacttctt | ctacatgtac | gaagggcctg | ccccccgcat | 1260 |
| ccgagctcat | aatatacctc | atgactttt | tagttttaat | tctgaggaaa | ttgttagaaa | 1320 |
| cctcagttgc | cgaaaacctg | atcagcattt | caagccctat | ttgactcctg | atttgccaaa | 1380 |
| gcgactgcac | tatgccaaga | acgtcagaat | cgacaaagtt | catctctttg | tggatcaaca | 1440 |
| gtggctggct | gttaggagta | aatcaaatac | aaattgtgga | ggaggcaacc | atggttataa | 1500 |
| caatgagttt | aggagcatgg | aggctatctt | tctggcacat | ggacccagtt | ttaaagagaa | 1560 |
| gactgaagtt | gaaccatttg | aaaatattga | agtctataac | ctaatgtgtg | atcttctacg | 1620 |
| cattcaacca | gcaccaaaca | atggaaccca | tggtagttta | aaccatcttc | tgaaggtgcc | 1680 |
| tttttatgag | ccatcccatg | cagaggaggt | gtcaaagttt | tctgtttgtg | gctttgctaa | 1740 |
| tccattgccc | acagagtctc | ttgactgttt | ctgccctcac | ctacaaaata | gtactcagct | 1800 |
| ggaacaagtg | aatcagatgc | taaatctcac | ccaagaagaa | ataacagcaa | cagtgaaagt | 1860 |
| aaatttgcca | tttgggaggc | ctagggtact | gcagaagaac | gtggaccact | gtctccttta | 1920 |
| ccacagggaa | tatgtcagtg | gatttggaaa | agctatgagg | atgcccatgt | ggagttcata | 1980 |
| cacagtcccc | cagttgggag | acacatcgcc | tctgcctccc | actgtcccag | actgtctgcg | 2040 |
| ggctgatgtc | agggttcctc | cttctgagag | ccaaaaatgt | tccttctatt | tagcagacaa | 2100 |
| gaatatcacc | cacggcttcc | tctatcctcc | tgccagcaat | agaacatcag | atagccaata | 2160 |
| tgatgcttta | attactagca | atttggtacc | tatgtatgaa | gaattcagaa | aaatgtggga | 2220 |

```
ctacttccac agtgttcttc ttataaaaca tgccacagaa agaaatggag taaatgtggt      2280
tagtggacca atatttgatt ataattatga tggccatttt gatgctccag atgaaattac      2340
caaacattta gccaacactg atgttcccat cccaacacac tactttgtgg tgctgaccag      2400
ttgtaaaaac aagagccaca caccggaaaa ctgccctggg tggctggatg tcctacccct      2460
tatcatccct caccgaccta ccaacgtgga gagctgtcct gaaggtaaac cagaagctct      2520
ttgggttgaa gaaagattta cagctcacat tgcccgggtc cgtgatgtag aacttctcac      2580
tgggcttgac ttctatcagg ataaagtgca gcctgtctct gaatttttgc aactaaagac      2640
atatttacca acatttgaaa cccctattta acttaataat gtctacttaa tatataattt      2700
actgtataaa gtaattttgg caaaatataa gtgattttt ctggagaatt gtaaaataaa       2760
gttttctatt tttccttaaa aaaaaaaccg gaattccggg cttgggaggc tgaggcagga      2820
gactcgcttg aacccgggag gcagaggttg cagtgagcca agattgcgcc attgcactcc      2880
agagcctggg tgacagagca agactacatc tcaaaaaata aataaataaa ataaagtaa       2940 caataaaaat aaaagaaca gcagagagaa tgagcaagga gaaatgtcac aaactattgc       3000
aaaatactgt tacactgggt tggctctcca agaagatact ggaatctctt cagccatttg      3060
cttttcagaa gtagaaacca gcaaaccacc tctaagcgga gaacatacga ttctttatta      3120
agtagctctg gggaaggaaa gaataaaagt tgatagctcc ctgattggga aaaaatgcac      3180
aattaataaa gaatgaagat gaaagaaagc atgcttatgt tgtaacacaa aaaaaattca      3240
caaacgttgg tggaaggaaa acagtataga aacattact ttaactaaaa gctggaaaaa       3300
ttttcagttg ggatgcgact gacaaaaaga acgggatttc caggcataaa gttggcgtga      3360
gctacagagg gcaccatgtg gctcagtgga agacccttca agattcaaag ttccatttga      3420
cagagcaaag gcacttcgca aggagaaggg tttaaattat gggtccaaaa gccaagtggt      3480
aaagcgagca atttgcagca taactgcttc tcctagacag ggctgagtgg gcaaaatacg      3540
acagtacaca cagtgactat tagccactgc cagaaacagg ctgaacagcc ctgggagaca      3600
agggaaggca ggtggtggga gttgttcatg gagagaaagg agagtttag aaccagcaca       3660 tccactggag atgctgggcc accagacccc tcccagtcaa taaagtctgg tgcctcattt      3720
gatctcagcc tcatcatgac cctggagaga ccctgatacc atctgccagt ccccgacagc      3780
ttaggcactc cttgccatca acctgacccc ccgagtggtt ctccaggctc cctgccccac      3840
ccattcaggc cggaattc                                                    3858
```

<210> SEQ ID NO 8
<211> LENGTH: 875
<212> TYPE: PRT
<213> ORGANISM: Homo sapiens

<400> SEQUENCE: 8

```
Met Glu Ser Thr Leu Thr Leu Ala Thr Glu Gln Pro Val Lys Lys Asn
1               5                   10                  15

Thr Leu Lys Lys Tyr Lys Ile Ala Cys Ile Val Leu Ala Leu Leu
            20                  25                  30

Val Ile Met Ser Leu Gly Leu Gly Leu Gly Leu Arg Lys Leu
        35                  40                  45

Glu Lys Gln Gly Ser Cys Arg Lys Lys Cys Phe Asp Ala Ser Phe Arg
    50                  55                  60

Gly Leu Glu Asn Cys Arg Cys Asp Val Ala Cys Lys Asp Arg Gly Asp
65                  70                  75                  80
```

-continued

Cys Cys Trp Asp Phe Glu Asp Thr Cys Val Glu Ser Thr Arg Ile Trp
                85                  90                  95
Met Cys Asn Lys Phe Arg Cys Gly Glu Thr Arg Leu Glu Ala Ser Leu
            100                 105                 110
Cys Ser Cys Ser Asp Asp Cys Leu Gln Lys Lys Asp Cys Cys Ala Asp
            115                 120                 125
Tyr Lys Ser Val Cys Gln Gly Glu Thr Ser Trp Leu Glu Glu Asn Cys
            130                 135                 140
Asp Thr Ala Gln Gln Ser Gln Cys Pro Glu Gly Phe Asp Leu Pro Pro
145                 150                 155                 160
Val Ile Leu Phe Ser Met Asp Gly Phe Arg Ala Glu Tyr Leu Tyr Thr
                165                 170                 175
Trp Asp Thr Leu Met Pro Asn Ile Asn Lys Leu Lys Thr Cys Gly Ile
                180                 185                 190
His Ser Lys Tyr Met Arg Ala Met Tyr Pro Thr Lys Thr Phe Pro Asn
                195                 200                 205
His Tyr Thr Ile Val Thr Gly Leu Tyr Pro Glu Ser His Gly Ile Ile
                210                 215                 220
Asp Asn Asn Met Tyr Asp Val Asn Leu Asn Lys Asn Phe Ser Leu Ser
225                 230                 235                 240
Ser Lys Glu Gln Asn Asn Pro Ala Trp Trp His Gly Gln Pro Met Trp
                245                 250                 255
Leu Thr Ala Met Tyr Gln Gly Leu Lys Ala Ala Thr Tyr Phe Trp Pro
                260                 265                 270
Gly Ser Glu Val Ala Ile Asn Gly Ser Phe Pro Ser Ile Tyr Met Pro
                275                 280                 285
Tyr Asn Gly Ser Val Pro Phe Glu Glu Arg Ile Ser Thr Leu Leu Lys
                290                 295                 300
Trp Leu Asp Leu Pro Lys Ala Glu Arg Pro Arg Phe Tyr Thr Met Tyr
305                 310                 315                 320
Phe Glu Glu Pro Asp Ser Ser Gly His Ala Gly Gly Pro Val Ser Ala
                325                 330                 335
Arg Val Ile Lys Ala Leu Gln Val Asp His Ala Phe Gly Met Leu
                340                 345                 350
Met Glu Gly Leu Lys Gln Arg Asn Leu His Asn Cys Val Asn Ile Ile
            355                 360                 365
Leu Leu Ala Asp His Gly Met Asp Gln Thr Tyr Cys Asn Lys Met Glu
370                 375                 380
Tyr Met Thr Asp Tyr Phe Pro Arg Ile Asn Phe Tyr Met Tyr Glu
385                 390                 395                 400
Gly Pro Ala Pro Arg Ile Arg Ala His Asn Ile Pro His Asp Phe Phe
                405                 410                 415
Ser Phe Asn Ser Glu Glu Ile Val Arg Asn Leu Ser Cys Arg Lys Pro
            420                 425                 430
Asp Gln His Phe Lys Pro Tyr Leu Thr Pro Asp Leu Pro Lys Arg Leu
            435                 440                 445
His Tyr Ala Lys Asn Val Arg Ile Asp Lys Val His Leu Phe Val Asp
            450                 455                 460
Gln Gln Trp Leu Ala Val Arg Ser Lys Ser Asn Thr Asn Cys Gly Gly
465                 470                 475                 480
Gly Asn His Gly Tyr Asn Asn Glu Phe Arg Ser Met Glu Ala Ile Phe
                485                 490                 495
Leu Ala His Gly Pro Ser Phe Lys Glu Lys Thr Glu Val Glu Pro Phe
                500                 505                 510

```
Glu Asn Ile Glu Val Tyr Asn Leu Met Cys Asp Leu Leu Arg Ile Gln
            515                 520                 525

Pro Ala Pro Asn Asn Gly Thr His Gly Ser Leu Asn His Leu Leu Lys
        530                 535                 540

Val Pro Phe Tyr Glu Pro Ser His Ala Glu Val Ser Lys Phe Ser
545                 550                 555                 560

Val Cys Gly Phe Ala Asn Pro Leu Pro Thr Glu Ser Leu Asp Cys Phe
                565                 570                 575

Cys Pro His Leu Gln Asn Ser Thr Gln Leu Glu Gln Val Asn Gln Met
            580                 585                 590

Leu Asn Leu Thr Gln Glu Glu Ile Thr Ala Thr Val Lys Val Asn Leu
        595                 600                 605

Pro Phe Gly Arg Pro Arg Val Leu Gln Lys Asn Val Asp His Cys Leu
    610                 615                 620

Leu Tyr His Arg Glu Tyr Val Ser Gly Phe Gly Lys Ala Met Arg Met
625                 630                 635                 640

Pro Met Trp Ser Ser Tyr Thr Val Pro Gln Leu Gly Asp Thr Ser Pro
                645                 650                 655

Leu Pro Pro Thr Val Pro Asp Cys Leu Arg Ala Asp Val Arg Val Pro
            660                 665                 670

Pro Ser Glu Ser Gln Lys Cys Ser Phe Tyr Leu Ala Asp Lys Asn Ile
        675                 680                 685

Thr His Gly Phe Leu Tyr Pro Pro Ala Ser Asn Arg Thr Ser Asp Ser
    690                 695                 700

Gln Tyr Asp Ala Leu Ile Thr Ser Asn Leu Val Pro Met Tyr Glu Glu
705                 710                 715                 720

Phe Arg Lys Met Trp Asp Tyr Phe His Ser Val Leu Leu Ile Lys His
                725                 730                 735

Ala Thr Glu Arg Asn Gly Val Asn Val Val Ser Gly Pro Ile Phe Asp
            740                 745                 750

Tyr Asn Tyr Asp Gly His Phe Asp Ala Pro Asp Glu Ile Thr Lys His
        755                 760                 765

Leu Ala Asn Thr Asp Val Pro Ile Pro Thr His Tyr Phe Val Val Leu
    770                 775                 780

Thr Ser Cys Lys Asn Lys Ser His Thr Pro Glu Asn Cys Pro Gly Trp
785                 790                 795                 800

Leu Asp Val Leu Pro Phe Ile Ile Pro His Arg Pro Thr Asn Val Glu
                805                 810                 815

Ser Cys Pro Glu Gly Lys Pro Glu Ala Leu Trp Val Glu Glu Arg Phe
            820                 825                 830

Thr Ala His Ile Ala Arg Val Arg Asp Val Glu Leu Leu Thr Gly Leu
        835                 840                 845

Asp Phe Tyr Gln Asp Lys Val Gln Pro Val Ser Glu Ile Leu Gln Leu
    850                 855                 860

Lys Thr Tyr Leu Pro Thr Phe Glu Thr Pro Ile
865                 870                 875

<210> SEQ ID NO 9
<211> LENGTH: 3858
<212> TYPE: DNA
<213> ORGANISM: Homo sapiens

<400> SEQUENCE: 9
ctactttatt ctgataaaac aggtctatgc agctaccagg acaatggaat ctacgttgac    60
```

-continued

```
tttagcaacg gaacaacctg ttaagaagaa cactcttaag aaatataaaa tagcttgcat    120
tgttcttctt gctttgctgg tgatcatgtc acttggatta ggcctggggc ttggactcag    180
gaaactggaa aagcaaggca gctgcaggaa gaagtgcttt gatgcatcat ttagaggact    240
ggagaactgc cggtgtgatg tggcatgtaa agaccgaggt gattgctgct gggattttga    300
agacacctgt gtggaatcaa ctcgaatatg gatgtgcaat aaatttcgtt gtggagagac    360
cagattagag gccagccttt gctcttgttc agatgactgt ttgcagaaga aagattgctg    420
tgctgactat aagagtgttt gccaaggaga aacctcatgg ctggaagaaa actgtgacac    480
agcccagcag tctcagtgcc cagaagggtt tgacctgcca ccagttatct tgttttctat    540
ggatggattt agagctgaat atttatacac atgggatact ttaatgccaa atatcaataa    600
actgaaaaca tgtggaattc attcaaaata catgagagct atgtatccta ccaaaacctt    660
cccaaatcat tacaccattg tcacgggctt gtatccagag tcacatggca tcattgacaa    720
taatatgtat gatgtaaatc tcaacaagaa ttttttcactt tcttcaaagg aacaaaataa    780
tccagcctgg tggcatgggc aaccaatgtg gctgacagca atgtatcaag gtttaaaagc    840
cgctacctac ttttggcccg gatcagaagt ggctataaat ggctcctttc cttccatata    900
catgccttac aacggaagtg tcccatttga agagaggatt tctacactgt taaaatggct    960
ggacctgccc aaagctgaaa gacccaggtt ttataccatg tattttgaag aacctgattc   1020
ctctggacat gcaggtggac cagtcagtgc cagagtaatt aaagccttac aggtagtaga   1080
tcatgctttt gggatgttga tggaaggcct gaagcagcgg aatttgcaca actgtgtcaa   1140
tatcatcctt ctggctgacc atggaatgga ccagacttat tgtaacaaga tggaatacat   1200
gactgattat tttcccagaa taaacttctt ctacatgtac aagggcctg cccccccgcat   1260 ccgagctcat aatatacctc atgactttttt tagttttaat tctgaggaaa ttgttagaaa   1320
cctcagttgc cgaaaacctg atcagcattt caagccctat ttgactcctg atttgccaaa   1380
gcgactgcac tatgccaaga acgtcagaat cgacaaagtt catctctttg tggatcaaca   1440
gtggctggct gttaggagta aatcaaatac aaattgtgga ggaggcaacc atggttataa   1500
caatgagttt aggagcatgg aggctatctt tctggcacat ggacccagtt ttaaagagaa   1560
gactgaagtt gaaccatttg aaaatattga agtctataac ctaatgtgtg atcttctacg   1620
cattcaacca gcaccaaaca atggaaccca tggtagttta aaccatcttc tgaaggtgcc   1680 ttttttatgag ccatcccatg cagaggaggt gtcaaagttt tctgtttgtg gctttgctaa   1740
tccattgccc acagagtctc ttgactgttt ctgccctcac ctacaaaata gtactcagct   1800
ggaacaagtg aatcagatgc taaatctcac ccaagaagaa ataacagcaa cagtgaaagt   1860
aaatttgcca tttgggaggc ctagggtact gcagaagaac gtggaccact gtctccttta   1920
ccacagggaa tatgtcagtg gatttggaaa agctatgagg atgcccatgt ggagttcata   1980
cacagtcccc cagttgggag acacatcgcc tctgcctccc actgtcccag actgtctgcg   2040
ggctgatgtc agggttcctc cttctgagag ccaaaaatgt tccttctatt tagcagacaa   2100
gaatatcacc cacggcttcc tctatcctcc tgccagcaat agaacatcag atagccaata   2160
tgatgcttta attactagca atttggtacc tatgtatgaa gaattcagaa aaatgtggga   2220
ctacttccac agtgttcttc ttataaaaca tgccacagaa agaaatggag taaatgtggt   2280
tagtggacca atatttgatt ataattatga tggccatttt gatgctccag atgaaattac   2340 caaacatttta gccaacactg atgttcccat cccaacacac tactttgtgg tgctgaccag   2400
ttgtaaaaac aagagccaca caccggaaaa ctgccctggg tggctggatg tcctacccct   2460
```

```
tatcatccct caccgaccta ccaacgtgga gagctgtcct gaaggtaaac cagaagctct    2520
ttgggttgaa gaaagattta cagctcacat tgcccgggtc cgtgatgtag aacttctcac    2580
tgggcttgac ttctatcagg ataaagtgca gcctgtctct gaaattttgc aactaaagac    2640
atatttacca acatttgaaa ccactatttt acttaataat gtctacttaa tatataattt    2700
actgtataaa gtaattttgg caaaatataa gtgatttttt ctggagaatt gtaaaataaa    2760
gttttctatt tttccttaaa aaaaaaccg gaattccggg cttgggaggc tgaggcagga    2820
gactcgcttg aacccgggag gcagaggttg cagtgagcca agattgcgcc attgcactcc    2880
agagcctggg tgacagagca agactacatc tcaaaaaata aataaataaa ataaagtaa    2940 caataaaaat aaaaagaaca gcagagagaa tgagcaagga gaaatgtcac aaactattgc    3000
aaaatactgt tacactgggt tggctctcca agaagatact ggaatctctt cagccatttg    3060
cttttcagaa gtagaaacca gcaaaccacc tctaagcgga gaacatacga ttctttatta    3120
agtagctctg gggaaggaaa gaataaaagt tgatagctcc ctgattggga aaaaatgcac    3180
aattaataaa gaatgaagat gaaagaaagc atgcttatgt tgtaacacaa aacaaattca    3240
caaacgttgg tggaaggaaa acagtataga aaacattact ttaactaaaa gctggaaaaa    3300
ttttcagttg ggatgcgact gacaaaaaga acgggatttc caggcataaa gttggcgtga    3360
gctacagagg gcaccatgtg gctcagtgga agacccttca agattcaaag ttccatttga    3420
cagagcaaag gcacttcgca aggagaaggg tttaaattat gggtccaaaa gccaagtggt    3480
aaagcgagca atttgcagca taactgcttc tcctagacag ggctgagtgg gcaaaatacg    3540
acagtacaca cagtgactat tagccactgc cagaaacagg ctgaacagcc ctgggagaca    3600
agggaaggca ggtggtggga gttgttcatg gagagaaagg agagttttag aaccagcaca    3660
tccactggag atgctgggcc accagacccc tcccagtcaa taaagtctgg tgcctcattt    3720
gatctcagcc tcatcatgac cctggagaga ccctgatacc atctgccagt ccccgacagc    3780
ttaggcactc cttgccatca acctgacccc ccgagtggtt ctccaggctc cctgccccac    3840
ccattcaggc cggaattc                                                 3858
```

<210> SEQ ID NO 10
<211> LENGTH: 875
<212> TYPE: PRT
<213> ORGANISM: Homo sapiens

<400> SEQUENCE: 10

```
Met Glu Ser Thr Leu Thr Leu Ala Thr Glu Gln Pro Val Lys Lys Asn
1               5                   10                  15

Thr Leu Lys Lys Tyr Lys Ile Ala Cys Ile Val Leu Leu Ala Leu Leu
                20                  25                  30

Val Ile Met Ser Leu Gly Leu Gly Leu Gly Leu Arg Lys Leu
            35                  40                  45

Glu Lys Gln Gly Ser Cys Arg Lys Lys Cys Phe Asp Ala Ser Phe Arg
    50                  55                  60

Gly Leu Glu Asn Cys Arg Cys Asp Val Ala Cys Lys Asp Arg Gly Asp
65                  70                  75                  80

Cys Cys Trp Asp Phe Glu Asp Thr Cys Val Glu Ser Thr Arg Ile Trp
                85                  90                  95

Met Cys Asn Lys Phe Arg Cys Gly Glu Thr Arg Leu Glu Ala Ser Leu
                100                 105                 110

Cys Ser Cys Ser Asp Asp Cys Leu Gln Lys Lys Asp Cys Cys Ala Asp
            115                 120                 125
```

```
Tyr Lys Ser Val Cys Gln Gly Glu Thr Ser Trp Leu Glu Glu Asn Cys
    130                 135                 140

Asp Thr Ala Gln Gln Ser Gln Cys Pro Glu Gly Phe Asp Leu Pro Pro
145                 150                 155                 160

Val Ile Leu Phe Ser Met Asp Gly Phe Arg Ala Glu Tyr Leu Tyr Thr
                165                 170                 175

Trp Asp Thr Leu Met Pro Asn Ile Asn Lys Leu Lys Thr Cys Gly Ile
            180                 185                 190

His Ser Lys Tyr Met Arg Ala Met Tyr Pro Thr Lys Thr Phe Pro Asn
        195                 200                 205

His Tyr Thr Ile Val Thr Gly Leu Tyr Pro Glu Ser His Gly Ile Ile
    210                 215                 220

Asp Asn Asn Met Tyr Asp Val Asn Leu Asn Lys Asn Phe Ser Leu Ser
225                 230                 235                 240

Ser Lys Glu Gln Asn Asn Pro Ala Trp Trp His Gly Gln Pro Met Trp
                245                 250                 255

Leu Thr Ala Met Tyr Gln Gly Leu Lys Ala Ala Thr Tyr Phe Trp Pro
            260                 265                 270

Gly Ser Glu Val Ala Ile Asn Gly Ser Phe Pro Ser Ile Tyr Met Pro
        275                 280                 285

Tyr Asn Gly Ser Val Pro Phe Glu Glu Arg Ile Ser Thr Leu Leu Lys
    290                 295                 300

Trp Leu Asp Leu Pro Lys Ala Glu Arg Pro Arg Phe Tyr Thr Met Tyr
305                 310                 315                 320

Phe Glu Glu Pro Asp Ser Ser Gly His Ala Gly Gly Pro Val Ser Ala
                325                 330                 335

Arg Val Ile Lys Ala Leu Gln Val Val Asp His Ala Phe Gly Met Leu
            340                 345                 350

Met Glu Gly Leu Lys Gln Arg Asn Leu His Asn Cys Val Asn Ile Ile
        355                 360                 365

Leu Leu Ala Asp His Gly Met Asp Gln Thr Tyr Cys Asn Lys Met Glu
    370                 375                 380

Tyr Met Thr Asp Tyr Phe Pro Arg Ile Asn Phe Phe Tyr Met Tyr Glu
385                 390                 395                 400

Gly Pro Ala Pro Arg Ile Arg Ala His Asn Ile Pro His Asp Phe Phe
                405                 410                 415

Ser Phe Asn Ser Glu Glu Ile Val Arg Asn Leu Ser Cys Arg Lys Pro
            420                 425                 430

Asp Gln His Phe Lys Pro Tyr Leu Thr Pro Asp Leu Pro Lys Arg Leu
        435                 440                 445

His Tyr Ala Lys Asn Val Arg Ile Asp Lys Val His Leu Phe Val Asp
    450                 455                 460

Gln Gln Trp Leu Ala Val Arg Ser Lys Ser Asn Thr Asn Cys Gly Gly
465                 470                 475                 480

Gly Asn His Gly Tyr Asn Asn Glu Phe Arg Ser Met Glu Ala Ile Phe
                485                 490                 495

Leu Ala His Gly Pro Ser Phe Lys Glu Lys Thr Glu Val Glu Pro Phe
            500                 505                 510

Glu Asn Ile Glu Val Tyr Asn Leu Met Cys Asp Leu Leu Arg Ile Gln
        515                 520                 525

Pro Ala Pro Asn Asn Gly Thr His Gly Ser Leu Asn His Leu Leu Lys
    530                 535                 540

Val Pro Phe Tyr Glu Pro Ser His Ala Glu Glu Val Ser Lys Phe Ser
545                 550                 555                 560
```

Val Cys Gly Phe Ala Asn Pro Leu Pro Thr Glu Ser Leu Asp Cys Phe
            565                 570                 575

Cys Pro His Leu Gln Asn Ser Thr Gln Leu Glu Gln Val Asn Gln Met
            580                 585                 590

Leu Asn Leu Thr Gln Glu Glu Ile Thr Ala Thr Val Lys Val Asn Leu
            595                 600                 605

Pro Phe Gly Arg Pro Arg Val Leu Gln Lys Asn Val Asp His Cys Leu
610                 615                 620

Leu Tyr His Arg Glu Tyr Val Ser Gly Phe Gly Lys Ala Met Arg Met
625                 630                 635                 640

Pro Met Trp Ser Ser Tyr Thr Val Pro Gln Leu Gly Asp Thr Ser Pro
            645                 650                 655

Leu Pro Pro Thr Val Pro Asp Cys Leu Arg Ala Asp Val Arg Val Pro
            660                 665                 670

Pro Ser Glu Ser Gln Lys Cys Ser Phe Tyr Leu Ala Asp Lys Asn Ile
            675                 680                 685

Thr His Gly Phe Leu Tyr Pro Pro Ala Ser Asn Arg Thr Ser Asp Ser
            690                 695                 700

Gln Tyr Asp Ala Leu Ile Thr Ser Asn Leu Val Pro Met Tyr Glu Glu
705                 710                 715                 720

Phe Arg Lys Met Trp Asp Tyr Phe His Ser Val Leu Leu Ile Lys His
            725                 730                 735

Ala Thr Glu Arg Asn Gly Val Asn Val Val Ser Gly Pro Ile Phe Asp
            740                 745                 750

Tyr Asn Tyr Asp Gly His Phe Asp Ala Pro Asp Glu Ile Thr Lys His
            755                 760                 765

Leu Ala Asn Thr Asp Val Pro Ile Pro Thr His Tyr Phe Val Val Leu
            770                 775                 780

Thr Ser Cys Lys Asn Lys Ser His Thr Pro Glu Asn Cys Pro Gly Trp
785                 790                 795                 800

Leu Asp Val Leu Pro Phe Ile Ile Pro His Arg Pro Thr Asn Val Glu
            805                 810                 815

Ser Cys Pro Glu Gly Lys Pro Glu Ala Leu Trp Val Glu Glu Arg Phe
            820                 825                 830

Thr Ala His Ile Ala Arg Val Arg Asp Val Glu Leu Leu Thr Gly Leu
            835                 840                 845

Asp Phe Tyr Gln Asp Lys Val Gln Pro Val Ser Glu Ile Leu Gln Leu
850                 855                 860

Lys Thr Tyr Leu Pro Thr Phe Glu Thr Thr Ile
865                 870                 875

<210> SEQ ID NO 11
<211> LENGTH: 3165
<212> TYPE: DNA
<213> ORGANISM: Homo sapiens

<400> SEQUENCE: 11
atacagtttc tctttgccag actagactaa agaaggagca ctactttatt ctgataaaac     60
aggtctatgc agctaccagg acaatggaat ctacgttgac tttagcaacg gaacaacctg    120
ttaagaagaa cactcttaag aaatatataaaa tagcttgcat tgttcttctt gctttgctgg    180
tgatcatgtc acttggatta ggcctggggc ttggactcag gaaactggaa aagcaaggca    240
gctgcaggaa gaagtgcttt gatgcatcat ttagaggact ggagaactgc cggtgtgatg    300
tggcatgtaa agaccgaggt gattgctgct gggattttga agacacctgt gtggaatcaa    360

```
ctcgaatatg gatgtgcaat aaatttcgtt gtggagagac cagattagag gccagccttt    420
gctcttgttc agatgactgt ttgcagagga aagattgctg tgctgactat aagagtgttt    480
gccaaggaga aacctcatgg ctggaagaaa actgtgacac agcccagcag tctcagtgcc    540
cagaagggtt tgacctgcca ccagttatct tgttttctat ggatggattt agagctgaat    600
atttatacac atgggatact ttaatgccaa atatcaataa actgaaaaca tgtggaattc    660
attcaaaata catgagagct atgtatccta ccaaaacctt cccaaatcat tacaccattg    720
tcacgggctt gtatccggag tcacatggca tcattgacaa taatatgtat gatgtaaatc    780
tcaacaagaa ttttttcactt tcttcaaagg aacaaaataa tccagcctgg tggcatgggc    840
aaccaatgtg gctgacagca atgtatcaag gtttaaaagc cgctacctac ttttggcccg    900
gatcagaagt ggctataaat ggctcctttc cttccatata catgccttac aacgaaagtg    960
tcccatttga agagaggatt tctacactgt taaaatggct ggacctgccc aaagctgaga   1020
gacccaggtt ttataccatg ttttttgaag aacctgattc ctctggacat gcaggtggac   1080
cagtcagtgc cagagtaatt aaagccttac aggtagtaga tcatgctttt gggatgttga   1140
tggaaggcct gaagcagcgg aatttgcaca actgtgtcaa tatcatcctt ctggctgacc   1200
atggaatgga ccagacttat tgtaacaaga tggaatacat gactgattat tttcccagaa   1260
taaacttctt ctcatgtac gaagggcctg ccccccgcgt ccgagctcat aatataccctc   1320
atgactttt tagttttaat tctgaggaaa ttgttagaaa cctcagttgc cgaaaacctg   1380
atcagcattt caagccctat ttgactcctg atttgccaaa gcgactgcac tatgccaaga   1440
acgtcagaat cgacaaagtt catctctttg tggatcaaca gtggctggct gttaggagta   1500
aatcaaatac aaattgtgga ggaggcaacc atggttataa caatgagttt aggagcatgg   1560
aggctatctt tctggcacat ggacccagtt ttaaagagaa gactgaagtt gaaccatttg   1620
aaaatattga agtctataac ctaatgtgtg atcttctacg cattcaacca gcaccaaaca   1680
atggaaccca tggtagttta aaccatcttc tgaaggtgcc ttttatgag ccatcccatg    1740
cagaggaggt gtcaaagttt tctgtttgtg gctttgctaa tccattgccc acagagtctc    1800
ttgactgttt ctgccctcac ctacaaaata gtactcagct ggaacaagtg aatcagatgc   1860
taaatctcac ccaagaagaa ataacagcaa cagtgaaagt aaatttgcca tttgggaggc   1920
ctagggtact gcagaagaac gtggaccact gtctccttta ccacagggaa tatgtcagtg   1980
gatttggaaa agctatgagg atgcccatgt ggagttcata cacagtcccc cagttgggag   2040
acacatcgcc tctgcctccc actgtcccag actgtctgcg ggctgatgtc agggttcctc   2100
cttctgagag ccaaaaatgt tccttctatt tagcagacaa gaatatcacc cacggcttcc   2160
tctatcctcc tgccagcaat agaacatcag atagccaata tgatgcttta attactagca   2220
atttggtacc tatgtatgaa gaattcagaa aaatgtggga ctacttccac agtgttcttc   2280
ttataaaaca tgccacagaa agaaatggag taaatgtggt tagtggacca atatttgatt   2340
ataattatga tggccatttt gatgctccag atgaaattac caaacattta gccaacactg   2400
atgttcccat cccaacacac tactttgtgg tgctgaccag ttgtaaaaac aagagccaca   2460
caccggaaaa ctgccctggg tggctggatg tcctacccctt tatcatccct caccgaccta   2520
ccaacgtgga gagctgtcct gaaggtaaac cagaagctct ttgggttgaa gaaagattta   2580
cagctcacat tgcccgggtc cgtgatgtag aacttctcac tgggcttgac ttctatcagg   2640
ataaagtgca gcctgtctct gaaatttttgc aactaaagac atatttacca acatttgaaa   2700
ccactatttta acttaataat gtctacttaa tatataattt actgtataaa gtaattttgg   2760
```

```
caaaatataa gtgatttttt tctggagaat tgtaaaataa agttttctat ttttccttaa    2820
gtcccctaaa agccataatt tttattattc cttttctct ttttcaatt ctatgaatat     2880 gtattatttt aaagttatat ttttcacaca gagatgatgc tatattacac cttccctttt    2940
ttgttggttt cttaaactct aatctcatga cagattatac cttccttatt acttgtttta    3000
tcttactcag aatctttgaa tatatttttc tgcccagaat tatctaaaca aaagggagaa    3060
caaaagaagt atgtctcact tgggaactga atcaactcta aatcagtttt gtcacaaaac    3120
tttttgtatt tgactggcaa tgctgattaa aattaaaaat gcaca                  3165
```

```
<210> SEQ ID NO 12
<211> LENGTH: 875
<212> TYPE: PRT
<213> ORGANISM: Homo sapiens

<400> SEQUENCE: 12
```

```
Met Glu Ser Thr Leu Thr Leu Ala Thr Glu Gln Pro Val Lys Lys Asn
  1               5                  10                  15

Thr Leu Lys Lys Tyr Lys Ile Ala Cys Ile Val Leu Leu Ala Leu Leu
             20                  25                  30

Val Ile Met Ser Leu Gly Leu Gly Leu Gly Leu Arg Lys Leu
         35                  40                  45

Glu Lys Gln Gly Ser Cys Arg Lys Lys Cys Phe Asp Ala Ser Phe Arg
 50                  55                  60

Gly Leu Glu Asn Cys Arg Cys Asp Val Ala Cys Lys Asp Arg Gly Asp
 65                  70                  75                  80

Cys Cys Trp Asp Phe Glu Asp Thr Cys Val Glu Ser Thr Arg Ile Trp
                 85                  90                  95

Met Cys Asn Lys Phe Arg Cys Gly Glu Thr Arg Leu Glu Ala Ser Leu
            100                 105                 110

Cys Ser Cys Ser Asp Asp Cys Leu Gln Arg Lys Asp Cys Cys Ala Asp
        115                 120                 125

Tyr Lys Ser Val Cys Gln Gly Glu Thr Ser Trp Leu Glu Glu Asn Cys
    130                 135                 140

Asp Thr Ala Gln Gln Ser Gln Cys Pro Glu Gly Phe Asp Leu Pro Pro
145                 150                 155                 160

Val Ile Leu Phe Ser Met Asp Gly Phe Arg Ala Glu Tyr Leu Tyr Thr
                165                 170                 175

Trp Asp Thr Leu Met Pro Asn Ile Asn Lys Leu Lys Thr Cys Gly Ile
            180                 185                 190

His Ser Lys Tyr Met Arg Ala Met Tyr Pro Thr Lys Thr Phe Pro Asn
        195                 200                 205

His Tyr Thr Ile Val Thr Gly Leu Tyr Pro Glu Ser His Gly Ile Ile
    210                 215                 220

Asp Asn Asn Met Tyr Asp Val Asn Leu Asn Lys Asn Phe Ser Leu Ser
225                 230                 235                 240

Ser Lys Glu Gln Asn Asn Pro Ala Trp Trp His Gly Gln Pro Met Trp
                245                 250                 255

Leu Thr Ala Met Tyr Gln Gly Leu Lys Ala Ala Thr Tyr Phe Trp Pro
            260                 265                 270

Gly Ser Glu Val Ala Ile Asn Gly Ser Phe Pro Ser Ile Tyr Met Pro
        275                 280                 285

Tyr Asn Gly Ser Val Pro Phe Glu Arg Ile Ser Thr Leu Leu Lys
    290                 295                 300
```

-continued

```
Trp Leu Asp Leu Pro Lys Ala Glu Arg Pro Arg Phe Tyr Thr Met Phe
305                 310                 315                 320

Phe Glu Glu Pro Asp Ser Ser Gly His Ala Gly Gly Pro Val Ser Ala
            325                 330                 335

Arg Val Ile Lys Ala Leu Gln Val Val Asp His Ala Phe Gly Met Leu
        340                 345                 350

Met Glu Gly Leu Lys Gln Arg Asn Leu His Asn Cys Val Asn Ile Ile
    355                 360                 365

Leu Leu Ala Asp His Gly Met Asp Gln Thr Tyr Cys Asn Lys Met Glu
370                 375                 380

Tyr Met Thr Asp Tyr Phe Pro Arg Ile Asn Phe Phe Tyr Met Tyr Glu
385                 390                 395                 400

Gly Pro Ala Pro Arg Val Arg Ala His Asn Ile Pro His Asp Phe Phe
            405                 410                 415

Ser Phe Asn Ser Glu Glu Ile Val Arg Asn Leu Ser Cys Arg Lys Pro
        420                 425                 430

Asp Gln His Phe Lys Pro Tyr Leu Thr Pro Asp Leu Pro Lys Arg Leu
    435                 440                 445

His Tyr Ala Lys Asn Val Arg Ile Asp Lys Val His Leu Phe Val Asp
450                 455                 460

Gln Gln Trp Leu Ala Val Arg Ser Lys Ser Asn Thr Asn Cys Gly Gly
465                 470                 475                 480

Gly Asn His Gly Tyr Asn Asn Glu Phe Arg Ser Met Glu Ala Ile Phe
            485                 490                 495

Leu Ala His Gly Pro Ser Phe Lys Glu Lys Thr Glu Val Glu Pro Phe
        500                 505                 510

Glu Asn Ile Glu Val Tyr Asn Leu Met Cys Asp Leu Leu Arg Ile Gln
    515                 520                 525

Pro Ala Pro Asn Asn Gly Thr His Gly Ser Leu Asn His Leu Leu Lys
530                 535                 540

Val Pro Phe Tyr Glu Pro Ser His Ala Glu Glu Val Ser Lys Phe Ser
545                 550                 555                 560

Val Cys Gly Phe Ala Asn Pro Leu Pro Thr Glu Ser Leu Asp Cys Phe
            565                 570                 575

Cys Pro His Leu Gln Asn Ser Thr Gln Leu Glu Gln Val Asn Gln Met
        580                 585                 590

Leu Asn Leu Thr Gln Glu Glu Ile Thr Ala Thr Val Lys Val Asn Leu
    595                 600                 605

Pro Phe Gly Arg Pro Arg Val Leu Gln Lys Asn Val Asp His Cys Leu
610                 615                 620

Leu Tyr His Arg Glu Tyr Val Ser Gly Phe Gly Lys Ala Met Arg Met
625                 630                 635                 640

Pro Met Trp Ser Ser Tyr Thr Val Pro Gln Leu Gly Asp Thr Ser Pro
            645                 650                 655

Leu Pro Pro Thr Val Pro Asp Cys Leu Arg Ala Asp Val Arg Val Pro
        660                 665                 670

Pro Ser Glu Ser Gln Lys Cys Ser Phe Tyr Leu Ala Asp Lys Asn Ile
    675                 680                 685

Thr His Gly Phe Leu Tyr Pro Pro Ala Ser Asn Arg Thr Ser Asp Ser
690                 695                 700

Gln Tyr Asp Ala Leu Ile Thr Ser Asn Leu Val Pro Met Tyr Glu Glu
705                 710                 715                 720

Phe Arg Lys Met Trp Asp Tyr Phe His Ser Val Leu Leu Ile Lys His
            725                 730                 735
```

```
Ala Thr Glu Arg Asn Gly Val Asn Val Val Ser Gly Pro Ile Phe Asp
            740                 745                 750
Tyr Asn Tyr Asp Gly His Phe Asp Ala Pro Asp Glu Ile Thr Lys His
        755                 760                 765
Leu Ala Asn Thr Asp Val Pro Ile Pro Thr His Tyr Phe Val Val Leu
    770                 775                 780
Thr Ser Cys Lys Asn Lys Ser His Thr Pro Glu Asn Cys Pro Gly Trp
785                 790                 795                 800
Leu Asp Val Leu Pro Phe Ile Ile Pro His Arg Pro Thr Asn Val Glu
                805                 810                 815
Ser Cys Pro Glu Gly Lys Pro Glu Ala Leu Trp Val Glu Glu Arg Phe
            820                 825                 830
Thr Ala His Ile Ala Arg Val Arg Asp Val Glu Leu Leu Thr Gly Leu
        835                 840                 845
Asp Phe Tyr Gln Asp Lys Val Gln Pro Val Ser Glu Ile Leu Gln Leu
    850                 855                 860
Lys Thr Tyr Leu Pro Thr Phe Glu Thr Thr Ile
865                 870                 875

<210> SEQ ID NO 13
<211> LENGTH: 3988
<212> TYPE: DNA
<213> ORGANISM: Homo sapiens

<400> SEQUENCE: 13
```

| | | | | | |
|---|---|---|---|---|---|
| ctactttatt | ctgataaaac | aggtctatgc | agctaccagg | acaatggaat | ctacgttgac | 60 |
| tttagcaacg | gaacaacctg | ttaagaagaa | cactcttaag | aaatataaaa | tagcttgcat | 120 |
| tacagggtct | ctctcctttg | ggatctcacc | tcaccacaac | ctctgtttcc | caggctcaag | 180 |
| tgatcctcct | gcctcagcct | cctgagtagc | ttggaccaca | ggcacatgcc | acaaggctca | 240 |
| gctaagtttt | tgttcttctt | gctttgctgg | tgatcatgtc | acttggatta | ggcctggggc | 300 |
| ttggactcag | gaaactggaa | aagcaaggca | gctgcaggaa | gaagtgcttt | gatgcatcat | 360 |
| ttagaggact | ggagaactgc | cggtgtgatg | tggcatgtaa | agaccgaggt | gattgctgct | 420 |
| gggattttga | agacacctgt | gtggaatcaa | ctcgaatatg | gatgtgcaat | aaatttcgtt | 480 |
| gtggagagac | cagattagag | gccagccttt | gctcttgttc | agatgactgt | ttgcagaaga | 540 |
| aagattgctg | tgctgactat | aagagtgttt | gccaaggaga | aacctcatgg | ctggaagaaa | 600 |
| actgtgcaca | agcccagcag | tctcagtgcc | cagaagggtt | tgacctgcca | ccagttatct | 660 |
| tgttttctat | ggatggattt | agagctgaat | atttatacac | atgggatact | ttaatgccaa | 720 |
| atatcaataa | actgaaaaca | tgtggaattc | attcaaaata | catgagagct | atgtatccta | 780 |
| ccaaaacctt | cccaaatcat | taccattg | tcacgggctt | gtatccagag | tcacatggca | 840 |
| tcattgacaa | taatatgtat | gatgtaaatc | tcaacaagaa | ttttcacctt | tcttcaaagg | 900 |
| aacaaaataa | tccagcctgg | tggcatgggc | aaccaatgtg | gctgacagca | atgtatcaag | 960 |
| gtttaaaagc | cgctacctac | ttttggcccg | gatcagaagt | ggctataaat | ggctcctttc | 1020 |
| cttccatata | catgccttac | aacggaagtg | tcccatttga | agagaggatt | tctacactgt | 1080 |
| taaaatggct | ggacctgccc | aaagctgaaa | gacccaggtt | ttataccatg | tattttgaag | 1140 |
| aacctgattc | ctctggacat | gcaggtggac | cagtcagtgc | cagagtaatt | aaagccttac | 1200 |
| aggtagtaga | tcatgctttt | gggatgttga | tggaaggcct | gaagcagcgg | aatttgcaca | 1260 |
| actgtgtcaa | tatcatcctt | ctggctgacc | atggaatgga | ccagacttat | tgtaacaaga | 1320 |

```
tggaatacat gactgattat tttcccagaa taaacttctt ctacatgtac gaagggcctg    1380 cccccccgcat ccgagctcat aatataccte atgactttt tagttttaat tctgaggaaa    1440
ttgttagaaa cctcagttgc cgaaaacctg atcagcattt caagccctat ttgactcctg    1500
atttgccaaa gcgactgcac tatgccaaga acgtcagaat cgacaaagtt catctctttg    1560
tggatcaaca gtggctggct gttaggagta aatcaaatac aaattgtgga ggaggcaacc    1620
atggttataa caatgagttt aggagcatgg aggctatctt tctggcacat ggacccagtt    1680
ttaaagagaa gactgaagtt gaaccatttg aaaatattga agtctataac ctaatgtgtg    1740
atcttctacg cattcaacca gcaccaaaca atggaaccca tggtagttta aaccatcttc    1800
tgaaggtgcc tttttatgag ccatcccatg cagaggaggt gtcaaagttt tctgtttgtg    1860
gctttgctaa tccattgccc acagagtctc ttgactgttt ctgccctcac ctacaaaata    1920
gtactcagct ggaacaagtg aatcagatgc taaatctcac ccaagaagaa ataacagcaa    1980
cagtgaaagt aaatttgcca tttgggaggc ctagggtact gcagaagaac gtggaccact    2040 gtctcccttta ccacagggaa tatgtcagtg gatttggaaa agctatgagg atgcccatgt    2100
ggagttcata cacagtcccc cagttgggag acacatcgcc tctgcctccc actgtcccag    2160
actgtctgcg ggctgatgtc agggttcctc cttctgagag ccaaaaatgt tccttctatt    2220
tagcagacaa gaatatcacc cacggcttcc tctatcctcc tgccagcaat agaacatcag    2280
atagccaata tgatgcttta attactagca atttggtacc tatgtatgaa gaattcagaa    2340
aaatgtggga ctacttccac agtgttcttc ttataaaaca tgccacagaa agaaatggag    2400
taaatgtggt tagtggacca atatttgatt ataattatga tggccatttt gatgctccag    2460
atgaaattac caaacattta gccaacactg atgttcccat cccaacacac tactttgtgg    2520
tgctgaccag ttgtaaaaac aagagccaca caccggaaaa ctgccctggg tggctggatg    2580 tcctacccctt tatcatccct caccgaccta ccaacgtgga gagctgtcct gaaggtaaac    2640
cagaagctct ttgggttgaa gaaagattta cagctcacat tgcccgggtc cgtgatgtag    2700
aacttctcac tgggcttgac ttctatcagg ataaagtgca gcctgtctct gaaattttgc    2760
aactaaagac atatttacca acatttgaaa ccactattta acttaataat gtctacttaa    2820
tatataattt actgtataaa gtaattttgg caaaatataa gtgatttttt ctggagaatt    2880
gtaaaataaa gttttctatt tttccttaaa aaaaaaccg gaattccggg cttgggaggc    2940
tgaggcagga gactcgcttg aacccgggag gcagaggttg cagtgagcca agattgcgcc    3000
attgcactcc agagcctggg tgacagagca agactacatc tcaaaaaata aataaataaa    3060 ataaagtaa caataaaaat aaaagaaca gcagagagaa tgagcaagga gaaatgtcac    3120
aaactattgc aaaatactgt tacactgggt tggctctcca agaagatact ggaatctctt    3180
cagccatttg cttttcagaa gtagaaacca gcaaccacc tctaagcgga gaacatacga    3240
ttctttatta agtagctctg gggaaggaaa gaataaaagt tgatagctcc ctgattggga    3300
aaaaatgcac aattaataaa gaatgaagat gaaagaaagc atgcttatgt tgtaacacaa    3360
aaaaaattca caaacgttgg tggaaggaaa acagtataga aaacattact ttaactaaaa    3420
gctggaaaaa ttttcagttg ggatgcgact gacaaaaaga acgggatttc caggcataaa    3480
gttggcgtga gctacagagg gcaccatgtg gctcagtgga agacccttca agattcaaag    3540
ttccatttga cagagcaaag gcacttcgca aggagaaggg tttaaattat gggtccaaaa    3600
gccaagtggt aaagcgagca atttgcagca taactgcttc tcctagacag ggctgagtgg    3660
gcaaaatacg acagtacaca cagtgactat tagccactgc cagaaacagg ctgaacagcc    3720
```

-continued

```
ctgggagaca agggaaggca ggtggtggga gttgttcatg gagagaaagg agagttttag      3780
aaccagcaca tccactggag atgctgggcc accagacccc tcccagtcaa taaagtctgg      3840
tgcctcattt gatctcagcc tcatcatgac cctggagaga ccctgatacc atctgccagt      3900
ccccgacagc ttaggcactc cttgccatca acctgacccc ccgagtggtt ctccaggctc      3960
cctgccccac ccattcaggc cggaattc                                          3988
```

<210> SEQ ID NO 14
<211> LENGTH: 841
<212> TYPE: PRT
<213> ORGANISM: Homo sapiens

<400> SEQUENCE: 14

```
Met Ser Leu Gly Leu Gly Leu Gly Leu Arg Lys Leu Glu Lys
1               5                   10                  15

Gln Gly Ser Cys Arg Lys Cys Phe Asp Ala Ser Phe Arg Gly Leu
            20                  25                  30

Glu Asn Cys Arg Cys Asp Val Ala Cys Lys Asp Arg Gly Asp Cys Cys
        35                  40                  45

Trp Asp Phe Glu Asp Thr Cys Val Glu Ser Thr Arg Ile Trp Met Cys
50                  55                  60

Asn Lys Phe Arg Cys Gly Glu Thr Arg Leu Glu Ala Ser Leu Cys Ser
65                  70                  75                  80

Cys Ser Asp Asp Cys Leu Gln Lys Lys Asp Cys Cys Ala Asp Tyr Lys
                85                  90                  95

Ser Val Cys Gln Gly Glu Thr Ser Trp Leu Glu Glu Asn Cys Asp Thr
            100                 105                 110

Ala Gln Gln Ser Gln Cys Pro Glu Gly Phe Asp Leu Pro Pro Val Ile
        115                 120                 125

Leu Phe Ser Met Asp Gly Phe Arg Ala Glu Tyr Leu Tyr Thr Trp Asp
130                 135                 140

Thr Leu Met Pro Asn Ile Asn Lys Leu Lys Thr Cys Gly Ile His Ser
145                 150                 155                 160

Lys Tyr Met Arg Ala Met Tyr Pro Thr Lys Thr Phe Pro Asn His Tyr
                165                 170                 175

Thr Ile Val Thr Gly Leu Tyr Pro Glu Ser His Gly Ile Ile Asp Asn
            180                 185                 190

Asn Met Tyr Asp Val Asn Leu Asn Lys Asn Phe Ser Leu Ser Ser Lys
        195                 200                 205

Glu Gln Asn Asn Pro Ala Trp Trp His Gly Gln Pro Met Trp Leu Thr
210                 215                 220

Ala Met Tyr Gln Gly Leu Lys Ala Ala Thr Tyr Phe Trp Pro Gly Ser
225                 230                 235                 240

Glu Val Ala Ile Asn Gly Ser Phe Pro Ser Ile Tyr Met Pro Tyr Asn
                245                 250                 255

Gly Ser Val Pro Phe Glu Glu Arg Ile Ser Thr Leu Leu Lys Trp Leu
            260                 265                 270

Asp Leu Pro Lys Ala Glu Arg Pro Arg Phe Tyr Thr Met Tyr Phe Glu
        275                 280                 285

Glu Pro Asp Ser Ser Gly His Ala Gly Gly Pro Val Ser Ala Arg Val
290                 295                 300

Ile Lys Ala Leu Gln Val Val Asp His Ala Phe Gly Met Leu Met Glu
305                 310                 315                 320

Gly Leu Lys Gln Arg Asn Leu His Asn Cys Val Asn Ile Ile Leu Leu
                325                 330                 335
```

```
Ala Asp His Gly Met Asp Gln Thr Tyr Cys Asn Lys Met Glu Tyr Met
            340                 345                 350

Thr Asp Tyr Phe Pro Arg Ile Asn Phe Phe Tyr Met Tyr Glu Gly Pro
            355                 360                 365

Ala Pro Arg Ile Arg Ala His Asn Ile Pro His Asp Phe Phe Ser Phe
370                 375                 380

Asn Ser Glu Glu Ile Val Arg Asn Leu Ser Cys Arg Lys Pro Asp Gln
385                 390                 395                 400

His Phe Lys Pro Tyr Leu Thr Pro Asp Leu Pro Lys Arg Leu His Tyr
                405                 410                 415

Ala Lys Asn Val Arg Ile Asp Lys Val His Leu Phe Val Asp Gln Gln
                420                 425                 430

Trp Leu Ala Val Arg Ser Lys Ser Asn Thr Asn Cys Gly Gly Gly Asn
            435                 440                 445

His Gly Tyr Asn Asn Glu Phe Arg Ser Met Glu Ala Ile Phe Leu Ala
            450                 455                 460

His Gly Pro Ser Phe Lys Glu Lys Thr Glu Val Glu Pro Phe Glu Asn
465                 470                 475                 480

Ile Glu Val Tyr Asn Leu Met Cys Asp Leu Leu Arg Ile Gln Pro Ala
                485                 490                 495

Pro Asn Asn Gly Thr His Gly Ser Leu Asn His Leu Leu Lys Val Pro
                500                 505                 510

Phe Tyr Glu Pro Ser His Ala Glu Glu Val Ser Lys Phe Ser Val Cys
            515                 520                 525

Gly Phe Ala Asn Pro Leu Pro Thr Glu Ser Leu Asp Cys Phe Cys Pro
            530                 535                 540

His Leu Gln Asn Ser Thr Gln Leu Glu Gln Val Asn Gln Met Leu Asn
545                 550                 555                 560

Leu Thr Gln Glu Glu Ile Thr Ala Thr Val Lys Val Asn Leu Pro Phe
                565                 570                 575

Gly Arg Pro Arg Val Leu Gln Lys Asn Val Asp His Cys Leu Leu Tyr
            580                 585                 590

His Arg Glu Tyr Val Ser Gly Phe Gly Lys Ala Met Arg Met Pro Met
            595                 600                 605

Trp Ser Ser Tyr Thr Val Pro Gln Leu Gly Asp Thr Ser Pro Leu Pro
            610                 615                 620

Pro Thr Val Pro Asp Cys Leu Arg Ala Asp Val Arg Val Pro Pro Ser
625                 630                 635                 640

Glu Ser Gln Lys Cys Ser Phe Tyr Leu Ala Asp Lys Asn Ile Thr His
                645                 650                 655

Gly Phe Leu Tyr Pro Pro Ala Ser Asn Arg Thr Ser Asp Ser Gln Tyr
            660                 665                 670

Asp Ala Leu Ile Thr Ser Asn Leu Val Pro Met Tyr Glu Glu Phe Arg
            675                 680                 685

Lys Met Trp Asp Tyr Phe His Ser Val Leu Leu Ile Lys His Ala Thr
            690                 695                 700

Glu Arg Asn Gly Val Asn Val Val Ser Gly Pro Ile Phe Asp Tyr Asn
705                 710                 715                 720

Tyr Asp Gly His Phe Asp Ala Pro Asp Glu Ile Thr Lys His Leu Ala
                725                 730                 735

Asn Thr Asp Val Pro Ile Pro Thr His Tyr Phe Val Val Leu Thr Ser
                740                 745                 750

Cys Lys Asn Lys Ser His Thr Pro Glu Asn Cys Pro Gly Trp Leu Asp
```

```
                755             760             765
Val Leu Pro Phe Ile Ile Pro His Arg Pro Thr Asn Val Glu Ser Cys
    770             775             780

Pro Glu Gly Lys Pro Glu Ala Leu Trp Val Glu Arg Phe Thr Ala
785             790             795             800

His Ile Ala Arg Val Arg Asp Val Glu Leu Leu Thr Gly Leu Asp Phe
                805             810             815

Tyr Gln Asp Lys Val Gln Pro Val Ser Glu Ile Leu Gln Leu Lys Thr
            820             825             830

Tyr Leu Pro Thr Phe Glu Thr Thr Ile
        835             840

<210> SEQ ID NO 15
<211> LENGTH: 1266
<212> TYPE: DNA
<213> ORGANISM: Homo sapiens

<400> SEQUENCE: 15
ctggggcctc agtgaggtct cctgcaaggc ttctggatac accttcaccg gctactatat    60
gcactgggtg cgacaggccc ctggacaagg cttgagtgg atgggatgga tcaaccctaa   120
cagtggtggc acaaactatg cacagaagtt tcagggcaga gtcaccatga ccagggacac   180
gtccatcagc acagcctaca tggagctgag caggctgaga tctgacgaca cggccgtgta   240
ttactgtgcg cgagaattac gatattttgg ctggttatta tcctcccttg actactgggg   300
ccagggaacc ctggtcaccg tctcctcagc ctccaccaag ggcccatcgg tcttcccccct  360
ggcgccctgc tccaggagca cctccgagag cacagcggcc ctgggctgcc tggtcaagga   420
ctacttcccc gaaccggtga cggtgtcgtg gaactcaggc gctctgacca gcggcgtgca   480
caccttccca gctgtcctac agtcctcagg actctactcc ctcagcagcg tggtgaccgt   540
gccctccagc aacttcggca cccagaccta cacctgcaac gtagatcaca agcccagcaa   600
caccaaggtg gacaagacag ttgagcgcaa atgttgtgtc gagtgcccac cgtgcccagc   660
accacctgtg gcaggaccgt cagtcttcct cttccccca aaacccaagg acaccctcat    720
gatctcccgg acccctgagg tcacgtgcgt ggtggtggac gtgagccacg aagaccccga   780
ggtccagttc aactggtacg tggacggcgt ggaggtgcat aatgccaaga caaagccacg   840
ggaggagcag ttcaacagca cgttccgtgt ggtcagcgtc ctcaccgttg tgcaccagga   900
ctggctgaac ggcaaggagt acaagtgcaa ggtctccaac aaaggcctcc cagcccccat   960
cgagaaaacc atctccaaaa ccaaagggca gccccgagaa ccacaggtgt acaccctgcc  1020
cccatcccgg gaggagatga ccaagaacca ggtcagcctg acctgcctgg tcaaaggctt  1080
ctaccccagc gacatcgccg tggagtggga gagcaatggg cagccggaga acaactacaa  1140
gaccacacct cccatgctgg actccgacgg ctccttcttc ctttacagca agctcaccgt  1200
ggacaagagc aggtggcagc aggggaacgt cttctcatgc tccgtgatgc atgaggctct  1260
gcacaa                                                             1266

<210> SEQ ID NO 16
<211> LENGTH: 421
<212> TYPE: PRT
<213> ORGANISM: Homo sapiens

<400> SEQUENCE: 16

Trp Gly Leu Ser Glu Val Ser Cys Lys Ala Ser Gly Tyr Thr Phe Thr
1               5                   10                  15
```

Gly Tyr Tyr Met His Trp Val Arg Gln Ala Pro Gly Gln Gly Leu Glu
             20                  25                  30

Trp Met Gly Trp Ile Asn Pro Asn Ser Gly Gly Thr Asn Tyr Ala Gln
         35                  40                  45

Lys Phe Gln Gly Arg Val Thr Met Thr Arg Asp Thr Ser Ile Ser Thr
 50                  55                  60

Ala Tyr Met Glu Leu Ser Arg Leu Arg Ser Asp Asp Thr Ala Val Tyr
 65                  70                  75                  80

Tyr Cys Ala Arg Glu Leu Arg Tyr Phe Gly Trp Leu Leu Ser Ser Leu
                 85                  90                  95

Asp Tyr Trp Gly Gln Gly Thr Leu Val Thr Val Ser Ser Ala Ser Thr
            100                 105                 110

Lys Gly Pro Ser Val Phe Pro Leu Ala Pro Cys Ser Arg Ser Thr Ser
        115                 120                 125

Glu Ser Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Asn Phe Gly Thr Gln Thr Tyr Thr Cys
            180                 185                 190

Asn Val Asp His Lys Pro Ser Asn Thr Lys Val Asp Lys Thr Val Glu
        195                 200                 205

Arg Lys Cys Cys Val Glu Cys Pro Pro Cys Pro Ala Pro Pro Val Ala
    210                 215                 220

Gly Pro Ser Val Phe Leu Phe Pro Pro Lys Pro Lys Asp Thr Leu Met
225                 230                 235                 240

Ile Ser Arg Thr Pro Glu Val Thr Cys Val Val Val Asp Val Ser His
                245                 250                 255

Glu Asp Pro Glu Val Gln Phe Asn Trp Tyr Val Asp Gly Val Glu Val
            260                 265                 270

His Asn Ala Lys Thr Lys Pro Arg Glu Glu Gln Phe Asn Ser Thr Phe
        275                 280                 285

Arg Val Val Ser Val Leu Thr Val Val His Gln Asp Trp Leu Asn Gly
    290                 295                 300

Lys Glu Tyr Lys Cys Lys Val Ser Asn Lys Gly Leu Pro Ala Pro Ile
305                 310                 315                 320

Glu Lys Thr Ile Ser Lys Thr Lys Gly Gln Pro Arg Glu Pro Gln Val
                325                 330                 335

Tyr Thr Leu Pro Pro Ser Arg Glu Glu Met Thr Lys Asn Gln Val Ser
            340                 345                 350

Leu Thr Cys Leu Val Lys Gly Phe Tyr Pro Ser Asp Ile Ala Val Glu
        355                 360                 365

Trp Glu Ser Asn Gly Gln Pro Glu Asn Asn Tyr Lys Thr Thr Pro Pro
    370                 375                 380

Met Leu Asp Ser Asp Gly Ser Phe Phe Leu Tyr Ser Lys Leu Thr Val
385                 390                 395                 400

Asp Lys Ser Arg Trp Gln Gln Gly Asn Val Phe Ser Cys Ser Val Met
                405                 410                 415

His Glu Ala Leu His
            420

<210> SEQ ID NO 17

```
<211> LENGTH: 680
<212> TYPE: DNA
<213> ORGANISM: Homo sapiens

<400> SEQUENCE: 17
agctcctggg gctcctgcta ctctggctcc gaggtgccag atgtgacatc cagatgaccc      60
agtctccatc ctccctgtct gcatctgtag gagacagagt caccatcact tgccgggcaa     120
gtcagagcat tagcagctat ttaaattggt ttcagcagaa accagggaaa gcccctaagc     180
tcctgatcta tgctgcatcc agtttgcaaa gtggggtccc atcaaggttc agtggcagtg     240
aatctgggac agatttcact ctcaccatca gcagtctgca acctgaagat tttgctactt     300
actcctgtca acagagttac agtttcccgc tcactttcgg cggagggacc aaggtggaga     360
tcaaacgaac tgtggctgca ccatctgtct tcatcttccc gccatctgat gagcagttga     420
aatctggaac tgcctctgtt gtgtgcctgc tgaataactt ctatcccaga gaggccaaag     480
tacagtggaa ggtggataac gccctccaat cgggtaactc ccaggagagt gtcacagagc     540
aggacagcaa ggacagcacc tacagcctca gcagcaccct gacgctgagc aaagcagact     600
acgagaaaca caaagtctac gcctgcgaag tcacccatca gggcctgagc tcgcccgtca     660
caaagagctt caacagggga                                                 680

<210> SEQ ID NO 18
<211> LENGTH: 226
<212> TYPE: PRT
<213> ORGANISM: Homo sapiens

<400> SEQUENCE: 18

Leu Leu Gly Leu Leu Leu Trp Leu Arg Gly Ala Arg Cys Asp Ile
1               5                   10                  15

Gln Met Thr Gln Ser Pro Ser Ser Leu Ser Ala Ser Val Gly Asp Arg
            20                  25                  30

Val Thr Ile Thr Cys Arg Ala Ser Gln Ser Ile Ser Ser Tyr Leu Asn
        35                  40                  45

Trp Phe Gln Gln Lys Pro Gly Lys Ala Pro Lys Leu Leu Ile Tyr Ala
    50                  55                  60

Ala Ser Ser Leu Gln Ser Gly Val Pro Ser Arg Phe Ser Gly Ser Glu
65                  70                  75                  80

Ser Gly Thr Asp Phe Thr Leu Thr Ile Ser Ser Leu Gln Pro Glu Asp
                85                  90                  95

Phe Ala Thr Tyr Ser Cys Gln Gln Ser Tyr Ser Phe Pro Leu Thr Phe
            100                 105                 110

Gly Gly Gly Thr Lys Val Glu Ile Lys Arg Thr Val Ala Ala Pro Ser
        115                 120                 125

Val Phe Ile Phe Pro Pro Ser Asp Glu Gln Leu Lys Ser Gly Thr Ala
    130                 135                 140

Ser Val Val Cys Leu Leu Asn Asn Phe Tyr Pro Arg Glu Ala Lys Val
145                 150                 155                 160

Gln Trp Lys Val Asp Asn Ala Leu Gln Ser Gly Asn Ser Gln Glu Ser
                165                 170                 175

Val Thr Glu Gln Asp Ser Lys Asp Ser Thr Tyr Ser Leu Ser Ser Thr
            180                 185                 190

Leu Thr Leu Ser Lys Ala Asp Tyr Glu Lys His Lys Val Tyr Ala Cys
        195                 200                 205

Glu Val Thr His Gln Gly Leu Ser Ser Pro Val Thr Lys Ser Phe Asn
    210                 215                 220
```

Arg Gly
225

<210> SEQ ID NO 19
<211> LENGTH: 1405
<212> TYPE: DNA
<213> ORGANISM: Homo sapiens
<220> FEATURE:
<221> NAME/KEY: misc_feature
<222> LOCATION: 1351
<223> OTHER INFORMATION: n = a, t, c, or g.

<400> SEQUENCE: 19

```
ctcaacaacc acatctgtcc tctagagaaa accctgtgag cacagctcct caccatggac      60
tggacctgga ggatcctctt cttggtggca gcagctacaa gtgcccactc ccaggtgcag     120
ctggtgcagt ctggggctga ggtgaagaag cctgggcct cagtgaaggt ctcctgcaag      180
gcttctggat acaccttcac cagttatgat atccactggg tgcgacaggc cactggacaa     240
gggcttgagt ggatgggatg gatgaaccct aacagtggta acacagtcta tgcacagaag     300
ttccagggca gagtcaccat gaccaggaac acctccataa gcacagccta catggagctg     360
agcagcctga gatctgagga cacggccgtg tattactgtg cgagaacagt attactatgg     420
ccctttgact actggggcca gggaaccctg gtcaccgtct cctcagcctc caccaagggc     480
ccatcggtct tccccctggc gccctgctcc aggagcacct ccgagagcac agcggccctg     540
ggctgcctgg tcaaggacta cttccccgaa ccggtgacgg tgtcgtggaa ctcaggcgct     600
ctgaccagcg gcgtgcacac cttcccagct gtcctacagt cctcaggact ctactccctc     660
agcagcgtgg tgaccgtgcc ctccagcaac ttcggcaccc agacctacac ctgcaacgta     720
gatcacaagc ccagcaacac caaggtggac aagacagttg agcgcaaatg ttgtgtcgag     780
tgcccaccgt gcccagcacc acctgtggca ggaccgtcag tcttcctctt cccccccaaaa     840
cccaaggaca ccctcatgat ctcccggacc cctgaggtca cgtgcgtggt ggtggacgtg     900
agccacgaag accccgaggt ccagttcaac tggtacgtgg acggcgtgga ggtgcataat     960
gccaagacaa agccacggga ggagcagttc aacagcacgt tccgtgtggt cagcgtcctc    1020
accgttgtgc accaggactg gctgaacggc aaggagtaca agtgcaaggt ctccaacaaa    1080
ggcctcccag cccccatcga gaaaaccatc tccaaaacca agggcagccc cgagaaccca    1140
caggtgtaca ccctgccccc atcccgggag gagatgacca agaaccaggt cagcctgacc    1200
tgcctggtca aaggcttcta ccccagcgac atcgccgtgg agtgggagag caatgggcag    1260
ccggagaaca actacaagac cacacctccc atgctggact ccgacggctc cttcttcctt    1320
tacagcaagc tcaccgtgga caagagcagg nggcagcagg ggaacgtctt ctcatgctcc    1380
gtgatgcatg aggctctgca caacc                                          1405
```

<210> SEQ ID NO 20
<211> LENGTH: 450
<212> TYPE: PRT
<213> ORGANISM: Homo sapiens
<220> FEATURE:
<221> NAME/KEY: VARIANT
<222> LOCATION: 433
<223> OTHER INFORMATION: Xaa = Any amino acid.

<400> SEQUENCE: 20

Met Asp Trp Thr Trp Arg Ile Leu Phe Leu Val Ala Ala Thr Ser
1               5                   10                  15

Ala His Ser Gln Val Gln Leu Val Gln Ser Gly Ala Glu Val Lys Lys
            20                  25                  30

```
Pro Gly Ala Ser Val Lys Val Ser Cys Lys Ala Ser Gly Tyr Thr Phe
            35                  40                  45
Thr Ser Tyr Asp Ile His Trp Val Arg Gln Ala Thr Gly Gln Gly Leu
 50                  55                  60
Glu Trp Met Gly Trp Met Asn Pro Asn Ser Gly Asn Thr Val Tyr Ala
 65                  70                  75                  80
Gln Lys Phe Gln Gly Arg Val Thr Met Thr Arg Asn Thr Ser Ile Ser
                    85                  90                  95
Thr Ala Tyr Met Glu Leu Ser Ser Leu Arg Ser Glu Asp Thr Ala Val
                100                 105                 110
Tyr Tyr Cys Ala Arg Thr Val Leu Leu Trp Pro Phe Asp Tyr Trp Gly
            115                 120                 125
Gln Gly Thr Leu Val Thr Val Ser Ser Ala Ser Thr Lys Gly Pro Ser
        130                 135                 140
Val Phe Pro Leu Ala Pro Cys Ser Arg Ser Thr Ser Glu Ser Thr Ala
145                 150                 155                 160
Ala Leu Gly Cys Leu Val Lys Asp Tyr Phe Pro Glu Pro Val Thr Val
                165                 170                 175
Ser Trp Asn Ser Gly Ala Leu Thr Ser Gly Val His Thr Phe Pro Ala
            180                 185                 190
Val Leu Gln Ser Ser Gly Leu Tyr Ser Leu Ser Ser Val Val Thr Val
        195                 200                 205
Pro Ser Ser Asn Phe Gly Thr Gln Thr Tyr Thr Cys Asn Val Asp His
        210                 215                 220
Lys Pro Ser Asn Thr Lys Val Asp Lys Thr Val Glu Arg Lys Cys Cys
225                 230                 235                 240
Val Glu Cys Pro Pro Cys Pro Ala Pro Val Ala Gly Pro Ser Val
                245                 250                 255
Phe Leu Phe Pro Pro Lys Pro Lys Asp Thr Leu Met Ile Ser Arg Thr
                260                 265                 270
Pro Glu Val Thr Cys Val Val Val Asp Val Ser His Glu Asp Pro Glu
            275                 280                 285
Val Gln Phe Asn Trp Tyr Val Asp Gly Val Glu Val His Asn Ala Lys
        290                 295                 300
Thr Lys Pro Arg Glu Glu Gln Phe Asn Ser Thr Phe Arg Val Val Ser
305                 310                 315                 320
Val Leu Thr Val Val His Gln Asp Trp Leu Asn Gly Lys Glu Tyr Lys
                325                 330                 335
Cys Lys Val Ser Asn Lys Gly Leu Pro Ala Pro Ile Glu Lys Thr Ile
            340                 345                 350
Ser Lys Thr Lys Gly Gln Pro Arg Glu Pro Gln Val Tyr Thr Leu Pro
        355                 360                 365
Pro Ser Arg Glu Glu Met Thr Lys Asn Gln Val Ser Leu Thr Cys Leu
    370                 375                 380
Val Lys Gly Phe Tyr Pro Ser Asp Ile Ala Val Glu Trp Glu Ser Asn
385                 390                 395                 400
Gly Gln Pro Glu Asn Asn Tyr Lys Thr Thr Pro Pro Met Leu Asp Ser
                405                 410                 415
Asp Gly Ser Phe Phe Leu Tyr Ser Lys Leu Thr Val Asp Lys Ser Arg
            420                 425                 430
Xaa Gln Gln Gly Asn Val Phe Ser Cys Ser Val Met His Glu Ala Leu
        435                 440                 445
His Asn
```

<210> SEQ ID NO 21
<211> LENGTH: 685
<212> TYPE: DNA
<213> ORGANISM: Homo sapiens

<400> SEQUENCE: 21

```
tctggatctc tggtgcctac ggggacatcg tgatgaccca gtctccagac tccctggctg    60
tgtctctggg cgagagggcc accatcaact gcaagtccag ccagagtgtt ttatacagct   120
ccaagaataa gaactactta gcttggtacc agcagaaacc aggacagcct cctaagctgc   180
tcatttactg ggcatctacc cgggaatccg gggtccctga ccgattcagt ggcagcgggt   240
ctgggacaga tttcactctc accatcagca gcctgcaggc tgaagatgtg gcagtttatt   300
actgtcagca atattatagt actcctccgt ggacgttcgg ccaagggacc aaggtggaaa   360
tcaaacgaac tgtggctgca ccatctgtct tcatcttccc gccatctgat gagcagttga   420
aatctggaac tgcctctgtt gtgtgcctgc tgaataactt ctatcccaga gaggccaaag   480
tacagtggaa ggtggataac gccctccaat cgggtaactc ccaggagagt gtcacagagc   540
aggacagcaa ggacagcacc tacagcctca gcagcaccct gacgctgagc aaagcagact   600
acgagaaaca caaagtctac gcctgcgaag tcacccatca gggcctgagc tcgcccgtca   660
caaagagctt caacagggga gagtg                                         685
```

<210> SEQ ID NO 22
<211> LENGTH: 227
<212> TYPE: PRT
<213> ORGANISM: Homo sapiens

<400> SEQUENCE: 22

```
Trp Ile Ser Gly Ala Tyr Gly Asp Ile Val Met Thr Gln Ser Pro Asp
1               5                   10                  15
Ser Leu Ala Val Ser Leu Gly Glu Arg Ala Thr Ile Asn Cys Lys Ser
            20                  25                  30
Ser Gln Ser Val Leu Tyr Ser Ser Lys Asn Lys Asn Tyr Leu Ala Trp
        35                  40                  45
Tyr Gln Gln Lys Pro Gly Gln Pro Pro Lys Leu Leu Ile Tyr Trp Ala
    50                  55                  60
Ser Thr Arg Glu Ser Gly Val Pro Asp Arg Phe Ser Gly Ser Gly Ser
65                  70                  75                  80
Gly Thr Asp Phe Thr Leu Thr Ile Ser Ser Leu Gln Ala Glu Asp Val
                85                  90                  95
Ala Val Tyr Tyr Cys Gln Gln Tyr Tyr Ser Thr Pro Pro Trp Thr Phe
            100                 105                 110
Gly Gln Gly Thr Lys Val Glu Ile Lys Arg Thr Val Ala Ala Pro Ser
        115                 120                 125
Val Phe Ile Phe Pro Pro Ser Asp Glu Gln Leu Lys Ser Gly Thr Ala
    130                 135                 140
Ser Val Val Cys Leu Leu Asn Asn Phe Tyr Pro Arg Glu Ala Lys Val
145                 150                 155                 160
Gln Trp Lys Val Asp Asn Ala Leu Gln Ser Gly Asn Ser Gln Glu Ser
                165                 170                 175
Val Thr Glu Gln Asp Ser Lys Asp Ser Thr Tyr Ser Leu Ser Ser Thr
            180                 185                 190
Leu Thr Leu Ser Lys Ala Asp Tyr Glu Lys His Lys Val Tyr Ala Cys
        195                 200                 205
```

Glu Val Thr His Gln Gly Leu Ser Ser Pro Val Thr Lys Ser Phe Asn
    210                 215                 220

Arg Gly Glu
225

<210> SEQ ID NO 23
<211> LENGTH: 387
<212> TYPE: DNA
<213> ORGANISM: Homo sapiens

<400> SEQUENCE: 23
agtctggggg aggcttggta cagcctgggg ggtccctgag actctcctgt gcagcctctg      60
gattcacctt tagcagctat gccatgagct gggtccgcca ggctccaggg aaggggctgg     120
agtgggtctc agctattagt ggtagtgatg gtagcccata ctacgcagac tccgtgaagg     180
gccggttcac catctccaga gacaattcca agaacacgct gtatctgcaa atgaacagcc     240
tgagagccga ggacacggcc gtatattact gtgcgaaaga tggttatagc agtggctgga     300
actactttga ctactggggc cagggaaccc tggtcaccgt ctcctcagcc tccaccaagg     360
gcccatcggt cttccccctg gcaccct                                         387

<210> SEQ ID NO 24
<211> LENGTH: 128
<212> TYPE: PRT
<213> ORGANISM: Homo sapiens

<400> SEQUENCE: 24

Ser Gly Gly Gly Leu Val Gln Pro Gly Gly Ser Leu Arg Leu Ser Cys
1               5                   10                  15

Ala Ala Ser Gly Phe Thr Phe Ser Ser Tyr Ala Met Ser Trp Val Arg
            20                  25                  30

Gln Ala Pro Gly Lys Gly Leu Glu Trp Val Ser Ala Ile Ser Gly Ser
        35                  40                  45

Asp Gly Ser Pro Tyr Tyr Ala Asp Ser Val Lys Gly Arg Phe Thr Ile
    50                  55                  60

Ser Arg Asp Asn Ser Lys Asn Thr Leu Tyr Leu Gln Met Asn Ser Leu
65                  70                  75                  80

Arg Ala Glu Asp Thr Ala Val Tyr Tyr Cys Ala Lys Asp Gly Tyr Ser
                85                  90                  95

Ser Gly Trp Asn Tyr Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

<210> SEQ ID NO 25
<211> LENGTH: 680
<212> TYPE: DNA
<213> ORGANISM: Homo sapiens

<400> SEQUENCE: 25
tggatctctg gtgcctacgg ggacatcgtg atgacccagt ctccagactc cctggctgtg      60
tctctgggcg agagggccac catcaactgc aagtccagcc agagtgtttt atacagctcc     120
aacaataaga actacttagc ttggtaccag cagaaaccag gacagcctcc caagctgctc     180
atttactggg catctacccg ggaatccggg gtccctgacc gattcagtgg cagcgggtct     240
gggacagatt tcactctcac catcagcagc ctgcaggctg aagatgtggc agtttattac     300
tgtcaggaat attatagtac catgtgcagt tttggccagg ggaccaagct ggagatcaaa     360

```
cgaactgtgg ctgcaccatc tgtcttcatc ttcccgccat ctgatgagca gttgaaatct    420
ggaactgcct ctgttgtgtg cctgctgaat aacttctatc ccagagaggc caaagtacag    480
tggaaggtgg ataacgccct ccaatcgggt aactcccagg agagtgtcac agagcaggac    540
agcaaggaca gcacctacag cctcagcagc accctgacgc tgagcaaagc agactacgag    600
aaacacaaag tctacgcctg cgaagtcacc catcagggcc tgagctcgcc cgtcacaaag    660
agcttcaaca ggggagagtg                                                680
```

\<210\> SEQ ID NO 26  
\<211\> LENGTH: 226  
\<212\> TYPE: PRT  
\<213\> ORGANISM: Homo sapiens

\<400\> SEQUENCE: 26

```
Trp Ile Ser Gly Ala Tyr Gly Asp Ile Val Met Thr Gln Ser Pro Asp
1               5                   10                  15

Ser Leu Ala Val Ser Leu Gly Glu Arg Ala Thr Ile Asn Cys Lys Ser
            20                  25                  30

Ser Gln Ser Val Leu Tyr Ser Ser Asn Asn Lys Asn Tyr Leu Ala Trp
        35                  40                  45

Tyr Gln Gln Lys Pro Gly Gln Pro Pro Lys Leu Leu Ile Tyr Trp Ala
    50                  55                  60

Ser Thr Arg Glu Ser Gly Val Pro Asp Arg Phe Ser Gly Ser Gly Ser
65                  70                  75                  80

Gly Thr Asp Phe Thr Leu Thr Ile Ser Ser Leu Gln Ala Glu Asp Val
                85                  90                  95

Ala Val Tyr Tyr Cys Gln Glu Tyr Tyr Ser Thr Met Cys Ser Phe Gly
            100                 105                 110

Gln Gly Thr Lys Leu Glu Ile Lys Arg Thr Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
    210                 215                 220

Gly Glu
225
```

\<210\> SEQ ID NO 27  
\<211\> LENGTH: 408  
\<212\> TYPE: DNA  
\<213\> ORGANISM: Homo sapiens

\<400\> SEQUENCE: 27

```
gtggagtctg ggggaggcgt ggtccagcct gggaggtccc tgagactctc ctgtgcagcg     60
tctggattca ccttcagaag ctatggcatg cactgggtcc gccaggctcc aggcaagggg    120
ctggagtggg tggcagttat atggtctgat ggaagtaata atactatgc  agactccgtg    180
```

```
aagggccgat ttaccatctc cagagacaat tccaagaaca cgctgtatct gcaaatgaac    240
agcctgagag ccgaggacac ggctgtgtat tactgtgcga gagagggta ctatggttcg     300 gggagttatt actactacta cggtatggac gtctggggcc aagggaccac ggtcaccgtc    360
tcctcagcct ccaccaaggg cccatcggtc ttccccctgg caccctcc                 408
```

<210> SEQ ID NO 28
<211> LENGTH: 136
<212> TYPE: PRT
<213> ORGANISM: Homo sapiens

<400> SEQUENCE: 28

Val Glu Ser Gly Gly Gly Val Val Gln Pro Gly Arg Ser Leu Arg Leu
1               5                   10                  15

Ser Cys Ala Ala Ser Gly Phe Thr Phe Arg Ser Tyr Gly Met His Trp
            20                  25                  30

Val Arg Gln Ala Pro Gly Lys Gly Leu Glu Trp Val Ala Val Ile Trp
        35                  40                  45

Ser Asp Gly Ser Asn Lys Tyr Tyr Ala Asp Ser Val Lys Gly Arg Phe
    50                  55                  60

Thr Ile Ser Arg Asp Asn Ser Lys Asn Thr Leu Tyr Leu Gln Met Asn
65                  70                  75                  80

Ser Leu Arg Ala Glu Asp Thr Ala Val Tyr Tyr Cys Ala Arg Glu Gly
                85                  90                  95

Tyr Tyr Gly Ser Gly Ser Tyr Tyr Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser
    130                 135

<210> SEQ ID NO 29
<211> LENGTH: 678
<212> TYPE: DNA
<213> ORGANISM: Homo sapiens

<400> SEQUENCE: 29

```
ctcctgaccc tcctcactca ctctgcagtg tcagtggtcc aggcagggct gactcagcca    60
ccctcggtgt ccaagggctt gagacagacc gccacactca cctgcactgg aacagcaac    120 aatgttggca cccaaggagc agcttggctg cagcagcacc agggccaccc tcccaaactc    180
ctttcctaca ggaataacaa ccggccctca gggatctcag agagattatc tgcatccacg    240
tcaggaaaca cagcctccct gaccattact ggactccagc tgaggacga ggctgactat    300 tactgctcag catgggacag cagcctcagt gctgtggtat cggcggagg gaccaagctg    360 accgtcctag gtcagcccaa ggctgccccc tcggtcactc tgttcccgcc ctcctctgag    420
gagcttcaag ccaacaaggc cacactggtg tgtctcataa gtgacttcta cccgggagcc    480
gtgacagtgg cctggaaggc agatagcagc cccgtcaagg cgggagtgga gaccaccaca    540
ccctccaaac aaagcaacaa caagtacgcg gccagcagct atctgagcct gacgcctgag    600
cagtggaagt cccacagaag ctacagctgc caggtcacgc atgaaggag caccgtggag    660 aagacagtgg cccctaca                                                  678
```

<210> SEQ ID NO 30
<211> LENGTH: 226
<212> TYPE: PRT
<213> ORGANISM: Homo sapiens

<400> SEQUENCE: 30

| Leu | Leu | Thr | Leu | Leu | Thr | His | Ser | Ala | Val | Ser | Val | Gln | Ala | Gly |
| 1 | | | | 5 | | | | | 10 | | | | | 15 |
| Leu | Thr | Gln | Pro | Pro | Ser | Val | Ser | Lys | Gly | Leu | Arg | Gln | Thr | Ala | Thr |
| | | | 20 | | | | | 25 | | | | | 30 | | |
| Leu | Thr | Cys | Thr | Gly | Asn | Ser | Asn | Asn | Val | Gly | Thr | Gln | Gly | Ala | Ala |
| | | | 35 | | | | | 40 | | | | | 45 | | |
| Trp | Leu | Gln | Gln | His | Gln | Gly | His | Pro | Pro | Lys | Leu | Leu | Ser | Tyr | Arg |
| | 50 | | | | | 55 | | | | | 60 | | | | |
| Asn | Asn | Asn | Arg | Pro | Ser | Gly | Ile | Ser | Glu | Arg | Leu | Ser | Ala | Ser |
| 65 | | | | | 70 | | | | | 75 | | | | | 80 |
| Ser | Gly | Asn | Thr | Ala | Ser | Leu | Thr | Ile | Thr | Gly | Leu | Gln | Pro | Glu | Asp |
| | | | | 85 | | | | | 90 | | | | | 95 | |
| Glu | Ala | Asp | Tyr | Tyr | Cys | Ser | Ala | Trp | Asp | Ser | Ser | Leu | Ser | Ala | Val |
| | | | 100 | | | | | 105 | | | | | 110 | | |
| Val | Phe | Gly | Gly | Gly | Thr | Lys | Leu | Thr | Val | Leu | Gly | Gln | Pro | Lys | Ala |
| | | 115 | | | | | 120 | | | | | 125 | | | |
| Ala | Pro | Ser | Val | Thr | Leu | Phe | Pro | Pro | Ser | Ser | Glu | Glu | Leu | Gln | Ala |
| | | 130 | | | | | 135 | | | | | 140 | | | |
| Asn | Lys | Ala | Thr | Leu | Val | Cys | Leu | Ile | Ser | Asp | Phe | Tyr | Pro | Gly | Ala |
| 145 | | | | | 150 | | | | | 155 | | | | | 160 |
| Val | Thr | Val | Ala | Trp | Lys | Ala | Asp | Ser | Ser | Pro | Val | Lys | Ala | Gly | Val |
| | | | | 165 | | | | | 170 | | | | | 175 | |
| Glu | Thr | Thr | Thr | Pro | Ser | Lys | Gln | Ser | Asn | Asn | Lys | Tyr | Ala | Ala | Ser |
| | | | 180 | | | | | 185 | | | | | 190 | | |
| Ser | Tyr | Leu | Ser | Leu | Thr | Pro | Glu | Gln | Trp | Lys | Ser | His | Arg | Ser | Tyr |
| | | 195 | | | | | 200 | | | | | 205 | | | |
| Ser | Cys | Gln | Val | Thr | His | Glu | Gly | Ser | Thr | Val | Glu | Lys | Thr | Val | Ala |
| | | 210 | | | | | 215 | | | | | 220 | | | |
| Pro | Thr |
| 225 | |

<210> SEQ ID NO 31
<211> LENGTH: 1250
<212> TYPE: DNA
<213> ORGANISM: Homo sapiens

<400> SEQUENCE: 31

```
cctgtccctc acctgcactg tctctggtgg ctccatcagt agttactact ggagctggat     60
ccggcagtcc gccgggaagg gactggagtg gattggcgt atctataccg tgtgagcac    120
caactacaac ccctccctca agagtcgagt caccatgtca gtagacacgt ccaagaacca    180
gttctccctg aagctgagct ctgtgaccgc cgcggacacg gccgtgtatt actgtgcgag    240
agattactat gatagtagtg gttattaccc ctttgactac tggggccagg gaaccctggt    300
caccgtctcc tcagcctcca ccaagggccc atcggtcttc cccctggcgc cctgctccag    360
gagcacctcc gagagcacag cggccctggg ctgcctggtc aaggactact ccccgaacc    420
ggtgacggtg tcgtggaact caggcgctct gaccagcggc gtgcacacct tcccagctgt    480
cctacagtcc tcaggactct actccctcag cagcgtggtg accgtgccct ccagcaactt    540
cggcacccag acctacacct gcaacgtaga tcacaagccc agcaacacca aggtggacaa    600
gacagttgag cgcaaatgtt gtgtcgagtg cccaccgtgc ccagcaccac ctgtggcagg    660
accgtcagtc ttcctcttcc ccccaaaacc caaggacacc ctcatgatct cccggacccc    720
```

```
tgaggtcacg tgcgtggtgg tggacgtgag ccacgaagac cccgaggtcc agttcaactg    780
gtacgtggac ggcgtggagg tgcataatgc caagacaaag ccacgggagg agcagttcaa    840
cagcacgttc cgtgtggtca gcgtcctcac cgttgtgcac caggactggc tgaacggcaa    900
ggagtacaag tgcaaggtct ccaacaaagg cctcccagcc cccatcgaga aaaccatctc    960
caaaaccaaa gggcagcccc gagaaccaca ggtgtacacc ctgcccccat cccgggagga   1020
gatgaccaag aaccaggtca gcctgacctg cctggtcaaa ggcttctacc ccagcgacat   1080
cgccgtggag tgggagagca atgggcagcc ggagaacaac tacaagacca cactcccat    1140 gctggactcc gacggctcct tcttccttta cagcaagctc accgtggaca gagcaggtg    1200 gcagcagggg aacgtcttct catgctccgt gatgcatgag gctctgcaca              1250
```

<210> SEQ ID NO 32
<211> LENGTH: 416
<212> TYPE: PRT
<213> ORGANISM: Homo sapiens

<400> SEQUENCE: 32

```
Leu Ser Leu Thr Cys Thr Val Ser Gly Gly Ser Ile Ser Ser Tyr Tyr
1               5                   10                  15

Trp Ser Trp Ile Arg Gln Ser Ala Gly Lys Gly Leu Glu Trp Ile Gly
            20                  25                  30

Arg Ile Tyr Thr Gly Val Ser Thr Asn Tyr Asn Pro Ser Leu Lys Ser
        35                  40                  45

Arg Val Thr Met Ser Val Asp Thr Ser Lys Asn Gln Phe Ser Leu Lys
    50                  55                  60

Leu Ser Ser Val Thr Ala Ala Asp Thr Ala Val Tyr Tyr Cys Ala Arg
65                  70                  75                  80

Asp Tyr Tyr Asp Ser Gly Tyr Tyr Pro Phe Asp Tyr Trp Gly Gln
                85                  90                  95

Gly Thr Leu Val Thr Val Ser Ser Ala Ser Thr Lys Gly Pro Ser Val
            100                 105                 110

Phe Pro Leu Ala Pro Cys Ser Arg Ser Thr Ser Glu Ser Thr Ala Ala
        115                 120                 125

Leu Gly Cys Leu Val Lys Asp Tyr Phe Pro Glu Pro Val Thr Val Ser
    130                 135                 140

Trp Asn Ser Gly Ala Leu Thr Ser Gly Val His Thr Phe Pro Ala Val
145                 150                 155                 160

Leu Gln Ser Ser Gly Leu Tyr Ser Leu Ser Ser Val Val Thr Val Pro
                165                 170                 175

Ser Ser Asn Phe Gly Thr Gln Thr Tyr Thr Cys Asn Val Asp His Lys
            180                 185                 190

Pro Ser Asn Thr Lys Val Asp Lys Thr Val Glu Arg Lys Cys Cys Val
        195                 200                 205

Glu Cys Pro Pro Cys Pro Ala Pro Pro Val Ala Gly Pro Ser Val Phe
    210                 215                 220

Leu Phe Pro Pro Lys Pro Lys Asp Thr Leu Met Ile Ser Arg Thr Pro
225                 230                 235                 240

Glu Val Thr Cys Val Val Val Asp Val Ser His Glu Asp Pro Glu Val
                245                 250                 255

Gln Phe Asn Trp Tyr Val Asp Gly Val Glu Val His Asn Ala Lys Thr
            260                 265                 270

Lys Pro Arg Glu Glu Gln Phe Asn Ser Thr Phe Arg Val Val Ser Val
        275                 280                 285
```

```
Leu Thr Val Val His Gln Asp Trp Leu Asn Gly Lys Glu Tyr Lys Cys
            290                 295                 300
Lys Val Ser Asn Lys Gly Leu Pro Ala Pro Ile Glu Lys Thr Ile Ser
305                 310                 315                 320
Lys Thr Lys Gly Gln Pro Arg Glu Pro Gln Val Tyr Thr Leu Pro Pro
                325                 330                 335
Ser Arg Glu Glu Met Thr Lys Asn Gln Val Ser Leu Thr Cys Leu Val
            340                 345                 350
Lys Gly Phe Tyr Pro Ser Asp Ile Ala Val Glu Trp Glu Ser Asn Gly
        355                 360                 365
Gln Pro Glu Asn Asn Tyr Lys Thr Thr Pro Pro Met Leu Asp Ser Asp
    370                 375                 380
Gly Ser Phe Phe Leu Tyr Ser Lys Leu Thr Val Asp Lys Ser Arg Trp
385                 390                 395                 400
Gln Gln Gly Asn Val Phe Ser Cys Ser Val Met His Glu Ala Leu His
                405                 410                 415

<210> SEQ ID NO 33
<211> LENGTH: 678
<212> TYPE: DNA
<213> ORGANISM: Homo sapiens

<400> SEQUENCE: 33
ctcctggggc tcctgctgct ctgtttccca ggtgccagat gtgacatcca gatgacccag      60
tctccatcct cactgtctgc atctgtagga gacagagtca ccatcagttg tcgggcgagt     120
cagggcatta gcaattattt agcctggttt cagcagaaac agggaaaagc ccctaagtcc     180
ctgatctatg ctgcatccag tttgaaaat ggggtcccat caaagttcag cggcagtgga     240
tctgggacag atttcactct caccatcagc agcctgcagc ctgaagattt tgcaacttat     300
tactgccaac agtataatag ttccccattc actttcggcc tgggaccaa agtggatatc      360
agacgaactg tggctgcacc atctgtcttc atcttcccgc catctgatga gcagttgaaa     420
tctggaactg cctctgttgt gtgcctgctg aataacttct atcccagaga ggccaaagta     480
cagtggaagg tggataacgc cctccaatcg ggtaactccc aggagagtgt cacagagcag     540
gacagcaagg acagcaccta cagcctcagc agcaccctga cgctgagcaa agcagactac     600
gagaaacaca aagtctacgc ctgcgaagtc acccatcagg gcctgagctc gcccgtcaca     660
aagagcttca acagggga                                                   678

<210> SEQ ID NO 34
<211> LENGTH: 226
<212> TYPE: PRT
<213> ORGANISM: Homo sapiens

<400> SEQUENCE: 34

Leu Leu Gly Leu Leu Leu Leu Cys Phe Pro Gly Ala Arg Cys Asp Ile
1               5                   10                  15
Gln Met Thr Gln Ser Pro Ser Ser Leu Ser Ala Ser Val Gly Asp Arg
            20                  25                  30
Val Thr Ile Ser Cys Arg Ala Ser Gln Gly Ile Ser Asn Tyr Leu Ala
        35                  40                  45
Trp Phe Gln Gln Lys Pro Gly Lys Ala Pro Lys Ser Leu Ile Tyr Ala
    50                  55                  60
Ala Ser Ser Leu Glu Asn Gly Val Pro Ser Lys Phe Ser Gly Ser Gly
65                  70                  75                  80
Ser Gly Thr Asp Phe Thr Leu Thr Ile Ser Ser Leu Gln Pro Glu Asp
```

```
                85                  90                  95
Phe Ala Thr Tyr Tyr Cys Gln Gln Tyr Asn Ser Ser Pro Phe Thr Phe
            100                 105                 110

Gly Pro Gly Thr Lys Val Asp Ile Arg Arg Thr Val Ala Ala Pro Ser
            115                 120                 125

Val Phe Ile Phe Pro Pro Ser Asp Glu Gln Leu Lys Ser Gly Thr Ala
            130                 135                 140

Ser Val Val Cys Leu Leu Asn Asn Phe Tyr Pro Arg Glu Ala Lys Val
145                 150                 155                 160

Gln Trp Lys Val Asp Asn Ala Leu Gln Ser Gly Asn Ser Gln Glu Ser
                165                 170                 175

Val Thr Glu Gln Asp Ser Lys Asp Ser Thr Tyr Ser Leu Ser Ser Thr
            180                 185                 190

Leu Thr Leu Ser Lys Ala Asp Tyr Glu Lys His Lys Val Tyr Ala Cys
            195                 200                 205

Glu Val Thr His Gln Gly Leu Ser Ser Pro Val Thr Lys Ser Phe Asn
            210                 215                 220

Arg Gly
225

<210> SEQ ID NO 35
<211> LENGTH: 407
<212> TYPE: DNA
<213> ORGANISM: Homo sapiens

<400> SEQUENCE: 35
tggtggagtc tggcccagga ctggtgaagc cttcacagac cctgtccctc acctgcactg    60
tctctggtgg ctccatcaac agttttggtt actactggag ctggatccgc cagtatccag   120
gaaagggcct ggagtggatt gggttcctct atttcactgg agcacctac  tacaacccgt   180 ccctcaagag tcgagttacc atatcagtag acacgtctaa gagccagttc tccctgaagc   240
tgagctctgt gactgccgcg gacacggccg tgtattactg tgcgagagca ggtactatgg   300
ttcggggagc ccactactac ggtatggacg tctggggcca agggaccacg gtcaccgtct   360
cctcagcctc caccaagggc ccatcggtct tccccctggc accctcc              407

<210> SEQ ID NO 36
<211> LENGTH: 135
<212> TYPE: PRT
<213> ORGANISM: Homo sapiens

<400> SEQUENCE: 36

Val Glu Ser Gly Pro Gly Leu Val Lys Pro Ser Gln Thr Leu Ser Leu
1               5                   10                  15

Thr Cys Thr Val Ser Gly Gly Ser Ile Asn Ser Phe Gly Tyr Tyr Trp
            20                  25                  30

Ser Trp Ile Arg Gln Tyr Pro Gly Lys Gly Leu Glu Trp Ile Gly Phe
            35                  40                  45

Leu Tyr Phe Thr Gly Ser Thr Tyr Tyr Asn Pro Ser Leu Lys Ser Arg
        50                  55                  60

Val Thr Ile Ser Val Asp Thr Ser Lys Ser Gln Phe Ser Leu Lys Leu
65                  70                  75                  80

Ser Ser Val Thr Ala Ala Asp Thr Ala Val Tyr Tyr Cys Ala Arg Ala
            85                  90                  95

Gly Thr Met Val Arg Gly Ala His Tyr Tyr Gly Met Asp Val Trp Gly
            100                 105                 110
```

Gln Gly Thr Thr Val Thr Val Ser Ser Ala Ser Thr Lys Gly Pro Ser
            115                 120                 125

Val Phe Pro Leu Ala Pro Ser
        130                 135

<210> SEQ ID NO 37
<211> LENGTH: 700
<212> TYPE: DNA
<213> ORGANISM: Homo sapiens

<400> SEQUENCE: 37
ctcagctcct ggggctcctg ctactctggc tccgaggagg cagatgtgac atccagatga    60
cccagtctcc atcctccctg tctgcatctg taggagacag agtcaccatc acttgccggg   120
caagtcagag tattagtaac tatttaaatt ggtatcagca gaaaccaggg aaagccccta   180
agctcctgat ctatgctgca tccagtttgc aaagtggggt cccatcaagg ttcagtggca   240
gtggatctgg gacagatttc actctcacca tcagcagtct gcaacctgaa gattttgcaa   300
cttactactg tcaacagatt tacagtaccc ctccggagtg gacgttcggc caagggacca   360
aggtggaaat caaacgaact gtggctgcac catctgtctt catcttcccg ccatctgatg   420
agcagttgaa atctggaact gcctctgttg tgtgcctgct gaataacttc tatcccagag   480
aggccaaagt acagtggaag gtggataacg ccctccaatc gggtaactcc caggagagtg   540
tcacagagca ggacagcaag acagcacct acagcctcag cagcaccctg acgctgagca   600
aagcagacta cgagaaacac aaagtctacg cctgcgaagt cacccatcag ggcctgagct   660
cgcccgtcac aaagagcttc aacaggggag agtgttagag                         700

<210> SEQ ID NO 38
<211> LENGTH: 231
<212> TYPE: PRT
<213> ORGANISM: Homo sapiens

<400> SEQUENCE: 38

Gln Leu Leu Gly Leu Leu Leu Trp Leu Arg Gly Gly Arg Cys Asp
1               5                   10                  15

Ile Gln Met Thr Gln Ser Pro Ser Ser Leu Ser Ala Ser Val Gly Asp
            20                  25                  30

Arg Val Thr Ile Thr Cys Arg Ala Ser Gln Ser Ile Ser Asn Tyr Leu
        35                  40                  45

Asn Trp Tyr Gln Gln Lys Pro Gly Lys Ala Pro Lys Leu Leu Ile Tyr
    50                  55                  60

Ala Ala Ser Ser Leu Gln Ser Gly Val Pro Ser Arg Phe Ser Gly Ser
65                  70                  75                  80

Gly Ser Gly Thr Asp Phe Thr Leu Thr Ile Ser Ser Leu Gln Pro Glu
                85                  90                  95

Asp Phe Ala Thr Tyr Tyr Cys Gln Gln Ile Tyr Ser Thr Pro Pro Glu
            100                 105                 110

Trp Thr Phe Gly Gln Gly Thr Lys Val Glu Ile Lys Arg Thr Val Ala
        115                 120                 125

Ala Pro Ser Val Phe Ile Phe Pro Pro Ser Asp Glu Gln Leu Lys Ser
    130                 135                 140

Gly Thr Ala Ser Val Val Cys Leu Leu Asn Asn Phe Tyr Pro Arg Glu
145                 150                 155                 160

Ala Lys Val Gln Trp Lys Val Asp Asn Ala Leu Gln Ser Gly Asn Ser
                165                 170                 175

Gln Glu Ser Val Thr Glu Gln Asp Ser Lys Asp Ser Thr Tyr Ser Leu

```
                    180                 185                 190
Ser Ser Thr Leu Thr Leu Ser Lys Ala Asp Tyr Glu Lys His Lys Val
        195                 200                 205

Tyr Ala Cys Glu Val Thr His Gln Gly Leu Ser Ser Pro Val Thr Lys
        210                 215                 220

Ser Phe Asn Arg Gly Glu Cys
225                 230

<210> SEQ ID NO 39
<211> LENGTH: 408
<212> TYPE: DNA
<213> ORGANISM: Homo sapiens

<400> SEQUENCE: 39
gaggtgcagc tggtggagtc tgggcccagga ctggtgaagc cttcggagac cctgtccctc      60
acctgcactg tctctggtgg ctccatcagc agtagtagtt attactgggg ctggatccgc     120
cagcccccag ggaaggggct ggagtggatt gggagtatgt attatagtgg agcacctac      180 cacaacccgt ccctcaagag tcgagtcatc atatccgtag acacgtccaa gaaccagttc     240
tccctgaagc tgagctctgt gaccgccgca gacacggctg tgtattactg tgcgagacat     300
tatataacag tggctggtat ctttgactac tggggccagg gaaccctggt caccgtctcc     360
tcagcctcca ccaagggccc atcggtcttc ccctggcac cctcctcc               408

<210> SEQ ID NO 40
<211> LENGTH: 136
<212> TYPE: PRT
<213> ORGANISM: Homo sapiens

<400> SEQUENCE: 40

Glu Val Gln Leu Val Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Met Tyr Tyr Ser Gly Ser Thr Tyr His Asn Pro Ser
    50                  55                  60

Leu Lys Ser Arg Val Ile Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Tyr Ile Thr Val Ala Gly Ile Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser
        130                 135

<210> SEQ ID NO 41
<211> LENGTH: 680
<212> TYPE: DNA
<213> ORGANISM: Homo sapiens

<400> SEQUENCE: 41
tcctcctcac cctcctcact cactgtgcag ggtcctgggc ccagtctgta ctgactcagc      60
caccctcagc gtctgggacc cccgggcaga gggccaccat ctcttgttct ggaagcagca    120
```

```
ccaatatcgg aagtactatt gtaaactggt accagcaggt cccaggaacg gcccccaaac    180
tcctcatcta tagtaataat cagcggccct caggggtccc tgaccgattc tctggctcca    240
agtctggcac ctcagcctcc ctggccatca gtgggctcca gtctgaggat gaggctgatt    300
attactgtgc agcatgggat gccagcctga atggtccggt attcggcgga gggaccaagc    360
tgaccgtcct aggtcagccc aaggctgccc cctcggtcac tctgttcccg ccctcctctg    420
aggagcttca agccaacaag gccacactgg tgtgtctcat aagtgacttc tacccgggag    480
ccgtgacagt ggcctggaag gcagatagca gccccgtcaa ggcgggagtg gagaccacca    540
caccctccaa acaaagcaac aacaagtacg cggccagcag ctatctgagc ctgacgcctg    600
agcagtggaa gtcccacaga agctacagct gccaggtcac gcatgaaggg agcaccgtgg    660
agaagacagt ggcccctaca                                                680

<210> SEQ ID NO 42
<211> LENGTH: 226
<212> TYPE: PRT
<213> ORGANISM: Homo sapiens

<400> SEQUENCE: 42

Leu Leu Thr Leu Leu Thr His Cys Ala Gly Ser Trp Ala Gln Ser Val
1               5                   10                  15

Leu Thr Gln Pro Pro Ser Ala Ser Gly Thr Pro Gly Gln Arg Ala Thr
            20                  25                  30

Ile Ser Cys Ser Gly Ser Ser Thr Asn Ile Gly Ser Thr Ile Val Asn
        35                  40                  45

Trp Tyr Gln Gln Val Pro Gly Thr Ala Pro Lys Leu Leu Ile Tyr Ser
    50                  55                  60

Asn Asn Gln Arg Pro Ser Gly Val Pro Asp Arg Phe Ser Gly Ser Lys
65                  70                  75                  80

Ser Gly Thr Ser Ala Ser Leu Ala Ile Ser Gly Leu Gln Ser Glu Asp
                85                  90                  95

Glu Ala Asp Tyr Tyr Cys Ala Ala Trp Asp Ala Ser Leu Asn Gly Pro
            100                 105                 110

Val Phe Gly Gly Gly Thr Lys Leu Thr Val Leu Gly Gln Pro Lys Ala
        115                 120                 125

Ala Pro Ser Val Thr Leu Phe Pro Pro Ser Ser Glu Glu Leu Gln Ala
    130                 135                 140

Asn Lys Ala Thr Leu Val Cys Leu Ile Ser Asp Phe Tyr Pro Gly Ala
145                 150                 155                 160

Val Thr Val Ala Trp Lys Ala Asp Ser Ser Pro Val Lys Ala Gly Val
                165                 170                 175

Glu Thr Thr Thr Pro Ser Lys Gln Ser Asn Asn Lys Tyr Ala Ala Ser
            180                 185                 190

Ser Tyr Leu Ser Leu Thr Pro Glu Gln Trp Lys Ser His Arg Ser Tyr
        195                 200                 205

Ser Cys Gln Val Thr His Glu Gly Ser Thr Val Glu Lys Thr Val Ala
    210                 215                 220

Pro Thr
225

<210> SEQ ID NO 43
<211> LENGTH: 389
<212> TYPE: DNA
<213> ORGANISM: Homo sapiens

<400> SEQUENCE: 43
```

```
gtggagtctg gcccaggact ggtgaagcct tcggagaccc tgtccctcac ctgcactgtc      60
tctggtggct ccatcagtag ttactactgg agctggatcc ggcagccccc agggaaggga     120
ctggagtgga ttgggtatat ctattacagt gggagcacca actacaaccc ctccctcaag     180
agtcgagtca ccatatcagt agacacgtcc aagaaccagt tctccctgaa gctgagctct     240
gtgaccgctg cggacacggc cgtgtattac tgtgcgagag cctacggcta ctactactac     300
ggtatggacg tctggggcca agggaccacg gtcaccgtct cctcagcctc caccaagggc     360
ccatcggtct tccccctggc accctcctc                                       389
```

<210> SEQ ID NO 44
<211> LENGTH: 129
<212> TYPE: PRT
<213> ORGANISM: Homo sapiens

<400> SEQUENCE: 44

```
Val Glu Ser Gly Pro Gly Leu Val Lys Pro Ser Glu Thr Leu Ser Leu
1               5                   10                  15

Thr Cys Thr Val Ser Gly Gly Ser Ile Ser Ser Tyr Tyr Trp Ser Trp
            20                  25                  30

Ile Arg Gln Pro Pro Gly Lys Gly Leu Glu Trp Ile Gly Tyr Ile Tyr
        35                  40                  45

Tyr Ser Gly Ser Thr Asn Tyr Asn Pro Ser Leu Lys Ser Arg Val Thr
    50                  55                  60

Ile Ser Val Asp Thr Ser Lys Asn Gln Phe Ser Leu Lys Leu Ser Ser
65                  70                  75                  80

Val Thr Ala Ala Asp Thr Ala Val Tyr Tyr Cys Ala Arg Ala Tyr Gly
                85                  90                  95

Tyr Tyr Tyr Tyr Gly Met Asp Val Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Ser
```

<210> SEQ ID NO 45
<211> LENGTH: 684
<212> TYPE: DNA
<213> ORGANISM: Homo sapiens

<400> SEQUENCE: 45

```
cagctcctgg ggctcctgct actctggctc cgaggtgcca gatgtgacat ccagatgacc      60
cagtctccat cctccctgtc tgcatctgta ggagacagag tcaccatcac ttgccggaca     120
agtcagagca ttagcagcta tttaaattgg tatcagcaga accagggaa agcccctaac     180 ctcctgatct atgctgcatc cagtttgcaa agtggggtcc catcaaggtt cagtggcagt     240
ggatctggga cagatttcac tctcaccatc agcagtctgc aacctgaaga ttttgcaact     300
tactactgtc aacagactta cagttcccct ccgtggacgt tcggccaagg gaccaaggtg     360
gaaatcaaac gaactgtggc tgcaccatct gtcttcatct tcccgccatc tgatgagcag     420
ttgaaatctg gaactgcctc tgttgtgtgc ctgctgaata acttctatcc cagagaggcc     480
aaagtacagt ggaaggtgga taacgccctc caatcgggta actcccagga gagtgtcaca     540
gagcaggaca gcaaggacag cacctacagc ctcagcagca ccctgacgct gagcaaagca     600
gactacgaga aacacaaagt ctacgcctgc gaagtcaccc atcagggcct gagctcgccc     660
gtcacaaaga gcttcaacag ggga                                            684
```

<210> SEQ ID NO 46
<211> LENGTH: 228
<212> TYPE: PRT
<213> ORGANISM: Homo sapiens

<400> SEQUENCE: 46

Gln Leu Leu Gly Leu Leu Leu Trp Leu Arg Gly Ala Arg Cys Asp
1               5                   10                  15

Ile Gln Met Thr Gln Ser Pro Ser Leu Ser Ala Ser Val Gly Asp
            20                  25                  30

Arg Val Thr Ile Thr Cys Arg Thr Ser Gln Ser Ile Ser Ser Tyr Leu
        35                  40                  45

Asn Trp Tyr Gln Gln Lys Pro Gly Lys Ala Pro Asn Leu Leu Ile Tyr
50                  55                  60

Ala Ala Ser Ser Leu Gln Ser Gly Val Pro Ser Arg Phe Ser Gly Ser
65                  70                  75                  80

Gly Ser Gly Thr Asp Phe Thr Leu Thr Ile Ser Ser Leu Gln Pro Glu
                85                  90                  95

Asp Phe Ala Thr Tyr Tyr Cys Gln Gln Thr Tyr Ser Ser Pro Pro Trp
            100                 105                 110

Thr Phe Gly Gln Gly Thr Lys Val Glu Ile Lys Arg Thr Val Ala Ala
        115                 120                 125

Pro Ser Val Phe Ile Phe Pro Pro Ser Asp Glu Gln Leu Lys Ser Gly
130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
                165                 170                 175

Glu Ser Val Thr Glu Gln Asp Ser Lys Asp Ser Thr Tyr Ser Leu Ser
            180                 185                 190

Ser Thr Leu Thr Leu Ser Lys Ala Asp Tyr Glu Lys His Lys Val Tyr
        195                 200                 205

Ala Cys Glu Val Thr His Gln Gly Leu Ser Ser Pro Val Thr Lys Ser
    210                 215                 220

Phe Asn Arg Gly
225

<210> SEQ ID NO 47
<211> LENGTH: 364
<212> TYPE: DNA
<213> ORGANISM: Homo sapiens

<400> SEQUENCE: 47
ctgttggagt ctggtccagg actggtgaag ccctcgcaga ccctctcact cacctgtgcc      60
atctccgggg acagtgtctc tagcaacagt gctgcttgga actggatcag gcagtcccca     120
tcgagaggcc ttgagtggct gggaaggaca tactacaggt ccaagtggta taatgcttat     180
gcagtatctg tgaaaagtcg aatgaccatc aacccagaca catccaagaa ccagttctcc     240
ctgcagctga actctgtgac tcccgaggac acggctgtgt attactgtgc aagagaggcg     300
gggggctggt tcgaccctg gggccaggga accctggtca ccgtctcctc agcctccacc     360
aagg                                                                  364

<210> SEQ ID NO 48
<211> LENGTH: 121
<212> TYPE: PRT

<213> ORGANISM: Homo sapiens

<400> SEQUENCE: 48

| Leu | Leu | Glu | Ser | Gly | Pro | Gly | Leu | Val | Lys | Pro | Ser | Gln | Thr | Leu | Ser |
|---|---|---|---|---|---|---|---|---|---|---|---|---|---|---|---|
| 1 | | | | 5 | | | | | 10 | | | | | 15 | |

| Leu | Thr | Cys | Ala | Ile | Ser | Gly | Asp | Ser | Val | Ser | Ser | Asn | Ser | Ala | Ala |
|---|---|---|---|---|---|---|---|---|---|---|---|---|---|---|---|
| | | | 20 | | | | | 25 | | | | | 30 | | |

| Trp | Asn | Trp | Ile | Arg | Gln | Ser | Pro | Ser | Arg | Gly | Leu | Glu | Trp | Leu | Gly |
|---|---|---|---|---|---|---|---|---|---|---|---|---|---|---|---|
| | | | | 35 | | | | | 40 | | | | | 45 | |

| Arg | Thr | Tyr | Tyr | Arg | Ser | Lys | Trp | Tyr | Asn | Ala | Tyr | Ala | Val | Ser | Val |
|---|---|---|---|---|---|---|---|---|---|---|---|---|---|---|---|
| | 50 | | | | | 55 | | | | | 60 | | | | |

| Lys | Ser | Arg | Met | Thr | Ile | Asn | Pro | Asp | Thr | Ser | Lys | Asn | Gln | Phe | Ser |
|---|---|---|---|---|---|---|---|---|---|---|---|---|---|---|---|
| 65 | | | | | 70 | | | | | 75 | | | | | 80 |

| Leu | Gln | Leu | Asn | Ser | Val | Thr | Pro | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Glu | Ala | Gly | Gly | Trp | Phe | Asp | Pro | Trp | Gly | Gln | Gly | Thr | Leu |
|---|---|---|---|---|---|---|---|---|---|---|---|---|---|---|---|
| | | | 100 | | | | | 105 | | | | | 110 | | |

| Val | Thr | Val | Ser | Ser | Ala | Ser | Thr | Lys |
|---|---|---|---|---|---|---|---|---|
| | | | 115 | | | | | 120 |

<210> SEQ ID NO 49
<211> LENGTH: 683
<212> TYPE: DNA
<213> ORGANISM: Homo sapiens

<400> SEQUENCE: 49

```
ctcagctcct ggggctcctg ctgctctggt tcccaggttc cagatgcgac atccagatga      60
cccagtctcc atcttccgtg tctgcatctg taggagacag agtcaccatc acttgtcggg     120
cgagtcaggg tattcgcagc tggttagcct ggtatcagca gaaaccaggg aaagccccta     180
agctcctgat ctatgctgca tccagtttgc aaagtggggt cccatcaagg ttcagcggca     240
gtggatctgg gacagatttc actctcacca tcagcagcct gcagcctgaa gattttgcaa     300
cttactattg tcaacaggct aacagtttcc ctcccacttt cggcggaggg accaaggtgg     360
agatcaaacg aactgtggct gcaccatctg tcttcatctt cccgccatct gatgagcagt     420
tgaaatctgg aactgcctct gttgtgtgcc tgctgaataa cttctatccc agagaggcca     480
aagtacagtg gaaggtggat aacgccctcc aatcgggtaa ctcccaggag agtgtcacag     540
agcaggacag caaggacagc acctacagcc tcagcagcac cctgacgctg agcaaagcag     600
actacgagaa acacaaagtc tacgcctgcg aagtcaccca tcagggcctg agctcgcccg     660
tcacaaagag cttcaacagg gga                                             683
```

<210> SEQ ID NO 50
<211> LENGTH: 227
<212> TYPE: PRT
<213> ORGANISM: Homo sapiens

<400> SEQUENCE: 50

| Gln | Leu | Leu | Gly | Leu | Leu | Leu | Trp | Phe | Pro | Gly | Ser | Arg | Cys | Asp |
|---|---|---|---|---|---|---|---|---|---|---|---|---|---|---|
| 1 | | | | 5 | | | | | 10 | | | | | 15 |

| Ile | Gln | Met | Thr | Gln | Ser | Pro | Ser | Ser | Val | Ser | Ala | Ser | Val | Gly | Asp |
|---|---|---|---|---|---|---|---|---|---|---|---|---|---|---|---|
| | | | 20 | | | | | 25 | | | | | 30 | | |

| Arg | Val | Thr | Ile | Thr | Cys | Arg | Ala | Ser | Gln | Gly | Ile | Arg | Ser | Trp | Leu |
|---|---|---|---|---|---|---|---|---|---|---|---|---|---|---|---|
| | | | | 35 | | | | | 40 | | | | | 45 | |

| Ala | Trp | Tyr | Gln | Gln | Lys | Pro | Gly | Lys | Ala | Pro | Lys | Leu | Leu | Ile | Tyr |
|---|---|---|---|---|---|---|---|---|---|---|---|---|---|---|---|
| | 50 | | | | | 55 | | | | | 60 | | | | |

```
Ala Ala Ser Ser Leu Gln Ser Gly Val Pro Ser Arg Phe Ser Gly Ser
 65                  70                  75                  80

Gly Ser Gly Thr Asp Phe Thr Leu Thr Ile Ser Ser Leu Gln Pro Glu
             85                   90                  95

Asp Phe Ala Thr Tyr Tyr Cys Gln Gln Ala Asn Ser Phe Pro Pro Thr
            100                 105                 110

Phe Gly Gly Gly Thr Lys Val Glu Ile Lys Arg Thr Val Ala Ala Pro
        115                 120                 125

Ser Val Phe Ile Phe Pro Pro Ser Asp Glu Gln Leu Lys Ser Gly Thr
    130                 135                 140

Ala Ser Val Val Cys Leu Leu Asn Asn Phe Tyr Pro Arg Glu Ala Lys
145                 150                 155                 160

Val Gln Trp Lys Val Asp Asn Ala Leu Gln Ser Gly Asn Ser Gln Glu
                165                 170                 175

Ser Val Thr Glu Gln Asp Ser Lys Asp Ser Thr Tyr Ser Leu Ser Ser
            180                 185                 190

Thr Leu Thr Leu Ser Lys Ala Asp Tyr Glu Lys His Lys Val Tyr Ala
        195                 200                 205

Cys Glu Val Thr His Gln Gly Leu Ser Ser Pro Val Thr Lys Ser Phe
210                 215                 220

Asn Arg Gly
225

<210> SEQ ID NO 51
<211> LENGTH: 371
<212> TYPE: DNA
<213> ORGANISM: Homo sapiens

<400> SEQUENCE: 51
gaggtgcagc tgttggagtc tggtccagga ctggtgaagc cctcgcagac cctctcactc      60
acctgtgcca tctccgggga cagtgtctct agcaacagtg ctgcttggaa ctggatcagg     120
cagtccccat cgagaggcct tgagtggctg gaaggacat actacaggtc caagtattat      180
aatgcttatc cagtatctgt gaaaagtcga ataaccatca cccagacac atccaagaac      240 cagttctccc tgcagctgaa ctctgtgact cccgaggaca cggctgtgta ttactgtgca     300
agagaggcgg ggggctggtt cgaccctgg ggccagggaa ccctggtcac cgtctcctca      360
gcctccacca a                                                          371

<210> SEQ ID NO 52
<211> LENGTH: 123
<212> TYPE: PRT
<213> ORGANISM: Homo sapiens

<400> SEQUENCE: 52

Glu Val Gln Leu Leu Glu Ser Gly Pro Gly Leu Val Lys Pro Ser Gln
  1               5                  10                  15

Thr Leu Ser Leu Thr Cys Ala Ile Ser Gly Asp Ser Val Ser Ser Asn
             20                  25                  30

Ser Ala Ala Trp Asn Trp Ile Arg Gln Ser Pro Ser Arg Gly Leu Glu
         35                  40                  45

Trp Leu Gly Arg Thr Tyr Tyr Arg Ser Lys Tyr Tyr Asn Ala Tyr Pro
 50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
             85                  90                  95
```

Tyr Tyr Cys Ala Arg Glu Ala Gly Gly Trp Phe Asp Pro Trp Gly Gln
                100                 105                 110

Gly Thr Leu Val Thr Val Ser Ser Ala Ser Thr
            115                 120

<210> SEQ ID NO 53
<211> LENGTH: 679
<212> TYPE: DNA
<213> ORGANISM: Homo sapiens

<400> SEQUENCE: 53
agctcctggg gctcctgctg ctctggttcc caggttccag atgcgacatc cagatgaccc    60
agtctccatc ttccgtgtct gcatctgtag gagacagagt caccatcact tgtcgggcga   120
atcagggtat taggagttgg ttagcctggt atcagcagaa accagggaaa gccccaaagc   180
tcctgatcta tgctgcatcc agtttgcaaa gtggggtccc atcaaggttc agcggcagtg   240
gatctgggac agatttcact ctcaccatca gcagcctgca gcctgaagat tttgcaactt   300
actattgtca acaggctaac agtttccctc ccactttcgg cggagggacc aaggtggaga   360
tcaaacgaac tgtggctgca ccatctgtct tcatcttccc gccatctgat gagcagttga   420
aatctggaac tgcctctgtt gtgtgcctgc tgaataactt ctatcccaga gaggccaaag   480
tacagtggaa ggtggataac gccctccaat cgggtaactc ccaggagagt gtcacagagc   540
aggacagcaa ggacagcacc tacagcctca gcagcaccct gacgctgagc aaagcagact   600
acgagaaaca caaagtctac gcctgcgaag tcacccatca gggcctgagc tcgcccgtca   660
caaagagctt caacagggg                                                 679

<210> SEQ ID NO 54
<211> LENGTH: 225
<212> TYPE: PRT
<213> ORGANISM: Homo sapiens

<400> SEQUENCE: 54

Leu Leu Gly Leu Leu Leu Leu Trp Phe Pro Gly Ser Arg Cys Asp Ile
1               5                   10                  15

Gln Met Thr Gln Ser Pro Ser Ser Val Ser Ala Ser Val Gly Asp Arg
            20                  25                  30

Val Thr Ile Thr Cys Arg Ala Asn Gln Gly Ile Arg Ser Trp Leu Ala
        35                  40                  45

Trp Tyr Gln Gln Lys Pro Gly Lys Ala Pro Lys Leu Leu Ile Tyr Ala
    50                  55                  60

Ala Ser Ser Leu Gln Ser Gly Val Pro Ser Arg Phe Ser Gly Ser Gly
65                  70                  75                  80

Ser Gly Thr Asp Phe Thr Leu Thr Ile Ser Ser Leu Gln Pro Glu Asp
                85                  90                  95

Phe Ala Thr Tyr Tyr Cys Gln Gln Ala Asn Ser Phe Pro Pro Thr Phe
            100                 105                 110

Gly Gly Gly Thr Lys Val Glu Ile Lys Arg Thr Val Ala Ala Pro Ser
        115                 120                 125

Val Phe Ile Phe Pro Pro Ser Asp Glu Gln Leu Lys Ser Gly Thr Ala
    130                 135                 140

Ser Val Val Cys Leu Leu Asn Asn Phe Tyr Pro Arg Glu Ala Lys Val
145                 150                 155                 160

Gln Trp Lys Val Asp Asn Ala Leu Gln Ser Gly Asn Ser Gln Glu Ser
                165                 170                 175

Val Thr Glu Gln Asp Ser Lys Asp Ser Thr Tyr Ser Leu Ser Ser Thr
            180                 185                 190

Leu Thr Leu Ser Lys Ala Asp Tyr Glu Lys His Lys Val Tyr Ala Cys
        195                 200                 205

Glu Val Thr His Gln Gly Leu Ser Ser Pro Val Thr Lys Ser Phe Asn
    210                 215                 220

Arg
225

<210> SEQ ID NO 55
<211> LENGTH: 427
<212> TYPE: DNA
<213> ORGANISM: Homo sapiens

<400> SEQUENCE: 55
gaggtgcatc tggtggagtc tgggggaggc gtggtccagc ctggagggtc cctgagactc      60
tcctgtgcag cgtctggatt caccttcaga agctatggca tgcactgggt ccgccaggct     120
ccaggcaagg ggctggagtg ggtggcagtt atatggtatg atggaagtaa taaatactat     180
gcagactccg tgaagggccg attcaccatc tccagagaca attccaagaa cacgctgtat     240
ctgcaaatga acagcctgag agccgaggac atggctatgt attactgtgc gaggtccaga     300
attacgattt ttggagtggt tcactacggt atggacgtct ggggccaagg gaccacggtc     360
accgtctcct cagcctccac caagggccca tcggtcttcc cctggcaccc tcctccaag      420 agcacct                                                                427

<210> SEQ ID NO 56
<211> LENGTH: 142
<212> TYPE: PRT
<213> ORGANISM: Homo sapiens

<400> SEQUENCE: 56

Glu Val His Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Met Ala Met Tyr Tyr Cys
                85                  90                  95

Ala Arg Ser Arg Ile Thr Ile Phe Gly Val Val His Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr
    130                 135                 140

<210> SEQ ID NO 57
<211> LENGTH: 468
<212> TYPE: DNA
<213> ORGANISM: Homo sapiens

<400> SEQUENCE: 57
acgcagctga cgcagtctcc atcctccctg tctgcatctg ttggagacag agtcaccatc      60

```
acttgccggg caagtcagaa cattaacagc tatttaaatt ggtatcagca gaaaccaggg    120
aaagccccta agctcctgat ctatgctgca tccagtttgc aaagtggggt cccatcaagg    180
ttcagtggca gtggatctgg gacagatttc actctcacca tcagcagtct acaacctgaa    240
gattttacaa cttactactg tcagcagagt tacagttccg ccccactttt cggcggcggg    300
accaagctgg agatcaaacg aactgtggct gcaccatctg tcttcatctt cccgccatct    360
gatgagcagt tgaaatctgg aactgcctct gttgtgtgcc tgctgaataa cttctatccc    420
agagaggcca agtacagtg gaaggtggat aacgccctcc aatcgggt              468

<210> SEQ ID NO 58
<211> LENGTH: 156
<212> TYPE: PRT
<213> ORGANISM: Homo sapiens

<400> SEQUENCE: 58

Thr Gln Leu Thr Gln Ser Pro Ser Ser Leu Ser Ala Ser Val Gly Asp
1               5                   10                  15

Arg Val Thr Ile Thr Cys Arg Ala Ser Gln Asn Ile Asn Ser Tyr Leu
            20                  25                  30

Asn Trp Tyr Gln Gln Lys Pro Gly Lys Ala Pro Lys Leu Leu Ile Tyr
        35                  40                  45

Ala Ala Ser Ser Leu Gln Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Thr Thr Tyr Tyr Cys Gln Gln Ser Tyr Ser Ser Ala Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly
145                 150                 155

<210> SEQ ID NO 59
<211> LENGTH: 392
<212> TYPE: DNA
<213> ORGANISM: Homo sapiens

<400> SEQUENCE: 59
ggcccaggac tggtgaagcc ttcggagacc ctgtccctca cctgcactgt ctctggtggc     60
tccatcagta gttactactg gagctggatc cggcagcccc cagggaaggg actggagtgg    120
attgggtata tctattacag tgggagcacc aactacaacc cctccctcaa gagtcgagtc    180
accatatcag tagacacgtc caagaaccag ttctccctga agctgagctc tgtgaccgct    240
gcggacacgg ccgtgtatta ctgtgcgaga gcggtgtcct actactacta cggtatggac    300
gtctggggcc aagggaccac ggtcaccgtc tcctcagcct ccaccaaggg cccatcggtc    360
ttccccctgg cacctcctc caagagcacc ta                                   392

<210> SEQ ID NO 60
<211> LENGTH: 130
<212> TYPE: PRT
<213> ORGANISM: Homo sapiens
```

<400> SEQUENCE: 60

Gly Pro Gly Leu Val Lys Pro Ser Glu Thr Leu Ser Leu Thr Cys Thr
1               5                   10                  15

Val Ser Gly Gly Ser Ile Ser Ser Tyr Tyr Trp Ser Trp Ile Arg Gln
            20                  25                  30

Pro Pro Gly Lys Gly Leu Glu Trp Ile Gly Tyr Ile Tyr Tyr Ser Gly
        35                  40                  45

Ser Thr Asn Tyr Asn Pro Ser Leu Lys Ser Arg Val Thr Ile Ser Val
    50                  55                  60

Asp Thr Ser Lys Asn Gln Phe Ser Leu Lys Leu Ser Ser Val Thr Ala
65                  70                  75                  80

Ala Asp Thr Ala Val Tyr Tyr Cys Ala Arg Ala Val Ser Tyr Tyr Tyr
                85                  90                  95

Tyr Gly Met Asp Val Trp Gly Gln Gly Thr Thr Val Thr Val Ser Ser
            100                 105                 110

Ala Ser Thr Lys Gly Pro Ser Val Phe Pro Leu Ala Pro Ser Ser Lys
        115                 120                 125

Ser Thr
    130

<210> SEQ ID NO 61
<211> LENGTH: 703
<212> TYPE: DNA
<213> ORGANISM: Homo sapiens

<400> SEQUENCE: 61
gtccccgctc agctcctggg gctcctgcta ctctggctcc gaggtgccag atgtgacatc      60
cagatgaccc agtctccatc ctccctgtct gcatctgtag gagacagagt caccatcact    120
tgccggacaa ttcagaacat taacagctat ttaaattggt atcagcagag accagggaaa    180
gcccctaagc tcctgatcta tgctacatcc agtttgcaaa gtggggtccc atcaaggttc    240
agtggcagtg gatctgggac agatttcact ctcaccatca gcagtctgca acctgaagat    300
tttgcaactt actactgtca acagacttac agtaccctat tcactttcgg ccctgggacc    360
aaagtggata tcaaacgaac tgtggctgca ccatctgtct tcatcttccc gccatctgat    420
gagcagttga aatctggaac tgcctctgtt gtgtgcctgc tgaataactt ctatcccaga    480
gaggccaaag tacagtggaa ggtggataac gccctccaat cgggtaactc ccaggagagt    540
gtcacagagc aggacagcaa ggacagcacc tacagcctca gcagcaccct gacgctgagc    600
aaagcagact acgagaaaca caaagtctac gcctgcgaag tcacccatca gggcctgagc    660
tcgcccgtca caaagagctt caacagggga gagtggttag aga                      703

<210> SEQ ID NO 62
<211> LENGTH: 234
<212> TYPE: PRT
<213> ORGANISM: Homo sapiens

<400> SEQUENCE: 62

Val Pro Ala Gln Leu Leu Gly Leu Leu Leu Leu Trp Leu Arg Gly Ala
1               5                   10                  15

Arg Cys Asp Ile Gln Met Thr Gln Ser Pro Ser Ser Leu Ser Ala Ser
            20                  25                  30

Val Gly Asp Arg Val Thr Ile Thr Cys Arg Thr Ile Gln Asn Ile Asn
        35                  40                  45

Ser Tyr Leu Asn Trp Tyr Gln Gln Arg Pro Gly Lys Ala Pro Lys Leu

```
                50                  55                  60
Leu Ile Tyr Ala Thr Ser Ser Leu Gln Ser Gly Val Pro Ser Arg Phe
 65                  70                  75                  80

Ser Gly Ser Gly Ser Gly Thr Asp Phe Thr Leu Thr Ile Ser Ser Leu
                 85                  90                  95

Gln Pro Glu Asp Phe Ala Thr Tyr Tyr Cys Gln Gln Thr Tyr Ser Thr
            100                 105                 110

Leu Phe Thr Phe Gly Pro Gly Thr Lys Val Asp Ile Lys Arg Thr Val
        115                 120                 125

Ala Ala Pro Ser Val Phe Ile Phe Pro Pro Ser Asp Glu Gln Leu Lys
130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
210                 215                 220

Lys Ser Phe Asn Arg Gly Glu Trp Leu Glu
225                 230

<210> SEQ ID NO 63
<211> LENGTH: 398
<212> TYPE: DNA
<213> ORGANISM: Homo sapiens

<400> SEQUENCE: 63
ggcccaggac tggtgaagcc ttcggagacc ctgtccctca cctgcactgt ccctggtggc    60
tccatcagga gttacttctg gagctggatc cggcagcccg ccgggaaggg actggagtgg   120
attgggcgtt ctatttcagt gggagcacca actacaaccc ctccctcaa gagtcgagtc    180 accatgtcag tagacacgtc caagaaccag ttctccctga agttgagctc tgtgaccgcc   240
gcggacacgg ccgtgtatta ctgtgcgaga gactacggtg accactacta ctactacggt   300
atggacgtct ggggccaagg gaccacggtc accgtctcct cagcctccac caagggccca   360
tcggtcttcc ccctggcacc ctcctccaag agcaccta                          398

<210> SEQ ID NO 64
<211> LENGTH: 132
<212> TYPE: PRT
<213> ORGANISM: Homo sapiens

<400> SEQUENCE: 64

Gly Pro Gly Leu Val Lys Pro Ser Glu Thr Leu Ser Leu Thr Cys Thr
 1               5                  10                  15

Val Pro Gly Gly Ser Ile Arg Ser Tyr Phe Trp Ser Trp Ile Arg Gln
                 20                  25                  30

Pro Ala Gly Lys Gly Leu Glu Trp Ile Gly Arg Phe Tyr Phe Ser Gly
            35                  40                  45

Ser Thr Asn Tyr Asn Pro Ser Leu Lys Ser Arg Val Thr Met Ser Val
        50                  55                  60

Asp Thr Ser Lys Asn Gln Phe Ser Leu Lys Leu Ser Ser Val Thr Ala
 65                  70                  75                  80
```

```
Ala Asp Thr Ala Val Tyr Tyr Cys Ala Arg Asp Tyr Gly Asp His Tyr
            85                  90                  95

Tyr Tyr Tyr Gly Met Asp Val Trp Gly Gln Gly Thr Thr Val Thr Val
            100                 105                 110

Ser Ser Ala Ser Thr Lys Gly Pro Ser Val Phe Pro Leu Ala Pro Ser
            115                 120                 125

Ser Lys Ser Thr
            130

<210> SEQ ID NO 65
<211> LENGTH: 633
<212> TYPE: DNA
<213> ORGANISM: Homo sapiens

<400> SEQUENCE: 65
gtgctgacgc agccgccctc agtgtctgcg gccccaggac agaaggtcac catctcctgc      60
tctggaagca gctccaatat tgggaataat tatgtatcct ggtaccagca gttcccagga     120
acagccccca aattctcat ttatgacaat aataagcgat cctcagggat tcctgaccga      180
ttctctggct ccaagtctgg cacgtcagcc accctgggca tcaccggact ccagactggg     240
gacgaggccg attattactg cggaacatgg gatagcagcc tgagtgctgt gatattcggc     300
ggagggacca gcctgaccgt cctaggtcag cccaaggctg cccccctcggt cactctgttc     360 ccgcccctcct ctgaggagct tcaagccaac aaggccacac tggtgtgtct cataagtgac     420
ttctacccgg gagccgtgac agtggcctgg aaggcagata gcagccccgt caaggcggga     480
gtggagacca ccacaccctc caaacaaagc aacaacaagt acgcggccag cagctatctg     540
agcctgacgc ctgagcagtg gaagtccac agaaagctaca gctgccaggt cacgcatgaa     600
gggagcaccg tggagaagac agtggcccct aca                                  633

<210> SEQ ID NO 66
<211> LENGTH: 211
<212> TYPE: PRT
<213> ORGANISM: Homo sapiens

<400> SEQUENCE: 66

Val Leu Thr Gln Pro Pro Ser Val Ser Ala Pro Gly Gln Lys Val
1               5                   10                  15

Thr Ile Ser Cys Ser Gly Ser Ser Asn Ile Gly Asn Asn Tyr Val
                20                  25                  30

Ser Trp Tyr Gln Gln Phe Pro Gly Thr Ala Pro Lys Phe Leu Ile Tyr
            35                  40                  45

Asp Asn Asn Lys Arg Ser Ser Gly Ile Pro Asp Arg Phe Ser Gly Ser
    50                  55                  60

Lys Ser Gly Thr Ser Ala Thr Leu Gly Ile Thr Gly Leu Gln Thr Gly
65                  70                  75                  80

Asp Glu Ala Asp Tyr Tyr Cys Gly Thr Trp Asp Ser Ser Leu Ser Ala
                85                  90                  95

Val Ile Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
        130                 135                 140

Ala Val Thr Val Ala Trp Lys Ala Asp Ser Ser Pro Val Lys Ala Gly
145                 150                 155                 160
```

```
Val Glu Thr Thr Thr Pro Ser Lys Gln Ser Asn Asn Lys Tyr Ala Ala
            165                 170                 175

Ser Ser Tyr Leu Ser Leu Thr Pro Glu Gln Trp Lys Ser His Arg Ser
        180                 185                 190

Tyr Ser Cys Gln Val Thr His Glu Gly Ser Thr Val Glu Lys Thr Val
        195                 200                 205

Ala Pro Thr
    210

<210> SEQ ID NO 67
<211> LENGTH: 260
<212> TYPE: DNA
<213> ORGANISM: Homo sapiens

<400> SEQUENCE: 67
ggattcacct tcagtagcta tggcatgcac tgggtccgcc aggctccagg caaggggctg      60
gagtgggtgg caattatatg gtatgatgaa agtaataaat actatgcaga ctccgtgaag     120
ggccgattca ccatctccag agacaattcc aagaacacgc tgtatctgca aatgaacagc     180
ctgagagccg aggacacggc tgtgtattac tgtgcgagag cttatagtgg gagctacggg     240
tactcctact acggtatgga                                                  260

<210> SEQ ID NO 68
<211> LENGTH: 86
<212> TYPE: PRT
<213> ORGANISM: Homo sapiens

<400> SEQUENCE: 68

Gly Phe Thr Phe Ser Ser Tyr Gly Met His Trp Val Arg Gln Ala Pro
1               5                   10                  15

Gly Lys Gly Leu Glu Trp Val Ala Ile Ile Trp Tyr Asp Glu Ser Asn
            20                  25                  30

Lys Tyr Tyr Ala Asp Ser Val Lys Gly Arg Phe Thr Ile Ser Arg Asp
        35                  40                  45

Asn Ser Lys Asn Thr Leu Tyr Leu Gln Met Asn Ser Leu Arg Ala Glu
    50                  55                  60

Asp Thr Ala Val Tyr Tyr Cys Ala Arg Ala Tyr Ser Gly Ser Tyr Gly
65                  70                  75                  80

Tyr Ser Tyr Tyr Gly Met
                85

<210> SEQ ID NO 69
<211> LENGTH: 543
<212> TYPE: DNA
<213> ORGANISM: Homo sapiens

<400> SEQUENCE: 69
caggacagac agccagcatc acctggctct ggagataaat tgggggataa atatgcttgc      60
tggtatcagc agaagccagg ccagtcccct gtgctggtca tctatcaaga tagcaagcgg     120
ccctcaggga tccctgagcg attctctggc tccaactctg ggaacacagc cactctgacc     180
atcagcggga cccaggctat ggatgaggct gactattact gtcaggcgtg gacaacaga     240 actgcggtat tcggcggagg gaccaagctg accgtcctag gtcagcccaa ggctgccccc     300
tcggtcactc tgttcccgcc ctcctctgag gagcttcaag ccaacaaggc cacactggtg     360
tgtctcataa gtgacttcta cccgggagcc gtgacagtgg cctggaaggc agatagcagc     420
cccgtcaagg cgggagtgga gaccaccaca cctccaaac aaagcaacaa caagtacgcg      480
```

```
gccagcagct atctgagcct gacgcctgag cagtggaagt cccacagaag ctacagctgc    540
cag                                                                   543
```

```
<210> SEQ ID NO 70
<211> LENGTH: 181
<212> TYPE: PRT
<213> ORGANISM: Homo sapiens

<400> SEQUENCE: 70
```

Gln Asp Arg Gln Pro Ala Ser Pro Gly Ser Gly Asp Lys Leu Gly Asp
1               5                   10                  15

Lys Tyr Ala Cys Trp Tyr Gln Gln Lys Pro Gly Gln Ser Pro Val Leu
            20                  25                  30

Val Ile Tyr Gln Asp Ser Lys Arg Pro Ser Gly Ile Pro Glu Arg Phe
        35                  40                  45

Ser Gly Ser Asn Ser Gly Asn Thr Ala Thr Leu Thr Ile Ser Gly Thr
    50                  55                  60

Gln Ala Met Asp Glu Ala Asp Tyr Tyr Cys Gln Ala Trp Asp Asn Arg
65                  70                  75                  80

Thr Ala Val Phe Gly Gly Gly Thr Lys Leu Thr Val Leu Gly Gln Pro
                85                  90                  95

Lys Ala Ala Pro Ser Val Thr Leu Phe Pro Pro Ser Ser Glu Glu Leu
            100                 105                 110

Gln Ala Asn Lys Ala Thr Leu Val Cys Leu Ile Ser Asp Phe Tyr Pro
        115                 120                 125

Gly Ala Val Thr Val Ala Trp Lys Ala Asp Ser Ser Pro Val Lys Ala
    130                 135                 140

Gly Val Glu Thr Thr Thr Pro Ser Lys Gln Ser Asn Asn Lys Tyr Ala
145                 150                 155                 160

Ala Ser Ser Tyr Leu Ser Leu Thr Pro Glu Gln Trp Lys Ser His Arg
                165                 170                 175

Ser Tyr Ser Cys Gln
            180

```
<210> SEQ ID NO 71
<211> LENGTH: 401
<212> TYPE: DNA
<213> ORGANISM: Homo sapiens

<400> SEQUENCE: 71
aggtgcaggc tggtggagtc tggagcagag gtgaaaaagc ccggggagtc tctgaagatc    60
tcctgtaagg gttctggata cagatttacc agctactgga tcggctgggt gcgccagatg    120
cccgggaaag gcctggagtg gatggggatc atctatcctg gtgactctga taccagatac    180
agcccgtcct tccaaggcca ggtcaccatc tcagccgaca gtccatcag caccgcctac    240 ctgcagtggc gcagcctgaa ggcctcggac accgccatgt attactgtgc gagaaaggac    300
tactactact acgttatgga cgtctggggc caagggacca cggtcaccgt ctcctcagcc    360
tccaccaagg gcccatcggt cttccccctg gcaccctcct c                       401
```

```
<210> SEQ ID NO 72
<211> LENGTH: 133
<212> TYPE: PRT
<213> ORGANISM: Homo sapiens

<400> SEQUENCE: 72
```

Arg Cys Arg Leu Val Glu Ser Gly Ala Glu Val Lys Lys Pro Gly Glu
1               5                   10                  15

```
Ser Leu Lys Ile Ser Cys Lys Gly Ser Gly Tyr Arg Phe Thr Ser Tyr
         20                  25                  30

Trp Ile Gly Trp Val Arg Gln Met Pro Gly Lys Gly Leu Glu Trp Met
         35                  40                  45

Gly Ile Ile Tyr Pro Gly Asp Ser Asp Thr Arg Tyr Ser Pro Ser Phe
50                       55                  60

Gln Gly Gln Val Thr Ile Ser Ala Asp Lys Ser Ile Ser Thr Ala Tyr
65                  70                  75                  80

Leu Gln Trp Arg Ser Leu Lys Ala Ser Asp Thr Ala Met Tyr Tyr Cys
                 85                  90                  95

Ala Arg Lys Asp Tyr Tyr Tyr Val Met Asp Val Trp Gly Gln Gly
                100                 105                 110

Thr Thr Val Thr Val Ser Ser Ala Ser Thr Lys Gly Pro Ser Val Phe
         115                 120                 125

Pro Leu Ala Pro Ser
    130
```

<210> SEQ ID NO 73
<211> LENGTH: 591
<212> TYPE: DNA
<213> ORGANISM: Homo sapiens

<400> SEQUENCE: 73

```
gataccatct cctgcactgg aaccagcagt gacgttggta attataacta tgtctcctgg      60
taccaacaac acccaggcaa agccccccaaa ctcatgattt atgcggtcaa taatcggccc    120
tcagggggttt ctaatcgctt ctctggctcc aagtctggca acacggcctc cctgaccatc    180
tctgggctcc aggctgagga cgaggctgat tattactgca gctcatatac aagcagcagg    240
aatcttgtag ttttcggcgg cgggaccaag ctgaccgtcc taggtcagcc caaggctgcc    300
ccctcggtca ctctgttccc gccctcctct gaggagcttc aagccaacaa ggccacactg    360
gtgtgtctca taagtgactt ctacccggga gccgtgacag tggcctggaa ggcagatagc    420
agccccgtca aggcgggagt ggagaccacc acaccctcca aacaaagcaa caacaagtac    480
gcggccagca gctatctgag cctgacgcct gagcagtgga agtcccacag aagctacagc    540
tgccaggtca cgcatgaagg gagcaccgtg gagaagacag tggccccta c              591
```

<210> SEQ ID NO 74
<211> LENGTH: 197
<212> TYPE: PRT
<213> ORGANISM: Homo sapiens

<400> SEQUENCE: 74

```
Asp Thr Ile Ser Cys Thr Gly Thr Ser Ser Asp Val Gly Asn Tyr Asn
1               5                  10                  15

Tyr Val Ser Trp Tyr Gln Gln His Pro Gly Lys Ala Pro Lys Leu Met
             20                  25                  30

Ile Tyr Ala Val Asn Asn Arg Pro Ser Gly Val Ser Asn Arg Phe Ser
         35                  40                  45

Gly Ser Lys Ser Gly Asn Thr Ala Ser Leu Thr Ile Ser Gly Leu Gln
50                  55                  60

Ala Glu Asp Glu Ala Asp Tyr Tyr Cys Ser Ser Tyr Thr Ser Ser Arg
65                  70                  75                  80

Asn Leu Val Val Phe Gly Gly Gly Thr Lys Leu Thr Val Leu Gly Gln
                 85                  90                  95

Pro Lys Ala Ala Pro Ser Val Thr Leu Phe Pro Pro Ser Ser Glu Glu
```

```
                100             105             110
Leu Gln Ala Asn Lys Ala Thr Leu Val Cys Leu Ile Ser Asp Phe Tyr
        115                 120                 125

Pro Gly Ala Val Thr Val Ala Trp Lys Ala Asp Ser Ser Pro Val Lys
130                 135                 140

Ala Gly Val Glu Thr Thr Thr Pro Ser Lys Gln Ser Asn Asn Lys Tyr
145                 150                 155                 160

Ala Ala Ser Ser Tyr Leu Ser Leu Thr Pro Glu Gln Trp Lys Ser His
                165                 170                 175

Arg Ser Tyr Ser Cys Gln Val Thr His Glu Gly Ser Thr Val Glu Lys
                180                 185                 190

Thr Val Ala Pro Thr
        195

<210> SEQ ID NO 75
<211> LENGTH: 660
<212> TYPE: DNA
<213> ORGANISM: Homo sapiens

<400> SEQUENCE: 75
ggagcacgag gacactgaca tggactgaag gagtagaaaa cccaaaaacc acacccctcc    60
ttgggagaat ccctagatc acagctcctc accatggact ggacctggag catccttttc    120
ttggtggcag cagcaacagg tgcccactcc caggttcagc tggtgcagtc tggagctgag    180
gtgaagaagc ctggggcctc agtgaaggtc tcctgcaagg cttctggtta cacctttacc    240
agctatggta tcagctgggt gcgacaggcc cctggacaag gcttgagtg gatgggatgg    300 atcagcgctt acaatggtaa cacatactat gcacagaagc tccaggccag agtcaccatg    360
accacagaca catccacgag cacagcctac atggagctga ggagcctgag atctgacgac    420
acggccgtgt attactgtgc gagagatggg tatagcagca gctggtccct cctgcactac    480
tacggtatgg acgtctgggg ccaagggacc acggtcaccg tctcctcagc ctccaccaag    540
ggcccatcgg tcttcccct ggcaccctcc tccaagagca cctctggggg cacagcggcc    600
ctgggctgcc tggtcaagga ctacttcccc gaaccggtga cggtgtcgtg gaactcagcg    660

<210> SEQ ID NO 76
<211> LENGTH: 189
<212> TYPE: PRT
<213> ORGANISM: Homo sapiens

<400> SEQUENCE: 76

Met Asp Trp Thr Trp Ser Ile Leu Phe Leu Val Ala Ala Thr Gly
1               5                   10                  15

Ala His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Ser Tyr Gly Ile Ser Trp Val Arg Gln Ala Pro Gly Gln Gly Leu
        50                  55                  60

Glu Trp Met Gly Trp Ile Ser Ala Tyr Asn Gly Asn Thr Tyr Tyr Ala
65                  70                  75                  80

Gln Lys Leu Gln Ala Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Asp Gly Tyr Ser Ser Ser Trp Ser Leu Leu His
```

```
              115                 120                 125
Tyr Tyr Gly Met Asp Val Trp Gly Gln Gly Thr Thr Val Thr Val Ser
130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Ala
            180                 185

<210> SEQ ID NO 77
<211> LENGTH: 651
<212> TYPE: DNA
<213> ORGANISM: Homo sapiens

<400> SEQUENCE: 77
tcagatacca gatgtgacat ccagatgacc cagtctccat cctccctgtc tgcatctgta      60
ggagacagaa tcaccatcac ttggcggtcg agtcagggca tttacaattc tttagcctgg     120
tatcagcaga aaccagggaa agttcctaag ctcctgatct atgctgcatc cactttgcac     180
tcagggttcc catctcggtt cagtggcagt ggatctggga cagatttcac tctcaccatc     240
agcagcctgc agcctgaaga tgttgcaact tattactgtc aaaaatataa cagtgcccca     300
ttcactttcg gccctgggac caaagtggat atcaaacgaa ctgtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg a              651

<210> SEQ ID NO 78
<211> LENGTH: 217
<212> TYPE: PRT
<213> ORGANISM: Homo sapiens

<400> SEQUENCE: 78

Ser Asp Thr Arg Cys Asp Ile Gln Met Thr Gln Ser Pro Ser Ser Leu
1               5                   10                  15

Ser Ala Ser Val Gly Asp Arg Ile Thr Ile Thr Trp Arg Ser Ser Gln
                20                  25                  30

Gly Ile Tyr Asn Ser Leu Ala Trp Tyr Gln Gln Lys Pro Gly Lys Val
            35                  40                  45

Pro Lys Leu Leu Ile Tyr Ala Ala Ser Thr Leu His Ser Gly Val Pro
        50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Val Ala Thr Tyr Tyr Cys Gln Lys Tyr
                85                  90                  95

Asn Ser Ala Pro Phe Thr Phe Gly Pro Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
```

```
                  145                 150                 155                 160
Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly
    210                 215

<210> SEQ ID NO 79
<211> LENGTH: 1396
<212> TYPE: DNA
<213> ORGANISM: Homo sapiens

<400> SEQUENCE: 79
tttctgagag tcctggacct cctgtgcaag aacatgaaac acctgtggtt cttcctcctg      60
ctggtggcag ctcccagatg ggtcctgtcc caggtgcagc tgcaggagtc gggcccagga     120
ctggtgaagc cttcacagac cctgtccctc acctgcactg tctctggtgg ctccatcagc     180
agtggtggtt actactggag ctggatccgc cagcacccag ggaagggcct ggagtggatt     240
gggatcatct attacagtgg gagcacctac tacaacccgt ccctcaagag tcgagttacc     300
atatcagtag acacgtctaa gaaccagttc tccctgaagc tgaactctgt gactgccgcg     360
gacacggccg tgttttactg tgcgagagtg gctatagtga ctacgatccc gggcggtatg     420
gacgtctggg gccaagggac cacggtcacc gtctcctcag cctccaccaa gggcccatcg     480
gtcttccccc tggcgccctg ctccaggagc acctccgaga gcacagcggc cctgggctgc     540
ctggtcaagg actacttccc cgaaccggtg acggtgtcgt ggaactcagg cgctctgacc     600
agcggcgtgc acaccttccc agctgtccta cagtcctcag gactctactc cctcagcagc     660
gtggtgaccg tgccctccag caacttcggc acccagacct acacctgcaa cgtagatcac     720
aagcccagca acaccaaggt ggacaagaca gttgagcgca aatgttgtgt cgagtgccca     780
ccgtgcccag caccacctgt ggcaggaccg tcagtcttcc tcttcccccc aaaacccaag     840
gacaccctca tgatctcccg gacccctgag gtcacgtgcg tggtggtgga cgtgagccac     900
gaagaccccg aggtccagtt caactggtac gtggacggcg tggaggtgca taatgccaag     960
acaaagccac gggaggagca gttcaacagc acgttccgtg tggtcagcgt cctcaccgtt    1020
gtgcaccagg actggctgaa cggcaaggag tacaagtgca aggtctccaa caaaggcctc    1080
ccagccccca tcgagaaaac catctccaaa accaaagggc agccccgaga accacaggtg    1140
tacaccctgc ccccatcccg ggaggagatg accaagaacc aggtcagcct gacctgcctg    1200
gtcaaaggct tctaccccag cgacatcgcc gtggagtggg agagcaatgg gcagccggag    1260
aacaactaca agaccacacc tcccatgctg gactccgacg gctccttctt cctttacagc    1320
aagctcaccg tggacaagag caggtggcag caggggaacg tcttctcatg ctccgtgatg    1380
catgaggctc tgcaca                                                    1396

<210> SEQ ID NO 80
<211> LENGTH: 454
<212> TYPE: PRT
<213> ORGANISM: Homo sapiens

<400> SEQUENCE: 80

Met Lys His Leu Trp Phe Phe Leu Leu Leu Val Ala Ala Pro Arg Trp
1               5                   10                  15
```

Val Leu Ser Gln Val Gln Leu Gln Glu Ser Gly Pro Gly Leu Val Lys
                20                  25                  30

Pro Ser Gln Thr Leu Ser Leu Thr Cys Thr Val Ser Gly Gly Ser Ile
            35                  40                  45

Ser Ser Gly Gly Tyr Tyr Trp Ser Trp Ile Arg Gln His Pro Gly Lys
    50                  55                  60

Gly Leu Glu Trp Ile Gly Ile Ile Tyr Tyr Ser Gly Ser Thr Tyr Tyr
65                  70                  75                  80

Asn Pro Ser Leu Lys Ser Arg Val Thr Ile Ser Val Asp Thr Ser Lys
                85                  90                  95

Asn Gln Phe Ser Leu Lys Leu Asn Ser Val Thr Ala Ala Asp Thr Ala
            100                 105                 110

Val Phe Tyr Cys Ala Arg Val Ala Ile Val Thr Thr Ile Pro Gly Gly
        115                 120                 125

Met Asp Val Trp Gly Gln Gly Thr Thr Val Thr Val Ser Ser Ala Ser
130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Gln Phe Asn Trp Tyr Val Asp Gly Val Glu
290                 295                 300

Val His Asn Ala Lys Thr Lys Pro Arg Glu Glu Gln Phe Asn Ser Thr
305                 310                 315                 320

Phe Arg Val Val Ser Val Leu Thr Val Val His Gln Asp Trp Leu Asn
                325                 330                 335

Gly Lys Glu Tyr Lys Cys Lys Val Ser Asn Lys Gly Leu Pro Ala Pro
            340                 345                 350

Ile Glu Lys Thr Ile Ser Lys Thr Lys Gly Gln Pro Arg Glu Pro Gln
        355                 360                 365

Val Tyr Thr Leu Pro Pro Ser Arg Glu Glu Met Thr Lys Asn Gln Val
370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Met Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val

Met His Glu Ala Leu His
            450

<210> SEQ ID NO 81
<211> LENGTH: 700
<212> TYPE: DNA
<213> ORGANISM: Homo sapiens

<400> SEQUENCE: 81
aggagtagaa aatgagcaaa actgacaagt caaggcagga agatgttgcc atcacaactc       60
attgggtttc tgctgctctg ggttccagcc tccaggggtg aaattgtgct gactcagtct      120
ccagactttc agtctgtgac tccaaaggag aaagtcacca tcacctgccg ggccagtcag      180
agcattggta ttagcttaca ctggtaccag cagaaaccag atcagtctcc aaagctcctc      240
atcaagtatg cttcccagtc cttctcaggg gtcccctcga ggttcagtgg cagtggatct      300
gggacagatt tcaccctcac catcaatagc ctggaagctg aagatgctgc aacgtattac      360
tgtcatcaga gtaggagttt cccgtggacg ttcggccaag ggaccaaggt ggaaatcaaa      420
cgaactgtgg ctgcaccatc tgtcttcatc ttcccgccat ctgatgagca gttgaaatct      480
ggaactgcct ctgttgtgtg cctgctgaat aacttctatc ccagagaggc caaagtacag      540
tggaaggtgg ataacgccct ccaatcgggt aactcccagg agagtgtcac agagcaggac      600
agcaaggaca gcacctacag cctcagcagc accctgacgc tgagcaaagc agactacgag      660
aaacacaaag tctacgcctg cgaagtcacc catcagggcc                            700

<210> SEQ ID NO 82
<211> LENGTH: 219
<212> TYPE: PRT
<213> ORGANISM: Homo sapiens

<400> SEQUENCE: 82

Met Leu Pro Ser Gln Leu Ile Gly Phe Leu Leu Leu Trp Val Pro Ala
1               5                   10                  15

Ser Arg Gly Glu Ile Val Leu Thr Gln Ser Pro Asp Phe Gln Ser Val
            20                  25                  30

Thr Pro Lys Glu Lys Val Thr Ile Thr Cys Arg Ala Ser Gln Ser Ile
        35                  40                  45

Gly Ile Ser Leu His Trp Tyr Gln Gln Lys Pro Asp Gln Ser Pro Lys
    50                  55                  60

Leu Leu Ile Lys Tyr Ala Ser Gln Ser Phe Ser Gly Val Pro Ser Arg
65                  70                  75                  80

Phe Ser Gly Ser Gly Ser Gly Thr Asp Phe Thr Leu Thr Ile Asn Ser
                85                  90                  95

Leu Glu Ala Glu Asp Ala Ala Thr Tyr Tyr Cys His Gln Ser Arg Ser
            100                 105                 110

Phe Pro Trp Thr Phe Gly Gln Gly Thr Lys Val Glu Ile Lys Arg Thr
        115                 120                 125

Val Ala Ala Pro Ser Val Phe Ile Phe Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

```
Ser Leu Ser Ser Thr Leu Thr Leu Ser Lys Ala Asp Tyr Glu Lys His
        195                 200                 205
Lys Val Tyr Ala Cys Glu Val Thr His Gln Gly
    210                 215
```

<210> SEQ ID NO 83
<211> LENGTH: 396
<212> TYPE: DNA
<213> ORGANISM: Homo sapiens

<400> SEQUENCE: 83

```
ttggtggagt ctggagcaga ggtgaaaaag cccggggagt ctctgaagat ctcctgtaag     60
ggttctggat acagatttac cagctactgg atcggctggg tgcgccagat gcccgggaaa    120
ggcctggagt ggatggggat catctatcct ggtgactctg ataccagata cagcccgtcc    180
ttccaaggcc aggtcaccat ctcagccgac aagtccatca gtaccgccta cctgcagtgg    240
agcagcctga aggcctcgga caccgccatg tattactgtg cgagaaagga ctactactac    300
tacagtatgg acgtctgggg ccaagggacc acggtcaccg tctcctcagc tccaccaag     360
ggcccatcgg tcttcccct ggaaccctcc tccaaa                               396
```

<210> SEQ ID NO 84
<211> LENGTH: 132
<212> TYPE: PRT
<213> ORGANISM: Homo sapiens

<400> SEQUENCE: 84

```
Leu Val Glu Ser Gly Ala Glu Val Lys Lys Pro Gly Glu Ser Leu Lys
1               5                   10                  15
Ile Ser Cys Lys Gly Ser Gly Tyr Arg Phe Thr Ser Tyr Trp Ile Gly
            20                  25                  30
Trp Val Arg Gln Met Pro Gly Lys Gly Leu Glu Trp Met Gly Ile Ile
        35                  40                  45
Tyr Pro Gly Asp Ser Asp Thr Arg Tyr Ser Pro Ser Phe Gln Gly Gln
    50                  55                  60
Val Thr Ile Ser Ala Asp Lys Ser Ile Ser Thr Ala Tyr Leu Gln Trp
65                  70                  75                  80
Ser Ser Leu Lys Ala Ser Asp Thr Ala Met Tyr Tyr Cys Ala Arg Lys
                85                  90                  95
Asp Tyr Tyr Tyr Tyr Ser Met Asp Val Trp Gly Gln Gly Thr Thr Val
            100                 105                 110
Thr Val Ser Ser Ala Ser Thr Lys Gly Pro Ser Val Phe Pro Leu Glu
        115                 120                 125
Pro Ser Ser Lys
    130
```

<210> SEQ ID NO 85
<211> LENGTH: 570
<212> TYPE: DNA
<213> ORGANISM: Homo sapiens

<400> SEQUENCE: 85

```
ggccagtctg ccctgactca acctgcctcc gtgtctgggt ctcctggaca gtcgatcacc     60
atctcctgca ctggaaccag cagtgacgtt ggtggttata attatgtctc ctggtaccaa    120
cagcacccag gcaagccccc caaactcctg atttatgggg tcaatattcg gccctcaggg    180
gtttctactc gcttctctgg ctccaagtct ggcaacacgg cctccctgac catctctggg    240
```

```
ctccaggctg aggacgaggc cgattattat tgtagttcat atacaagaag cagcattctt      300
gtggttttcg ccggagggac caaactgacc gtcctaggtc agcccaaggc tgccccctcg      360
gtcactctgt tcccgccctc ctctgaggag cttcaagcca acaaggccac actggtgtgt      420
ctcataagtg acttctaccc gggagccgtg acagtggcct ggaaggcaga tagcagcccc      480
gtcaaggcgg gagtggagac caccacaccc tccaaacaaa gcaacaacaa gtacgcggcc      540
agcagctatc tgagcctgac gcctgagcag                                       570
```

<210> SEQ ID NO 86
<211> LENGTH: 190
<212> TYPE: PRT
<213> ORGANISM: Homo sapiens

<400> SEQUENCE: 86

```
Gly Gln Ser Ala Leu Thr Gln Pro Ala Ser Val Gly Ser Pro Gly
1               5                  10                  15
Gln Ser Ile Thr Ile Ser Cys Thr Gly Thr Ser Asp Val Gly Gly
            20                  25                  30
Tyr Asn Tyr Val Ser Trp Tyr Gln Gln His Pro Gly Gln Ala Pro Lys
        35                  40                  45
Leu Leu Ile Tyr Gly Val Asn Ile Arg Pro Ser Gly Val Ser Thr Arg
    50                  55                  60
Phe Ser Gly Ser Lys Ser Gly Asn Thr Ala Ser Leu Thr Ile Ser Gly
65                  70                  75                  80
Leu Gln Ala Glu Asp Glu Ala Asp Tyr Tyr Cys Ser Ser Tyr Thr Arg
                85                  90                  95
Ser Ser Ile Leu Val Val Phe Ala Gly Gly Thr Lys Leu Thr Val Leu
            100                 105                 110
Gly Gln Pro Lys Ala Ala Pro Ser Val Thr Leu Phe Pro Pro Ser Ser
        115                 120                 125
Glu Glu Leu Gln Ala Asn Lys Ala Thr Leu Val Cys Leu Ile Ser Asp
    130                 135                 140
Phe Tyr Pro Gly Ala Val Thr Val Ala Trp Lys Ala Asp Ser Ser Pro
145                 150                 155                 160
Val Lys Ala Gly Val Glu Thr Thr Thr Pro Ser Lys Gln Ser Asn Asn
                165                 170                 175
Lys Tyr Ala Ala Ser Ser Tyr Leu Ser Leu Thr Pro Glu Gln
            180                 185                 190
```

<210> SEQ ID NO 87
<211> LENGTH: 427
<212> TYPE: DNA
<213> ORGANISM: Homo sapiens

<400> SEQUENCE: 87

```
gaggtgcagc tggtggagtc tgggggaggc gtggtccagc ctggaggtc cctgagactc       60
tcctgtgcag cgtctggatt caccttcagt agctatggca tgcactgggt ccgccaggct      120
ccaggcaagg gctggagtg gtggcagtt atatggtatg atggaagtaa taaatactat       180
gcagactccg tgaagggccg attcaccatc tccagagaca attccaagaa cacgctgtat      240
ctgcaaatga acagcctgag agccgaggac acggctgtgt attactgtgc gaggtccaga      300
attacgattt ttggagtggt tcactacggt atggacgtct ggggccaagg gaccacggtc      360
accgtctcct cagcctccac caagggccca tcggtcttcc cctggcacc ctcctccaag      420
agcacct                                                                427
```

<210> SEQ ID NO 88
<211> LENGTH: 142
<212> TYPE: PRT
<213> ORGANISM: Homo sapiens

<400> SEQUENCE: 88

Glu Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Arg Ile Thr Ile Phe Gly Val Val His Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr
    130                 135                 140

<210> SEQ ID NO 89
<211> LENGTH: 470
<212> TYPE: DNA
<213> ORGANISM: Homo sapiens

<400> SEQUENCE: 89
gacacgcagc tgactcagtc tccatcctcc ctgtctgcat ctgtaggaga cagagtcacc      60
atcacttgcc gggcaagtca gagcattagc agctatttaa attggtatca gctgaaacca    120
gggaaagccc ctaagctcct gatctatgct gcatccagtt tagaaagtgg ggtcccatca    180
aggttcagtg gcagtgaatc tgggacagat ttcactctca ccatcagcag tctgcaacct    240
gaagattttg caacttacta ctgtcaacag agttacaatt ccccaatcac tttcggccct    300
gggaccaaag tggatatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg                470

<210> SEQ ID NO 90
<211> LENGTH: 156
<212> TYPE: PRT
<213> ORGANISM: Homo sapiens

<400> SEQUENCE: 90

Asp Thr Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Leu Lys Pro Gly Lys Ala Pro Lys Leu Leu Ile
        35                  40                  45

Tyr Ala Ala Ser Ser Leu Glu Ser Gly Val Pro Ser Arg Phe Ser Gly
    50                  55                  60

Ser Glu Ser Gly Thr Asp Phe Thr Leu Thr Ile Ser Ser Leu Gln Pro

```
                65                  70                  75                  80
Glu Asp Phe Ala Thr Tyr Tyr Cys Gln Gln Ser Tyr Asn Ser Pro Ile
                    85                  90                  95

Thr Phe Gly Pro Gly Thr Lys Val Asp Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser
145                 150                 155

<210> SEQ ID NO 91
<211> LENGTH: 594
<212> TYPE: DNA
<213> ORGANISM: Homo sapiens

<400> SEQUENCE: 91
agaagagtct ccctcactgc ccagctggga tctcagggct tcattttctg tcctccacca      60
atggggtcaa ccgccatcct cgccctcctc ctggctgttc tccaaggagt ctgtgccgag     120
gtgcaactag tgcagtctgg agcagaggtg aaaaagcccg gggagtctct gaagatctcc     180
tgtaagggtt ctggatacag gtttaccagc tactggatcg gctgggtgcg ccagatgccc     240
gggaaaggcc tggagtggat ggggatcatc tatcctggtg actctgatac cagatacagc     300
ccgtccttcc aaggccaggt caccatctca gccgacaagt ccatcagcac cgcctacctg     360
cagtggagca gcctgaaggc ctcggacacc gccatgtatt actgtgcgag aaaggactac     420
tactactaca ctatggacgt ctggggccaa gggaccacgg tcaccgtctc ctcagcctcc     480
accaagggcc catcggtctt ccccctggca ccctcctcca agagcacctc tgggggcaca     540
gcggccctgg gctgcctggt caaggactac ttccccgaac cggtgacggt gtcg           594

<210> SEQ ID NO 92
<211> LENGTH: 178
<212> TYPE: PRT
<213> ORGANISM: Homo sapiens

<400> SEQUENCE: 92

Met Gly Ser Thr Ala Ile Leu Ala Leu Leu Leu Ala Val Leu Gln Gly
1               5                   10                  15

Val Cys Ala Glu Val Gln Leu Val Gln Ser Gly Ala Glu Val Lys Lys
                20                  25                  30

Pro Gly Glu Ser Leu Lys Ile Ser Cys Lys Gly Ser Gly Tyr Arg Phe
            35                  40                  45

Thr Ser Tyr Trp Ile Gly Trp Val Arg Gln Met Pro Gly Lys Gly Leu
        50                  55                  60

Glu Trp Met Gly Ile Ile Tyr Pro Gly Asp Ser Asp Thr Arg Tyr Ser
65                  70                  75                  80

Pro Ser Phe Gln Gly Gln Val Thr Ile Ser Ala Asp Lys Ser Ile Ser
                85                  90                  95

Thr Ala Tyr Leu Gln Trp Ser Ser Leu Lys Ala Ser Asp Thr Ala Met
                100                 105                 110

Tyr Tyr Cys Ala Arg Lys Asp Tyr Tyr Tyr Thr Met Asp Val Trp
            115                 120                 125

Gly Gln Gly Thr Thr Val Thr Val Ser Ser Ala Ser Thr Lys Gly Pro
        130                 135                 140
```

```
Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser

<210> SEQ ID NO 93
<211> LENGTH: 648
<212> TYPE: DNA
<213> ORGANISM: Homo sapiens

<400> SEQUENCE: 93
ctgggccagt ctgccctgac tcagcctgcc tccgtgtctg ggtctcctgg acagtcgatc      60
accatctcct gcactggaaa cagcagtgac gttggtggtt ataactatgt ctcctggtac     120
caacaacacc caggcaaagc ccccaaactc atgatttatg cggtcagtaa tcggccctca     180
ggggtttcta atcgcttctc tggctccaag tctggcaaca cggcctccct gaccatctct     240
gggctccagg ctgaggacga ggctgattat tactgcagct catatacaat cagcaggatt     300
cttgtggttt tcggcggggg gaccaagctg accgtcctag gtcagcccaa ggctgccccc     360
tcggtcactc tgttcccgcc ctcctctgag gagcttcaag ccaacaaggc cacactggtg     420
tgtctcataa gtgacttcta cccgggagcc gtgacagtgg cctggaaggc agatagcagc     480
cccgtcaagg cgggagtgga gaccaccaca cctccaaac aaagcaacaa caagtacgcg     540
gccagcagct atctgagcct gacgcctgag cagtggaagt cccacagaag ctacagctgc     600
caggtcacgc atgaagggag caccgtggag aagacagtgg cccctaca                 648

<210> SEQ ID NO 94
<211> LENGTH: 216
<212> TYPE: PRT
<213> ORGANISM: Homo sapiens

<400> SEQUENCE: 94

Leu Gly Gln Ser Ala Leu Thr Gln Pro Ala Ser Val Ser Gly Ser Pro
1               5                   10                  15

Gly Gln Ser Ile Thr Ile Ser Cys Thr Gly Thr Ser Ser Asp Val Gly
                20                  25                  30

Gly Tyr Asn Tyr Val Ser Trp Tyr Gln Gln His Pro Gly Lys Ala Pro
            35                  40                  45

Lys Leu Met Ile Tyr Ala Val Ser Asn Arg Pro Ser Gly Val Ser Asn
        50                  55                  60

Arg Phe Ser Gly Ser Lys Ser Gly Asn Thr Ala Ser Leu Thr Ile Ser
65                  70                  75                  80

Gly Leu Gln Ala Glu Asp Glu Ala Asp Tyr Tyr Cys Ser Ser Tyr Thr
                85                  90                  95

Ile Ser Arg Ile Leu Val Val Phe Gly Gly Gly Thr Lys Leu Thr Val
            100                 105                 110

Leu Gly Gln Pro Lys Ala Ala Pro Ser Val Thr Leu Phe Pro Pro Ser
        115                 120                 125

Ser Glu Glu Leu Gln Ala Asn Lys Ala Thr Leu Val Cys Leu Ile Ser
    130                 135                 140

Asp Phe Tyr Pro Gly Ala Val Thr Val Ala Trp Lys Ala Asp Ser Ser
145                 150                 155                 160

Pro Val Lys Ala Gly Val Glu Thr Thr Thr Pro Ser Lys Gln Ser Asn
                165                 170                 175

Asn Lys Tyr Ala Ala Ser Ser Tyr Leu Ser Leu Thr Pro Glu Gln Trp
```

```
              180                 185                 190
Lys Ser His Arg Ser Tyr Ser Cys Gln Val Thr His Glu Gly Ser Thr
            195                 200                 205

Val Glu Lys Thr Val Ala Pro Thr
        210                 215

<210> SEQ ID NO 95
<211> LENGTH: 686
<212> TYPE: DNA
<213> ORGANISM: Homo sapiens

<400> SEQUENCE: 95
aaatactttc tgagagtcct ggacctcctg tgcaagaaca tgaaacacct gtggttcttc      60
ctcctgctgg tggcagctcc cagatgggtc ctgtcccagg tgcagctgca ggagtcgggc     120
ccaggactgg tgaagccttc acagaccctg tccctcacct gcactgtctc tggtggctcc     180
atcaccagtg gtgattacta ctggagctgg atccgccagc acccagggaa gggcctggag     240
tggtttgggt tcatctatta cagtgggagc gcctactaca acccgtccct caagagtcga     300
attaccatat cagtagacac gtctaagaac cagttctccc tgaagctgag ctctgtgact     360
gccgcggaca cggccgtgta ttactgtgcg agagaggga actacggtgg taactcgttt      420
gactactggg gccagggaac cctggtcacc gtctcctcag cctccaccaa gggcccatcg     480
gtcttccccc tggcgccctg ctccaggagc acctccgaga gcacagcggc cctgggctgc     540
ctggtcaagg actacttccc cgaaccggtg acggtgtcgt ggaactcagg cgctctgacc     600
agcggcgtgc acaccttccc agctgtccta cagtcctcag gactctactc cctcagcagc     660
gtggtgaccg tgccctccag cactcg                                         686

<210> SEQ ID NO 96
<211> LENGTH: 215
<212> TYPE: PRT
<213> ORGANISM: Homo sapiens

<400> SEQUENCE: 96

Met Lys His Leu Trp Phe Phe Leu Leu Leu Val Ala Ala Pro Arg Trp
1               5                  10                  15

Val Leu Ser Gln Val Gln Leu Gln Glu Ser Gly Pro Gly Leu Val Lys
            20                  25                  30

Pro Ser Gln Thr Leu Ser Leu Thr Cys Thr Val Ser Gly Gly Ser Ile
        35                  40                  45

Thr Ser Gly Asp Tyr Tyr Trp Ser Trp Ile Arg Gln His Pro Gly Lys
    50                  55                  60

Gly Leu Glu Trp Phe Gly Phe Ile Tyr Tyr Ser Gly Ser Ala Tyr Tyr
65                  70                  75                  80

Asn Pro Ser Leu Lys Ser Arg Ile Thr Ile Ser Val Asp Thr Ser Lys
                85                  90                  95

Asn Gln Phe Ser Leu Lys Leu Ser Ser Val Thr Ala Ala Asp Thr Ala
            100                 105                 110

Val Tyr Tyr Cys Ala Arg Glu Arg Asn Tyr Gly Gly Asn Ser Phe Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175
```

```
Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Thr
        210                 215
```

<210> SEQ ID NO 97
<211> LENGTH: 671
<212> TYPE: DNA
<213> ORGANISM: Homo sapiens

<400> SEQUENCE: 97

```
tggatctctg gatccagtgg ggatattgtg atgactcagt ctccactctc cctgcccgtc    60
acccctggag agccggcctc catctcctgc aggtctagtc agagcctcct gcatagtaat   120
ggatacaact atttggattg gtacctgcag aagccaggcc agtctccaca gctcctgatc   180
tatttgggtt ctaatcgggc ctccggggtc cctgacaggt tcagtggcag tggatcaggc   240
acagatttta cactgaaaat cagcagagtg gaggctgagg atgttggggt ttattactgc   300
atgcaagctc tacaaactat taccttcggc caagggacac gactggagat taaacgaact   360
gtggctgcac catctgtctt catcttcccg ccatctgatg agcagttgaa atctggaact   420
gcctctgttg tgtgcctgct gaataacttc tatcccagag aggccaaagt acagtggaag   480
gtggataacg ccctccaatc gggtaactcc caggagagtg tcacagagca ggacagcaag   540
gacagcacct acagcctcag cagcaccctg acgctgagca agcagactac gagaaacac    600
aaagtctacg cctgcgaagt cacccatcag gscctgagct cgcccgtcac aaagagcttc   660
aacaggggag a                                                        671
```

<210> SEQ ID NO 98
<211> LENGTH: 223
<212> TYPE: PRT
<213> ORGANISM: Homo sapiens
<220> FEATURE:
<221> NAME/KEY: VARIANT
<222> LOCATION: 211
<223> OTHER INFORMATION: Xaa = Any amino acid.

<400> SEQUENCE: 98

```
Trp Ile Ser Gly Ser Ser Gly Asp Ile Val Met Thr Gln Ser Pro Leu
1               5                   10                  15

Ser Leu Pro Val Thr Pro Gly Glu Pro Ala Ser Ile Ser Cys Arg Ser
            20                  25                  30

Ser Gln Ser Leu Leu His Ser Asn Gly Tyr Asn Tyr Leu Asp Trp Tyr
        35                  40                  45

Leu Gln Lys Pro Gly Gln Ser Pro Gln Leu Leu Ile Tyr Leu Gly Ser
    50                  55                  60

Asn Arg Ala Ser Gly Val Pro Asp Arg Phe Ser Gly Ser Gly Ser Gly
65                  70                  75                  80

Thr Asp Phe Thr Leu Lys Ile Ser Arg Val Glu Ala Glu Asp Val Gly
                85                  90                  95

Val Tyr Tyr Cys Met Gln Ala Leu Gln Thr Ile Thr Phe Gly Gln Gly
            100                 105                 110

Thr Arg Leu Glu Ile Lys Arg Thr Val Ala Ala Pro Ser Val Phe Ile
        115                 120                 125

Phe Pro Pro Ser Asp Glu Gln Leu Lys Ser Gly Thr Ala Ser Val Val
    130                 135                 140
```

Cys Leu Leu Asn Asn Phe Tyr Pro Arg Glu Ala Lys Val Gln Trp Lys
145                 150                 155                 160

Val Asp Asn Ala Leu Gln Ser Gly Asn Ser Gln Glu Ser Val Thr Glu
            165                 170                 175

Gln Asp Ser Lys Asp Ser Thr Tyr Ser Leu Ser Ser Thr Leu Thr Leu
        180                 185                 190

Ser Lys Ala Asp Tyr Glu Lys His Lys Val Tyr Ala Cys Glu Val Thr
    195                 200                 205

His Gln Xaa Leu Ser Ser Pro Val Thr Lys Ser Phe Asn Arg Gly
210                 215                 220

<210> SEQ ID NO 99
<211> LENGTH: 604
<212> TYPE: DNA
<213> ORGANISM: Homo sapiens

<400> SEQUENCE: 99
agtctccctc actgcccagc tgggatctca gggcttcatt ttctgtcctc caccatcatg      60
gggtcaaccg ccatcctcgc cctcctcctg gctgttctcc aaggagtctg tgccgaggtg     120
cagctggtgc agtctggagc agaggtgaaa agcccggggg agtctctgaa gatctcctgt     180
aagggttctg gatacaggtt taccagctac tggatcggct gggtgcgcca gatgcccggg     240
aaaggcctgg agtggatggg gatcatctat cctggtgact ctgataccag atacagcccg     300
tccttccaag gccaggtcac catctcagcc gacaagtcca tcagcaccgc ctacctgcag     360
tggagtagcc tgaaggcctc ggacaccgcc atgtattact gtgcgagaaa ggactactac     420
tactacagta tggacgtctg gggccaaggg accacggtca ccgtctcctc agcctccacc     480
aagggcccat cggtcttccc cctggcaccc tcctccaaga gcacctctgg gggcacagcg     540
gccctgggct gcctggtcaa ggactacttc cccgaaccga gtgacgagtg tcgtgaactc     600
agcg     604

<210> SEQ ID NO 100
<211> LENGTH: 182
<212> TYPE: PRT
<213> ORGANISM: Homo sapiens

<400> SEQUENCE: 100

Met Gly Ser Thr Ala Ile Leu Ala Leu Leu Leu Ala Val Leu Gln Gly
1               5                   10                  15

Val Cys Ala Glu Val Gln Leu Val Gln Ser Gly Ala Glu Val Lys Lys
            20                  25                  30

Pro Gly Glu Ser Leu Lys Ile Ser Cys Lys Gly Ser Gly Tyr Arg Phe
        35                  40                  45

Thr Ser Tyr Trp Ile Gly Trp Val Arg Gln Met Pro Gly Lys Gly Leu
    50                  55                  60

Glu Trp Met Gly Ile Ile Tyr Pro Gly Asp Ser Asp Thr Arg Tyr Ser
65                  70                  75                  80

Pro Ser Phe Gln Gly Gln Val Thr Ile Ser Ala Asp Lys Ser Ile Ser
            85                  90                  95

Thr Ala Tyr Leu Gln Trp Ser Ser Leu Lys Ala Ser Asp Thr Ala Met
        100                 105                 110

Tyr Tyr Cys Ala Arg Lys Asp Tyr Tyr Tyr Ser Met Asp Val Trp
    115                 120                 125

Gly Gln Gly Thr Thr Val Thr Val Ser Ser Ala Ser Thr Lys Gly Pro
130                 135                 140

```
Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Ser Asp
            165                 170                 175

Glu Cys Arg Glu Leu Ser
            180
```

```
<210> SEQ ID NO 101
<211> LENGTH: 651
<212> TYPE: DNA
<213> ORGANISM: Homo sapiens

<400> SEQUENCE: 101
ggtctgggcc agtctgccct gactcagcct gcctccgtgt ctgggtctcc tggacagtcg      60
atcaccatct cctgcactgg aaccagcagt gacgttggtc gttttaacta tgtctcctgg     120
taccaacagc gcccaggcaa agcccccaaa ctcatgattt atgcggtcaa tattcggccc     180
tcaggggttt ctaatcgctt ctctggctcc aagtctggca acacggcctc cctgaccatc     240
tctgggctcc aggctgagga cgaggctggt tattactgca gctcatatac aagcagcagc     300
actcttctgg ttttcggcgg agggaccaag ctgaccgtcc tgggtcagcc caaggctgcc     360
ccctcggtca ctctgttccc gccctcctct gaggagcttc aagccaacaa ggccacactg     420
gtgtgtctca taagtgactt ctacccggga gccgtgacag tggcctggaa ggcagatagc     480
agccccgtca aggcgggagt ggagaccacc acaccctcca aacaaagcaa caacaagtac     540
gcggccagca gctatctgag cctgacgcct gagcagtgga agtcccacag aagctacagc     600
tgccaggtca cgcatgaagg gagcaccgtg gagaagacag tggcccctac a             651
```

```
<210> SEQ ID NO 102
<211> LENGTH: 217
<212> TYPE: PRT
<213> ORGANISM: Homo sapiens

<400> SEQUENCE: 102

Gly Leu Gly Gln Ser Ala Leu Thr Gln Pro Ala Ser Val Ser Gly Ser
1               5                   10                  15

Pro Gly Gln Ser Ile Thr Ile Ser Cys Thr Gly Thr Ser Ser Asp Val
                20                  25                  30

Gly Arg Phe Asn Tyr Val Ser Trp Tyr Gln Gln Arg Pro Gly Lys Ala
            35                  40                  45

Pro Lys Leu Met Ile Tyr Ala Val Asn Ile Arg Pro Ser Gly Val Ser
        50                  55                  60

Asn Arg Phe Ser Gly Ser Lys Ser Gly Asn Thr Ala Ser Leu Thr Ile
65                  70                  75                  80

Ser Gly Leu Gln Ala Glu Asp Glu Ala Gly Tyr Tyr Cys Ser Ser Tyr
                85                  90                  95

Thr Ser Ser Ser Thr Leu Leu Val Phe Gly Gly Gly Thr Lys Leu Thr
            100                 105                 110

Val Leu Gly Gln Pro Lys Ala Ala Pro Ser Val Thr Leu Phe Pro Pro
        115                 120                 125

Ser Ser Glu Glu Leu Gln Ala Asn Lys Ala Thr Leu Val Cys Leu Ile
    130                 135                 140

Ser Asp Phe Tyr Pro Gly Ala Val Thr Val Ala Trp Lys Ala Asp Ser
145                 150                 155                 160

Ser Pro Val Lys Ala Gly Val Glu Thr Thr Thr Pro Ser Lys Gln Ser
                165                 170                 175
```

```
Asn Asn Lys Tyr Ala Ala Ser Ser Tyr Leu Ser Leu Thr Pro Glu Gln
            180                 185                 190

Trp Lys Ser His Arg Ser Tyr Ser Cys Gln Val Thr His Glu Gly Ser
        195                 200                 205

Thr Val Glu Lys Thr Val Ala Pro Thr
    210                 215
```

<210> SEQ ID NO 103
<211> LENGTH: 603
<212> TYPE: DNA
<213> ORGANISM: Homo sapiens

<400> SEQUENCE: 103

```
ctgggagagg agcccagcac tagaagtcgg cggtgtttcc attcggtgat cagcactgaa    60
cacagaggac tcaccatgga gtttgggctg agctgggttt cctcgttgc tcttttaaga    120
ggtgtccagt gtcaggtgca gctggtggag tctgggggag gcgtggtcca gcctggggagg   180
tccctgagac tctcctgtgc agcgtctgga ttcaccttca gtagctatgg catgcactgg   240
gtccgccagg ctccaggcaa ggggctggag tgggtggcaa ctatatggtt tgatggaagt   300
aatggatact atgcagactc cgtgaagggc cgattcacca tctccagaga caattccaag   360
aacacgttgt atctgcaaat gaacagcctg agagccgagg acacggctgt gtattactgt   420
gcgagagaca gcagtgggag ctacgaccac tttgactact ggggccaggg aaccctggtc   480
accgtctcct cagcctccac caagggccca tcggtcttcc ccctggcgcc ctgctccagg   540
agcacctccg agagcacagc ggccctgggc tgcctggtca aggactactt ccccgaaccg   600
gtg                                                                 603
```

<210> SEQ ID NO 104
<211> LENGTH: 176
<212> TYPE: PRT
<213> ORGANISM: Homo sapiens

<400> SEQUENCE: 104

```
Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Thr Ile Trp Phe Asp Gly Ser Asn Gly Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Ser Ser Gly Ser Tyr Asp His Phe Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175
```

<210> SEQ ID NO 105
<211> LENGTH: 668
<212> TYPE: DNA
<213> ORGANISM: Homo sapiens

<400> SEQUENCE: 105

```
gatcagtggg atattgtgat gactcagtct ccactctccc tgcccgtcac ccctggagag    60
ccggcctcca tctcctgcag gtctagtcag agcctcctgc atagtaatgg atacaactgt   120
ttggattggt acctgcagaa gccagggcag tctccacagc tcctgatcta tttgggttct   180
aatcgggcct ccggggtccc tgacaggttc agtggcagtg gatcaggcac agattttaca   240
ctgaaaatca gcagagtgga ggctgaggat gttggggttt attactgcat gcaagcacta   300
caaactccga tcaccttcgg ccaagggaca cgagtggaga ttaaacgaac tgtggctgca   360
ccatctgtct tcatcttccc gccatctgat gagcagttga aatctggaac tgcctctgtt   420
gtgtgcctgc tgaataactt ctatcccaga gaggccaaag tacagtggaa ggtggataac   480
gccctccaat cgggtaactc ccaggagagt gtcacagagc aggacagcaa ggacagcacc   540
tacagcctca gcagcaccct gacgctgagc aaagcagact acgagaaaca caaagtctac   600
gcctgcgaag tcacccatca gggcctgagc tcgcccgtca caaagagctt caacagggga   660
gagtgtta                                                           668
```

<210> SEQ ID NO 106
<211> LENGTH: 222
<212> TYPE: PRT
<213> ORGANISM: Homo sapiens

<400> SEQUENCE: 106

```
Asp Gln Trp Asp Ile Val Met Thr Gln Ser Pro Leu Ser Leu Pro Val
1               5                  10                  15

Thr Pro Gly Glu Pro Ala Ser Ile Ser Cys Arg Ser Ser Gln Ser Leu
            20                  25                  30

Leu His Ser Asn Gly Tyr Asn Cys Leu Asp Trp Tyr Leu Gln Lys Pro
        35                  40                  45

Gly Gln Ser Pro Gln Leu Leu Ile Tyr Leu Gly Ser Asn Arg Ala Ser
    50                  55                  60

Gly Val Pro Asp Arg Phe Ser Gly Ser Gly Ser Gly Thr Asp Phe Thr
65                  70                  75                  80

Leu Lys Ile Ser Arg Val Glu Ala Glu Asp Val Gly Val Tyr Tyr Cys
                85                  90                  95

Met Gln Ala Leu Gln Thr Pro Ile Thr Phe Gly Gln Gly Thr Arg Val
            100                 105                 110

Glu Ile Lys Arg Thr Val Ala Ala Pro Ser Val Phe Ile Phe Pro Pro
        115                 120                 125

Ser Asp Glu Gln Leu Lys Ser Gly Thr Ala Ser Val Val Cys Leu Leu
    130                 135                 140

Asn Asn Phe Tyr Pro Arg Glu Ala Lys Val Gln Trp Lys Val Asp Asn
145                 150                 155                 160

Ala Leu Gln Ser Gly Asn Ser Gln Glu Ser Val Thr Glu Gln Asp Ser
                165                 170                 175

Lys Asp Ser Thr Tyr Ser Leu Ser Ser Thr Leu Thr Leu Ser Lys Ala
            180                 185                 190

Asp Tyr Glu Lys His Lys Val Tyr Ala Cys Glu Val Thr His Gln Gly
        195                 200                 205
```

Leu Ser Ser Pro Val Thr Lys Ser Phe Asn Arg Gly Glu Cys
210                 215                 220

<210> SEQ ID NO 107
<211> LENGTH: 435
<212> TYPE: DNA
<213> ORGANISM: Homo sapiens

<400> SEQUENCE: 107

```
tgcaggctgg tggagtctgg ggctgaggtg aagaagcctg gggcctcagt gaaggtctcc      60
tgcaaggctt ctggatacac cttcaccggc tactatatgc actgggtgcg acaggcccct     120
ggacaagggc ttgagtggat gggatggatc aaccctaaca gtggtggcac aaactatgca     180
cagaagtttc agggcagggt caccatgacc agggacacgt ccatcagcac agcctacatg     240
gagctgagca ggctgagatc tgacgacacg gccgtgtatt actgtgcgag agatcaggtg     300
gatatagtgg ctacccgtta ttactactac tactacggta tggacgtctg gggccaaggg     360
accacggtca ccgtctcctc agcctccacc aagggcccat cggtcttccc cctggcaccc     420
tcctccaaga gcacc                                                      435
```

<210> SEQ ID NO 108
<211> LENGTH: 145
<212> TYPE: PRT
<213> ORGANISM: Homo sapiens

<400> SEQUENCE: 108

Cys Arg Leu Val Glu Ser Gly Ala Glu Val Lys Lys Pro Gly Ala Ser
1               5                   10                  15

Val Lys Val Ser Cys Lys Ala Ser Gly Tyr Thr Phe Thr Gly Tyr Tyr
            20                  25                  30

Met His Trp Val Arg Gln Ala Pro Gly Gln Gly Leu Glu Trp Met Gly
        35                  40                  45

Trp Ile Asn Pro Asn Ser Gly Gly Thr Asn Tyr Ala Gln Lys Phe Gln
    50                  55                  60

Gly Arg Val Thr Met Thr Arg Asp Thr Ser Ile Ser Thr Ala Tyr Met
65                  70                  75                  80

Glu Leu Ser Arg Leu Arg Ser Asp Asp Thr Ala Val Tyr Tyr Cys Ala
                85                  90                  95

Arg Asp Gln Val Asp Ile Val Ala Thr Arg Tyr Tyr Tyr Tyr Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr
145

<210> SEQ ID NO 109
<211> LENGTH: 397
<212> TYPE: DNA
<213> ORGANISM: Homo sapiens

<400> SEQUENCE: 109

```
gtggagtctg gcccaggact ggtgaagcct tcacagaccc tgtccctcac ctgcactgtc      60
tctggtggct ccatcagcag tggtggttac tactggagct ggatccgcca gcacccaggg     120
aagggcctgg agtggattgg gtacatctat tacagtggga gcacctacta caacccgtcc     180
ctcaagagtc gagttaccat atcagtagac acgtctaaga accagttctc cctgaagctg     240
```

```
agctctgtga ctgccgcgga cacggccgtg tattactgtg cgagagtgga tatagtggct    300
acgatcccac ttatctttga ctactggggc cagggaaccc tggtcaccgt ctcctcagcc    360
tccaccaagg gcccatcggt cttcccctg gcaccct                              397
```

<210> SEQ ID NO 110
<211> LENGTH: 132
<212> TYPE: PRT
<213> ORGANISM: Homo sapiens

<400> SEQUENCE: 110

```
Val Glu Ser Gly Pro Gly Leu Val Lys Pro Ser Gln Thr Leu Ser Leu
1               5                   10                  15

Thr Cys Thr Val Ser Gly Gly Ser Ile Ser Ser Gly Gly Tyr Tyr Trp
            20                  25                  30

Ser Trp Ile Arg Gln His Pro Gly Lys Gly Leu Glu Trp Ile Gly Tyr
        35                  40                  45

Ile Tyr Tyr Ser Gly Ser Thr Tyr Tyr Asn Pro Ser Leu Lys Ser Arg
    50                  55                  60

Val Thr Ile Ser Val Asp Thr Ser Lys Asn Gln Phe Ser Leu Lys Leu
65                  70                  75                  80

Ser Ser Val Thr Ala Ala Asp Thr Ala Val Tyr Tyr Cys Ala Arg Val
                85                  90                  95

Asp Ile Val Ala Thr Ile Pro Leu Ile Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro
    130
```

<210> SEQ ID NO 111
<211> LENGTH: 406
<212> TYPE: DNA
<213> ORGANISM: Homo sapiens

<400> SEQUENCE: 111

```
gaggtgctgc tggtggagtc tggcccagga ctggtgaagc cttcggagac cctgtccctc     60
acctgcactg tctctggtgg ctccatcagc agtagtagtt acttctgggg ctggatccgc    120
cagcccccag ggaaggggct ggagtggatt gggagtatct attatagtgg aaacacctac    180
tacaacccgt ccctcaagag tcgagtcacc atatccgtag acacgtccaa gaaccggttc    240
tccctgaagc tgagctctgt gaccgccgca gacacggctg tgtattgctg tgcgagcgcc    300
actacagtaa ctacagcttt tgatatctgg ggccaaggga caatggtcac cgtctcttca    360
gcctccacca agggcccatc ggtcttcccc ctggcaccct cctcca                   406
```

<210> SEQ ID NO 112
<211> LENGTH: 135
<212> TYPE: PRT
<213> ORGANISM: Homo sapiens

<400> SEQUENCE: 112

```
Glu Val Leu Leu Val Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Phe Trp Gly Trp Ile Arg Gln Pro Pro Gly Lys Gly Leu Glu
        35                  40                  45
```

Trp Ile Gly Ser Ile Tyr Tyr Ser Gly Asn Thr Tyr Tyr Asn Pro Ser
            50                  55                  60

Leu Lys Ser Arg Val Thr Ile Ser Val Asp Thr Ser Lys Asn Arg Phe
65                  70                  75                  80

Ser Leu Lys Leu Ser Ser Val Thr Ala Ala Asp Thr Ala Val Tyr Cys
                85                  90                  95

Cys Ala Ser Ala Thr Thr Val Thr Thr Ala Phe Asp Ile Trp Gly Gln
            100                 105                 110

Gly Thr Met Val Thr Val Ser Ser Ala Ser Thr Lys Gly Pro Ser Val
            115                 120                 125

Phe Pro Leu Ala Pro Ser Ser
            130             135

<210> SEQ ID NO 113
<211> LENGTH: 648
<212> TYPE: DNA
<213> ORGANISM: Homo sapiens

<400> SEQUENCE: 113
ctgggccagt ctgccctgac tcagcctgcc tccgtgtctg ggtctcctgg acagtcgatc      60
accatctcct gtactggaac cagcagtgac gttggtcgtt ataactatgt ctcctggtac     120
caacagcacc caggccaagc ccccaaactc atgatttatg ggatcagtat tcggccctca     180
ggggtttctc ctcgcttctc tggctccaag tctggcaaca cggcctccct gaccatctct     240
gggctccagg ctgaggacga ggctgattat tactgcagct cacatacaag caacagcact     300
cttgtggtat tcgccggagg gaccaaactg accgtcctag gtcagcccaa ggctgccccc     360
tcggtcactc tgttcccgcc ctcctctgag gagcttcaag ccaacaaggc cacactggtg     420
tgtctcataa gtgacttcta cccgggagcc gtgacagtgg cctggaaggc agatagcagc     480
cccgtcaagg cgggagtgga gaccaccaca ccctccaaac aaagcaacaa caagtacgcg     540
gccagcagct atctgagcct gacgcctgag cagtggaagt cccacagaag ctacagctgc     600
caggtcacgc atgaagggag caccgtggag aagacagtgg cccctaca                  648

<210> SEQ ID NO 114
<211> LENGTH: 216
<212> TYPE: PRT
<213> ORGANISM: Homo sapiens

<400> SEQUENCE: 114

Leu Gly Gln Ser Ala Leu Thr Gln Pro Ala Ser Val Ser Gly Ser Pro
1               5                   10                  15

Gly Gln Ser Ile Thr Ile Ser Cys Thr Gly Thr Ser Ser Asp Val Gly
            20                  25                  30

Arg Tyr Asn Tyr Val Ser Trp Tyr Gln Gln His Pro Gly Gln Ala Pro
            35                  40                  45

Lys Leu Met Ile Tyr Gly Ile Ser Ile Arg Pro Ser Gly Val Ser Pro
            50                  55                  60

Arg Phe Ser Gly Ser Lys Ser Gly Asn Thr Ala Ser Leu Thr Ile Ser
65                  70                  75                  80

Gly Leu Gln Ala Glu Asp Glu Ala Asp Tyr Tyr Cys Ser Ser His Thr
                85                  90                  95

Ser Asn Ser Thr Leu Val Val Phe Ala Gly Gly Thr Lys Leu Thr Val
            100                 105                 110

Leu Gly Gln Pro Lys Ala Ala Pro Ser Val Thr Leu Phe Pro Pro Ser
            115                 120                 125

```
Ser Glu Glu Leu Gln Ala Asn Lys Ala Thr Leu Val Cys Leu Ile Ser
    130                 135                 140

Asp Phe Tyr Pro Gly Ala Val Thr Val Ala Trp Lys Ala Asp Ser Ser
145                 150                 155                 160

Pro Val Lys Ala Gly Val Glu Thr Thr Thr Pro Ser Lys Gln Ser Asn
                165                 170                 175

Asn Lys Tyr Ala Ala Ser Ser Tyr Leu Ser Leu Thr Pro Glu Gln Trp
            180                 185                 190

Lys Ser His Arg Ser Tyr Ser Cys Gln Val Thr His Glu Gly Ser Thr
        195                 200                 205

Val Glu Lys Thr Val Ala Pro Thr
    210                 215

<210> SEQ ID NO 115
<211> LENGTH: 421
<212> TYPE: PRT
<213> ORGANISM: Homo sapiens

<400> SEQUENCE: 115

Trp Gly Leu Ser Glu Val Ser Cys Lys Ala Ser Gly Tyr Thr Phe Thr
1               5                   10                  15

Gly Tyr Tyr Met His Trp Val Arg Gln Ala Pro Gly Gln Gly Leu Glu
            20                  25                  30

Trp Met Gly Trp Ile Asn Pro Asn Ser Gly Gly Thr Asn Tyr Ala Gln
        35                  40                  45

Lys Phe Gln Gly Arg Val Thr Met Thr Arg Asp Thr Ser Ile Ser Thr
50                  55                  60

Ala Tyr Met Glu Leu Ser Arg Leu Arg Ser Asp Asp Thr Ala Val Tyr
65                  70                  75                  80

Tyr Cys Ala Arg Glu Leu Arg Tyr Phe Gly Trp Leu Leu Ser Ser Leu
                85                  90                  95

Asp Tyr Trp Gly Gln Gly Thr Leu Val Thr Val Ser Ser Ala Ser Thr
            100                 105                 110

Lys Gly Pro Ser Val Phe Pro Leu Ala Pro Cys Ser Arg Ser Thr Ser
        115                 120                 125

Glu Ser Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Asn Phe Gly Thr Gln Thr Tyr Thr Cys
            180                 185                 190

Asn Val Asp His Lys Pro Ser Asn Thr Lys Val Asp Lys Thr Val Glu
        195                 200                 205

Arg Lys Cys Cys Val Glu Cys Pro Pro Cys Pro Ala Pro Pro Val Ala
    210                 215                 220

Gly Pro Ser Val Phe Leu Phe Pro Pro Lys Pro Lys Asp Thr Leu Met
225                 230                 235                 240

Ile Ser Arg Thr Pro Glu Val Thr Cys Val Val Val Asp Val Ser His
                245                 250                 255

Glu Asp Pro Glu Val Gln Phe Asn Trp Tyr Val Asp Gly Val Glu Val
            260                 265                 270

His Asn Ala Lys Thr Lys Pro Arg Glu Glu Gln Phe Asn Ser Thr Phe
        275                 280                 285
```

```
Arg Val Val Ser Val Leu Thr Val His Gln Asp Trp Leu Asn Gly
    290                 295                 300

Lys Glu Tyr Lys Cys Lys Val Ser Asn Lys Gly Leu Pro Ala Pro Ile
305                 310                 315                 320

Glu Lys Thr Ile Ser Lys Thr Lys Gly Gln Pro Arg Glu Pro Gln Val
                325                 330                 335

Tyr Thr Leu Pro Pro Ser Arg Glu Glu Met Thr Lys Asn Gln Val Ser
            340                 345                 350

Leu Thr Cys Leu Val Lys Gly Phe Tyr Pro Ser Asp Ile Ala Val Glu
        355                 360                 365

Trp Glu Ser Asn Gly Gln Pro Glu Asn Asn Tyr Lys Thr Thr Pro Pro
    370                 375                 380

Met Leu Asp Ser Asp Gly Ser Phe Phe Leu Tyr Ser Lys Leu Thr Val
385                 390                 395                 400

Asp Lys Ser Arg Trp Gln Gln Gly Asn Val Phe Ser Cys Ser Val Met
                405                 410                 415

His Glu Ala Leu His
            420

<210> SEQ ID NO 116
<211> LENGTH: 226
<212> TYPE: PRT
<213> ORGANISM: Homo sapiens

<400> SEQUENCE: 116

Leu Leu Gly Leu Leu Leu Leu Trp Leu Arg Gly Ala Arg Cys Asp Ile
1               5                   10                  15

Gln Met Thr Gln Ser Pro Ser Ser Leu Ser Ala Ser Val Gly Asp Arg
            20                  25                  30

Val Thr Ile Thr Cys Arg Ala Ser Gln Ser Ile Ser Ser Tyr Leu Asn
        35                  40                  45

Trp Phe Gln Gln Lys Pro Gly Lys Ala Pro Lys Leu Leu Ile Tyr Ala
    50                  55                  60

Ala Ser Ser Leu Gln Ser Gly Val Pro Ser Arg Phe Ser Gly Ser Glu
65                  70                  75                  80

Ser Gly Thr Asp Phe Thr Leu Thr Ile Ser Ser Leu Gln Pro Glu Asp
                85                  90                  95

Phe Ala Thr Tyr Ser Cys Gln Gln Ser Tyr Ser Phe Pro Leu Thr Phe
            100                 105                 110

Gly Gly Gly Thr Lys Val Glu Ile Lys Arg Thr Val Ala Ala Pro Ser
        115                 120                 125

Val Phe Ile Phe Pro Pro Ser Asp Glu Gln Leu Lys Ser Gly Thr Ala
    130                 135                 140

Ser Val Val Cys Leu Leu Asn Asn Phe Tyr Pro Arg Glu Ala Lys Val
145                 150                 155                 160

Gln Trp Lys Val Asp Asn Ala Leu Gln Ser Gly Asn Ser Gln Glu Ser
                165                 170                 175

Val Thr Glu Gln Asp Ser Lys Asp Ser Thr Tyr Ser Leu Ser Ser Thr
            180                 185                 190

Leu Thr Leu Ser Lys Ala Asp Tyr Glu Lys His Lys Val Tyr Ala Cys
        195                 200                 205

Glu Val Thr His Gln Gly Leu Ser Ser Pro Val Thr Lys Ser Phe Asn
    210                 215                 220

Arg Gly
225
```

```
<210> SEQ ID NO 117
<211> LENGTH: 399
<212> TYPE: PRT
<213> ORGANISM: Homo sapiens

<400> SEQUENCE: 117

Trp Gly Leu Ser Glu Val Ser Cys Lys Ala Ser Gly Tyr Thr Phe Thr
1               5                   10                  15

Ser Tyr Asp Ile His Trp Val Arg Gln Ala Thr Gly Gln Gly Leu Glu
            20                  25                  30

Trp Met Gly Trp Met Asn Pro Asn Ser Gly Asn Thr Val Tyr Ala Gln
        35                  40                  45

Lys Phe Gln Gly Arg Val Thr Met Thr Arg Asn Thr Ser Ile Ser Thr
50                  55                  60

Ala Tyr Met Glu Leu Ser Ser Leu Arg Ser Glu Asp Thr Ala Val Tyr
65                  70                  75                  80

Tyr Cys Ala Arg Thr Val Leu Leu Trp Pro Phe Asp Tyr Trp Gly Gln
                85                  90                  95

Gly Thr Leu Val Thr Val Ser Ser Ala Ser Thr Lys Gly Pro Ser Val
            100                 105                 110

Phe Pro Leu Ala Pro Cys Ser Arg Ser Thr Ser Glu Ser Thr Ala Ala
        115                 120                 125

Leu Gly Cys Leu Val Lys Asp Tyr Phe Pro Glu Pro Val Thr Val Ser
130                 135                 140

Trp Asn Ser Gly Ala Leu Thr Ser Gly Val His Thr Phe Pro Ala Val
145                 150                 155                 160

Leu Gln Ser Ser Gly Leu Tyr Ser Leu Ser Ser Val Val Thr Val Pro
                165                 170                 175

Ser Ser Asn Phe Gly Thr Gln Thr Tyr Thr Cys Asn Val Asp His Lys
            180                 185                 190

Pro Ser Asn Thr Lys Val Asp Lys Thr Val Glu Arg Lys Cys Cys Val
        195                 200                 205

Glu Cys Pro Pro Cys Pro Ala Pro Pro Val Ala Gly Pro Ser Val Phe
210                 215                 220

Leu Phe Pro Pro Lys Pro Lys Asp Thr Leu Met Ile Ser Arg Thr Pro
225                 230                 235                 240

Glu Val Thr Cys Val Val Val Asp Val Ser His Glu Asp Pro Glu Val
                245                 250                 255

Gln Phe Asn Trp Tyr Val Asp Gly Val Glu Val His Asn Ala Lys Thr
            260                 265                 270

Lys Pro Arg Glu Glu Gln Phe Asn Ser Thr Phe Arg Val Val Ser Val
        275                 280                 285

Leu Thr Val Val His Gln Asp Trp Leu Asn Gly Lys Glu Tyr Lys Cys
290                 295                 300

Lys Val Ser Asn Lys Gly Leu Pro Ala Pro Ile Glu Lys Thr Ile Ser
305                 310                 315                 320

Lys Thr Lys Gly Gln Pro Arg Glu Pro Gln Val Tyr Thr Leu Pro Pro
                325                 330                 335

Ser Arg Glu Glu Met Thr Lys Asn Gln Val Ser Leu Thr Cys Leu Val
            340                 345                 350

Lys Gly Phe Tyr Pro Ser Asp Ile Ala Val Glu Trp Glu Ser Asn Gly
        355                 360                 365

Gln Pro Glu Asn Asn Tyr Lys Thr Thr Pro Pro Met Leu Asp Ser Asp
370                 375                 380
```

Gly Ser Phe Phe Leu Tyr Ser Lys Leu Thr Val Asp Lys Ser Arg
385 390 395

<210> SEQ ID NO 118
<211> LENGTH: 227
<212> TYPE: PRT
<213> ORGANISM: Homo sapiens

<400> SEQUENCE: 118

Trp Ile Ser Gly Ala Tyr Gly Asp Ile Val Met Thr Gln Ser Pro Asp
1 5 10 15

Ser Leu Ala Val Ser Leu Gly Glu Arg Ala Thr Ile Asn Cys Lys Ser
20 25 30

Ser Gln Ser Val Leu Tyr Ser Ser Lys Asn Lys Asn Tyr Leu Ala Trp
35 40 45

Tyr Gln Gln Lys Pro Gly Gln Pro Pro Lys Leu Leu Ile Tyr Trp Ala
50 55 60

Ser Thr Arg Glu Ser Gly Val Pro Asp Arg Phe Ser Gly Ser Gly Ser
65 70 75 80

Gly Thr Asp Phe Thr Leu Thr Ile Ser Ser Leu Gln Ala Glu Asp Val
85 90 95

Ala Val Tyr Tyr Cys Gln Gln Tyr Tyr Ser Thr Pro Pro Trp Thr Phe
100 105 110

Gly Gln Gly Thr Lys Val Glu Ile Lys Arg Thr Val Ala Ala Pro Ser
115 120 125

Val Phe Ile Phe Pro Pro Ser Asp Glu Gln Leu Lys Ser Gly Thr Ala
130 135 140

Ser Val Val Cys Leu Leu Asn Asn Phe Tyr Pro Arg Glu Ala Lys Val
145 150 155 160

Gln Trp Lys Val Asp Asn Ala Leu Gln Ser Gly Asn Ser Gln Glu Ser
165 170 175

Val Thr Glu Gln Asp Ser Lys Asp Ser Thr Tyr Ser Leu Ser Ser Thr
180 185 190

Leu Thr Leu Ser Lys Ala Asp Tyr Glu Lys His Lys Val Tyr Ala Cys
195 200 205

Glu Val Thr His Gln Gly Leu Ser Ser Pro Val Thr Lys Ser Phe Asn
210 215 220

Arg Gly Glu
225

<210> SEQ ID NO 119
<211> LENGTH: 128
<212> TYPE: PRT
<213> ORGANISM: Homo sapiens

<400> SEQUENCE: 119

Ser Gly Gly Gly Leu Val Gln Pro Gly Gly Ser Leu Arg Leu Ser Cys
1 5 10 15

Ala Ala Ser Gly Phe Thr Phe Ser Ser Tyr Ala Met Ser Trp Val Arg
20 25 30

Gln Ala Pro Gly Lys Gly Leu Glu Trp Val Ser Ala Ile Ser Gly Ser
35 40 45

Asp Gly Ser Pro Tyr Tyr Ala Asp Ser Val Lys Gly Arg Phe Thr Ile
50 55 60

Ser Arg Asp Asn Ser Lys Asn Thr Leu Tyr Leu Gln Met Asn Ser Leu
65 70 75 80

Arg Ala Glu Asp Thr Ala Val Tyr Tyr Cys Ala Lys Asp Gly Tyr Ser
                85                  90                  95

Ser Gly Trp Asn Tyr Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

<210> SEQ ID NO 120
<211> LENGTH: 226
<212> TYPE: PRT
<213> ORGANISM: Homo sapiens

<400> SEQUENCE: 120

Trp Ile Ser Gly Ala Tyr Gly Asp Ile Val Met Thr Gln Ser Pro Asp
1               5                   10                  15

Ser Leu Ala Val Ser Leu Gly Glu Arg Ala Thr Ile Asn Cys Lys Ser
            20                  25                  30

Ser Gln Ser Val Leu Tyr Ser Ser Asn Asn Lys Asn Tyr Leu Ala Trp
        35                  40                  45

Tyr Gln Gln Lys Pro Gly Gln Pro Pro Lys Leu Leu Ile Tyr Trp Ala
    50                  55                  60

Ser Thr Arg Glu Ser Gly Val Pro Asp Arg Phe Ser Gly Ser Gly Ser
65                  70                  75                  80

Gly Thr Asp Phe Thr Leu Thr Ile Ser Ser Leu Gln Ala Glu Asp Val
                85                  90                  95

Ala Val Tyr Tyr Cys Gln Glu Tyr Tyr Ser Thr Met Cys Ser Phe Gly
            100                 105                 110

Gln Gly Thr Lys Leu Glu Ile Lys Arg Thr Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
    210                 215                 220

Gly Glu
225

<210> SEQ ID NO 121
<211> LENGTH: 136
<212> TYPE: PRT
<213> ORGANISM: Homo sapiens

<400> SEQUENCE: 121

Val Glu Ser Gly Gly Gly Val Val Gln Pro Gly Arg Ser Leu Arg Leu
1               5                   10                  15

Ser Cys Ala Ala Ser Gly Phe Thr Phe Arg Ser Tyr Gly Met His Trp
            20                  25                  30

Val Arg Gln Ala Pro Gly Lys Gly Leu Glu Trp Val Ala Val Ile Trp
        35                  40                  45

Ser Asp Gly Ser Asn Lys Tyr Tyr Ala Asp Ser Val Lys Gly Arg Phe

```
              50                  55                  60
Thr Ile Ser Arg Asp Asn Ser Lys Asn Thr Leu Tyr Leu Gln Met Asn
 65                  70                  75                  80

Ser Leu Arg Ala Glu Asp Thr Ala Val Tyr Tyr Cys Ala Arg Glu Gly
                 85                  90                  95

Tyr Tyr Gly Ser Gly Ser Tyr Tyr Tyr Tyr Gly Met Asp Val Trp
                100                 105                 110

Gly Gln Gly Thr Thr Val Thr Val Ser Ser Ala Ser Thr Lys Gly Pro
                115                 120                 125

Ser Val Phe Pro Leu Ala Pro Ser
                130                 135
```

<210> SEQ ID NO 122
<211> LENGTH: 226
<212> TYPE: PRT
<213> ORGANISM: Homo sapiens

<400> SEQUENCE: 122

```
Leu Leu Thr Leu Leu Thr His Ser Ala Val Ser Val Val Gln Ala Gly
 1               5                  10                  15

Leu Thr Gln Pro Pro Ser Val Ser Lys Gly Leu Arg Gln Thr Ala Thr
                20                  25                  30

Leu Thr Cys Thr Gly Asn Ser Asn Asn Val Gly Thr Gln Gly Ala Ala
                35                  40                  45

Trp Leu Gln Gln His Gln Gly His Pro Pro Lys Leu Leu Ser Tyr Arg
 50                  55                  60

Asn Asn Asn Arg Pro Ser Gly Ile Ser Glu Arg Leu Ser Ala Ser Thr
 65                  70                  75                  80

Ser Gly Asn Thr Ala Ser Leu Thr Ile Thr Gly Leu Gln Pro Glu Asp
                 85                  90                  95

Glu Ala Asp Tyr Tyr Cys Ser Ala Trp Asp Ser Ser Leu Ser Ala Val
                100                 105                 110

Val Phe Gly Gly Gly Thr Lys Leu Thr Val Leu Gly Gln Pro Lys Ala
                115                 120                 125

Ala Pro Ser Val Thr Leu Phe Pro Pro Ser Ser Glu Glu Leu Gln Ala
                130                 135                 140

Asn Lys Ala Thr Leu Val Cys Leu Ile Ser Asp Phe Tyr Pro Gly Ala
145                 150                 155                 160

Val Thr Val Ala Trp Lys Ala Asp Ser Ser Pro Val Lys Ala Gly Val
                165                 170                 175

Glu Thr Thr Thr Pro Ser Lys Gln Ser Asn Asn Lys Tyr Ala Ala Ser
                180                 185                 190

Ser Tyr Leu Ser Leu Thr Pro Glu Gln Trp Lys Ser His Arg Ser Tyr
                195                 200                 205

Ser Cys Gln Val Thr His Glu Gly Ser Thr Val Glu Lys Thr Val Ala
                210                 215                 220

Pro Thr
225
```

<210> SEQ ID NO 123
<211> LENGTH: 416
<212> TYPE: PRT
<213> ORGANISM: Homo sapiens

<400> SEQUENCE: 123

```
Leu Ser Leu Thr Cys Thr Val Ser Gly Gly Ser Ile Ser Ser Tyr Tyr
 1               5                  10                  15
```

-continued

Trp Ser Trp Ile Arg Gln Ser Ala Gly Lys Gly Leu Glu Trp Ile Gly
           20                  25                  30

Arg Ile Tyr Thr Gly Val Ser Thr Asn Tyr Asn Pro Ser Leu Lys Ser
       35                  40                  45

Arg Val Thr Met Ser Val Asp Thr Ser Lys Asn Gln Phe Ser Leu Lys
50                  55                  60

Leu Ser Ser Val Thr Ala Ala Asp Thr Ala Val Tyr Tyr Cys Ala Arg
65                  70                  75                  80

Asp Tyr Tyr Asp Ser Ser Gly Tyr Tyr Pro Phe Asp Tyr Trp Gly Gln
               85                  90                  95

Gly Thr Leu Val Thr Val Ser Ser Ala Ser Thr Lys Gly Pro Ser Val
           100                 105                 110

Phe Pro Leu Ala Pro Cys Ser Arg Ser Thr Ser Glu Ser Thr Ala Ala
       115                 120                 125

Leu Gly Cys Leu Val Lys Asp Tyr Phe Pro Glu Pro Val Thr Val Ser
130                 135                 140

Trp Asn Ser Gly Ala Leu Thr Ser Gly Val His Thr Phe Pro Ala Val
145                 150                 155                 160

Leu Gln Ser Ser Gly Leu Tyr Ser Leu Ser Ser Val Val Thr Val Pro
               165                 170                 175

Ser Ser Asn Phe Gly Thr Gln Thr Tyr Thr Cys Asn Val Asp His Lys
           180                 185                 190

Pro Ser Asn Thr Lys Val Asp Lys Thr Val Glu Arg Lys Cys Cys Val
       195                 200                 205

Glu Cys Pro Pro Cys Pro Ala Pro Pro Val Ala Gly Pro Ser Val Phe
210                 215                 220

Leu Phe Pro Pro Lys Pro Lys Asp Thr Leu Met Ile Ser Arg Thr Pro
225                 230                 235                 240

Glu Val Thr Cys Val Val Val Asp Val Ser His Glu Asp Pro Glu Val
               245                 250                 255

Gln Phe Asn Trp Tyr Val Asp Gly Val Glu Val His Asn Ala Lys Thr
           260                 265                 270

Lys Pro Arg Glu Glu Gln Phe Asn Ser Thr Phe Arg Val Val Ser Val
       275                 280                 285

Leu Thr Val Val His Gln Asp Trp Leu Asn Gly Lys Glu Tyr Lys Cys
290                 295                 300

Lys Val Ser Asn Lys Gly Leu Pro Ala Pro Ile Glu Lys Thr Ile Ser
305                 310                 315                 320

Lys Thr Lys Gly Gln Pro Arg Glu Pro Gln Val Tyr Thr Leu Pro Pro
               325                 330                 335

Ser Arg Glu Glu Met Thr Lys Asn Gln Val Ser Leu Thr Cys Leu Val
           340                 345                 350

Lys Gly Phe Tyr Pro Ser Asp Ile Ala Val Glu Trp Glu Ser Asn Gly
       355                 360                 365

Gln Pro Glu Asn Asn Tyr Lys Thr Thr Pro Pro Met Leu Asp Ser Asp
370                 375                 380

Gly Ser Phe Phe Leu Tyr Ser Lys Leu Thr Val Asp Lys Ser Arg Trp
385                 390                 395                 400

Gln Gln Gly Asn Val Phe Ser Cys Ser Val Met His Glu Ala Leu His
               405                 410                 415

<210> SEQ ID NO 124
<211> LENGTH: 226
<212> TYPE: PRT

<213> ORGANISM: Homo sapiens

<400> SEQUENCE: 124

Leu Leu Gly Leu Leu Leu Cys Phe Pro Gly Ala Arg Cys Asp Ile
1               5                   10                  15

Gln Met Thr Gln Ser Pro Ser Ser Leu Ser Ala Ser Val Gly Asp Arg
            20                  25                  30

Val Thr Ile Ser Cys Arg Ala Ser Gln Gly Ile Ser Asn Tyr Leu Ala
        35                  40                  45

Trp Phe Gln Gln Lys Pro Gly Lys Ala Pro Lys Ser Leu Ile Tyr Ala
    50                  55                  60

Ala Ser Ser Leu Glu Asn Gly Val Pro Ser Lys Phe Ser Gly Ser Gly
65                  70                  75                  80

Ser Gly Thr Asp Phe Thr Leu Thr Ile Ser Ser Leu Gln Pro Glu Asp
                85                  90                  95

Phe Ala Thr Tyr Tyr Cys Gln Gln Tyr Asn Ser Ser Pro Phe Thr Phe
            100                 105                 110

Gly Pro Gly Thr Lys Val Asp Ile Arg Arg Thr Val Ala Ala Pro Ser
        115                 120                 125

Val Phe Ile Phe Pro Pro Ser Asp Glu Gln Leu Lys Ser Gly Thr Ala
    130                 135                 140

Ser Val Val Cys Leu Leu Asn Asn Phe Tyr Pro Arg Glu Ala Lys Val
145                 150                 155                 160

Gln Trp Lys Val Asp Asn Ala Leu Gln Ser Gly Asn Ser Gln Glu Ser
                165                 170                 175

Val Thr Glu Gln Asp Ser Lys Asp Ser Thr Tyr Ser Leu Ser Ser Thr
            180                 185                 190

Leu Thr Leu Ser Lys Ala Asp Tyr Glu Lys His Lys Val Tyr Ala Cys
        195                 200                 205

Glu Val Thr His Gln Gly Leu Ser Ser Pro Val Thr Lys Ser Phe Asn
    210                 215                 220

Arg Gly
225

<210> SEQ ID NO 125
<211> LENGTH: 135
<212> TYPE: PRT
<213> ORGANISM: Homo sapiens

<400> SEQUENCE: 125

Val Glu Ser Gly Pro Gly Leu Val Lys Pro Ser Gln Thr Leu Ser Leu
1               5                   10                  15

Thr Cys Thr Val Ser Gly Gly Ser Ile Asn Ser Phe Gly Tyr Tyr Trp
            20                  25                  30

Ser Trp Ile Arg Gln Tyr Pro Gly Lys Gly Leu Glu Trp Ile Gly Phe
        35                  40                  45

Leu Tyr Phe Thr Gly Ser Thr Tyr Tyr Asn Pro Ser Leu Lys Ser Arg
    50                  55                  60

Val Thr Ile Ser Val Asp Thr Ser Lys Ser Gln Phe Ser Leu Lys Leu
65                  70                  75                  80

Ser Ser Val Thr Ala Ala Asp Thr Ala Val Tyr Tyr Cys Ala Arg Ala
                85                  90                  95

Gly Thr Met Val Arg Gly Ala His Tyr Tyr Gly Met Asp Val Trp Gly
            100                 105                 110

Gln Gly Thr Thr Val Thr Val Ser Ser Ala Ser Thr Lys Gly Pro Ser
        115                 120                 125

```
Val Phe Pro Leu Ala Pro Ser
    130             135
```

```
<210> SEQ ID NO 126
<211> LENGTH: 231
<212> TYPE: PRT
<213> ORGANISM: Homo sapiens

<400> SEQUENCE: 126

Gln Leu Leu Gly Leu Leu Leu Trp Leu Arg Gly Arg Cys Asp
1               5                   10                  15

Ile Gln Met Thr Gln Ser Pro Ser Leu Ser Ala Ser Val Gly Asp
            20                  25                  30

Arg Val Thr Ile Thr Cys Arg Ala Ser Gln Ser Ile Ser Asn Tyr Leu
            35                  40                  45

Asn Trp Tyr Gln Gln Lys Pro Gly Lys Ala Pro Lys Leu Leu Ile Tyr
        50                  55                  60

Ala Ala Ser Ser Leu Gln Ser Gly Val Pro Ser Arg Phe Ser Gly Ser
65                  70                  75                  80

Gly Ser Gly Thr Asp Phe Thr Leu Thr Ile Ser Ser Leu Gln Pro Glu
                85                  90                  95

Asp Phe Ala Thr Tyr Tyr Cys Gln Gln Ile Tyr Ser Thr Pro Pro Glu
            100                 105                 110

Trp Thr Phe Gly Gln Gly Thr Lys Val Glu Ile Lys Arg Thr Val Ala
        115                 120                 125

Ala Pro Ser Val Phe Ile Phe Pro Pro Ser Asp Glu Gln Leu Lys Ser
    130                 135                 140

Gly Thr Ala Ser Val Val Cys Leu Leu Asn Asn Phe Tyr Pro Arg Glu
145                 150                 155                 160

Ala Lys Val Gln Trp Lys Val Asp Asn Ala Leu Gln Ser Gly Asn Ser
                165                 170                 175

Gln Glu Ser Val Thr Glu Gln Asp Ser Lys Asp Ser Thr Tyr Ser Leu
            180                 185                 190

Ser Ser Thr Leu Thr Leu Ser Lys Ala Asp Tyr Glu Lys His Lys Val
        195                 200                 205

Tyr Ala Cys Glu Val Thr His Gln Gly Leu Ser Ser Pro Val Thr Lys
    210                 215                 220

Ser Phe Asn Arg Gly Glu Cys
225                 230
```

```
<210> SEQ ID NO 127
<211> LENGTH: 136
<212> TYPE: PRT
<213> ORGANISM: Homo sapiens

<400> SEQUENCE: 127

Glu Val Gln Leu Val Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Met Tyr Tyr Ser Gly Ser Thr Tyr His Asn Pro Ser
    50                  55                  60

Leu Lys Ser Arg Val Ile Ile Ser Val Asp Thr Ser Lys Asn Gln Phe
65                  70                  75                  80
```

```
Ser Leu Lys Leu Ser Ser Val Thr Ala Ala Asp Thr Ala Val Tyr Tyr
                85                  90                  95

Cys Ala Arg His Tyr Ile Thr Val Ala Gly Ile Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser
    130                 135

<210> SEQ ID NO 128
<211> LENGTH: 226
<212> TYPE: PRT
<213> ORGANISM: Homo sapiens

<400> SEQUENCE: 128

Leu Leu Thr Leu Leu Thr His Cys Ala Gly Ser Trp Ala Gln Ser Val
1               5                   10                  15

Leu Thr Gln Pro Pro Ser Ala Ser Gly Thr Pro Gly Arg Ala Thr
            20                  25                  30

Ile Ser Cys Ser Gly Ser Ser Thr Asn Ile Gly Ser Thr Ile Val Asn
            35                  40                  45

Trp Tyr Gln Gln Val Pro Gly Thr Ala Pro Lys Leu Leu Ile Tyr Ser
    50                  55                  60

Asn Asn Gln Arg Pro Ser Gly Val Pro Asp Arg Phe Ser Gly Ser Lys
65                  70                  75                  80

Ser Gly Thr Ser Ala Ser Leu Ala Ile Ser Gly Leu Gln Ser Glu Asp
                85                  90                  95

Glu Ala Asp Tyr Tyr Cys Ala Ala Trp Asp Ala Ser Leu Asn Gly Pro
            100                 105                 110

Val Phe Gly Gly Gly Thr Lys Leu Thr Val Leu Gly Gln Pro Lys Ala
        115                 120                 125

Ala Pro Ser Val Thr Leu Phe Pro Pro Ser Ser Glu Glu Leu Gln Ala
    130                 135                 140

Asn Lys Ala Thr Leu Val Cys Leu Ile Ser Asp Phe Tyr Pro Gly Ala
145                 150                 155                 160

Val Thr Val Ala Trp Lys Ala Asp Ser Ser Pro Val Lys Ala Gly Val
                165                 170                 175

Glu Thr Thr Thr Pro Ser Lys Gln Ser Asn Asn Lys Tyr Ala Ala Ser
            180                 185                 190

Ser Tyr Leu Ser Leu Thr Pro Glu Gln Trp Lys Ser His Arg Ser Tyr
        195                 200                 205

Ser Cys Gln Val Thr His Glu Gly Ser Thr Val Glu Lys Thr Val Ala
    210                 215                 220

Pro Thr
225

<210> SEQ ID NO 129
<211> LENGTH: 129
<212> TYPE: PRT
<213> ORGANISM: Homo sapiens

<400> SEQUENCE: 129

Val Glu Ser Gly Pro Gly Leu Val Lys Pro Ser Glu Thr Leu Ser Leu
1               5                   10                  15

Thr Cys Thr Val Ser Gly Gly Ser Ile Ser Ser Tyr Tyr Trp Ser Trp
            20                  25                  30

Ile Arg Gln Pro Pro Gly Lys Gly Leu Glu Trp Ile Gly Tyr Ile Tyr
```

```
                35                  40                  45
Tyr Ser Gly Ser Thr Asn Tyr Asn Pro Ser Leu Lys Ser Arg Val Thr
    50                  55                  60

Ile Ser Val Asp Thr Ser Lys Asn Gln Phe Ser Leu Lys Leu Ser Ser
65                  70                  75                  80

Val Thr Ala Ala Asp Thr Ala Val Tyr Tyr Cys Ala Arg Ala Tyr Gly
                85                  90                  95

Tyr Tyr Tyr Tyr Gly Met Asp Val Trp Gly Gln Gly Thr Thr Val Thr
                100                 105                 110

Val Ser Ser Ala Ser Thr Lys Gly Pro Ser Val Phe Pro Leu Ala Pro
            115                 120                 125

Ser

<210> SEQ ID NO 130
<211> LENGTH: 228
<212> TYPE: PRT
<213> ORGANISM: Homo sapiens

<400> SEQUENCE: 130

Gln Leu Leu Gly Leu Leu Leu Trp Leu Arg Gly Ala Arg Cys Asp
1               5                   10                  15

Ile Gln Met Thr Gln Ser Pro Ser Ser Leu Ser Ala Ser Val Gly Asp
                20                  25                  30

Arg Val Thr Ile Thr Cys Arg Thr Ser Gln Ser Ile Ser Ser Tyr Leu
            35                  40                  45

Asn Trp Tyr Gln Gln Lys Pro Gly Lys Ala Pro Asn Leu Leu Ile Tyr
    50                  55                  60

Ala Ala Ser Ser Leu Gln Ser Gly Val Pro Ser Arg Phe Ser Gly Ser
65                  70                  75                  80

Gly Ser Gly Thr Asp Phe Thr Leu Thr Ile Ser Ser Leu Gln Pro Glu
                85                  90                  95

Asp Phe Ala Thr Tyr Tyr Cys Gln Gln Thr Tyr Ser Ser Pro Pro Trp
                100                 105                 110

Thr Phe Gly Gln Gly Thr Lys Val Glu Ile Lys Arg Thr Val Ala Ala
            115                 120                 125

Pro Ser Val Phe Ile Phe Pro Pro Ser Asp Glu Gln Leu Lys Ser Gly
    130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
                165                 170                 175

Glu Ser Val Thr Glu Gln Asp Ser Lys Asp Ser Thr Tyr Ser Leu Ser
                180                 185                 190

Ser Thr Leu Thr Leu Ser Lys Ala Asp Tyr Glu Lys His Lys Val Tyr
            195                 200                 205

Ala Cys Glu Val Thr His Gln Gly Leu Ser Ser Pro Val Thr Lys Ser
    210                 215                 220

Phe Asn Arg Gly
225

<210> SEQ ID NO 131
<211> LENGTH: 121
<212> TYPE: PRT
<213> ORGANISM: Homo sapiens

<400> SEQUENCE: 131
```

```
Leu Leu Glu Ser Gly Pro Gly Leu Val Lys Pro Ser Gln Thr Leu Ser
1               5                   10                  15

Leu Thr Cys Ala Ile Ser Gly Asp Ser Val Ser Ser Asn Ser Ala Ala
                20                  25                  30

Trp Asn Trp Ile Arg Gln Ser Pro Ser Arg Gly Leu Glu Trp Leu Gly
            35                  40                  45

Arg Thr Tyr Tyr Arg Ser Lys Trp Tyr Asn Ala Tyr Ala Val Ser Val
        50                  55                  60

Lys Ser Arg Met Thr Ile Asn Pro Asp Thr Ser Lys Asn Gln Phe Ser
65              70                  75                  80

Leu Gln Leu Asn Ser Val Thr Pro Glu Asp Thr Ala Val Tyr Tyr Cys
                85                  90                  95

Ala Arg Glu Ala Gly Gly Trp Phe Asp Pro Trp Gly Gln Gly Thr Leu
            100                 105                 110

Val Thr Val Ser Ser Ala Ser Thr Lys
            115                 120
```

<210> SEQ ID NO 132
<211> LENGTH: 227
<212> TYPE: PRT
<213> ORGANISM: Homo sapiens

<400> SEQUENCE: 132

```
Gln Leu Leu Gly Leu Leu Leu Trp Phe Pro Gly Ser Arg Cys Asp
1               5                   10                  15

Ile Gln Met Thr Gln Ser Pro Ser Ser Val Ser Ala Ser Val Gly Asp
                20                  25                  30

Arg Val Thr Ile Thr Cys Arg Ala Ser Gln Gly Ile Arg Ser Trp Leu
            35                  40                  45

Ala Trp Tyr Gln Gln Lys Pro Gly Lys Ala Pro Lys Leu Leu Ile Tyr
        50                  55                  60

Ala Ala Ser Ser Leu Gln Ser Gly Val Pro Ser Arg Phe Ser Gly Ser
65              70                  75                  80

Gly Ser Gly Thr Asp Phe Thr Leu Thr Ile Ser Ser Leu Gln Pro Glu
                85                  90                  95

Asp Phe Ala Thr Tyr Tyr Cys Gln Gln Ala Asn Ser Phe Pro Pro Thr
            100                 105                 110

Phe Gly Gly Gly Thr Lys Val Glu Ile Lys Arg Thr Val Ala Ala Pro
        115                 120                 125

Ser Val Phe Ile Phe Pro Pro Ser Asp Glu Gln Leu Lys Ser Gly Thr
    130                 135                 140

Ala Ser Val Val Cys Leu Leu Asn Asn Phe Tyr Pro Arg Glu Ala Lys
145                 150                 155                 160

Val Gln Trp Lys Val Asp Asn Ala Leu Gln Ser Gly Asn Ser Gln Glu
                165                 170                 175

Ser Val Thr Glu Gln Asp Ser Lys Asp Ser Thr Tyr Ser Leu Ser Ser
            180                 185                 190

Thr Leu Thr Leu Ser Lys Ala Asp Tyr Glu Lys His Lys Val Tyr Ala
        195                 200                 205

Cys Glu Val Thr His Gln Gly Leu Ser Ser Pro Val Thr Lys Ser Phe
    210                 215                 220

Asn Arg Gly
225
```

<210> SEQ ID NO 133
<211> LENGTH: 123

```
<212> TYPE: PRT
<213> ORGANISM: Homo sapiens

<400> SEQUENCE: 133

Glu Val Gln Leu Leu Glu Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Tyr Tyr Asn Ala Tyr Pro
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Ala Gly Gly Trp Phe Asp Pro Trp Gly Gln
            100                 105                 110

Gly Thr Leu Val Thr Val Ser Ser Ala Ser Thr
        115                 120

<210> SEQ ID NO 134
<211> LENGTH: 225
<212> TYPE: PRT
<213> ORGANISM: Homo sapiens

<400> SEQUENCE: 134

Leu Leu Gly Leu Leu Leu Leu Trp Phe Pro Gly Ser Arg Cys Asp Ile
1               5                   10                  15

Gln Met Thr Gln Ser Pro Ser Ser Val Ser Ala Ser Val Gly Asp Arg
            20                  25                  30

Val Thr Ile Thr Cys Arg Ala Asn Gln Gly Ile Arg Ser Trp Leu Ala
        35                  40                  45

Trp Tyr Gln Gln Lys Pro Gly Lys Ala Pro Lys Leu Leu Ile Tyr Ala
    50                  55                  60

Ala Ser Ser Leu Gln Ser Gly Val Pro Ser Arg Phe Ser Gly Ser Gly
65                  70                  75                  80

Ser Gly Thr Asp Phe Thr Leu Thr Ile Ser Ser Leu Gln Pro Glu Asp
                85                  90                  95

Phe Ala Thr Tyr Tyr Cys Gln Gln Ala Asn Ser Phe Pro Pro Thr Phe
            100                 105                 110

Gly Gly Gly Thr Lys Val Glu Ile Lys Arg Thr Val Ala Ala Pro Ser
        115                 120                 125

Val Phe Ile Phe Pro Pro Ser Asp Glu Gln Leu Lys Ser Gly Thr Ala
    130                 135                 140

Ser Val Val Cys Leu Leu Asn Asn Phe Tyr Pro Arg Glu Ala Lys Val
145                 150                 155                 160

Gln Trp Lys Val Asp Asn Ala Leu Gln Ser Gly Asn Ser Gln Glu Ser
                165                 170                 175

Val Thr Glu Gln Asp Ser Lys Asp Ser Thr Tyr Ser Leu Ser Ser Thr
            180                 185                 190

Leu Thr Leu Ser Lys Ala Asp Tyr Glu Lys His Lys Val Tyr Ala Cys
        195                 200                 205

Glu Val Thr His Gln Gly Leu Ser Ser Pro Val Thr Lys Ser Phe Asn
    210                 215                 220

Arg
```

-continued

<210> SEQ ID NO 135
<211> LENGTH: 142
<212> TYPE: PRT
<213> ORGANISM: Homo sapiens

<400> SEQUENCE: 135

Glu Val His Leu Val Glu Ser Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Met Ala Met Tyr Tyr Cys
                85                  90                  95

Ala Arg Ser Arg Ile Thr Ile Phe Gly Val Val His Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr
    130                 135                 140

<210> SEQ ID NO 136
<211> LENGTH: 156
<212> TYPE: PRT
<213> ORGANISM: Homo sapiens

<400> SEQUENCE: 136

Thr Gln Leu Thr Gln Ser Pro Ser Ser Leu Ser Ala Ser Val Gly Asp
1               5                   10                  15

Arg Val Thr Ile Thr Cys Arg Ala Ser Gln Asn Ile Asn Ser Tyr Leu
            20                  25                  30

Asn Trp Tyr Gln Gln Lys Pro Gly Lys Ala Pro Lys Leu Leu Ile Tyr
        35                  40                  45

Ala Ala Ser Ser Leu Gln Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Thr Thr Tyr Tyr Cys Gln Gln Ser Tyr Ser Ser Ala Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly
145                 150                 155

<210> SEQ ID NO 137
<211> LENGTH: 130
<212> TYPE: PRT
<213> ORGANISM: Homo sapiens

<400> SEQUENCE: 137

Gly Pro Gly Leu Val Lys Pro Ser Glu Thr Leu Ser Leu Thr Cys Thr
1               5                   10                  15

Val Ser Gly Gly Ser Ile Ser Ser Tyr Tyr Trp Ser Trp Ile Arg Gln
            20                  25                  30

Pro Pro Gly Lys Gly Leu Glu Trp Ile Gly Tyr Ile Tyr Tyr Ser Gly
        35                  40                  45

Ser Thr Asn Tyr Asn Pro Ser Leu Lys Ser Arg Val Thr Ile Ser Val
    50                  55                  60

Asp Thr Ser Lys Asn Gln Phe Ser Leu Lys Leu Ser Ser Val Thr Ala
65                  70                  75                  80

Ala Asp Thr Ala Val Tyr Tyr Cys Ala Arg Ala Val Ser Tyr Tyr Tyr
                85                  90                  95

Tyr Gly Met Asp Val Trp Gly Gln Gly Thr Thr Val Thr Val Ser Ser
            100                 105                 110

Ala Ser Thr Lys Gly Pro Ser Val Phe Pro Leu Ala Pro Ser Ser Lys
            115                 120                 125

Ser Thr
    130

<210> SEQ ID NO 138
<211> LENGTH: 234
<212> TYPE: PRT
<213> ORGANISM: Homo sapiens

<400> SEQUENCE: 138

Val Pro Ala Gln Leu Leu Gly Leu Leu Leu Leu Trp Leu Arg Gly Ala
1               5                   10                  15

Arg Cys Asp Ile Gln Met Thr Gln Ser Pro Ser Ser Leu Ser Ala Ser
            20                  25                  30

Val Gly Asp Arg Val Thr Ile Thr Cys Arg Thr Ile Gln Asn Ile Asn
            35                  40                  45

Ser Tyr Leu Asn Trp Tyr Gln Gln Arg Pro Gly Lys Ala Pro Lys Leu
    50                  55                  60

Leu Ile Tyr Ala Thr Ser Ser Leu Gln Ser Gly Val Pro Ser Arg Phe
65                  70                  75                  80

Ser Gly Ser Gly Ser Gly Thr Asp Phe Thr Leu Thr Ile Ser Ser Leu
                85                  90                  95

Gln Pro Glu Asp Phe Ala Thr Tyr Tyr Cys Gln Gln Tyr Tyr Ser Thr
            100                 105                 110

Leu Phe Thr Phe Gly Pro Gly Thr Lys Val Asp Ile Lys Arg Thr Val
            115                 120                 125

Ala Ala Pro Ser Val Phe Ile Phe Pro Pro Ser Asp Glu Gln Leu Lys
            130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
            195                 200                 205

Val Tyr Ala Cys Glu Val Thr His Gln Gly Leu Ser Ser Pro Val Thr
    210                 215                 220

```
Lys Ser Phe Asn Arg Gly Glu Trp Leu Glu
225                 230
```

<210> SEQ ID NO 139
<211> LENGTH: 132
<212> TYPE: PRT
<213> ORGANISM: Homo sapiens

<400> SEQUENCE: 139

```
Gly Pro Gly Leu Val Lys Pro Ser Glu Thr Leu Ser Leu Thr Cys Thr
1               5                   10                  15

Val Pro Gly Gly Ser Ile Arg Ser Tyr Phe Trp Ser Trp Ile Arg Gln
                20                  25                  30

Pro Ala Gly Lys Gly Leu Glu Trp Ile Gly Arg Phe Tyr Phe Ser Gly
            35                  40                  45

Ser Thr Asn Tyr Asn Pro Ser Leu Lys Ser Arg Val Thr Met Ser Val
        50                  55                  60

Asp Thr Ser Lys Asn Gln Phe Ser Leu Lys Leu Ser Ser Val Thr Ala
65                  70                  75                  80

Ala Asp Thr Ala Val Tyr Tyr Cys Ala Arg Asp Tyr Gly Asp His Tyr
                85                  90                  95

Tyr Tyr Tyr Gly Met Asp Val Trp Gly Gln Gly Thr Thr Val Thr Val
                100                 105                 110

Ser Ser Ala Ser Thr Lys Gly Pro Ser Val Phe Pro Leu Ala Pro Ser
            115                 120                 125

Ser Lys Ser Thr
        130
```

<210> SEQ ID NO 140
<211> LENGTH: 211
<212> TYPE: PRT
<213> ORGANISM: Homo sapiens

<400> SEQUENCE: 140

```
Val Leu Thr Gln Pro Pro Ser Val Ser Ala Ala Pro Gly Gln Lys Val
1               5                   10                  15

Thr Ile Ser Cys Ser Gly Ser Ser Asn Ile Gly Asn Asn Tyr Val
                20                  25                  30

Ser Trp Tyr Gln Gln Phe Pro Gly Thr Ala Pro Lys Phe Leu Ile Tyr
            35                  40                  45

Asp Asn Asn Lys Arg Ser Ser Gly Ile Pro Asp Arg Phe Ser Gly Ser
        50                  55                  60

Lys Ser Gly Thr Ser Ala Thr Leu Gly Ile Thr Gly Leu Gln Thr Gly
65                  70                  75                  80

Asp Glu Ala Asp Tyr Tyr Cys Gly Thr Trp Asp Ser Ser Leu Ser Ala
                85                  90                  95

Val Ile Phe Gly Gly Gly Thr Lys Leu Thr Val Leu Gly Gln Pro Lys
                100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
        130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
```

180                 185                 190
Tyr Ser Cys Gln Val Thr His Glu Gly Ser Thr Val Glu Lys Thr Val
        195                 200                 205

Ala Pro Thr
    210

<210> SEQ ID NO 141
<211> LENGTH: 86
<212> TYPE: PRT
<213> ORGANISM: Homo sapiens

<400> SEQUENCE: 141

Gly Phe Thr Phe Ser Ser Tyr Gly Met His Trp Val Arg Gln Ala Pro
1               5                   10                  15

Gly Lys Gly Leu Glu Trp Val Ala Ile Ile Trp Tyr Asp Glu Ser Asn
            20                  25                  30

Lys Tyr Tyr Ala Asp Ser Val Lys Gly Arg Phe Thr Ile Ser Arg Asp
        35                  40                  45

Asn Ser Lys Asn Thr Leu Tyr Leu Gln Met Asn Ser Leu Arg Ala Glu
    50                  55                  60

Asp Thr Ala Val Tyr Tyr Cys Ala Arg Ala Tyr Ser Gly Ser Tyr Gly
65                  70                  75                  80

Tyr Ser Tyr Tyr Gly Met
            85

<210> SEQ ID NO 142
<211> LENGTH: 181
<212> TYPE: PRT
<213> ORGANISM: Homo sapiens

<400> SEQUENCE: 142

Gln Asp Arg Gln Pro Ala Ser Pro Gly Ser Gly Asp Lys Leu Gly Asp
1               5                   10                  15

Lys Tyr Ala Cys Trp Tyr Gln Gln Lys Pro Gly Gln Ser Pro Val Leu
            20                  25                  30

Val Ile Tyr Gln Asp Ser Lys Arg Pro Ser Gly Ile Pro Glu Arg Phe
        35                  40                  45

Ser Gly Ser Asn Ser Gly Asn Thr Ala Thr Leu Thr Ile Ser Gly Thr
    50                  55                  60

Gln Ala Met Asp Glu Ala Asp Tyr Tyr Cys Gln Ala Trp Asp Asn Arg
65                  70                  75                  80

Thr Ala Val Phe Gly Gly Gly Thr Lys Leu Thr Val Leu Gly Gln Pro
            85                  90                  95

Lys Ala Ala Pro Ser Val Thr Leu Phe Pro Pro Ser Ser Glu Glu Leu
        100                 105                 110

Gln Ala Asn Lys Ala Thr Leu Val Cys Leu Ile Ser Asp Phe Tyr Pro
    115                 120                 125

Gly Ala Val Thr Val Ala Trp Lys Ala Asp Ser Ser Pro Val Lys Ala
130                 135                 140

Gly Val Glu Thr Thr Thr Pro Ser Lys Gln Ser Asn Asn Lys Tyr Ala
145                 150                 155                 160

Ala Ser Ser Tyr Leu Ser Leu Thr Pro Glu Gln Trp Lys Ser His Arg
            165                 170                 175

Ser Tyr Ser Cys Gln
        180

<210> SEQ ID NO 143

```
<211> LENGTH: 133
<212> TYPE: PRT
<213> ORGANISM: Homo sapiens

<400> SEQUENCE: 143

Arg Cys Arg Leu Val Glu Ser Gly Ala Glu Val Lys Lys Pro Gly Glu
1               5                   10                  15

Ser Leu Lys Ile Ser Cys Lys Gly Ser Gly Tyr Arg Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Arg Ser Leu Lys Ala Ser Asp Thr Ala Met Tyr Tyr Cys
                85                  90                  95

Ala Arg Lys Asp Tyr Tyr Tyr Val Met Asp Val Trp Gly Gln Gly
            100                 105                 110

Thr Thr Val Thr Val Ser Ser Ala Ser Thr Lys Gly Pro Ser Val Phe
            115                 120                 125

Pro Leu Ala Pro Ser
        130

<210> SEQ ID NO 144
<211> LENGTH: 197
<212> TYPE: PRT
<213> ORGANISM: Homo sapiens

<400> SEQUENCE: 144

Asp Thr Ile Ser Cys Thr Gly Thr Ser Ser Asp Val Gly Asn Tyr Asn
1               5                   10                  15

Tyr Val Ser Trp Tyr Gln Gln His Pro Gly Lys Ala Pro Lys Leu Met
            20                  25                  30

Ile Tyr Ala Val Asn Asn Arg Pro Ser Gly Val Ser Asn Arg Phe Ser
        35                  40                  45

Gly Ser Lys Ser Gly Asn Thr Ala Ser Leu Thr Ile Ser Gly Leu Gln
    50                  55                  60

Ala Glu Asp Glu Ala Asp Tyr Tyr Cys Ser Ser Tyr Thr Ser Ser Arg
65                  70                  75                  80

Asn Leu Val Val Phe Gly Gly Gly Thr Lys Leu Thr Val Leu Gly Gln
                85                  90                  95

Pro Lys Ala Ala Pro Ser Val Thr Leu Phe Pro Pro Ser Ser Glu Glu
            100                 105                 110

Leu Gln Ala Asn Lys Ala Thr Leu Val Cys Leu Ile Ser Asp Phe Tyr
            115                 120                 125

Pro Gly Ala Val Thr Val Ala Trp Lys Ala Asp Ser Ser Pro Val Lys
        130                 135                 140

Ala Gly Val Glu Thr Thr Thr Pro Ser Lys Gln Ser Asn Asn Lys Tyr
145                 150                 155                 160

Ala Ala Ser Ser Tyr Leu Ser Leu Thr Pro Glu Gln Trp Lys Ser His
                165                 170                 175

Arg Ser Tyr Ser Cys Gln Val Thr His Glu Gly Ser Thr Val Glu Lys
            180                 185                 190

Thr Val Ala Pro Thr
        195
```

<210> SEQ ID NO 145
<211> LENGTH: 454
<212> TYPE: PRT
<213> ORGANISM: Homo sapiens

<400> SEQUENCE: 145

```
Met Lys His Leu Trp Phe Phe Leu Leu Val Ala Ala Pro Arg Trp
1               5                  10                  15

Val Leu Ser Gln Val Gln Leu Gln Glu Ser Gly Pro Gly Leu Val Lys
            20                  25                  30

Pro Ser Gln Thr Leu Ser Leu Thr Cys Thr Val Ser Gly Gly Ser Ile
        35                  40                  45

Ser Ser Gly Gly Tyr Tyr Trp Ser Trp Ile Arg Gln His Pro Gly Lys
    50                  55                  60

Gly Leu Glu Trp Ile Gly Ile Ile Tyr Tyr Ser Gly Ser Thr Tyr Tyr
65                  70                  75                  80

Asn Pro Ser Leu Lys Ser Arg Val Thr Ile Ser Val Asp Thr Ser Lys
                85                  90                  95

Asn Gln Phe Ser Leu Lys Leu Asn Ser Val Thr Ala Ala Asp Thr Ala
            100                 105                 110

Val Phe Tyr Cys Ala Arg Val Ala Ile Val Thr Thr Ile Pro Gly Gly
        115                 120                 125

Met Asp Val Trp Gly Gln Gly Thr Thr Val Thr Val Ser Ser Ala Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Asn Ser Thr
305                 310                 315                 320

Phe Arg Val Val Ser Val Leu Thr Val Val His Gln Asp Trp Leu Asn
                325                 330                 335

Gly Lys Glu Tyr Lys Cys Lys Val Ser Asn Lys Gly Leu Pro Ala Pro
            340                 345                 350

Ile Glu Lys Thr Ile Ser Lys Thr Lys Gly Gln Pro Arg Glu Pro Gln
        355                 360                 365

Val Tyr Thr Leu Pro Pro Ser Arg Glu Glu Met Thr Lys Asn Gln Val
    370                 375                 380
```

```
Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
            405                 410                 415

Pro Met Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His
        450

<210> SEQ ID NO 146
<211> LENGTH: 219
<212> TYPE: PRT
<213> ORGANISM: Homo sapiens

<400> SEQUENCE: 146

Met Leu Pro Ser Gln Leu Ile Gly Phe Leu Leu Leu Trp Val Pro Ala
1               5                   10                  15

Ser Arg Gly Glu Ile Val Leu Thr Gln Ser Pro Asp Phe Gln Ser Val
            20                  25                  30

Thr Pro Lys Glu Lys Val Thr Ile Thr Cys Arg Ala Ser Gln Ser Ile
        35                  40                  45

Gly Ile Ser Leu His Trp Tyr Gln Gln Lys Pro Asp Gln Ser Pro Lys
    50                  55                  60

Leu Leu Ile Lys Tyr Ala Ser Gln Ser Phe Ser Gly Val Pro Ser Arg
65                  70                  75                  80

Phe Ser Gly Ser Gly Ser Gly Thr Asp Phe Thr Leu Thr Ile Asn Ser
                85                  90                  95

Leu Glu Ala Glu Asp Ala Ala Thr Tyr Tyr Cys His Gln Ser Arg Ser
            100                 105                 110

Phe Pro Trp Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly
    210                 215

<210> SEQ ID NO 147
<211> LENGTH: 189
<212> TYPE: PRT
<213> ORGANISM: Homo sapiens

<400> SEQUENCE: 147

Met Asp Trp Thr Trp Ser Ile Leu Phe Leu Val Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
```

-continued

```
            35                  40                  45
Thr Ser Tyr Gly Ile Ser Trp Val Arg Gln Ala Pro Gly Gln Gly Leu
 50                  55                  60

Glu Trp Met Gly Trp Ile Ser Ala Tyr Asn Gly Asn Thr Tyr Tyr Ala
 65                  70                  75                  80

Gln Lys Leu Gln Ala Arg Val Thr Met Thr Thr Asp Thr Ser Thr Ser
                 85                  90                  95

Thr Ala Tyr Met Glu Leu Arg Ser Leu Arg Ser Asp Asp Thr Ala Val
                100                 105                 110

Tyr Tyr Cys Ala Arg Asp Gly Tyr Ser Ser Ser Trp Ser Leu Leu His
                115                 120                 125

Tyr Tyr Gly Met Asp Val Trp Gly Gln Gly Thr Thr Val Thr Val Ser
                130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Ala
                180                 185

<210> SEQ ID NO 148
<211> LENGTH: 217
<212> TYPE: PRT
<213> ORGANISM: Homo sapiens

<400> SEQUENCE: 148

Ser Asp Thr Arg Cys Asp Ile Gln Met Thr Gln Ser Pro Ser Ser Leu
 1               5                  10                  15

Ser Ala Ser Val Gly Asp Arg Ile Thr Ile Thr Trp Arg Ser Ser Gln
                 20                  25                  30

Gly Ile Tyr Asn Ser Leu Ala Trp Tyr Gln Gln Lys Pro Gly Lys Val
                 35                  40                  45

Pro Lys Leu Leu Ile Tyr Ala Ala Ser Thr Leu His Ser Gly Val Pro
 50                  55                  60

Ser Arg Phe Ser Gly Ser Gly Ser Gly Thr Asp Phe Thr Leu Thr Ile
 65                  70                  75                  80

Ser Ser Leu Gln Pro Glu Asp Val Ala Thr Tyr Tyr Cys Gln Lys Tyr
                 85                  90                  95

Asn Ser Ala Pro Phe Thr Phe Gly Pro Gly Thr Lys Val Asp Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
                130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly
210                 215
```

```
<210> SEQ ID NO 149
<211> LENGTH: 132
<212> TYPE: PRT
<213> ORGANISM: Homo sapiens

<400> SEQUENCE: 149

Leu Val Glu Ser Gly Ala Glu Val Lys Lys Pro Gly Glu Ser Leu Lys
1               5                   10                  15

Ile Ser Cys Lys Gly Ser Gly Tyr Arg Phe Thr Ser Tyr Trp Ile Gly
            20                  25                  30

Trp Val Arg Gln Met Pro Gly Lys Gly Leu Glu Trp Met Gly Ile Ile
        35                  40                  45

Tyr Pro Gly Asp Ser Asp Thr Arg Tyr Ser Pro Ser Phe Gln Gly Gln
    50                  55                  60

Val Thr Ile Ser Ala Asp Lys Ser Ile Ser Thr Ala Tyr Leu Gln Trp
65                  70                  75                  80

Ser Ser Leu Lys Ala Ser Asp Thr Ala Met Tyr Tyr Cys Ala Arg Lys
                85                  90                  95

Asp Tyr Tyr Tyr Ser Met Asp Val Trp Gly Gln Gly Thr Thr Val
            100                 105                 110

Thr Val Ser Ser Ala Ser Thr Lys Gly Pro Ser Val Phe Pro Leu Glu
            115                 120                 125

Pro Ser Ser Lys
    130

<210> SEQ ID NO 150
<211> LENGTH: 190
<212> TYPE: PRT
<213> ORGANISM: Homo sapiens

<400> SEQUENCE: 150

Gly Gln Ser Ala Leu Thr Gln Pro Ala Ser Val Ser Gly Ser Pro Gly
1               5                   10                  15

Gln Ser Ile Thr Ile Ser Cys Thr Gly Thr Ser Ser Asp Val Gly Gly
            20                  25                  30

Tyr Asn Tyr Val Ser Trp Tyr Gln Gln His Pro Gly Gln Ala Pro Lys
        35                  40                  45

Leu Leu Ile Tyr Gly Val Asn Ile Arg Pro Ser Gly Val Ser Thr Arg
    50                  55                  60

Phe Ser Gly Ser Lys Ser Gly Asn Thr Ala Ser Leu Thr Ile Ser Gly
65                  70                  75                  80

Leu Gln Ala Glu Asp Glu Ala Asp Tyr Tyr Cys Ser Ser Tyr Thr Arg
                85                  90                  95

Ser Ser Ile Leu Val Val Phe Ala Gly Gly Thr Lys Leu Thr Val Leu
            100                 105                 110

Gly Gln Pro Lys Ala Ala Pro Ser Val Thr Leu Phe Pro Pro Ser Ser
            115                 120                 125

Glu Glu Leu Gln Ala Asn Lys Ala Thr Leu Val Cys Leu Ile Ser Asp
        130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln
            180                 185                 190

<210> SEQ ID NO 151
```

```
<211> LENGTH: 142
<212> TYPE: PRT
<213> ORGANISM: Homo sapiens

<400> SEQUENCE: 151

Glu Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Arg Ile Thr Ile Phe Gly Val Val His Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr
    130                 135                 140

<210> SEQ ID NO 152
<211> LENGTH: 156
<212> TYPE: PRT
<213> ORGANISM: Homo sapiens

<400> SEQUENCE: 152

Asp Thr Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Leu Lys Pro Gly Lys Ala Pro Lys Leu Leu Ile
        35                  40                  45

Tyr Ala Ala Ser Ser Leu Glu Ser Gly Val Pro Ser Arg Phe Ser Gly
    50                  55                  60

Ser Glu Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asn Ser Pro Ile
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser
145                 150                 155

<210> SEQ ID NO 153
<211> LENGTH: 178
<212> TYPE: PRT
<213> ORGANISM: Homo sapiens

<400> SEQUENCE: 153

Met Gly Ser Thr Ala Ile Leu Ala Leu Leu Leu Ala Val Leu Gln Gly
```

-continued

```
                1               5                   10                  15
Val Cys Ala Glu Val Gln Leu Val Gln Ser Gly Ala Glu Val Lys Lys
                20                  25                  30

Pro Gly Glu Ser Leu Lys Ile Ser Cys Lys Gly Ser Gly Tyr Arg Phe
                35                  40                  45

Thr Ser Tyr Trp Ile Gly Trp Val Arg Gln Met Pro Gly Lys Gly Leu
        50                  55                  60

Glu Trp Met Gly Ile Ile Tyr Pro Gly Asp Ser Asp Thr Arg Tyr Ser
65                  70                  75                  80

Pro Ser Phe Gln Gly Gln Val Thr Ile Ser Ala Asp Lys Ser Ile Ser
                85                  90                  95

Thr Ala Tyr Leu Gln Trp Ser Ser Leu Lys Ala Ser Asp Thr Ala Met
                100                 105                 110

Tyr Tyr Cys Ala Arg Lys Asp Tyr Tyr Tyr Thr Met Asp Val Trp
                115                 120                 125

Gly Gln Gly Thr Thr Val Thr Val Ser Ser Ala Ser Thr Lys Gly Pro
                130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser

<210> SEQ ID NO 154
<211> LENGTH: 216
<212> TYPE: PRT
<213> ORGANISM: Homo sapiens

<400> SEQUENCE: 154

Leu Gly Gln Ser Ala Leu Thr Gln Pro Ala Ser Val Ser Gly Ser Pro
1               5                   10                  15

Gly Gln Ser Ile Thr Ile Ser Cys Thr Gly Thr Ser Ser Asp Val Gly
                20                  25                  30

Gly Tyr Asn Tyr Val Ser Trp Tyr Gln Gln His Pro Gly Lys Ala Pro
                35                  40                  45

Lys Leu Met Ile Tyr Ala Val Ser Asn Arg Pro Ser Gly Val Ser Asn
                50                  55                  60

Arg Phe Ser Gly Ser Lys Ser Gly Asn Thr Ala Ser Leu Thr Ile Ser
65                  70                  75                  80

Gly Leu Gln Ala Glu Asp Glu Ala Asp Tyr Tyr Cys Ser Ser Tyr Thr
                85                  90                  95

Ile Ser Arg Ile Leu Val Val Phe Gly Gly Gly Thr Lys Leu Thr Val
                100                 105                 110

Leu Gly Gln Pro Lys Ala Ala Pro Ser Val Thr Leu Phe Pro Pro Ser
                115                 120                 125

Ser Glu Glu Leu Gln Ala Asn Lys Ala Thr Leu Val Cys Leu Ile Ser
                130                 135                 140

Asp Phe Tyr Pro Gly Ala Val Thr Val Ala Trp Lys Ala Asp Ser Ser
145                 150                 155                 160

Pro Val Lys Ala Gly Val Glu Thr Thr Thr Pro Ser Lys Gln Ser Asn
                165                 170                 175

Asn Lys Tyr Ala Ala Ser Ser Tyr Leu Ser Leu Thr Pro Glu Gln Trp
                180                 185                 190

Lys Ser His Arg Ser Tyr Ser Cys Gln Val Thr His Glu Gly Ser Thr
                195                 200                 205
```

```
Val Glu Lys Thr Val Ala Pro Thr
    210                 215

<210> SEQ ID NO 155
<211> LENGTH: 215
<212> TYPE: PRT
<213> ORGANISM: Homo sapiens

<400> SEQUENCE: 155

Met Lys His Leu Trp Phe Phe Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Gln Thr Leu Ser Leu Thr Cys Thr Val Ser Gly Gly Ser Ile
            35                  40                  45

Thr Ser Gly Asp Tyr Tyr Trp Ser Trp Ile Arg Gln His Pro Gly Lys
        50                  55                  60

Gly Leu Glu Trp Phe Gly Phe Ile Tyr Tyr Ser Gly Ser Ala Tyr Tyr
65                  70                  75                  80

Asn Pro Ser Leu Lys Ser Arg Ile Thr Ile Ser Val Asp Thr Ser Lys
                85                  90                  95

Asn Gln Phe Ser Leu Lys Leu Ser Ser Val Thr Ala Ala Asp Thr Ala
            100                 105                 110

Val Tyr Tyr Cys Ala Arg Glu Arg Asn Tyr Gly Gly Asn Ser Phe Asp
        115                 120                 125

Tyr Trp Gly Gln Gly Thr Leu Val Thr Val Ser Ser Ala Ser Thr Lys
130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Thr
    210                 215

<210> SEQ ID NO 156
<211> LENGTH: 223
<212> TYPE: PRT
<213> ORGANISM: Homo sapiens
<220> FEATURE:
<221> NAME/KEY: VARIANT
<222> LOCATION: 211
<223> OTHER INFORMATION: Xaa = Any amino acid.

<400> SEQUENCE: 156

Trp Ile Ser Gly Ser Ser Gly Asp Ile Val Met Thr Gln Ser Pro Leu
1               5                   10                  15

Ser Leu Pro Val Thr Pro Gly Glu Pro Ala Ser Ile Ser Cys Arg Ser
            20                  25                  30

Ser Gln Ser Leu Leu His Ser Asn Gly Tyr Asn Tyr Leu Asp Trp Tyr
        35                  40                  45

Leu Gln Lys Pro Gly Gln Ser Pro Gln Leu Leu Ile Tyr Leu Gly Ser
    50                  55                  60

Asn Arg Ala Ser Gly Val Pro Asp Arg Phe Ser Gly Ser Gly Ser Gly
65                  70                  75                  80
```

```
Thr Asp Phe Thr Leu Lys Ile Ser Arg Val Glu Ala Glu Asp Val Gly
                 85                  90                  95
Val Tyr Tyr Cys Met Gln Ala Leu Gln Thr Ile Thr Phe Gly Gln Gly
            100                 105                 110
Thr Arg Leu Glu Ile Lys Arg Thr Val Ala Ala Pro Ser Val Phe Ile
        115                 120                 125
Phe Pro Pro Ser Asp Glu Gln Leu Lys Ser Gly Thr Ala Ser Val Val
130                 135                 140
Cys Leu Leu Asn Asn Phe Tyr Pro Arg Glu Ala Lys Val Gln Trp Lys
145                 150                 155                 160
Val Asp Asn Ala Leu Gln Ser Gly Asn Ser Gln Glu Ser Val Thr Glu
                165                 170                 175
Gln Asp Ser Lys Asp Ser Thr Tyr Ser Leu Ser Ser Thr Leu Thr Leu
            180                 185                 190
Ser Lys Ala Asp Tyr Glu Lys His Lys Val Tyr Ala Cys Glu Val Thr
        195                 200                 205
His Gln Xaa Leu Ser Ser Pro Val Thr Lys Ser Phe Asn Arg Gly
210                 215                 220

<210> SEQ ID NO 157
<211> LENGTH: 182
<212> TYPE: PRT
<213> ORGANISM: Homo sapiens

<400> SEQUENCE: 157

Met Gly Ser Thr Ala Ile Leu Ala Leu Leu Ala Val Leu Gln Gly
1               5                   10                  15
Val Cys Ala Glu Val Gln Leu Val Gln Ser Gly Ala Glu Val Lys Lys
            20                  25                  30
Pro Gly Glu Ser Leu Lys Ile Ser Cys Lys Gly Ser Gly Tyr Arg Phe
        35                  40                  45
Thr Ser Tyr Trp Ile Gly Trp Val Arg Gln Met Pro Gly Lys Gly Leu
    50                  55                  60
Glu Trp Met Gly Ile Ile Tyr Pro Gly Asp Ser Asp Thr Arg Tyr Ser
65                  70                  75                  80
Pro Ser Phe Gln Gly Gln Val Thr Ile Ser Ala Asp Lys Ser Ile Ser
                85                  90                  95
Thr Ala Tyr Leu Gln Trp Ser Ser Leu Lys Ala Ser Asp Thr Ala Met
            100                 105                 110
Tyr Tyr Cys Ala Arg Lys Asp Tyr Tyr Tyr Ser Met Asp Val Trp
        115                 120                 125
Gly Gln Gly Thr Thr Val Thr Val Ser Ser Ala Ser Thr Lys Gly Pro
130                 135                 140
Ser Val Phe Pro Leu Ala Pro Ser Ser Lys Ser Thr Ser Gly Gly Thr
145                 150                 155                 160
Ala Ala Leu Gly Cys Leu Val Lys Asp Tyr Phe Pro Glu Pro Ser Asp
                165                 170                 175
Glu Cys Arg Glu Leu Ser
            180

<210> SEQ ID NO 158
<211> LENGTH: 217
<212> TYPE: PRT
<213> ORGANISM: Homo sapiens

<400> SEQUENCE: 158
```

```
Gly Leu Gly Gln Ser Ala Leu Thr Gln Pro Ala Ser Val Ser Gly Ser
1               5                   10                  15

Pro Gly Gln Ser Ile Thr Ile Ser Cys Thr Gly Thr Ser Ser Asp Val
            20                  25                  30

Gly Arg Phe Asn Tyr Val Ser Trp Tyr Gln Gln Arg Pro Gly Lys Ala
        35                  40                  45

Pro Lys Leu Met Ile Tyr Ala Val Asn Ile Arg Pro Ser Gly Val Ser
50                  55                  60

Asn Arg Phe Ser Gly Ser Lys Ser Gly Asn Thr Ala Ser Leu Thr Ile
65                  70                  75                  80

Ser Gly Leu Gln Ala Glu Asp Glu Ala Gly Tyr Tyr Cys Ser Ser Tyr
                85                  90                  95

Thr Ser Ser Ser Thr Leu Leu Val Phe Gly Gly Gly Thr Lys Leu Thr
            100                 105                 110

Val Leu Gly Gln Pro Lys Ala Ala Pro Ser Val Thr Leu Phe Pro Pro
        115                 120                 125

Ser Ser Glu Glu Leu Gln Ala Asn Lys Ala Thr Leu Val Cys Leu Ile
130                 135                 140

Ser Asp Phe Tyr Pro Gly Ala Val Thr Val Ala Trp Lys Ala Asp Ser
145                 150                 155                 160

Ser Pro Val Lys Ala Gly Val Glu Thr Thr Thr Pro Ser Lys Gln Ser
                165                 170                 175

Asn Asn Lys Tyr Ala Ala Ser Ser Tyr Leu Ser Leu Thr Pro Glu Gln
            180                 185                 190

Trp Lys Ser His Arg Ser Tyr Ser Cys Gln Val Thr His Glu Gly Ser
        195                 200                 205

Thr Val Glu Lys Thr Val Ala Pro Thr
210                 215

<210> SEQ ID NO 159
<211> LENGTH: 176
<212> TYPE: PRT
<213> ORGANISM: Homo sapiens

<400> SEQUENCE: 159

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
50                  55                  60

Glu Trp Val Ala Thr Ile Trp Phe Asp Gly Ser Asn Gly Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Ser Ser Gly Ser Tyr Asp His Phe Asp Tyr
        115                 120                 125

Trp Gly Gln Gly Thr Leu Val Thr Val Ser Ser Ala Ser Thr Lys Gly
130                 135                 140

Pro Ser Val Phe Pro Leu Ala Pro Cys Ser Arg Ser Thr Ser Glu Ser
145                 150                 155                 160
```

Thr Ala Ala Leu Gly Cys Leu Val Lys Asp Tyr Phe Pro Glu Pro Val
            165                 170                 175

<210> SEQ ID NO 160
<211> LENGTH: 222
<212> TYPE: PRT
<213> ORGANISM: Homo sapiens

<400> SEQUENCE: 160

Asp Gln Trp Asp Ile Val Met Thr Gln Ser Pro Leu Ser Leu Pro Val
1               5                   10                  15

Thr Pro Gly Glu Pro Ala Ser Ile Ser Cys Arg Ser Ser Gln Ser Leu
            20                  25                  30

Leu His Ser Asn Gly Tyr Asn Cys Leu Asp Trp Tyr Leu Gln Lys Pro
        35                  40                  45

Gly Gln Ser Pro Gln Leu Leu Ile Tyr Leu Gly Ser Asn Arg Ala Ser
    50                  55                  60

Gly Val Pro Asp Arg Phe Ser Gly Ser Gly Ser Gly Thr Asp Phe Thr
65                  70                  75                  80

Leu Lys Ile Ser Arg Val Glu Ala Glu Asp Val Gly Val Tyr Tyr Cys
                85                  90                  95

Met Gln Ala Leu Gln Thr Pro Ile Thr Phe Gly Gln Gly Thr Arg Val
            100                 105                 110

Glu Ile Lys Arg Thr Val Ala Ala Pro Ser Val Phe Ile Phe Pro Pro
        115                 120                 125

Ser Asp Glu Gln Leu Lys Ser Gly Thr Ala Ser Val Val Cys Leu Leu
    130                 135                 140

Asn Asn Phe Tyr Pro Arg Glu Ala Lys Val Gln Trp Lys Val Asp Asn
145                 150                 155                 160

Ala Leu Gln Ser Gly Asn Ser Gln Glu Ser Val Thr Glu Gln Asp Ser
                165                 170                 175

Lys Asp Ser Thr Tyr Ser Leu Ser Ser Thr Leu Thr Leu Ser Lys Ala
            180                 185                 190

Asp Tyr Glu Lys His Lys Val Tyr Ala Cys Glu Val Thr His Gln Gly
        195                 200                 205

Leu Ser Ser Pro Val Thr Lys Ser Phe Asn Arg Gly Glu Cys
    210                 215                 220

<210> SEQ ID NO 161
<211> LENGTH: 145
<212> TYPE: PRT
<213> ORGANISM: Homo sapiens

<400> SEQUENCE: 161

Cys Arg Leu Val Glu Ser Gly Ala Glu Val Lys Lys Pro Gly Ala Ser
1               5                   10                  15

Val Lys Val Ser Cys Lys Ala Ser Gly Tyr Thr Phe Thr Gly Tyr Tyr
            20                  25                  30

Met His Trp Val Arg Gln Ala Pro Gly Gln Gly Leu Glu Trp Met Gly
        35                  40                  45

Trp Ile Asn Pro Asn Ser Gly Gly Thr Asn Tyr Ala Gln Lys Phe Gln
    50                  55                  60

Gly Arg Val Thr Met Thr Arg Asp Thr Ser Ile Ser Thr Ala Tyr Met
65                  70                  75                  80

Glu Leu Ser Arg Leu Arg Ser Asp Asp Thr Ala Val Tyr Tyr Cys Ala
                85                  90                  95

Arg Asp Gln Val Asp Ile Val Ala Thr Arg Tyr Tyr Tyr Tyr Tyr Tyr

```
                    100                 105                 110
Gly Met Asp Val Trp Gly Gln Gly Thr Thr Val Thr Val Ser Ser Ala
            115                 120                 125
Ser Thr Lys Gly Pro Ser Val Phe Pro Leu Ala Pro Ser Ser Lys Ser
            130                 135                 140
Thr
145

<210> SEQ ID NO 162
<211> LENGTH: 132
<212> TYPE: PRT
<213> ORGANISM: Homo sapiens

<400> SEQUENCE: 162

Val Glu Ser Gly Pro Gly Leu Val Lys Pro Ser Gln Thr Leu Ser Leu
1               5                   10                  15
Thr Cys Thr Val Ser Gly Gly Ser Ile Ser Ser Gly Gly Tyr Tyr Trp
            20                  25                  30
Ser Trp Ile Arg Gln His Pro Gly Lys Gly Leu Glu Trp Ile Gly Tyr
        35                  40                  45
Ile Tyr Tyr Ser Gly Ser Thr Tyr Tyr Asn Pro Ser Leu Lys Ser Arg
    50                  55                  60
Val Thr Ile Ser Val Asp Thr Ser Lys Asn Gln Phe Ser Leu Lys Leu
65                  70                  75                  80
Ser Ser Val Thr Ala Ala Asp Thr Ala Val Tyr Tyr Cys Ala Arg Val
                85                  90                  95
Asp Ile Val Ala Thr Ile Pro Leu Ile Phe Asp Tyr Trp Gly Gln Gly
            100                 105                 110
Thr Leu Val Thr Val Ser Ser Ala Ser Thr Lys Gly Pro Ser Val Phe
            115                 120                 125
Pro Leu Ala Pro
    130

<210> SEQ ID NO 163
<211> LENGTH: 135
<212> TYPE: PRT
<213> ORGANISM: Homo sapiens

<400> SEQUENCE: 163

Glu Val Leu Leu Val Glu Ser Gly Pro Gly Leu Val Lys Pro Ser Glu
1               5                   10                  15
Thr Leu Ser Leu Thr Cys Thr Val Ser Gly Gly Ser Ile Ser Ser Ser
            20                  25                  30
Ser Tyr Phe Trp Gly Trp Ile Arg Gln Pro Pro Gly Lys Gly Leu Glu
        35                  40                  45
Trp Ile Gly Ser Ile Tyr Tyr Ser Gly Asn Thr Tyr Tyr Asn Pro Ser
    50                  55                  60
Leu Lys Ser Arg Val Thr Ile Ser Val Asp Thr Ser Lys Asn Arg Phe
65                  70                  75                  80
Ser Leu Lys Leu Ser Ser Val Thr Ala Ala Asp Thr Ala Val Tyr Cys
                85                  90                  95
Cys Ala Ser Ala Thr Thr Val Thr Thr Ala Phe Asp Ile Trp Gly Gln
            100                 105                 110
Gly Thr Met Val Thr Val Ser Ser Ala Ser Thr Lys Gly Pro Ser Val
            115                 120                 125
Phe Pro Leu Ala Pro Ser Ser
    130                 135
```

<210> SEQ ID NO 164
<211> LENGTH: 216
<212> TYPE: PRT
<213> ORGANISM: Homo sapiens

<400> SEQUENCE: 164

Leu Gly Gln Ser Ala Leu Thr Gln Pro Ala Ser Val Ser Gly Ser Pro
1               5                   10                  15

Gly Gln Ser Ile Thr Ile Ser Cys Thr Gly Thr Ser Ser Asp Val Gly
            20                  25                  30

Arg Tyr Asn Tyr Val Ser Trp Tyr Gln Gln His Pro Gly Gln Ala Pro
        35                  40                  45

Lys Leu Met Ile Tyr Gly Ile Ser Ile Arg Pro Ser Gly Val Ser Pro
    50                  55                  60

Arg Phe Ser Gly Ser Lys Ser Gly Asn Thr Ala Ser Leu Thr Ile Ser
65                  70                  75                  80

Gly Leu Gln Ala Glu Asp Glu Ala Asp Tyr Tyr Cys Ser Ser His Thr
                85                  90                  95

Ser Asn Ser Thr Leu Val Val Phe Ala Gly Gly Thr Lys Leu Thr Val
            100                 105                 110

Leu Gly Gln Pro Lys Ala Ala Pro Ser Val Thr Leu Phe Pro Pro Ser
        115                 120                 125

Ser Glu Glu Leu Gln Ala Asn Lys Ala Thr Leu Val Cys Leu Ile Ser
    130                 135                 140

Asp Phe Tyr Pro Gly Ala Val Thr Val Ala Trp Lys Ala Asp Ser Ser
145                 150                 155                 160

Pro Val Lys Ala Gly Val Glu Thr Thr Thr Pro Ser Lys Gln Ser Asn
                165                 170                 175

Asn Lys Tyr Ala Ala Ser Ser Tyr Leu Ser Leu Thr Pro Glu Gln Trp
            180                 185                 190

Lys Ser His Arg Ser Tyr Ser Cys Gln Val Thr His Glu Gly Ser Thr
        195                 200                 205

Val Glu Lys Thr Val Ala Pro Thr
    210                 215

<210> SEQ ID NO 165
<211> LENGTH: 24
<212> TYPE: DNA
<213> ORGANISM: Artificial Sequence
<220> FEATURE:
<223> OTHER INFORMATION: Flag Tag

<400> SEQUENCE: 165
gattacaagg atgacgacga taag                                          24

<210> SEQ ID NO 166
<211> LENGTH: 21
<212> TYPE: DNA
<213> ORGANISM: Artificial Sequence
<220> FEATURE:
<223> OTHER INFORMATION: RNAi Primer

<400> SEQUENCE: 166
aattctccga acgtgtcacg t                                             21

<210> SEQ ID NO 167
<211> LENGTH: 23
<212> TYPE: DNA
<213> ORGANISM: Artificial Sequence

```
<220> FEATURE:
<223> OTHER INFORMATION: RNAi Primer

<400> SEQUENCE: 167
aactgaagac ctgaagacaa taa                                             23

<210> SEQ ID NO 168
<211> LENGTH: 21
<212> TYPE: DNA
<213> ORGANISM: Artificial Sequence
<220> FEATURE:
<223> OTHER INFORMATION: RNAi Primer

<400> SEQUENCE: 168
aacctcatgg ctggaagaaa a                                               21

<210> SEQ ID NO 169
<211> LENGTH: 552
<212> TYPE: DNA
<213> ORGANISM: Homo sapiens

<400> SEQUENCE: 169
tgacatggac tgaaggagta gaaaagaagt ctccctcact gcccagctgg gatctcaggg     60
cttcattttc tgtcctccac catcatgggg tcaaccgcca tcctcgccct cctcctggct    120
gttctccaag gagtctgtgc cgaggtgcag ctggtgcagt ctggagcaga ggtgaaaaag    180
cccggggagt ctctgaagat ctcctgtaag ggttctggat acaggtttac cagctactgg    240
atcggctggg tgcgccagat gcccgggaaa ggcctggagt ggatggggat catctatcct    300
ggtgactctg ataccagata cagcccgtcc ttccaaggcc aggtcaccat ctcagccgac    360
aagtccatca gtaccgccta cctgcagtgg agcagcctga aggcctcgga caccgccatg    420
tattactgtg cgagaaagga ctactactac tacgctatgg acgtctgggg ccaagggacc    480
acggtcaccg tctcctcagc ctccaccaag ggcccatcgg tcttccccct ggcaccctcc    540
tccaaaagca cc                                                        552

<210> SEQ ID NO 170
<211> LENGTH: 156
<212> TYPE: PRT
<213> ORGANISM: Homo sapiens

<400> SEQUENCE: 170

Met Gly Ser Thr Ala Ile Leu Ala Leu Leu Leu Ala Val Leu Gln Gly
1               5                   10                  15

Val Cys Ala Glu Val Gln Leu Val Gln Ser Gly Ala Glu Val Lys Lys
            20                  25                  30

Pro Gly Glu Ser Leu Lys Ile Ser Cys Lys Gly Ser Gly Tyr Arg Phe
        35                  40                  45

Thr Ser Tyr Trp Ile Gly Trp Val Arg Gln Met Pro Gly Lys Gly Leu
    50                  55                  60

Glu Trp Met Gly Ile Ile Tyr Pro Gly Asp Ser Asp Thr Arg Tyr Ser
65                  70                  75                  80

Pro Ser Phe Gln Gly Gln Val Thr Ile Ser Ala Asp Lys Ser Ile Ser
                85                  90                  95

Thr Ala Tyr Leu Gln Trp Ser Ser Leu Lys Ala Ser Asp Thr Ala Met
            100                 105                 110

Tyr Tyr Cys Ala Arg Lys Asp Tyr Tyr Tyr Tyr Ala Met Asp Val Trp
        115                 120                 125

Gly Gln Gly Thr Thr Val Thr Val Ser Ser Ala Ser Thr Lys Gly Pro
```

Ser Val Phe Pro Leu Ala Pro Ser Ser Lys Ser Thr
145                 150                 155

<210> SEQ ID NO 171
<211> LENGTH: 589
<212> TYPE: DNA
<213> ORGANISM: Homo sapiens

<400> SEQUENCE: 171

```
aaaaactttt tgagagtcct ggacctcctg tgcaagaaca tgaaacatct gtggttcttc      60
cttctcctgg tggcagctcc cagatgggtc ctgtcccagg tgcagctgca ggagtcgggc     120
ccaggactgg tgaagccttc ggagaccctg tccctcacct gcactgtctc tggtggctcc     180
atcagtagtt actactggag ctggatccgg cagcccccag ggaagggact ggagtggatt     240
gggtatgtct atttcagtgg gagcaccaac tacaacccct ccctcaagag tcgagtcacc     300
atatcagtag acacgtccaa gaaccagttc tccctgaagc tgagctctgt gaccgctgcg     360
gacacggccg tgtattactg tgcgagagct acaagagact actactacta cggtatggac     420
gtctggggcc aagggaccac ggtcaccgtc tcctcagcct ccaccaaggg cccatcggtc     480
ttccccctgg caccctcctc caagagcacc tctgggggca cagcggccct gggctgcctg     540
gtcaaggact acttccccga accggtgacg gtgtcgtggg aactcagcg               589
```

<210> SEQ ID NO 172
<211> LENGTH: 183
<212> TYPE: PRT
<213> ORGANISM: Homo sapiens

<400> SEQUENCE: 172

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Ile
        35                  40                  45

Ser Ser Tyr Tyr Trp Ser Trp Ile Arg Gln Pro Pro Gly Lys Gly Leu
    50                  55                  60

Glu Trp Ile Gly Tyr Val Tyr Phe Ser Gly Ser Thr Asn Tyr Asn Pro
65                  70                  75                  80

Ser Leu Lys Ser Arg Val Thr Ile Ser Val Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Ala Thr Arg Asp Tyr Tyr Tyr Tyr Gly Met Asp Val
        115                 120                 125

Trp Gly Gln Gly Thr Thr Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Glu Leu Ser
            180

<210> SEQ ID NO 173
<211> LENGTH: 679

```
<212> TYPE: DNA
<213> ORGANISM: Homo sapiens

<400> SEQUENCE: 173
cagctcctgg ggctcctgct actctggctc cgaggtgcca gatgtgacat ccagatgacc        60
cagtctccat cctccctgtc tgcatctgta ggagacagag tcaccatcac ttgccggaca       120
agtcatgaca ttagtaacta tttaaattgg tatcagcaga aaccagggaa agcccctaag       180
ctcctgatct atgctgcatc cagtttgcaa agtggggtcc catcaaggtt cagtggcagt       240
agatctggga cagatttcac tctcaccatc agcagtctgc aacctgaaga ttttgcaact       300
tactactgtc aacagactta cagtaccctc ttcactttcg gccctgggac caaagtggat       360
atcaaacgaa ctgtggctgc accatctgtc ttcatcttcc cgccatctga tgagcagttg       420
aaatctggaa ctgcctctgt tgtgtgcctg ctgaataact tctatcccag agaggccaaa       480
gtacagtgga aggtggataa cgccctccaa tcgggtaact cccaggagag tgtcacagag       540
caggacagca aggacagcac ctacagcctc agcagcaccc tgacgctgag caaagcagac       600
tacgagaaac acaaagtcta cgcctgcgaa gtcacccatc agggcctgag ctcgcccgtc       660
acaaagagct tcaacaggg                                                   679

<210> SEQ ID NO 174
<211> LENGTH: 226
<212> TYPE: PRT
<213> ORGANISM: Homo sapiens

<400> SEQUENCE: 174

Gln Leu Leu Gly Leu Leu Leu Trp Leu Arg Gly Ala Arg Cys Asp
1               5                   10                  15

Ile Gln Met Thr Gln Ser Pro Ser Ser Leu Ser Ala Ser Val Gly Asp
            20                  25                  30

Arg Val Thr Ile Thr Cys Arg Thr Ser His Asp Ile Ser Asn Tyr Leu
        35                  40                  45

Asn Trp Tyr Gln Gln Lys Pro Gly Lys Ala Pro Lys Leu Leu Ile Tyr
    50                  55                  60

Ala Ala Ser Ser Leu Gln Ser Gly Val Pro Ser Arg Phe Ser Gly Ser
65                  70                  75                  80

Arg Ser Gly Thr Asp Phe Thr Leu Thr Ile Ser Ser Leu Gln Pro Glu
                85                  90                  95

Asp Phe Ala Thr Tyr Tyr Cys Gln Gln Thr Tyr Ser Thr Leu Phe Thr
            100                 105                 110

Phe Gly Pro Gly Thr Lys Val Asp Ile Lys Arg Thr Val Ala Ala Pro
        115                 120                 125

Ser Val Phe Ile Phe Pro Pro Ser Asp Glu Gln Leu Lys Ser Gly Thr
    130                 135                 140

Ala Ser Val Val Cys Leu Leu Asn Asn Phe Tyr Pro Arg Glu Ala Lys
145                 150                 155                 160

Val Gln Trp Lys Val Asp Asn Ala Leu Gln Ser Gly Asn Ser Gln Glu
                165                 170                 175

Ser Val Thr Glu Gln Asp Ser Lys Asp Ser Thr Tyr Ser Leu Ser Ser
            180                 185                 190

Thr Leu Thr Leu Ser Lys Ala Asp Tyr Glu Lys His Lys Val Tyr Ala
        195                 200                 205

Cys Glu Val Thr His Gln Gly Leu Ser Ser Pro Val Thr Lys Ser Phe
    210                 215                 220

Asn Arg
```

<210> SEQ ID NO 175
<211> LENGTH: 156
<212> TYPE: PRT
<213> ORGANISM: Homo sapiens

<400> SEQUENCE: 175

Met Gly Ser Thr Ala Ile Leu Ala Leu Leu Ala Val Leu Gln Gly
1               5                   10                  15

Val Cys Ala Glu Val Gln Leu Val Gln Ser Gly Ala Glu Val Lys Lys
            20                  25                  30

Pro Gly Glu Ser Leu Lys Ile Ser Cys Lys Gly Ser Gly Tyr Arg Phe
        35                  40                  45

Thr Ser Tyr Trp Ile Gly Trp Val Arg Gln Met Pro Gly Lys Gly Leu
    50                  55                  60

Glu Trp Met Gly Ile Ile Tyr Pro Gly Asp Ser Asp Thr Arg Tyr Ser
65                  70                  75                  80

Pro Ser Phe Gln Gly Gln Val Thr Ile Ser Ala Asp Lys Ser Ile Ser
                85                  90                  95

Thr Ala Tyr Leu Gln Trp Ser Ser Leu Lys Ala Ser Asp Thr Ala Met
            100                 105                 110

Tyr Tyr Cys Ala Arg Lys Asp Tyr Tyr Tyr Ala Met Asp Val Trp
        115                 120                 125

Gly Gln Gly Thr Thr Val Thr Val Ser Ser Ala Ser Thr Lys Gly Pro
    130                 135                 140

Ser Val Phe Pro Leu Ala Pro Ser Ser Lys Ser Thr
145                 150                 155

<210> SEQ ID NO 176
<211> LENGTH: 226
<212> TYPE: PRT
<213> ORGANISM: Homo sapiens

<400> SEQUENCE: 176

Gln Leu Leu Gly Leu Leu Leu Trp Leu Arg Gly Ala Arg Cys Asp
1               5                   10                  15

Ile Gln Met Thr Gln Ser Pro Ser Ser Leu Ser Ala Ser Val Gly Asp
            20                  25                  30

Arg Val Thr Ile Thr Cys Arg Thr Ser His Asp Ile Ser Asn Tyr Leu
        35                  40                  45

Asn Trp Tyr Gln Gln Lys Pro Gly Lys Ala Pro Lys Leu Leu Ile Tyr
    50                  55                  60

Ala Ala Ser Ser Leu Gln Ser Gly Val Pro Ser Arg Phe Ser Gly Ser
65                  70                  75                  80

Arg Ser Gly Thr Asp Phe Thr Leu Thr Ile Ser Ser Leu Gln Pro Glu
                85                  90                  95

Asp Phe Ala Thr Tyr Tyr Cys Gln Gln Thr Tyr Ser Thr Leu Phe Thr
            100                 105                 110

Phe Gly Pro Gly Thr Lys Val Asp Ile Lys Arg Thr Val Ala Ala Pro
        115                 120                 125

Ser Val Phe Ile Phe Pro Pro Ser Asp Glu Gln Leu Lys Ser Gly Thr
    130                 135                 140

Ala Ser Val Val Cys Leu Leu Asn Asn Phe Tyr Pro Arg Glu Ala Lys
145                 150                 155                 160

Val Gln Trp Lys Val Asp Asn Ala Leu Gln Ser Gly Asn Ser Gln Glu
                165                 170                 175

```
Ser Val Thr Glu Gln Asp Ser Lys Asp Ser Thr Tyr Ser Leu Ser Ser
            180                 185                 190

Thr Leu Thr Leu Ser Lys Ala Asp Tyr Glu Lys His Lys Val Tyr Ala
        195                 200                 205

Cys Glu Val Thr His Gln Gly Leu Ser Ser Pro Val Thr Lys Ser Phe
    210                 215                 220

Asn Arg
225

<210> SEQ ID NO 177
<211> LENGTH: 183
<212> TYPE: PRT
<213> ORGANISM: Homo sapiens

<400> SEQUENCE: 177

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Ile
        35                  40                  45

Ser Ser Tyr Tyr Trp Ser Trp Ile Arg Gln Pro Pro Gly Lys Gly Leu
    50                  55                  60

Glu Trp Ile Gly Tyr Val Tyr Phe Ser Gly Ser Thr Asn Tyr Asn Pro
65                  70                  75                  80

Ser Leu Lys Ser Arg Val Thr Ile Ser Val Asp Thr Ser Lys Asn Gln
            85                  90                  95

Phe Ser Leu Lys Leu Ser Ser Val Thr Ala Ala Asp Thr Ala Val Tyr
        100                 105                 110

Tyr Cys Ala Arg Ala Thr Arg Asp Tyr Tyr Tyr Gly Met Asp Val
            115                 120                 125

Trp Gly Gln Gly Thr Thr Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
            165                 170                 175

Thr Val Ser Trp Glu Leu Ser
            180
```